US012668598B2

(12) United States Patent
Hu et al.

(10) Patent No.: US 12,668,598 B2
(45) Date of Patent: Jun. 30, 2026

(54) MK2 INHIBITORS AND USES THEREOF

(71) Applicant: Bristol-Myers Squibb Company, Princeton, NJ (US)

(72) Inventors: Xirui Hu, Cambridge, MA (US); Lixin Qiao, Andover, MA (US); Boris Seletsky, Cambridge, MA (US); Matthew Patton, Cambridge, MA (US); Min Cao, Cambridge, MA (US); Farid van der Mei, Summit, NJ (US); Guobin Miao, Lexington, MA (US); Ivar McDonald, Cambridge, MA (US); Carolyn Dzierba, Cambridge, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 236 days.

(21) Appl. No.: 18/495,004

(22) Filed: Oct. 26, 2023

(65) Prior Publication Data

US 2024/0190890 A1 Jun. 13, 2024

Related U.S. Application Data

(60) Provisional application No. 63/381,195, filed on Oct. 27, 2022.

(51) Int. Cl.
*C07D 495/14* (2006.01)

(52) U.S. Cl.
CPC .................................. *C07D 495/14* (2013.01)

(58) Field of Classification Search
None
See application file for complete search history.

(56) References Cited

U.S. PATENT DOCUMENTS

| | | | |
|---|---|---|---|
| 2016/0263187 A1 | 9/2016 | Lander et al. | |
| 2019/0135835 A1 | 5/2019 | Alexander et al. | |
| 2019/0375762 A1 | 12/2019 | Alexander et al. | |
| 2023/0135894 A1* | 5/2023 | Yang .................... | C07D 519/00 514/210.16 |

FOREIGN PATENT DOCUMENTS

WO 2023278759 A1 1/2023

OTHER PUBLICATIONS

Anderson et al., Benzothiophene inhibitors of MK2. Part 2: Improvements in kinase selectivity and cell potency, Bioorganic & Medicinal Chemistry Letters, vol. 19, Issue 16, 2009, pp. 4882-4884 (Year: 2009).*
Brown, Bioisosteres in Medicinal Chemistry, 2012 (Year: 2012).*
International Search Report & Written Opinion Issued in PCT Application No. PCT/US23/77897, Mailed Date: May 10, 2024, 14 Pages.
Invitation to Pay Additional Fees Issued in PCT Application No. PCT/US23/77897, Mailed Date: Feb. 23, 2024, 2 Pages.

* cited by examiner

*Primary Examiner* — Jeffrey S Lundgren
*Assistant Examiner* — Anthony Joseph Seitz
(74) *Attorney, Agent, or Firm* — Mintz Levin Cohn Ferris Glovsky and Popeo, P.C.

(57) ABSTRACT

The present invention provides compounds, compositions thereof, and methods of using the MK2 inhibitors of the Formula:

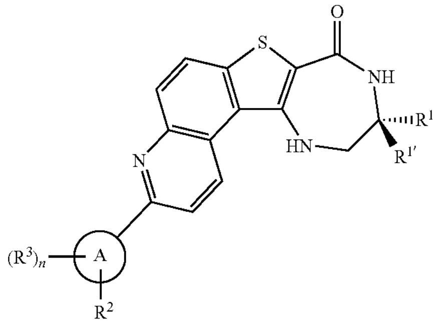

13 Claims, No Drawings

Specification includes a Sequence Listing.

SEQUENCE LISTING

```
Sequence total quantity: 2
SEQ ID NO: 1           moltype = AA  length = 400
FEATURE                Location/Qualifiers
source                 1..400
                       mol_type = protein
                       organism = Homo sapiens
SEQUENCE: 1
MLSNSQGQSP PVPFPAPAPP PQPPTPALPH PPAQPPPPPP QQFPQFHVKS GLQIKKNAII  60
DDYKVTSQVL GLGINGKVLQ IFNKRTQEKF ALKMLQDCPK ARREVELHWR ASQCPHIVRI  120
VDVYENLYAG RKCLLIVMEC LDGGELFSRI QDRGDQAFTE REASEIMKSI GEAIQYLHSI  180
NIAHRDVKPE NLLYTSKRPN AILKLTDFGF AKETTSHNSL TTPCYTPYYV APEVLGPEKY  240
DKSCDMWSLG VIMYILLCGY PPFYSNHGLA ISPGMKTRIR MGQYEFPNPE WSEVSEEVKM  300
LIRNLLKTEP TQRMTITEFM NHPWIMQSTK VPQTPLHTSR VLKEDKERWE DVKEEMTSAL  360
ATMRVDYEQI KIKKIEDASN PLLLKRRKKA RALEAAALAH                     400

SEQ ID NO: 2           moltype = AA  length = 28
FEATURE                Location/Qualifiers
source                 1..28
                       mol_type = protein
                       organism = synthetic construct
SEQUENCE: 2
NLYAGRKCLL IVMECLDGGE LFSRIQDR                                  28
```

MK2 INHIBITORS AND USES THEREOF

RELATED APPLICATIONS

This application claims priority to, and benefit of, U.S. Provisional Patent Application No. 63/381,195, filed Oct. 27, 2022, the contents of which are incorporated by reference in their entirety.

INCORPORATION BY REFERENCE OF SEQUENCE LISTING

The present application is being filed with a Sequence Listing in electronic format. The Sequence Listing is provided as a file entitled 055920-569001US-ST26.xml, created on Oct. 26, 2023, and is 4 kilobytes in size. The information in electronic format of the Sequence Listing is incorporated herein by reference in its entirety.

TECHNICAL FIELD OF THE INVENTION

The present invention relates to compounds useful as inhibitors of MK2 kinases. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

Mitogen-activated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNF-α), interleukin 6 (IL-6) and interferon gamma (IFNγ), that are involved in many acute and chronic inflammatory diseases, e.g. rheumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-α. (see Deak et al., EMBO. 17:4426-4441 (1998); Shi et al., Biol. Chem. 383:1519-1536 (2002); Staklatvala., Curr. Opin. Pharmacol. 4:372-377 (2004), and Shiroto et al., J. Mol. Cardiol. 38:93-97 (2005)).

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases.

Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of MK2. Such compounds have general formula

I

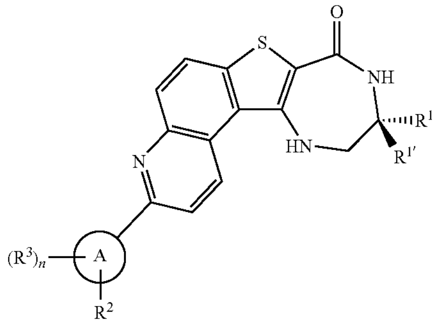

or a pharmaceutically acceptable salt thereof, wherein each of Ring A, $R^1$, $R^{1'}$, $R^2$, $R^3$, and n is as defined and described in embodiments herein.

Compounds of the present invention, and pharmaceutically acceptable compositions thereof, are useful for treating a variety of diseases, disorders or conditions, associated with abnormal cellular responses triggered by protein kinase-mediated events. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF CERTAIN EMBODIMENTS

1. General Description of Compounds of the Invention

In certain embodiments, the present invention provides irreversible inhibitors of MK2. In some embodiments, such compounds include those of the formulae described herein, or a pharmaceutically acceptable salt thereof, wherein each variable is as defined and described herein.

In some embodiments, the present invention provides a compound of formula I:

I

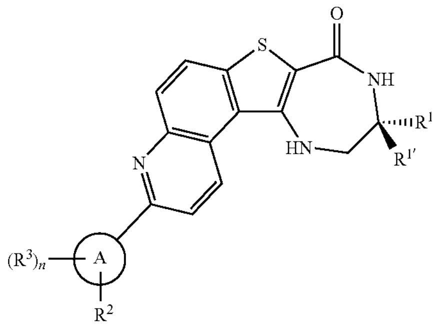

or a pharmaceutically acceptable salt thereof, wherein:

Ring A is a 5-6 membered heteroaryl ring having 1-3 heteroatoms independently selected from nitrogen, oxygen, and sulfur, provided that when Ring A is a 6-membered heteroaryl ring the heteroatom is nitrogen;

each of $R^1$ and $R^{1'}$ is independently selected from hydrogen and $C_{1-4}$ aliphatic substituted with 0-3 instances of $R^x$, or:

$R^1$ and $R^{1'}$ may, together with the intervening atom to which they are attached, form an optionally substituted 3- to 6-membered saturated, partially unsaturated heterocyclyl, or aryl ring having 0-3 heteroatoms independently selected from nitrogen, oxygen, and sulfur;

$R^x$ is —CN, —$NO_2$, halogen, —OR, —SR, —$N(R)_2$, —$C(O)N(R)_2$, —C(O)OR, —C(O)R, —N(R)C(O)R, —$SO_2N(R)_2$, or —$N(R)SO_2$;

$R^2$ is halogen, $C_2$-$C_6$ alkenyl, or $C_2$-$C_6$ alkynyl, wherein the alkenyl or alkynyl is optionally substituted with m instances of $R^y$;

each $R^y$ is independently selected from D, halogen, —CN, —$CO_2R$, —$N(R)_2$, and a 3- to 6-membered saturated or partially unsaturated heterocyclic ring having 1-3 heteroatoms independently selected from nitrogen, oxygen, and sulfur;

$R^3$ is optionally substituted $C_{1-6}$ aliphatic, —CN, halogen, —$(CH_2)_q$—$OR^4$, —$N(R)_2$, —C(O)OR, —$(CH_2)_r$-Cy, or —O—$(CH_2)_t$—$R^5$; or:

two $R^3$ groups on adjacent atoms, together with the intervening atoms to which they are attached, form an optionally substituted 5- to 6-membered saturated, partially unsaturated, or aryl ring having 0-3 heteroatoms independently selected from nitrogen, oxygen, and sulfur;

each $R^4$ is independently selected from hydrogen, optionally substituted $C_{1-6}$ aliphatic, and -Cy;

each $R^5$ is independently selected from —OR and -Cy;

each Cy is independently an optionally substituted ring selected from a 3- to 9-membered saturated or partially unsaturated monocyclic carbocyclic ring, a 3- to 9-membered saturated or partially unsaturated monocyclic heterocyclic ring having 1-3 heteroatoms independently selected from nitrogen, oxygen, and sulfur, phenyl, a 5- to 6-membered heteroaryl ring having 1-3 heteroatoms independently selected from nitrogen, oxygen, and sulfur, a 7- to 12-membered saturated or partially unsaturated fused, spirofused, or bridged bicyclic carbocyclic ring, or a 7- to 12-membered saturated or partially unsaturated fused, spirofused, or bridged bicyclic heterocyclic ring having 1-3 heteroatoms independently selected from nitrogen, oxygen, and sulfur;

each R is independently hydrogen or an optionally substituted $C_{1-6}$ aliphatic, or:

two R groups on the same nitrogen are taken together with the nitrogen to form a 3-7 membered saturated or partially unsaturated heterocyclic ring having 1-3 heteroatoms selected from nitrogen, oxygen, or sulfur;

each of m, n, q, and r is independently 0-4; and is 1-4.

2. Compounds and Definitions

Compounds of this invention include those described generally above, and are further illustrated by the classes, subclasses, and species disclosed herein. As used herein, the following definitions shall apply unless otherwise indicated.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic $C_3$-$C_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

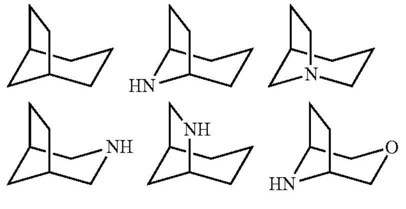

-continued

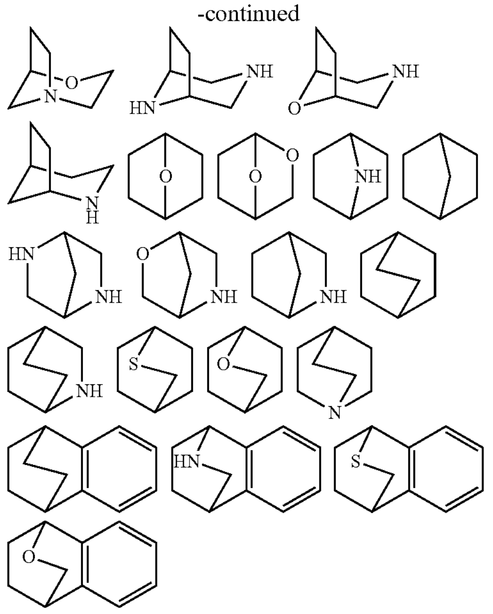

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

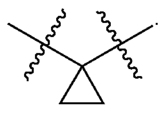

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system and exemplary groups include phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Exemplary heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Exemplary groups include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted.

Examples of such saturated or partially unsaturated heterocyclic radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

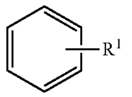

refers to at least

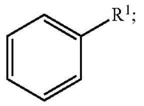

and

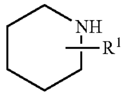

refers to at least

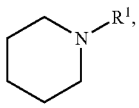,
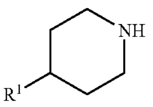
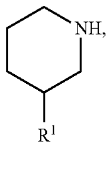, or
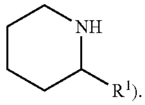).

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium, halogen; $-(CH_2)_{0-4}R^{\circ}$; $-(CH_2)_{0-4}OR^{\circ}$; $-O(CH_2)_{0-4}R^{\circ}$, $-O-(CH_2)_{0-4}C(O)OR^{\circ}$; $-(CH_2)_{0-4}CH(OR^{\circ})_2$; $-(CH_2)_{0-4}SR^{\circ}$; $-(CH_2)_{0-4}Ph$, which may be substituted with $R^{\circ}$; $-(CH_2)_{0-4}O(CH_2)_{0-1}Ph$ which may be substituted with $R^{\circ}$; $-CH{=}CHPh$, which may be substituted with $R^{\circ}$; $-(CH_2)_{0-4}O(CH_2)_{0-1}$-pyridyl which may be substituted with $R^{\circ}$; $-NO_2$; $-CN$; $-N_3$; $-(CH_2)_{0-4}N(R^{\circ})_2$; $-(CH_2)_{0-4}N(R^{\circ})C(O)R^{\circ}$; $-N(R^{\circ})C(S)R^{\circ}$; $-(CH_2)_{0-4}N(R^{\circ})C(O)NR^{\circ}_2$; $-N(R^{\circ})C(S)NR^{\circ}_2$; $-(CH_2)_{0-4}N(R^{\circ})C(O)OR^{\circ}$; $-N(R^{\circ})N(R^{\circ})C(O)R^{\circ}$; $-N(R^{\circ})N(R^{\circ})C(O)NR^{\circ}_2$; $-N(R^{\circ})N(R^{\circ})C(O)OR^{\circ}$; $-(CH_2)_{0-4}C(O)R^{\circ}$; $-C(S)R^{\circ}$; $-(CH_2)_{0-4}C(O)OR^{\circ}$; $-(CH_2)_{0-4}C(O)SR^{\circ}$; $-(CH_2)_{0-4}C(O)OSiR^{\circ}_3$; $-(CH_2)_{0-4}OC(O)R^{\circ}$; $-OC(O)(CH_2)_{0-4}SR^{\circ}$; $-(CH_2)_{0-4}SC(O)R^{\circ}$; $-(CH_2)_{0-4}C(O)NR^{\circ}_2$; $-C(S)NR^{\circ}_2$; $-C(S)SR^{\circ}$; $-SC(S)SR^{\circ}$, $-(CH_2)_{0-4}OC(O)NR^{\circ}_2$; $-C(O)N(OR^{\circ})R^{\circ}$; $-C(O)C(O)R^{\circ}$; $-C(O)CH_2C(O)R^{\circ}$; $-C(NOR^{\circ})R^{\circ}$; $-(CH_2)_{0-4}SSR^{\circ}$; $-(CH_2)_{0-4}S(O)_2R^{\circ}$; $-(CH_2)_{0-4}S(O)_2OR^{\circ}$; $-(CH_2)_{0-4}OS(O)_2R^{\circ}$; $-S(O)_2NR^{\circ}_2$; $-(CH_2)_{0-4}S(O)R^{\circ}$; $-N(R^{\circ})S(O)_2NR^{\circ}_2$; $-N(R^{\circ})S(O)_2R^{\circ}$; $-N(OR^{\circ})R^{\circ}$; $-C(NH)NR^{\circ}_2$; $-P(O)_2R^{\circ}$; $-P(O)R^{\circ}_2$; $-OP(O)R^{\circ}_2$; $-OP(O)(OR^{\circ})_2$; $SiR^{\circ}_3$; $-(C_{1-4}$ straight or branched alkylene)$O-N(R^{\circ})_2$; or $-(C_{1-4}$ straight or branched alkylene)$C(O)O-N(R^{\circ})_2$, wherein each $R^{\circ}$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, $-(CH_2)_{0-2}R^{\bullet}$, -(halo$R^{\bullet}$), $-(CH_2)_{0-2}OH$, $-(CH_2)_{0-2}OR^{\bullet}$, $-(CH_2)_{0-2}CH(OR^{\bullet})_2$; $-O$(halo$R^{\bullet}$), $-CN$, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\circ}_3$, $-OSiR^{\circ}_3$, $-C(O)SR^{\bullet}$, $-(C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include $=O$ and $=S$.

Suitable divalent substituents on a saturated carbon atom of an "optionally substituted" group include the following: $=O$ ("oxo"), $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^•$ include halogen, $—R^•$, -(halo$R^•$), —OH, $—OR^•$, —O(halo$R^•$), —CN, —C(O)OH, $—C(O)OR^•$, $—NH_2$, $—NHR^•$, $—NR^•_2$, or $—NO_2$, wherein each $R^•$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^†$, $—NR^†_2$, $—C(O)R^†$, $—C(O)OR^†$, $—C(O)C(O)R^†$, $—C(O)CH_2C(O)R^†$, $—S(O)_2R^†$, $—S(O)_2NR^†_2$, $—C(S)NR^†_2$, $—C(NH)NR^†_2$, or $—N(R)S(O)_2R^†$; wherein each R is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R are independently halogen, $—R^•$, -(halo$R^•$), —OH, $—OR^•$, —O(halo$R^•$), —CN, —C(O)OH, $—C(O)OR^•$, $—NH_2$, —NHR, $—NR^•_2$, or $—NO_2$, wherein each $R^•$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention.

Such compounds are useful, for example, as analytical tools, as probes in biological assays, or as therapeutic agents in accordance with the present invention. In certain embodiments, a warhead moiety, Ring $A(R^2)(R^3)$, of a provided compound comprises one or more deuterium atoms.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The term "biological sample", as used herein, includes, without limitation, cell cultures or extracts thereof; biopsied material obtained from a mammal or extracts thereof, and blood, saliva, urine, feces, semen, tears, or other body fluids or extracts thereof. Inhibition of activity of a protein kinase, for example, MK2 or a mutant thereof, in a biological sample is useful for a variety of purposes that are known to one of skill in the art. Examples of such purposes include, but are not limited to, blood transfusion, organ transplantation, biological specimen storage, and biological assays.

As used herein, a "disease or disorder associated with MK2" or, alternatively, "an MK2-mediated disease or disorder" means any disease or other deleterious condition in which MK2, or a mutant thereof, is known or suspected to play a role.

The term "subject", as used herein, means a mammal and includes human and animal subjects, such as domestic animals (e.g., horses, dogs, cats, etc.). The terms "subject" and "patient" are used interchangeably. In some embodiments, the "patient" or "subject" means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The amount of compounds of the present invention that may be combined with the carrier materials to produce a composition in a single dosage form will vary depending upon the host treated, the particular mode of administration, etc. Preferably, provided compositions are formulated so that a dosage of between 0.01 to about 100 mg/kg, or about 0.1 mg/kg to about 50 mg/kg, and preferably from about 1 mg/kg to about 25 mg/kg, of subject body weight/day of the inhibitor can be administered to a patient receiving these compositions to obtain the desired therapeutic effect. The amount of a compound of the present invention in the composition will also depend upon the particular compound in the composition.

The expression "unit dosage form" as used herein refers to a physically discrete unit of a provided compound and/or compositions thereof appropriate for the subject to be treated. It will be understood, however, that the total daily usage of the active agent (i.e., compounds and compositions of the present invention) will be decided by the attending physician within the scope of sound medical judgment. The specific effective dose level for any particular subject (i.e., patient) or organism will depend upon a variety of factors including the disorder being treated and the severity of the disorder; activity of specific active agent employed; specific composition employed; age, body weight, general health, sex and diet of the subject; time of administration, route of administration, and rate of excretion of the specific active agent employed; duration of the treatment; and like factors well known in the medical arts.

The term "parenteral" as used herein includes subcutaneous, intravenous, intramuscular, intra-articular, intra-synovial, intrasternal, intrathecal, intrahepatic, intralesional and intracranial injection or infusion techniques.

As used herein, a "therapeutically effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a provided compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a "therapeutically effective amount" is at least a minimal amount of a provided compound, or composition containing a provided compound, which is sufficient for treating one or more symptoms of an MK2-mediated disease or disorder.

As used herein, the terms "treatment," "treat," and "treating" refer to partially or completely alleviating, inhibiting, delaying onset of, preventing, ameliorating and/or relieving a disorder or condition, or one or more symptoms of the disorder or condition, as described herein.

In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

As used herein, the term "inhibitor" is defined as a compound that binds to and/or inhibits the target protein kinase, MK2, with measurable affinity. In certain embodiments, an inhibitor has an $IC_{50}$ and/or binding constant of less than about 50 μM, less than about 1 μM, less than about 500 nM, less than about 100 nM, or less than about 10 nM.

The terms "measurable affinity" and "measurably inhibit," as used herein, means a measurable change in MK2 activity between a sample comprising a compound of the present invention, or composition thereof, and MK2, and an equivalent sample comprising MK2, in the absence of said compound, or composition thereof.

As used herein, the term "irreversible" or "irreversible inhibitor" refers to an inhibitor (i.e. a compound) that is able to be covalently bonded to a kinase in a substantially non-reversible manner. That is, whereas a reversible inhibitor is able to bind to (but is generally unable to form a covalent bond with) a kinase, and therefore can become dissociated from the kinase, an irreversible inhibitor will remain substantially bound to a kinase once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to a kinase once covalent bond formation has occurred and will remain bound for a time period that is longer than the life of the protein.

Methods for identifying if a compound is acting as an irreversible inhibitor are known to one of ordinary skill in the art. Such methods include, but are not limited to, enzyme kinetic analysis of the inhibition profile of the compound with a kinase, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

As used herein, the term "drug resistance" refers to changes in the wild-type nucleic acid sequence coding a target protein, and/or the amino acid sequence of the target protein, and/or the amino acid sequence of another protein, which changes decrease or abolish the inhibitory effect of the inhibitor on the target protein. Without wishing to be bound by any particular theory, it is believed that certain compounds of the present invention, i.e., compounds that are irreversible kinase inhibitors, may be effective inhibitors of drug resistant forms of protein kinases.

3. Description of Exemplary Embodiments

As described herein, the present invention provides irreversible inhibitors of MK2 kinase. Without wishing to be bound by any particular theory, it is believed that compounds of the invention comprise a moiety capable of covalently binding to a key cysteine residue in the binding domain of MK2 kinase. Such a moiety is referred to herein as a "reactive moiety." One of ordinary skill in the art will appreciate that MK2 kinase, and mutants thereof, have a cysteine residue in the binding domain. Without wishing to be bound by any particular theory, it is believed that proximity of a reactive moiety, present on a provided MK2 inhibitor, to the cysteine of interest facilitates covalent modification of that cysteine by the reactive moiety.

The cysteine residues of interest can also be described by an identifying portion of the amino acid sequence of MK2 kinase which includes the cysteine of interest. Thus, in certain embodiments, Cys140 of MK2 is characterized in that Cys140 is the cysteine embedded in the following amino acid sequence of MK2:

SEQ ID NO. 1:
MLSNSQGQSPPVPFPAPAPPPQPPTPALPHPPAQPPPPPPQQFPQ

FHVKSGLQIKKNAIIDDYKVTSQVLGLGINGKVLQIFNKRTQEKF

ALKMLQDCPKARREVELHWRASQCPHIVRIVDVYENLYAGRKCLL

IVMECLDGGELFSRIQDRGDQAFTEREASEIMKSIGEAIQYLHSI

NIAHRDVKPENLLYTSKRPNAILKLTDFGFAKETTSHNSLTTPCY

TPYYVAPEVLGPEKYDKSCDMWSLGVIMYILLCGYPPFYSNHGLA

ISPGMKTRIRMGQYEFPNPEWSEVSEEVKMLIRNLLKTEPTQRMT

ITEFMNHPWIMQSTKVPQTPLHTSRVLKEDKERWEDVKEEMTSAL

ATMRVDYEQIKIKKIEDASNPLLLKRRKKARALEAAALAH.

For the purpose of clarity, Cys140 is provided in the abbreviated amino acid sequence below:

SEQ ID NO. 2:
NLYAGRKCLLIVMEC(140)LDGGELFSRIQDR.

In both SEQ ID NOS. 1 and 2, Cysteine 140 is highlighted in bold with underlining.

In some embodiments, compounds of the present invention include a reactive moiety characterized in that provided compounds covalently modify Cys140 of MK2.

In certain embodiments, compounds of the present invention include a reactive moiety characterized in that a compound covalently modifies a target of Cys140 of MK2, thereby irreversibly inhibiting the kinase.

Thus, in some embodiments, a reactive moiety present on a provided MK2 inhibitor compound is capable of covalently binding to a cysteine residue thereby irreversibly inhibiting the enzyme. In some embodiments, the cysteine residue is Cys140 of MK2. One of ordinary skill in the art will recognize that a variety of reactive moieties, as defined herein, are suitable for such covalent bonding. Such reactive moieties include, but are not limited to, those described herein and depicted infra.

According to one aspect, the present invention provides a compound of formula I,

I

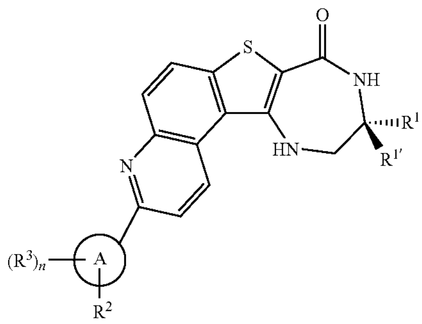

or a pharmaceutically acceptable salt thereof, wherein:

Ring A is phenyl or a 5-6 membered heteroaryl ring having 1-3 heteroatoms independently selected from nitrogen, oxygen, and sulfur;

each of $R^1$ and $R^{1'}$ is independently selected from hydrogen and $C_{1-4}$ aliphatic substituted with 0-3 instances of $R^x$, or:

$R^1$ and $R^{1'}$ may, together with the intervening atoms to which they are attached, form an optionally substituted 3- to 6-membered saturated, partially unsaturated, or aryl ring having 0-3 heteroatoms independently selected from nitrogen, oxygen, and sulfur;

$R^x$ is —CN, —$NO_2$, halogen, —OR, —SR, —$N(R)_2$, —C(O)$N(R)_2$, —C(O)OR, —C(O)R, —N(R)C(O)R, —$SO_2N(R)_2$, or —$N(R)SO_2$;

$R^2$ is halogen, —CN, or $C_{1-6}$ aliphatic substituted with m instances of $R^y$;

each $R^y$ is independently selected from halogen, —CN, —$CO_2R$, —$N(R)_2$, and a 3- to 6-membered heterocyclic ring having 1-3 heteroatoms independently selected from nitrogen, oxygen, and sulfur;

$R^3$ is optionally substituted $C_{1-6}$ aliphatic, —CN, halogen, —$(CH_2)_q$—$OR^4$, —$N(R)_2$, —C(O)OR, —$(CH_2)_r$-Cy, or —O—$(CH_2)_t$—$R^5$; or:

two $R^3$ groups, together with the intervening atoms to which they are attached, form an optionally substituted 5- to 6-membered saturated, partially unsaturated, or aryl ring having 0-3 heteroatoms independently selected from nitrogen, oxygen, and sulfur;

each $R^4$ is independently selected from hydrogen, optionally substituted $C_{1-6}$ aliphatic, and -Cy;

each $R^5$ is independently selected from —OR and -Cy;

each Cy is independently an optionally substituted ring selected from a 3- to 9-membered saturated or partially unsaturated monocyclic carbocyclic ring, a 3- to 9-membered saturated or partially unsaturated monocyclic heterocyclic ring having 1-3 heteroatoms independently selected from nitrogen, oxygen, and sulfur, phenyl, a 5- to 6-membered heteroaryl ring having 1-3 heteroatoms independently selected from nitrogen, oxygen, and sulfur, a 7- to 12-membered saturated or partially unsaturated fused, spirofused, or bridged bicyclic carbocyclic ring, or a 7- to 12-membered saturated or partially unsaturated fused, spirofused, or bridged bicyclic heterocyclic ring having 1-3 heteroatoms independently selected from nitrogen, oxygen, and sulfur;

each R is independently hydrogen or an optionally substituted $C_{1-6}$ aliphatic, or:

two R groups on the same nitrogen are taken together with the nitrogen to form a 3-7 membered saturated or partially unsaturated heterocyclic ring having 1-3 heteroatoms selected from nitrogen, oxygen, or sulfur;

each of m, n, q, and r is independently 0-4; and t is 1-4.

As defined generally above, each of $R^1$ and $R^{1'}$ is independently selected from hydrogen and $C_{1-4}$ aliphatic substituted with 0-3 instances of $R^x$, or $R^1$ and $R^{1'}$ may, together with the intervening atoms to which they are attached, form an optionally substituted 3- to 6-membered saturated, partially unsaturated, or aryl ring having 0-3 heteroatoms independently selected from nitrogen, oxygen, and sulfur.

In some embodiments, $R^{1'}$ is hydrogen. Accordingly, in some embodiments, the present disclosure provides a compound of formula I-a:

I-a

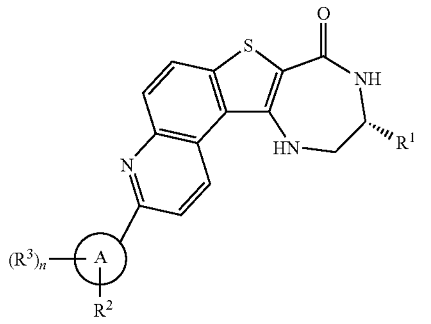

or a pharmaceutically acceptable salt thereof, wherein each of $R^1$, $R^2$, $R^3$, and n is as defined above and described herein.

In some embodiments of formula I or I-a, $R^1$ is $C_{1-4}$ aliphatic substituted with 0-3 instances of $R^x$. In some embodiments, $R^1$ is $C_{1-4}$ aliphatic substituted with 1 instance of $R^x$. In some embodiments, $R^1$ is $C_{1-4}$ aliphatic substituted with 2 instances of $R^x$. In some embodiments, $R^1$ is $C_{1-4}$ aliphatic substituted with 3 instances of $R^x$. In some embodiments, $R^1$ is $C_{1-2}$ aliphatic substituted with 1 instance of $R^x$. In some embodiments, $R^1$ is $C_{1-2}$ aliphatic substituted with 2 instances of $R^x$. In some embodiments, $R^1$ is $C_{1-2}$ aliphatic substituted with 3 instances of $R^x$.

As defined generally above, $R^x$ is —CN, —$NO_2$, halogen, —OR, —SR, —$N(R)_2$, —$C(O)N(R)_2$, —C(O)OR, —C(O)R, —N(R)C(O)R, —$SO_2N(R)_2$, or —$N(R)SO_2$. In some embodiments, $R^x$ is halogen.

In some embodiments, $R^x$ is —OR. In some embodiments, $R^x$ is —$N(R)_2$.

In some embodiments of formula I or I-a, $R^1$ is —$CH_3$. In some embodiments of formula I or I-a, $R^1$ is —$CH_2OH$. In some embodiments of formula I or I-a, $R^1$ is —$CH_2F$.

In some embodiments of formula I, $R^1$ and $R^{1'}$ are each $C_{1-4}$ aliphatic substituted with 0-3 instances of R. In some embodiments, $R^1$ and $R^{1'}$ are each $C_{1-4}$ aliphatic. In some embodiments, $R^1$ and $R^{1'}$ are each $C_{1-2}$ aliphatic. In some embodiments, $R^1$ and $R^{1'}$ are each —$CH_3$.

In some embodiments of formula I, $R^1$ and $R^{1'}$ together with the intervening atoms to which they are attached, form an optionally substituted 3- to 6-membered saturated, partially unsaturated, or aryl ring having 0-3 heteroatoms independently selected from nitrogen, oxygen, and sulfur. In some embodiments of formula I, $R^1$ and $R^{1'}$ together with the intervening atoms to which they are attached, form an optionally substituted 3-membered saturated ring having 0-1 heteroatoms independently selected from nitrogen, oxygen, and sulfur. In some embodiments of formula I, $R^1$ and $R^{1'}$ together with the intervening atoms to which they are attached, form an optionally substituted 4-membered saturated ring having 0-1 heteroatoms independently selected from nitrogen, oxygen, and sulfur. In some embodiments of formula I, $R^1$ and $R^{1'}$ together with the intervening atoms to which they are attached, form an optionally substituted 5-membered saturated ring having 0-1 heteroatoms independently selected from nitrogen, oxygen, and sulfur.

In some embodiments of formula I, $R^1$ and $R^{1'}$ together with the intervening atoms to which they are attached, form an optionally substituted 6-membered saturated ring having 0-1 heteroatoms independently selected from nitrogen, oxygen, and sulfur. In some embodiments of formula I, $R^1$ and $R^{1'}$ together with the intervening atoms to which they are attached, form an optionally substituted

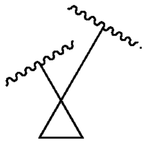

As defined generally above, Ring A is phenyl or a 5-6 membered heteroaryl ring having 1-3 heteroatoms independently selected from nitrogen, oxygen, and sulfur. In some embodiments, Ring A is phenyl. In some embodiments, Ring A is phenyl and $R^2$ is at a meta position of the phenyl ring.

In some embodiments, Ring A is a 5-6 membered heteroaryl ring having 1-3 heteroatoms independently selected from nitrogen, oxygen, and sulfur.

In some embodiments, Ring A is a 5-membered heteroaryl ring having 1-3 heteroatoms independently selected from nitrogen, oxygen, and sulfur. In some embodiments, Ring A is a 5-membered heteroaryl ring having 1-2 heteroatoms independently selected from nitrogen, oxygen, and sulfur. In some embodiments, Ring A is a 5-membered heteroaryl ring having 2 heteroatoms independently selected from nitrogen, oxygen, and sulfur.

In some embodiments, Ring A is a 6-membered heteroaryl ring having 1-3 nitrogen atoms. In some embodiments, Ring A is a 6-membered heteroaryl ring having 1-2 nitrogen atoms.

In some embodiments, Ring A is a 6-membered heteroaryl ring having 1 nitrogen. In some embodiments, Ring A is a 6-membered heteroaryl ring having 2 nitrogens.

In some embodiments,

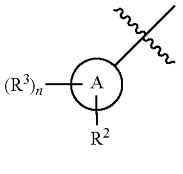

is selected from the group consisting of
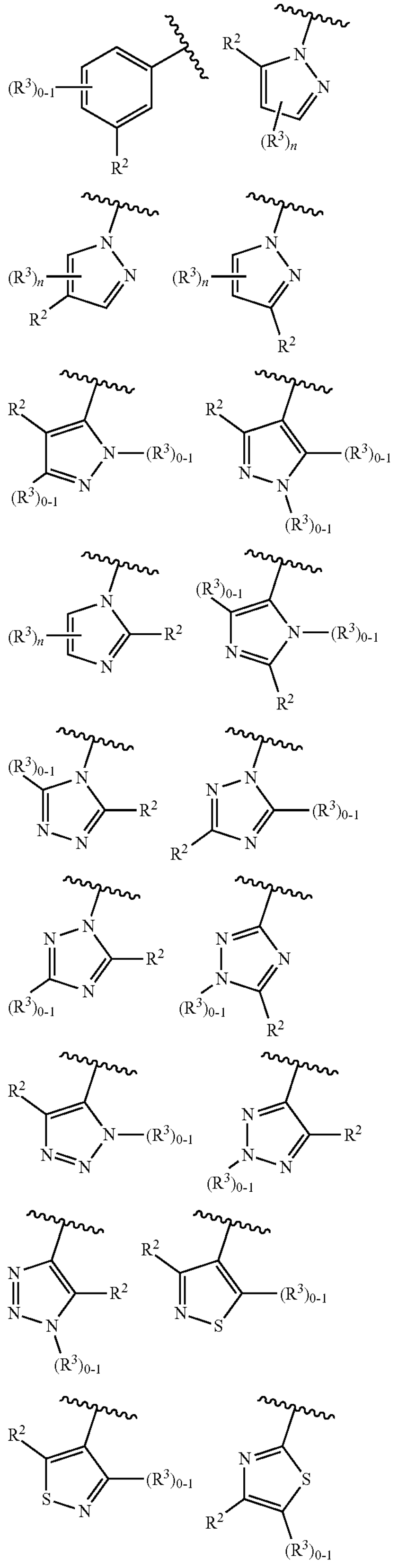
-continued
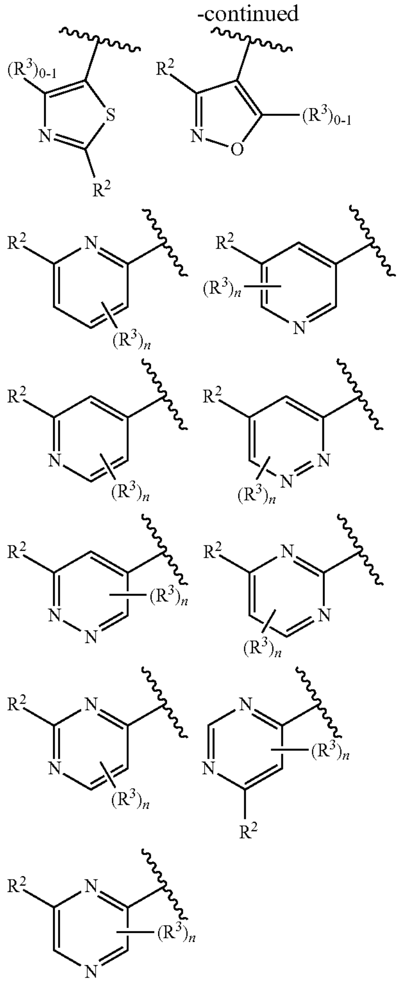
In some embodiments,
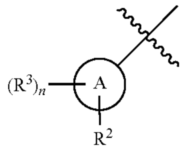
is selected from the group consisting of
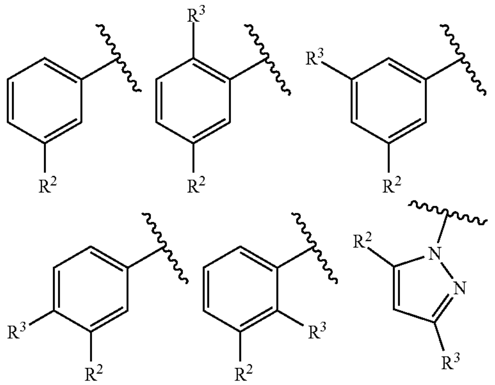

-continued
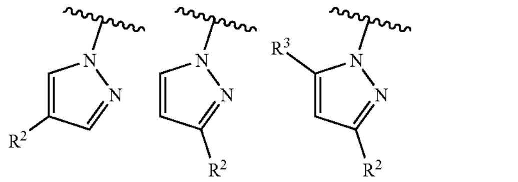
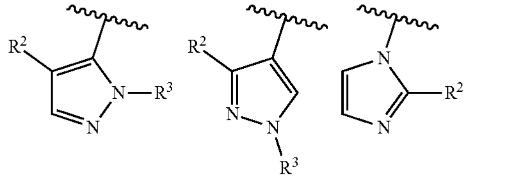
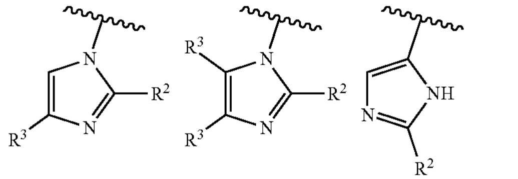
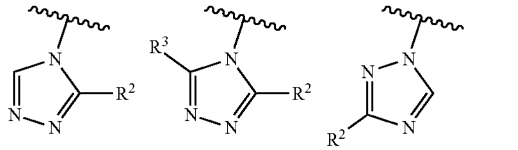
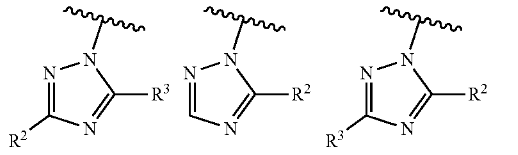
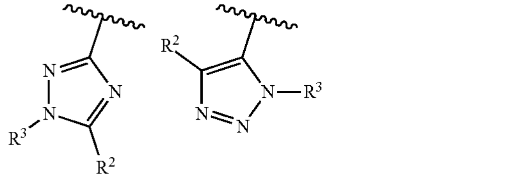
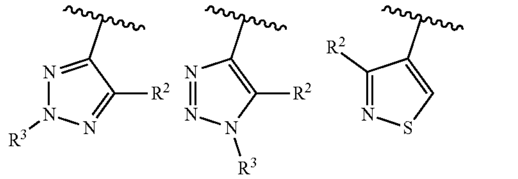
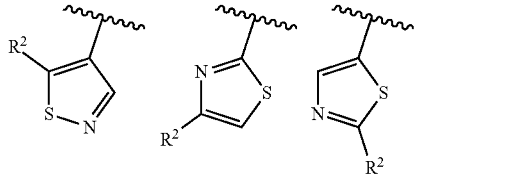
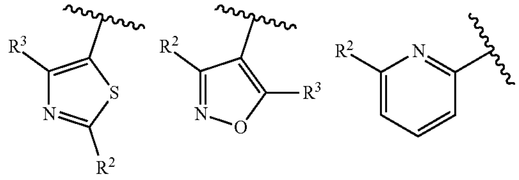
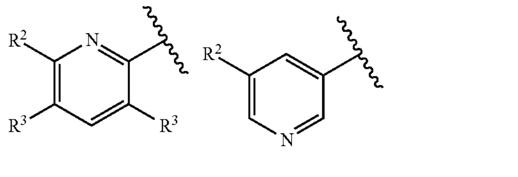
-continued
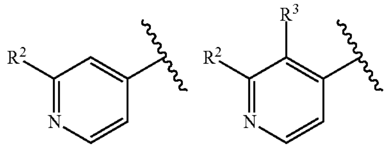
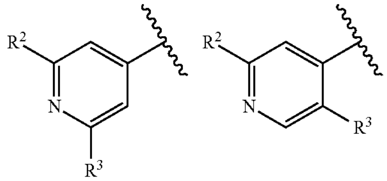
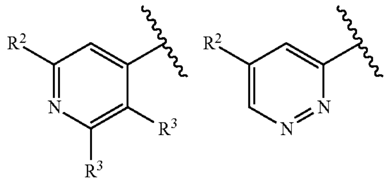
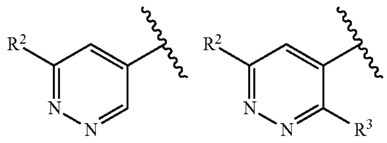
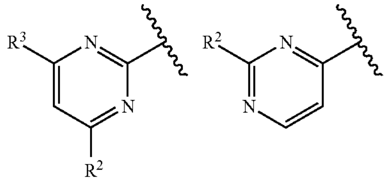
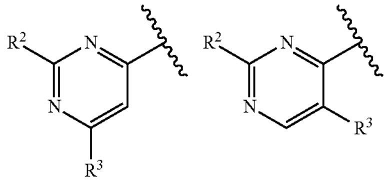
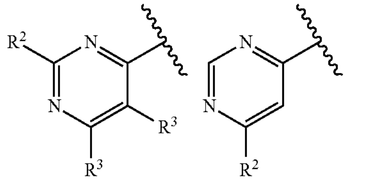
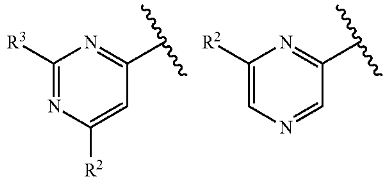
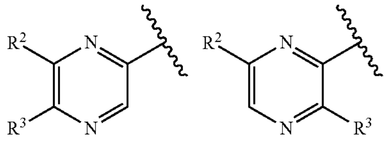
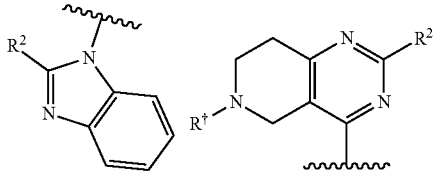

-continued

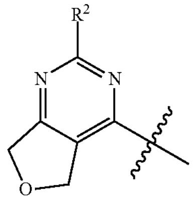

As defined generally above, $R^2$ is halogen, —CN, or $C_{1-6}$ aliphatic substituted with m instances of $R^y$. In some embodiments, $R^2$ is halogen. In some such embodiments, $R^2$ is fluoro, chloro, or bromo. In some embodiments, $R^2$ is fluoro or chloro. In some embodiments, $R^2$ is —CN.

In some embodiments, $R^2$ is $C_{1-6}$ aliphatic substituted with m instances of $R^y$. In some embodiments, $R^2$ is $C_{1-4}$ aliphatic substituted with m instances of $R^y$. In some embodiments, $R^2$ is $C_{1-2}$ aliphatic substituted with m instances of $R^y$.

In some embodiments, $R^2$ is $C_{2-6}$ aliphatic substituted with m instances of $R^y$, wherein the $C_{2-6}$ aliphatic has at least one unit of unsaturation. In some embodiments, $R^2$ is $C_{2-4}$ aliphatic substituted with m instances of $R^y$, wherein the $C_{2-4}$ aliphatic has at least one unit of unsaturation. In some embodiments, $R^2$ is $C_{2-3}$ aliphatic substituted with m instances of $R^y$, wherein the $C_{2-3}$ aliphatic has one unit of unsaturation.

In some embodiments, $R^2$ is selected from the group consisting of $—CH_2—R^y$, $—CH{=}CH_2$, —C≡CH, $—C{\equiv}CCH_3$, $—CH{=}CHCH_3$ (e.g.,

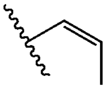 or 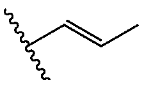), $—CH{=}CH—R^y$ (e.g.,

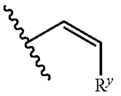 or 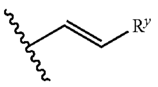), $—CH{=}CHCH_2—R^y$ (e.g.,

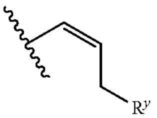 or 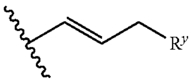), $—CH{=}CHCH(R^y)_2$ (e.g.,

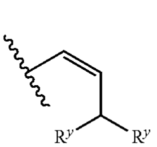 or 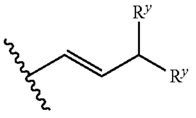), $—CH{=}CHC(R^y)_3$ (e.g.

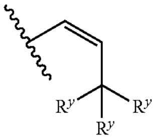 or 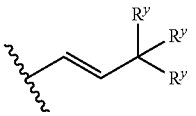),

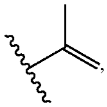, 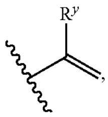, 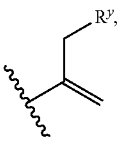

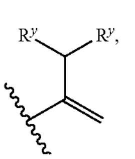 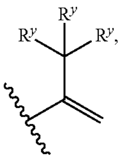 and

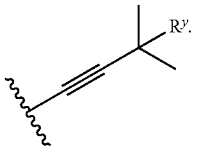

As defined generally above, each $R^y$ is independently selected from halogen, —CN, $—CO_2R$, $—N(R)_2$, and a 3- to 6-membered saturated or partially unsaturated heterocyclic ring having 1-3 heteroatoms independently selected from nitrogen, oxygen, and sulfur. In some embodiments, $R^y$ is halogen. In some embodiments, $R^y$ is fluoro. In some embodiments, $R^y$ is —CN. In some embodiments, $R^y$ is $—CO_2R$. In some embodiments, $R^y$ is $—N(R)_2$.

In some embodiments, $R^y$ is a 3- to 6-membered saturated or partially unsaturated heterocyclic ring having 1-3 heteroatoms independently selected from nitrogen, oxygen, and sulfur. In some embodiments, $R^y$ is a 5-membered saturated heterocyclic ring having 1-3 heteroatoms independently selected from nitrogen, oxygen, and sulfur. In some embodiments, $R^y$ is a 5-membered saturated heterocyclic ring having 1 heteroatom selected from nitrogen, oxygen, and sulfur. In some embodiments, $R^y$ is a 6-membered saturated heterocyclic ring having 1-3 heteroatoms independently selected from nitrogen, oxygen, and sulfur. In some embodiments, $R^y$ is a 6-membered saturated heterocyclic ring having 1-2 heteroatoms independently selected from nitrogen, oxygen, and sulfur. In some embodiments, $R^y$ is pyrrolidinyl or morpholinyl.

In some embodiments, $R^y$ is selected from fluoro, —CN, $—NH_2$, $—N(CH_3)_2$, $—C(O)OCH_3$,

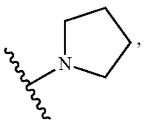, and 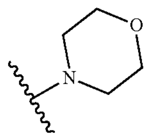.

In some embodiments, m is 0-4. In some embodiments, m is 0. In some embodiments, m is 1-4. In some embodiments, m is 1-3. In some embodiments, m is 1. In some embodiments, m is 2. In some embodiments, m is 3.

In some embodiments, n is 0. In some embodiments, n is 1. In some embodiments, n is 2. In some embodiments, n is 3. In some embodiments, n is 4. In some embodiments, n is 0-2. In some embodiments, n is 0-3. In some embodiments, n is 1-3.

As defined generally above, $R^3$ is optionally substituted $C_{1-6}$ aliphatic, —CN, halogen, $—(CH_2)_q—OR^4$, $—N(R)_2$, —C(O)OR, $—(CH_2)_r$-Cy, or $—O—(CH_2)_t—R^5$, or two $R^3$ groups, together with the intervening atoms to which they are attached, form an optionally substituted 5- to 6-membered saturated, partially unsaturated, or aryl ring having 0-3 heteroatoms independently selected from nitrogen, oxygen, and sulfur. In some embodiments, $R^3$ is optionally substituted $C_{1-6}$ aliphatic, —CN, halogen, $—(CH_2)_q—OR^4$, $—N(R)_2$, —C(O)OR, $—(CH_2)_r$-Cy, or $—O—(CH_2)_t—R^5$.

In some embodiments, $R^3$ is optionally substituted $C_{1-6}$ aliphatic. In some embodiments, $R^3$ is optionally substituted $C_{1-4}$ aliphatic. In some embodiments, $R^3$ is optionally substituted $C_{1-2}$ aliphatic. In some embodiments, $R^3$ is $C_{1-6}$ aliphatic optionally substituted with halogen. In some embodiments, $R^3$ is $C_{1-6}$ aliphatic optionally substituted with $—(CH_2)_{0-4}OR^\circ$. In some such embodiments, $R^\circ$ is hydrogen. In some embodiments, $R^3$ is $C_{1-6}$ aliphatic optionally substituted with —OH. In some embodiments, $R^3$ is $C_{1-4}$ aliphatic optionally substituted with halogen. In some embodiments, $R^3$ is $C_{1-4}$ aliphatic optionally substituted with $—(CH_2)_{0-4}OR^\circ$. In some such embodiments, $R^\circ$ is hydrogen. In some embodiments, $R^3$ is $C_{1-4}$ aliphatic optionally substituted with —OH. In some embodiments, $R^3$ is $C_{1-2}$ aliphatic optionally substituted with halogen. In some embodiments, $R^3$ is $C_{1-2}$ aliphatic optionally substituted with $—(CH_2)_{0-4}OR^\circ$. In some such embodiments, $R^\circ$ is hydrogen. In some embodiments, $R^3$ is $C_{1-2}$ aliphatic optionally substituted with —OH.

In some embodiments, $R^3$ is —CN. In some embodiments, $R^3$ is halogen. In some such embodiments, $R^3$ is fluoro or chloro. In some embodiments, $R^3$ is $—(CH_2)_q—OR^4$. In some embodiments, $R^3$ is $—N(R)_2$. In some embodiments, $R^3$ is —C(O)OR. In some embodiments, $R^3$ is $—(CH_2)_r$-Cy. In some embodiments, $R^3$ is $—O—(CH_2)_t—R^5$.

In some embodiments, two $R^3$ groups on adjacent atoms, together with the intervening atoms to which they are attached, form an optionally substituted 5- to 6-membered saturated, partially unsaturated, or aryl ring having 0-3 heteroatoms independently selected from nitrogen, oxygen, and sulfur. In some embodiments, two $R^3$ groups on adjacent atoms, together with the intervening atoms to which they are attached, form an optionally substituted 5-membered saturated ring having 0-3 heteroatoms independently selected from nitrogen, oxygen, and sulfur. In some embodiments, two $R^3$ groups on adjacent atoms, together with the intervening atoms to which they are attached, form an optionally substituted 6-membered saturated ring having 0-3 heteroatoms independently selected from nitrogen, oxygen, and sulfur. In some embodiments, two $R^3$ groups on adjacent atoms, together with the intervening atoms to which they are attached, form an optionally substituted 6-membered aryl ring having 0-3 heteroatoms independently selected from nitrogen, oxygen, and sulfur.

In some embodiments, q is 0. Accordingly, in some embodiments, $R^3$ is $—OR^4$. In some embodiments, q is 1-4. In some embodiments, q is 1. Accordingly, in some embodiments, $R^3$ is $—CH_2OR^4$. In some embodiments, q is 2. In some embodiments, q is 3.

As defined generally above, each $R^4$ is independently selected from hydrogen, optionally substituted $C_{1-6}$ aliphatic, and -Cy. In some embodiments, $R^4$ is hydrogen. In some embodiments, $R^4$ is selected from optionally substituted $C_{1-6}$ aliphatic and -Cy. In some embodiments, $R^4$ is optionally substituted $C_{1-6}$ aliphatic. In some embodiments, $R^4$ is optionally substituted $C_{1-4}$ aliphatic. In some embodiments, $R^4$ is optionally substituted $C_{1-2}$ aliphatic.

In some embodiments, $R^4$ is $C_{1-6}$ aliphatic optionally substituted with halogen. In some embodiments, $R^4$ is $C_{1-4}$ aliphatic optionally substituted with halogen. In some embodiments, $R^4$ is $C_{1-2}$ aliphatic optionally substituted with halogen.

In some embodiments, $R^4$ is -Cy.

In some embodiments, r is 0. Accordingly, in some embodiments, $R^3$ is -Cy In some embodiments, r is 1-4. In some embodiments, r is 1. Accordingly, in some embodiments, $R^3$ is $—CH_2Cy$. In some embodiments, r is 2. Accordingly, in some embodiments, $R^3$ is $—CH_2CH_2Cy$. In some embodiments, r is 3.

As defined generally above, t is 1-4. In some embodiments, t is 1. Accordingly, in some embodiments, $R^3$ is $—OCH_2R^5$. In some embodiments, t is 2. Accordingly, in some embodiments, $R^3$ is $—OCH_2CH_2R^5$. In some embodiments, t is 3. In some embodiments, t is 4.

As defined generally above, each R is independently hydrogen or an optionally substituted $C_{1-6}$ aliphatic, or two R groups on the same nitrogen are taken together with the nitrogen to form a 3-7 membered saturated or partially unsaturated heterocyclic ring having 1-3 heteroatoms selected from nitrogen, oxygen, or sulfur. In some embodiments, R is hydrogen. In some embodiments, R is an optionally substituted $C_{1-6}$ aliphatic, or two R groups on the same nitrogen are taken together with the nitrogen to form a 3-7 membered saturated or partially unsaturated heterocyclic ring having 1-3 heteroatoms selected from nitrogen, oxygen, or sulfur. In some embodiments, R is an optionally substituted $C_{1-6}$ aliphatic. In some embodiments, R is an optionally substituted $C_{1-4}$ aliphatic. In some embodiments, R is an optionally substituted $C_{1-2}$ aliphatic. In some embodiments, R is an $C_{1-6}$ aliphatic optionally substituted with $—(CH_2)_{0-4}OR^\circ$ or halogen. In some embodiments, R is an $C_{1-4}$ aliphatic optionally substituted with $—(CH_2)_{0-4}OR^\circ$ or halogen. In some embodiments, R is an $C_{1-2}$ aliphatic optionally substituted with $—(CH_2)_{0-4}OR^\circ$ or halogen. In some embodiments, R is hydrogen, $—CH_3$, $CH_2CH_3$, or $—CH_2CH_2CH_3$.

As defined generally above, each $R^5$ is independently selected from —OR and -Cy. In some embodiments, $R^5$ is —OR. In some embodiments, $R^5$ is -Cy.

As defined generally above, each Cy is independently an optionally substituted ring selected from a 3- to 9-membered saturated or partially unsaturated monocyclic carbocyclic ring, a 3- to 9-membered saturated or partially unsaturated monocyclic heterocyclic ring having 1-3 heteroatoms independently selected from nitrogen, oxygen, and sulfur, phenyl, a 5- to 6-membered heteroaryl ring having 1-3 heteroatoms independently selected from nitrogen, oxygen, and sulfur, a 7- to 12-membered saturated or partially unsaturated fused, spirofused, or bridged bicyclic carbocyclic ring, or a 7- to 12-membered saturated or partially unsaturated fused, spirofused, or bridged bicyclic heterocyclic ring having 1-3 heteroatoms independently selected from nitrogen, oxygen, and sulfur.

In some embodiments, Cy is an optionally substituted 3- to 9-membered saturated or partially unsaturated monocyclic carbocyclic ring. In some embodiments, Cy is an optionally substituted 3-membered saturated carbocyclic ring. In some embodiments, Cy is an optionally substituted 4-membered saturated carbocyclic ring. In some embodiments, Cy is an optionally substituted 5-membered saturated carbocyclic ring. In some embodiments, Cy is an optionally substituted 6-membered saturated monocyclic carbocyclic ring.

In some embodiments, Cy is an optionally substituted 3- to 9-membered saturated or partially unsaturated monocyclic heterocyclic ring having 1-3 heteroatoms independently selected from nitrogen, oxygen, and sulfur. In some embodiments, Cy is an optionally substituted 3-membered saturated heterocyclic ring having 1 heteroatom selected from nitrogen, oxygen, and sulfur. In some embodiments, Cy is an optionally substituted 4-membered saturated heterocyclic ring having 1 heteroatom selected from nitrogen, oxygen, and sulfur. In some embodiments, Cy is an optionally substituted 5-membered saturated heterocyclic ring having 1 heteroatom selected from nitrogen, oxygen, and sulfur. In some embodiments, Cy is an optionally substituted 6-membered saturated heterocyclic ring having 1-2 heteroatoms independently selected from nitrogen, oxygen, and sulfur.

In some embodiments, Cy is an optionally substituted phenyl.

In some embodiments, Cy is an optionally substituted 5- to 6-membered heteroaryl ring having 1-3 heteroatoms independently selected from nitrogen, oxygen, and sulfur. In some embodiments, Cy is an optionally substituted 5-membered heteroaryl ring having 1-3 heteroatoms independently selected from nitrogen, oxygen, and sulfur. In some embodiments, Cy is an optionally substituted 6-membered heteroaryl ring having 1-2 nitrogen atoms.

In some embodiments, Cy is an optionally substituted 7- to 12-membered saturated or partially unsaturated fused, spirofused, or bridged bicyclic carbocyclic ring. In some embodiments, Cy is an optionally substituted 7- to 12-membered saturated or partially unsaturated fused bicyclic carbocyclic ring. In some embodiments, Cy is an optionally substituted 7- to 12-membered saturated or partially unsaturated spirofused bicyclic carbocyclic ring. In some embodiments, Cy is an optionally substituted 7- to 12-membered saturated or partially unsaturated bridged bicyclic carbocyclic ring.

In some embodiments, Cy is an optionally substituted 7- to 12-membered saturated or partially unsaturated fused, spirofused, or bridged bicyclic heterocyclic ring having 1-3 heteroatoms independently selected from nitrogen, oxygen, and sulfur. In some embodiments, Cy is an optionally substituted 7- to 12-membered saturated or partially unsaturated fused bicyclic heterocyclic ring having 1-3 heteroatoms independently selected from nitrogen, oxygen, and sulfur. In some embodiments, Cy is an optionally substituted 7- to 12-membered saturated or partially unsaturated spirofused bicyclic heterocyclic ring having 1-3 heteroatoms independently selected from nitrogen, oxygen, and sulfur. In some embodiments, Cy is an optionally substituted 7-membered saturated spirofused bicyclic heterocyclic ring having 1-3 heteroatoms independently selected from nitrogen, oxygen, and sulfur. In some embodiments, Cy is an optionally substituted 8-membered saturated spirofused bicyclic heterocyclic ring having 1-3 heteroatoms independently selected from nitrogen, oxygen, and sulfur. In some embodiments, Cy is an optionally substituted 9-membered saturated spirofused bicyclic heterocyclic ring having 1-3 heteroatoms independently selected from nitrogen, oxygen, and sulfur. In some embodiments, Cy is an optionally substituted 10-membered saturated spirofused bicyclic heterocyclic ring having 1-3 heteroatoms independently selected from nitrogen, oxygen, and sulfur.

In some embodiments, Cy is an optionally substituted 7- to 12-membered saturated or partially unsaturated bridged bicyclic heterocyclic ring having 1-3 heteroatoms independently selected from nitrogen, oxygen, and sulfur. In some embodiments, Cy is an optionally substituted 7-membered saturated bridged bicyclic heterocyclic ring having 1-3 heteroatoms independently selected from nitrogen, oxygen, and sulfur.

In some embodiments, Cy is selected from

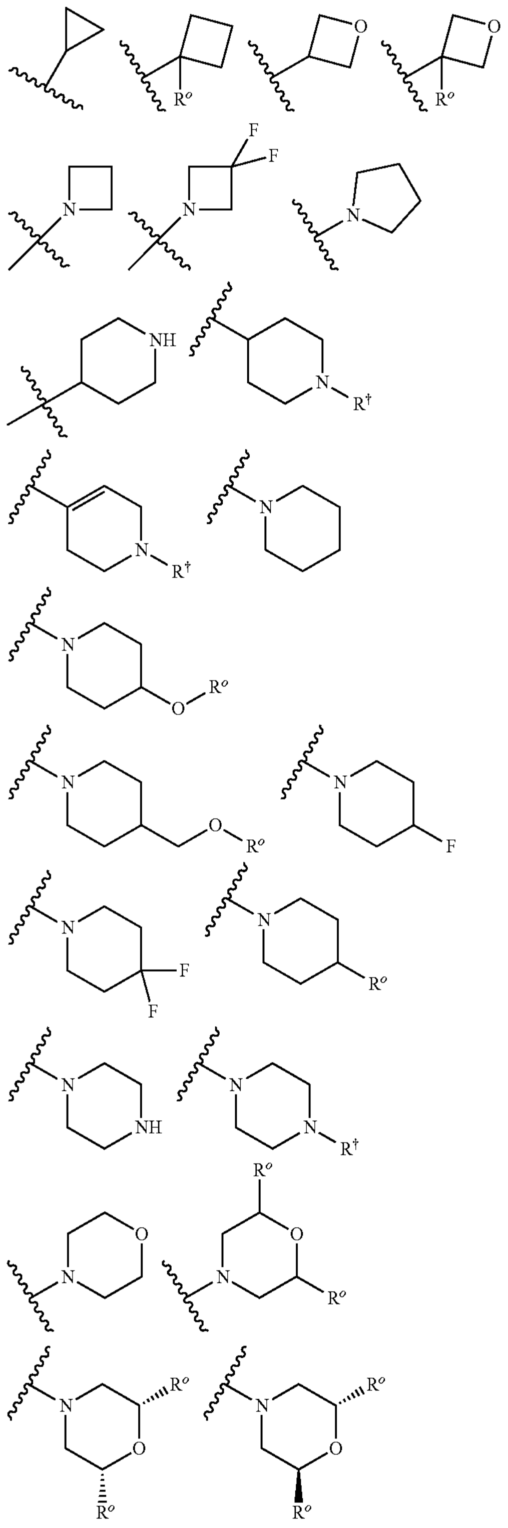

-continued

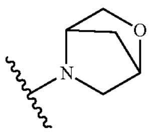
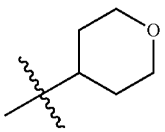
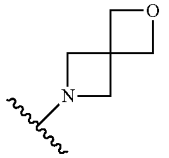
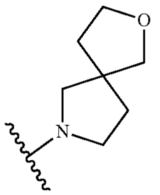
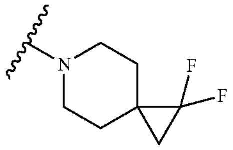
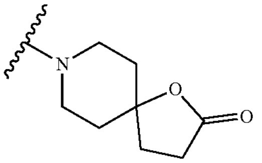

In some embodiments, Cy is selected from

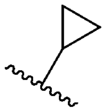
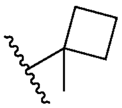
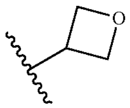
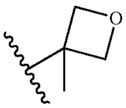
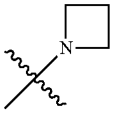
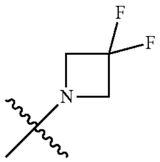
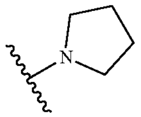
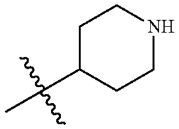
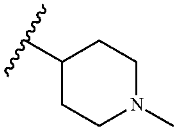
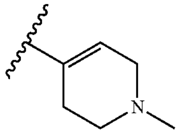
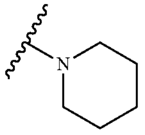
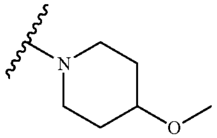
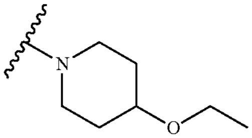
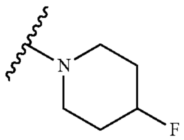
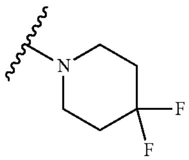
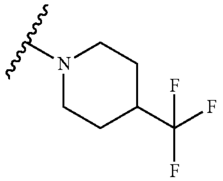
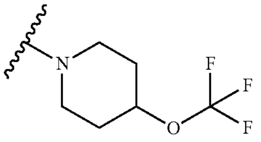

-continued

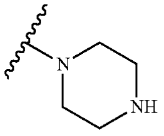
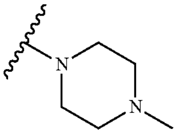
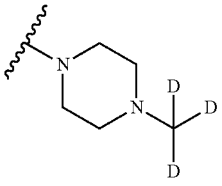
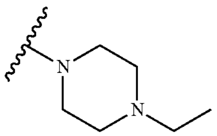
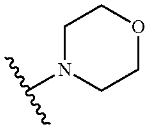
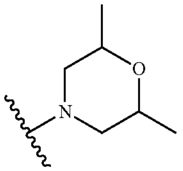
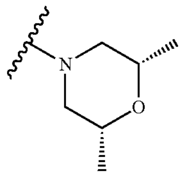
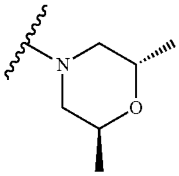
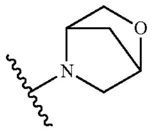
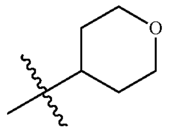
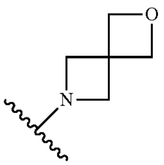
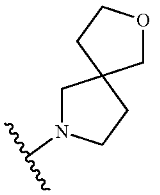
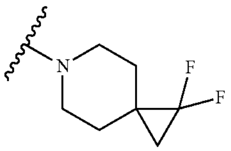
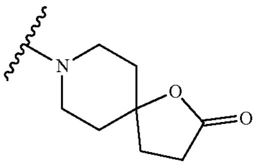

In some embodiments, $R^3$ is selected from halogen, $-CN$, $-N(R)_2$, $-C(O)OR$, $-(CH_2)_q-OR^4$ (e.g., $-OR^4$ or $-CH_2OR^4$), $-(CH_2)_r$-Cy (e.g., -Cy, $-CH_2Cy$, or $-CH_2CH_2Cy$), $-O-(CH_2)_t-R^5$ (e.g., $-OCH_2R^5$ or $-OCH_2CH_2R^5$) and $C_{1-6}$ aliphatic optionally substituted with halogen or $-OR^{\circ}$.

In some embodiments, $R^3$ is selected from: fluoro, chloro, $-CH_3$, $-CD_3$, $-CH_2CH_3$, $-CF_3$, $-CF_2H$, $-CN$, $-CH_2OH$, $-CH_2OCH_3$, $-CH_2OCH_2CH_3$, $-CH(OH)CD_3$, $-C(OH)(CD_3)_2$, $-OCH_3$, $-OCF_3$, $-OCF_2H$, $-OCH_2CH_2CH_3$, $-OCH_2CH_2OCH_2CH_3$, $-NHCH_3$, $-N(CH_3)_2$, $-C(O)OCH_3$, $-C(O)OCH_2CH_3$,

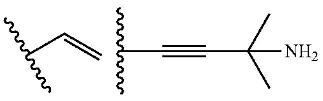
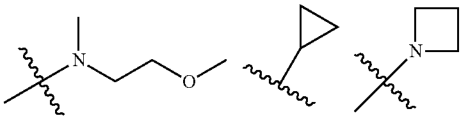

-continued
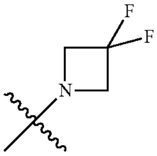
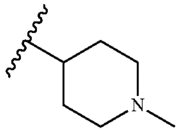
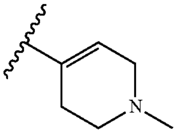
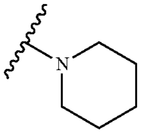
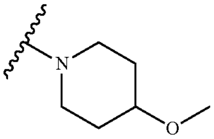
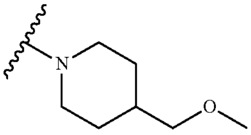
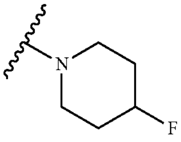
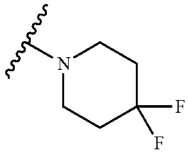
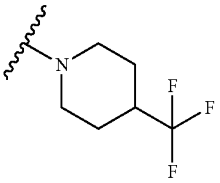
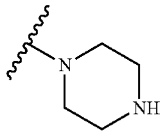
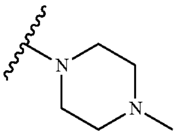
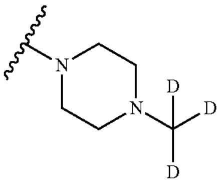
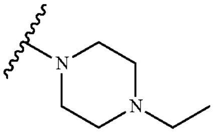
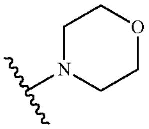
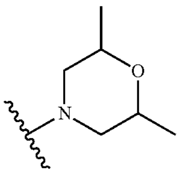
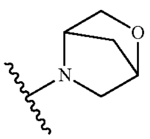
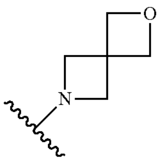
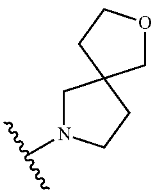
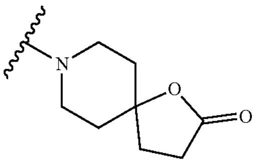
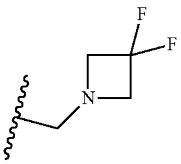
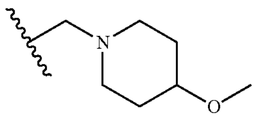
-continued
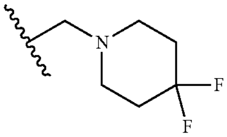
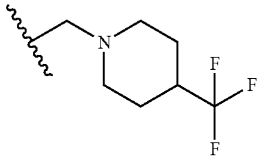
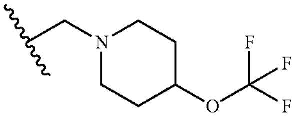
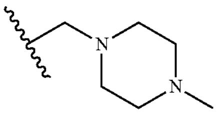
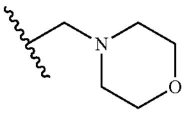
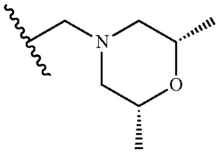
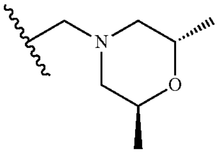
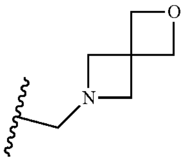
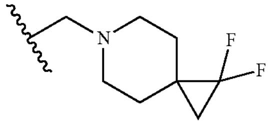
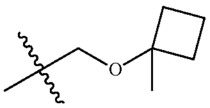
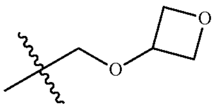
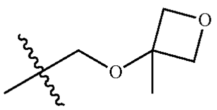
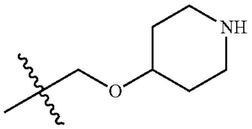
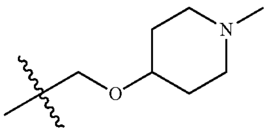
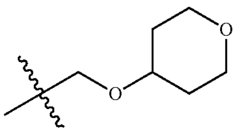
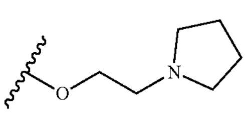
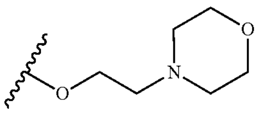
In some embodiments,
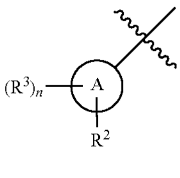

is selected from
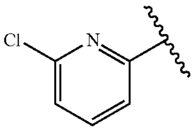
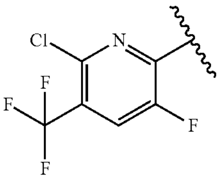
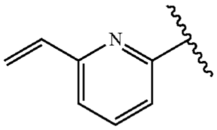
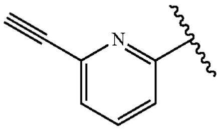
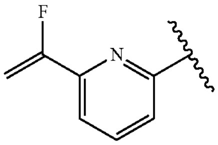
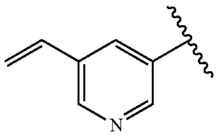
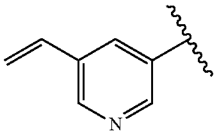
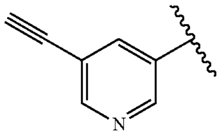
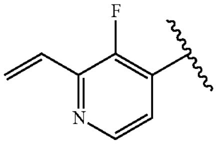
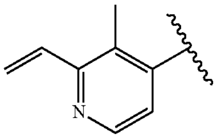
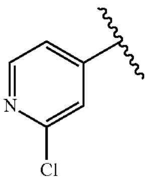
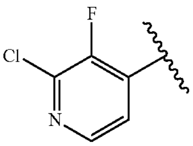
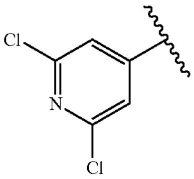
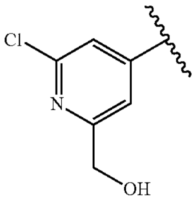
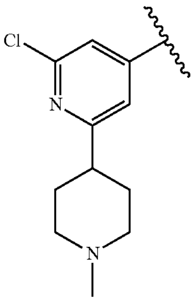
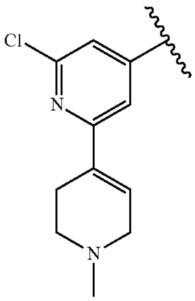
-continued
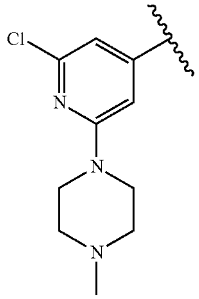
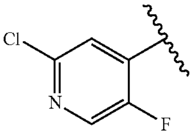
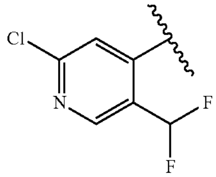
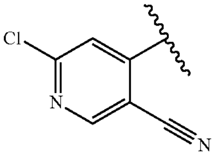
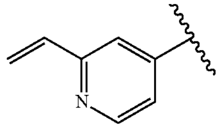
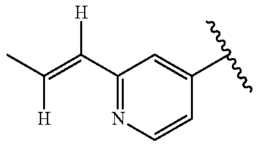
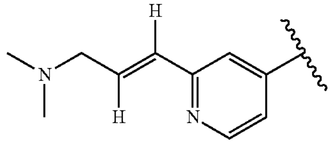
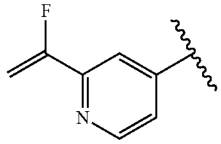
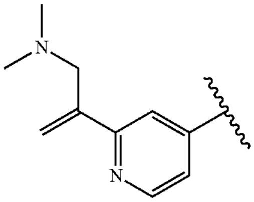
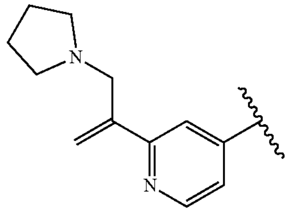
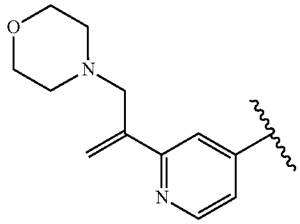
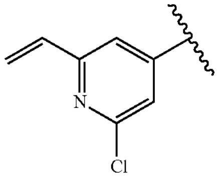
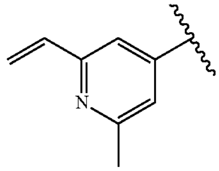
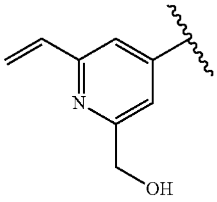

-continued
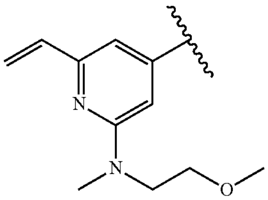
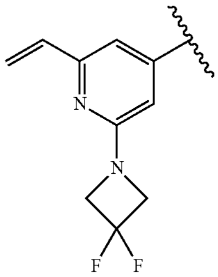
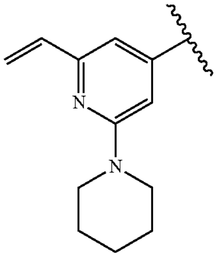
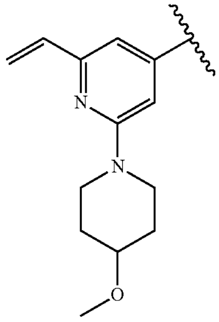
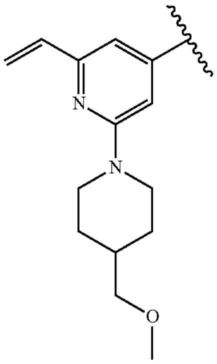
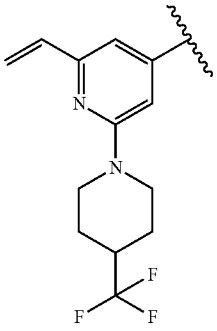
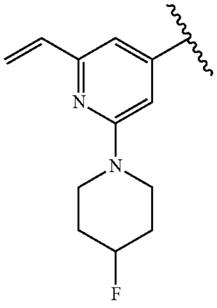
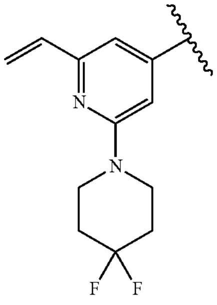
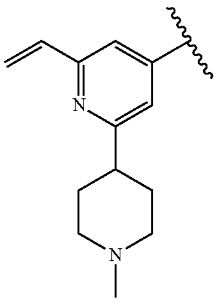
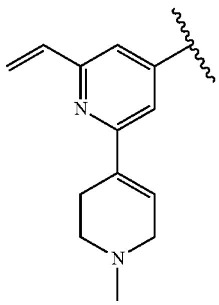
-continued
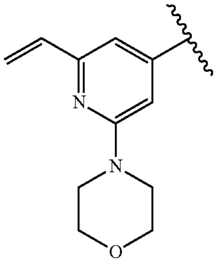
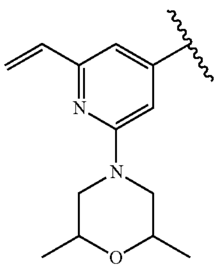
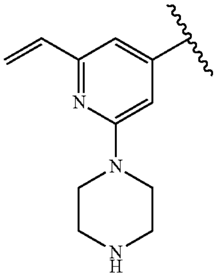
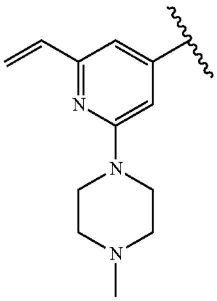
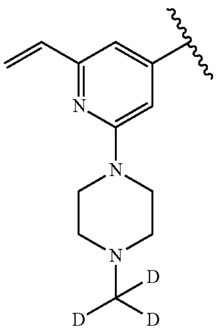
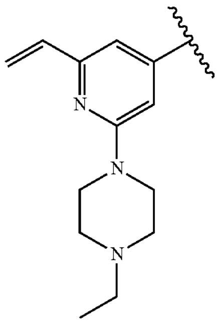
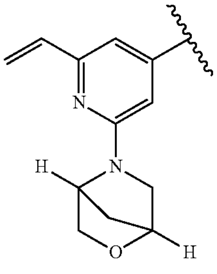
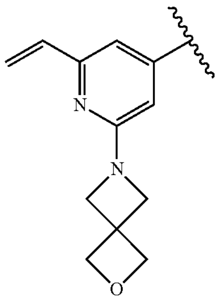
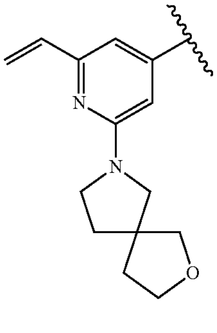
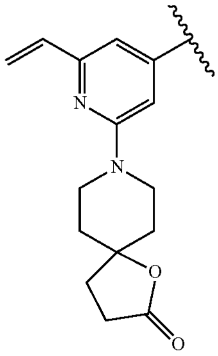

-continued
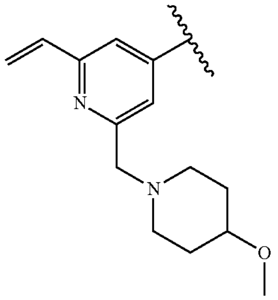
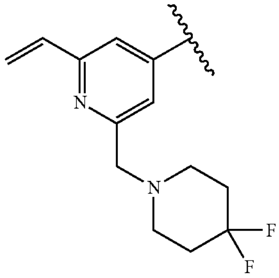
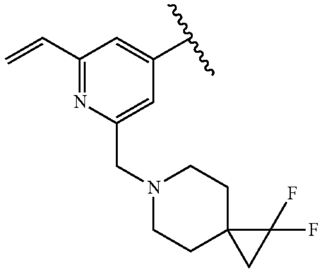
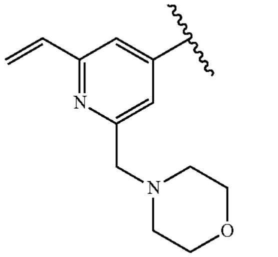
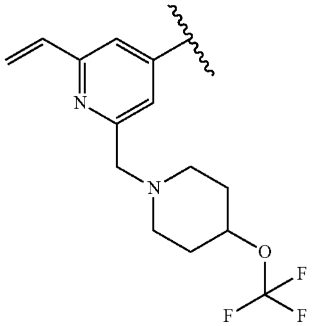
-continued
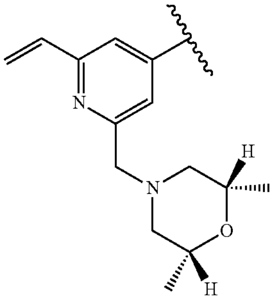
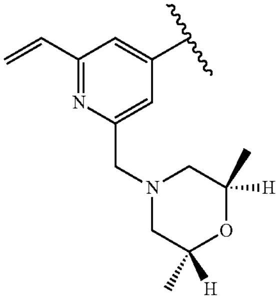
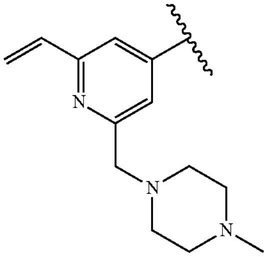
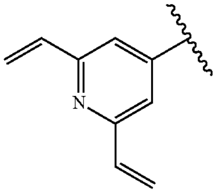
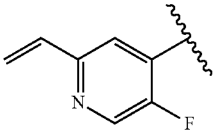
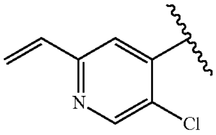
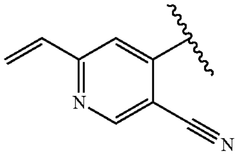
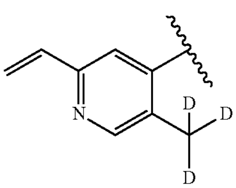
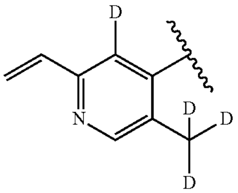
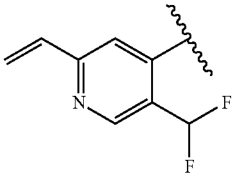
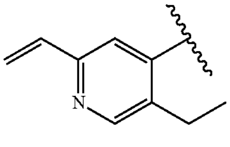

-continued
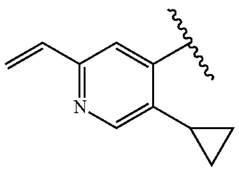
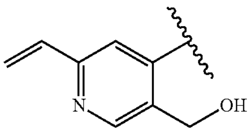
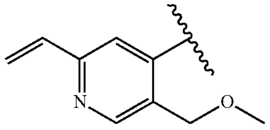
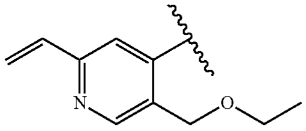
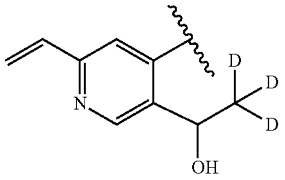
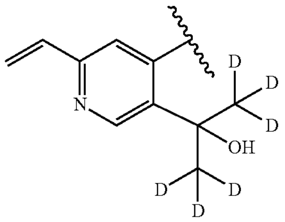
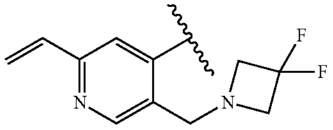
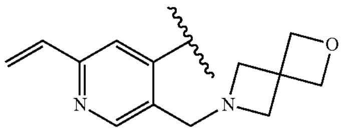
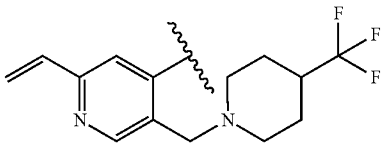
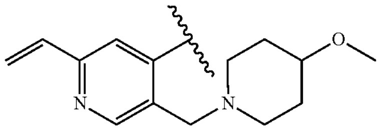
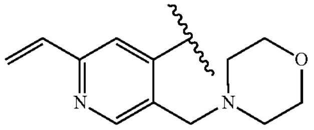
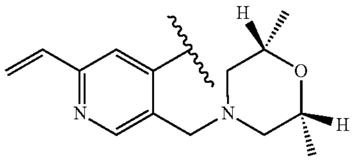
-continued
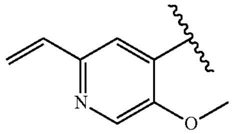
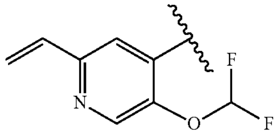
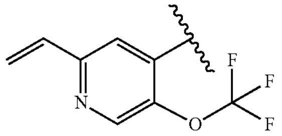
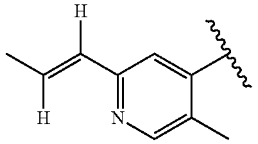
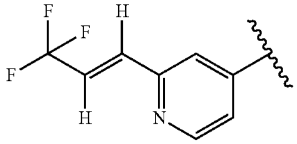
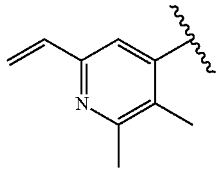
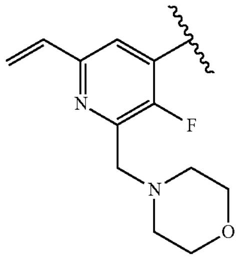
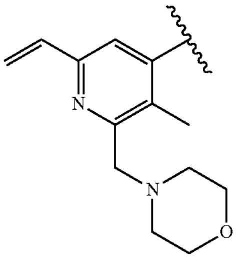
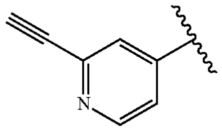
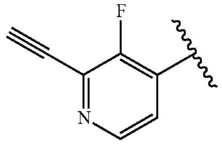
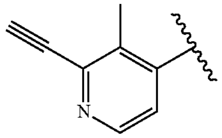
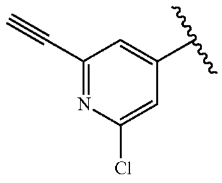
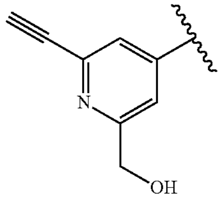
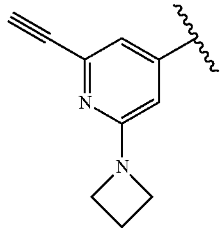
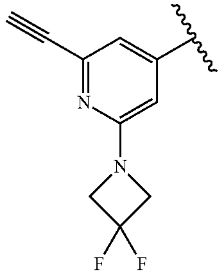
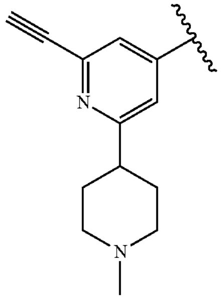

-continued
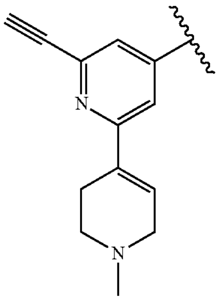
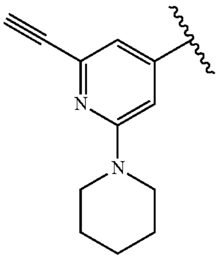
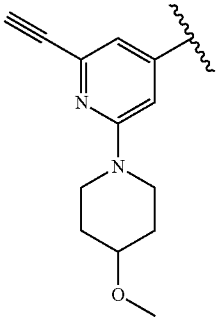
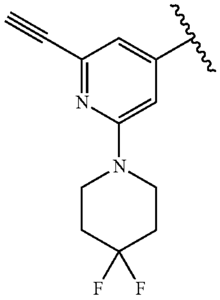
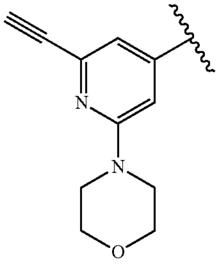
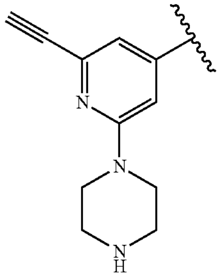
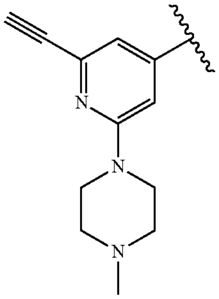
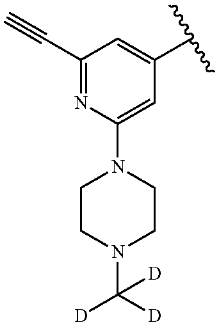
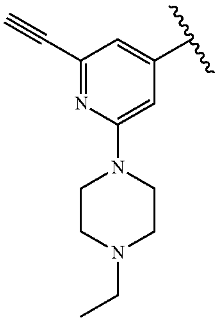
-continued
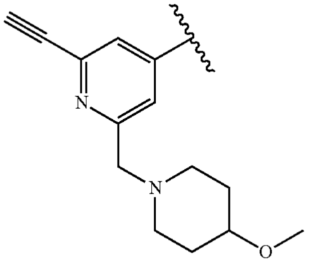
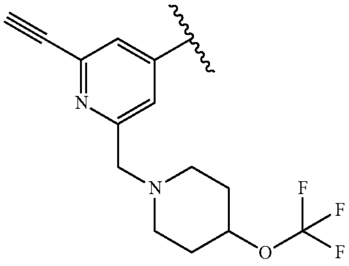
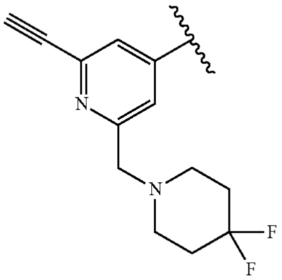
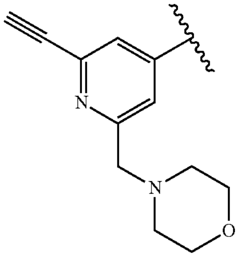
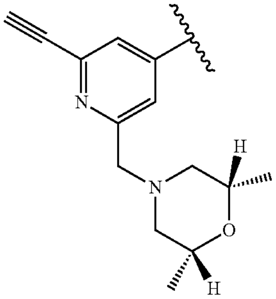
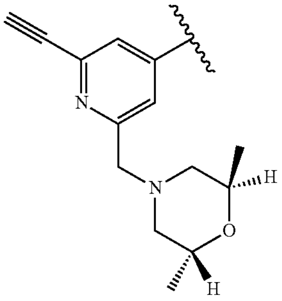
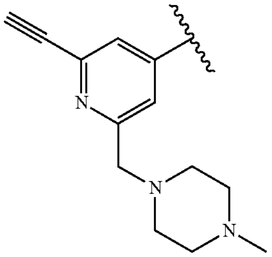

-continued
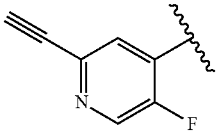
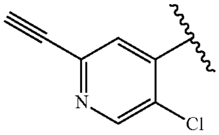
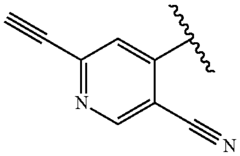
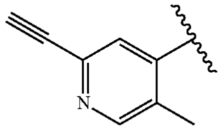
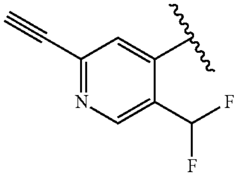
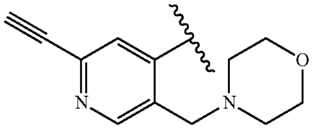
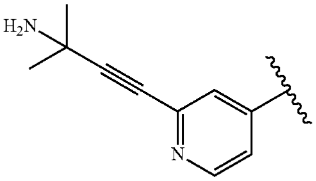
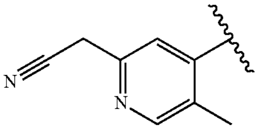
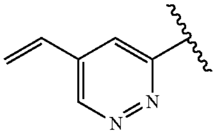
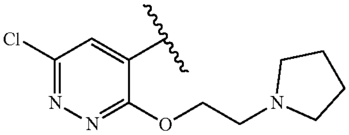
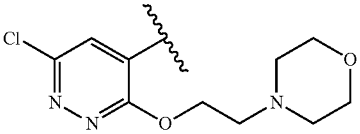
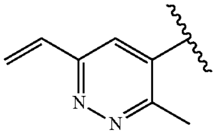
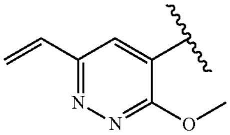
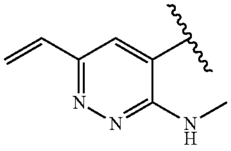
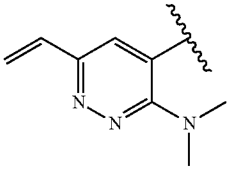
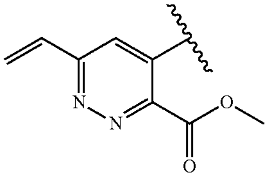
-continued
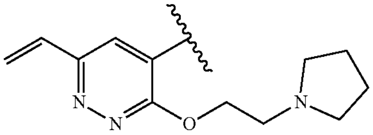
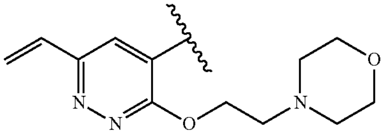
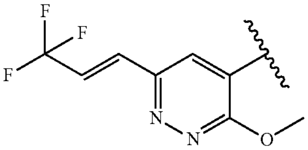
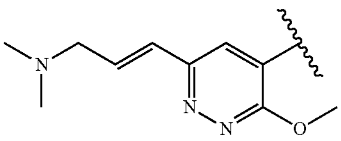
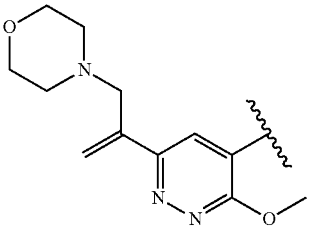
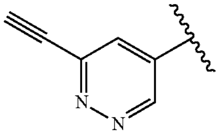
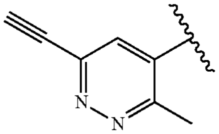
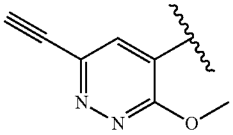
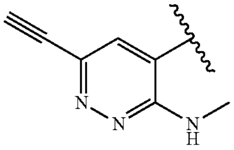
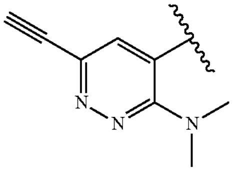
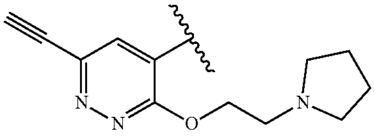
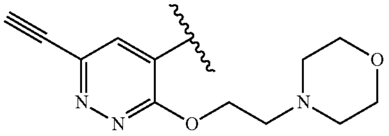
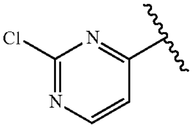
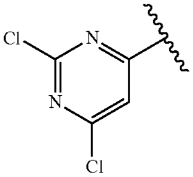

-continued
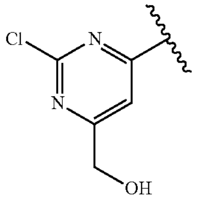
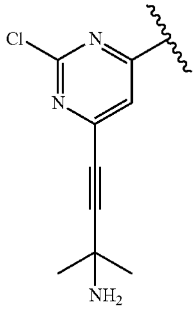
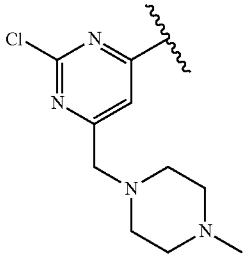
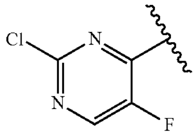
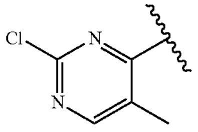
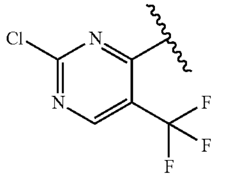
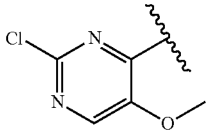
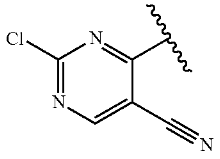
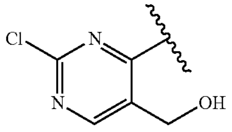
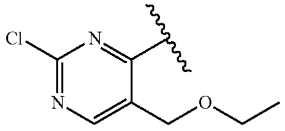
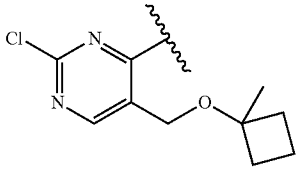
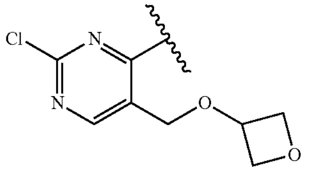
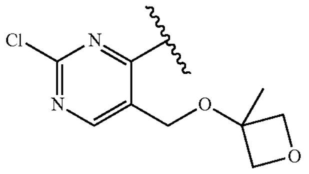
-continued
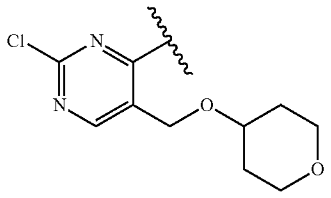
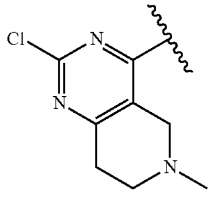
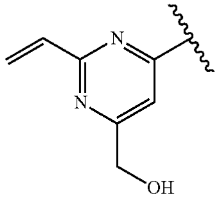
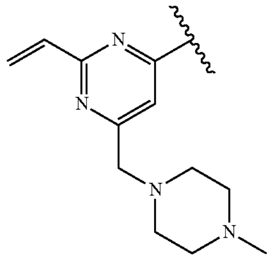
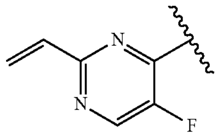
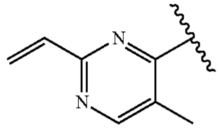
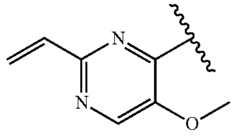
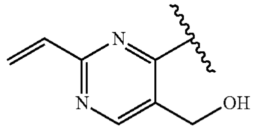
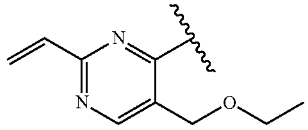
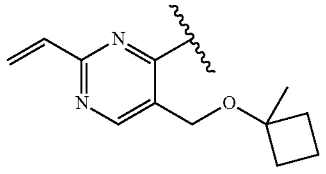
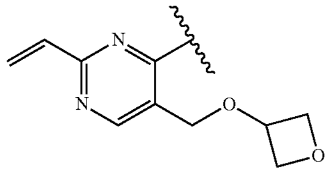 [SMILES: *c1nc(C=C)ncc1COC1(C)COC1]
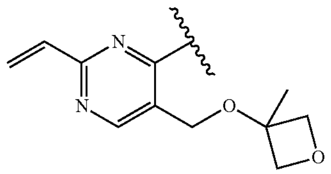

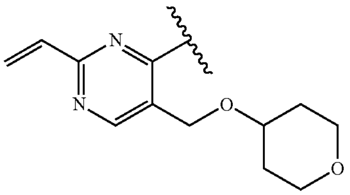
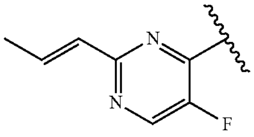
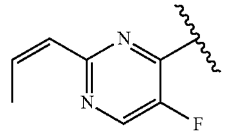
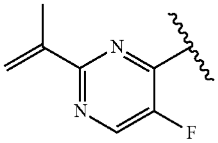
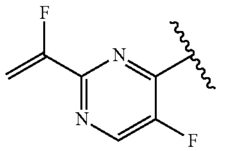
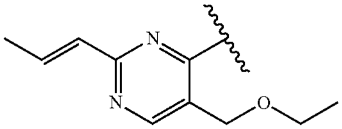
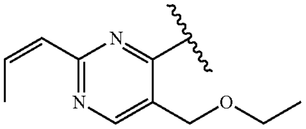
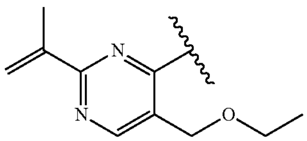
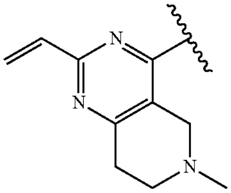
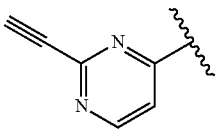
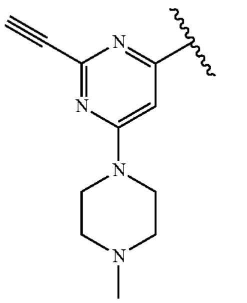
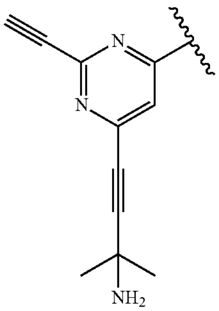
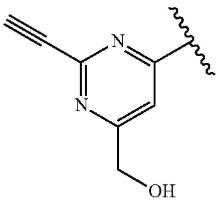
-continued
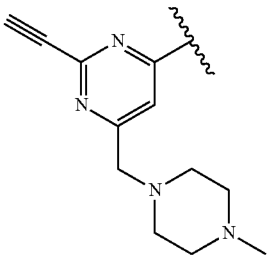
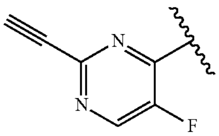
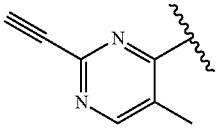
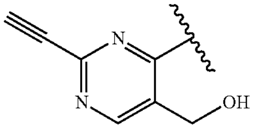
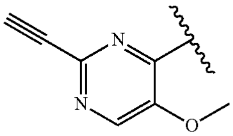
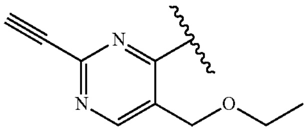
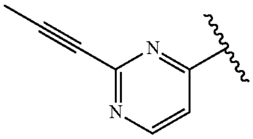
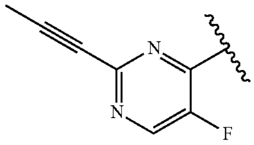
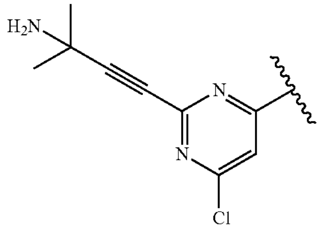
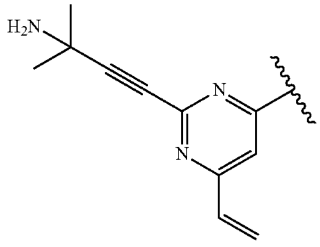
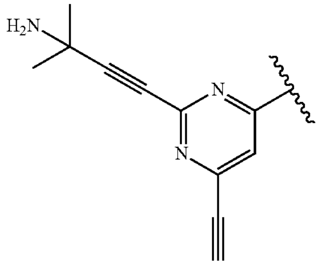
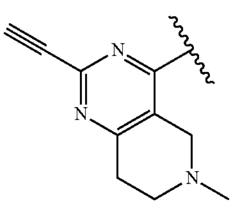
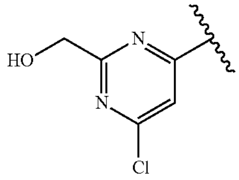
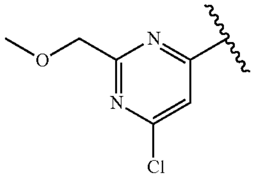

-continued
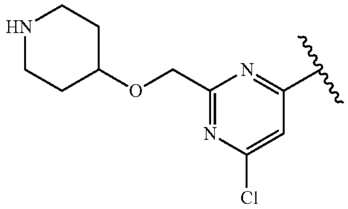
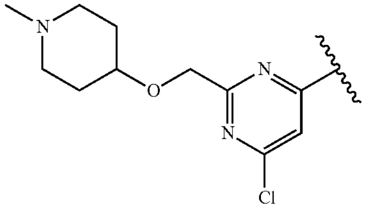
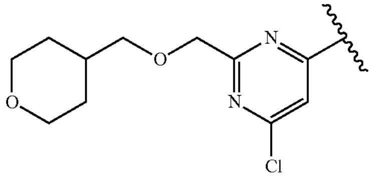
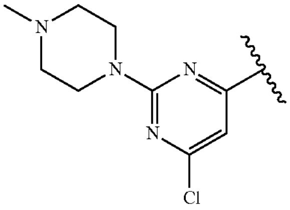
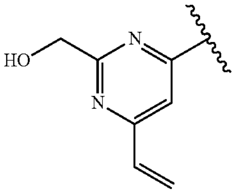
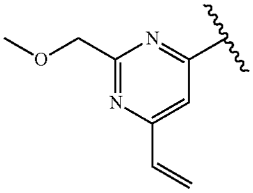
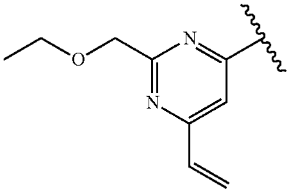
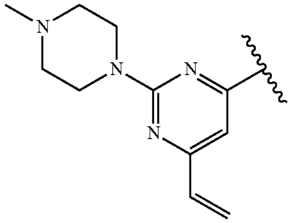
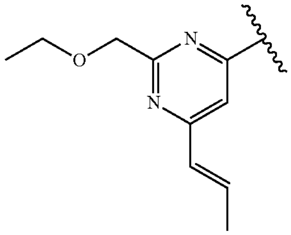
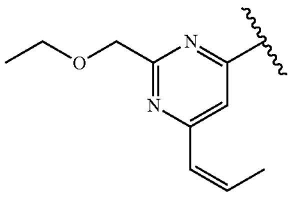
-continued
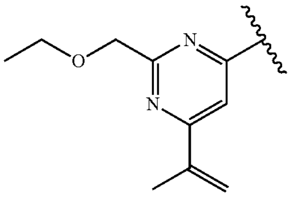
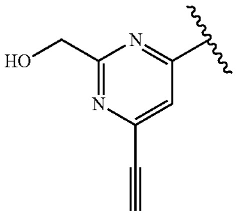
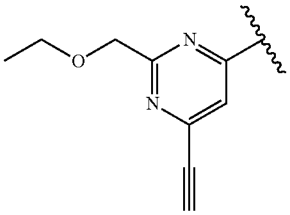
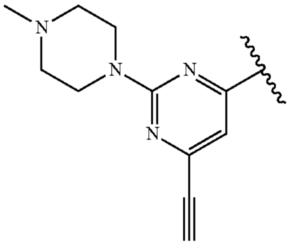
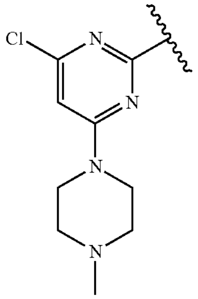
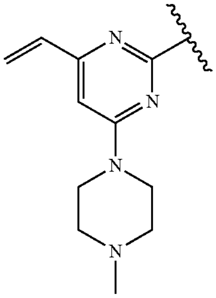
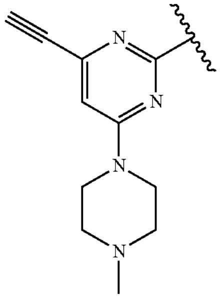
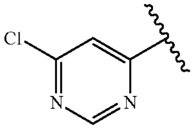
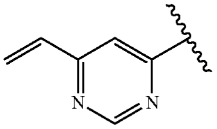
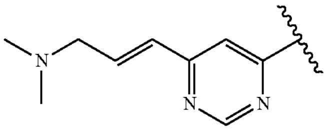
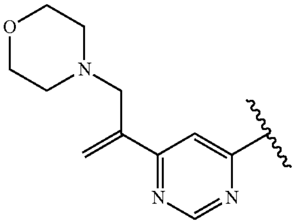
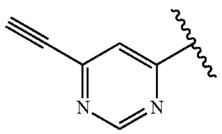
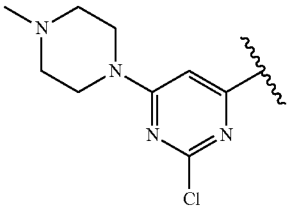

-continued
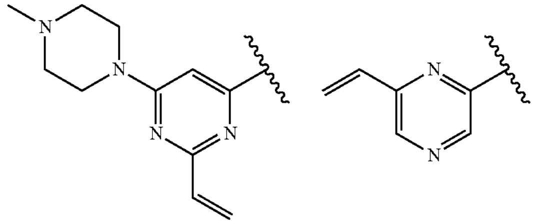
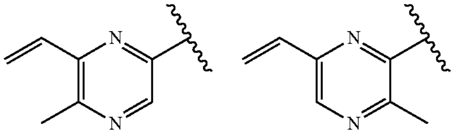
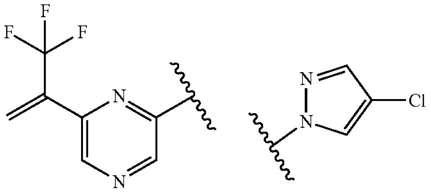
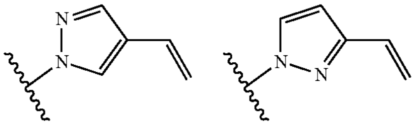
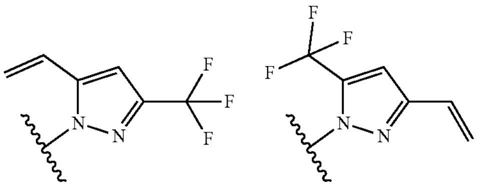
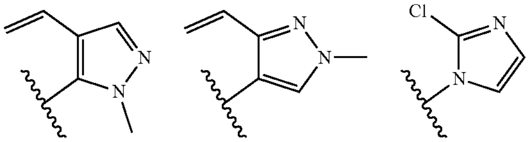
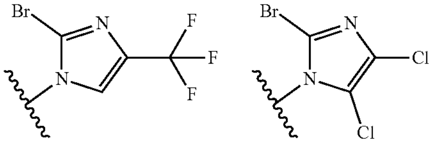
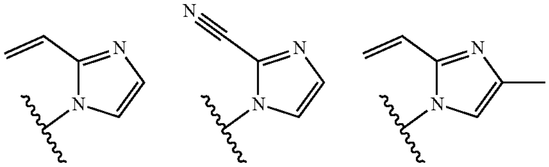
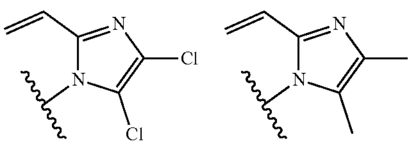
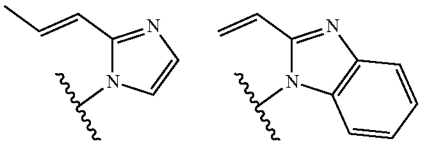
-continued
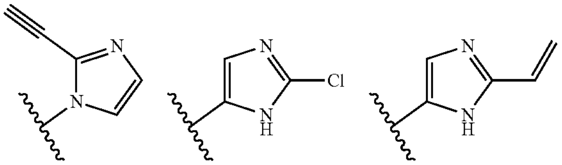
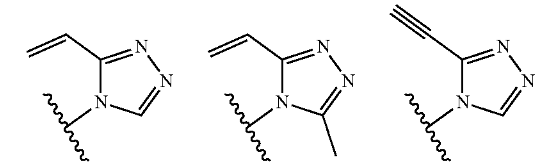
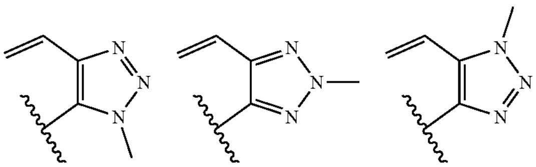
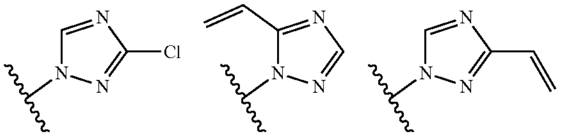
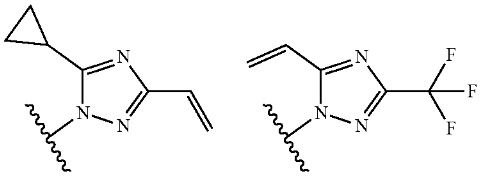
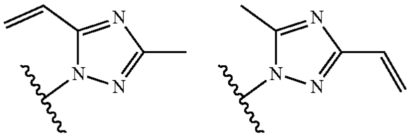
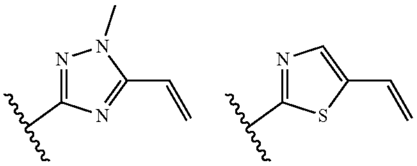
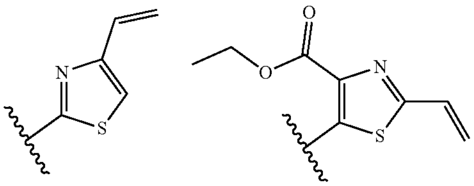
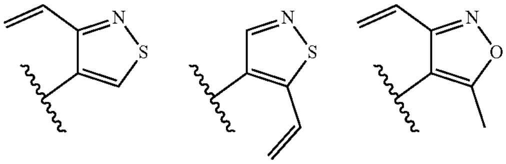
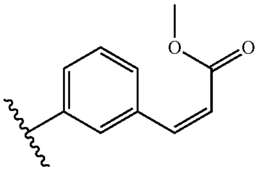

-continued
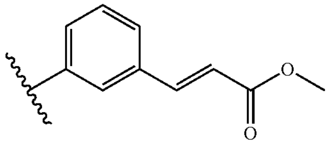
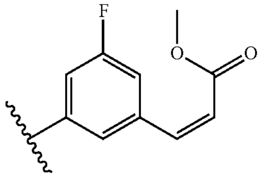
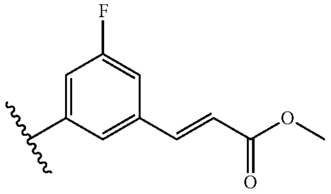
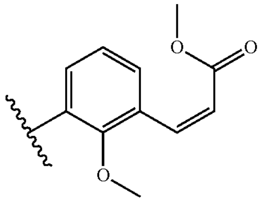
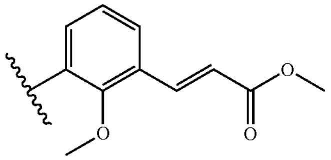
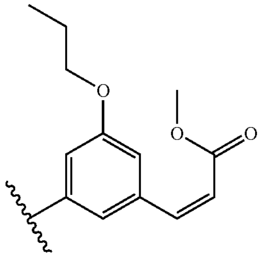
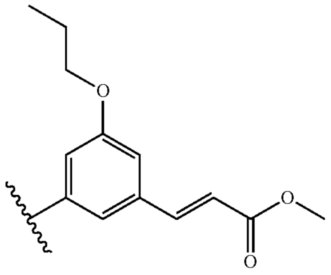
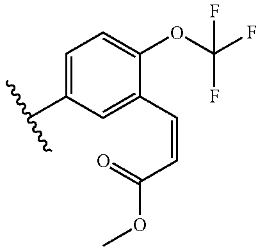
-continued
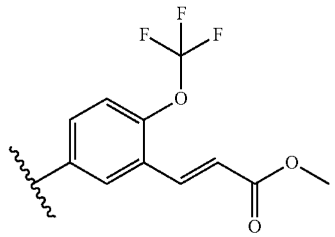
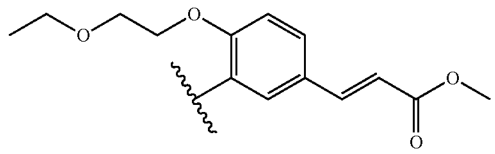
In some embodiments, the present disclosure provides a compound of any one of formulas II, III, IV, or V:
II
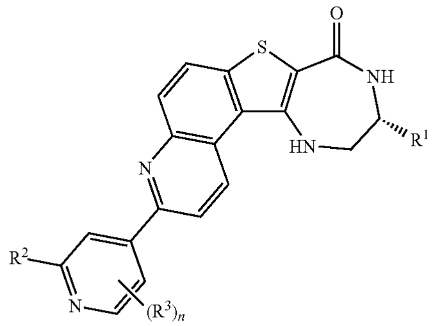
III
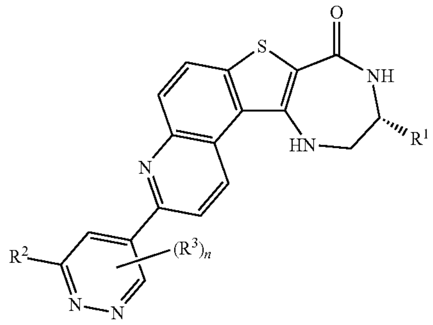
IV
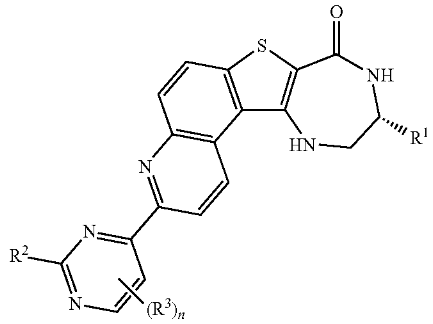

-continued
V
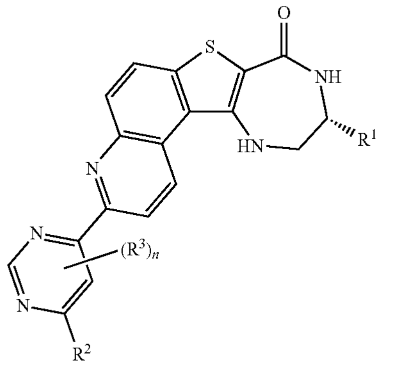
or a pharmaceutically acceptable salt thereof, wherein each of $R^1$, $R^2$, $R^3$, and n is as defined above and described herein.
In some embodiments, the present disclosure provides a compound of any one of
II-a
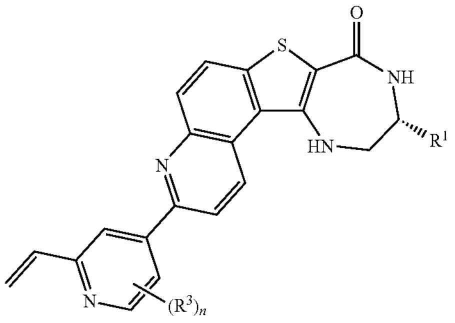
II-b
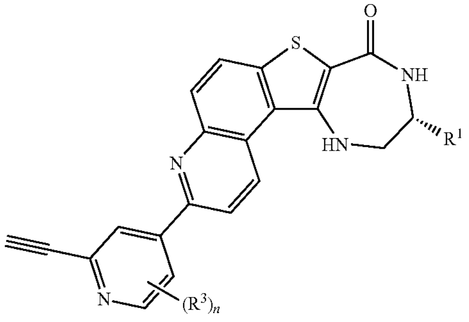
II-c
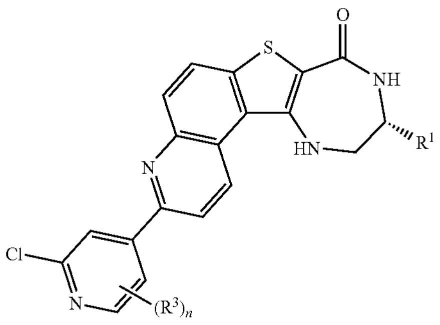
-continued
III-a
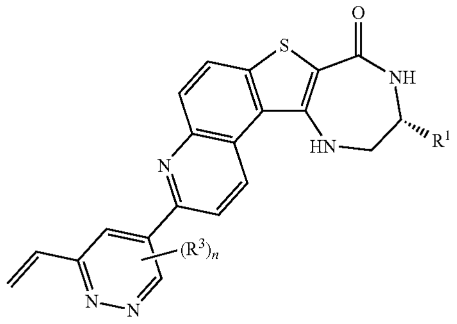
III-b
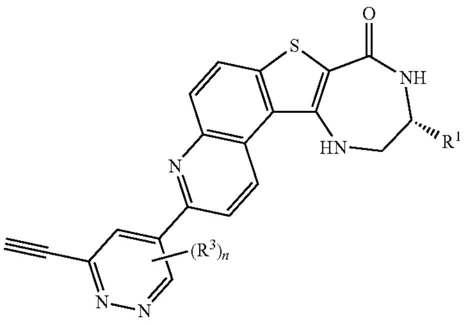
IV-a
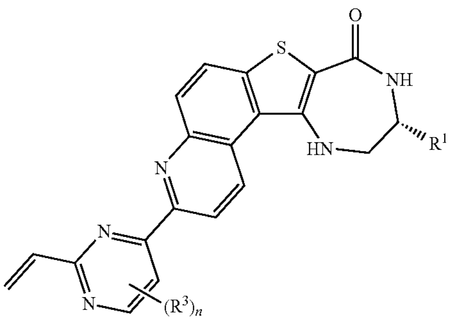
IV-b
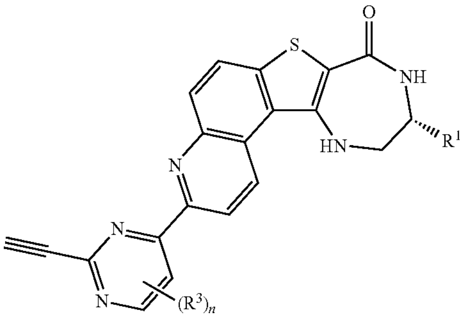
IV-c
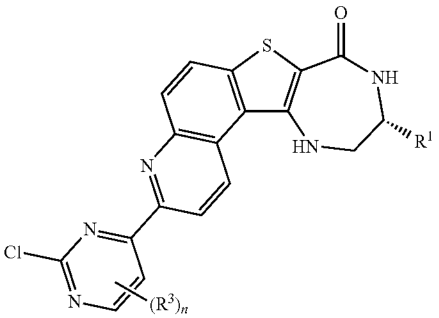

-continued
V-a
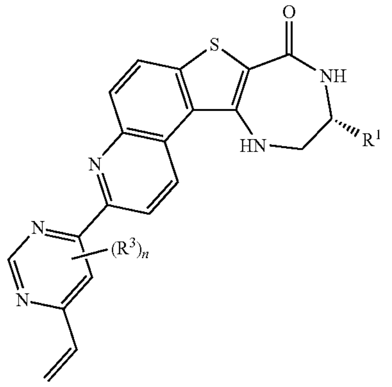
V-b
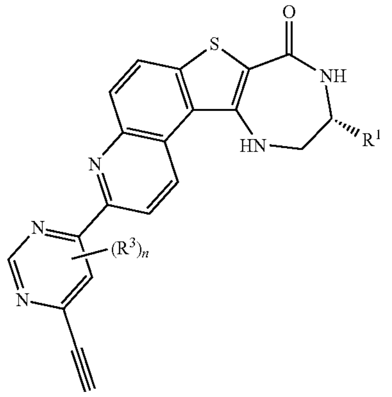
V-c
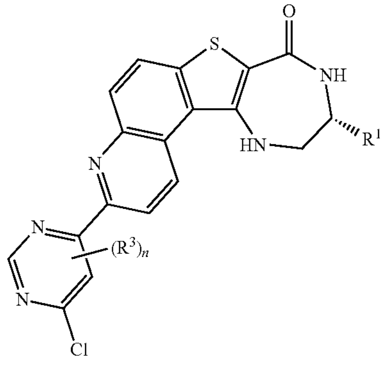
or a pharmaceutically acceptable salt thereof, wherein each of $R^1$, $R^3$, and n is as defined above and described herein.
In some embodiments, the present disclosure provides a compound of any one of formulae II-a-i, II-a-ii, II-b-i, II-b-ii, II-c-i, II-c-ii, III-a-i, III-b-i, IV-a-i, IV-a-ii, IV-b-i, IV-b-ii, IV-c-i, IV-c-ii, V-a-i, V-b-i, or V-c-i:
II-a-i
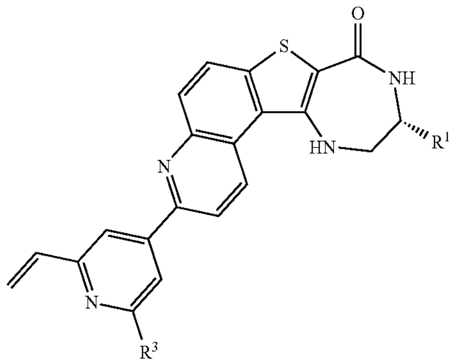
II-a-ii
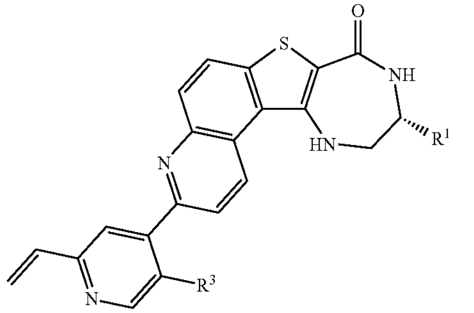
II-b-i
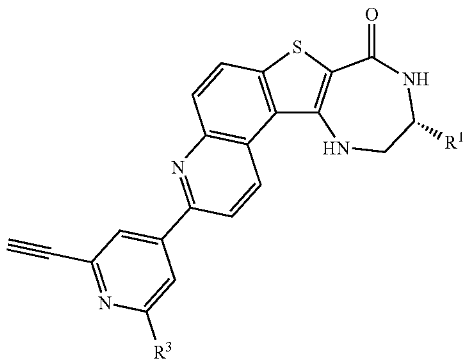
II-b-ii
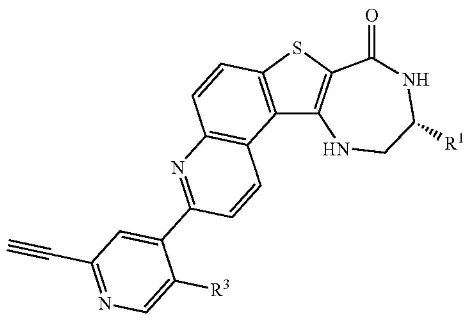

-continued
II-c-i
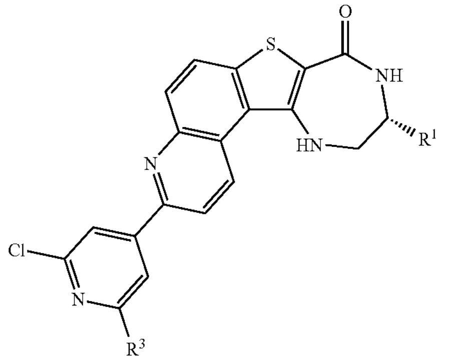
II-c-ii
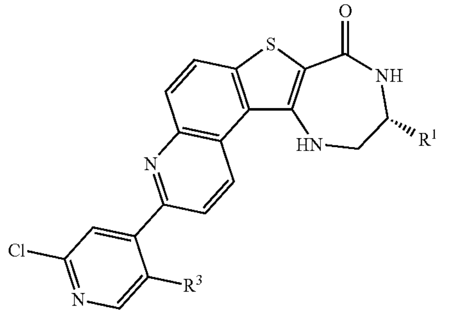
III-a-i
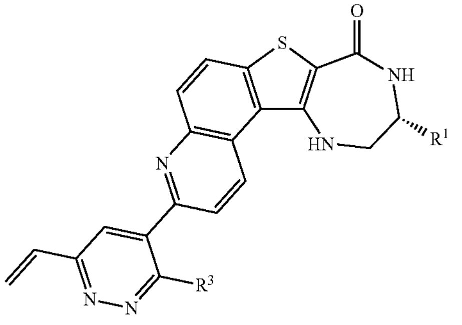
III-b-i
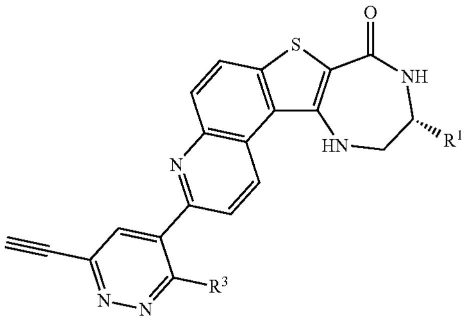
-continued
IV-a-i
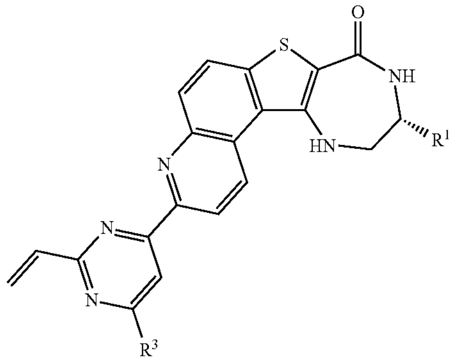
IV-a-ii
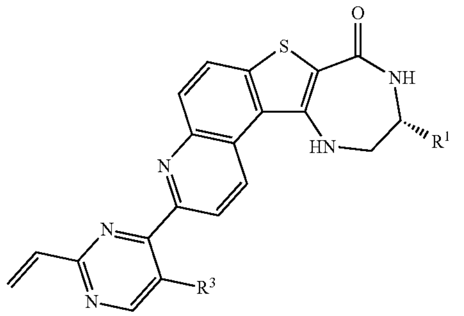
IV-b-i
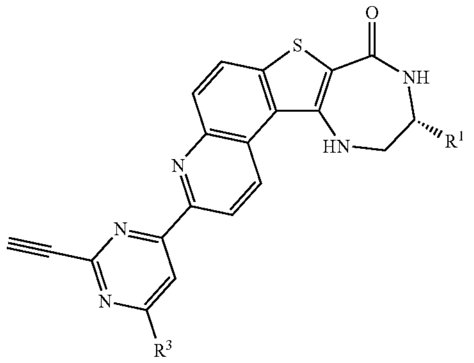
IV-b-ii
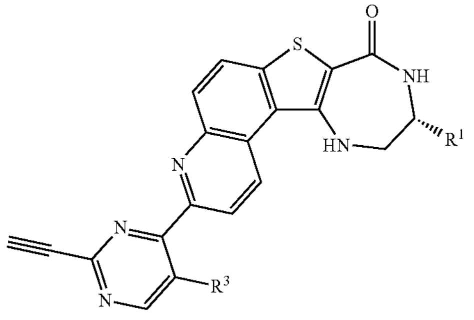

-continued

IV-c-i

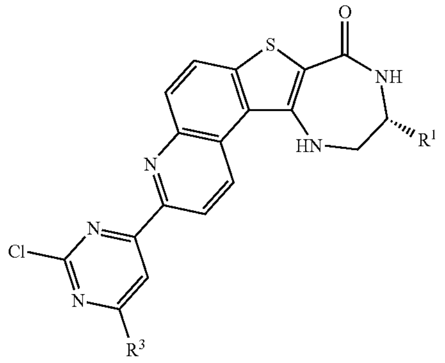

IV-c-ii

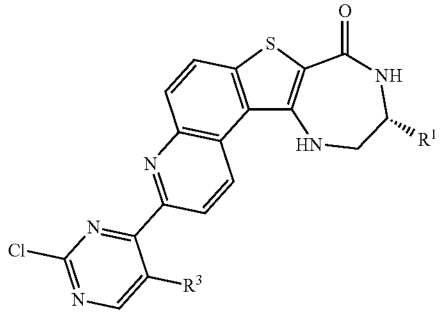

V-a-i

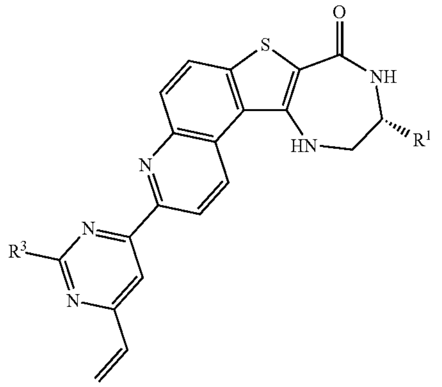

V-b-i

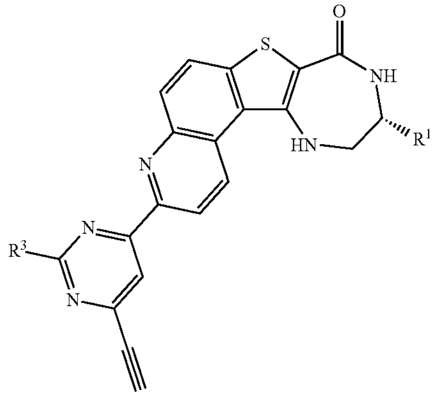

-continued

V-c-i

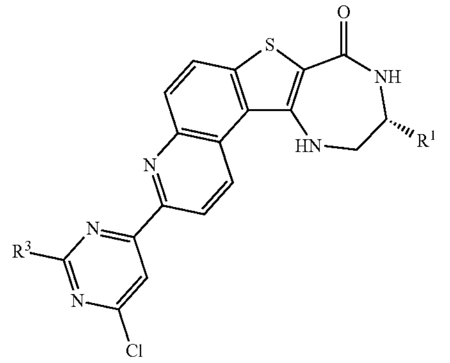

or a pharmaceutically acceptable salt thereof, wherein each of $R^1$ and $R^3$ is as defined above and described herein.

In some embodiments of any of formulae I, II, II-a, II-a-i, II-a-ii, II-b, II-b-i, II-b-ii, II-c, II-c-i, II-c-ii, III, III-a, III-a-i, III-b, III-b-i, IV, IV-a, IV-a-i, IV-a-ii, IV-b, IV-b-i, IV-b-ii, IV-c, IV-c-i, IV-c-ii, V, V-a, V-a-i, V-b, V-b-i, V-c, and V-c-i, $R^1$ is —$CH_3$.

In some embodiments of any of formulae I, II, III, IV, and V, $R^2$ is selected from halogen, —$CH_2$—$R^y$, —$C(CH_3)$═$CH_2$, —C≡$CCH_3$, —CH═$CHCH_3$ (e.g.,

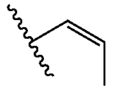 or 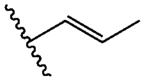 ),

—CH═CH—$R^y$ (e.g.,

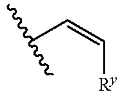 or 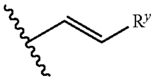 ),

—CH═$CHCH_2$—$R^y$ (e.g., R

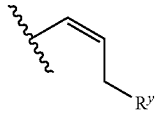 or 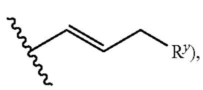

—CH═$CHCH(R^y)_2$ (e.g.,

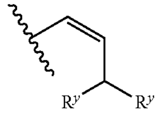 or 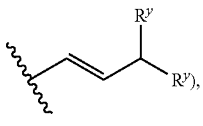

—CH═$CHC(R^y)_3$ (e.g.,

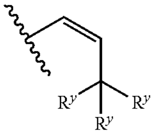 or 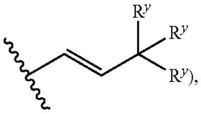 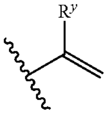,

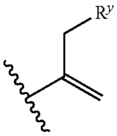, 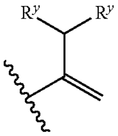, 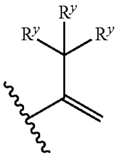, and

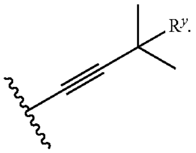

In some embodiments of any of formulae I, II, II-a, II-a-i, II-a-ii, II-b, II-b-i, II-b-ii, II-c, II-c-i, II-c-ii, III, III-a, III-a-i, III-b, III-b-i, IV, IV-a, IV-a-i, IV-a-ii, IV-b, IV-b-i, IV-b-ii, IV-c, IV-c-i, IV-c-ii, V, V-a, V-a-i, V-b, V-b-i, V-c, and V-c-i, $R^3$ is selected from fluoro, chloro, $—CH_3$, $-CD_3$, $—CH_2CH_3$, $—CF_3$, $—CF_2H$, —CN, $—CH_2OH$, $—CH_2OCH_3$, $—CH_2OCH_2CH_3$, $—CH(OH)CD_3$, $—C(OH)(CD_3)_2$, $—OCH_3$, $—OCF_3$, $—OCF_2H$, $—OCH_2CH_2CH_3$, $—OCH_2CH_2OCH_2CH_3$, $—NHCH_3$, $—N(CH_3)_2$, $—C(O)OCH_3$, $—C(O)OCH_2CH_3$,

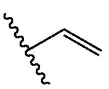 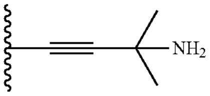

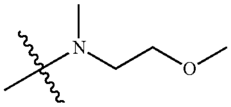 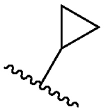 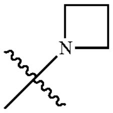

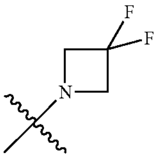 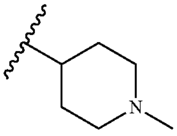

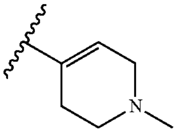 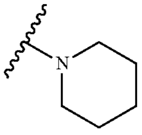

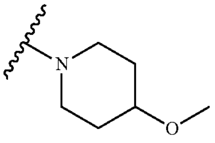 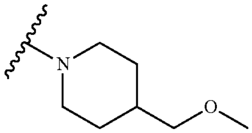

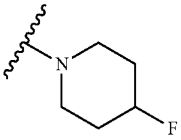 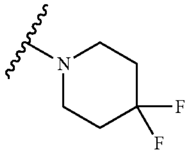

-continued

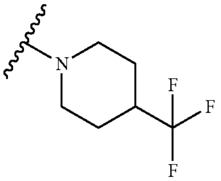 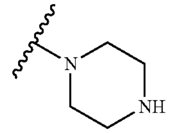

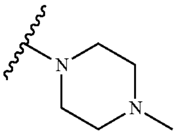 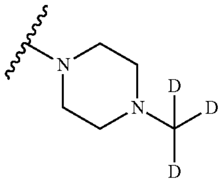

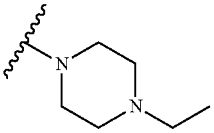 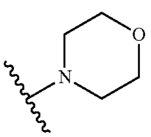

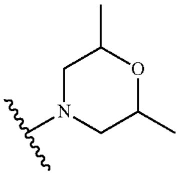 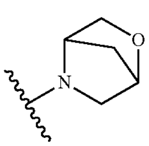 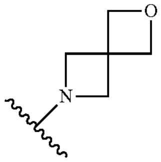

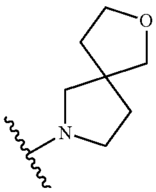 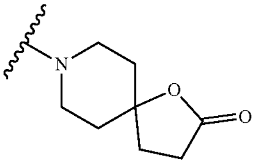

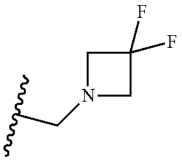 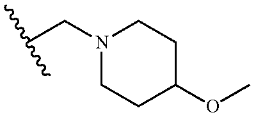

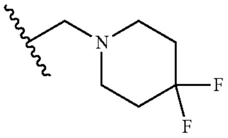 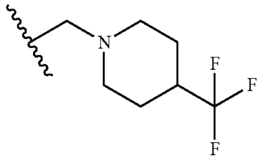

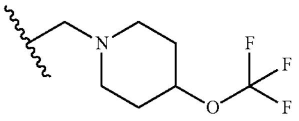

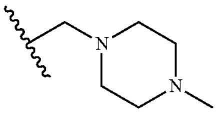 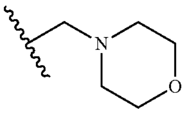

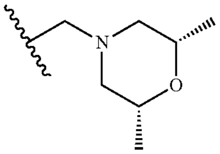 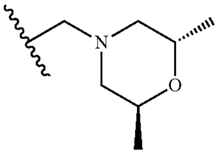

-continued

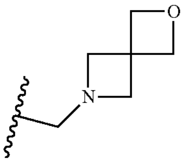
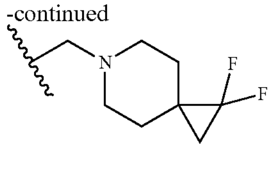
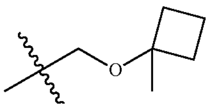
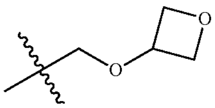
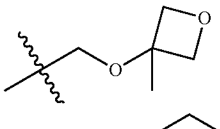
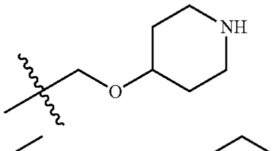
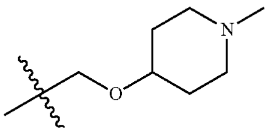
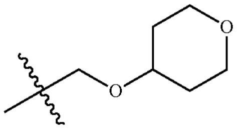
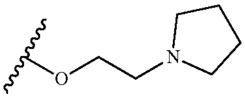
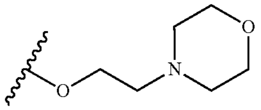

In some embodiments, the present disclosure provides a compound or a pharmaceutically acceptable salt thereof from the group:

(R)-3-(2-ethynyl-5-fluoropyrimidin-4-yl)-10-methyl-9,10,11,12-tetrahydro-8H-[1,4]diazepino[5',6':4,5]thieno[3,2-f]quinolin-8-one (I-1)

(R)-3-(5-fluoro-2-vinylpyrimidin-4-yl)-10-methyl-9,10,11,12-tetrahydro-8H-[1,4]diazepino[5',6':4,5]thieno[3,2-f]quinolin-8-one (I-2)

(R)-3-(2-chloro-5-(ethoxymethyl)pyrimidin-4-yl)-10-methyl-9,10,11,12-tetrahydro-8H-[1,4]diazepino[5',6':4,5]thieno[3,2-f]quinolin-8-one (I-3)

(R)-3-(2-chloro-5-(trifluoromethyl)pyrimidin-4-yl)-10-methyl-9,10,11,12-tetrahydro-8H-[1,4]diazepino[5',6':4,5]thieno[3,2-f]quinolin-8-one (I-4)

(R)-3-(5-(ethoxymethyl)-2-vinylpyrimidin-4-yl)-10-methyl-9,10,11,12-tetrahydro-8H-[1,4]diazepino[5',6':4,5]thieno[3,2-f]quinolin-8-one (I-5)

(R)-3-(2-chloro-5-methylpyrimidin-4-yl)-10-methyl-9,10,11,12-tetrahydro-8H-[1,4]diazepino[5',6':4,5]thieno[3,2-f]quinolin-8-one (I-6)

(R)-3-(6-chloro-2-(methoxymethyl)pyrimidin-4-yl)-10-methyl-9,10,11,12-tetrahydro-8H-[1,4]diazepino[5',6':4,5]thieno[3,2-f]quinolin-8-one (I-7)

(R)-3-(2-chloropyrimidin-4-yl)-10-methyl-9,10,11,12-tetrahydro-8H-[1,4]diazepino[5',6':4,5]thieno[3,2-f]quinolin-8-one (1-8)

(R)-2-chloro-4-(10-methyl-8-oxo-9,10,11,12-tetrahydro-8H-[1,4]diazepino[5',6':4,5]thieno[3,2-f]quinolin-3-yl)pyrimidine-5-carbonitrile (I-9)

(R)-3-(2-chloro-5-methoxypyrimidin-4-yl)-10-methyl-9,10,11,12-tetrahydro-8H-[1,4]diazepino[5',6':4,5]thieno[3,2-f]quinolin-8-one (I-10)

(R)-3-(6-chloropyrimidin-4-yl)-10-methyl-9,10,11,12-tetrahydro-8H-[1,4]diazepino[5',6':4,5]thieno[3,2-f]quinolin-8-one (I-11)

(R)-3-(5-(ethoxymethyl)-2-ethynylpyrimidin-4-yl)-10-methyl-9,10,11,12-tetrahydro-8H-[1,4]diazepino[5',6':4,5]thieno[3,2-f]quinolin-8-one (I-12)

(R)-3-(2-(methoxymethyl)-6-vinylpyrimidin-4-yl)-10-methyl-9,10,11,12-tetrahydro-8H-[1,4]diazepino[5',6':4,5]thieno[3,2-f]quinolin-8-one (I-13)

(R)-3-(6-chloro-2-((piperidin-4-yloxy)methyl)pyrimidin-4-yl)-10-methyl-9,10,11,12-tetrahydro-8H-[1,4]diazepino[5',6':4,5]thieno[3,2-f]quinolin-8-one (I-14)

(R)-3-(6-chloro-2-(((1-methylpiperidin-4-yl)oxy)methyl)pyrimidin-4-yl)-10-methyl-9,10,11,12-tetrahydro-8H-[1,4]diazepino[5',6':4,5]thieno[3,2-f]quinolin-8-one (I-15)

(R)-3-(2-chloro-6-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-16)

(R)-3-(6-chloro-2-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-17)

(R)-10-methyl-3-(6-(4-methylpiperazin-1-yl)-2-vinylpyrimidin-4-yl)-9,10,11,12-tetrahydro-8H-[1,4]diazepino[5',6':4,5]thieno[3,2-f]quinolin-8-one (I-18)

(R)-10-methyl-3-(2-(4-methylpiperazin-1-yl)-6-vinylpyrimidin-4-yl)-9,10,11,12-tetrahydro-8H-[1,4]diazepino[5',6':4,5]thieno[3,2-f]quinolin-8-one (I-19)

(R)-3-(2-chloro-5-((oxetan-3-yloxy)methyl)pyrimidin-4-yl)-10-methyl-9,10,11,12-tetrahydro-8H-[1,4]diazepino[5',6':4,5]thieno[3,2-f]quinolin-8-one (I-20)

(R)-10-methyl-3-(5-((oxetan-3-yloxy)methyl)-2-vinylpyrimidin-4-yl)-9,10,11,12-tetrahydro-8H-[1,4]diazepino[5',6':4,5]thieno[3,2-f]quinolin-8-one (I-21)

(R)-3-(2-(ethoxymethyl)-6-vinylpyrimidin-4-yl)-10-methyl-9,10,11,12-tetrahydro-8H-[1,4]diazepino[5',6':4,5]thieno[3,2-f]quinolin-8-one (I-22)

(R)-3-(6-chloro-2-(((tetrahydro-2H-pyran-4-yl)oxy)methyl)pyrimidin-4-yl)-10-methyl-9,10,11,12-tetrahydro-8H-[1,4]diazepino[5',6':4,5]thieno[3,2-f]quinolin-8-one (I-23)

(R)-3-(2-chloro-5-(((tetrahydro-2H-pyran-4-yl)oxy)methyl)pyrimidin-4-yl)-10-methyl-9,10,11,12-tetrahydro-8H-[1,4]diazepino[5',6':4,5]thieno[3,2-f]quinolin-8-one (I-24)

(R)-10-methyl-3-(5-(((tetrahydro-2H-pyran-4-yl)oxy)methyl)-2-vinylpyrimidin-4-yl)-9,10,11,12-tetrahydro-8H-[1,4]diazepino[5',6':4,5]thieno[3,2-f]quinolin-8-one (I-25)

(R)-10-methyl-3-(5-((1-methylcyclobutoxy)methyl)-2-vinylpyrimidin-4-yl)-9,10,11,12-tetrahydro-8H-[1,4]diazepino[5',6':4,5]thieno[3,2-f]quinolin-8-one (I-26)

(R)-3-(2-chloro-5-((1-methylcyclobutoxy)methyl)pyrimidin-4-yl)-10-methyl-9,10,11,12-tetrahydro-8H-[1,4]diazepino[5',6':4,5]thieno[3,2-f]quinolin-8-one (I-27)

(R)-3-(2-chloro-5-(((3-methyloxetan-3-yl)oxy)methyl)pyrimidin-4-yl)-10-methyl-9,10,11,12-tetrahydro-8H-[1,4]diazepino[5',6':4,5]thieno[3,2-f]quinolin-8-one (I-28)

(R)-10-methyl-3-(5-(((3-methyloxetan-3-yl)oxy)methyl)-2-vinylpyrimidin-4-yl)-9,10,11,12-tetrahydro-8H-[1,4]diazepino[5',6':4,5]thieno[3,2-f]quinolin-8-one (I-29)

(R)-3-(6-chloro-2-(ethoxymethyl)pyrimidin-4-yl)-10-methyl-9,10,11,12-tetrahydro-8H-[1,4]diazepino[5',6':4,5]thieno[3,2-f]quinolin-8-one (I-30)

(R)-3-(5-fluoro-2-(1-fluorovinyl)pyrimidin-4-yl)-10-methyl-9,10,11,12-tetrahydro-8H-[1,4]diazepino[5',6':4,5]thieno[3,2-f]quinolin-8-one (I-31)

(R)-3-(5-methoxy-2-vinylpyrimidin-4-yl)-10-methyl-9,10,11,12-tetrahydro-8H-[1,4]diazepino[5',6':4,5]thieno[3,2-f]quinolin-8-one (I-32)

(R)-10-methyl-3-(5-methyl-2-vinylpyrimidin-4-yl)-9,10,11,12-tetrahydro-8H-[1,4]diazepino[5',6':4,5]thieno[3,2-f]quinolin-8-one (I-33)

(R)-10-methyl-3-(6-vinylpyrimidin-4-yl)-9,10,11,12-tetrahydro-8H-[1,4]diazepino[5',6':4,5]thieno[3,2-f]quinolin-8-one (I-34)

(R,E)-3-(2-(ethoxymethyl)-6-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-35)

(R,Z)-3-(2-(ethoxymethyl)-6-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-36)

(R)-3-(2-(ethoxymethyl)-6-(prop-1-en-2-yl)pyrimidin-4-yl)-10-methyl-9,10,11,12-tetrahydro-8H-[1,4]diazepino[5',6':4,5]thieno[3,2-f]quinolin-8-one (I-37)

(R)-3-(6-ethynylpyrimidin-4-yl)-10-methyl-9,10,11,12-tetrahydro-8H-[1,4]diazepino[5',6':4,5]thieno[3,2-f]quinolin-8-one (I-38)

(R)-3-(2-(ethoxymethyl)-6-ethynylpyrimidin-4-yl)-10-methyl-9,10,11,12-tetrahydro-8H-[1,4]diazepino[5',6':4,5]thieno[3,2-f]quinolin-8-one (I-39)

(R)-3-(2-ethynylpyrimidin-4-yl)-10-methyl-9,10,11,12-tetrahydro-8H-[1,4]diazepino[5',6':4,5]thieno[3,2-f]quinolin-8-one (I-40)

(R)-3-(2-ethynyl-5-methylpyrimidin-4-yl)-10-methyl-9,10,11,12-tetrahydro-8H-[1,4]diazepino[5',6':4,5]thieno[3,2-f]quinolin-8-one (I-41)

(R)-3-(2-ethynyl-5-methoxypyrimidin-4-yl)-10-methyl-9,10,11,12-tetrahydro-8H-[1,4]diazepino[5',6':4,5]thieno[3,2-f]quinolin-8-one (I-42)

(R)-3-(4-chloro-6-(4-methylpiperazin-1-yl)pyrimidin-2-yl)-10-methyl-9,10,11,12-tetrahydro-8H-[1,4]diazepino[5',6':4,5]thieno[3,2-f]quinolin-8-one (I-43)

(R)-3-(5-fluoro-2-(prop-1-yn-1-yl)pyrimidin-4-yl)-10-methyl-9,10,11,12-tetrahydro-8H-[1,4]diazepino[5',6':4,5]thieno[3,2-f]quinolin-8-one (I-44)

(R,E)-3-(5-fluoro-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-45)

(R,Z)-3-(5-fluoro-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-46)

(R)-3-(5-fluoro-2-(prop-1-en-2-yl)pyrimidin-4-yl)-10-methyl-9,10,11,12-tetrahydro-8H-[1,4]diazepino[5',6':4,5]thieno[3,2-f]quinolin-8-one (I-47)

(R,E)-3-(5-(ethoxymethyl)-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-48)

(R,Z)-3-(5-(ethoxymethyl)-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-49)

(R)-3-(5-(ethoxymethyl)-2-(prop-1-en-2-yl)pyrimidin-4-yl)-10-methyl-9,10,11,12-tetrahydro-8H-[1,4]diazepino[5',6':4,5]thieno[3,2-f]quinolin-8-one (I-50)

(R)-3-(6-ethynylpyridazin-4-yl)-10-methyl-9,10,11,12-tetrahydro-8H-[1,4]diazepino[5',6':4,5]thieno[3,2-f]quinolin-8-one (I-51)

(R)-3-(6-chloropyridin-2-yl)-10-methyl-9,10,11,12-tetrahydro-8H-[1,4]diazepino[5',6':4,5]thieno[3,2-f]quinolin-8-one (I-52)

(R)-10-methyl-3-(2-(prop-1-yn-1-yl)pyrimidin-4-yl)-9,10,11,12-tetrahydro-8H-[1,4]diazepino[5',6':4,5]thieno[3,2-f]quinolin-8-one (I-53)

(R)-10-methyl-3-(6-vinylpyridin-2-yl)-9,10,11,12-tetrahydro-8H-[1,4]diazepino[5',6':4,5]thieno[3,2-f]quinolin-8-one (I-54)

(R)-10-methyl-3-(2-vinylpyridin-4-yl)-9,10,11,12-tetrahydro-8H-[1,4]diazepino[5',6':4,5]thieno[3,2-f]quinolin-8-one (I-55)

(R)-3-(6-ethynylpyridin-2-yl)-10-methyl-9,10,11,12-tetrahydro-8H-[1,4]diazepino[5',6':4,5]thieno[3,2-f]quinolin-8-one (I-56)

(R)-3-(2-ethynylpyridin-4-yl)-10-methyl-9,10,11,12-tetrahydro-8H-[1,4]diazepino[5',6':4,5]thieno[3,2-f]quinolin-8-one (I-57)

(R)-3-(2,6-dichloropyrimidin-4-yl)-10-methyl-9,10,11,12-tetrahydro-8H-[1,4]diazepino[5',6':4,5]thieno[3,2-f]quinolin-8-one (I-58)

(R)-3-(6-ethynyl-2-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-59)

(R)-3-(2-ethynyl-6-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-60)

(R)-3-(4-ethynyl-6-(4-methylpiperazin-1-yl)pyrimidin-2-yl)-10-methyl-9,10,11,12-tetrahydro-8H-[1,4]diazepino[5',6':4,5]thieno[3,2-f]quinolin-8-one (I-61)

(R)-10-methyl-3-(4-(4-methylpiperazin-1-yl)-6-vinylpyrimidin-2-yl)-9,10,11,12-tetrahydro-8H-[1,4]diazepino[5',6':4,5]thieno[3,2-f]quinolin-8-one (I-62)

(R)-3-(6-(3-amino-3-methylbut-1-yn-1-yl)-2-chloropyrimidin-4-yl)-10-methyl-9,10,11,12-tetrahydro-8H-[1,4]diazepino[5',6':4,5]thieno[3,2-f]quinolin-8-one (I-63)

(R)-3-(2-(3-amino-3-methylbut-1-yn-1-yl)-6-chloropyrimidin-4-yl)-10-methyl-9,10,11,12-tetrahydro-8H-[1,4]diazepino[5',6':4,5]thieno[3,2-f]quinolin-8-one (I-64)

(R)-3-(6-(3-amino-3-methylbut-1-yn-1-yl)-2-ethynylpyrimidin-4-yl)-10-methyl-9,10,11,12-tetrahydro-8H-[1,4]diazepino[5',6':4,5]thieno[3,2-f]quinolin-8-one (I-65)

(R)-3-(2-(3-amino-3-methylbut-1-yn-1-yl)-6-vinylpyrimidin-4-yl)-10-methyl-9,10,11,12-tetrahydro-8H-[1,4]diazepino[5',6':4,5]thieno[3,2-f]quinolin-8-one (I-66)

(R)-3-(2-(3-amino-3-methylbut-1-yn-1-yl)-6-ethynylpyrimidin-4-yl)-10-methyl-9,10,11,12-tetrahydro-8H-[1,4]diazepino[5',6':4,5]thieno[3,2-f]quinolin-8-one (I-67)

(R)-3-(2,6-dichloropyridin-4-yl)-10-methyl-9,10,11,12-tetrahydro-8H-[1,4]diazepino[5',6':4,5]thieno[3,2-f]quinolin-8-one (I-68)

(R)-3-(2-chloro-5-fluoropyridin-4-yl)-10-methyl-9,10,11,12-tetrahydro-8H-[1,4]diazepino[5',6':4,5]thieno[3,2-f]quinolin-8-one (I-69)

(R)-3-(5-fluoro-2-vinylpyridin-4-yl)-10-methyl-9,10,11,12-tetrahydro-8H-[1,4]diazepino[5',6':4,5]thieno[3,2-f]quinolin-8-one (I-70)

(R)-3-(2-ethynyl-5-fluoropyridin-4-yl)-10-methyl-9,10,11,12-tetrahydro-8H-[1,4]diazepino[5',6':4,5]thieno[3,2-f]quinolin-8-one (I-71)

(R)-3-(2-chloro-6-vinylpyridin-4-yl)-10-methyl-9,10,11,12-tetrahydro-8H-[1,4]diazepino[5',6':4,5]thieno[3,2-f]quinolin-8-one (I-72)

(R)-3-(2-chloro-6-ethynylpyridin-4-yl)-10-methyl-9,10,11,12-tetrahydro-8H-[1,4]diazepino[5',6':4,5]thieno[3,2-f]quinolin-8-one (I-73)

(R)-3-(6-chloro-2-(hydroxymethyl)pyrimidin-4-yl)-10-methyl-9,10,11,12-tetrahydro-8H-[1,4]diazepino[5',6':4,5]thieno[3,2-f]quinolin-8-one (I-74)

(R)-3-(2-chloro-5-(hydroxymethyl)pyrimidin-4-yl)-10-methyl-9,10,11,12-tetrahydro-8H-[1,4]diazepino[5',6':4,5]thieno[3,2-f]quinolin-8-one (I-75)

(R)-3-(2-(hydroxymethyl)-6-vinylpyrimidin-4-yl)-10-methyl-9,10,11,12-tetrahydro-8H-[1,4]diazepino[5',6':4,5]thieno[3,2-f]quinolin-8-one (I-76)

(R)-3-(5-(hydroxymethyl)-2-vinylpyrimidin-4-yl)-10-methyl-9,10,11,12-tetrahydro-8H-[1,4]diazepino[5',6':4,5]thieno[3,2-f]quinolin-8-one (I-77)

(R)-3-(6-ethynyl-2-(hydroxymethyl)pyrimidin-4-yl)-10-methyl-9,10,11,12-tetrahydro-8H-[1,4]diazepino[5',6':4,5]thieno[3,2-f]quinolin-8-one (I-78)

(R)-3-(2-ethynyl-5-(hydroxymethyl)pyrimidin-4-yl)-10-methyl-9,10,11,12-tetrahydro-8H-[1,4]diazepino[5',6':4,5]thieno[3,2-f]quinolin-8-one (I-79)

(R)-3-(2,6-divinylpyridin-4-yl)-10-methyl-9,10,11,12-tetrahydro-8H-[1,4]diazepino[5',6':4,5]thieno[3,2-f]quinolin-8-one (I-80)

(R)-3-(5-chloropyridin-3-yl)-10-methyl-9,10,11,12-tetrahydro-8H-[1,4]diazepino[5',6':4,5]thieno[3,2-f]quinolin-8-one (I-81)

(R)-10-methyl-3-(5-vinylpyridin-3-yl)-9,10,11,12-tetrahydro-8H-[1,4]diazepino[5',6':4,5]thieno[3,2-f]quinolin-8-one (I-82)

(R)-3-(5-ethynylpyridin-3-yl)-10-methyl-9,10,11,12-tetrahydro-8H-[1,4]diazepino[5',6':4,5]thieno[3,2-f]quinolin-8-one (I-83)

(R)-3-(2-chloro-6-(hydroxymethyl)pyrimidin-4-yl)-10-methyl-9,10,11,12-tetrahydro-8H-[1,4]diazepino[5',6':4,5]thieno[3,2-f]quinolin-8-one (I-84)

(R)-3-(6-(hydroxymethyl)-2-vinylpyrimidin-4-yl)-10-methyl-9,10,11,12-tetrahydro-8H-[1,4]diazepino[5',6':4,5]thieno[3,2-f]quinolin-8-one (I-85)

(R)-3-(2-ethynyl-6-(hydroxymethyl)pyrimidin-4-yl)-10-methyl-9,10,11,12-tetrahydro-8H-[1,4]diazepino[5',6':4,5]thieno[3,2-f]quinolin-8-one (I-86)

(R)-3-(2-chloro-6-((4-methylpiperazin-1-yl)methyl)pyrimidin-4-yl)-10-methyl-9,10,11,12-tetrahydro-8H-[1,4]diazepino[5',6':4,5]thieno[3,2-f]quinolin-8-one (I-87)

(R)-10-methyl-3-(6-((4-methylpiperazin-1-yl)methyl)-2-vinylpyrimidin-4-yl)-9,10,11,12-tetrahydro-8H-[1,4]diazepino[5',6':4,5]thieno[3,2-f]quinolin-8-one (I-88)

(R)-3-(2-ethynyl-6-((4-methylpiperazin-1-yl)methyl)pyrimidin-4-yl)-10-methyl-9,10,11,12-tetrahydro-8H-[1,4]diazepino[5',6':4,5]thieno[3,2-f]quinolin-8-one (I-89)

(R)-3-(6-(1-fluorovinyl)pyridin-2-yl)-10-methyl-9,10,11,12-tetrahydro-8H-[1,4]diazepino[5',6':4,5]thieno[3,2-f]quinolin-8-one (I-90)

(R)-3-(6-ethynyl-3-methoxypyridazin-4-yl)-10-methyl-9,10,11,12-tetrahydro-8H-[1,4]diazepino[5',6':4,5]thieno[3,2-f]quinolin-8-one (I-91)

(R)-3-(5-(difluoromethyl)-2-ethynylpyridin-4-yl)-10-methyl-9,10,11,12-tetrahydro-8H-[1,4]diazepino[5',6':4,5]thieno[3,2-f]quinolin-8-one (I-92)

(R)-3-(2-chloro-5-(difluoromethyl)pyridin-4-yl)-10-methyl-9,10,11,12-tetrahydro-8H-[1,4]diazepino[5',6':4,5]thieno[3,2-f]quinolin-8-one (I-93)

(R)-3-(2-chloro-6-(4-methylpiperazin-1-yl)pyridin-4-yl)-10-methyl-9,10,11,12-tetrahydro-8H-[1,4]diazepino[5',6':4,5]thieno[3,2-f]quinolin-8-one (I-94)

(R)-3-(2-ethynyl-6-(4-methylpiperazin-1-yl)pyridin-4-yl)-10-methyl-9,10,11,12-tetrahydro-8H-[1,4]diazepino[5',6':4,5]thieno[3,2-f]quinolin-8-one (I-95)

(R)-10-methyl-3-(2-(4-methylpiperazin-1-yl)-6-vinylpyridin-4-yl)-9,10,11,12-tetrahydro-8H-[1,4]diazepino[5',6':4,5]thieno[3,2-f]quinolin-8-one (I-96)

(R)-3-(2-chloro-6-(hydroxymethyl)pyridin-4-yl)-10-methyl-9,10,11,12-tetrahydro-8H-[1,4]diazepino[5',6':4,5]thieno[3,2-f]quinolin-8-one (I-97)

(R)-3-(2-ethynyl-6-(hydroxymethyl)pyridin-4-yl)-10-methyl-9,10,11,12-tetrahydro-8H-[1,4]diazepino[5',6':4,5]thieno[3,2-f]quinolin-8-one (I-98)

(R)-3-(2-(hydroxymethyl)-6-vinylpyridin-4-yl)-10-methyl-9,10,11,12-tetrahydro-8H-[1,4]diazepino[5',6':4,5]thieno[3,2-f]quinolin-8-one (I-99)

(R)-3-(6-chloro-1'-methyl-1',2',3',6'-tetrahydro-[2,4'-bipyridin]-4-yl)-10-methyl-9,10,11,12-tetrahydro-8H-[1,4]diazepino[5',6':4,5]thieno[3,2-f]quinolin-8-one (I-100)

(R)-10-methyl-3-(1'-methyl-6-vinyl-1',2',3',6'-tetrahydro-[2,4'-bipyridin]-4-yl)-9,10,11,12-tetrahydro-8H-[1,4]diazepino[5',6':4,5]thieno[3,2-f]quinolin-8-one (I-101)

(R)-3-(6-ethynyl-1'-methyl-1',2',3',6'-tetrahydro-[2,4'-bipyridin]-4-yl)-10-methyl-9,10,11,12-tetrahydro-8H-[1,4]diazepino[5',6':4,5]thieno[3,2-f]quinolin-8-one (I-102)

(R)-3-(2-chloro-6-(1-methylpiperidin-4-yl)pyridin-4-yl)-10-methyl-9,10,11,12-tetrahydro-8H-[1,4]diazepino[5',6':4,5]thieno[3,2-f]quinolin-8-one (I-103)

(R)-3-(6-ethynyl-3-(methylamino)pyridazin-4-yl)-10-methyl-9,10,11,12-tetrahydro-8H-[1,4]diazepino[5',6':4,5]thieno[3,2-f]quinolin-8-one (I-104)

(R)-3-(3-(dimethylamino)-6-ethynylpyridazin-4-yl)-10-methyl-9,10,11,12-tetrahydro-8H-[1,4]diazepino[5',6':4,5]thieno[3,2-f]quinolin-8-one (I-105)

(R)-10-methyl-3-(2-(1-methylpiperidin-4-yl)-6-vinylpyridin-4-yl)-9,10,11,12-tetrahydro-8H-[1,4]diazepino[5',6':4,5]thieno[3,2-f]quinolin-8-one (I-106)

(R)-3-(2-ethynyl-6-(1-methylpiperidin-4-yl)pyridin-4-yl)-10-methyl-9,10,11,12-tetrahydro-8H-[1,4]diazepino[5',6':4,5]thieno[3,2-f]quinolin-8-one (I-107)

(R)-3-(2-(1-fluorovinyl)pyridin-4-yl)-10-methyl-9,10,11,12-tetrahydro-8H-[1,4]diazepino[5',6':4,5]thieno[3,2-f]quinolin-8-one (I-108)

(R)-10-methyl-3-(5-methyl-2-vinylpyridin-4-yl)-9,10,11,12-tetrahydro-8H-[1,4]diazepino[5',6':4,5]thieno[3,2-f]quinolin-8-one (I-109)

(R)-10-methyl-3-(2-methyl-6-vinylpyridin-4-yl)-9,10,11,12-tetrahydro-8H-[1,4]diazepino[5',6':4,5]thieno[3,2-f]quinolin-8-one (I-110)

(R)-3-(2-ethynyl-5-methylpyridin-4-yl)-10-methyl-9,10,11,12-tetrahydro-8H-[1,4]diazepino[5',6':4,5]thieno[3,2-f]quinolin-8-one (I-111)

(R)-3-(2-ethynyl-6-methylpyridin-4-yl)-10-methyl-9,10,11,12-tetrahydro-8H-[1,4]diazepino[5',6':4,5]thieno[3,2-f]quinolin-8-one (I-112)

(R,E)-10-methyl-3-(2-(prop-1-en-1-yl)pyridin-4-yl)-9,10,11,12-tetrahydro-8H-[1,4]diazepino[5',6':4,5]thieno[3,2-f]quinolin-8-one (I-113)

(R,E)-3-(2-(3-(dimethylamino)prop-1-en-1-yl)pyridin-4-yl)-10-methyl-9,10,11,12-tetrahydro-8H-[1,4]diazepino[5',6':4,5]thieno[3,2-f]quinolin-8-one (I-114)

(R,E)-3-(6-(3-(dimethylamino)prop-1-en-1-yl)pyrimidin-4-yl)-10-methyl-9,10,11,12-tetrahydro-8H-[1,4]diazepino[5',6':4,5]thieno[3,2-f]quinolin-8-one (I-115)

(R)-10-methyl-3-(2-(3-(pyrrolidin-1-yl)prop-1-en-2-yl)pyridin-4-yl)-9,10,11,12-tetrahydro-8H-[1,4]diazepino[5',6':4,5]thieno[3,2-f]quinolin-8-one (I-116)

(R)-3-(2-(3-(dimethylamino)prop-1-en-2-yl)pyridin-4-yl)-10-methyl-9,10,11,12-tetrahydro-8H-[1,4]diazepino[5',6':4,5]thieno[3,2-f]quinolin-8-one (I-117)

(R)-10-methyl-3-(3-(2-(pyrrolidin-1-yl)ethoxy)-6-vinylpyridazin-4-yl)-9,10,11,12-tetrahydro-8H-[1,4]diazepino[5',6':4,5]thieno[3,2-f]quinolin-8-one (I-118)

(R)-3-(6-chloro-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one (I-119)

(R)-3-(6-ethynyl-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one (I-120)

(R)-3-(2-((4-methoxypiperidin-1-yl)methyl)-6-vinylpyridin-4-yl)-10-methyl-9,10,11,12-tetrahydro-8H-[1,4]diazepino[5',6':4,5]thieno[3,2-f]quinolin-8-one (I-121)

(R)-3-(2-ethynyl-6-((4-methoxypiperidin-1-yl)methyl)pyridin-4-yl)-10-methyl-9,10,11,12-tetrahydro-8H-[1,4]diazepino[5',6':4,5]thieno[3,2-f]quinolin-8-one (I-122)

(R)-3-(2-((4,4-difluoropiperidin-1-yl)methyl)-6-vinylpyridin-4-yl)-10-methyl-9,10,11,12-tetrahydro-8H-[1,4]diazepino[5',6':4,5]thieno[3,2-f]quinolin-8-one (I-123)

(R)-3-(2-((4,4-difluoropiperidin-1-yl)methyl)-6-ethynylpyridin-4-yl)-10-methyl-9,10,11,12-tetrahydro-8H-[1,4]diazepino[5',6':4,5]thieno[3,2-f]quinolin-8-one (I-124)

(R)-10-methyl-3-(2-((4-methylpiperazin-1-yl)methyl)-6-vinylpyridin-4-yl)-9,10,11,12-tetrahydro-8H-[1,4]diazepino[5',6':4,5]thieno[3,2-f]quinolin-8-one (I-125)

(R)-3-(2-ethynyl-6-((4-methylpiperazin-1-yl)methyl)pyridin-4-yl)-10-methyl-9,10,11,12-tetrahydro-8H-[1,4]diazepino[5',6':4,5]thieno[3,2-f]quinolin-8-one (I-126)

(R)-3-(3-methoxy-6-vinylpyridazin-4-yl)-10-methyl-9,10,11,12-tetrahydro-8H-[1,4]diazepino[5',6':4,5]thieno[3,2-f]quinolin-8-one (I-127)

(R)-10-methyl-3-(3-(methylamino)-6-vinylpyridazin-4-yl)-9,10,11,12-tetrahydro-8H-[1,4]diazepino[5',6':4,5]thieno[3,2-f]quinolin-8-one (I-128)

(R)-3-(3-(dimethylamino)-6-vinylpyridazin-4-yl)-10-methyl-9,10,11,12-tetrahydro-8H-[1,4]diazepino[5',6':4,5]thieno[3,2-f]quinolin-8-one (I-129)

(R)-3-(5-(difluoromethyl)-2-vinylpyridin-4-yl)-10-methyl-9,10,11,12-tetrahydro-8H-[1,4]diazepino[5',6':4,5]thieno[3,2-f]quinolin-8-one (I-130)

(R)-10-methyl-3-(2-(3-morpholinoprop-1-en-2-yl)pyridin-4-yl)-9,10,11,12-tetrahydro-8H-[1,4]diazepino[5',6':4,5]thieno[3,2-f]quinolin-8-one (I-131)

(R)-3-(6-chloro-3-(2-morpholinoethoxy)pyridazin-4-yl)-10-methyl-9,10,11,12-tetrahydro-8H-[1,4]diazepino[5',6':4,5]thieno[3,2-f]quinolin-8-one (I-132)

(R)-10-methyl-3-(3-(2-morpholinoethoxy)-6-vinylpyridazin-4-yl)-9,10,11,12-tetrahydro-8H-[1,4]diazepino[5',6':4,5]thieno[3,2-f]quinolin-8-one (I-133)

(R)-3-(6-ethynyl-3-(2-morpholinoethoxy)pyridazin-4-yl)-10-methyl-9,10,11,12-tetrahydro-8H-[1,4]diazepino[5',6':4,5]thieno[3,2-f]quinolin-8-one (I-134)

(R)-3-(2-(3-amino-3-methylbut-1-yn-1-yl)pyridin-4-yl)-10-methyl-9,10,11,12-tetrahydro-8H-[1,4]diazepino[5',6':4,5]thieno[3,2-f]quinolin-8-one (I-135)

(R)-10-methyl-3-(3-methyl-6-vinylpyridazin-4-yl)-9,10,11,12-tetrahydro-8H-[1,4]diazepino[5',6':4,5]thieno[3,2-f]quinolin-8-one (I-136)

methyl (R)-4-(10-methyl-8-oxo-9,10,11,12-tetrahydro-8H-[1,4]diazepino[5',6':4,5]thieno[3,2-f]quinolin-3-yl)-6-vinylpyridazine-3-carboxylate (I-137)

(R)-3-(3-methoxy-6-(3-morpholinoprop-1-en-2-yl)pyridazin-4-yl)-10-methyl-9,10,11,12-tetrahydro-8H-[1,4]diazepino[5',6':4,5]thieno[3,2-f]quinolin-8-one (I-138)

(R)-10-methyl-3-(6-(3-morpholinoprop-1-en-2-yl)pyrimidin-4-yl)-9,10,11,12-tetrahydro-8H-[1,4]diazepino[5',6':4,5]thieno[3,2-f]quinolin-8-one (I-139)

(R)-10-methyl-3-(2-(morpholinomethyl)-6-vinylpyridin-4-yl)-9,10,11,12-tetrahydro-8H-[1,4]diazepino[5',6':4,5]thieno[3,2-f]quinolin-8-one (I-140)

(R)-3-(2-((1,1-difluoro-6-azaspiro[2.5]octan-6-yl)methyl)-6-vinylpyridin-4-yl)-10-methyl-9,10,11,12-tetrahydro-8H-[1,4]diazepino[5',6':4,5]thieno[3,2-f]quinolin-8-one (I-141)

(R)-10-methyl-3-(5-(methyl-d3)-2-vinylpyridin-4-yl)-9,10,11,12-tetrahydro-8H-[1,4]diazepino[5',6':4,5]thieno[3,2-f]quinolin-8-one (I-142)

(R)-3-(5-chloro-2-vinylpyridin-4-yl)-10-methyl-9,10,11,12-tetrahydro-8H-[1,4]diazepino[5',6':4,5]thieno[3,2-f]quinolin-8-one (I-143)

(R)-3-(5-chloro-2-ethynylpyridin-4-yl)-10-methyl-9,10,11,12-tetrahydro-8H-[1,4]diazepino[5',6':4,5]thieno[3,2-f]quinolin-8-one (I-144)

(R,E)-3-(6-(3-(dimethylamino)prop-1-en-1-yl)-3-methoxypyridazin-4-yl)-10-methyl-9,10,11,12-tetrahydro-8H-[1,4]diazepino[5',6':4,5]thieno[3,2-f]quinolin-8-one (I-145)

(R)-10-methyl-3-(1-methyl-4-vinyl-1H-pyrazol-5-yl)-9,10,11,12-tetrahydro-8H-[1,4]diazepino[5',6':4,5]thieno[3,2-f]quinolin-8-one (I-146)

(R)-10-methyl-3-(3-vinyl-1H-pyrazol-1-yl)-9,10,11,12-tetrahydro-8H-[1,4]diazepino[5',6':4,5]thieno[3,2-f]quinolin-8-one (I-147)

(R)-10-methyl-3-(4-vinyl-1H-pyrazol-1-yl)-9,10,11,12-tetrahydro-8H-[1,4]diazepino[5',6':4,5]thieno[3,2-f]quinolin-8-one (I-148)

(R)-10-methyl-3-(4-vinylthiazol-2-yl)-9,10,11,12-tetrahydro-8H-[1,4]diazepino[5',6':4,5]thieno[3,2-f]quinolin-8-one (I-149)

(R)-10-methyl-3-(2-vinyl-1H-imidazol-5-yl)-9,10,11,12-tetrahydro-8H-[1,4]diazepino[5',6':4,5]thieno[3,2-f]quinolin-8-one (I-150)

(R)-3-(2-chloro-1H-imidazol-5-yl)-10-methyl-9,10,11,12-tetrahydro-8H-[1,4]diazepino[5',6':4,5]thieno[3,2-f]quinolin-8-one (I-151)

(R)-3-(4-chloro-1H-pyrazol-1-yl)-10-methyl-9,10,11,12-tetrahydro-8H-[1,4]diazepino[5',6':4,5]thieno[3,2-f]quinolin-8-one (I-152)

(R)-10-methyl-3-(5-(morpholinomethyl)-2-vinylpyridin-4-yl)-9,10,11,12-tetrahydro-8H-[1,4]diazepino[5',6':4,5]thieno[3,2-f]quinolin-8-one (I-153)

(R)-3-(2-ethynyl-5-(morpholinomethyl)pyridin-4-yl)-10-methyl-9,10,11,12-tetrahydro-8H-[1,4]diazepino[5',6':4,5]thieno[3,2-f]quinolin-8-one (I-154)

(R)-3-(5-((4-methoxypiperidin-1-yl)methyl)-2-vinylpyridin-4-yl)-10-methyl-9,10,11,12-tetrahydro-8H-[1,4]diazepino[5',6':4,5]thieno[3,2-f]quinolin-8-one (I-155)

(R)-10-methyl-3-(2-morpholino-6-vinylpyridin-4-yl)-9,10,11,12-tetrahydro-8H-[1,4]diazepino[5',6':4,5]thieno[3,2-f]quinolin-8-one (I-156)

(R)-3-(2-ethynyl-6-morpholinopyridin-4-yl)-10-methyl-9,10,11,12-tetrahydro-8H-[1,4]diazepino[5',6':4,5]thieno[3,2-f]quinolin-8-one (I-157)

(R)-3-(2-(4-methoxypiperidin-1-yl)-6-vinylpyridin-4-yl)-10-methyl-9,10,11,12-tetrahydro-8H-[1,4]diazepino[5',6':4,5]thieno[3,2-f]quinolin-8-one (I-158)

(R)-3-(2-ethynyl-6-(4-methoxypiperidin-1-yl)pyridin-4-yl)-10-methyl-9,10,11,12-tetrahydro-8H-[1,4]diazepino[5',6':4,5]thieno[3,2-f]quinolin-8-one (I-159)

(R)-6-chloro-4-(10-methyl-8-oxo-9,10,11,12-tetrahydro-8H-[1,4]diazepino[5',6':4,5]thieno[3,2-f]quinolin-3-yl)nicotinonitrile (I-160)

(R)-4-(10-methyl-8-oxo-9,10,11,12-tetrahydro-8H-[1,4]diazepino[5',6':4,5]thieno[3,2-f]quinolin-3-yl)-6-vinylnicotinonitrile (I-161)

(R)-6-ethynyl-4-(10-methyl-8-oxo-9,10,11,12-tetrahydro-8H-[1,4]diazepino[5',6':4,5]thieno[3,2-f]quinolin-3-yl)nicotinonitrile (I-162)

(R)-10-methyl-3-(6-vinylpyrazin-2-yl)-9,10,11,12-tetrahydro-8H-[1,4]diazepino[5',6':4,5]thieno[3,2-f]quinolin-8-one (I-163)

(R)-10-methyl-3-(2-vinyl-1H-imidazol-1-yl)-9,10,11,12-tetrahydro-8H-[1,4]diazepino[5',6':4,5]thieno[3,2-f]quinolin-8-one (I-164)

(R)-3-(3-chloro-1H-pyrazol-1-yl)-10-methyl-9,10,11,12-tetrahydro-8H-[1,4]diazepino[5',6':4,5]thieno[3,2-f]quinolin-8-one (I-165)

(R)-10-methyl-3-(5-methyl-6-vinylpyrazin-2-yl)-9,10,11,12-tetrahydro-8H-[1,4]diazepino[5',6':4,5]thieno[3,2-f]quinolin-8-one (I-166)

(R)-10-methyl-3-(3-methyl-6-vinylpyrazin-2-yl)-9,10,11,12-tetrahydro-8H-[1,4]diazepino[5',6':4,5]thieno[3,2-f]quinolin-8-one (I-167)

(R)-3-(2-(4,4-difluoropiperidin-1-yl)-6-vinylpyridin-4-yl)-10-methyl-9,10,11,12-tetrahydro-8H-[1,4]diazepino[5',6':4,5]thieno[3,2-f]quinolin-8-one (I-168)

(R)-3-(2-ethynyl-6-(morpholinomethyl)pyridin-4-yl)-10-methyl-9,10,11,12-tetrahydro-8H-[1,4]diazepino[5',6':4,5]thieno[3,2-f]quinolin-8-one (I-169)

(R)-3-(6-ethynyl-3-methylpyridazin-4-yl)-10-methyl-9,10,11,12-tetrahydro-8H-[1,4]diazepino[5',6':4,5]thieno[3,2-f]quinolin-8-one (I-170)

(R)-10-methyl-3-(2-(4-(methyl-d3)piperazin-1-yl)-6-vinylpyridin-4-yl)-9,10,11,12-tetrahydro-8H-[1,4]diazepino[5',6':4,5]thieno[3,2-f]quinolin-8-one (I-171)

(R)-3-(2-ethynyl-6-(4-(methyl-d3)piperazin-1-yl)pyridin-4-yl)-10-methyl-9,10,11,12-tetrahydro-8H-[1,4]diazepino[5',6':4,5]thieno[3,2-f]quinolin-8-one (I-172)

(R)-3-(2-(4-ethylpiperazin-1-yl)-6-vinylpyridin-4-yl)-10-methyl-9,10,11,12-tetrahydro-8H-[1,4]diazepino[5',6':4,5]thieno[3,2-f]quinolin-8-one (I-173)

(R)-3-(2-(4-ethylpiperazin-1-yl)-6-ethynylpyridin-4-yl)-10-methyl-9,10,11,12-tetrahydro-8H-[1,4]diazepino[5',6':4,5]thieno[3,2-f]quinolin-8-one (I-174)

(R)-10-methyl-3-(2-(piperazin-1-yl)-6-vinylpyridin-4-yl)-9,10,11,12-tetrahydro-8H-[1,4]diazepino[5',6':4,5]thieno[3,2-f]quinolin-8-one (I-175)

(R)-3-(2-ethynyl-6-(piperazin-1-yl)pyridin-4-yl)-10-methyl-9,10,11,12-tetrahydro-8H-[1,4]diazepino[5',6':4,5]thieno[3,2-f]quinolin-8-one (I-176)

(R)-10-methyl-3-(2-(piperidin-1-yl)-6-vinylpyridin-4-yl)-9,10,11,12-tetrahydro-8H-[1,4]diazepino[5',6':4,5]thieno[3,2-f]quinolin-8-one (I-177)

(R)-3-(2-ethynyl-6-(piperidin-1-yl)pyridin-4-yl)-10-methyl-9,10,11,12-tetrahydro-8H-[1,4]diazepino[5',6':4,5]thieno[3,2-f]quinolin-8-one (I-178)

(R)-3-(2-(azetidin-1-yl)-6-vinylpyridin-4-yl)-10-methyl-9,10,11,12-tetrahydro-8H-[1,4]diazepino[5',6':4,5]thieno[3,2-f]quinolin-8-one (I-179)

(R)-3-(2-(azetidin-1-yl)-6-ethynylpyridin-4-yl)-10-methyl-9,10,11,12-tetrahydro-8H-[1,4]diazepino[5',6':4,5]thieno[3,2-f]quinolin-8-one (I-180)

(R)-10-methyl-3-(3-methyl-6-vinylpyrazin-2-yl)-9,10,11,12-tetrahydro-8H-[1,4]diazepino[5',6':4,5]thieno[3,2-f]quinolin-8-one (I-181)

(R)-3-(2-(4,4-difluoropiperidin-1-yl)-6-ethynylpyridin-4-yl)-10-methyl-9,10,11,12-tetrahydro-8H-[1,4]diazepino[5',6':4,5]thieno[3,2-f]quinolin-8-one (I-182)

(R)-3-(2-(3,3-difluoroazetidin-1-yl)-6-ethynylpyridin-4-yl)-10-methyl-9,10,11,12-tetrahydro-8H-[1,4]diazepino[5',6':4,5]thieno[3,2-f]quinolin-8-one (I-183)

(R)-3-(2-(3,3-difluoroazetidin-1-yl)-6-vinylpyridin-4-yl)-10-methyl-9,10,11,12-tetrahydro-8H-[1,4]diazepino[5',6':4,5]thieno[3,2-f]quinolin-8-one (I-184)

(R)-3-(2-(((2S,6R)-2,6-dimethylmorpholino)methyl)-6-vinylpyridin-4-yl)-10-methyl-9,10,11,12-tetrahydro-8H-[1,4]diazepino[5',6':4,5]thieno[3,2-f]quinolin-8-one (I-185)

(R)-3-(2-(((2S,6R)-2,6-dimethylmorpholino)methyl)-6-ethynylpyridin-4-yl)-10-methyl-9,10,11,12-tetrahydro-8H-[1,4]diazepino[5',6':4,5]thieno[3,2-f]quinolin-8-one (I-186)

(R)-3-(2-(((2R,6R)-2,6-dimethylmorpholino)methyl)-6-vinylpyridin-4-yl)-10-methyl-9,10,11,12-tetrahydro-8H-[1,4]diazepino[5',6':4,5]thieno[3,2-f]quinolin-8-one (I-187)

(R)-3-(2-(((2R,6R)-2,6-dimethylmorpholino)methyl)-6-ethynylpyridin-4-yl)-10-methyl-9,10,11,12-tetrahydro-8H-[1,4]diazepino[5',6':4,5]thieno[3,2-f]quinolin-8-one (I-188)

(R)-10-methyl-3-(2-((4-(trifluoromethoxy)piperidin-1-yl)methyl)-6-vinylpyridin-4-yl)-9,10,11,12-tetrahydro-8H-[1,4]diazepino[5',6':4,5]thieno[3,2-f]quinolin-8-one (I-189)

(R)-3-(2-ethynyl-6-((4-(trifluoromethoxy)piperidin-1-yl)methyl)pyridin-4-yl)-10-methyl-9,10,11,12-tetrahydro-8H-[1,4]diazepino[5',6':4,5]thieno[3,2-f]quinolin-8-one (I-190)

(R)-10-methyl-3-(6-methyl-2-vinyl-5,6,7,8-tetrahydro-pyrido[4,3-d]pyrimidin-4-yl)-9,10,11,12-tetrahydro-8H-[1,4]diazepino[5',6':4,5]thieno[3,2-f]quinolin-8-one (I-191)

(R)-3-(2-chloro-6-methyl-5,6,7,8-tetrahydropyrido[4,3-d]pyrimidin-4-yl)-10-methyl-9,10,11,12-tetrahydro-8H-[1,4]diazepino[5',6':4,5]thieno[3,2-f]quinolin-8-one (I-192)

(R)-3-(2-ethynyl-6-methyl-5,6,7,8-tetrahydropyrido[4,3-d]pyrimidin-4-yl)-10-methyl-9,10,11,12-tetrahydro-8H-[1,4]diazepino[5',6':4,5]thieno[3,2-f]quinolin-8-one (I-193)

(R)-3-(2,3-dimethyl-6-vinylpyridin-4-yl)-10-methyl-9,10,11,12-tetrahydro-8H-[1,4]diazepino[5',6':4,5]thieno[3,2-f]quinolin-8-one (I-194)

(R)-3-(5-ethyl-2-vinylpyridin-4-yl)-10-methyl-9,10,11,12-tetrahydro-8H-[1,4]diazepino[5',6':4,5]thieno[3,2-f]quinolin-8-one (I-195)

(R)-3-(5-cyclopropyl-2-vinylpyridin-4-yl)-10-methyl-9,10,11,12-tetrahydro-8H-[1,4]diazepino[5',6':4,5]thieno[3,2-f]quinolin-8-one (I-196)

(R)-10-methyl-3-(3-methyl-2-(morpholinomethyl)-6-vinylpyridin-4-yl)-9,10,11,12-tetrahydro-8H-[1,4]diazepino[5',6':4,5]thieno[3,2-f]quinolin-8-one (I-197)

(R)-3-(3-fluoro-2-(morpholinomethyl)-6-vinylpyridin-4-yl)-10-methyl-9,10,11,12-tetrahydro-8H-[1,4]diazepino[5',6':4,5]thieno[3,2-f]quinolin-8-one (I-198)

(R,E)-10-methyl-3-(2-(3,3,3-trifluoroprop-1-en-1-yl)pyridin-4-yl)-9,10,11,12-tetrahydro-8H-[1,4]diazepino[5',6':4,5]thieno[3,2-f]quinolin-8-one (I-199)

(R,E)-3-(3-methoxy-6-(3,3,3-trifluoroprop-1-en-1-yl)pyridazin-4-yl)-10-methyl-9,10,11,12-tetrahydro-8H-[1,4]diazepino[5',6':4,5]thieno[3,2-f]quinolin-8-one (I-200)

(10R)-3-(2-(2,6-dimethylmorpholino)-6-vinylpyridin-4-yl)-10-methyl-9,10,11,12-tetrahydro-8H-[1,4]diazepino[5',6':4,5]thieno[3,2-f]quinolin-8-one (I-201)

(R)-10-methyl-3-(2-(4-(trifluoromethyl)piperidin-1-yl)-6-vinylpyridin-4-yl)-9,10,11,12-tetrahydro-8H-[1,4]diazepino[5',6':4,5]thieno[3,2-f]quinolin-8-one (I-202)

(R)-10-methyl-3-(3-vinyl-4H-1,2,4-triazol-4-yl)-9,10,11,12-tetrahydro-8H-[1,4]diazepino[5',6':4,5]thieno[3,2-f]quinolin-8-one (I-203)

(R)-3-(3-ethynyl-4H-1,2,4-triazol-4-yl)-10-methyl-9,10,11,12-tetrahydro-8H-[1,4]diazepino[5',6':4,5]thieno[3,2-f]quinolin-8-one (I-204)

(R)-3-(2-chloro-1H-imidazol-1-yl)-10-methyl-9,10,11,12-tetrahydro-8H-[1,4]diazepino[5',6':4,5]thieno[3,2-f]quinolin-8-one (I-205)

(R)-10-methyl-3-(4-methyl-2-vinyl-1H-imidazol-1-yl)-9,10,11,12-tetrahydro-8H-[1,4]diazepino[5',6':4,5]thieno[3,2-f]quinolin-8-one (I-206)

(R)-10-methyl-3-(3-vinyl-1H-1,2,4-triazol-1-yl)-9,10,11,12-tetrahydro-8H-[1,4]diazepino[5',6':4,5]thieno[3,2-f]quinolin-8-one (I-207)

(R)-10-methyl-3-(1-methyl-5-vinyl-1H-1,2,4-triazol-3-yl)-9,10,11,12-tetrahydro-8H-[1,4]diazepino[5',6':4,5]thieno[3,2-f]quinolin-8-one (I-208)

(R)-10-methyl-3-(2-vinylthiazol-5-yl)-9,10,11,12-tetrahydro-8H-[1,4]diazepino[5',6':4,5]thieno[3,2-f]quinolin-8-one (I-209)

(R)-3-(3-chloro-1H-1,2,4-triazol-1-yl)-10-methyl-9,10,11,12-tetrahydro-8H-[1,4]diazepino[5',6':4,5]thieno[3,2-f]quinolin-8-one (I-210)

(R)-3-(5-((3,3-difluoroazetidin-1-yl)methyl)-2-vinylpyridin-4-yl)-10-methyl-9,10,11,12-tetrahydro-8H-[1,4]diazepino[5',6':4,5]thieno[3,2-f]quinolin-8-one (I-211)

(R)-10-methyl-3-(5-((4-(trifluoromethyl)piperidin-1-yl)methyl)-2-vinylpyridin-4-yl)-9,10,11,12-tetrahydro-8H-[1,4]diazepino[5',6':4,5]thieno[3,2-f]quinolin-8-one (I-212)

(R)-3-(5-(((2S,6R)-2,6-dimethylmorpholino)methyl)-2-vinylpyridin-4-yl)-10-methyl-9,10,11,12-tetrahydro-8H-[1,4]diazepino[5',6':4,5]thieno[3,2-f]quinolin-8-one (I-213)

(R)-10-methyl-3-(5-vinyl-1H-1,2,4-triazol-1-yl)-9,10,11,12-tetrahydro-8H-[1,4]diazepino[5',6':4,5]thieno[3,2-f]quinolin-8-one (I-214)

rac-(R)-8-(4-(10-methyl-8-oxo-9,10,11,12-tetrahydro-8H-[1,4]diazepino[5',6':4,5]thieno[3,2-f]quinolin-3-yl)-6-vinylpyridin-2-yl)-1-oxa-8-azaspiro[4.5]decan-2-one (I-215)

rac-(10R)-3-(2-(2-oxa-5-azabicyclo[2.2.1]heptan-5-yl)-6-vinylpyridin-4-yl)-10-methyl-9,10,11,12-tetrahydro-8H-[1,4]diazepino[5',6':4,5]thieno[3,2-f]quinolin-8-one (I-216)

(R)-3-(3-fluoro-2-vinylpyridin-4-yl)-10-methyl-9,10,11,12-tetrahydro-8H-[1,4]diazepino[5',6':4,5]thieno[3,2-f]quinolin-8-one (I-217)

(R)-3-(2-ethynyl-3-fluoropyridin-4-yl)-10-methyl-9,10,11,12-tetrahydro-8H-[1,4]diazepino[5',6':4,5]thieno[3,2-f]quinolin-8-one (I-218)

(R)-10-methyl-3-(3-methyl-2-vinylpyridin-4-yl)-9,10,11,12-tetrahydro-8H-[1,4]diazepino[5',6':4,5]thieno[3,2-f]quinolin-8-one (I-219)

(R)-3-(2-ethynyl-3-methylpyridin-4-yl)-10-methyl-9,10,11,12-tetrahydro-8H-[1,4]diazepino[5',6':4,5]thieno[3,2-f]quinolin-8-one (I-220)

(R)-3-(2-chloro-3-fluoropyridin-4-yl)-10-methyl-9,10,11,12-tetrahydro-8H-[1,4]diazepino[5',6':4,5]thieno[3,2-f]quinolin-8-one (I-221)

(R)-3-(2-ethynyl-1H-imidazol-1-yl)-10-methyl-9,10,11,12-tetrahydro-8H-[1,4]diazepino[5',6':4,5]thieno[3,2-f]quinolin-8-one (I-222)

(R)-10-methyl-3-(3-methyl-5-vinyl-4H-1,2,4-triazol-4-yl)-9,10,11,12-tetrahydro-8H-[1,4]diazepino[5',6':4,5]thieno[3,2-f]quinolin-8-one (I-223)

(R)-10-methyl-3-(3-methyl-5-vinyl-1H-1,2,4-triazol-1-yl)-9,10,11,12-tetrahydro-8H-[1,4]diazepino[5',6':4,5]thieno[3,2-f]quinolin-8-one (I-224)

(R)-10-methyl-3-(6-(3,3,3-trifluoroprop-1-en-2-yl)pyrazin-2-yl)-9,10,11,12-tetrahydro-8H-[1,4]diazepino[5',6':4,5]thieno[3,2-f]quinolin-8-one (I-225)

(R)-10-methyl-3-(3-(trifluoromethyl)-5-vinyl-1H-1,2,4-triazol-1-yl)-9,10,11,12-tetrahydro-8H-[1,4]diazepino[5',6':4,5]thieno[3,2-f]quinolin-8-one (I-226)

(R)-10-methyl-3-(5-methyl-3-vinylisoxazol-4-yl)-9,10,11,12-tetrahydro-8H-[1,4]diazepino[5',6':4,5]thieno[3,2-f]quinolin-8-one (I-227)

(R)-10-methyl-3-(3-vinylisothiazol-4-yl)-9,10,11,12-tetrahydro-8H-[1,4]diazepino[5',6':4,5]thieno[3,2-f]quinolin-8-one (I-228)

(R)-10-methyl-3-(5-vinylisothiazol-4-yl)-9,10,11,12-tetrahydro-8H-[1,4]diazepino[5',6':4,5]thieno[3,2-f]quinolin-8-one (I-229)

(R)-10-methyl-3-(1-methyl-3-vinyl-1H-pyrazol-4-yl)-9,10,11,12-tetrahydro-8H-[1,4]diazepino[5',6':4,5]thieno[3,2-f]quinolin-8-one (I-230)

(R)-3-(4,5-dimethyl-2-vinyl-1H-imidazol-1-yl)-10-methyl-9,10,11,12-tetrahydro-8H-[1,4]diazepino[5',6':4,5]thieno[3,2-f]quinolin-8-one (I-231)

(R)-10-methyl-3-(2-methyl-5-vinyl-2H-1,2,3-triazol-4-yl)-9,10,11,12-tetrahydro-8H-[1,4]diazepino[5',6':4,5]thieno[3,2-f]quinolin-8-one (I-232)

(R)-10-methyl-3-(1-methyl-4-vinyl-1H-1,2,3-triazol-5-yl)-9,10,11,12-tetrahydro-8H-[1,4]diazepino[5',6':4,5]thieno[3,2-f]quinolin-8-one (I-233)

(R)-5-(10-methyl-8-oxo-9,10,11,12-tetrahydro-8H-[1,4]diazepino[5',6':4,5]thieno[3,2-f]quinolin-3-yl)-2-vinylthiazole-4-carboxylate (I-234)

(R)-10-methyl-3-(1-methyl-5-vinyl-1H-1,2,3-triazol-4-yl)-9,10,11,12-tetrahydro-8H-[1,4]diazepino[5',6':4,5]thieno[3,2-f]quinolin-8-one (I-235)

(R)-10-methyl-3-(3-methyl-5-vinyl-1H-pyrazol-1-yl)-9,10,11,12-tetrahydro-8H-[1,4]diazepino[5',6':4,5]thieno[3,2-f]quinolin-8-one (I-236)

(R)-3-(2-((2-methoxyethyl)(methyl)amino)-6-vinylpyridin-4-yl)-10-methyl-9,10,11,12-tetrahydro-8H-[1,4]diazepino[5',6':4,5]thieno[3,2-f]quinolin-8-one (I-237)

(R)-3-(2-(2-oxa-6-azaspiro[3.3]heptan-6-yl)-6-vinylpyridin-4-yl)-10-methyl-9,10,11,12-tetrahydro-8H-[1,4]diazepino[5',6':4,5]thieno[3,2-f]quinolin-8-one (I-238)

(R)-3-(2-(4-fluoropiperidin-1-yl)-6-vinylpyridin-4-yl)-10-methyl-9,10,11,12-tetrahydro-8H-[1,4]diazepino[5',6':4,5]thieno[3,2-f]quinolin-8-one (I-239)

(R)-3-(2-(4-(methoxymethyl)piperidin-1-yl)-6-vinylpyridin-4-yl)-10-methyl-9,10,11,12-tetrahydro-8H-[1,4]diazepino[5',6':4,5]thieno[3,2-f]quinolin-8-one (I-240)

(R)-10-methyl-3-(3-(trifluoromethyl)-5-vinyl-1H-pyrazol-1-yl)-9,10,11,12-tetrahydro-8H-[1,4]diazepino[5',6':4,5]thieno[3,2-f]quinolin-8-one (I-241)

(R)-3-(2-bromo-4-(trifluoromethyl)-1H-imidazol-1-yl)-10-methyl-9,10,11,12-tetrahydro-8H-[1,4]diazepino[5',6':4,5]thieno[3,2-f]quinolin-8-one (I-242)

(10R)-3-(5-(1-hydroxyethyl-2,2,2-d3)-2-vinylpyridin-4-yl)-10-methyl-9,10,11,12-tetrahydro-8H-[1,4]diazepino[5',6':4,5]thieno[3,2-f]quinolin-8-one (I-243)

di-tert-butyl (R)-10-methyl-3-(5-methyl-2-vinylpyridin-4-yl)-8-oxo-10,11-dihydro-8H-[1,4]diazepino[5',6':4,5]thieno[3,2-f]quinoline-9,12-dicarboxylate (I-244)

(R)-10-methyl-3-(5-(trifluoromethoxy)-2-vinylpyridin-4-yl)-9,10,11,12-tetrahydro-8H-[1,4]diazepino[5',6':4,5]thieno[3,2-f]quinolin-8-one (I-245)

(R)-1-(10-methyl-8-oxo-9,10,11,12-tetrahydro-8H-[1,4]diazepino[5',6':4,5]thieno[3,2-f]quinolin-3-yl)-1H-imidazole-2-carbonitrile (I-246)

(R)-3-(5-(difluoromethoxy)-2-vinylpyridin-4-yl)-10-methyl-9,10,11,12-tetrahydro-8H-[1,4]diazepino[5',6':4,5]thieno[3,2-f]quinolin-8-one (I-247)

(R)-3-(5-cyclopropyl-3-vinyl-1H-1,2,4-triazol-1-yl)-10-methyl-9,10,11,12-tetrahydro-8H-[1,4]diazepino[5',6':4,5]thieno[3,2-f]quinolin-8-one (I-248)

(R)-10-methyl-3-(5-(methyl-d3)-2-vinylpyridin-4-yl-3-d)-9,10,11,12-tetrahydro-8H-[1,4]diazepino[5',6':4,5]thieno[3,2-f]quinolin-8-one (I-249)

(R)-3-(2-bromo-4,5-dichloro-1H-imidazol-1-yl)-10-methyl-9,10,11,12-tetrahydro-8H-[1,4]diazepino[5',6':4,5]thieno[3,2-f]quinolin-8-one (I-250)

(R)-3-(4,5-dichloro-2-vinyl-1H-imidazol-1-yl)-10-methyl-9,10,11,12-tetrahydro-8H-[1,4]diazepino[5',6':4,5]thieno[3,2-f]quinolin-8-one (I-251)

(R)-3-(5-(hydroxymethyl)-2-vinylpyridin-4-yl)-10-methyl-9,10,11,12-tetrahydro-8H-[1,4]diazepino[5',6':4,5]thieno[3,2-f]quinolin-8-one (I-252)

(R)-3-(5-(methoxymethyl)-2-vinylpyridin-4-yl)-10-methyl-9,10,11,12-tetrahydro-8H-[1,4]diazepino[5',6':4,5]thieno[3,2-f]quinolin-8-one (I-253)

(S)-10-(fluoromethyl)-3-(5-methyl-2-vinylpyridin-4-yl)-9,10,11,12-tetrahydro-8H-[1,4]diazepino[5',6':4,5]thieno[3,2-f]quinolin-8-one (I-254)

(S)-10-(fluoromethyl)-3-(2-vinyl-1H-imidazol-1-yl)-9,10,11,12-tetrahydro-8H-[1,4]diazepino[5',6':4,5]thieno[3,2-f]quinolin-8-one (I-255)

(R)-3-(5-methoxy-2-vinylpyridin-4-yl)-10-methyl-9,10,11,12-tetrahydro-8H-[1,4]diazepino[5',6':4,5]thieno[3,2-f]quinolin-8-one (I-256)

(R)-10-methyl-3-(5-(trifluoromethyl)-3-vinyl-1H-pyrazol-1-yl)-9,10,11,12-tetrahydro-8H-[1,4]diazepino[5',6':4,5]thieno[3,2-f]quinolin-8-one (I-257)

(R)-3-(5-(2-hydroxypropan-2-yl-1,1,1,3,3,3-d6)-2-vinylpyridin-4-yl)-10-methyl-9,10,11,12-tetrahydro-8H-[1,4]diazepino[5',6':4,5]thieno[3,2-f]quinolin-8-one (I-258)

(10R)-3-(5-(1-hydroxyethyl-2,2,2-d3)-2-vinylpyridin-4-yl)-10-methyl-9,10,11,12-tetrahydro-8H-[1,4]diazepino[5',6':4,5]thieno[3,2-f]quinolin-8-one (I-259)

(10R)-3-(5-(1-hydroxyethyl-2,2,2-d3)-2-vinylpyridin-4-yl)-10-methyl-9,10,11,12-tetrahydro-8H-[1,4]diazepino[5',6':4,5]thieno[3,2-f]quinolin-8-one (I-260)

(R)-10-methyl-3-(5-methyl-3-vinyl-1H-1,2,4-triazol-1-yl)-9,10,11,12-tetrahydro-8H-[1,4]diazepino[5',6':4,5]thieno[3,2-f]quinolin-8-one (I-261)

(R)-3-(5-(ethoxymethyl)-2-vinylpyridin-4-yl)-10-methyl-9,10,11,12-tetrahydro-8H-[1,4]diazepino[5',6':4,5]thieno[3,2-f]quinolin-8-one (I-262)

(R)-3-(5-((2-oxa-6-azaspiro[3.3]heptan-6-yl)methyl)-2-vinylpyridin-4-yl)-10-methyl-9,10,11,12-tetrahydro-8H-[1,4]diazepino[5',6':4,5]thieno[3,2-f]quinolin-8-one (I-263)

(R)-10-methyl-3-(5-vinylpyridazin-3-yl)-9,10,11,12-tetrahydro-8H-[1,4]diazepino[5',6':4,5]thieno[3,2-f]quinolin-8-one (I-264)

(R,E)-10-methyl-3-(5-methyl-2-(prop-1-en-1-yl)pyridin-4-yl)-9,10,11,12-tetrahydro-8H-[1,4]diazepino[5',6':4,5]thieno[3,2-f]quinolin-8-one (I-265)

(R,E)-10-methyl-3-(2-(prop-i-en-1-yl)-1H-imidazol-1-yl)-9,10,11,12-tetrahydro-8H-[1,4]diazepino[5',6':4,5]thieno[3,2-f]quinolin-8-one (I-266)

(R)-2-(5-methyl-4-(10-methyl-8-oxo-9,10,11,12-tetrahydro-8H-[1,4]diazepino[5',6':4,5]thieno[3,2-f]quinolin-3-yl)pyridin-2-yl)acetonitrile (I-267)

1'-fluoro-2'-(2-((2-methoxyethyl)(methyl)amino)-6-vinylpyridin-4-yl)-1-methyl-6',8',9',11'-tetrahydrospiro[azetidine-3,10'-pyrido[3',4':4,5]pyrrolo[2,3-f]isoquinolin]-7'(5'H)-one (I-268)

2'-(2-(2-oxa-7-azaspiro[4.4]nonan-7-yl)-6-vinylpyridin-4-yl)-1'-fluoro-1-methyl-6',8',9',11'-tetrahydrospiro[azetidine-3,10'-pyrido[3',4':4,5]pyrrolo[2,3-f]isoquinolin]-7'(5'H)-one (I-269)

1'-fluoro-2'-(2-(4-(methoxymethyl)piperidin-1-yl)-6-vinylpyridin-4-yl)-1-methyl-6',8',9',11'-tetrahydrospiro[azetidine-3,10'-pyrido[3',4':4,5]pyrrolo[2,3-f]isoquinolin]-7'(5'H)-one (I-270)

(R)-10-methyl-3-(2-vinyl-1H-benzo[d]imidazol-1-yl)-9,10,11,12-tetrahydro-8H-[1,4]diazepino[5',6':4,5]thieno[3,2-f]quinolin-8-one (I-271)

(R)-3-(2-chloropyridin-4-yl)-10-methyl-9,10,11,12-tetrahydro-8H-[1,4]diazepino[5',6':4,5]thieno[3,2-f]quinolin-8-one (I-272)

(R)-3-(2-chloro-5-fluoropyrimidin-4-yl)-10-methyl-9,10,11,12-tetrahydro-8H-[1,4]diazepino[5',6':4,5]thieno[3,2-f]quinolin-8-one (I-273)

(R)-3-(6-chloro-3-fluoro-5-(trifluoromethyl)pyridin-2-yl)-10-methyl-9,10,11,12-tetrahydro-8H-[1,4]diazepino[5',6':4,5]thieno[3,2-f]quinolin-8-one (I-274)

4. Uses, Formulation and Administration

Pharmaceutically Acceptable Compositions

According to another embodiment, the invention provides a composition comprising a compound of this invention or a pharmaceutically acceptable salt thereof and a pharmaceutically acceptable carrier, adjuvant, or vehicle. In certain embodiments, the amount of compound in compositions of this invention is such that it is effective to measurably inhibit MK2, or a mutant thereof, in a biological sample or in a patient. In certain embodiments, a composition of this invention is formulated for administration to a patient in need of such composition. In some embodiments, a composition of this invention is formulated for oral administration to a patient.

Compounds and compositions, according to method of the present invention, are administered using any amount and any route of administration effective for treating or lessening the severity of a disorder provided herein (i.e., an MK2-mediated disease or disorder). The exact amount required will vary from subject to subject, depending on the species, age, and general condition of the subject, the severity of the infection, the particular agent, its mode of administration, and the like. Compounds of the invention are preferably formulated in unit dosage form for ease of administration and uniformity of dosage.

Compositions of the present invention may be administered orally, parenterally, by inhalation spray, topically, rectally, nasally, buccally, vaginally, intraperitoneally, intracisternally or via an implanted reservoir. In some embodiments, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In some embodiments, provided pharmaceutically acceptable compositions are formulated for oral administration. Such formulations may be administered with or without food. In some embodiments, pharmaceutically acceptable compositions of this invention are administered without food. In other embodiments, pharmaceutically acceptable compositions of this invention are administered with food. Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

5. Uses of Compounds and Pharmaceutically Acceptable Compositions

Compounds and compositions described herein are generally useful for the inhibition of kinase activity of one or more enzymes. Examples of kinases that are inhibited by the compounds and compositions described herein and against which the methods described herein are useful include MK2, or a mutant thereof.

The activity of a compound utilized in this invention as an inhibitor of a MK2 kinase, or a mutant thereof, may be assayed in vitro, in vivo or in a cell line. In vitro assays include assays that determine inhibition of either the phosphorylation activity and/or the subsequent functional consequences, or ATPase activity of activated MK2 kinase, or a mutant thereof. Alternate in vitro assays quantitate the ability of the test compound to bind to MK2. Inhibitor binding may be measured by radiolabeling the test compound prior to binding, isolating the test compound/MK2 complex and determining the amount of radiolabel bound. Alternatively, inhibitor binding may be determined by running a competition experiment where test compounds are incubated with MK2 kinase bound to known radioligands. Detailed conditions for assaying a compound utilized in this invention as an inhibitor of MK2, or a mutant thereof, are set forth in the Examples, below.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting MK2 kinase, or a mutant thereof, activity in a biological sample comprising the step of contacting said biological sample with a compound of this invention, or a composition comprising said compound. In certain embodiments, the invention relates to a method of irreversibly inhibiting MK2 kinase, or a mutant thereof, activity in a biological sample comprising the step of contacting said biological sample with a compound of this invention, or a composition comprising said compound.

According to another embodiment, the invention relates to a method of inhibiting MK2 kinase, or a mutant thereof, activity in a patient comprising the step of administering to said patient a compound of the present invention, or a composition comprising said compound. According to certain embodiments, the invention relates to a method of irreversibly inhibiting MK2 kinase, or a mutant thereof, activity in a patient comprising the step of administering to said patient a compound of the present invention, or a composition comprising said compound. In other embodiments, the present invention provides a method for treating an MK2-mediated disease or disorder, in a patient in need thereof, comprising the step of administering to said patient a compound according to the present invention or pharmaceutically acceptable composition thereof. Such disorders are described in detail herein.

6. MK2 Kinase

MAP kinase-activated protein kinase 2 ("MK2") is an enzyme that in humans is encoded by the MAPKAPK2 gene. This gene encodes a member of the Ser/Thr protein kinase family. This kinase is regulated through direct phosphorylation by p38 MAP kinase. In conjunction with p38 MAP kinase, this kinase is known to be involved in many cellular processes including stress and inflammatory responses, nuclear export, gene expression regulation and cell proliferation. Heat shock protein HSP27 was shown to be one of the substrates of this kinase in vivo. Two transcript variants encoding two different isoforms have been found for this gene.

MK2 is a multi-domain protein consisting of an N-terminal proline-rich domain, a catalytic domain, an autoinhibitory domain and at the C-terminus a nuclear export signal (NES) and nuclear localization signal (NLS). Two isoforms of human MK2 have been characterized. One isoform consists of 400 amino acids and the other isoform 370 residues which is thought to be a splice variant missing the C-terminal NLS. MK2 is located in the nucleus of the cell and upon binding and phosphorylation by p38, the MK2 NES becomes functional and both kinases are co-transported out of the nucleus to the cytoplasm. Interestingly, transport of the MK2/p38 complex does not require catalytically active MK2, as the active site mutant, Asp207Ala, is still transported to the cytoplasm. Phosphorylation of human MK2 by p38 on residues T222, S272 and T334 is thought to activate the enzyme by inducing a conformational change of the autoinhibitory domain thus exposing the active site for substrate binding. Mutations of two autoinhibitory domain residues W332A and K326E in murine MK2 demonstrate an increase in basal activity and a C-terminal deletion of the autoinhibitory domain renders the enzyme constitutively active, providing additional evidence to the role of this domain in inhibition of MK2 activity.

Diseases or disorders associated with MK2 that are treated by compounds of the present invention include autoimmune disorders, chronic inflammatory disorders, acute inflammatory disorders, auto-inflammatory disorders, fibrotic disorders, metabolic disorders, neoplasias, or cardiovascular or cerebrovascular disorders. Thus, in some embodiments, the present invention provides a method for treating an MK2-mediated disease or disorder in a patient in need thereof, wherein said method comprises administering to said patient a therapeutically effective amount of a provided compound, or composition thereof. Such MK2-mediated diseases or disorders include, but are not limited to those described herein.

In some embodiments, the MK2-mediated disease or disorder is an autoimmune disorder, chronic and/or acute inflammatory disorder, and/or auto-inflammatory disorder. Exemplary autoimmune and/or inflammatory and/or auto-inflammatory disorders include: inflammatory bowel diseases (for example, ulcerative colitis or Crohn's disease), multiple sclerosis, psoriasis, arthritis, rheumatoid arthritis, osteoarthritis, juvenile arthritis, psoriatic arthritis, reactive arthritis, ankylosing spondylitis, cryopyrin associated periodic syndromes, Muckle-Wells syndrome, familial cold auto-inflammatory syndrome, neonatal-onset multisystem inflammatory disease, TNF receptor associated periodic syndrome, acute and chronic pancreatitis, atherosclerosis, gout, ankylosing spondylitis, fibrotic disorders (for example, hepatic fibrosis or idiopathic pulmonary fibrosis), nephropathy, sarcoidosis, scleroderma, anaphylaxis, diabetes (for example, diabetes mellitus type 1 or diabetes mellitus type 2), diabetic retinopathy, Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease, Sjogren's syndrome, familial Mediterranean fever, systemic lupus erythematosus, vasculitis syndromes (for example, temporal, Takayasu's and giant cell arteritis, Behçet's disease or Wegener's granulomatosis), vitiligo, secondary hematologic manifestation of autoimmune diseases (for example, anemias), drug-induced autoimmunity, Hashimoto's thyroiditis, hypophysitis, idiopathic thrombocytic pupura, metal-induced autoimmunity, myasthenia gravis, pemphigus, autoimmune deafness (for example, Meniere's disease), Goodpasture's syndrome, Graves' disease, HW-related autoimmune syndromes, Gullain-Barre disease, Addison's disease, anti-phospholipid syndrome, asthma, atopic dermatitis, Celiac disease, Cushing's syndrome, dermatomyositis, idiopathic adrenal adrenal atrophy, idiopathic thrombocytopenia, Kawasaki syndrome, Lambert-Eaton Syndrome, pernicious anemia, pollinosis, polyarteritis nodosa, primary biliary cirrhosis, primary sclerosing cholangitis, Raynaud's, Reiter's Syndrome, relapsing polychondritis, Schmidt's syndrome, thyrotoxidosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonary disease (COPD), vasculitis, graft vs. host reaction (for example, graft vs. host disease), allograft rejections (for example, acute allograft rejection or chronic allograft rejection), early transplantation rejection (for example, acute allograft rejection), reperfusion injury, pain (for example, acute pain, chronic pain, neuropathic pain, or fibromyalgia), chronic infections, meningitis, encephalitis, myocarditis, gingivitis, post surgical trauma, tissue injury, traumatic brain injury, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

In some embodiments, the MK2-mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension-induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis)), radiation-induced fibrosis (for example, head and neck, gastrointestinal or pulmonary), primary sclerosing cholangitis, restenosis, cardiac fibrosis (for example, endomyocardial fibrosis or atrial fibrosis), ophthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the MK2-mediated disease or disorder is a metabolic disorder. Exemplary metabolic disorders include obesity, steroid-resistance, glucose intolerance, and metabolic syndrome.

In some embodiments, the MK2-mediated disease or disorder is a neoplasia. Exemplary neoplasias include cancers. In some embodiments, exemplary neoplasias include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, fibrosarcoma, rhabdomyosarcoma; astrocytoma, neuroblastoma, glioma and schwannomas; melanoma, seminoma, teratocarcinoma, osteosarcoma, xenoderoma pigmentosum, keratoctanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the MK2-mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Enantioenriched compounds of the invention were prepared in enantioenriched form using chiral starting materials, or were separated after reaction with a racemic starting material, using chiral chromatography. For compounds prepared as racemic or diastereomeric mixtures, the single isomers can be prepared in optically pure form by either employing chiral starting materials or performing chiral chromatography.

In the illustrative examples that follow, reactions were carried out at room or ambient temperature, in the range of 18-25° C. unless otherwise stated. Organic solutions were dried over anhydrous magnesium sulfate or sodium sulfate and evaporation of solvent was carried out using a rotary evaporator under reduced pressure. In general, the courses of reactions were followed by TLC or LCMS and reaction times are representative. Yields are given for illustration only and are not necessarily those which can be obtained by diligent process development.

Microwave reactions were performed in a Biotage Explorer reaction microwave system. $^1$H NMR data is in delta values for major diagnostic protons, given in parts per million (ppm) relative to tetramethylsilane (TMS) or residual solvent. $^1$H NMR spectra were determined at 400 MHz. Solvent ratios are given in volume:volume (v/v) terms. Mass spectra (MS) data was generated on an LCMS system where the HPLC component comprised generally either an Agilent or Shimadzu LCMS-2020 Instrument and was run on a Sepax BR-C18 (4.6×50 mm, 3 μm) column or similar, eluting with acidic eluent (for example, using a gradient between 0-95% water acetonitrile with 0.1% formic acid or trifluoroacetic acid). Chromatograms were in electrospray (ESI) positive, negative and/or UV. LCMS values for m/z are provided throughout and generally, only ions which indicate the parent mass are reported. Unless otherwise stated the value quoted is the (M+H) or (M+1) for positive ion mode. Preparative HPLC was performed on $C_{18}$ reversed-phase silica using decreasingly polar mixtures as eluent, for example decreasingly polar mixtures of water and acetonitrile containing 1% trifluoroacetic acid.

Enantioenriched intermediates and final compounds were synthesized using commercially available chiral materials and their stereochemistry as recorded is absolute. Unless otherwise specified, starting materials were commercially available or synthesized according to known methods.

| Table of abbreviations | |
|---|---|
| TFA | trifluoroacetic acid |
| TLC | thin layer chromatography |
| THF | tetrahydrofuran |
| DMF | N,N-dimethylformamide |
| EtOAc | ethyl acetate |
| DCM | dichloromethane |
| DMSO | dimethylsulfoxide |
| ACN/MeCN | acetonitrile |
| mCPBA | m-chloroperoxybenzoic acid |
| DIPEA (Hünig's base) | N,N-diisopropylethylamine |
| TBAF | tetra-N-butylammonium fluoride |
| PMB | p-methoxybenzyl |
| rac | racemic |
| DMAP | 4-dimethylaminopyridine |
| dba | dibenzylideneacetone |
| dppf | 1,1'-bis(diphenylphosphino) ferrocene |
| Xantphos | 4,5-Bis(diphenylphosphino)-9,9-dimethylxanthene |
| DavePhos | 2-Dicyclohexylphosphino-2'-(N,N-dimethylamino)biphenyl |
| SPhos | 2-Dicyclohexylphosphino-2',6'-dimethoxybiphenyl |
| BINAP | (±)-2,2'-Bis(diphenylphosphino)-1,1'-binaphthyl |
| BrettPhos-G1 | Chloro[2-(dicyclohexylphosphino)-3,6-dimethoxy-2',4', 6'-triisopropyl-1,1'-biphenyl][2-(2-aminoethyl)phenyl]palladium(II) |
| h | hour |
| min | minute |
| aq | aqueous |
| g | gas |
| sat | saturated |

Example 1: Synthesis of (R)-3-(6-ethynylpyridin-2-yl)-10-methyl-9,10,11,12-tetrahydro-8H-[1,4]diazepino[5',6':4,5]thieno[3,2-f]quinolin-8-one

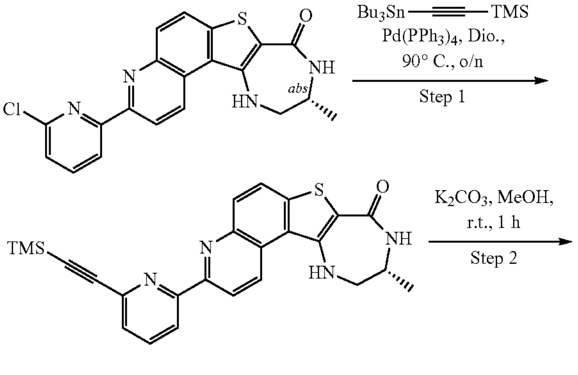

-continued

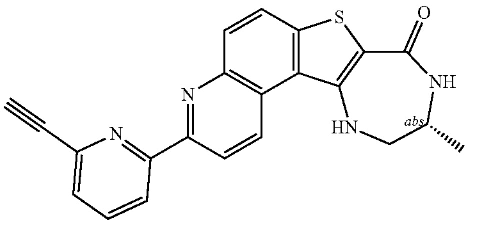

Step 1: Synthesis of (R)-10-methyl-3-(6-((trimethylsilyl)ethynyl)pyridin-2-yl)-9,10,11,12-tetrahydro-8H-[1,4]diazepino[5',6':4,5]thieno[3,2-f]quinolin-8-one

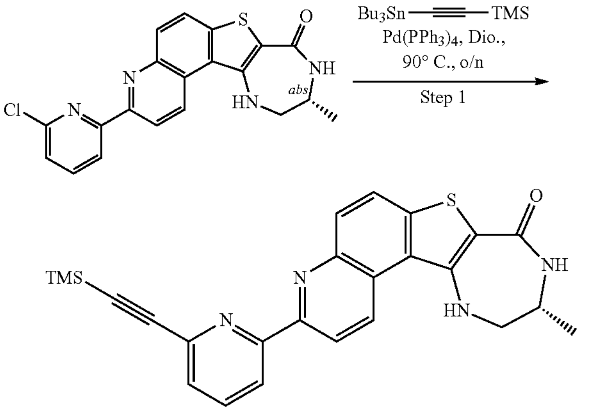

To a solution of (R)-3-(6-chloropyridin-2-yl)-10-methyl-9,10,11,12-tetrahydro-8H-[1,4]diazepino[5',6':4,5]thieno[3,2-f]quinolin-8-one (110 mg, 0.280 mmol, 1.00 equiv) in 1,4-dioxane (5.0 mL) was added trimethyl(2-tributylstannylethynyl)silane (323 mg, 0.840 mmol, 3.00 equiv) and $Pd(PPh_3)_4$ (32 mg, 0.030 mmol, 0.10 equiv). The resulting mixture was stirred at 90° C. under nitrogen atmosphere overnight. LCMS showed the reaction was completed. The resulting solution was diluted with EA (20 mL). The solid was collected by filtration and washed with EA (50 mL). Dried to give (R)-10-methyl-3-(6-((trimethylsilyl)ethynyl)pyridin-2-yl)-9,10,11,12-tetrahydro-8H-[1,4]diazepino[5',6':4,5]thieno[3,2-f]quinolin-8-one (70 mg, 55%) as a green solid. LCMS (ESI, m z): 457 $[M+H]^+$.

Step 2: Synthesis of (R)-3-(6-ethynylpyridin-2-yl)-10-methyl-9,10,11,12-tetrahydro-8H-[1,4]diazepino[5',6':4,5]thieno[3,2-f]quinolin-8-one

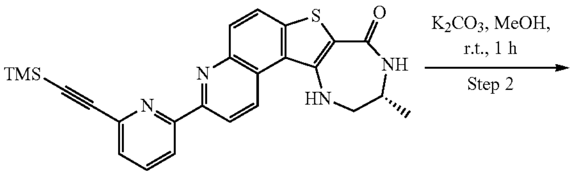

-continued

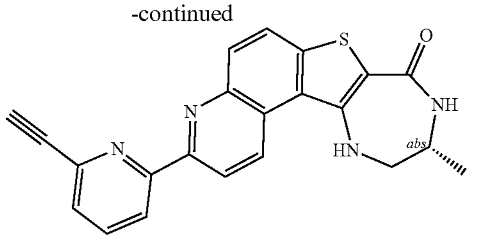

To a solution of (R)-10-methyl-3-(6-((trimethylsilyl)ethynyl)pyridin-2-yl)-9,10,11,12-tetrahydro-8H-[1,4]diazepino[5',6':4,5]thieno[3,2-f]quinolin-8-one (70 mg, 0.153 mmol, 1.00 equiv) in methanol (3.0 mL) was added $K_2CO_3$ (42 mg, 0.306 mmol, 2.00 equiv). The resulting mixture was stirred at room temperature for 1 h. LCMS showed the reaction was completed. The resulting mixture was concentrated under reduced pressure. The crude product was purified by preparative HPLC using the following gradient conditions: Column: Xselect CSH OBD Column 30*150 mm Sum, n; Mobile Phase A: Water (0.05% TFA), Mobile Phase B: ACN; Flow rate: 60 mL/min; Gradient: 37% B to 42% B in 10 min, 42% B; Wave Length: 254/220 nm; RT1 (min): 9.28. Purification resulted in (R)-3-(6-ethynylpyridin-2-yl)-10-methyl-9,10,11,12-tetrahydro-8H-[1,4]diazepino[5',6':4,5]thieno[3,2-f]quinolin-8-one (36 mg, 38%) as a red solid. Analytic Conditions: Column: HALO C18 100 A Column 3.0*30 mm, 2.0 um; Mobile Phase A: Water/0.05% TFA, Mobile Phase B: Acetonitrile/0.05% TFA; Flow rate: 1.2000 mL/min; Gradient: 5% B to 100% B in 1.95 min; 254 nm; Rt: 1.572 min.

$^1H$ NMR (400 MHz, DMSO-$d_6$) δ 9.33 (d, J=9.2 Hz, 1H), 8.65 (d, J=8.8 Hz, 1H), 8.57 (d, J=8.8 Hz, 1H), 8.19 (d, J=8.8 Hz, 1H), 8.11-8.05 (m, 3H), 7.71 (d, J=8.4 Hz, 1H), 7.18 (s, 1H), 4.48 (s, 1H), 3.66-3.60 (m, 1H), 3.53-3.50 (m, 2H), 1.22 (d, J=6.8 Hz, 3H). $^{19}F$ NMR (376 MHz, DMSO-$d_6$) δ-74.84.

Example 2: Synthesis of rac-(15R)-5-(2,6-dichloropyrimidin-4-yl)-15-methyl-11-thia-6,14,17-triazatetracyclo[8.8.0.0^,7.0^12,18]octadeca-1,3,5,7,9,12(18)-hexaen-13-one

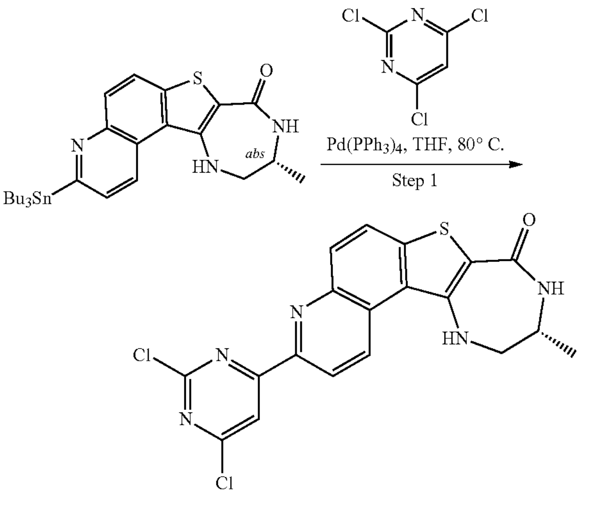

To a solution of 2,4,6-trichloropyrimidine (80 mg, 0.440 mmol, 1.00 equiv) and rac-(15R)-15-methyl-5-tributylstannyl-11-thia-6,14,17-triazatetracyclo[8.8.0.0^,7.0^12,18]octadeca-1,3,5,7,9,12(18)-hexaen-13-one (251 mg, 0.440 mmol, 1.00 equiv) in THF (1.0 mL) was added $Pd(PPh_3)_4$ (51 mg, 0.05 mmol, 0.10 equiv). The resulting mixture was stirred at 80° C. overnight under a nitrogen atmosphere. LCMS showed the reaction was completed. The resulting solution was concentrated under reduce pressure. The residue was purified by Prep-HPLC using the following gradient conditions: Column: SunFire Prep C18 OBD Column, 19×150 mm, 5 m 10 nm; Mobile Phase A: Water (0.05% TFA), Mobile Phase B: MeCN; Flow rate: 20 mL/min; Gradient: 25% B to 50% B in 4.5 min, 50% B; Wave Length: 254/210 nm; RT1(min): 4.35. Purification resulted in desired rac-(15R)-5-(2,6-dichloropyrimidin-4-yl)-15-methyl-11-thia-6,14,17-triazatetracyclo[8.8.0.0^,7.0^12,18]octadeca-1,3,5,7,9,12(18)-hexaen-13-one (3.9 mg, 2%) as a yellow solid. LCMS (ESI, m/z): 430 and 432 $(M+H)^+$. Analytic Conditions: Column: HALO C18 100A Column 3.0*30 mm, 2.7 um; Mobile Phase A: Water/0.05% TFA, Mobile Phase B: Acetonitrile/0.05% TFA; Flow rate: 1.2000 mL/min; Gradient: 5% B to 100% B in 1.30 min; 254 nm; Rt: 1.223 min.

$^1H$ NMR (400 MHz, DMSO-$d_6$) δ 9.38 (d, J=8.8 Hz, 1H), 8.63 (s, 1H), 8.52 (d, J=8.8 Hz, 1H), 8.27 (d, J=8.8 Hz, 1H), 8.17 (d, J=3.6 Hz, 1H), 8.11 (d, J=8.8 Hz, 1H), 7.22 (s, 1H), 3.67-3.60 (m, 1H), 3.50-3.40 (m, 1H), 1.21 (d, J=6.8 Hz, 3H).

Example 3: Synthesis of (15R)-5-[6-ethynyl-2-(4-methylpiperazin-1-yl)pyrimidin-4-yl]-15-methyl-11-thia-6,14,17-triazatetracyclo[8.8.0.0^,7.0^12,18]octadeca-1(10),2(7),3,5,8,12(18)-hexaen-13-one

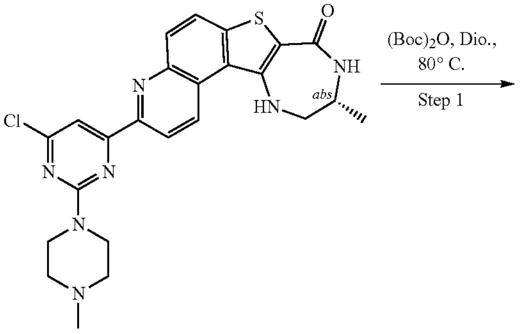

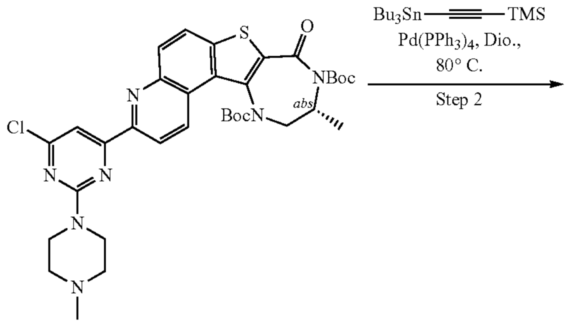

-continued

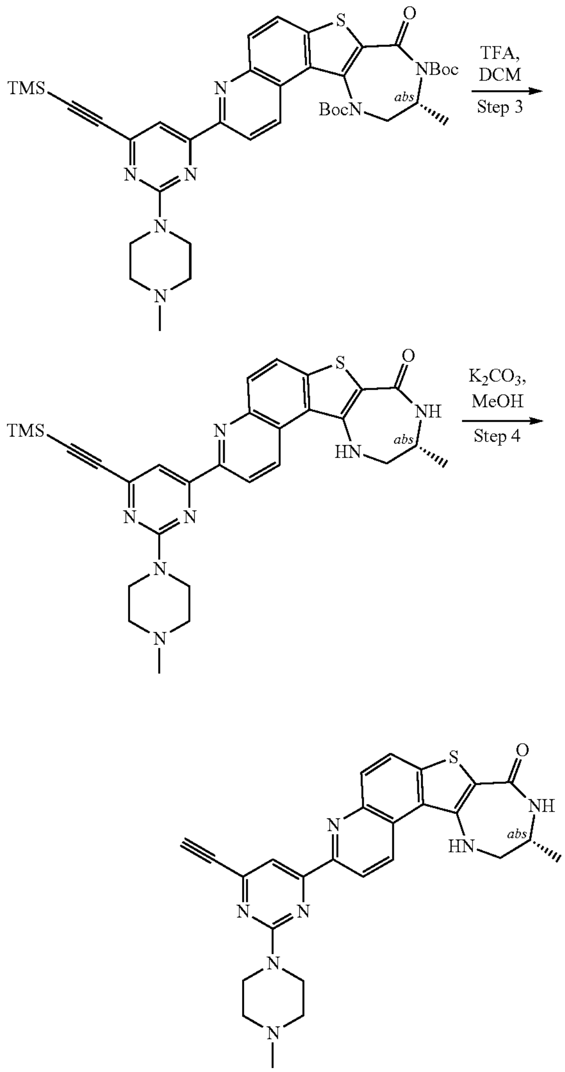

Step 1: Synthesis of ditert-butyl (15R)-5-[6-chloro-2-(4-methylpiperazin-1-yl)pyrimidin-4-yl]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate

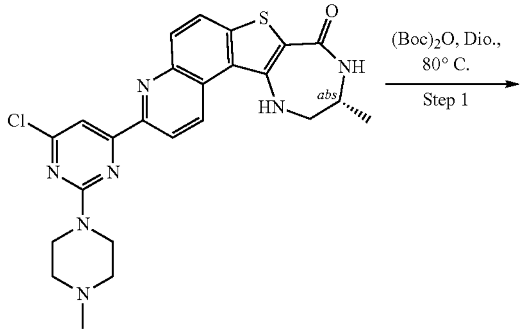

-continued

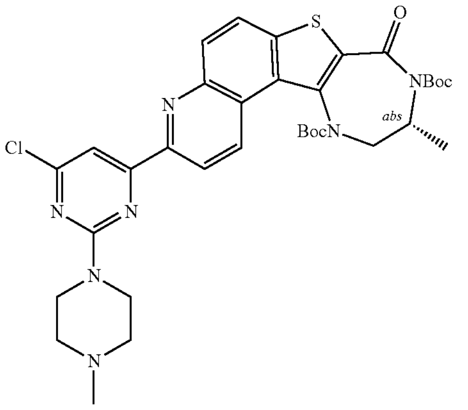

To a solution of (15R)-5-[6-chloro-2-(4-methylpiperazin-1-yl)pyrimidin-4-yl]-15-methyl-11-thia-6,14,17-triazatetracyclo[8.8.0.0^,7.0^12,18]octadeca-1(10),2(7),3,5,8,12(18)-hexaen-13-one (50 mg, 0.100 mmol, 1.00 equiv), $(Boc)_2O$ (109 mg, 0.500 mmol, 5.0 equiv) and DMAP (2 mg, 0.010 mmol, 0.10 equiv) in 1,4-dioxane (3.0 mL). The resulting solution was stirred overnight at 80° C. under a nitrogen atmosphere. LCMS showed the reaction was completed. The reaction was quenched with water (20 mL) and extracted with ethyl acetate (3×20 mL). The combined organic layers were washed with brine (2×20 mL), dried over sodium sulfate, filtered, concentrated under reduce pressure and the residue was purified by column chromatography on silica gel with petroleum ether/ethyl acetate (3:1) to give ditert-butyl (15R)-5-[6-chloro-2-(4-methylpiperazin-1-yl)pyrimidin-4-yl]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (60 mg, 85%) as a white solid. LCMS (ESI, m/z): 694 $(M+H)^+$.

Step 2: Synthesis of ditert-butyl(15R)-15-methyl-5-[2-(4-methylpiperazin-1-yl)-6-(2-trimethylsilylethynyl)pyrimidin-4-yl]-13-oxo-11-thia-6,14,17-triazatetracyclo[8.8.0.0^,7.0^12,18]octadeca-1(10),2(7),3,5,8,12(18)-hexaene-14,17-dicarboxylate -continued

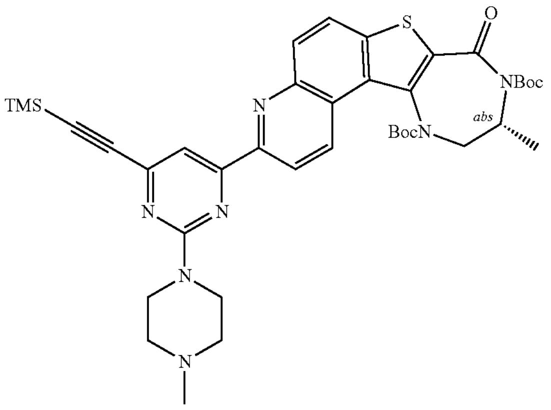

To a solution of ditert-butyl (15R)-5-[6-chloro-2-(4-methylpiperazin-1-yl)pyrimidin-4-yl]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (50 mg, 0.070 mmol, 1.00 equiv) and trimethyl(2-tributylstannylethynyl)silane (41 mg, 0.110 mmol, 1.50 equiv) in 1,4-dioxane (3.0 mL) was added $Pd(PPh_3)_4$(12 mg, 0.010 mmol, 0.20 equiv). The resulting solution was stirred overnight at 80° C. under a nitrogen atmosphere. LCMS showed the reaction was completed. The reaction was then quenched with water (20 mL) and extracted with ethyl acetate (3×20 mL). The combined organic layers were washed with brine (2×20 mL), dried over sodium sulfate, filtered, concentrated under reduce pressure and the residue was purified by column chromatography on silica gel with petroleum ether/ethyl acetate (1:4) to give ditert-butyl (15R)-15-methyl-5-[2-(4-methylpiperazin-1-yl)-6-(2-trimethylsilylethynyl)pyrimidin-4-yl]-13-oxo-11-thia-6,14,17-triazatetracyclo[8.8.0.0^,7.0^12,18]octadeca-1(10),2(7),3,5,8,12(18)-hexaene-14,17-dicarboxylate (50 mg, 92%) as a yellow solid. LCMS (ESI, m/z): 756$(M+H)^+$.

Step 3: Synthesis of (15R)-15-methyl-5-[2-(4-methylpiperazin-1-yl)-6-(2-trimethylsilylethynyl)pyrimidin-4-yl]-11-thia-6,14,17-triazatetracyclo[8.8.0.0^,7.0^12,18]octadeca-1(10),2(7),3,5,8,12(18)-hexaen-13-one

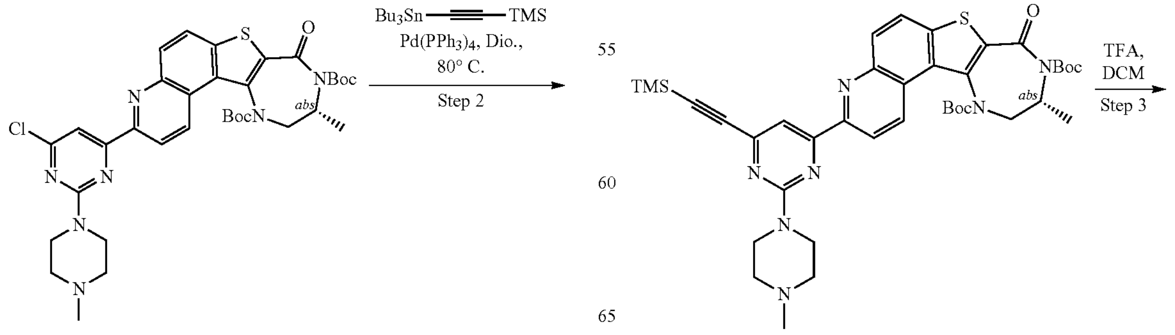

-continued

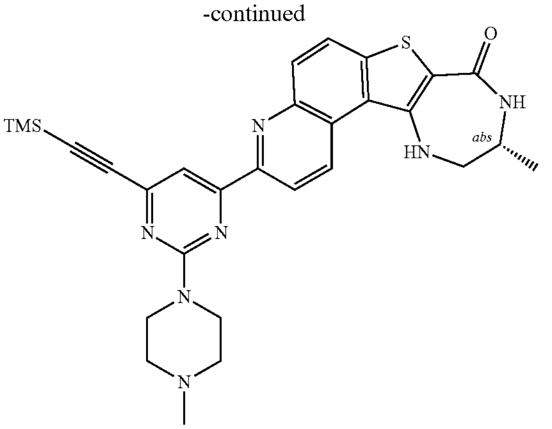

To a solution of ditert-butyl (15R)-15-methyl-5-[2-(4-methylpiperazin-1-yl)-6-(2-trimethylsilylethynyl)pyrimidin-4-yl]-13-oxo-11-thia-6,14,17-triazatetracyclo[8.8.0.0^,7.0^12,18]octadeca-1(10),2(7),3,5,8,12(18)-hexaene-14,17-dicarboxylate (50 mg, 0.070 mmol, 1.00 equiv) in DCM (4.0 mL) was added dropwise TFA (1.0 mL). The resulting solution was stirred for 1 h at room temperature. LCMS showed the reaction was completed. The resulting solution was concentrated under reduce pressure to give crude (15R)-15-methyl-5-[2-(4-methylpiperazin-1-yl)-6-(2-trimethylsilylethynyl)pyrimidin-4-yl]-11-thia-6,14,17-triazatetracyclo[8.8.0.0^,7.0^12,18]octadeca-1(10),2(7),3,5,8,12(18)-hexaen-13-one (30 mg, 83%) as a yellow solid. LCMS (ESI, m/z): 556(M+H)$^+$.

Step 4: Synthesis of (15R)-5-[6-ethynyl-2-(4-methylpiperazin-1-yl)pyrimidin-4-yl]-15-methyl-11-thia-6,14,17-triazatetracyclo[8.8.0.0^,7.0^12,18]octadeca-1(10),2(7),3,5,8,12(18)-hexaen-13-one

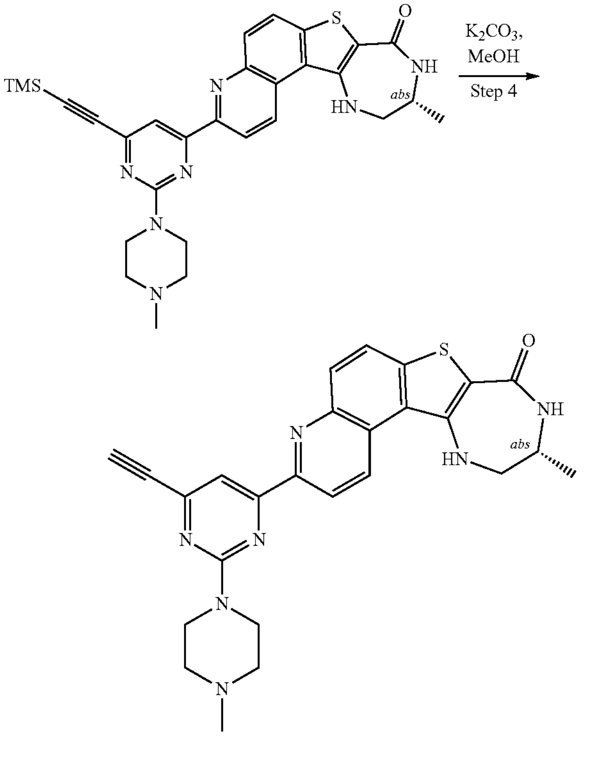

To a solution of (15R)-15-methyl-5-[2-(4-methylpiperazin-1-yl)-6-(2-trimethylsilylethynyl)pyrimidin-4-yl]-11-thia-6,14,17-triazatetracyclo[8.8.0.0^,7.0^12,18]octadeca-1(10),2(7),3,5,8,12(18)-hexaen-13-one (30 mg, 0.050 mmol, 1.00 equiv) and $K_2CO_3$ (11 mg, 0.080 mmol, 1.50 equiv) in methanol (2.0 mL). The resulting solution was stirred for 1 h at room temperature. LCMS showed the reaction was completed. The resulting solution was diluted with DMSO (5 mL). The solid was filtered out. The filtration was purified by Prep-HPLC using the following conditions: Column: SunFire Prep C18 OBD Column, 19*150 mm, 5 μm; Mobile Phase A: Water (0.05% TFA), Mobile Phase B: MeCN; Flow rate: 20 mL/min; Gradient: 30% B to 50% B in 4.5 min, 50% B; Wave Length: 254/210 nm; RT1. Purification resulted in desired (15R)-5-[6-ethynyl-2-(4-methylpiperazin-1-yl)pyrimidin-4-yl]-15-methyl-i 1-thia-6,14,17-triazatetracyclo[8.8.0.0^,7.0^12,18]octadeca-1(10),2(7),3,5,8,12(18)-hexaen-13-one (15.5 mg, 58% yield) as a brown solid. LCMS (ESI, m/z): 484 (M+H)$^+$. Analytic Conditions: Column: HALO C18 100A Column 3.0*30 mm, 2.7 um; Mobile Phase A: Water/0.05% TFA, Mobile Phase B: Acetonitrile/0.05% TFA; Flow rate: 1.5000 mL/min; Gradient: 5% B to 65% B in 1.7 min; 254 nm; Rt: 1.396 min.

$^1$H NMR (400 MHz, DMSO-$d_6$) δ 9.34 (d, J=8.8 Hz, 1H), 8.65 (d, J=8.8 Hz, 1H), 8.23 (d, J=9.2 Hz, 1H), 8.15 (d, J=4.0 Hz, 1H), 8.09 (d, J=8.8 Hz, 1H), 7.93 (s, 1H), 4.98-4.88 (m, 2H), 4.73 (s, 1H), 3.70-3.55 (m, 3H), 3.50-3.30 (m, 4H), 3.25-3.10 (m, 2H), 2.88 (s, 3H), 1.21 (d, J=6.8 Hz, 3H).

Example 4: Synthesis of (15R)-5-[2-ethynyl-6-(4-methylpiperazin-1-yl)pyrimidin-4-yl]-15-methyl-11-thia-6,14,17-triazatetracyclo[8.8.0.0^,7.0^12,18]octadeca-1(10),2(7),3,5,8,12(18)-hexaen-13-one

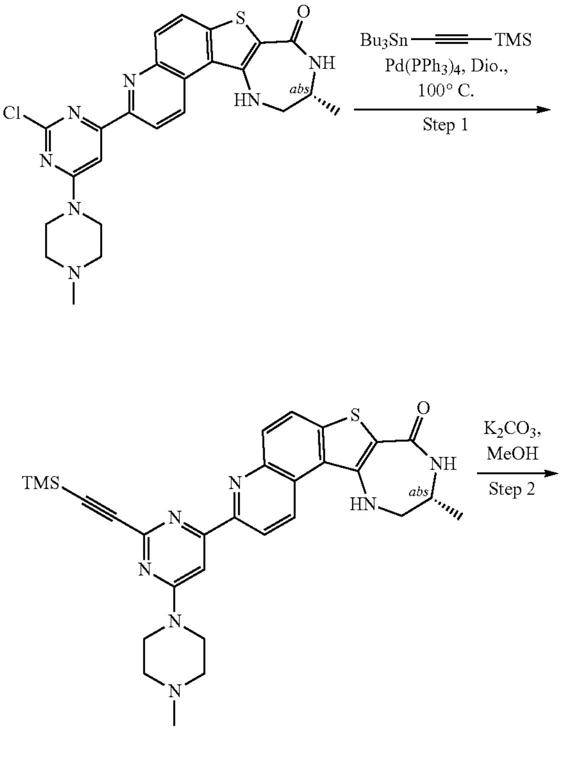

-continued

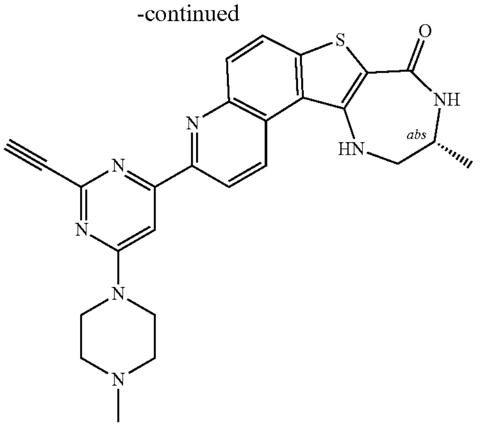

Step 1: Synthesis of (15R)-15-methyl-5-[6-(4-methylpiperazin-1-yl)-2-(2-trimethylsilylethynyl)pyrimidin-4-yl]-11-thia-6,14,17-triazatetracyclo[8.8.0.0^,7.0^12,18]octadeca-1(10),2(7),3,5,8,12(18)-hexaen-13-one

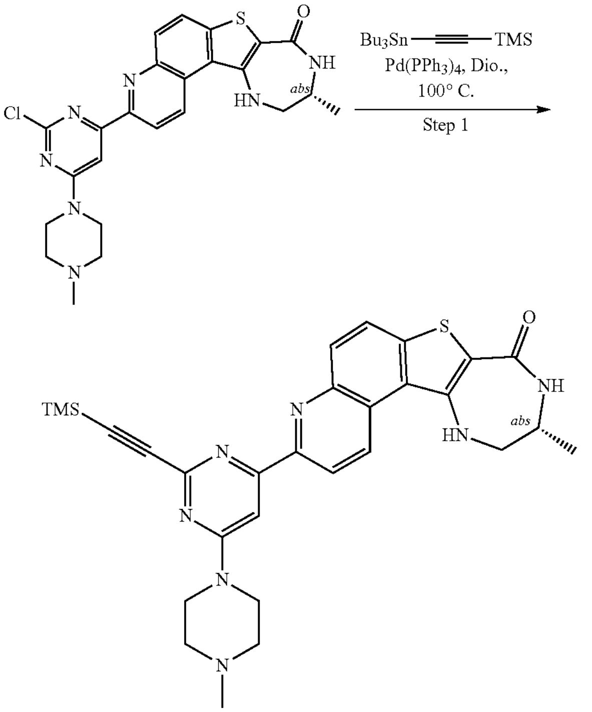

To a solution of (15R)-5-[2-chloro-6-(4-methylpiperazin-1-yl)pyrimidin-4-yl]-15-methyl-11-thia-6,14,17-triazatetracyclo[8.8.0.0^,7.0^12,18]octadeca-1(10),2(7),3,5,8,12(18)-hexaen-13-one (100 mg, 0.200 mmol, 1.00 equiv) and trimethyl(2-tributylstannylethynyl)silane (156 mg, 0.400 mmol, 2.00 equiv) in 1,4-dioxane (2.0 mL) was added $Pd(PPh_3)_4$(46 mg, 0.040 mmol, 0.10 equiv). The resulting mixture was stirred at 100° C. for 6 h under a nitrogen atmosphere. LCMS showed the reaction was completed. The resulting solution was diluted with water (50 mL), extracted with ethyl acetate (3×50 mL). The combined organic layers were dried over anhydrous sodium sulfate, filtered and concentrated under reduce pressure. The residue was purified by column chromatography on silica gel with ethyl acetate/petroleum ether (2:1) to give (15R)-15-methyl-5-[6-(4-methylpiperazin-1-yl)-2-(2-trimethylsilylethynyl)pyrimidin-4-yl]-11-thia-6,14,17-triazatetracyclo[8.8.0.0^,7.0^12,18]octadeca-1(10),2(7),3,5,8,12(18)-hexaen-13-one (40 mg, 35%) as a white solid. LCMS (ESI, m/z): 556 $(M+H)^+$.

Step 2: Synthesis of (15R)-5-[2-ethynyl-6-(4-methylpiperazin-1-yl)pyrimidin-4-yl]-15-methyl-11-thia-6,14,17-triazatetracyclo[8.8.0.0^,7.0^12,18]octadeca-1(10),2(7),3,5,8,12(18)-hexaen-13-one

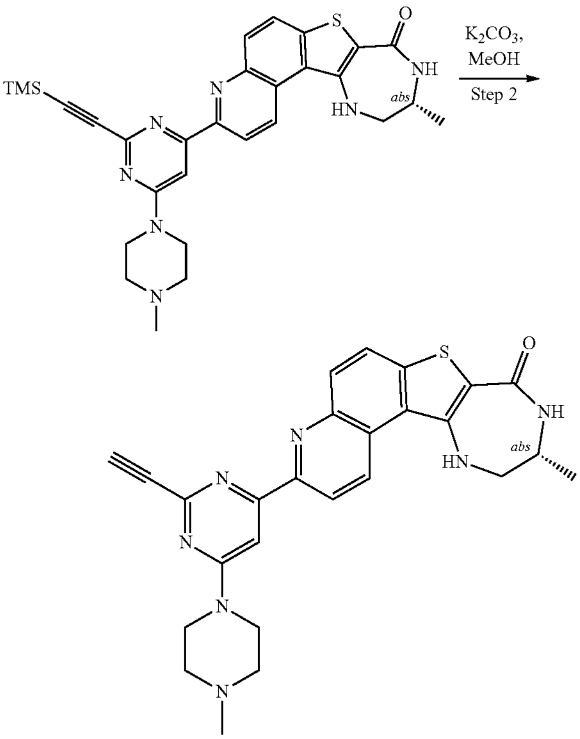

To a solution of (15R)-15-methyl-5-[6-(4-methylpiperazin-1-yl)-2-(2-trimethylsilylethynyl)pyrimidin-4-yl]-11-thia-6,14,17-triazatetracyclo[8.8.0.0^,7.0^12,18]octadeca-1(10),2(7),3,5,8,12(18)-hexaen-13-one (40 mg, 0.070 mmol, 1.00 equiv) in methanol (2.0 mL) was added $K_2CO_3$ (20 mg, 0.140 mmol, 2.00 equiv). The resulting mixture was stirred at room temperature for 1 h. LCMS showed the reaction was completed. The resulting solution was diluted with DMSO (2.0 mL). The solid was filtered out. The filtration was purified by Prep-HPLC using the following gradient conditions: Column: SunFire Prep C18 OBD Column, 19×150 mm, 5 μm; Mobile Phase A: Water (0.05% TFA), Mobile Phase B: MeCN; Flow rate: 20 mL/min; Gradient: 10% B to 40% B in 5 min, 40% B; Wave Length: 254/210 nm; RT1(min): 4.35. Purification resulted in desired (15R)-5-[2-ethynyl-6-(4-methylpiperazin-1-yl)pyrimidin-4-yl]-15-methyl-11-thia-6,14,17-triazatetracyclo[8.8.0.0^,7.0^12,18]octadeca-1(10),2(7),3,5,8,12(18)-hexaen-13-one (4.9 mg, 13%) as a red solid. LCMS (ESI, m/z): 484 $(M+H)^+$. Analytic Conditions: Column: HALO C18 100A Column 3.0*50 mm, 3.0 um; Mobile Phase A: Water/0.05% TFA, Mobile Phase B: Acetonitrile/0.05% TFA; Flow rate: 1.2000 mL/min; Gradient: 10% B to 55% B in 1.90 min; 254 nm; Rt: 1.852 min.

$^{1}H$ NMR (300 MHz, DMSO-$d_6$) δ 9.32 (d, J=8.8 Hz, 1H), 8.59 (d, J=8.8 Hz, 1H), 8.26-8.13 (m, 2H), 7.25 (s, 1H), 4.79 (s, 1H), 4.54 (s, 1H), 4.34-4.02 (m, 1H), 3.73-3.30 (m, 7H), 3.28-3.01 (m, 2H), 2.86 (s, 3H), 1.20 (d, J=6.6 Hz, 3H). $^{19}F$ NMR (282 MHz, DMSO-$d_6$) δ-74.09.

Example 5: Synthesis of (15R)-5-[4-ethynyl-6-(4-methylpiperazin-1-yl)pyrimidin-2-yl]-15-methyl-11-thia-6,14,17-triazatetracyclo[8.8.0.0^,7.0^12,18]octa-deca-1(10),2(7),3,5,8,12(18)-hexaen-13-one

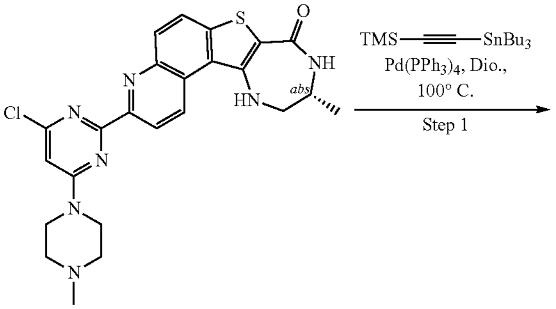

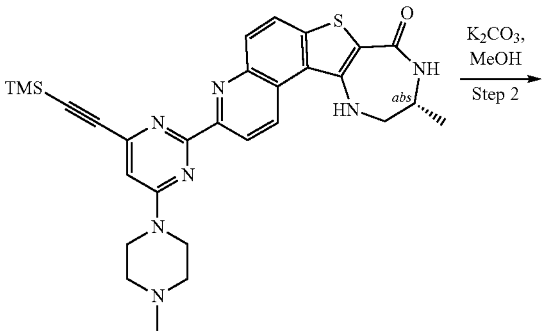

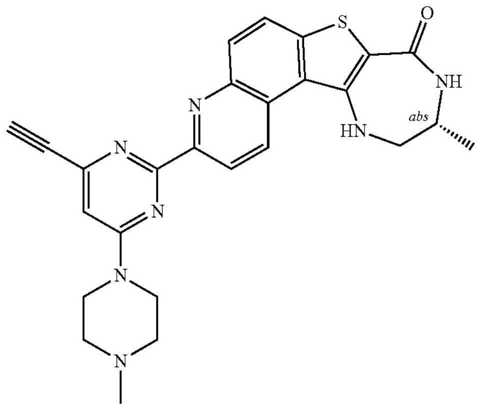

Step 1: Synthesis of (15R)-15-methyl-5-[4-(4-methylpiperazin-1-yl)-6-(2-trimethylsilylethynyl)pyrimidin-2-yl]-11-thia-6,14,17-triazatetracyclo[8.8.0.0^, 7.0^12,18]octadeca-1(10),2(7),3,5,8,12(18)-hexaen-13-one

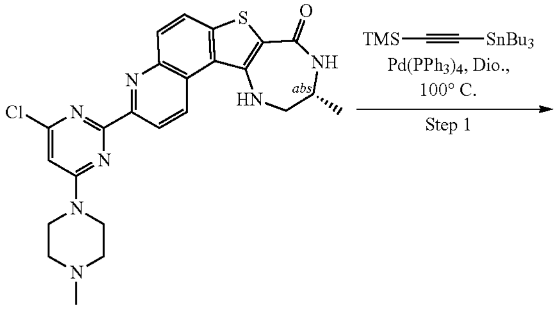

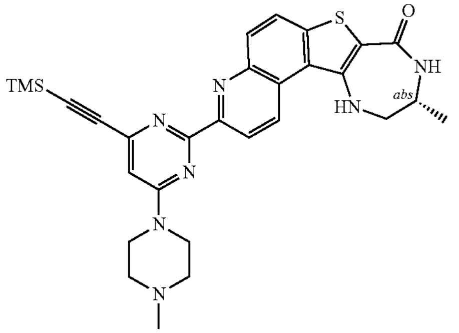

To a solution of (15R)-5-[4-chloro-6-(4-methylpiperazin-1-yl)pyrimidin-2-yl]-15-methyl-11-thia-6,14,17-triazatetracyclo[8.8.0.0^2,7.0^12,18]octadeca-1(10),2(7),3,5,8,12(18)-hexaen-13-one (100 mg, 0.200 mmol, 1.00 equiv) and trimethyl(2-tributylstannylethynyl)silane (156 mg, 0.400 mmol, 2.00 equiv) in 1,4-dioxane (2.0 mL) was added $Pd(PPh_3)_4$(23 mg, 0.020 mmol, 0.10 equiv). The resulting mixture was stirred at 100° C. for 5 h under a nitrogen atmosphere. LCMS showed the material was completed. The resulting solution was concentrated under reduce pressure and the residue was purified by column chromatography on silica gel with ethyl acetate to afford (15R)-15-methyl-5-[4-(4-methylpiperazin-1-yl)-6-(2-trimethylsilylethynyl)pyrimidin-2-yl]-11-thia-6,14,17-triazatetracyclo[8.8.0.0^2,7.0^12,18]octadeca-1(10),2(7),3,5,8,12(18)-hexaen-13-one (40 mg, 35%) as a brown solid. LCMS (ESI, m/z): 556 $(M+H)^{+}$.

Step 2: Synthesis of (15R)-5-[4-ethynyl-6-(4-methylpiperazin-1-yl)pyrimidin-2-yl]-15-methyl-11-thia-6,14,17-triazatetracyclo[8.8.0.0^,7.0^12,18]octadeca-1(10),2(7),3,5,8,12(18)-hexaen-13-one

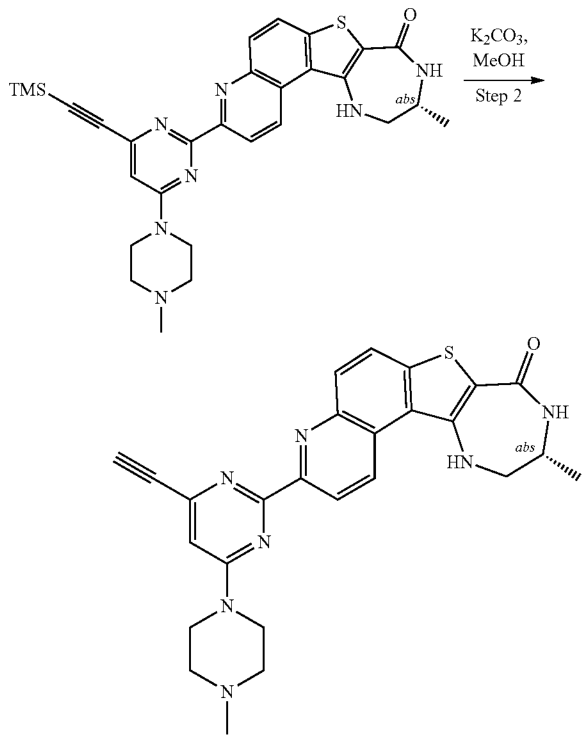

To a solution of (15R)-15-methyl-5-[4-(4-methylpiperazin-1-yl)-6-(2-trimethylsilylethynyl)pyrimidin-2-yl]-11-thia-6,14,17-triazatetracyclo[8.8.0.0^,7.0^12,18]octadeca-1(10),2(7),3,5,8,12(18)-hexaen-13-one (40 mg, 0.070 mmol, 1.00 equiv) in methanol (2.0 mL) was added $K_2CO_3$ (19 mg, 0.140 mmol, 2.00 equiv). The resulting mixture was stirred at room temperature for 2 h. LCMS showed the reaction was completed. The resulting solution was diluted with DMSO (3 mL). The solid was filtered out. The filtration was purified by Prep-HPLC using the following gradient conditions: Column: SunFire Prep C18 OBD Column, 19*150 mm, 5 μm; Mobile Phase A: Water (0.05% TFA), Mobile Phase B: MeCN; Flow rate: 20 mL/min; Gradient: 10% B to 40% B in 5 min, 40% B; Wave Length: 210/245 nm; RT1(min): 4.8. Purification resulted in desired (15R)-5-[4-ethynyl-6-(4-methylpiperazin-1-yl)pyrimidin-2-yl]-15-methyl-11-thia-6,14,17-triazatetracyclo[8.8.0.0^,7.0^12,18]octadeca-1(10),2(7),3,5,8,12(18)-hexaen-13-one (8.3 mg, 22%) as a brown solid. LCMS (ESI, m/z): 484 $(M+H)^+$. Analytic Conditions: Column: HALO C18 100A Column 3.0*30 mm, 2.7 um; Mobile Phase A: Water/0.05% TFA, Mobile Phase B: Acetonitrile/0.05% TFA; Flow rate: 1.5000 mL/min; Gradient: 5% B to 100% B in 1.30 min; 254 nm; Rt: 0.755 min.

$^1H$ NMR (400 MHz, DMSO-$d_6$) δ 9.85 (s, 1H), 9.34 (d, J=8.8 Hz, 1H), 8.51 (d, J=8.8 Hz, 1H), 8.23 (d, J=9.2 Hz, 1H), 8.14 (d, J=4.4 Hz, 1H), 8.08 (d, J=8.8 Hz, 1H), 8.00 (s, 1H), 7.19 (s, 1H), 4.71 (d, J=13.2 Hz, 2H), 4.33 (s, 1H), 3.69-3.59 (m, 3H), 3.55-3.49 (m, 2H), 3.42-3.31 (m, 2H), 3.20-3.15 (m, 2H), 2.88 (s, 3H), 1.22 (d, J=6.8 Hz, 3H). $^{19}F$ NMR (376 MHz, DMSO-$d_6$) δ-74.21.

Example 6: Synthesis of (15R)-15-methyl-5-[4-(4-methylpiperazin-1-yl)-6-vinyl-pyrimidin-2-yl]-11-thia-6,14,17-triazatetracyclo[8.8.0.0^,7.0^12,18]octadeca-1(10),2(7),3,5,8,12(18)-hexaen-13-one

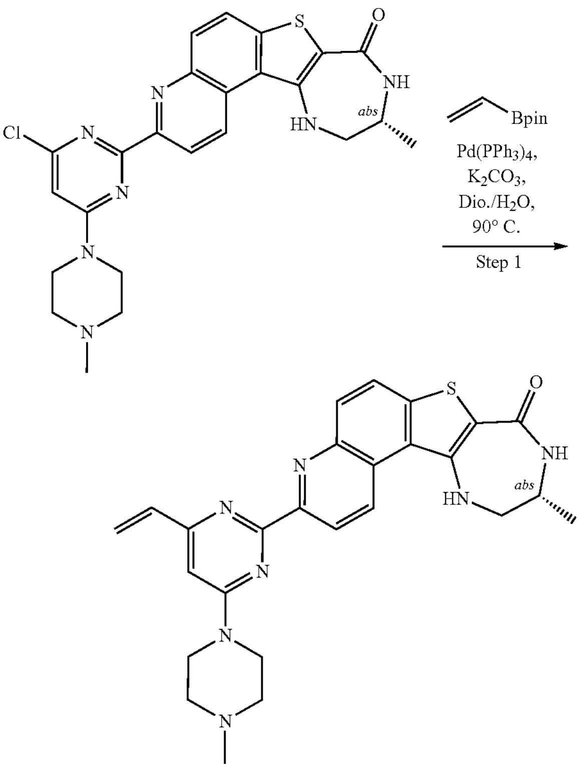

To a stirred a solution of (15R)-5-[4-chloro-6-(4-methylpiperazin-1-yl)pyrimidin-2-yl]-15-methyl-11-thia-6,14,17-triazatetracyclo[8.8.0.0^,7.0^12,18]octadeca-1(10),2(7),3,5,8,12(18)-hexaen-13-one (100 mg, 0.200 mmol, 1.00 equiv), 4,4,5,5-tetramethyl-2-vinyl-1,3,2-dioxaborolane (62 mg, 0.40 mmol, 2.00 equiv) and $K_2CO_3$ (83 mg, 0.600 mmol, 3.0 erquiv) in 1,4-dioxane (2.0 mL) and water (0.2 mL) was added $Pd(PPh_3)_4$(46 mg, 0.040 mmol, 0.20 equiv). The resulting mixture was stirred at 90° C. for 2 h under a nitrogen atmosphere. LCMS showed the reaction was completed. The resulting solution was diluted with water (20 mL). The solid was collected by filtration. The solid was purified by reverse flash chromatography with water (0.05% TFA)/MeCN (1:1) to afford 50 mg crude product. The crude product was purified by Prep-HPLC using the following gradient conditions: Column: SunFire Prep C18 OBD Column, 19*150 mm, 5 m 10 nm; Mobile Phase A: Water (0.05% TFA), Mobile Phase B: MeCN; Flow rate: 20 mL/min; Gradient: 10% B to 40% B in 5 min, 40% B; Wave Length: 210/245 nm; RT1(min): 4.8. Purification resulted in desired (15R)-15-methyl-5-[4-(4-methylpiperazin-1-yl)-6-vinyl-pyrimidin-2-yl]-11-thia-6,14,17-triazatetracyclo[8.8.0.0^,7.0^12,18]octadeca-1(10),2(7),3,5,8,12(18)-hexaen-13-one (26.5 mg, 25%) as an orange solid. LCMS (ESI, m/z): 486 $(M+H)^+$. Analytic Conditions: Column: Shim-pack ScepterC18 100A Column 3.0*33 mm, 3.0 um; Mobile Phase A: Water/5mMNH$_4$HCO$_3$, Mobile Phase B: Acetonitrile; Flow rate: 1.5000 mL/min; Gradient: 10% B to 95% B in 1.20 min; 254 nm; Rt: 1.046 min.

$^1$H NMR (400 MHz, DMSO-$d_6$) δ 10.03 (s, 1H), 9.35 (d, J=8.8 Hz, 1H), 8.63 (d, J=8.8 Hz, 1H), 8.23 (d, J=8.8 Hz, 1H), 8.14 (d, J=4.4 Hz, 1H), 8.09 (d, J=9.2 Hz, 1H), 7.90 (s, 1H), 7.19 (s, 1H), 6.85 (dd, J=17.2, 10.4 Hz, 1H), 6.68 (d, J=17.2 Hz, 1H), 5.81 (t, J=12.0 Hz, 1H), 4.79 (d, J=11.2 Hz, 2H), 3.67-3.57 (m, 3H), 3.55-3.49 (m, 2H), 3.42-3.30 (m, 2H), 3.18-3.10 (m, 2H), 2.90 (s, 3H), 1.22 (d, J=6.4 Hz, 3H). $^{19}$F NMR (376 MHz, DMSO-$d_6$) δ-74.53.

Example 7: Synthesis of (15R)-5-[6-(3-amino-3-methyl-but-1-ynyl)-2-chloro-pyrimidin-4-yl]-15-methyl-11-thia-6,14,17-triazatetracyclo[8.8.0.0^,7.0^12,18]octadeca-1(10),2(7),3,5,8,12(18)-hexaen-13-one

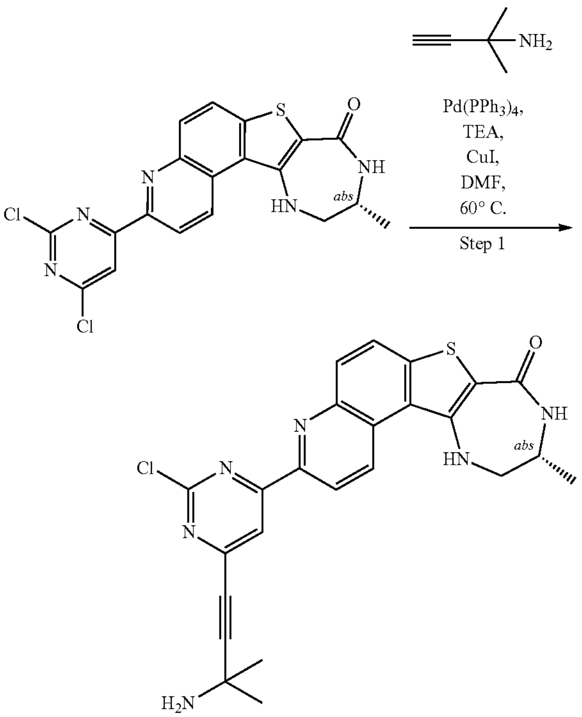

To a solution of (15R)-5-(2,6-dichloropyrimidin-4-yl)-15-methyl-11-thia-6,14,17-triazatetracyclo[8.8.0.0^,7.0^12,18]octadeca-1(10),2(7),3,5,8,12(18)-hexaen-13-one (60 mg, 0.140 mmol, 1.00 equiv), 2-methylbut-3-yn-2-amine (11 mg, 0.140 mmol, 1.00 equiv) and TEA (0.12 mL, 0.700 mmol, 5.00 equiv) in DMF (1.0 mL) was added CuI (11 mg, 0.056 mmol, 0.04 equiv) and $Pd(PPh_3)_4$(16 mg, 0.04 mmol, 0.10 equiv). The resulting mixture was stirred at 60° C. overnight under a nitrogen atmosphere. LCMS showed the reaction was completed. The resulting solution was diluted with DMSO (2.0 mL). The solid was filtered out. The filtration was purified by Prep-HPLC using the following gradient conditions: Column: SunFire Prep C18 OBD Column, 19×150 mm, 5 μm; Mobile Phase A: Water (0.05% TFA), Mobile Phase B: MeCN; Flow rate: 20 mL/min; Gradient: 25% B to 50% B in 4.5 min, 50% B; Wave Length: 254/210 nm; RT1(min): 4.3. Purification resulted in desired (15R)-5-[6-(3-amino-3-methyl-but-1-ynyl)-2-chloro-pyrimidin-4-yl]-15-methyl-11-thia-6,14,17-triazatetracyclo[8.8.0.0^,7.0^12,18]octadeca-1(10),2(7),3,5,8,12(18)-hexaen-13-one (9.0 mg, 12%) as a brown solid. LCMS (ESI, m/z): 477 $(M+H)^+$. Analytic Conditions: Column: Xselect HSS T3 Column 4.6*100 mm, 3.5 um; Mobile Phase A: Water/0.1% $H_3PO_4$, Mobile Phase B: Acetonitrile; Flow rate: 1.2000 mL/min; Gradient: 10% B to 95% B in 6.0 min; 254 nm; Rt: 3.071 min.

$^1$H NMR (300 MHz, DMSO-$d_6$) δ 9.40 (d, J=9.3 Hz, 1H), 8.78 (s, 3H), 8.61 (s, 1H), 8.55 (d, J=9.0 Hz, 1H), 8.28 (d, J=9.0 Hz, 1H), 8.18 (d, J=3.9 Hz, 1H), 8.08 (d, J=8.7 Hz, 1H), 7.23 (s, 1H), 3.70-3.60 (m, 1H), 3.55-3.45 (m, 1H), 1.73 (s, 6H), 1.22 (d, J=6.6 Hz, 3H). $^{19}$F NMR (282 MHz, DMSO-$d_6$) δ-73.89.

Example 8: Synthesis of (R)-3-(2-(3-amino-3-methylbut-1-yn-1-yl)-6-chloropyrimidin-4-yl)-10-methyl-9,10,11,12-tetrahydro-8H-[1,4]diazepino[5',6':4,5]thieno[3,2-f]quinolin-8-one

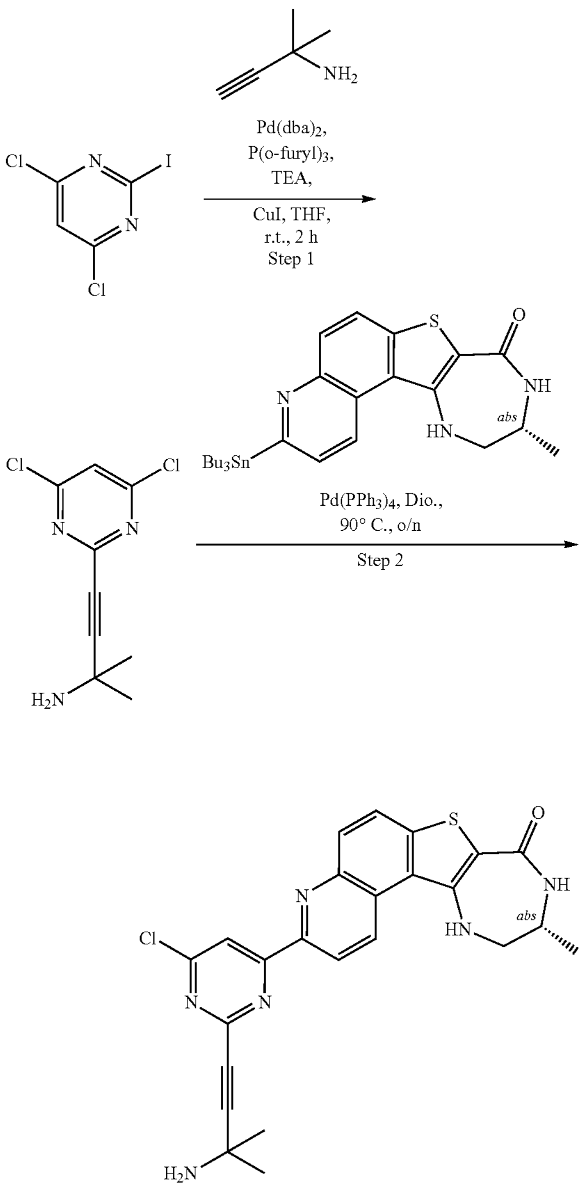

Step 1: Synthesis of 4-(4,6-dichloropyrimidin-2-yl)-2-methyl-but-3-yn-2-amine

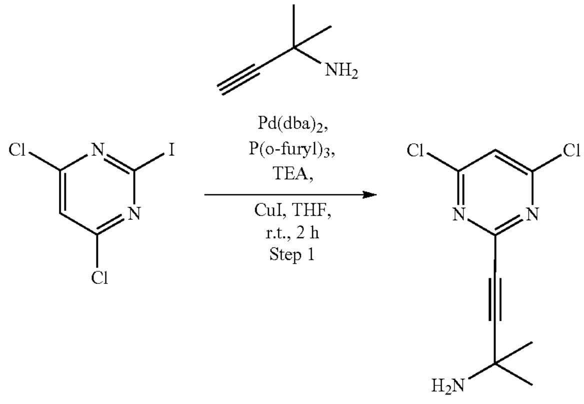

To a solution of 4,6-dichloro-2-iodo-pyrimidine (1.0 g, 3.640 mmol, 1.00 equiv), 2-methylbut-3-yn-2-amine (604 mg, 7.280 mmol, 2.00 equiv) and TEA (940 mg, 7.280 mmol, 2.00 equiv) in THF (30.0 mL) was added CuI (69 mg, 0.360 mmol, 0.10 equiv), $Pd(dba)_2$ (209 mg, 0.360 mmol, 0.10 equiv) and $P(o\text{-furyl})_3$ (84 mg, 0.360 mmol, 0.10 equiv). The resulting solution was stirred at room temperature for 2 h under nitrogen atmosphere. LCMS showed the reaction was completed. The resulting solution was diluted with water (50 mL) and extracted with ethyl acetate (3×50 mL). The combined organic layers were washed with brine (2×100 mL), dried over anhydrous sodium sulfate, filtered and concentrated under reduced pressure. The crude product was purified by column chromatography on silica gel with ethyl acetate/petroleum ether (1:1) to afford 4-(4,6-dichloropyrimidin-2-yl)-2-methyl-but-3-yn-2-amine (400 mg, 47%) as a yellow solid. LCMS (ESI, m z): 229 $[M+H]^+$.

Step 2: Synthesis of (R)-3-(2-(3-amino-3-methyl-but-1-yn-1-yl)-6-chloropyrimidin-4-yl)-10-methyl-9,10,11,12-tetrahydro-8H-[1,4]diazepino[5',6':4,5]thieno[3,2-f]quinolin-8-one

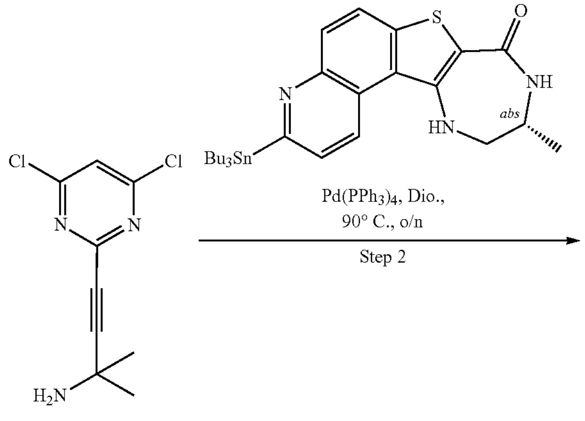

-continued

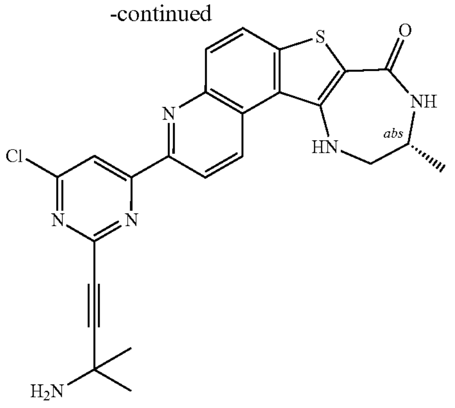

To a solution of (R)-10-methyl-3-(tributylstannyl)-9,10,11,12-tetrahydro-8H-[1,4]diazepino[5',6':4,5]thieno[3,2-f]quinolin-8-one (80 mg, 0.140 mmol, 1.00 equiv) and 4-(4,6-dichloro-2-pyridyl)-2-methyl-but-3-yn-2-amine (38 mg, 0.170 mmol, 1.20 equiv) in 1,4-dioxane (5.0 mL) was added $Pd(PPh_3)_4$(11 mg, 0.010 mmol, 0.10 equiv). The resulting solution was stirred at 90° C. under nitrogen atmosphere. LCMS showed the reaction was completed. The resulting solution was concentrated under reduced pressure. The residue product was purified by Prep-HPLC using the following gradient conditions: Column: SunFire Prep C18 OBD Column, 19*150 mm, 5 μm; Mobile Phase A: Water (0.05% TFA), Mobile Phase B: MeCN; Flow rate: 20 mL/min; Gradient: 20% B to 50% B in 4.5 min, 50% B; Wave Length: 254/210 nm; RT1(min): 4.35. Purification resulted in desired (R)-3-(2-(3-amino-3-methylbut-1-yn-1-yl)-6-chloropyrimidin-4-yl)-10-methyl-9,10,11,12-tetrahydro-8H-[1,4]diazepino[5',6':4,5]thieno[3,2-f]quinolin-8-one (16.9 mg, 24%) as a yellow solid. Analytic Conditions: Column: HALO C18 100 A Column 3.0*30 mm, 2.0 um; Mobile Phase A: Water/0.05% TFA, Mobile Phase B: Acetonitrile/0.05% TFA; Flow rate: 1.2000 mL/min; Gradient: 5% B to 100% B in 2.40 min; 254 nm; Rt: 1.613 min. $^1H$ NMR (400 MHz, DMSO-$d_6$+$D_2O$) δ 9.36 (d, J=8.8 Hz, 1H), 8.62 (d, J=2.8 Hz, 1H), 8.49 (d, J=8.8 Hz, 1H), 8.24 (d, J=8.8 Hz, 1H), 8.10 (d, J=8.8 Hz, 1H), 3.70-3.60 (m, 1H), 3.55-3.45 (m, 2H), 1.73 (s, 6H), 1.21 (d, J=6.8 Hz, 3H). $^{19}F$ NMR (376 MHz, DMSO-$d_6$) δ 73.70.

Example 9: Synthesis of (15R)-5-[6-(3-amino-3-methyl-but-1-ynyl)-2-ethynyl-pyrimidin-4-yl]-15-methyl-11-thia-6,14,17-triazatetracyclo[8.8.0.0^,7.0^12,18]octadeca-1(10),2(7),3,5,8,12(18)-hexaen-13-one

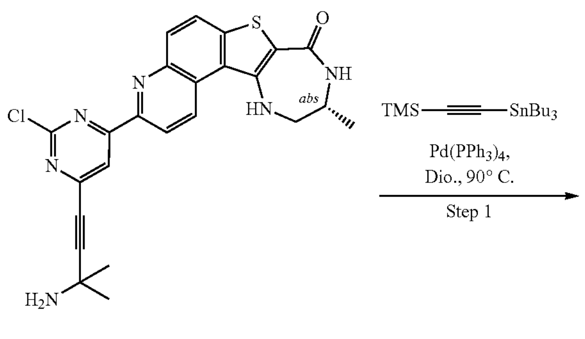

-continued

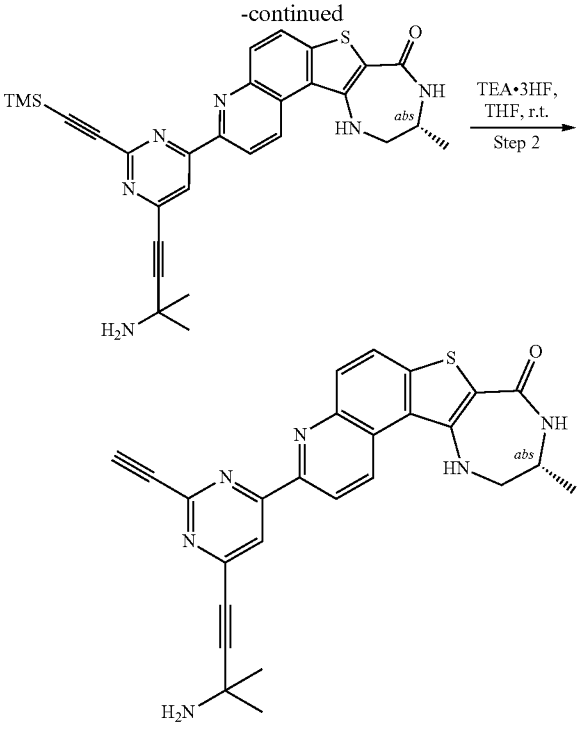

Step 1: Synthesis of (15R)-5-[6-(3-amino-3-methyl-but-1-ynyl)-2-chloro-pyrimidin-4-yl]-15-methyl-11-thia-6,14,17-triazatetracyclo[8.8.0.0^,7.0^12,18]octadeca-1(10),2(7),3,5,8,12(18)-hexaen-13-one

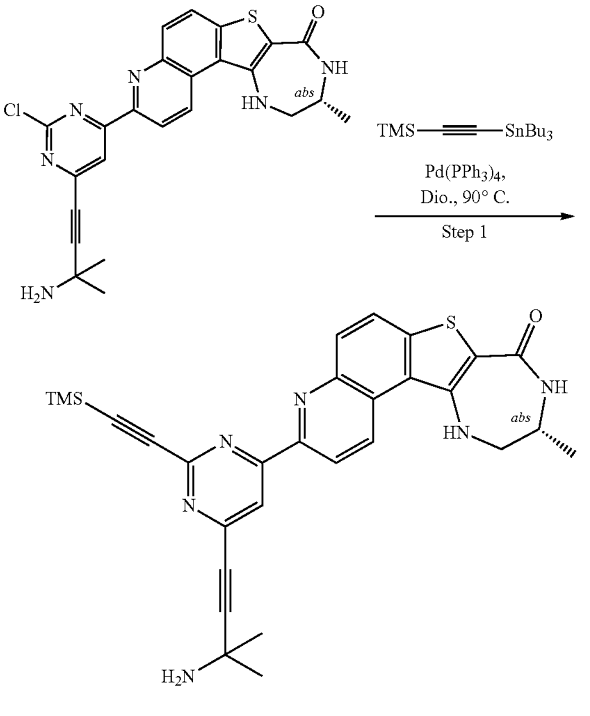

To a solution of (15R)-5-[6-(3-amino-3-methyl-but-1-ynyl)-2-chloro-pyrimidin-4-yl]-15-methyl-11-thia-6,14,17-triazatetracyclo[8.8.0.0^,7.0^12,18]octadeca-1(10),2(7),3,5,8,12(18)-hexaen-13-one (170 mg, 0.356 mmol, 1.00 equiv) and trimethyl((tributylstannyl)ethynyl)silane (275 mg, 0.713 mmol, 2.00 equiv) in 1,4-dioxane (3.0 mL) was added $Pd(PPh_3)_4$(41 mg, 0.036 mmol, 0.10 equiv). The resulting mixture was stirred at 60° C. overnight under a nitrogen atmosphere. LCMS showed the reaction was completed. The resulting solution was diluted with ethyl acetate (20 mL). The solid was filtered out. The filtration was concentrated under reduce pressure. The residue was purified by reverse flash chromatography with water (0.05% TFA)/MeCN (1:1) to give (15R)-5-[6-(3-amino-3-methyl-but-1-ynyl)-2-chloro-pyrimidin-4-yl]-15-methyl-11-thia-6,14,17-triazatetracyclo[8.8.0.0^,7.0^12,18]octadeca-1(10),2(7),3,5,8,12(18)-hexaen-13-one (45 mg, 23%) as a yellow solid. LCMS (ESI, m/z): 539 $(M+H)^+$.

Step 2: Synthesis of (15R)-5-[6-(3-amino-3-methyl-but-1-ynyl)-2-ethynyl-pyrimidin-4-yl]-15-methyl-11-thia-6,14,17-triazatetracyclo[8.8.0.0^,7.0^12,18]octadeca-1(10),2(7),3,5,8,12(18)-hexaen-13-one

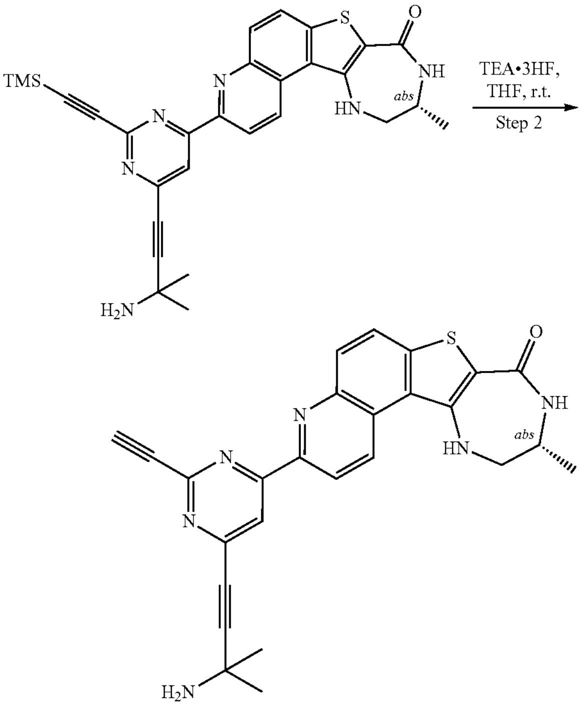

To a solution of (15R)-5-[6-(3-amino-3-methyl-but-1-ynyl)-2-(2-trimethylsilylethynyl)pyrimidin-4-yl]-15-methyl-11-thia-6,14,17-triazatetracyclo[8.8.0.0^,7.0^12,18]octadeca-1(10),2(7),3,5,8,12(18)-hexaen-13-one (35 mg, 0.065 mmol, 1.00 equiv) in THF (2.0 mL) was added dropwise TEA.3HF (0.1 mL). The resulting mixture was stirred at room temperature for 2 h. LCMS showed the reaction was completed. The resulting solution was concentrated under reduce pressure. The residue was purified by Prep-HPLC using the following gradient conditions: Column: SunFire Prep C18 OBD Column, 19×150 mm, 5 μm; Mobile Phase A: Water (0.05% TFA), Mobile Phase B: MeCN; Flow rate: 20 mL/min; Gradient: 22% B to 35% B in 5 min, 35% B; Wave Length: 254 nm; RT1(min): 4.95. Purification resulted in desired (15R)-5-[6-(3-amino-3-methyl-but-1-ynyl)-2-ethynyl-pyrimidin-4-yl]-15-methyl- 11l-thia-6,14,17-triazatetracyclo[8.8.0.0^2,7.0^12,18]octadeca-1(10),2(7),3,5,8,12(18)-hexaen-13-one (3.4 mg, 11%) as a yellow solid. LCMS (ESI, m/z): 467 $(M+H)^+$. Analytic Conditions: Column: HALO C18 100A Column 3.0*30 mm, 2.7 um; Mobile Phase A: Water/0.05% TFA, Mobile Phase B: Acetonitrile/0.05% TFA; Flow rate: 1.2000 mL/min; Gradient: 5% B to 60% B in 1.80 min; 254 nm; Rt: 1.312 min.

$^1H$ NMR (300 MHz, DMSO-$d_6$) δ 9.39 (d, J=9.0 Hz, 1H), 8.79 (s, 3H), 8.59 (s, 1H), 8.58 (d, J=9.0 Hz, 1H), 8.26 (8.55 (d, J=9.0 Hz, 1H), 8.15 (d, J=3.9 Hz, 1H), 8.08 (d, J=9.0 Hz, 1H), 7.23 (s, 1H), 4.64 (s, 1H), 3.70-3.40 (m, 3H), 1.73 (s, 6H), 1.21 (d, J=6.6 Hz, 3H). $^{19}F$ NMR (282 MHz, DMSO-$d_6$) δ-73.69.

Example 10: Synthesis of (R)-3-(2-(3-amino-3-methylbut-1-yn-1-yl)-6-vinylpyrimidin-4-yl)-10-methyl-9,10,11,12-tetrahydro-8H-[1,4]diazepino[5',6':4,5]thieno[3,2-f]quinolin-8-one

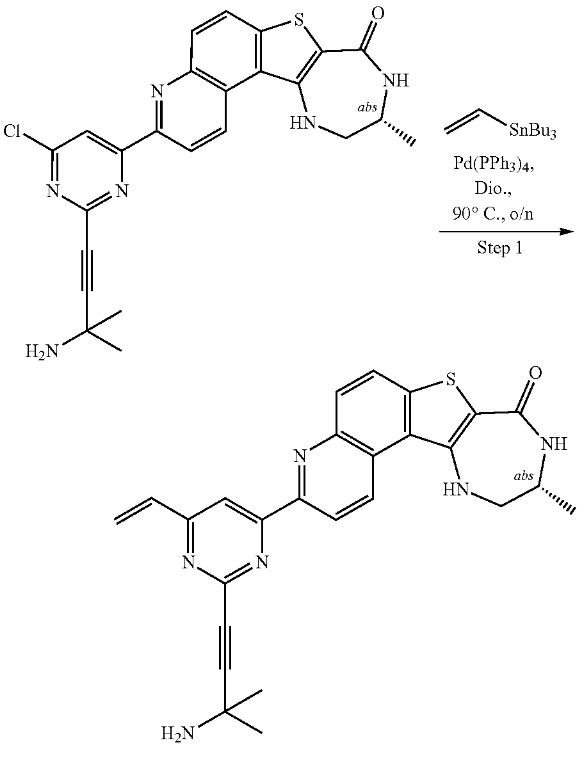

To a solution of (R)-3-(2-(3-amino-3-methylbut-1-yn-1-yl)-6-chloropyrimidin-4-yl)-10-methyl-9,10,11,12-tetrahydro-8H-[1,4]diazepino[5',6':4,5]thieno[3,2-f]quinolin-8-one (50 mg, 0.100 mmol, 1.00 equiv) and tributyl(vinyl) stannane (99 mg, 0.310 mmol, 3.00 equiv) in 1,4-dioxane (2.0 mL) was added $Pd(PPh_3)_4$(8 mg, 0.010 mmol, 0.10 equiv). The resulting solution was stirred at 90° C. under nitrogen atmosphere overnight. LCMS showed the reaction was completed. The resulting solution was concentrated under reduced pressure. The residue was purified by Prep-HPLC using the following gradient conditions: Column: SunFire Prep C18 OBD Column, 19*150 mm, 5 μm; Mobile Phase A: Water (0.05% TFA), Mobile Phase B: MeCN; Flow rate: 20 mL/min; Gradient: 20% B to 50% B in 4.5 min, 50% B; Wave Length: 254/210 nm; RT1(min): 4.350. Purification resulted in desired (R)-3-(2-(3-amino-3-methylbut-1-yn-1-yl)-6-vinylpyrimidin-4-yl)-10-methyl-9,10,11,12-tetrahydro-8H-[1,4]diazepino[5',6':4,5]thieno[3,2-f]quinolin-8-one (3.8 mg, 7%) as a red solid. LCMS (ESI, m/z): 469 $[M+H]^+$. Analytic Conditions: Column: HALO C18 100 A Column 3.0*30 mm, 2.0 um; Mobile Phase A: Water/0.05% TFA, Mobile Phase B: Acetonitrile/0.05% TFA; Flow rate: 1.2000 mL/min; Gradient: 5% B to 100% B in 2.40 min; 254 nm; Rt: 1.546 min.

$^1H$ NMR (400 MHz, DMSO-$d_6$+$D_2O$) δ 9.36 (d, J=8.8 Hz, 1H), 8.61 (s, 1H), 8.53 (d, J=8.8 Hz, 1H), 8.24 (d, J=9.2 Hz, 1H), 8.12 (d, J=9.2 Hz, 1H), 7.02 (dd, J=17.2, 10.4 Hz, 1H), 6.64 (d, J=17.2 Hz, 1H), 5.89 (d, J=11.6 Hz, 1H), 3.62-3.59 (m, 1H), 3.49 (s, 2H), 1.73 (s, 6H), 1.21 (d, J=6.8 Hz, 3H). $^{19}F$ NMR (376 MHz, DMSO-$d_6$) δ 74.57.

Example 11: Synthesis of (R)-3-(2-(3-amino-3-methylbut-1-yn-1-yl)-6-ethynylpyrimidin-4-yl)-10-methyl-9,10,11,12-tetrahydro-8H-[1,4]diazepino[5',6':4,5]thieno[3,2-f]quinolin-8-one

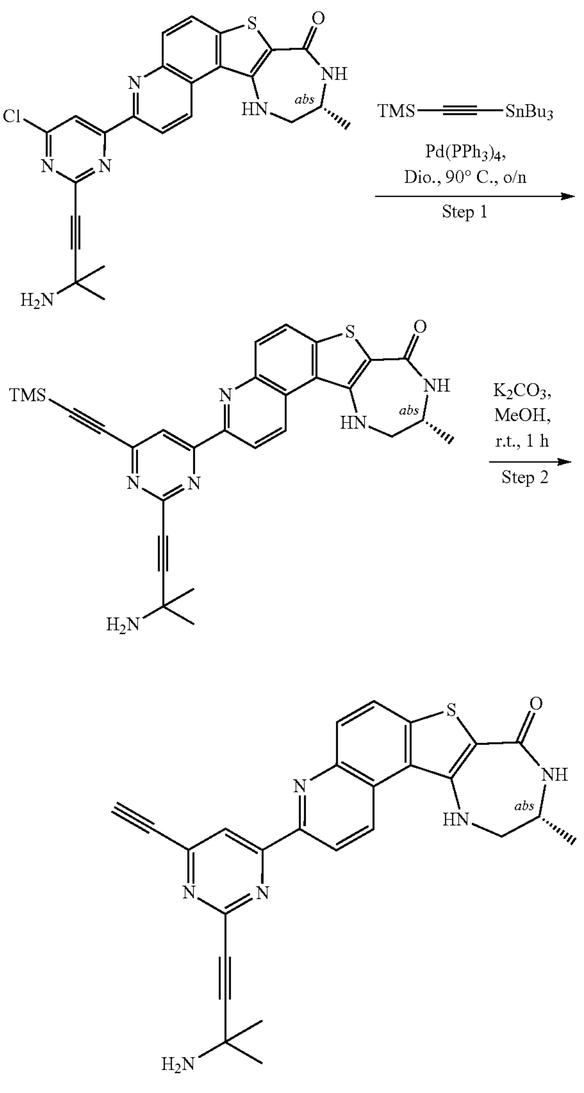

Step 1: Synthesis of (R)-3-(2-(3-amino-3-methylbut-1-yn-1-yl)-6-((trimethylsilyl)ethynyl)pyrimidin-4-yl)-10-methyl-9,10,11,12-tetrahydro-8H-[1,4]diazepino[5',6':4,5]thieno[3,2-f]quinolin-8-one

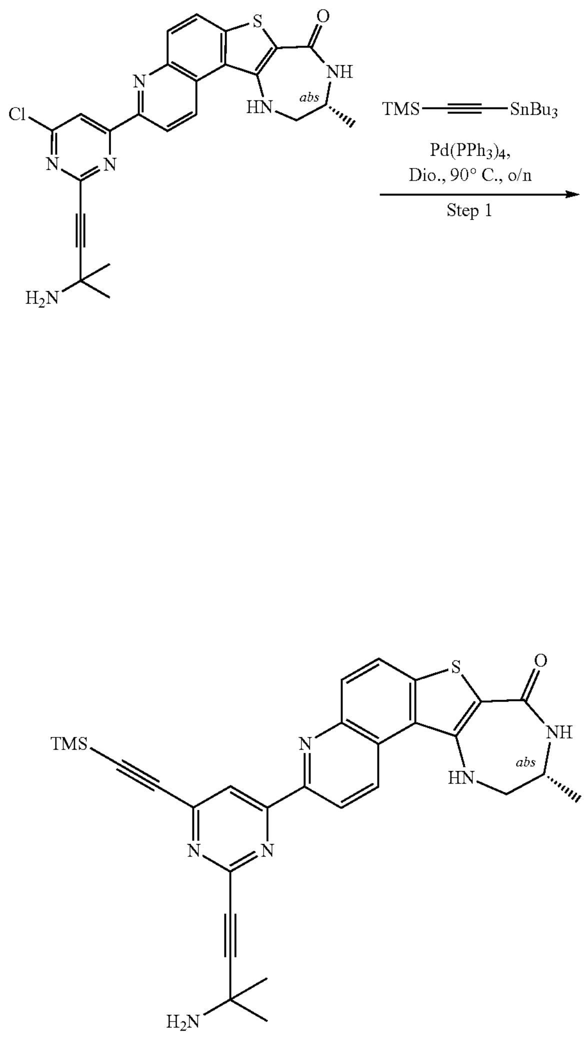

To a solution of (R)-3-(2-(3-amino-3-methylbut-1-yn-1-yl)-6-chloropyrimidin-4-yl)-10-methyl-9,10,11,12-tetrahydro-8H-[1,4]diazepino[5',6':4,5]thieno[3,2-f]quinolin-8-one (100 mg, 0.210 mmol, 1.00 equiv) and trimethyl(2-tributylstannylethynyl)silane (243 mg, 0.630 mmol, 3.00 equiv) in 1,4-dioxane (5.0 mL) was added $Pd(PPh_3)_4$(17 mg, 0.020 mmol, 0.10 equiv). The resulting solution was stirred at 90° C. under nitrogen atmosphere overnight. LCMS showed the reaction was completed. The resulting solution was concentrated under reduce pressure. The residue was purified by reverse flash chromatography with water (0.05% TFA)/MeCN (1:1) to afford (R)-3-(2-(3-amino-3-methylbut-1-yn-1-yl)-6-((trimethylsilyl)ethynyl)pyrimidin-4-yl)-10-methyl-9,10,11,12-tetrahydro-8H-[1,4]diazepino[5',6':4,5]thieno[3,2-f]quinolin-8-one (40 mg, 35%) as a red solid. LCMS (ESI, m z): 539 $[M+H]^+$.

Step 2: Synthesis of (R)-3-(2-(3-amino-3-methylbut-1-yn-1-yl)-6-ethynylpyrimidin-4-yl)-10-methyl-9,10,11,12-tetrahydro-8H-[1,4]diazepino[5',6':4,5]thieno[3,2-f]quinolin-8-one

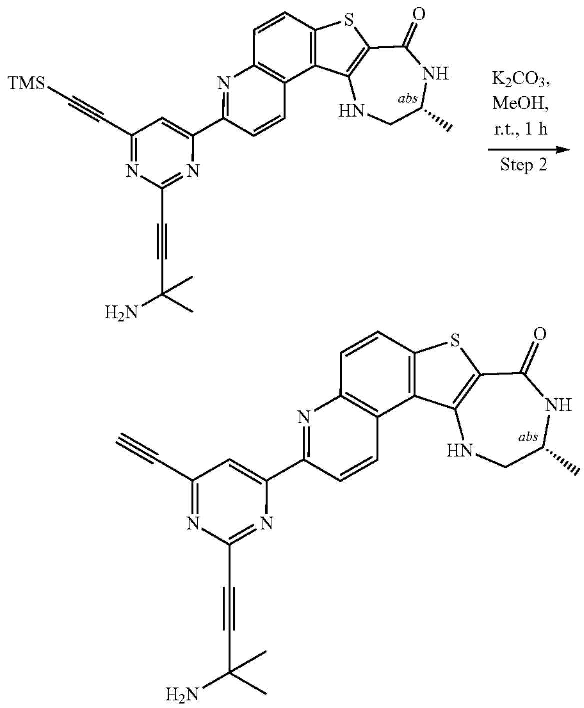

To a solution of (R)-3-(2-(3-amino-3-methylbut-1-yn-1-yl)-6-((trimethylsilyl)ethynyl)pyrimidin-4-yl)-10-methyl-9,10,11,12-tetrahydro-8H-[1,4]diazepino[5',6':4,5]thieno[3,2-f]quinolin-8-one (40 mg, 0.070 mmol, 1.00 equiv) in methanol (2.0 mL) was added $K_2CO_3$ (20 mg, 0.150 mmol, 2.00 equiv). The resulting solution was stirred at room temperature for 1 hour. LCMS showed the reaction was completed. The resulting solution was concentrated under reduced pressure. The residue was purified by Prep-HPLC using the following gradient conditions: Column: SunFire Prep C18 OBD Column, 19*150 mm, 5 μm; Mobile Phase A: Water (0.05% TFA), Mobile Phase B: MeCN; Flow rate: 20 mL/min; Gradient: 20% B to 50% B in 5 min, 50% B; Wave Length: 254 nm; RT1(min): 4.85. Purification resulted in desired (R)-3-(2-(3-amino-3-methylbut-1-yn-1-yl)-6-ethynylpyrimidin-4-yl)-10-methyl-9,10,11,12-tetrahydro-8H-[1,4]diazepino[5',6':4,5]thieno[3,2-f]quinolin-8-one (3.8 mg, 10%) as a yellow solid. LCMS (ESI, m/z): 467 $[M+H]^+$. Analytic Conditions: Column: HALO C18 100A Column 3.0*30 mm, 2.7 um; Mobile Phase A: Water/0.05% TFA, Mobile Phase B: Acetonitrile/0.05% TFA; Flow rate: 1.2000 mL/min; Gradient: 5% B to 100% B in 1.2 min; 254 nm; Rt: 0.932 min.

$^1H$ NMR (400 MHz, DMSO-$d_6$+$D_2O$) δ9.39 (d, J=8.8 Hz, 1H), 8.74 (s, 2H), 8.63 (s, 1H), 8.51 (d, J=8.4 Hz, 1H), 8.27 (d, J=8.8 Hz, 1H), 8.16-8.11 (m, 2H), 7.20 (s, 1H), 5.01 (s, 1H), 3.64 (s, 1H), 3.50 (s, 2H), 1.73 (s, 6H), 1.22 (d, J=5.6 Hz, 3H). $^{19}F$ NMR (376 MHz, DMSO-$d_6$) δ 73.45.

Example 12: Synthesis of (15R)-5-(2-chloro-5-fluoro-4-pyridyl)-15-methyl-11-thia-6,14,17-triazatetracyclo[8.8.0.0^,7.0^12,18]octadeca-1(10),2(7),3,5,8,12(18)-hexaen-13-one

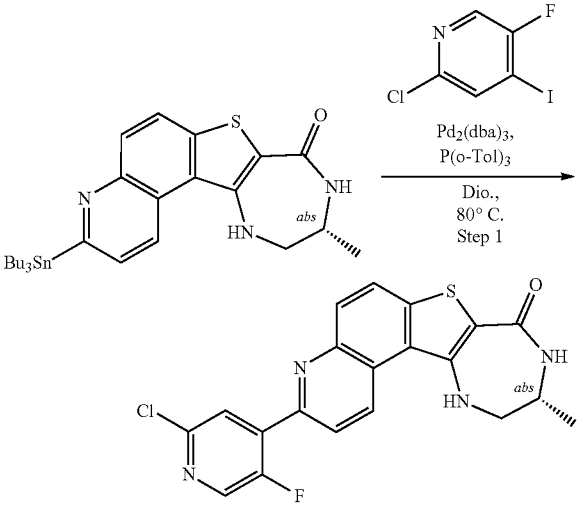

To a solution of (15R)-15-methyl-5-tributylstannyl-11-thia-6,14,17-triazatetracyclo[8.8.0.0^,7.0^12,18]octadeca-1(10),2(7),3,5,8,12(18)-hexaen-13-one (40 mg, 0.070 mmol, 1.00 equiv) and 2-chloro-5-fluoro-4-iodo-pyridine (21 mg, 0.080 mmol, 1.10 equiv) and in DMF (1.0 mL) was added $Pd_2(dba)_3$ (15 mg, 0.010 mmol, 0.20 equiv) and $P(o\text{-}Tol)_3$ (8 mg, 0.030 mmol, 0.40 equiv). The resulting solution was stirred at 80° C. overnight under a nitrogen atmosphere. LCMS showed the reaction was completed. The resulting solution was diluted with water (20 mL), and extracted with ethyl acetate (3×50 mL). The combined organic layers were washed with brine (2×40 mL), dried over anhydrous sodium sulfate, filtered and concentrated under reduced pressure. The residue was purified by flash chromatography on silica gel with ethyl acetate/petroleum ether (5:1) to afford 20 mg crude product. The crude product was purified by Prep-HPLC using following gradient conditions: Column: Xselect CSH OBD Column 30*150 mm Sum; Mobile Phase A: Water (0.05% TFA), Mobile Phase B: MeCN; Flow rate: 60 mL/min; Gradient: 38% B to 62% B in 7 min, 62% B; Wave Length: 254/220 nm; RT1(min): 6.5. Purification resulted in desired (15R)-5-(2-chloro-5-fluoro-4-pyridyl)-15-methyl-11-thia-6,14,17-triazatetracyclo[8.8.0.0^,7.0^12,18]octadeca-1(10),2(7),3,5,8,12(18)-hexaen-13-one (3.7 mg, 12%) as a yellow solid. LCMS (ESI, m z): 414 $[M+H]^+$. Analytic conditions: Column: HALO C18 Column 3.0*30 mm, 2.7 um; Mobile Phase A: Water/0.05% TFA, Mobile Phase B: Acetonitrile/0.05% TFA; Flow rate: 1.200 mL/min; Gradient: 20% B to 80% B in 2.1 min; 254/210 nm; RT: 1.518 min.

$^1$H NMR (400 MHz, DMSO-$d_6$) δ 9.34 (d, J=8.8 Hz, 1H), 8.68 (d, J=2.4 Hz, 1H), 8.28-8.04 (m, 5H), 7.20 (s, 1H), 3.62 (s, 1H), 3.48 (s, 2H), 1.20 (d, J=6.8 Hz, 3H). $^{19}$F NMR (376 MHz, DMSO-$d_6$) δ−74.71, −134.09.

Example 13: Synthesis of (15R)-5-(2-ethynyl-5-fluoro-4-pyridyl)-15-methyl-11-thia-6,14,17-triazatetracyclo[8.8.0.0^,7.0^12,18]octadeca-1(10),2(7),3,5,8,12(18)-hexaen-13-one

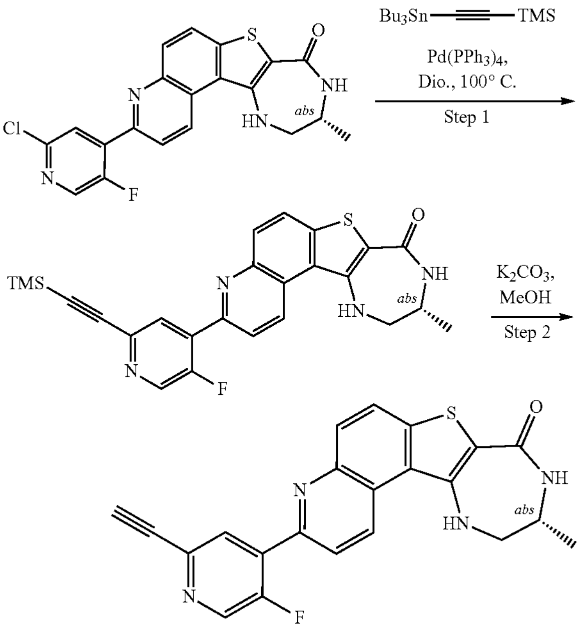

Step 1: Synthesis of (15R)-5-[5-fluoro-2-(2-trimethylsilylethynyl)-4-pyridyl]-15-methyl-11-thia-6,14,17-triazatetracyclo[8.8.0.0^,7.0^12,18]octadeca-1(10),2(7),3,5,8,12(18)-hexaen-13-one

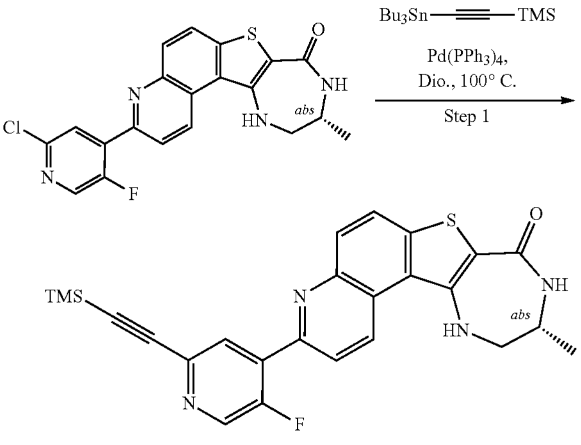

To a solution of (15R)-5-(2-chloro-5-fluoro-4-pyridyl)-15-methyl-11-thia-6,14,17-triazatetracyclo[8.8.0.0^,7.0^12,18]octadeca-1(10),2(7),3,5,8,12(18)-hexaen-13-one (40 mg, 0.100 mmol, 1.00 equiv) and trimethyl(2-tributylstannylethynyl)silane (56 mg, 0.150 mmol, 1.50 equiv) in 1,4-dioxane (2.0 mL) was added $Pd(PPh_3)_4$(11 mg, 0.010 mmol, 0.10 equiv). The resulting solution was stirred at 100° C. overnight under a nitrogen atmosphere. LCMS showed the reaction was completed. The reaction solution was diluted with ethyl acetate/petroleum ether (1:1) (10 mL). The solid was collected by filtered and washed with ethyl acetate/petroleum ether (1:1) (2×10 mL). The solid was dried to give (15R)-5-[5-fluoro-2-(2-trimethylsilylethynyl)-4-pyridyl]-15-methyl-11-thia-6,14,17-triazatetracyclo[8.8.0.0^,7.0^12,18]octadeca-1(10),2(7),3,5,8,12(18)-hexaen-13-one (20 mg, 43%) as a gray-green solid. LCMS (ESI, m z):475[M+H]+.

Step 2: Synthesis of (15R)-5-(2-ethynyl-5-fluoro-4-pyridyl)-15-methyl-11-thia-6,14,17-triazatetracyclo[8.8.0.0^,7.0^12,18]octadeca-1(10),2(7),3,5,8,12(18)-hexaen-13-one

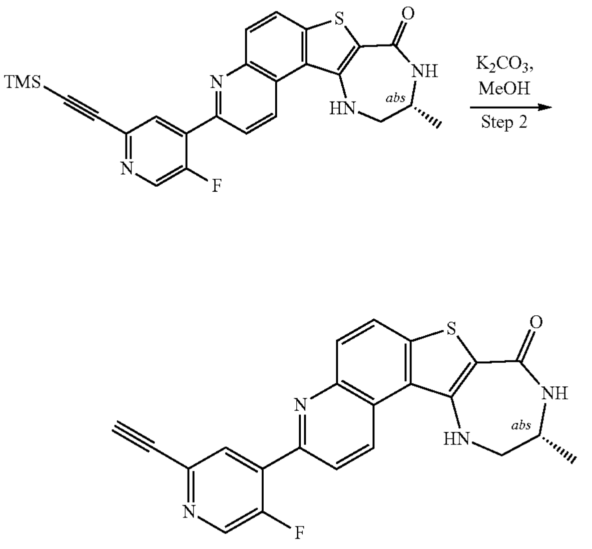

To a solution of (15R)-5-[5-fluoro-2-(2-trimethylsilylethynyl)-4-pyridyl]-15-methyl-1-thia-6,14,17-triazatetracyclo[8.8.0.0^,7.0^12,18]octadeca-1(10),2(7),3,5,8,12(18)-hexaen-13-one (20 mg, 0.040 mmol, 1.00 equiv) in methanol (1.0 mL) was added $K_2CO_3$ (12 mg, 0.090 mmol, 2.00 equiv). The solution was stirred at room temperature for 2 h under a nitrogen atmosphere. LCMS showed the reaction was completed. The resulting solution was diluted with DMSO (3.0 mL). The solid was filtered out and the filtration was purified by Prep-HPLC using following gradient conditions: Column: Xselect CSH C18 OBD Column 30*150 mm 5 μm, n; Mobile Phase A: Water (0.05% TFA), Mobile Phase B: MeCN; Flow rate: 60 mL/min; Gradient: 33% B to 57% B in 7 min, 57% B; Wave Length: 254/220 nm; RT1(min): 6.1. Purification resulted in desired (15R)-5-(2-ethynyl-5-fluoro-4-pyridyl)-15-methyl-11-thia-6,14,17-triazatetracyclo[8.8.0.0^,7.0^12,18]octadeca-1(10),2(7),3,5,8,12(18)-hexaen-13-one (2.1 mg, 11%) as a yellow solid. LCMS (ESI, m z): 403 [M+H]+. Analytic conditions: Column: HALO C18 Column 3.0*30 mm, 2.7 um; Mobile Phase A: Water/0.05% TFA, Mobile Phase B: Acetonitrile/0.05% TFA; Flow rate: 1.200 mL/min; Gradient: 5% B to 70% B in 1.7 min; 254/210 nm; RT: 1.538 min.

$^1$H NMR (400 MHz, DMSO-$d_6$) δ 9.34 (d, J=8.8 Hz, 1H), 8.79 (d, J=2.4 Hz, 1H), 8.32 (d, J=10.0 Hz, 1H), 8.23 (d, J=9.2 Hz, 1H), 8.18-8.08 (m, 3H), 7.22 (s, 1H), 4.46 (s, 1H), 3.70-3.60 (m, 1H), 3.54-3.44 (m, 1H), 1.20 (d, J=6.8 Hz, 3H). $^{19}$F NMR (376 MHz, DMSO-$d_6$) δ−74.67, −129.68.

Example 14: Synthesis of (15R)-5-(2-chloro-6-vinyl-4-pyridyl)-15-methyl-11-thia-6,14,17-triazatetracyclo[8.8.0.0^,7.0^12,18]octadeca-1(10),2(7),3,5,8,12(18)-hexaen-13-one

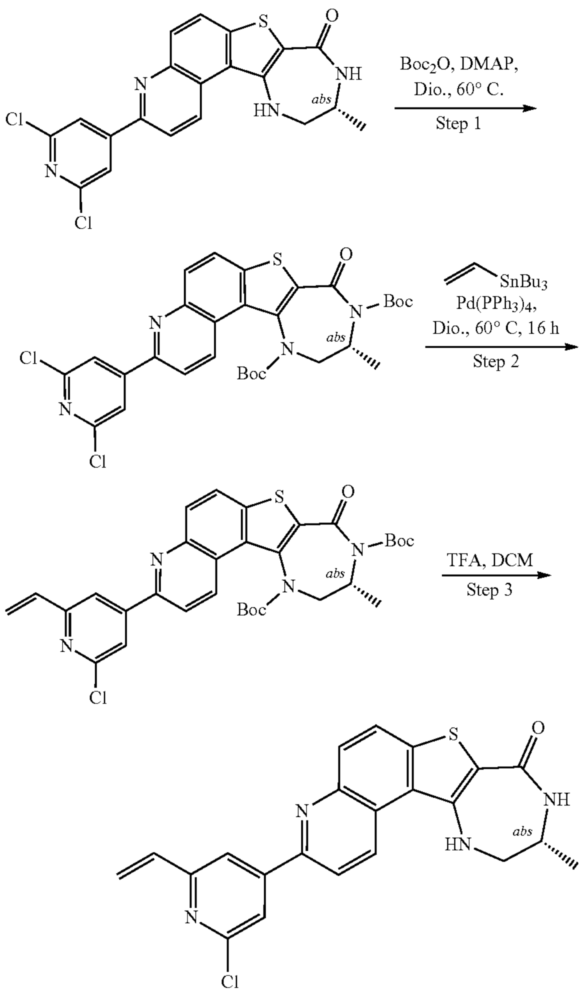

Step 1: Synthesis of ditert-butyl (15R)-5-(2,6-dichloro-4-pyridyl)-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate

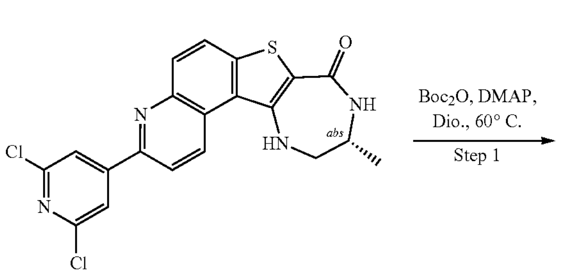

-continued

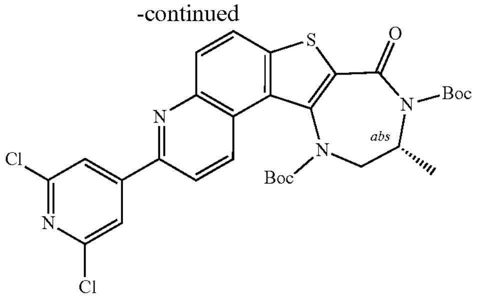

To a solution of (15R)-5-(2,6-dichloro-4-pyridyl)-15-methyl-11-thia-6,14,17-triazatetracyclo[8.8.0.0^,7.0^12,18] octadeca-1(10),2(7),3,5,8,12(18)-hexaen-13-one (200 mg, 0.467 mmol, 1.00 equiv) and $Boc_2O$ (251 mg, 1.168 mmol, 2.50 equiv) in 1,4-dioxane (5.0 mL) was added DMAP (6 mg, 0.047 mmol, 0.10 equiv). The resulting mixture was stirred at 60° C. overnight under a nitrogen atmosphere. LCMS showed the reaction was completed. The resulting solution was concentrated under reduce pressure. The residue was purified by column chromatography on silica gel with ethyl acetate/petroleum ether (1:3) to afford ditert-butyl (15R)-5-(2,6-dichloro-4-pyridyl)-15-methyl-13-oxo-11-thia-6,14,17-triazatetracyclo[8.8.0.0^,7.0^12,18]octadeca-1 (10),2(7),3,5,8,12(18)-hexaene-14,17-dicarboxylate (190 mg, 64%) as a yellow solid. LCMS (ESI, m/z): 629 $(M+H)^+$.

Step 2: Synthesis of ditert-butyl (15R)-5-(2-chloro-6-vinyl-4-pyridyl)-15-methyl-13-oxo-11-thia-6,14,17-triazatetracyclo[8.8.0.0^,7.0^12,18]octadeca-1 (10),2(7),3,5,8,12(18)-hexaene-14,17-dicarboxylate

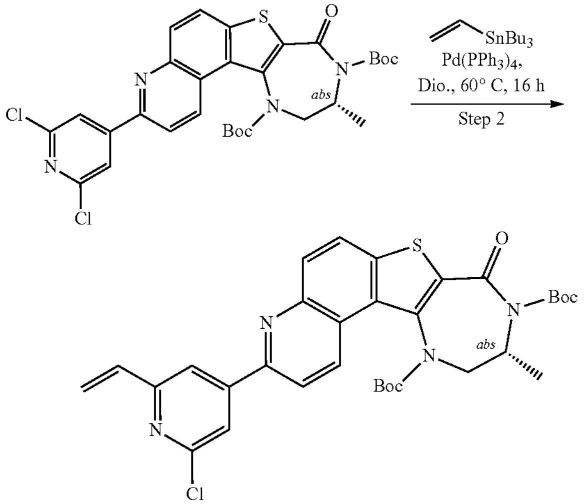

To a solution of ditert-butyl (15R)-5-(2,6-dichloro-4-pyridyl)-15-methyl-13-oxo-11-thia-6,14,17-triazatetracyclo [8.8.0.0^,7.0^12,18]octadeca-1(10),2(7),3,5,8,12(18)-hexaene-14,17-dicarboxylate (70 mg, 0.111 mmol, 1.00 equiv) and tributyl(vinyl)stannane (40 mg, 0.122 mmol, 1.10 equiv) in 1,4-dioxane (5.0 mL) was added $Pd(PPh_3)_4$(9 mg, 0.011 mmol, 0.10 equiv). The resulting mixture was stirred at 60° C. overnight under a nitrogen atmosphere. LCMS showed the reaction was completed. The resulting solution was diluted with water (10 mL) and extracted with ethyl acetate (3×10 mL). The combined organic layers were washed with brine (2×10 mL), dried over anhydrous sodium sulfate, filtered and concentrated under reduced pressure. The residue was purified by reverse flash chromatography with water (10 mmol/L $NH_4HCO_3$)/MeCN (1:1) to give ditert-butyl(15R)-5-(2-chloro-6-vinyl-4-pyridyl)-15-methyl-13-oxo-11-thia-6,14,17-triazatetracyclo[8.8.0.0^, 7.0^12,18]octadeca-1(10),2(7),3,5,8,12(18)-hexaene-14,17-dicarboxylate (25 mg, 36%) as a yellow oil. LCMS (ESI, m/z): 621 $(M+H)^+$.

Step 3: Synthesis of (15R)-5-(2-chloro-6-vinyl-4-pyridyl)-15-methyl-11-thia-6,14,17-triazatetracyclo [8.8.0.0^,7.0^12,18]octadeca-1(10),2(7),3,5,8,12(18)-hexaen-13-one

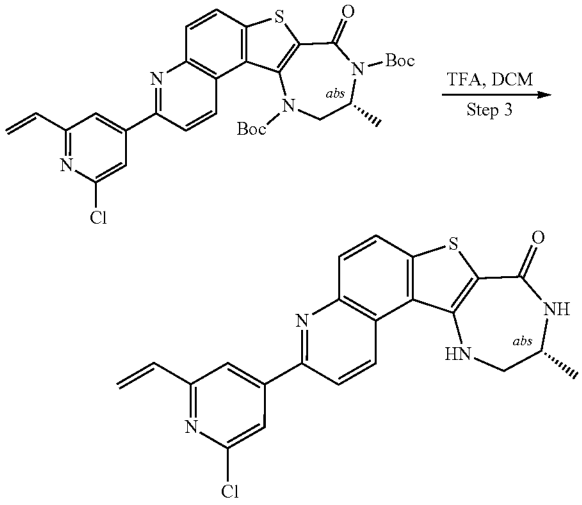

To a solution of ditert-butyl(15R)-5-(2-chloro-6-vinyl-4-pyridyl)-15-methyl-13-oxo-11-thia-6,14,17-triazatetracyclo [8.8.0.0^,7.0^12,18]octadeca-1(10),2(7),3,5,8,12(18)-hexaene-14,17-dicarboxylate (25 mg, 0.040 mmol, 1.00 equiv) in DCM (5.0 mL) was added dropwise TFA (1.0 mL). The resulting mixture was stirred at room temperature for 3 h under a nitrogen atmosphere. LCMS showed the reaction was completed. The resulting solution was concentrated under reduce pressure. The residue was purified by Prep-HPLC using the following gradient conditions: Column: XBridge Prep OBD C18 Column, 30*150 mm, 5 μm; Mobile Phase A: water (10 mmol/L $NH_4HCO_3$), Mobile Phase B: MeCN; Flow rate: 25 mL/min; Gradient: 45% B to 80% B in 5.2 min, 80% B; Wave Length: 254 nm; RT1(min): 4.76. Purification resulted in desired (15R)-5-(2-chloro-6-vinyl-4-pyridyl)-15-methyl-11-thia-6,14,17-triazatetracyclo [8.8.0.0^,7.0^12,18]octadeca-1(10),2(7),3,5,8,12(18)-hexaen-13-one (2 mg, 12%) as a yellow solid. LCMS (ESI, m/z): 421 $(M+H)^+$. Analytic Conditions: Column: HALO C18 Column 3.0*30 mm, 2.7 um; Mobile Phase A: water+0.05% TFA, Mobile Phase B: Acetonitrile+0.05% TFA; Flow rate: 1.5000 mL/min; Gradient: 30% B to 70% B in 1.75 min; 254 nm; Rt: 1.585 min.

$^1H$ NMR (300 MHz, DMSO-$d_6$) δ 9.34 (d, J=9.3 Hz, 1H), 8.47 (d, J=9.3 Hz, 1H), 8.40 (s, 1H), 8.29 (s, 1H), 8.23 (d, J=11.7 Hz, 1H), 8.16-8.07 (m, 2H), 7.23 (t, J=4.4 Hz, 1H), 6.99 (dd, J=17.1 Hz, 11.4 Hz, 1H), 6.42 (d, J=17.1 Hz, 1H), 5.67 (d, J=11.4 Hz, 1H), 3.70-3.60 (m, 1H), 3.52-3.40 (m, 2H), 1.22 (d, J=6.6 Hz, 3H)

Example 15: Synthesis of (15R)-5-(2-chloro-6-ethynyl-4-pyridyl)-15-methyl-11-thia-6,14,17-triazatetracyclo[8.8.0.0^,7.0^12,18]octadeca-1(10),2(7),3,5,8,12(18)-hexaen-13-one

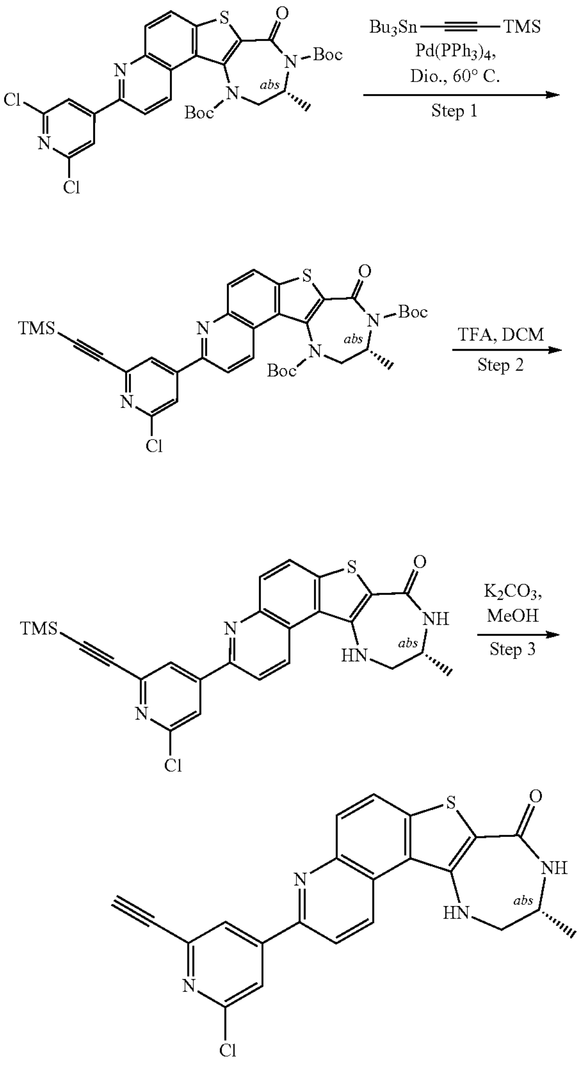

Step 1: Synthesis of ditert-butyl (15R)-5-[2-chloro-6-(2-trimethylsilylethynyl)-4-pyridyl]-15-methyl-13-oxo-11-thia-6,14,17-triazatetracyclo[8.8.0.0^2,7.0^12,18]octadeca-1(10),2(7),3,5,8,12(18)-hexaene-14,17-dicarboxylate

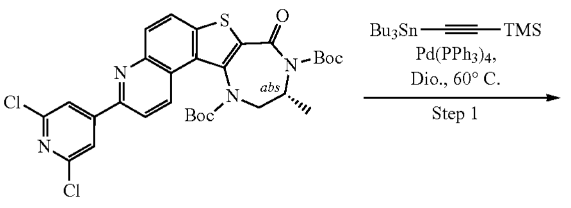

-continued

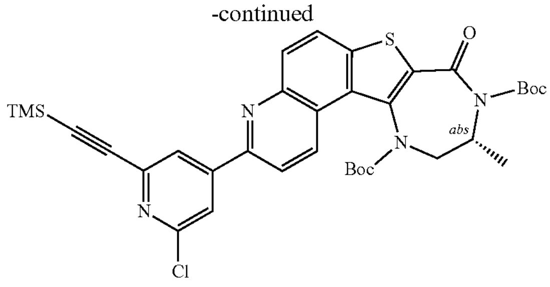

To a solution of ditert-butyl (15R)-5-(2,6-dichloro-4-pyridyl)-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (70 mg, 0.111 mmol, 1.00 equiv) and trimethyl (2-tributylstannylethynyl) silane (56 mg, 0.133 mmol, 1.20 equiv) in 1,4-dioxane (5.0 mL) was added $Pd(PPh_3)_4$(12 mg, 0.011 mmol, 0.10 equiv). The resulting mixture was stirred at 60° C. overnight under a nitrogen atmosphere. LCMS showed the reaction was completed. The resulting solution was diluted with water (10 mL) and extracted with ethyl acetate (3×10 mL). The combined organic layers were washed with brine (2×10 mL), dried over anhydrous sodium sulfate, filtered and concentrated under reduced pressure. The residue was purified by reverse flash chromatography with water(0.05% TFA)/MeCN (1:1) to give ditert-butyl (15R)-5-[2-chloro-6-(2-trimethylsilylethynyl)-4-pyridyl]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (40 mg, 51%) as a yellow oil. LCMS (ESI, m/z): 635 $(M+H-tBu)^+$.

Step 2: Synthesis of (15R)-5-[2-chloro-6-(2-trimethylsilylethynyl)-4-pyridyl]-15-methyl-11-thia-6,14,17-triazatetracyclo[8.8.0.0^,7.0^12,18]octadeca-1(10),2(7),3,5,8,12(18)-hexaen-13-one

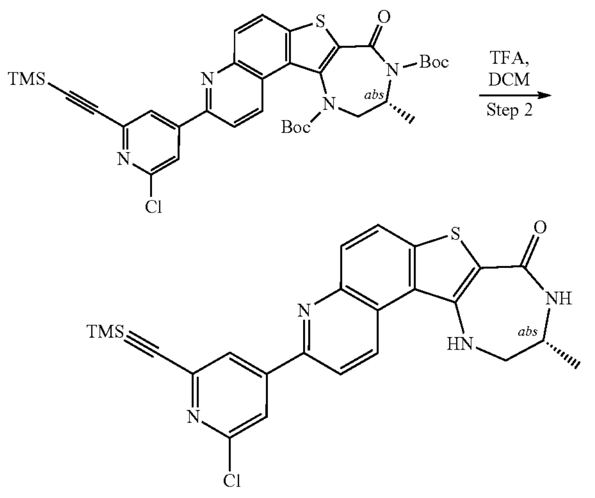

To a solution of ditert-butyl (15R)-5-[2-chloro-6-(2-trimethylsilylethynyl)-4-pyridyl]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (40 mg, 0.060 mmol, 1.00 equiv) in DCM (5.0 mL) was added dropwise TFA (1.0 mL). The resulting mixture was stirred at room temperature for 3 h under a nitrogen atmosphere.

LCMS showed the reaction was completed. The resulting solution was concentrated under reduce pressure to give crude product. The crude product was used in the next step directly without further purification. LCMS (ESI, m/z): 491 $(M+H)^+$.

Step 3: Synthesis of (15R)-5-(2-chloro-6-ethynyl-4-pyridyl)-15-methyl-11-thia-6,14,17-triazatetracyclo [8.8.0.0^,7.0^12,18]octadeca-1(10),2(7),3,5,8,12(18)-hexaen-13-one

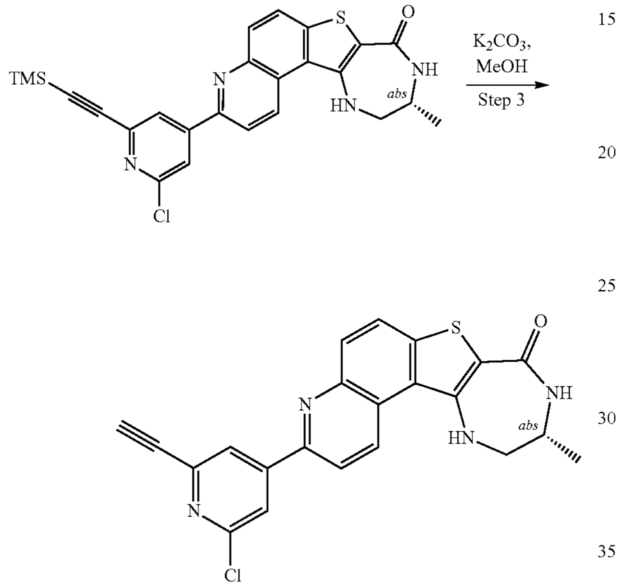

To a solution of (15R)-5-[2-chloro-6-(2-trimethylsilylethynyl)-4-pyridyl]-15-methyl-11-thia-6,14,17-triazatetracyclo[8.8.0.0^,7.0^12,18]octadeca-1(10),2(7),3,5,8,12(18)-hexaen-13-one (30 mg, 0.061 mmol, 1.00 equiv) in methanol (3.0 mL) was added $K_2CO_3$ (12 mg, 0.092 mmol, 1.50 equiv). The reaction mixture was stirred at room temperature for 15 minutes. LCMS showed the reaction was completed. The resulting solution was diluted with DMSO (3 mL). The solid was filtered out. The filtration was purified by Prep-HPLC using the following gradient conditions: Column: XBridge Prep OBD C18 Column, 30*150 mm, 5 μm; Mobile Phase A: water (0.05% TFA), Mobile Phase B: MeCN; Flow rate: 25 mL/min; Gradient: 30% B to 75% B in 5.2 min, 80% B; Wave Length: 254 nm; RT1(min): 4.62. Purification resulted in desired (15R)-5-(2-chloro-6-ethynyl-4-pyridyl)-15-methyl-11-thia-6,14,17-triazatetracyclo [8.8.0.0^,7.0^12,18]octadeca-1(10),2(7),3,5,8,12(18)-hexaen-13-one (2.7 mg, 10%) as a yellow solid. LCMS (ESI, m/z): 419 $(M+H)^+$. Analytic Conditions: Column: Shim-pack Scepter C18 Column 3.0*33 mm, 3.0 um; Mobile Phase A: water/5mMN$H_4HCO_3$, Mobile Phase B: Acetonitrile; Flow rate: 1.5000 mL/min; Gradient: 10% B to 95% B in 1.20 min; 254 nm; Rt: 1.106 min.

$^1$H NMR (300 MHz, DMSO-$d_6$) δ 9.33 (d, J=8.7 Hz, 1H), 8.52-8.46 (m, 3H), 8.23 (d, J=9.0 Hz, 1H), 8.13 (d, J=5.1 Hz, 1H), 8.11 (d, J=9.0 Hz, 1H), 7.23 (t, J=5.4 Hz, 1H), 4.65 (s, 1H), 3.64-3.60 (m, 1H), 3.50-3.40 (m, 2H), 1.22 (d, J=6.9 Hz, 3H)

Example 16: Synthesis of (15R)-5-[6-chloro-2-(hydroxymethyl)pyrimidin-4-yl]-15-methyl-11-thia-6, 14,17-triazatetracyclo[8.8.0.0^,7.0^12,18]octadeca-1 (10),2,4,6,8,12(18)-hexaen-13-one

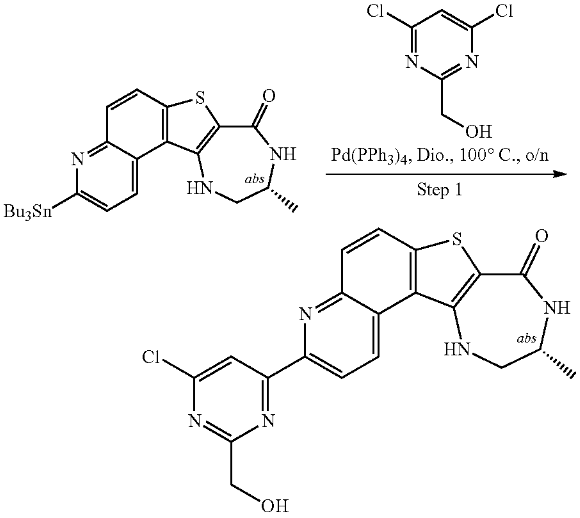

Step 1: Synthesis of (15R)-5-[6-chloro-2-(hydroxymethyl)pyrimidin-4-yl]-15-methyl-11-thia-6, 14,17-triazatetracyclo[8.8.0.0^,7.0^12,18]octadeca-1 (10),2,4,6,8,12(18)-hexaen-13-one

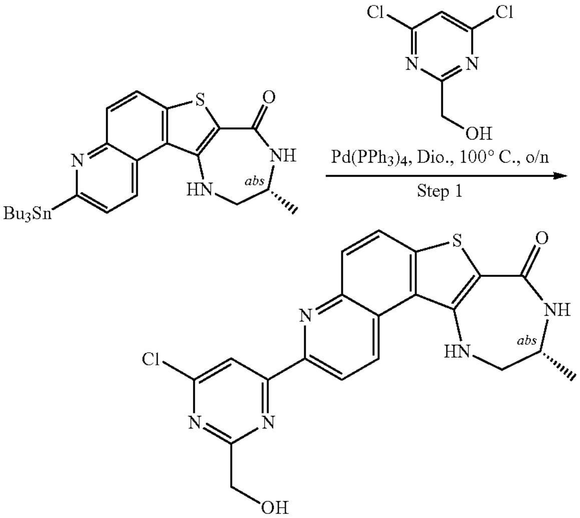

To a solution of (4,6-dichloropyrimidin-2-yl)methanol (200 mg, 1.117 mmol, 1.00 equiv) and (15R)-15-methyl-5-tributylstannyl-11-thia-6,14,17-triazatetracyclo[8.8.0.0^, 7.0^12,18]octadeca-1(10),2,4,6,8,12(18)-hexaen-13-one (640 mg, 1.117 mmol, 1.00 equiv) in 1,4-dioxane (10.0 mL) was added $Pd(PPh_3)_4$(95 mg, 0.110 mmol, 0.10 equiv). The resulting solution was stirred at 100° C. overnight under a nitrogen atmosphere. LCMS showed the reaction was completed. The resulting solution was diluted with dichloromethane (10 mL). The solid was collected by filtration and washed with dichloromethane (2×10 mL). The solid was purified by Prep-HPLC using the following the gradient conditions: Column: SunFire Prep C18 OBD Column, 19*150 mm, 5 μm; Mobile Phase A: Water (0.05% TFA), Mobile Phase B: ACN; Flow rate: 20 mL/min; Gradient: 20% B to 50% B in 4.5 min, 50% B; Wave Length: 254/210 nm; RT1(min): 4.35; Number Of Runs: 0. Purification resulted in desired (15R)-5-[6-chloro-2-(hydroxymethyl)pyrimidin-4-yl]-15-methyl-11-thia-6,14,17-triazatetracyclo [8.8.0.0^,7.0^12,18]octadeca-1(10),2,4,6,8,12(18)-hexaen-13-one (26.5 mg, 5.4%) as a yellow solid. LCMS (ESI, m/z): 426 $(M+H)^+$. Analytic Conditions: Column: HALO C18 100A Column 3.0*30 mm, 2.7 um; Mobile Phase A: Water+ 0.05% TFA, Mobile Phase B: Acetonitrile+0.05% TFA; Flow rate: 1.5000 mL/min; Gradient: 5% B to 70% B in 1.70 min; 254 nm; Rt: 1.531 min.

$^1$H NMR (400 MHz, DMSO-$d_6$+$D_2O$) δ 9.36 (d, J=9.2 Hz, 1H), 8.67 (d, J=8.8 Hz, 1H), 8.47 (s, 1H), 8.23 (d, J=8.4 Hz, 1H), 8.14-8.08 (m, 2H), 7.19 (s, 1H), 5.63 (d, J=5.6 Hz, 1H), 4.76 (d, J=4.8 Hz, 2H), 3.65-3.59 (m, 1H), 3.49 (s, 2H), 1.21 (d, J=6.8 Hz, 3H). $^{19}$F NMR (376 MHz, DMSO-$d_6$) δ 73.44.

Example 17: Synthesis of (15R)-5-[2-(hydroxymethyl)-6-vinyl-pyrimidin-4-yl]-15-methyl-11-thia-6,14,17-triazatetracyclo[8.8.0.0^,7.0^12,18]octadeca-1(10),2,4,6,8,12(18)-hexaen-13-one

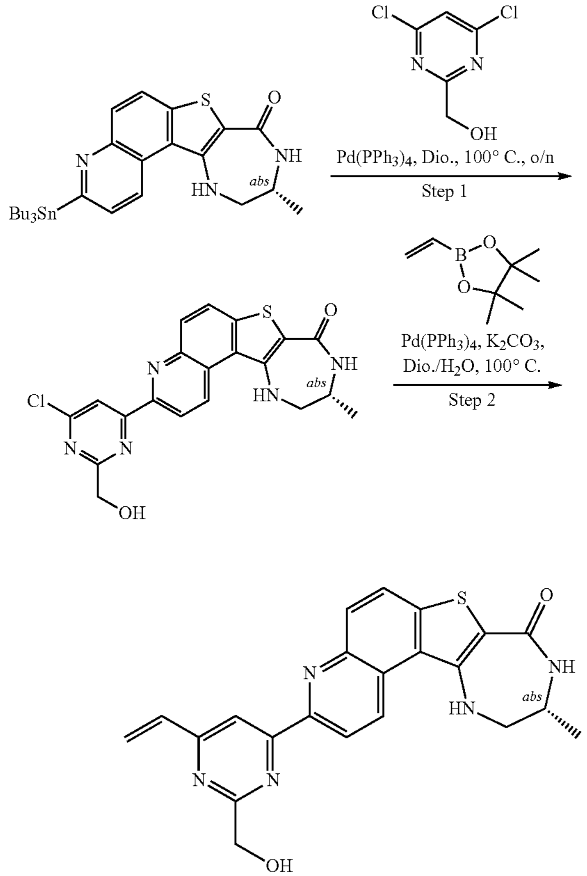

Step 1: Synthesis of (15R)-5-[6-chloro-2-(hydroxymethyl)pyrimidin-4-yl]-15-methyl-11-thia-6,14,17-triazatetracyclo[8.8.0.0^,7.0^12,18]octadeca-1(10),2,4,6,8,12(18)-hexaen-13-one

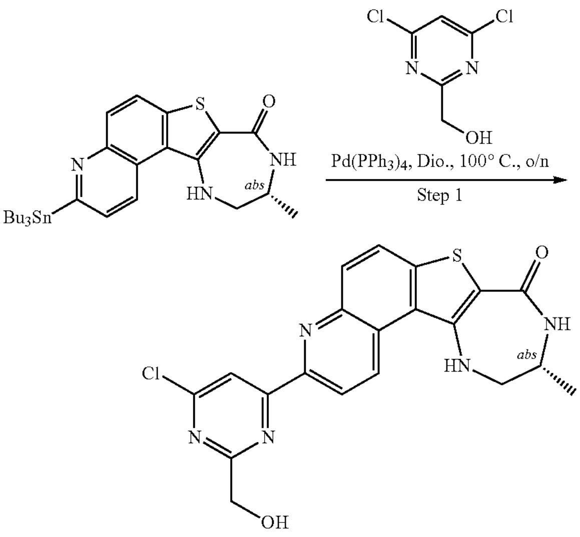

To a solution of (4,6-dichloropyrimidin-2-yl)methanol (200 mg, 1.117 mmol, 1.00 equiv) and (15R)-15-methyl-5-tributylstannyl-11-thia-6,14,17-triazatetracyclo[8.8.0.0^, 7.0^12,18]octadeca-1(10),2(7),3,5,8,12(18)-hexaen-13-one (640 mg, 1.117 mmol, 1.00 equiv) in 1,4-Dioxane (8.0 mL) was added $Pd(PPh_3)_4$(95 mg, 0.112 mmol, 0.10 equiv). The resulting mixture was stirred at 100° C. overnight under a nitrogen atmosphere. The reaction was monitored by LCMS. The solid was collected by filtration and washed with DCM. Dried to give (15R)-5-[6-chloro-2-(hydroxymethyl)pyrimidin-4-yl]-15-methyl-11-thia-6,14,17-triazatetracyclo [8.8.0.0^,7.0^12,18]octadeca-1(10),2,4,6,8,12(18)-hexaen-13-one (230 mg, 48%) as a yellow solid. LCMS (ESI, m/z): 426 $(M+H)^+$.

Step 2: Synthesis of (15R)-5-[2-(hydroxymethyl)-6-vinyl-pyrimidin-4-yl]-15-methyl-11-thia-6,14,17-triazatetracyclo[8.8.0.0^,7.0^12,18]octadeca-1(10),2,4,6,8,12(18)-hexaen-13-one

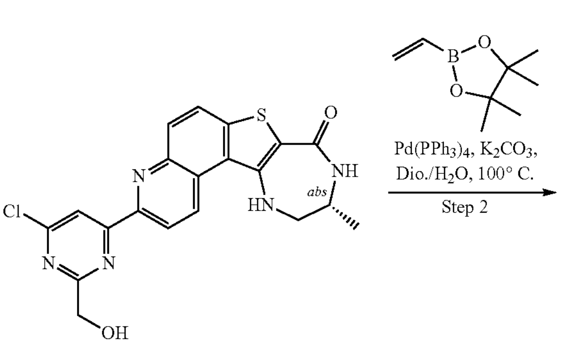

-continued

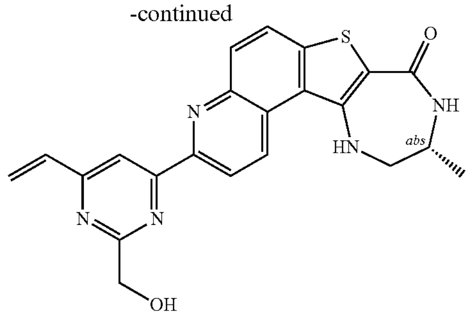

To a solution of (15R)-5-[6-chloro-2-(hydroxymethyl)pyrimidin-4-yl]-15-methyl-11-thia-6,14,17-triazatetracyclo[8.8.0.0^,7.0^12,18]octadeca-1(10),2,4,6,8,12(18)-hexaen-13-one (80 mg, 0.188 mmol, 1.00 equiv) and 4,4,5,5-tetramethyl-2-vinyl-1,3,2-dioxaborolane (35 mg, 0.225 mmol, 1.20 equiv) in 1,4-Dioxane (3.0 mL) and Water (0.3 mL) was added $Pd(PPh_3)_4$(16 mg, 0.019 mmol, 0.10 equiv). The resulting mixture was stirred at 100° C. overnight under a nitrogen atmosphere. LCMS showed the reaction was completed. The resulting solution was diluted with DCM. The solid was collected by filtration and washed with DCM. The solid was purified by Prep-HPLC using the following the gradient conditions: Column: SunFire Prep C18 OBD Column, 19*150 mm, 5 μm; Mobile Phase A: Water(0.1% FA), Mobile Phase B: ACN; Flow rate: 20 mL/min; Gradient: 25% B to 50% B in 4.5 min, 50% B, in 0.3 min; Wave Length: 254/210 nm; RT1(min): 4.35. Purification resulted in desired (15R)-5-[2-(hydroxymethyl)-6-vinyl-pyrimidin-4-yl]-15-methyl-11-thia-6,14,17-triazatetracyclo[8.8.0.0^, 7.0^12,18]octadeca-1(10),2,4,6,8,12(18)-hexaen-13-one (24.5 mg, 29%) as a yellow solid. LCMS (ESI, m/z): 418 $(M+H)^+$. Analytic Conditions: Column: HALO C18 100A Column 3.0*30 mm, 2.7 um; Mobile Phase A: Water/0.05% TFA, Mobile Phase B: Acetonitrile/0.05% TFA; Flow rate: 1.5000 mL/min; Gradient: 5% B to 60% B in 2.10 min; 254 nm; Rt: 1.533 min.

$^1H$ NMR (400 MHz, DMSO-$d_6$+$D_2O$) δ 9.36 (d, J=8.8 Hz, 1H), 8.72 (d, J=8.8 Hz, 1H), 8.47 (s, 1H), 8.23 (d, J=8.8 Hz, 1H), 8.15-8.03 (m, 2H), 7.21 (s, 1H), 7.04 (dd, J=17.2, 10.4 Hz, 1H), 6.69 (d, J=18.0 Hz, 1H), 5.83 (d, J=11.6 Hz, 1H), 5.40 (s, 1H), 4.77 (s, 2H), 3.68-3.59 (m, 1H), 3.50-3.40 (m, 2H), 1.21 (d, J=6.8 Hz, 3H).

Example 18: Synthesis of (R)-10-methyl-3-(3-(2-(pyrrolidin-1-yl)ethoxy)-6-vinylpyridazin-4-yl)-9,10,11,12-tetrahydro-8H-[1,4]diazepino[5',6':4,5]thieno[3,2-f]quinolin-8-one

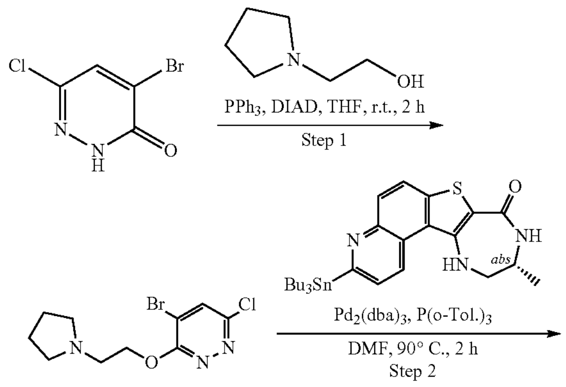

-continued

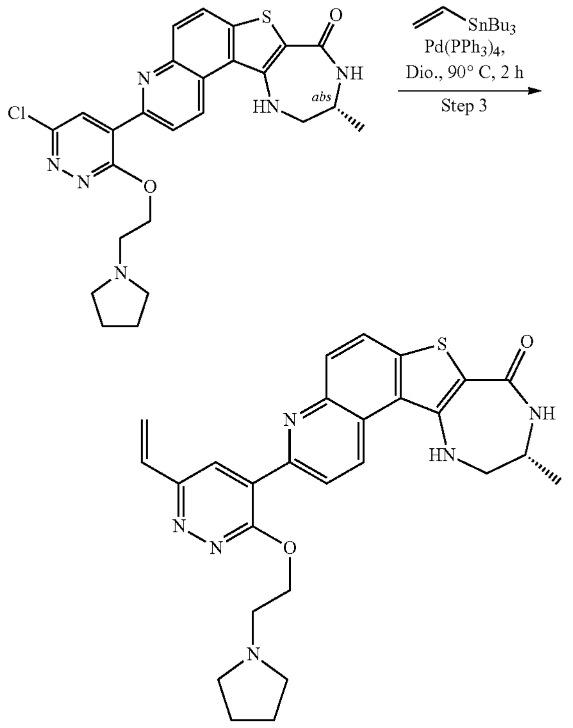

Step 1: Synthesis of 4-bromo-6-chloro-3-(2-pyrrolidin-1-ylethoxy)pyridazine

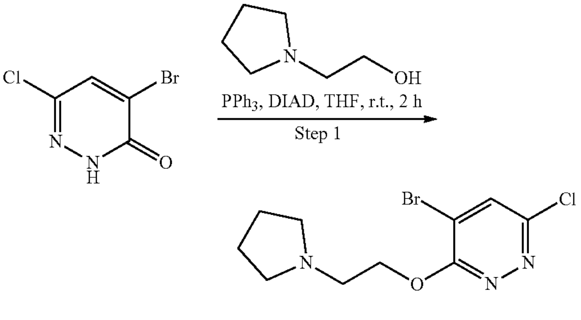

To a solution of 5-bromo-3-chloro-1H-pyridazin-6-one (1.5 g, 7.200 mmol, 1.00 equiv) and 2-pyrrolidin-1-ylethanol (0.8 g, 7.200 mmol, 1.00 equiv) and $PPh_3$ (3.8 g, 14.300, mmol, 2.00 equiv) in THF (40.0 mL) was added dropwise DIAD (2.8 mL, 14.300 mmol, 2.00 equiv). The resulting mixture was stirred at room temperature for 2 h under a nitrogen atmosphere. LCMS showed the reaction was completed. The resulting was diluted with water (100 ml), extracted with ethyl acetate (3×50 mL). The organic layers were washed with brine (2×50 mL), dried over anhydrous sodium sulfate, filtered and concentrated under reduce pressure. The residue was purified by Prep-HPLC using the following gradient conditions: Column: SunFire Prep C18 OBD Column, 19*150 mm, 5 μm; Mobile Phase A: Water (0.05% TFA), Mobile Phase B: MeCN; Flow rate: 25 mL/min; Gradient: 20% B to 40% B in 6 min, 40% B; Wave Length: 210/254 nm; RT1(min): 5.51. Purification resulted in desired 4-bromo-6-chloro-3-(2-pyrrolidin-1-ylethoxy) pyridazine (160 mg, 7.3%) as a yellow oil. LCMS (ESI, m/z): 306 $[M+H]^+$.

Step 2: Synthesis of (R)-3-(6-chloro-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one

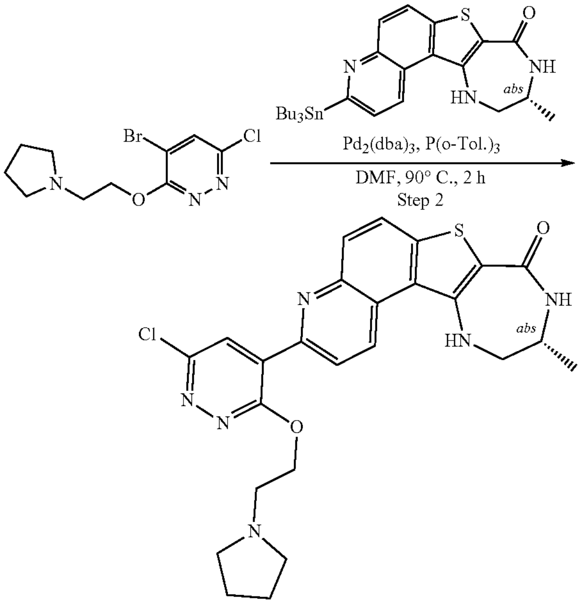

To a solution of 4-bromo-6-chloro-3-(2-pyrrolidin-1-ylethoxy)pyridazine (10 mg, 0.030 mmol, 1.00 equiv) and (R)-10-methyl-3-(tributylstannyl)-9,10,11,12-tetrahydro-8H-[1,4]diazepino[5',6':4,5]thieno[3,2-f]quinolin-8-one (22 mg, 0.040 mmol, 1.30 equiv) in 1,4-dioxane (1.0 mL) was added $Pd_2(dba)_3$ (7 mg, 0.010 mmol, 0.20 equiv) and P(o-Tol.)$_3$ (2 mg, 0.010 mmol, 0.20 equiv). The resulting mixture was stirred at 90° C. for 2 h under a nitrogen atmosphere. LCMS showed the reaction was completed. The resulting solution was diluted with water (10 ml), extracted with ethyl acetate (2×10 mL). The combined organic layer was washed with brine (2×20 mL), dried over anhydrous sodium sulfate, filtered and concentrated under reduce pressure. The residue was purified by Prep-HPLC using the following gradient conditions: Column: SunFire Prep C18 OBD Column, 19*150 mm, 5 μm; Mobile Phase A: Water (0.05% TFA), Mobile Phase B: MeCN; Flow rate: 25 mL/min; Gradient: 20% B to 40% B in 6 min, 40% B; Wave Length: 210/254 nm; RT1(min): 5.51. Purification resulted in desired (R)-3-(6-chloro-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one (1.8 mg, 10.3%) as a light yellow solid. LCMS (ESI, m/z): 509 $[M+H]^+$. Analytic Conditions: column: HALO C18 Column 3.0*30 mm, 1.9 □m; mobile phase A: water+0.05% TFA, mobile phase B: acetonitrile+0.05% TFA; flow rate: 1.5000 mL/min; gradient: 5% B to 65% in 2.10 min. 254 nm; Rt: 1.429 min.

$^1$H NMR (400 MHz, DMSO-$d_6$) δ 9.69 (s, 1H), 9.32 (d, J=9.2 Hz, 1H), 8.37 (s, 1H), 8.31 (d, J=9.2 Hz, 1H), 8.24 (d, J=8.8 Hz, 1H), 8.15 (d, J=4.4 Hz, 1H), 8.06 (d, J=8.8 Hz, 1H), 7.18 (t, J=5.2 Hz, 1H), 4.93 (t, J=4.8 Hz, 2H), 3.72 (d, J=4.0 Hz, 2H), 3.70-3.60 (m, 3H), 3.50-3.40 (m, 2H), 3.12-3.06 (m, 2H), 2.01-1.96 (m, 2H), 1.83-1.80 (m, 2H), 1.21 (d, J=6.4 Hz, 3H). $^{19}$F NMR (376 MHz, DMSO-$d_6$) δ-73.50

Step 3: Synthesis of (R)-10-methyl-3-(3-(2-(pyrrolidin-1-yl)ethoxy)-6-vinylpyridazin-4-yl)-9,10,11,12-tetrahydro-8H-[1,4]diazepino[5',6':4,5]thieno[3,2-f]quinolin-8-one

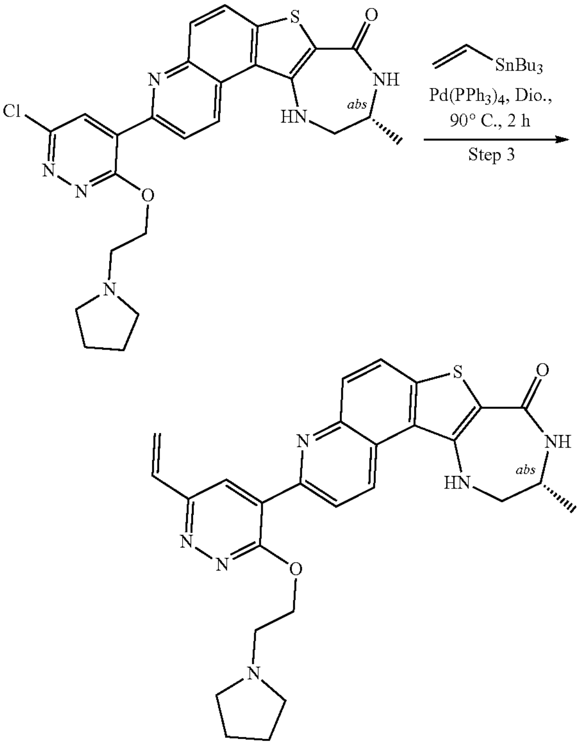

To a solution of (R)-3-(6-chloro-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one (20 mg, 0.040 mmol, 1.00 equiv) and tributyl(vinyl)stannane (19 mg, 0.060 mmol, 1.50 equiv) in 1,4-Dioxane (1.0 mL) was added $Pd(PPh_3)_4$(7 mg, 0.010 mmol, 0.20 equiv). The resulting mixture was stirred at 90° C. for 2 h under a nitrogen atmosphere. LCMS showed the reaction was completed. The resulting solution was diluted with water (5 mL) and extracted with ethyl acetate (3×5 mL). The organic layer was washed with brine (2×5 mL), dried over anhydrous sodium sulfate, filtered and concentrated under reduce pressure. The residue was purified by Prep-HPLC using the following conditions: Column: SunFire Prep C18 OBD Column, 19*150 mm, 5 μm; Mobile Phase A: Water (0.05% TFA), Mobile Phase B: MeCN; Flow rate: 25 mL/min; Gradient: 20% B to 40% B in 6 min, 40% B; Wave Length: 254 nm; RT1(min): Array. Purification resulted in desired (R)-10-methyl-3-(3-(2-(pyrrolidin-1-yl)ethoxy)-6-vinylpyridazin-4-yl)-9,10,11,12-tetrahydro-8H-[1,4]diazepino[5',6':4,5]thieno[3,2-f]quinolin-8-one (6.8 mg, 33%) as a yellow solid. LCMS (ESI, m/z): 501 $(M+H)^+$. Analytic Conditions: column: HALO C18 Column 3*30 mm, 1.9 □m; mobile phase A: water+0.05% TFA, mobile phase B: acetonitrile+0.05% TFA; flow rate: 1.5000 mL/min; gradient: 5% B to 60% B in 2.10 min; 254 nm; Rt: 1.432 min.

$^1$H NMR (400 MHz, DMSO-$d_6$) δ 9.65 (s, 1H), 9.30 (d, J=9.2 Hz, 1H), 8.42 (s, 1H), 8.26 (d, J=8.8 Hz, 1H), 8.23 (d, J=9.2 Hz, 1H), 8.15 (d, J=4.4 Hz, 1H), 8.06 (d, J=8.8 Hz, 1H), 7.21 (t, J=5.2 Hz, 1H), 7.09 (dd, J=17.6, 11.4 Hz, 1H), 6.39 (d, J=17.6 Hz, 1H), 5.70 (d, J=11.6 Hz, 1H), 4.94 (t, J=4.4 Hz, 2H), 3.72 (d, J=4.0 Hz, 2H), 3.70-3.60 (m, 3H), 3.50-3.42 (m, 2H), 3.12-3.02 (m, 2H), 2.00-1.90 (m, 2H), 1.86-1.78 (m, 2H), 1.21 (d, J=6.8 Hz, 3H). $^{19}$F NMR (376 MHz, DMSO-$d_6$) δ-73.65

Example 19: Synthesis of (R)-3-(6-ethynyl-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one

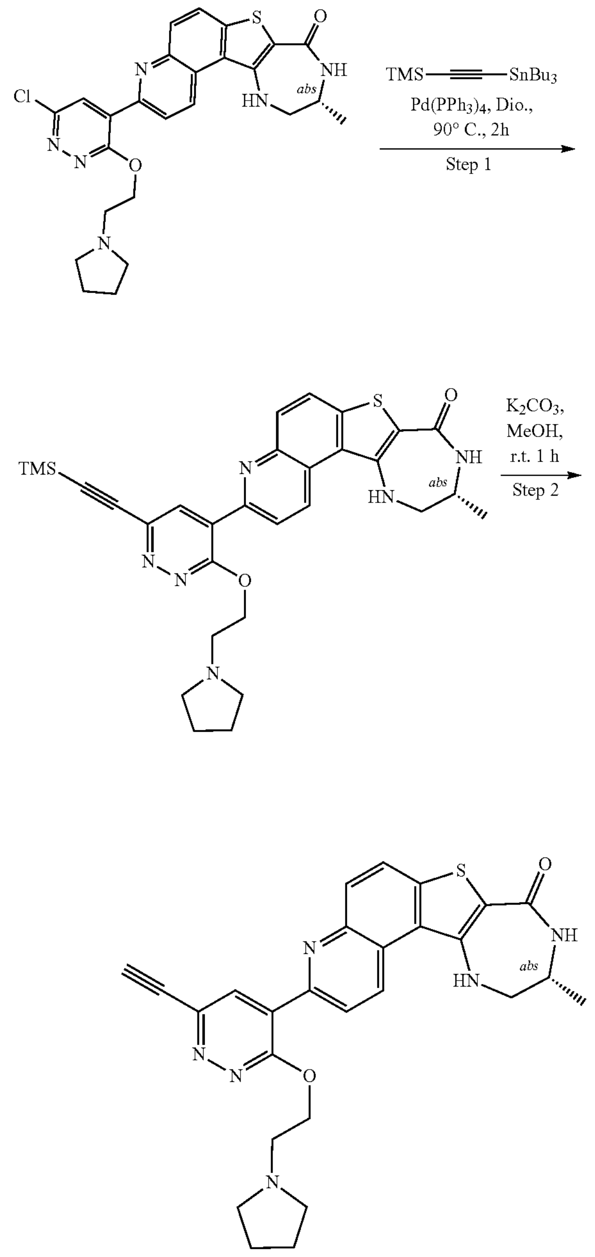

Step 1: Synthesis of (R)-10-methyl-3-(3-(2-(pyrrolidin-1-yl)ethoxy)-6-((trimethylsilyl)ethynyl)pyridazin-4-yl)-9,10,11,12-tetrahydro-8H-[1,4]diazepino[5',6':4,5]thieno[3,2-f]quinolin-8-one

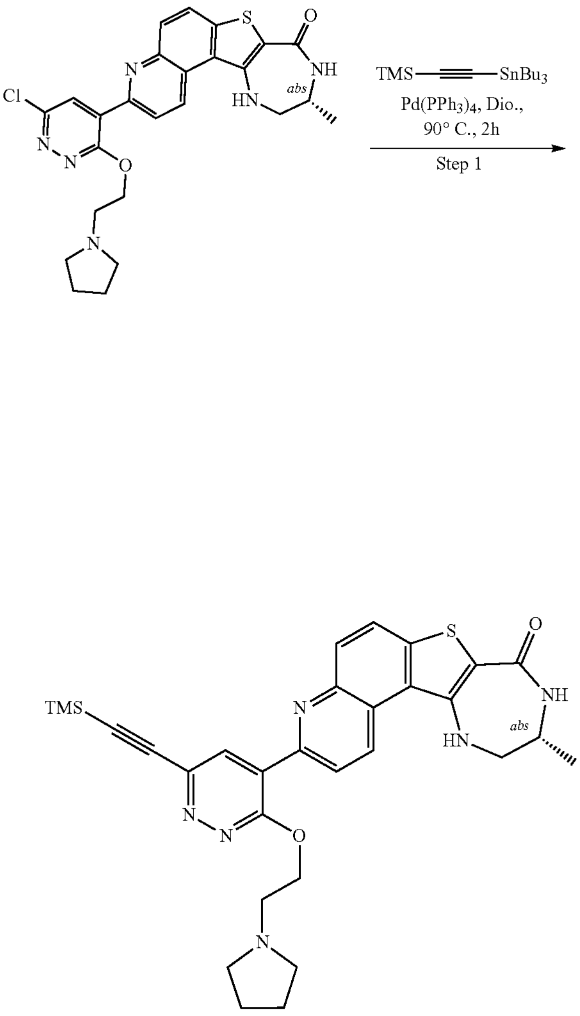

To a solution of (R)-3-(6-chloro-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one (35 mg, 0.070 mmol, 1.00 equiv) and trimethyl(2-tributylstannylethynyl)silane (133 mg, 0.340 mmol, 5.00 equiv) in 1,4-dioxane (1.0 mL) was added $Pd(PPh_3)_4$(11.6 mg, 0.01 mmol, 0.10 equiv). The resulting mixture was stirred at 90° C. for 2 h under a nitrogen atmosphere. LCMS showed the reaction was completed. The reaction was diluted with water (15 mL) and extracted with ethyl acetate (3×15 mL). The organic layers were washed with brine (2×10 mL), dried over anhydrous sodium sulfate, filtered and concentrated under reduce pressure. The residue was purified by reverse flash chromatography with water (0.05% TFA)/MeCN (2:1) to give (R)-10-methyl-3-(3-(2-(pyrrolidin-1-yl)ethoxy)-6-((trimethylsilyl)ethynyl)pyridazin-4-yl)-9,10,11,12-tetrahydro-8H-[1,4]diazepino[5',6':4,5]thieno[3,2-f]quinolin-8-one (30 mg, 76%) as a yellow solid. as a yellow solid. LCMS (ESI, m/z): 571 $[M+H]^+$.

Step 2: Synthesis of (R)-3-(6-ethynyl-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one

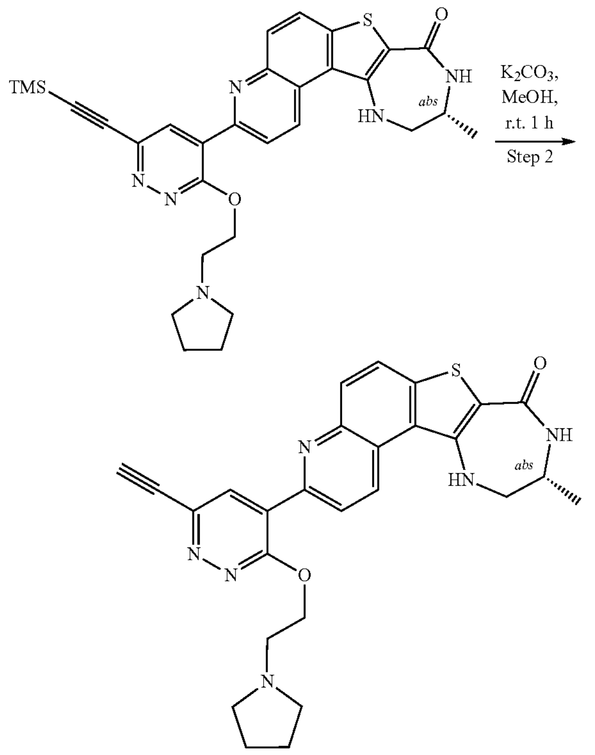

To a solution of (R)-10-methyl-3-(3-(2-(pyrrolidin-1-yl)ethoxy)-6-((trimethylsilyl)ethynyl)pyridazin-4-yl)-9,10,11,12-tetrahydro-8H-[1,4]diazepino[5',6':4,5]thieno[3,2-f]quinolin-8-one (20 mg, 0.040 mmol, 1.00 equiv) in methanol (1.0 mL) was added $K_2CO_3$ (10 mg, 0.08 mmol, 2.00 equiv). The resulting mixture was stirred at room temperature for 1 h. LCMS showed the reaction was completed. The resulting solution was diluted with DMSO (2 mL). The solid was filtered out. The filtration was purified by Prep-HPLC using the following conditions: Column: SunFire Prep C18 OBD Column, 19*150 mm, 5 μm; Mobile Phase A: Water (0.05% TFA), Mobile Phase B: MeCN; Flow rate: 25 mL/min; Gradient: 20% B to 40% B in 6 min, 40% B; Wave Length: 254 nm; RT1(min): 5.35. Purification resulted in desired (R)-3-(6-ethynyl-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one (3.4 mg, 18.9%) as a yellow solid. LCMS (ESI, m/z): 499 $[M+H]^+$. Analytic Conditions: column: HALO C18 Column 3*30 mm, 1.9 □m; mobile phase A: water+0.05% TFA, mobile phase B: acetonitrile+0.05% TFA; flow rate: 1.5000 mL/min; gradient: 5% B to 60% B in 2.10 min; 254 nm; Rt: 1.426 min.

$^1H$ NMR (400 MHz, DMSO-$d_6$) δ 9.65 (s, 1H), 9.31 (d, J=9.2 Hz, 1H), 8.35 (s, 1H), 8.31 (d, J=8.8 Hz, 1H), 8.23 (d, J=9.2 Hz, 1H), 8.15 (d, J=4.4 Hz, 1H), 8.06 (d, J=9.2 Hz, 1H), 7.19 (t, J=4.8 Hz, 1H), 4.93 (t, J=4.8 Hz, 2H), 4.72 (s, 1H), 3.80-3.70 (m, 2H), 3.68-3.56 (m, 2H), 3.50-3.40 (m, 3H), 3.17-3.08 (m, 2H), 1.95-1.91 (m, 2H), 1.89-1.81 (m, 2H), 1.22 (d, J=6.8 Hz, 3H). $^{19}F$ NMR (376 MHz, DMSO-$d_6$) δ-73.44.

Example 20: Synthesis of (R)-3-(6-chloro-3-methoxypyridazin-4-yl)-10-methyl-9,10,11,12-tetrahydro-8H-[1,4]diazepino[5',6':4,5]thieno[3,2-f]quinolin-8-one

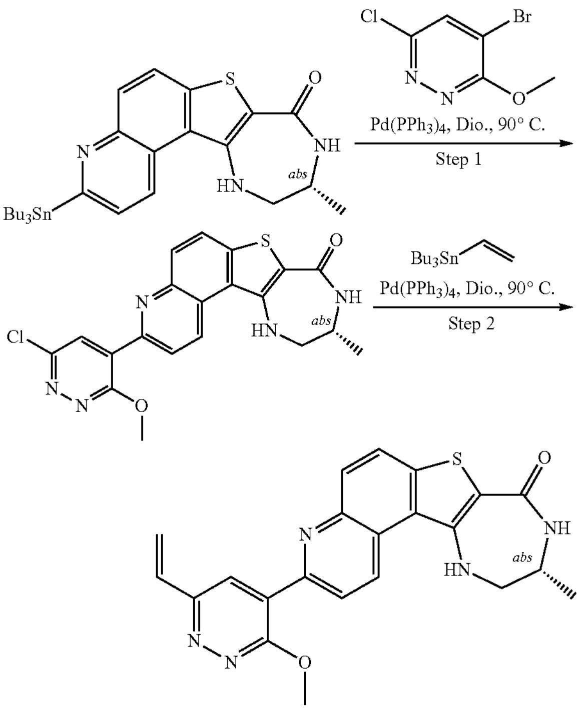

Step 1: Synthesis of (R)-3-(6-chloro-3-methoxypyridazin-4-yl)-10-methyl-9,10,11,12-tetrahydro-8H-[1,4]diazepino[5',6':4,5]thieno[3,2-f]quinolin-8-one

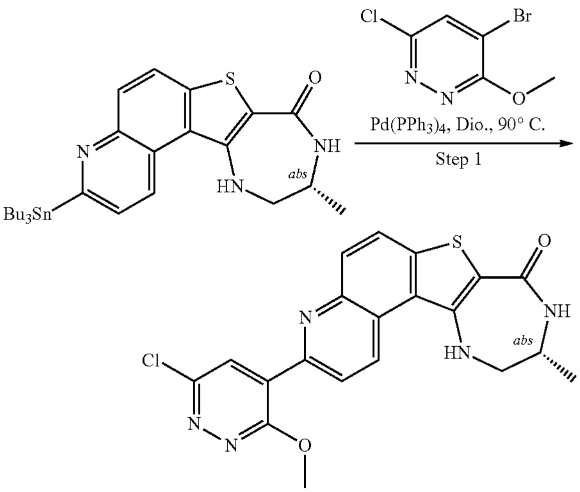

To a solution of (R)-10-methyl-3-(tributylstannyl)-9,10,11,12-tetrahydro-8H-[1,4]diazepino[5',6':4,5]thieno[3,2-f]quinolin-8-one (422 mg, 0.740 mmol, 1.10 equiv) and 4-bromo-6-chloro-3-methoxy-pyridazine (150 mg, 0.670 mmol, 1.00 equiv) in 1,4-dioxane (5.0 mL) was added $Pd(PPh_3)_4$(51 mg, 0.060 mmol, 0.10 equiv). The resulting solution was stirred at 90° C. overnight under a nitrogen atmosphere. LCMS showed the reaction was completed. The resulting solution was diluted with ethyl acetate/petroleum ether (1:1) (30 mL). The solid was collected by filtration and washed with ethyl acetate/petroleum ether (1:1) (100 mL), dichloromethane (50 mL) and hexane (50 mL). The solid was dried to give desired (R)-3-(6-chloro-3-methoxypyridazin-4-yl)-10-methyl-9,10,11,12-tetrahydro-8H-[1,4]diazepino[5',6':4,5]thieno[3,2-f]quinolin-8-one (160.4 mg, 53%) as a red solid. LCMS (ESI, m/z): 426 $[M+H]^+$. Analytic Conditions: Column: Shim-pack GIST C18-AQ Column 4.6*100 mm, 3.0 um; Mobile Phase A: 0.1% $H_3PO_4$+$H_2O$, Mobile Phase B: Acetonitrile; Flow rate: 1.5000 mL/min; Gradient: 10% B to 95% B in 6.00 min; 254 nm; Rt: 4.869 min.

$^1H$ NMR (400 MHz, DMSO-$d_6$) δ 9.25 (d, J=9.2 Hz, 1H), 8.78 (d, J=9.2 Hz, 1H), 8.36 (s, 1H), 8.18 (d, J=8.8 Hz, 1H), 8.10 (d, J=4.0 Hz, 1H), 8.04 (d, J=8.8 Hz, 1H), 7.18 (t, J=4.8 Hz, 1H), 3.78 (s, 3H), 3.66-3.58 (m, 1H), 3.54-3.42 (m, 2H), 1.20 (d, J=7.2 Hz, 3H).

Step 2: Synthesis of (R)-3-(3-methoxy-6-vinylpyridazin-4-yl)-10-methyl-9,10,11,12-tetrahydro-8H-[1,4]diazepino[5',6':4,5]thieno[3,2-f]quinolin-8-one

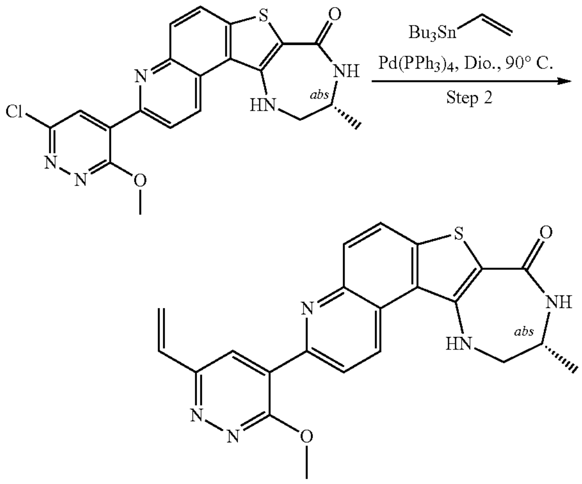

To a solution of (R)-3-(6-chloro-3-methoxypyridazin-4-yl)-10-methyl-9,10,11,12-tetrahydro-8H-[1,4]diazepino[5',6':4,5]thieno[3,2-f]quinolin-8-one (50 mg, 0.120 mmol, 1.00 equiv) and tributyl(vinyl)stannane (111 mg, 0.350 mmol, 3.00 equiv) in 1,4-dioxane (2.0 mL) was added $Pd(PPh_3)_4$(13 mg, 0.011 mmol, 0.10 equiv). The resulting solution was stirred at 100° C. overnight under a nitrogen atmosphere overnight. LCMS showed the reaction was completed. The resulting solution was concentrated under reduced pressure. The crude product was purified by preparative HPLC using the following gradient conditions: Column: SunFire Prep C18 OBD Column, 19*150 mm, 5 μm; Mobile Phase A: Water(0.05% TFA), Mobile Phase B: ACN; Flow rate: 20 mL/min; Gradient: 30% B to 65% B in 6 min, 65% B; Wave Length: 210/254 nm; RT1(min): 5.60. Purification resulted in desired (R)-3-(3-methoxy-6-vinylpyridazin-4-yl)-10-methyl-9,10,11,12-tetrahydro-8H-[1,4]diazepino[5',6':4,5]thieno[3,2-f]quinolin-8-one (6.2 mg, 12%) as a red solid. LCMS (ESI, m/z): 418 $[M+H]^+$. Analytic Conditions: Column: HALOWA C18 Column 3.0*30 mm, 1.9 um; Mobile Phase A: Water/0.05% TFA, Mobile Phase B: Acetonitrile/0.05% TFA; Flow rate: 1.2000 mL/min; Gradient: 5% B to 100% B in 2.40 min; 254 nm; Rt: 1.658 min.

$^1H$ NMR (400 MHz, DMSO-$d_6$) δ 9.25 (d, J=9.2 Hz, 1H), 8.73 (d, J=8.8 Hz, 1H), 8.63 (s, 1H), 8.18 (d, J=9.2 Hz, 1H), 8.12-8.04 (m, 3H), 7.19 (s, 1H), 6.75 (dd, J=17.6 Hz, 10.8 Hz, 1H), 6.14 (d, J=17.6 Hz, 1H), 5.62 (d, 11.2 Hz, 1H), 3.83 (s, 3H), 3.60-3.40 (m, 3H), 1.20 (d, J=7.2 Hz, 3H). $^{19}F$ NMR (376 MHz, DMSO-$d_6$) δ-74.54.

Example 21: Synthesis of (15R)-15-methyl-5-[3-(methylamino)-6-vinyl-pyridazin-4-yl]-11-thia-6,14,17-triazatetracyclo[8.8.0.0^,7.0^12,18]octadeca-1(10),2,4,6,8,12(18)-hexaen-13-one

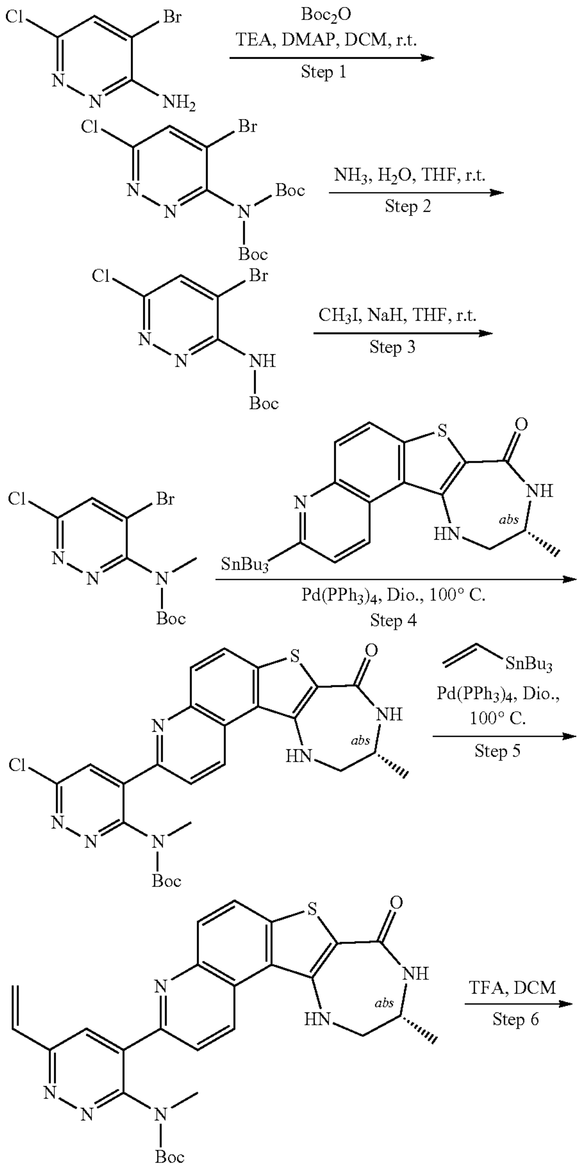

-continued

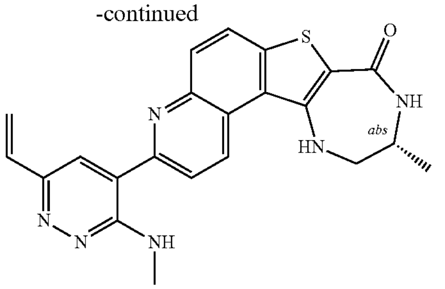

Step 1: Synthesis of tert-butyl N-(4-bromo-6-chloro-pyridazin-3-yl)-N-tert-butoxycarbonyl-carbamate

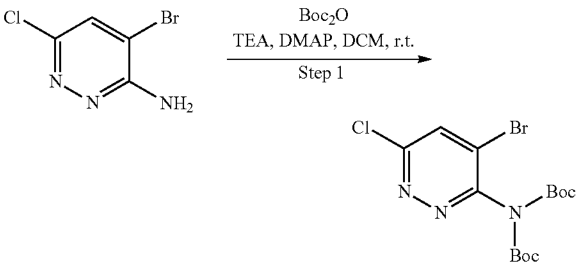

To a solution of 4-bromo-6-chloro-pyridazin-3-amine (2.0 g, 9.615 mmol, 1.00 equiv), $Boc_2O$ (4.2 g, 19.231 mmol, 2.00 equiv) and TEA (1.9 g, 2.880 mmol, 2.00 equiv) in DCM (100.0 mL) was added DMAP (117 mg, 0.962 mmol, 0.10 equiv). The resulting solution was stirred at room temperature for 2 h under a nitrogen atmosphere. LCMS showed the reaction was completed. The resulting solution was concentrated under reduced pressure. The residue was purified by column chromatography on silica gel with ethyl acetate/petroleum ether (1:1) to afford tert-butyl N-(4-bromo-6-chloro-pyridazin-3-yl)-N-tert-butoxycarbonyl-carbamate (2.5 g, 64%) as a white solid. LCMS (ESI, m/z): 408 and 410 $(M+H)^+$.

Step 2: Synthesis of tert-butyl N-(4-bromo-6-chloro-pyridazin-3-yl)carbamate

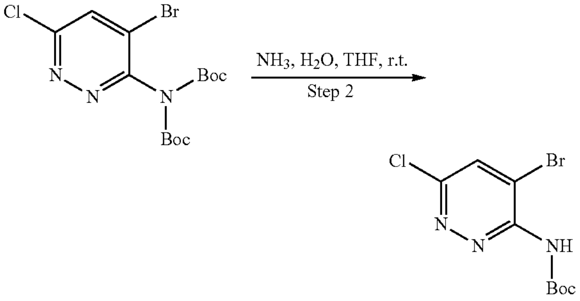

To a solution of tert-butyl N-(4-bromo-6-chloro-pyridazin-3-yl)-N-tert-butoxycarbonyl-carbamate (2.5 g, 6.112 mmol, 1.00 equiv) in THF (20.0 mL) was added $NH_3 \cdot H_2O$ (20.0 mL). The resulting solution was stirred at room temperature for 1 h. LCMS showed the reaction was completed. The reaction was diluted with water (100 mL) and extracted with ethyl acetate (3×200 ml). The combined organic layers were washed with brine (2×100 mL), dried over anhydrous sodium sulfate, filtered and concentrated under reduce pressure. The crude tert-butyl N-(4-bromo-6-chloro-pyridazin-3-yl)carbamate (2.0 g) was used directly for the next step without purification. LCMS (ESI, m/z): 308 and 309 $(M+H)^+$.

Step 3: Synthesis of tert-butyl N-(4-bromo-6-chloro-pyridazin-3-yl)-N-methyl-carbamate

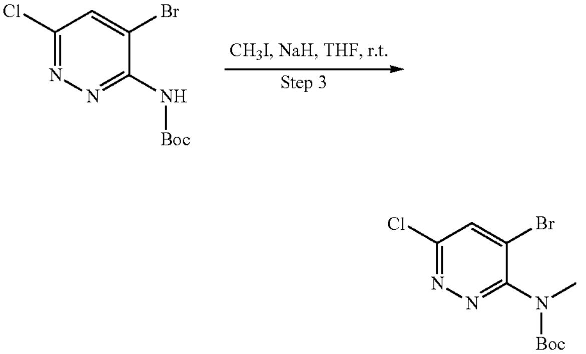

To a solution of tert-butyl N-(4-bromo-6-chloro-pyridazin-3-yl)carbamate (1.0 g, 3.236 mmol, 1.00 equiv) in THF (20.0 mL) was added NaH (116 mg, 0.730 mmol, 1.50 equiv) at 0° C. for 0.5 h. Then the $CH_3I$ (544 mg, 0.620 mmol, 1.20 equiv). The resulting solution was stirred at room temperature for 1 h. LCMS showed the reaction was completed. The reaction was quenched with water (50 mL) and extracted with ethyl acetate (3×100 mL). The organic layer was washed with brine (2×50 mL), dried over anhydrous sodium sulfate, filtered and concentrated under reduce pressure. The residue was purified by column chromatography on silica gel with ethyl acetate/petroleum ether (1:4) to afford tert-butyl N-(4-bromo-6-chloro-pyridazin-3-yl)-N-methyl-carbamate (850 mg, 81%) as a white solid. LCMS (ESI, m/z): 322 and 324 $(M+H)^+$.

Step 4: Synthesis of tert-butyl N-[6-chloro-4-[(15R)-15-methyl-13-oxo-11-thia-6,14,17-triazatetracyclo[8.8.0.0^,7.0^12,18]octadeca-1(10),2(7),3,5,8,12(18)-hexaen-5-yl]pyridazin-3-yl]-N-methyl-carbamate

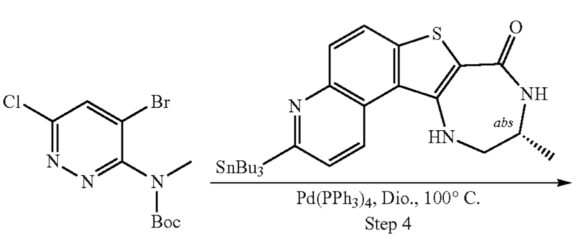

-continued

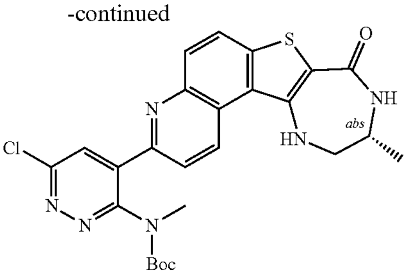

To a solution of (15R)-15-methyl-5-tributylstannyl-11-thia-6,14,17-triazatetracyclo[8.8.0.0^,7.0^12,18]octadeca-1(10),2(7),3,5,8,12(18)-hexaen-13-one (150 mg, 0.261 mmol, 1.00 equiv) and tert-butyl N-(4-bromo-6-chloro-pyridazin-3-yl)-N-methyl-carbamate (101 mg, 0.314 mmol, 1.20 equiv) in 1,4-dioxane (1.0 mL) was added $Pd(PPh_3)_4$ (30 mg, 0.026 mmol, 0.10 equiv). The resulting solution was stirred at 100° C. for 6 h under a nitrogen atmosphere. LCMS showed the reaction was completed. The resulting solution concentrated under reduced pressure. The residue was purified by column chromatography on silica gel with ethyl acetate/petroleum ether (1:2) to afford tert-butyl N-[6-chloro-4-[(15R)-15-methyl-13-oxo-11-thia-6,14,17-triazatetracyclo[8.8.0.0^,7.0^12,18]octadeca-1(10),2(7),3,5,8,12(18)-hexaen-5-yl]pyridazin-3-yl]-N-methyl-carbamate (50 mg, 36%) as a yellow solid. LCMS (ESI, m/z): 525 $(M+H)^+$.

Step 5: Synthesis of tert-butyl N-methyl-N-[4-[(15R)-15-methyl-13-oxo-11-thia-6,14,17-triazatetracyclo[8.8.0.0^,7.0^12,18]octadeca-1(10),2(7),3,5,8,12(18)-hexaen-5-yl]-6-vinyl-pyridazin-3-yl]carbamate

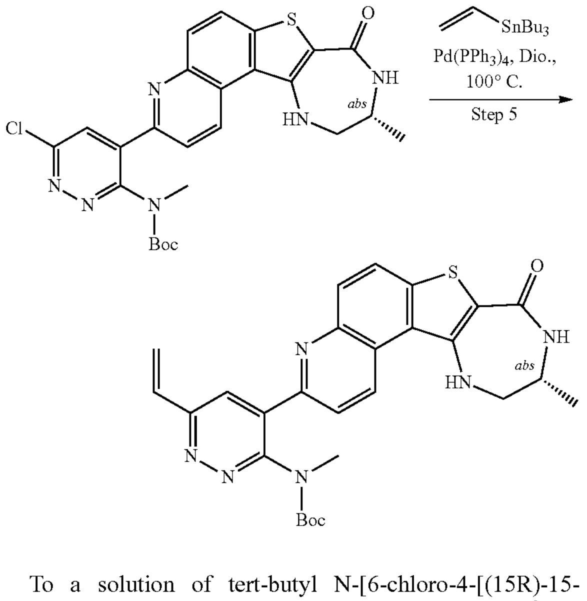

To a solution of tert-butyl N-[6-chloro-4-[(15R)-15-methyl-13-oxo-11-thia-6,14,17-triazatetracyclo[8.8.0.0^,7.0^12,18]octadeca-1(10),2(7),3,5,8,12(18)-hexaen-5-yl]pyridazin-3-yl]-N-methyl-carbamate (30 mg, 0.060 mmol, 1.00 equiv) and tributyl(vinyl)stannane (54 mg, 0.170 mmol, 3.00 equiv) in 1,4-dioxane (2.0 mL) was added $Pd(PPh_3)_4$ (4 mg, 0.010 mmol, 0.10 equiv). The resulting solution was stirred at 100° C. for 6 h under a nitrogen atmosphere. LCMS showed the reaction was completed. The resulting solution concentrated under reduced pressure. The residue was purified by column chromatography on silica gel with dichloromethane/methanol (15:1) to afford tert-butyl N-methyl-N-[4-[(15R)-15-methyl-13-oxo-11-thia-6,14,17-triazatetracyclo[8.8.0.0^,7.0^12,18]octadeca-1(10),2(7),3,5,8,12(18)-hexaen-5-yl]-6-vinyl-pyridazin-3-yl]carbamate (20 mg, 67%). LCMS (ESI, m/z): 517 $[M+H]^+$.

Step 6: Synthesis of (15R)-15-methyl-5-[3-(methylamino)-6-vinyl-pyridazin-4-yl]-11-thia-6,14,17-triazatetracyclo[8.8.0.0^,7.0^12,18]octadeca-1(10),2,4,6,8,12(18)-hexaen-13-one

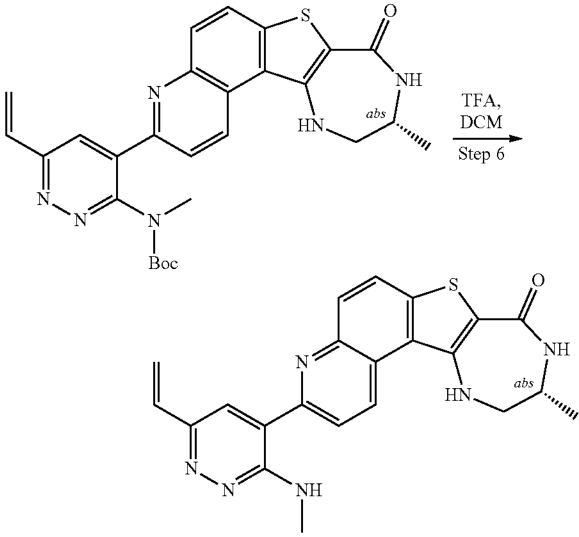

To a solution of tert-butyl N-methyl-N-[4-[(15R)-15-methyl-13-oxo-11-thia-6,14,17-triazatetracyclo[8.8.0.0^,7.0^12,18]octadeca-1(10),2,4,6,8,12(18)-hexaen-5-yl]-6-vinyl-pyridazin-3-yl]carbamate (20 mg, 0.0400 mmol, 1.00 equiv) in DCM (3.0 mL) was added dropwise TFA (0.5 mL). The resulting solution was stirred for 1 h at room temperature. LCMS showed the reaction was completed. The solution was concentrated by reduced pressure and the residue was purified by Prep-HPLC using the following conditions: Column: SunFire Prep C18 OBD Column, 19*150 mm, 5 μm; Mobile Phase A: Water (0.05% TFA), Mobile Phase B: MeCN; Flow rate: 20 mL/min; Gradient: 25% B to 43% B in 5 min, 43% B; Wave Length: 210/254 nm; RT1(min): 4.95. Purification resulted in desired (15R)-15-methyl-5-[3-(methylamino)-6-vinyl-pyridazin-4-yl]-11-thia-6,14,17-triazatetracyclo[8.8.0.0^,7.0^12,18]octadeca-1(10),2,4,6,8,12(18)-hexaen-13-one (8.7 mg, 52%) as an orange solid. LCMS (ESI, m z): 417 $[M+H]^+$. Analytic Conditions: Column: HALO C18 100A Column 3.0*30 mm, 1.9 um; Mobile Phase A: Water/0.05% TFA, Mobile Phase B: Acetonitrile/0.05% TFA; Flow rate: 1.2000 mL/min; Gradient: 5% B to 100% B in 2.40 min; 254 nm; Rt: 1.429 min.

$^1H$ NMR (400 MHz, DMSO-$d_6$) δ 10.75 (s, 1H), 9.40 (d, J=8.8 Hz, 1H), 8.70 (t, J=6.0 Hz, 2H), 8.37 (d, J=8.8 Hz, 1H), 8.30 (d, J=8.8 Hz, 1H), 8.17 (d, J=4.4 Hz, 1H), 7.23 (d, J=8.4 Hz, 1H), 6.95 (dd, J=17.6 Hz, 11.2 Hz, 1H), 6.49 (d, J=17.6 Hz, 1H), 5.77 (d, J=11.2 Hz, 1H), 3.51 (d, J=8.0 Hz, 2H), 3.27 (s, 3H), 1.21 (d, J=7.2 Hz, 3H). $^{19}F$ NMR (376 MHz, DMSO-$d_6$) δ−74.60.

Example 22: Synthesis of (R)-3-(3-(dimethylamino)-6-vinylpyridazin-4-yl)-10-methyl-9,10,11,12-tetrahydro-8H-[1,4]diazepino[5',6':4,5]thieno[3,2-f]quinolin-8-one

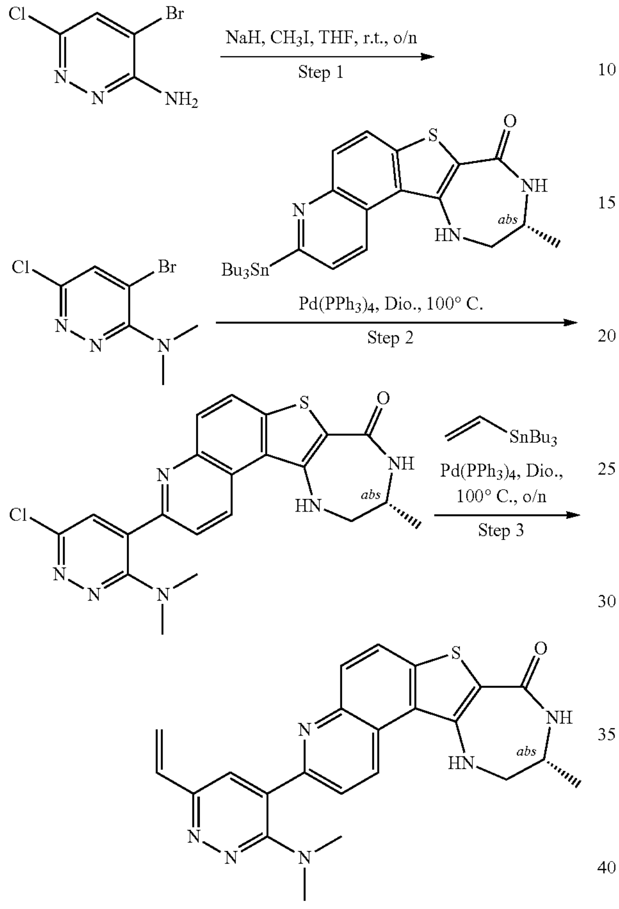

Step 1: Synthesis of 4-bromo-6-chloro-N,N'-dimethyl-pyridazin-3-amine

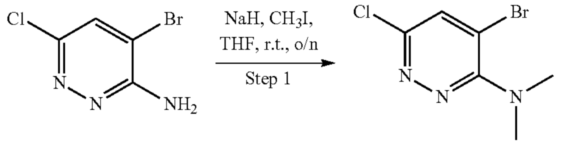

To a solution of 4-bromo-6-chloro-pyridazin-3-amine (300 mg, 1.440 mmol, 1.00 equiv) in THF (5.0 mL) was added NaH (41 mg, 1.730 mmol, 1.20 equiv) at ice bath and stirred for 30 min at 0° C. Then the $CH_3I$ (617 mg, 4.320 mmol, 3.00 equiv) was added the resulting solution and stirred at room temperature overnight. LCMS showed the reaction was completed. The resulting solution was quenched with water (30 mL) and extracted with ethyl acetate (3×50 mL). The combined organic layers were washed with brine (2×50 mL), dried over anhydrous sodium sulfate, filtered and concentrated under reduced pressure. The residue was purified by thin layer chromatography developed with ethyl acetate/petroleum ether (1:4) to afford 4-bromo-6-chloro-N,N'-dimethyl-pyridazin-3-amine (250 mg, 73%) as a yellow oil. LCMS (ESI, m z): 236 $[M+H]^+$.

Step 2: Synthesis of (R)-3-(6-chloro-3-(dimethylamino)pyridazin-4-yl)-10-methyl-9,10,11,12-tetrahydro-8H-[1,4]diazepino[5',6':4,5]thieno[3,2-f]quinolin-8-one

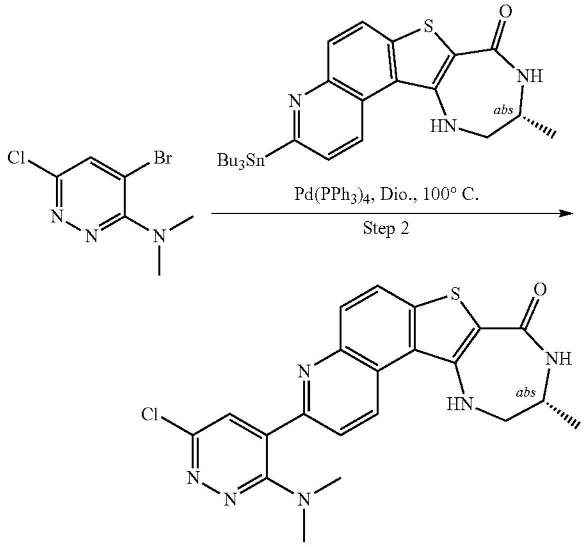

To a solution of (R)-10-methyl-3-(tributylstannyl)-9,10,11,12-tetrahydro-8H-[1,4]diazepino[5',6':4,5]thieno[3,2-f]quinolin-8-one (300 mg, 0.520 mmol, 1.00 equiv) and 4-bromo-6-chloro-N,N-dimethyl-pyridazin-3-amine (150 mg, 0.638 mmol, 1.20 equiv) in 1,4-dioxane (10.0 mL) was added $Pd(PPh_3)_4$(44 mg, 0.050 mmol, 0.10 equiv). The resulting solution was stirred at 100° C. under a nitrogen atmosphere overnight. LCMS showed the reaction was completed. The resulting solution was concentrated under reduced pressure. The residue was purified by reverse flash chromatography with water (0.05% TFA)/MeCN (2:1) to afford (R)-3-(6-chloro-3-(dimethylamino)pyridazin-4-yl)-10-methyl-9,10,11,12-tetrahydro-8H-[1,4]diazepino[5',6':4,5]thieno[3,2-f]quinolin-8-one (80 mg, 34%) as a yellow solid. LCMS (ESI, m z): 439 $[M+H]^+$.

Step 3: Synthesis of (R)-3-(3-(dimethylamino)-6-vinylpyridazin-4-yl)-10-methyl-9,10,11,12-tetrahydro-8H-[1,4]diazepino[5',6':4,5]thieno[3,2-f]quinolin-8-one

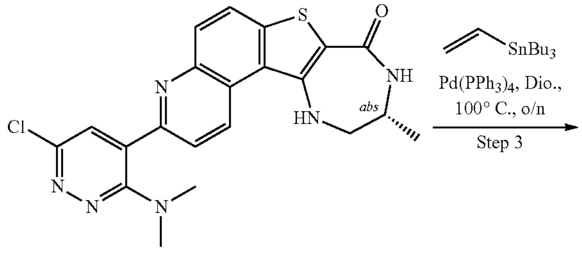

-continued

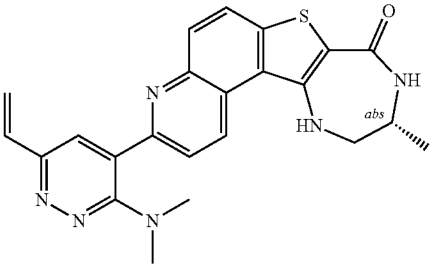

To a solution of (R)-3-(6-chloro-3-(dimethylamino)pyridazin-4-yl)-10-methyl-9,10,11,12-tetrahydro-8H-[1,4]diazepino[5',6':4,5]thieno[3,2-f]quinolin-8-one (30 mg, 0.070 mmol, 1.00 equiv) and tributyl(vinyl)stannane (65 mg, 0.210 mmol, 3.00 equiv) in 1,4-dioxane (2.0 mL) was added and $Pd(PPh_3)_4$(5 mg, 0.010 mmol, 0.10 equiv). The resulting solution was stirred at 100° C. under a nitrogen atmosphere overnight. LCMS showed the reaction was completed. The resulting solution was concentrated under reduced pressure. The residue was purified by Prep-HPLC using the following gradient conditions: Column: SunFire Prep C18 OBD Column, 19*150 mm, 5 μm; Mobile Phase A: Water (0.05% TFA), Mobile Phase B: MeCN; Flow rate: 20 mL/min; Gradient: 20% B to 40% B in 5 min, 40% B; Wave Length: 210/254 nm; RT1(min): 5.13. Purification resulted in desired (R)-3-(3-(dimethylamino)-6-vinylpyridazin-4-yl)-10-methyl-9,10,11,12-tetrahydro-8H-[1,4]diazepino[5',6':4,5]thieno[3,2-f]quinolin-8-one (5.6 mg, 18%) as an orange solid. LCMS (ESI, m/z): 431[M+H]$^+$. Analytic Conditions: Column: Shim-pack GIST C18-AQ Column 4.6*100 mm, 3.0 um; Mobile Phase A: 0.1% $H_3PO_4$+$H_2O$, Mobile Phase B: Acetonitrile; Flow rate: 1.5000 mL/min; Gradient: 10% B to 95% B in 8.00 min; 254 nm; Rt: 4.889 min.

$^1$H NMR (400 MHz, DMSO-$d_6$) δ 9.31 (d, J=8.8 Hz, 1H), 8.21 (d, J=8.8 Hz, 1H), 8.14 (d, J=4.4 Hz, 1H), 8.12-8.01 (m, 2H), 7.97 (d, J=8.8 Hz, 1H), 7.19 (s, 1H), 6.98 (dd, J=18.0 Hz, 11.2 Hz, 1H), 6.29 (d, J=18.0 Hz, 1H), 5.40 (d, J=11.2 Hz, 1H), 3.62-3.60 (m, 1H), 3.51-3.48 (m, 2H), 2.83 (s, 6H), 1.21 (d, J=6.8 Hz, 3H).

Example 23: Synthesis of (R)-3-(5-(difluoromethyl)-2-vinylpyridin-4-yl)-10-methyl-9,10,11,12-tetrahydro-8H-[1,4]diazepino[5',6':4,5]thieno[3,2-f]quinolin-8-one

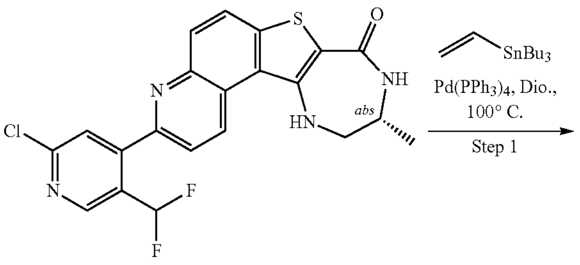

-continued

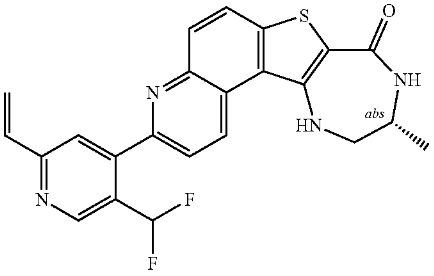

To a solution of (R)-3-(2-chloro-5-(difluoromethyl)pyridin-4-yl)-10-methyl-9,10,11,12-tetrahydro-8H-[1,4]diazepino[5',6':4,5]thieno[3,2-f]quinolin-8-one (50 mg, 0.110 mmol, 1.00 equiv) in 1,4-dioxane (2.0 mL) was added tributyl(vinyl)stannane (106 mg, 0.340 mmol, 3.00 equiv) and $Pd(PPh_3)_4$(9 mg, 0.010 mmol, 0.10 equiv). The resulting solution was stirred at 100° C. under nitrogen atmosphere overnight. LCMS showed the reaction was completed. The resulting mixture was concentrated under reduced pressure. The residue was purified by reverse flash chromatography with water(0.05% $NH_4HCO_3$)/MeCN(1:1). Purification resulted in (R)-3-(5-(difluoromethyl)-2-vinylpyridin-4-yl)-10-methyl-9,10,11,12-tetrahydro-8H-[1,4]diazepino[5',6':4,5]thieno[3,2-f]quinolin-8-one (8.3 mg, 16%) as a red solid. LCMS (ESI, m/z): 437 [M+H]$^+$. Analytic Conditions: Column: HALOWA C18 Column 3.0*30 mm, 1.9 um; Mobile Phase A: Water/0.05% TFA, Mobile Phase B: Acetonitrile/0.05% TFA; Flow rate: 1.2000 mL/min; Gradient: 5% B to 100% B in 2.40 min; 254 nm; Rt: 1.804 min.

$^1$H NMR (400 MHz, DMSO-$d_6$) δ 9.36 (d, J=8.8 Hz, 1H), 8.97 (s, 1H), 8.22 (d, J=8.8 Hz, 1H), 8.13 (d, J=8.8 Hz, 1H), 8.05 (d, J=8.8 Hz, 1H), 7.75 (t, J=54.4 Hz, 1H), 7.21 (t, J=5.2 Hz, 1H), 7.02 (dd, J=17.2, 10.8 Hz, 1H), 6.50 (d, J=17.2 Hz, 1H), 5.68 (d, J=11.2 Hz, 1H), 3.63-3.62 (m, 1H), 3.52-3.45 (m, 2H), 1.20 (d, J=6.8 Hz, 3H).

Example 24: Synthesis of (R)-10-methyl-3-(3-(2-morpholinoethoxy)-6-vinylpyridazin-4-yl)-9,10,11,12-tetrahydro-8H-[1,4]diazepino[5',6':4,5]thieno[3,2-f]quinolin-8-one

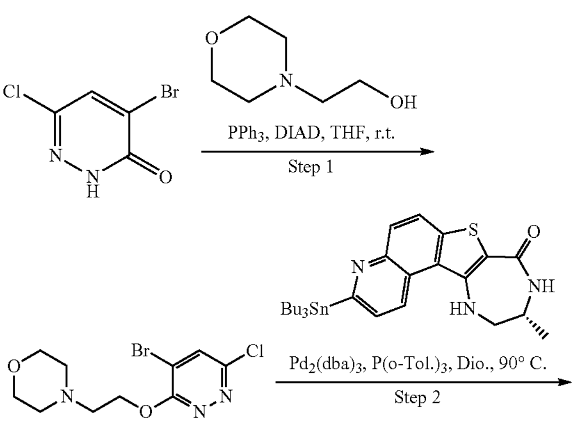

-continued

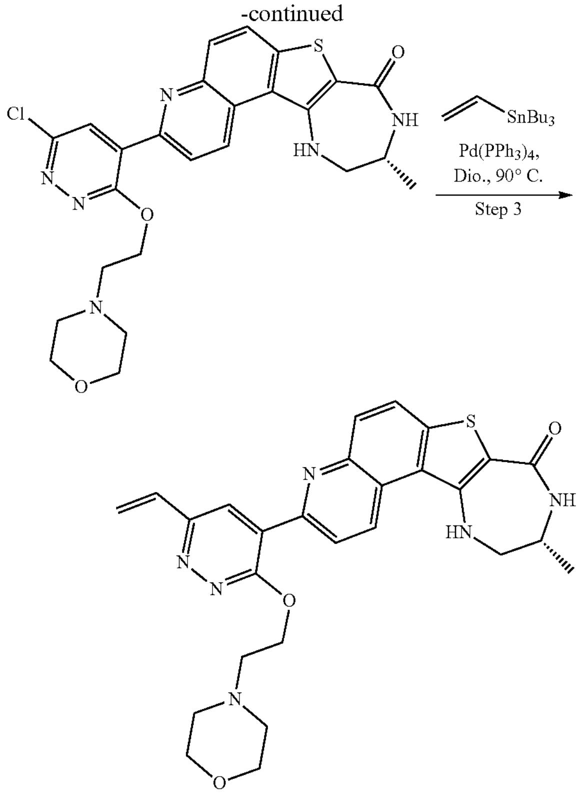

Step 1: Synthesis 4-[2-(4-bromo-6-chloro-pyridazin-3-yl)oxyethyl]morpholine

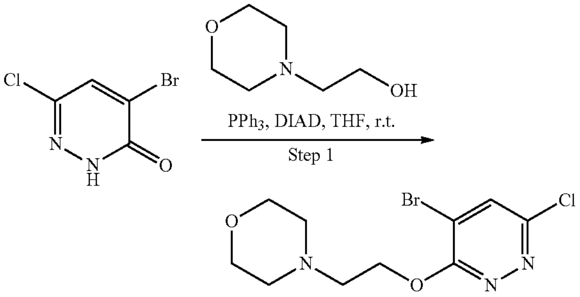

To a solution of 5-bromo-3-chloro-1H-pyridazin-6-one (1.5 g, 7.16 mmol), 2-morpholinoethanol (1.9 g, 14.320 mmol, 1.00 equiv) and $PPh_3$ (5 g, 17.910 mmol) in THF (80 mL) was added dropwise DIAD (3.5 mL, 17.910 mmol, 1.30 equiv). The resulting mixture was stirred at room temperature for 2 h under a nitrogen atmosphere. LCMS showed the reaction was completed. The resulting solution was diluted with water (300 mL) and extracted with ethyl acetate (2×500 mL). The combined organic layers were washed with brine (2×300 mL), dried over sodium sulfate, filtered and concentrated under reduce pressure. The residue was purified by reverse flash chromatography with water (0.05% TFA)/MeCN (1:2) to give crude product. The crude product was purified by Prep-HPLC using the following conditions: Column: Welch Utimate AQ-C18, 50*250 mm*10 μm; Mobile Phase A: Water (0.05% TFA), Mobile Phase B: MeCN; Flow rate: 100 mL/min; Gradient: 3% B to 13% B in 22 min, 13% B; Wave Length: 210/254 nm; RT1(min): 18.9. Purification resulted in desired 4-[2-(4-bromo-6-chloro-pyridazin-3-yl)oxyethyl]morpholine (200 mg, 8%) as a white solid. LCMS (ESI, m/z): 322 $[M+H]^+$.

Step 2: Synthesis of ((R)-3-(6-chloro-3-(2-morpholinoethoxy)pyridazin-4-yl)-10-methyl-9,10,11,12-tetrahydro-8H-[1,4]diazepino[5',6':4,5]thieno[3,2-f]quinolin-8-one

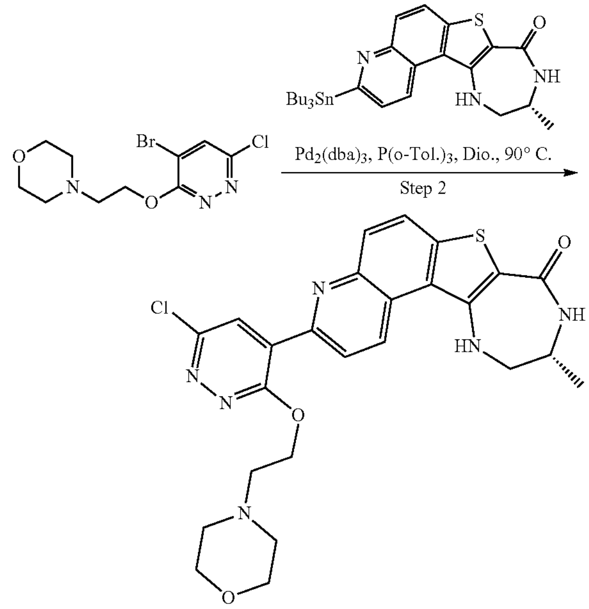

To a solution of 4-[2-(4-bromo-6-chloro-pyridazin-3-yl)oxyethyl]morpholine (30 mg, 0.090 mmol, 1.00 equiv) and (R)-10-methyl-3-(tributylstannyl)-9,10,11,12-tetrahydro-8H-[1,4]diazepino[5',6':4,5]thieno[3,2-f]quinolin-8-one (80 mg, 0.140 mmol, 1.50 equiv) in 1,4-dioxane (2.0 mL) was added $Pd_2(dba)_3$ (17 mg, 0.020 mmol, 0.20 equiv) and $P(o\text{-}Tol.)_3$ (6 mg, 0.020 mmol, 0.20 equiv). The resulting mixture was stirred at 90° C. for 2 h under a nitrogen atmosphere. LCMS showed the reaction was completed. The resulting solution was diluted with ethyl acetate (20 mL). The solid was filtered out and the filtration was concentrated under reduced pressure. The residue was purified by Prep-HPLC using the following conditions: Column: SunFire Prep C18 OBD Column, 19*150 mm, 5 μm; Mobile Phase A: Water(0.05% TFA), Mobile Phase B: MeCN; Flow rate: 20 mL/min; Gradient: 20% B to 40% B in 6 min, 40% B; Wave Length: 210/254 nm; RT1(min): 5.62. Purification resulted in desired ((R)-3-(6-chloro-3-(2-morpholinoethoxy)pyridazin-4-yl)-10-methyl-9,10,11,12-tetrahydro-8H-[1,4]diazepino[5',6':4,5]thieno[3,2-f]quinolin-8-one (9.6 mg, 19.5% yield) as a yellow solid. LCMS (ESI, m/z):525 $[M+H]^+$. Analytic Conditions: column: HALO C18 Column 3*30 mm, 2.7 □m; mobile phase A: water+0.05% TFA, mobile phase B: acetonitrile+0.05% TFA; flow rate: 1.5000 mL/min; gradient: 5% B to 65% B in 1.7 min; 254 nm; Rt: 1.300 min.

$^1H$ NMR (400 MHz, DMSO-$d_6$+$D_2O$) δ 9.30 (d, J=8.8 Hz, 1H), 8.37 (s, 1H), 8.30 (d, J=8.8 Hz, 1H), 8.24 (d, J=8.8 Hz, 1H), 8.07 (d, J=8.8 Hz, 1H), 4.97 (t, J=4.4 Hz, 2H), 3.92-3.82 (m, 2H), 3.72 (t, J=4.8 Hz, 3H), 3.69-3.59 (m, 3H), 3.52-3.44 (m, 3H), 3.31-3.20 (m, 2H), 1.22 (d, J=6.8 Hz, 3H).

Step 3: Synthesis of (R)-10-methyl-3-(3-(2-morpholinoethoxy)-6-vinylpyridazin-4-yl)-9,10,11,12-tetrahydro-8H-[1,4]diazepino[5',6':4,5]thieno[3,2-f]quinolin-8-one

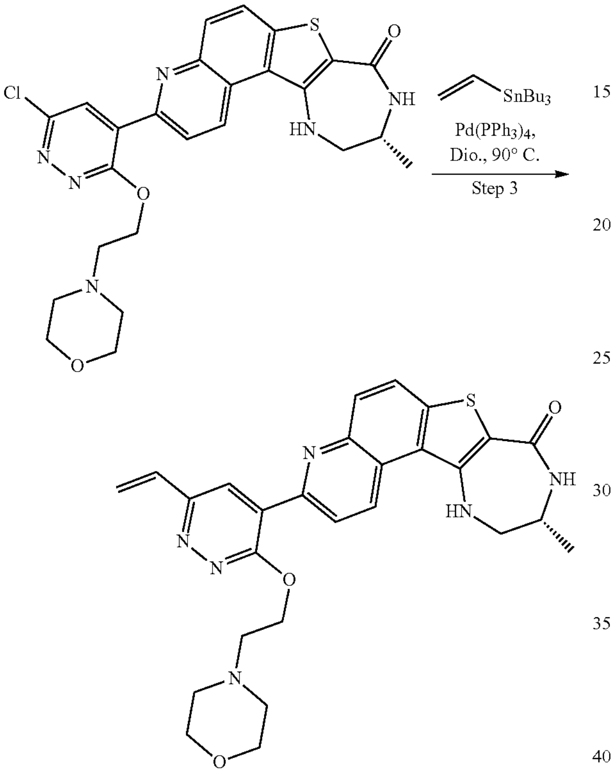

To a solution of ((R)-3-(6-chloro-3-(2-morpholinoethoxy)pyridazin-4-yl)-10-methyl-9,10,11,12-tetrahydro-8H-[1,4]diazepino[5',6':4,5]thieno[3,2-f]quinolin-8-one (20 mg, 0.040 mmol, 1.00 equiv) and tributyl(vinyl)stannane (36 mg, 0.110 mmol, 3.00 equiv) in 1,4-dioxane (2.0 mL) was added $Pd(PPh_3)_4$(9 mg, 0.010 mmol, 0.20 equiv). The resulting mixture was stirred at 90° C. for 3 h under a nitrogen atmosphere. LCMS showed the reaction was completed. The resulting solution was concentrated under reduce pressure. The residue was purified by column chromatography on silica gel with dichloromethane/methanol (20:1) to give crude product. The crude product was purified by Prep-HPLC using the following conditions: Column: SunFire Prep C18 OBD Column, 19*150 mm, 5 μm; Mobile Phase A: Water (0.05% TFA), Mobile Phase B: MeCN; Flow rate: 20 mL/min; Gradient: 20% B to 60% B in 6 min, 60% B; Wave Length: 254 nm; RT1(min): 5.56. Purification resulted in desired (R)-10-methyl-3-(3-(2-morpholinoethoxy)-6-vinylpyridazin-4-yl)-9,10,11,12-tetrahydro-8H-[1,4]diazepino[5',6':4,5]thieno[3,2-f]quinolin-8-one (4.5 mg, 22%) as a brown solid. LCMS (ESI, m/z):517 $[M+H]^+$. Analytic Conditions: column: HALO C18 Column 3*30 mm, 2.7 □m; mobile phase A: water+0.05% TFA, mobile phase B: acetonitrile+0.05% TFA; flow rate: 1.5000 mL/min; gradient: 5% B to 65% B in 1.70 min; 254 nm; Rt: 1.307 min.

$^1H$ NMR (400 MHz, DMSO-$d_6$+$D_2O$) δ 9.30 (d, J=8.8 Hz, 1H), 8.41 (s, 1H), 8.27 (d, J=8.8 Hz, 1H), 8.22 (d, J=8.8 Hz, 1H), 8.08 (d, J=8.8 Hz, 1H), 7.10 (dd, J=18.0, 11.2 Hz, 1H), 6.37 (d, J=18.0 Hz, 1H), 5.72 (d, J=11.2 Hz, 1H), 4.99 (t, J=4.4 Hz, 2H), 4.03-3.83 (m, 2H), 3.75-3.68 (m, 3H), 3.63-3.56 (m, 2H), 3.56-3.43 (m, 4H), 3.32-3.09 (m, 2H), 1.22 (d, J=6.8 Hz, 3H).

Example 25: Synthesis of (R)-3-(6-ethynyl-3-(2-morpholinoethoxy)pyridazin-4-yl)-10-methyl-9,10,11,12-tetrahydro-8H-[1,4]diazepino[5',6':4,5]thieno[3,2-f]quinolin-8-one

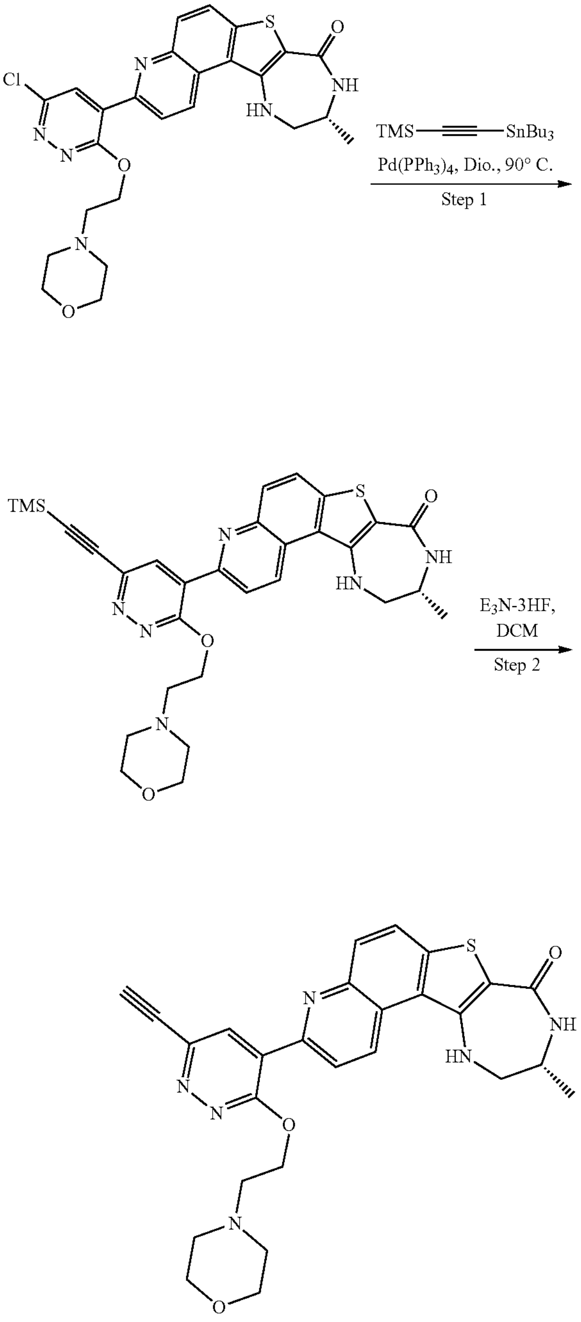

Step 1: Synthesis of (R)-10-methyl-3-(3-(2-morpholinoethoxy)-6-((trimethylsilyl)ethynyl)pyridazin-4-yl)-9,10,11,12-tetrahydro-8H-[1,4]diazepino[5',6':4,5]thieno[3,2-f]quinolin-8-one

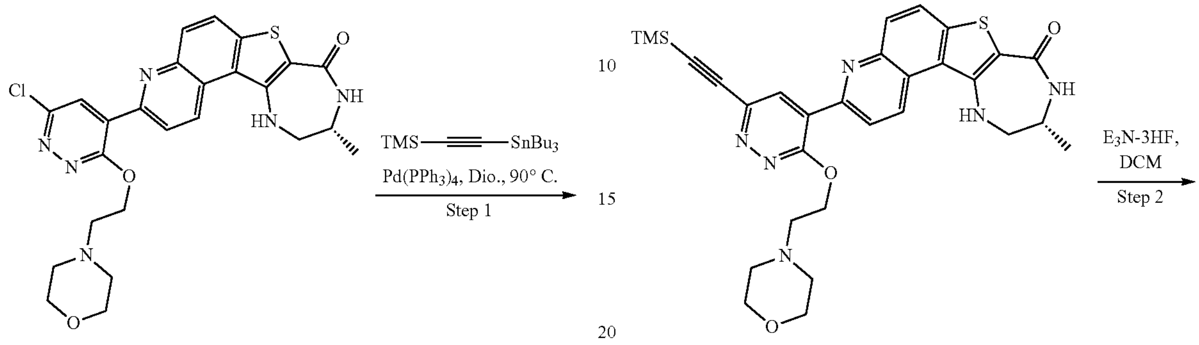

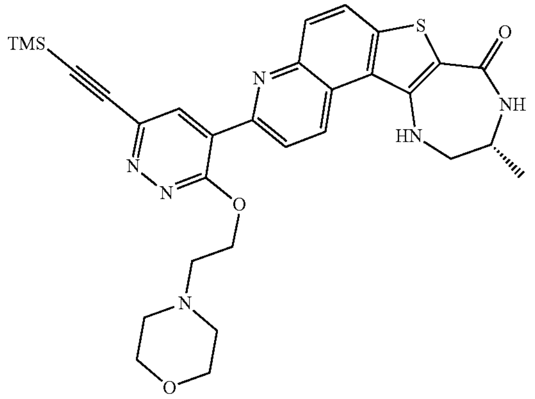

To a solution of ((R)-3-(6-chloro-3-(2-morpholinoethoxy)pyridazin-4-yl)-10-methyl-9,10,11,12-tetrahydro-8H-[1,4]diazepino[5',6':4,5]thieno[3,2-f]quinolin-8-one (30 mg, 0.060 mmol, 1.00 equiv) and trimethyl(2-tributylstannylethynyl)silane (66 mg, 0.170 mmol, 3.00 equiv) in 1,4-dioxane (2.0 mL) was added $Pd(PPh_3)_4$(13 mg, 0.010 mmol, 0.20 equiv). The resulting mixture was stirred at 90° C. for 3 h under a nitrogen atmosphere. LCMS showed the reaction was completed. The resulting solution was concentrated under reduce pressure and the residue was purified by column chromatography on silica gel with DCM/MeOH (20:1) to give (R)-10-methyl-3-(3-(2-morpholinoethoxy)-6-((trimethylsilyl)ethynyl)pyridazin-4-yl)-9,10,11,12-tetrahydro-8H-[1,4]diazepino[5',6':4,5]thieno[3,2-f]quinolin-8-one (15 mg, 45%) as a yellow oil. LCMS (ESI, m/z): 587 $[M+H]^+$.

Step 2: Synthesis of (R)-3-(6-ethynyl-3-(2-morpholinoethoxy)pyridazin-4-yl)-10-methyl-9,10,11,12-tetrahydro-8H-[1,4]diazepino[5',6':4,5]thieno[3,2-f]quinolin-8-one

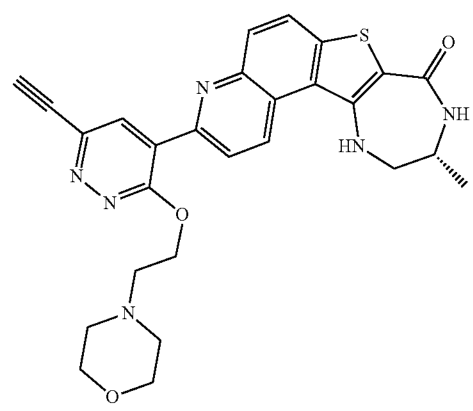

To a solution of (R)-10-methyl-3-(3-(2-morpholinoethoxy)-6-((trimethylsilyl)ethynyl)pyridazin-4-yl)-9,10,11,12-tetrahydro-8H-[1,4]diazepino[5',6':4,5]thieno[3,2-f]quinolin-8-one (13 mg, 0.020 mmol, 1.00 equiv) in DCM (2.0 mL), was added $Et_3N$-3HF (0.1 mL). The resulting mixture was stirred at room temperature for 1 h. LCMS showed the reaction was completed. The resulting solution was concentrated under reduce pressure and the residue was purified by Prep-HPLC using the following conditions: Column: SunFire Prep C18 OBD Column, 19*150 mm, 5 μm; Mobile Phase A: Water (0.05% TFA), Mobile Phase B: MeCN; Flow rate: 25 mL/min; Gradient: 15% B to 35% B in 5 min, 35% B; Wave Length: 254 nm; RT1(min): 5.56. Purification resulted in desired (R)-3-(6-ethynyl-3-(2-morpholinoethoxy)pyridazin-4-yl)-10-methyl-9,10,11,12-tetrahydro-8H-[1,4]diazepino[5',6':4,5]thieno[3,2-f]quinolin-8-one (1 mg, 8%) as a yellow solid. LCMS (ESI, m/z):515 $[M+H]^+$. Analytic Conditions: column: HALO C18 Column 3*30 mm, 2.7 □m; mobile phase A: water+0.05% TFA, mobile phase B: acetonitrile+0.05% TFA; flow rate: 1.5000 mL/min; gradient: 5% B to 60% B in 1.80 min; 254 nm; RT: 1.383 min.

$^1H$ NMR (400 MHz, DMSO-$d_6$+$D_2O$) δ 9.29 (d, J=8.8 Hz, 1H), 8.39 (s, 1H), 8.32 (d, J=8.8 Hz, 1H), 8.23 (d, J=8.8 Hz, 1H), 8.07 (d, J=9.2 Hz, 1H), 4.96 (s, 2H), 4.68 (s, 1H), 3.80-3.60 (m, 5H), 3.52-3.36 (m, 6H), 3.22-3.03 (m, 2H), 1.24 (d, J=6.4 Hz, 3H).

Example 26: Synthesis of (R)-10-methyl-3-(3-methyl-6-vinylpyridazin-4-yl)-9,10,11,12-tetrahydro-8H-[1,4]diazepino[5',6':4,5]thieno[3,2-f]quinolin-8-one

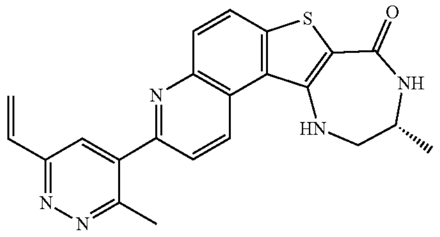 [SMILES: C=Cc1cc(-c2ccc3c(ccc4sc5c(c43)NC[C@@H](C)NC5=O)n2)c(C)nn1]

Step 1: Preparation of 4-chloro-3-methyl-6-vinylpyridazine

A 20 mL reaction vial was charged with a stir bar, potassium vinyltrifluoroborate (82 mg, 0.613 mmol), 4,6-dichloro-3-methylpyridazine (100 mg, 0.613 mmol), Pd(dppf)Cl2, DCM adduct (50.1 mg, 0.061 mmol), cesium carbonate (500 mg, 1.534 mmol), Dioxane (2454 μl), and Water (613 μl) to give a orange suspension. The resulting mixture was degassed by bubbling of nitrogen for 5 min and then stirred at 60° C. for 16 h. LC MS indicated significant product formation. The reaction mixture was concentrated under reduced pressure, diluted in ethyl acetate, and filtered through a pad of Celite. The filtrate was concentrated under reduced pressure to yield the crude product, which was purified by flash chromatography (0-100% ethyl acetate in heptane; desired product eluted ~50%). The pure fractions were combined and concentrated to yield 4-chloro-3-methyl-6-vinylpyridazine (26 mg, 0.168 mmol, 27.4% yield) as a clear oil. MS ESI m/z 155.2 and 157.2 $(M+H)^+$ Step 2: Preparation of (R)-10-methyl-3-(3-methyl-6-vinylpyridazin-4-yl)-9,10,11,12-tetrahydro-8H-[1,4]diazepino[5',6':4,5]thieno[3,2-f]quinolin-8-one A 4 mL reaction vial was charged with a stir bar, (R)-10-methyl-3-(tributylstannyl)-9,10,11,12-tetrahydro-8H-[1,4]diazepino[5',6':4,5]thieno[3,2-f]quinolin-8-one (33.3 mg, 0.058 mmol), 4-chloro-3-methyl-6-vinylpyridazine (9 mg, 0.058 mmol), PdCl2(dtbpf) (3.79 mg, 5.82 μmol), and Dioxane (291 μl) to give a brown solution. The reaction was degassed by evacuating and backfilling 3 times with nitrogen. The resulting mixture was stirred at 80° C. for 16 h. LC MS indicated significant starting material was consumed. The reaction mixture was concentrated under reduced pressure, dissolved in ethyl acetate, and filtered through a pad of Celite. The crude product was concentrated under reduced pressure. The crude material was purified via preparative Reverse Phase chromatography with the following conditions: Column: XBridge C18, 19 mm×200 mm, m particles; Mobile Phase A: 5:95 acetonitrile: water with 10 mM ammonium acetate; Mobile Phase B: 95:5 acetonitrile: water with 10 mM ammonium acetate; Gradient: a 0-min hold at 7% B, 7-47% B over 20 min, then a 4-min hold at 100% B; Flow Rate: 20 mL/min; Column Temperature: 25° C. Fraction collection was triggered by UV (220 nm) and MS (ESI+). Fractions containing the desired product were combined and dried via centrifugal evaporation, affording (R)-10-methyl-3-(3-methyl-6-vinylpyridazin-4-yl)-9,10,11,12-tetrahydro-8H-[1,4]diazepino[5',6':4,5]thieno[3,2-f]quinolin-8-one (1.4 mg, 0.003 mmol, 6% yield).

$^1$H NMR (500 MHz, DMSO-$d_6$) δ 9.35 (d, J=8.9 Hz, 1H), 8.22 (d, J=9.0 Hz, 1H), 8.12 (s, 2H), 8.08 (d, J=8.8 Hz, 1H), 8.05 (d, J=8.9 Hz, 1H), 7.21 (br s, 1H), 7.11 (dd, J=17.9, 11.1 Hz, 1H), 6.48 (d, J=17.8 Hz, 1H), 5.75 (d, J=11.2 Hz, 1H), 3.63 (br s, 2H), 2.80 (s, 3H), 1.21 (d, J=6.8 Hz, 3H). One proton obscured by water. MS ESI m/z 402.1 $(M+H)^+$ Example 27: Synthesis of Methyl (R)-4-(10-methyl-8-oxo-9,10,11,12-tetrahydro-8H-[1,4]diazepino[5',6':4,5]thieno[3,2-f]quinolin-3-yl)-6-vinylpyridazine-3-carboxylate

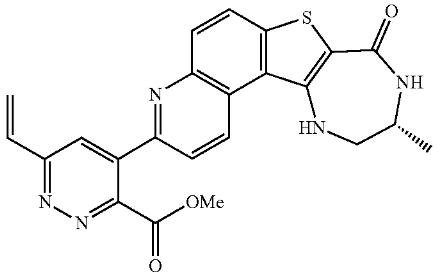 [SMILES: C=Cc1cc(-c2ccc3c(ccc4sc5c(c43)NC[C@@H](C)NC5=O)n2)c(C(=O)OC)nn1]

Step 1: Preparation of methyl 4-chloro-6-vinylpyridazine-3-carboxylate

A 20 mL reaction vial was charged with a stir bar, potassium vinyltrifluoroborate (81 mg, 0.604 mmol), methyl 4,6-dichloropyridazine-3-carboxylate (125 mg, 0.604 mmol), Pd(dppf)Cl2, DCM adduct (49.3 mg, 0.060 mmol), and cesium carbonate (492 mg, 1.510 mmol), Dioxane (2415 μl), and water (604 μl) to give a orange suspension. The resulting mixture was degassed by bubbling of nitrogen for 5 min and then stirred at 60° C. for 16 h. LC-MS indicated significant product present. The reaction mixture was concentrated under reduced pressure, diluted in ethyl acetate and filtered through a pad of celite. The filtrate was concentrated under reduced pressure to yield the crude product. The crude product was purified by flash chromatography (0-100% ethyl acetate in heptane). The pure fraction was concentrated under reduced pressure to yield methyl 4-chloro-6-vinylpyridazine-3-carboxylate (28 mg, 0.141 mmol, 23.35% yield). MS ESI m/z 199.2 $(M+H)^+$ Step 2: Preparation of methyl (R)-4-(10-methyl-8-oxo-9,10,11,12-tetrahydro-8H-[1,4]diazepino[5',6':4,5]thieno[3,2-f]quinolin-3-yl)-6-vinylpyridazine-3-carboxylate A 4 mL reaction vial was charged with a stir bar, (R)-10-methyl-3-(tributylstannyl)-9,10,11,12-tetrahydro-8H-[1,4]diazepino[5',6':4,5]thieno[3,2-f]quinolin-8-one (25.9 mg, 0.045 mmol), methyl 4-chloro-6-vinylpyridazine-3-carboxylate (9 mg, 0.045 mmol), and PdCl2(dtbpf) (29.5 mg, 0.045 mmol), and Dioxane (227 μl). The reaction mixture was degassed by evacuating and backfilling with nitrogen 3 times. The vial was sealed and heated to 80° C. overnight. The crude reaction mixture was concentrated under reduced pressure, dissolved in ethyl acetate, and filtered through a pad of Celite. The filtrate was concentrated under reduced pressure. The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 9% B, 9-49% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 9% B, 9-49% B over 20 minutes, then a 0-minute hold at 100% B; Flow Rate: 20 mL/min; Column Temperature: 25 C. Fraction collection was triggered by UV signals. Fractions containing the desired product were combined and dried via centrifugal evaporation, affording (R)-4-(10-methyl-8-oxo-9,10,11,12-tetrahydro-8H-[1,4]diazepino[5',6':4,5]thieno[3,2-f]quinolin-3-yl)-6-vinylpyridazine-3-carboxylate (0.5 mg, 0.001 mmol, 2.5% yield). MS ESI m/z 446.1 $(M+H)^+$. HPLC RT 1.34 min Example 28: Synthesis of (R)-10-methyl-3-(2-(morpholinomethyl)-6-vinylpyridin-4-yl)-9,10,11,12-tetrahydro-8H-[1,4]diazepino[5',6':4,5]thieno[3,2-f]quinolin-8-one

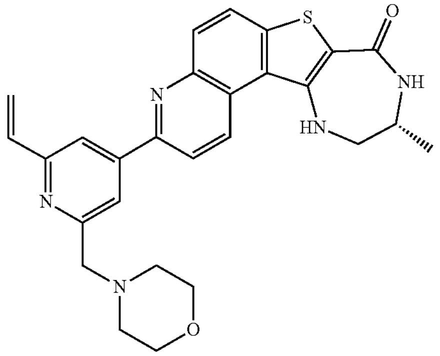 [SMILES: C=Cc1cc(-c2ccc3c(ccc4sc5c(c43)NC[C@@H](C)NC5=O)n2)cc(CN2CCOCC2)n1]

Step 1: Preparation of 4-((4,6-dichloropyridin-2-yl)methyl)morpholine

A 20 mL reaction vial was charged with a stir bar, morpholine (49.0 μl, 0.568 mmol), 4,6-dichloropicolinaldehyde (100 mg, 0.568 mmol), acetic acid (65.1 μl, 1.136 mmol), and DCM (2841 μl) to give a colorless solution. The reaction mixture was stirred for 10 m at room temperature. Sodium triacetoxyborohydride (241 mg, 1.136 mmol) was added and the reaction was stirred at room temperature overnight. LC/MS indicates the reaction is complete. The reaction was quenched by washing with saturated sodium bicarbonate. The suspension was diluted in DCM and the layers were separated. The aqueous layer was extracted twice more with DCM. The organic layers were combined and washed with brine. The organic phase was concentrated under reduced pressure to yield 4-((4,6-dichloropyridin-2-yl)methyl)morpholine (142 mg, 0.575 mmol, 101% yield) as an oil. MS ESI m/z 328.5 $(M+H)^+$ Step 2: Preparation of 4-((4-chloro-6-vinylpyridin-2-yl)methyl)morpholine A 20 mL reaction vial was charged with a stir bar, potassium vinyltrifluoroborate (72 mg, 0.538 mmol), 4-((4,6-dichloropyridin-2-yl)methyl)morpholine (140 mg, 0.567 mmol), Pd(dppf)Cl2, DCM adduct (46.3 mg, 0.057 mmol), cesium carbonate (461 mg, 1.416 mmol), Dioxane (2261 μl), and Water (567 μl) to give a orange suspension. The resulting mixture was degassed by bubbling of nitrogen for 5 min and then stirred at 60° C. for 16 h. LC MS indicated significant product formation. The reaction mixture was concentrated under reduced pressure, diluted in ethyl acetate, and filtered through a pad of Celite. The filtrate was concentrated under reduced pressure to yield the crude product, which was purified by flash chromatography (0-100% ethyl acetate in heptane; desired product eluted ~50%). The pure fractions were combined and concentrated to yield 4-((4-chloro-6-vinylpyridin-2-yl)methyl)morpholine (89 mg, 0.373 mmol, 66% yield) as a clear oil.

$^1$H NMR (400 MHz, CHLOROFORM-d) δ 7.40 (s, 1H), 7.28-7.25 (m, 1H), 6.78 (dd, J=17.4, 10.8 Hz, 1H), 6.22 (dd, J=17.4, 1.0 Hz, 1H), 5.55 (dd, J=10.9, 1.1 Hz, 1H), 3.79-3.76 (m, 4H), 3.67 (s, 2H), 2.56 (br s, 4H). MS ESI m/z 239.3, and 241.3 $(M+H)^+$ Step 3: Preparation of (2-(morpholinomethyl)-6-vinylpyridin-4-yl)boronic acid A 20 mL reaction vial was charged with a stir bar, bis(pinacolato)diboron (62.2 mg, 0.245 mmol), 4-((4-chloro-6-vinylpyridin-2-yl)methyl)morpholine (45 mg, 0.189 mmol), potassium acetate (27.8 mg, 0.283 mmol), Pd(dppf)Cl2, DCM adduct (15.39 mg, 0.019 mmol), and Dioxane (1885 μl) to give a orange suspension. The reaction mixture was degassed by bubbling with nitrogen for 5 m. The vial was sealed and heated to 80° C. for 16 hours. LC MS shows the reaction is incomplete. PdCl2(dtbpf) (12.29 mg, 0.019 mmol) was added, the reaction was degassed by evacuating and backfilling with nitrogen 3 times, and the reaction was heated to 80° C. for 2 hours. LC/MS indicated the starting material was consumed. The crude product was concentrated under reduced pressure and diluted in ethyl acetate and water The layers were separated and the aqueous layer was extracted twice more with ethyl acetate. The combined organic layers were washed with brine and concentrated under reduced pressure to yield (2-(morpholinomethyl)-6-vinylpyridin-4-yl)boronic acid. The product will be used as a crude reaction mixture without further isolation. MS ESI m/z 249.3 $(M+H)^+$ Step 4: Preparation of (R)-10-methyl-3-(2-(morpholinomethyl)-6-vinylpyridin-4-yl)-9,10,11,12-tetrahydro-8H-[1,4]diazepino[5',6':4,5]thieno[3,2-f]quinolin-8-one A 4 mL reaction vial was charged with a stir bar, (R)-3-chloro-10-methyl-9,10,11,12-tetrahydro-8H-[1,4]diazepino[5',6':4,5]thieno[3,2-f]quinolin-8-one (20 mg, 0.063 mmol), (2-(morpholinomethyl)-6-vinylpyridin-4-yl)boronic acid (629 μl as a 0.1 M crude mixture in dioxane, 0.094 mmol), and PdCl2(dtbpf) (4.10 mg, 6.29 μmol) to give a brown solution. Aqueous potassium phosphate, tribasic (94 μl, 0.189 mmol) was added. The reaction mixture was degassed by evacuating and backfilling with nitrogen 3 times. The vial was sealed and heated to 100° C. for 2 h. LC MS indicated significant product present. The reaction mixture was concentrated under reduced pressure. The crude material was dissolved in ethyl acetate and water. The phases were separated. The aqueous layer was extracted twice more with ethyl acetate. The combined organic layers were washed with brine and dried over sodium sulfate. The ethyl acetate was removed in vacuo. The crude Boc-protected product was dissolved in 1 ml 10% TFA (v/v) in DCM and stirred at room temperature overnight. The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 16% B, 16-56% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation, affording (R)-10-methyl-3-(2-(morpholinomethyl)-6-vinylpyridin-4-yl)-9,10,11,12-tetrahydro-8H-[1,4]diazepino[5',6':4,5]thieno[3,2-f]quinolin-8-one (5.1 mg, 0.11 mmol, 14% yield).

$^1$H NMR (500 MHz, DMSO-$d_6$) δ 9.32 (d, J=8.8 Hz, 1H), 8.37 (d, J=8.9 Hz, 1H), 8.24-8.18 (m, 3H), 8.10 (s, 2H), 7.20 (br t, J=5.2 Hz, 1H), 6.98 (dd, J=17.5, 10.8 Hz, 1H), 6.42-6.36 (m, 1H), 5.56 (d, J=12.1 Hz, 1H), 3.74 (s, 2H), 3.69-3.61 (m, 6H), 3.50 (br s, 3H), 1.22 (br d, J=6.8 Hz, 4H). One proton obscured by solvent peak. MS ESI m/z 486.2 $(M+H)^+$ Example 29: Synthesis of (15R)-5-(5-chloro-2-vinyl-4-pyridyl)-15-methyl-11-thia-6,14,17-triazatetracyclo[8.8.0.0^,7.0^12,18]octadeca-1(10),2(7),3,5,8,12(18)-hexaen-13-one

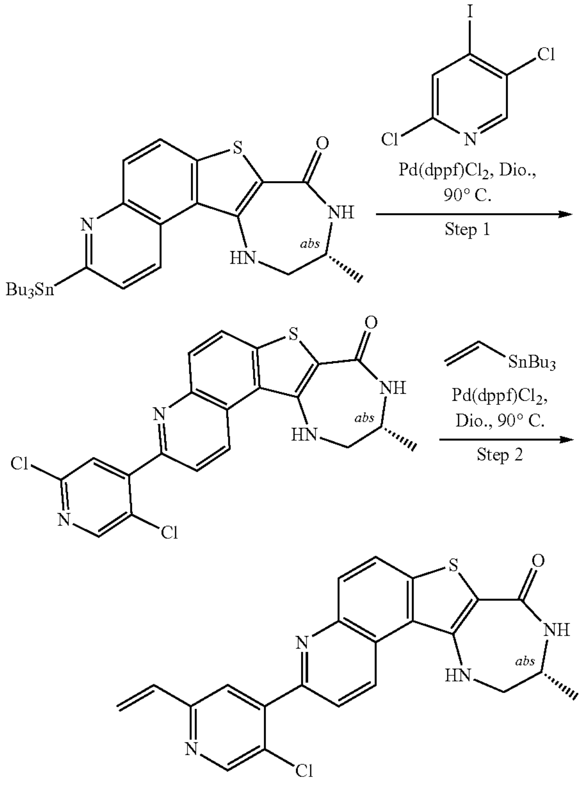

TABLE 1

Compounds in Table 1 were prepared in a similar fashion to (R)-10-methyl-3-(2-(morpholinomethyl)-6-vinylpyridin-4-yl)-9,10,11,12-tetrahydro-8H-[1,4]diazepino[5',6':4,5]thieno[3,2-f]quinolin-8-one.

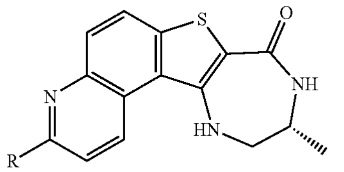

| Name | R | M + H+ | 1H NMR (500 MHz, DMSO-d6) □ |
|---|---|---|---|
| (R)-3-(2-((1,1-difluoro-6-azaspiro[2.5]octan-6-yl)methyl)-6-vinylpyridin-4-yl)-10-methyl-9,10,11,12-tetrahydro-8H-[1,4]diazepino[5',6':4,5]]thieno[3,2-f]quinolin-8-one | 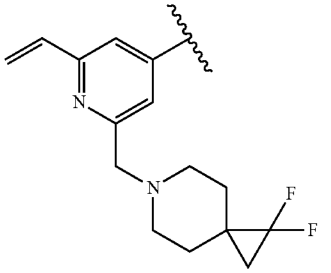 [SMILES: *c1cc(C=C)nc(CN2CCC3(CC2)CC3(F)F)c1] | 546.3 | $^1$H NMR (500 MHz, DMSO-$d_6$) δ 9.32 (d, J = 9.1 Hz, 1H), 8.37 (d, J = 9.0 Hz, 1H), 8.26-8.18 (m, 3H), 8.14-8.08 (m, 2H), 7.24-7.17 (m, 1H), 6.98 (dd, J = 17.3, 10.6 Hz, 1H), 6.39 (d, J = 17.6 Hz, 1H), 5.56 (d, J = 11.1 Hz, 1H), 3.64 (br s, 1H), 3.50 (br s, 1H), 3.44 (br s, 1H), 1.91 (s, 2H), 1.77-1.65 (m, 2H), 1.59 (br s, 2H), 1.28-1.14 (m, 10H) |

Step 1: Synthesis of (15R)-5-(2,5-dichloro-4-pyridyl)-15-methyl-11-thia-6,14,17-triazatetracyclo [8.8.0.0^,7.0^12,18]octadeca-1(10),2(7),3,5,8,12(18)-hexaen-13-one

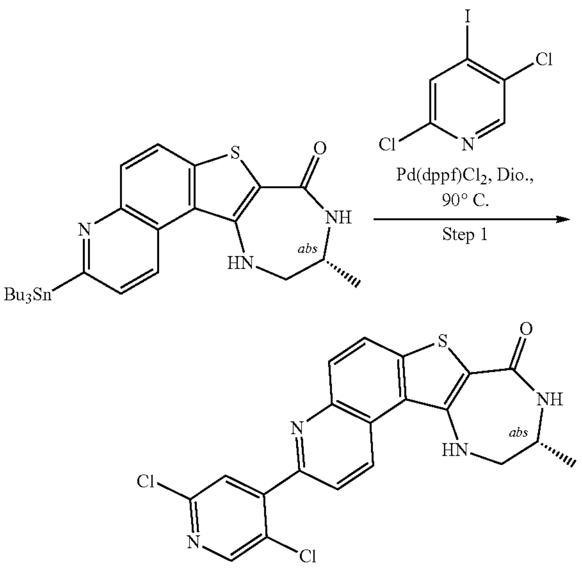

To a solution of (15R)-15-methyl-5-tributylstannyl-11-thia-6,14,17-triazatetracyclo[8.8.0.0^,7.0^12,18]octadeca-1(10),2(7),3,5,8,12(18)-hexaen-13-one (1.0 g, 1.750 mmol, 1.00 equiv) and 2,5-dichloro-4-iodo-pyridine (478 mg, 1.750 mmol, 1.00 equiv) in 1,4-dioxane (10.0 mL) was added Pd(dppf)$Cl_2$ (285 mg, 0.350 mmol, 0.20 equiv). The resulting mixture was stirred at 90° C. overnight under a nitrogen atmosphere. LCMS showed the reaction was completed. The resulting solution was diluted with ethyl acetate (100 mL). The solid was filtered out and the filtration was concentrated under reduced pressure. The residue was purified by reverse flash chromatography with water (0.05% TFA)/MeCN (2:1) to give (15R)-5-(2,5-dichloro-4-pyridyl)-15-methyl-11-thia-6,14,17-triazatetracyclo[8.8.0.0^2, 7.0^12,18]octadeca-1(10),2(7),3,5,8,12(18)-hexaen-13-one (350 mg, 46%) as a yellow solid. LCMS (ESI, m/z): 429 $(M+H)^+$.

Step 2: Synthesis of (15R)-5-(5-chloro-2-vinyl-4-pyridyl)-15-methyl-11-thia-6,14,17-triazatetracyclo [8.8.0.0^,7.0^12,18]octadeca-1(10),2(7),3,5,8,12(18)-hexaen-13-one

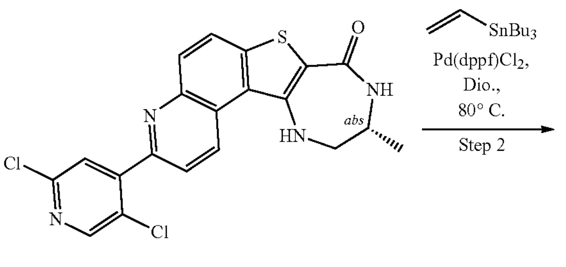

-continued

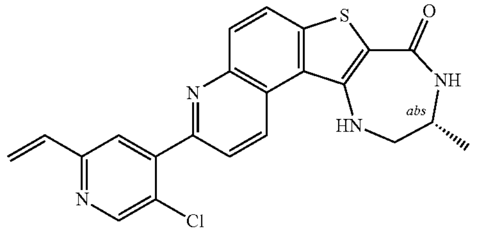

To a solution of (15R)-5-(2,5-dichloro-4-pyridyl)-15-methyl-11-thia-6,14,17-triazatetracyclo[8.8.0.0^,7.0^12,18] octadeca-1(10),2(7),3,5,8,12(18)-hexaen-13-one (85 mg, 0.200 mmol, 1.00 equiv) and tributyl(vinyl)stannane (94 mg, 0.300 mmol, 1.50 equiv) in 1,4-dioxane (10.0 mL) was added Pd(dppf)$Cl_2$ (32 mg, 0.040 mmol, 0.20 equiv). The resulting mixture was stirred at 90° C. for 8 h under a nitrogen atmosphere. LCMS showed the reaction was completed. The resulting solution was concentrated under reduce pressure. The residue was purified by Prep-HPLC using the following gradient conditions: Column: SunFire Prep C18 OBD Column, 19*150 mm, 5 μm; Mobile Phase A: Water (0.05% TFA), Mobile Phase B: MeCN; Flow rate: 20 mL/min; Gradient: 10% B to 40% B in 6 min, 40% B; Wave Length: 210/254 nm; RT1(min): Array. Purification resulted in desired (15R)-5-(5-chloro-2-vinyl-4-pyridyl)-15-methyl-11-thia-6,14,17-triazatetracyclo[8.8.0.0^2,7.0^12,18]octadeca-1(10),2(7),3,5,8,12(18)-hexaen-13-one (10.4 mg, 12%) as a yellow solid. LCMS (ESI, m/z): 421 $(M+H)^+$. Analytic Conditions: Column: HALO C18 Column 3.0*30 mm, 2.7 um; Mobile Phase A: Water/0.05% TFA, Mobile Phase B: Acetonitrile/0.05% TFA; Flow rate: 1.5000 mL/min; Gradient: 20% B to 70% B in 1.9 min; 254 nm; Rt: 1.364 min.

$^1H$ NMR (400 MHz, DMSO-$d_6$) δ 9.33 (d, J=8.8 Hz, 1H), 8.78 (s, 1H), 8.22 (d, J=9.2 Hz, 1H), 8.14 (d, J=4.0 Hz, 1H), 8.09-8.01 (m, 2H), 7.89 (s, 1H), 7.21 (s, 1H), 6.96 (dd, J=17.6 Hz, 10.8 Hz, 1H), 6.37 (dd, J=17.6 Hz, 1.2 Hz, 1H), 5.59 (dd, J=10.8 Hz, 1.2 Hz, 1H), 3.64-3.62 (s, 1H), 3.50-3.40 (m, 2H), 1.20 (d, J=6.8 Hz, 3H). $^{19}F$ NMR (376 MHz, DMSO-$d_6$) δ-73.89.

Example 30: Synthesis of (15R)-15-methyl-5-[5-(trideuteriomethyl)-2-vinyl-4-pyridyl]-11-thia-6,14,17-triazatetracyclo[8.8.0.0^,7.0^12,18]octadeca-1(10),2(7),3,5,8,12(18)-hexaen-13-one

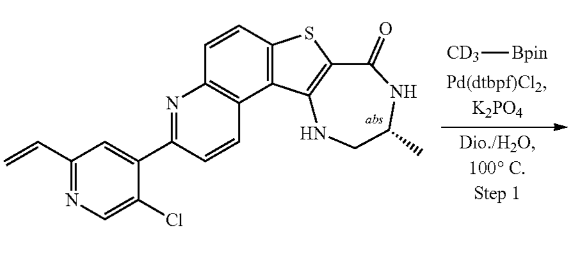

-continued

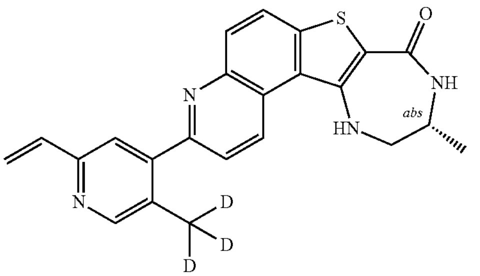

To a solution of (15R)-5-(5-chloro-2-vinyl-4-pyridyl)-15-methyl-11-thia-6,14,17-triazatetracyclo[8.8.0.0^,7.0^12,18] octadeca-1(10),2(7),3,5,8,12(18)-hexaen-13-one (40 mg, 0.095 mmol, 1.00 equiv), 4,4,5,5-tetramethyl-2-(trideuteriomethyl)-1,3,2-dioxaborolane (14 mg, 0.190 mmol, 2.00 equiy) and $K_2CO_3$ (26 mg, 0.190 mmol, 2.00 equiy) in 1,4-dioxane (2.0 mL) and water (0.2 mL) was added Pd(dtbpf)$Cl_2$ (15 mg, 0.019 mmol, 0.10 equiv). The resulting mixture was stirred at 100° C. for 3 h under a nitrogen atmosphere. LCMS showed the reaction was completed. The resulting solution was diluted with DMSO (3 mL). The solid was filtered out. The filtration was purified by Prep-HPLC using the following gradient conditions: Column: Welch Utimate HS-C18, 21.2*250 mm, 7 μm; Mobile Phase A: Water (0.05% TFA), Mobile Phase B: MeCN; Flow rate: 25 mL/min; Gradient: 15% B to 35% B in 6.3 min, 35% B; Wave Length: 254/210 nm; RT1(min): 5.56. Purification resulted in desired (15R)-15-methyl-5-[5-(trideuteriomethyl)-2-vinyl-4-pyridyl]-11-thia-6,14,17-triazatetracyclo [8.8.0.0^,7.0^12,18]octadeca-1(10),2(7),3,5,8,12(18)-hexaen-13-one (1.1 mg, 3%) as a yellow solid. LCMS (ESI, m/z): 404 $(M+H)^+$. Analytic Conditions: Column: HALO C18 Column 3.0*30 mm, 2.7 um; Mobile Phase A: Water/0.05% TFA, Mobile Phase B: Acetonitrile/0.05% TFA; Flow rate: 1.5000 mL/min; Gradient: 5% B to 60% B in 1.8 min; 254 nm; Rt: 1.249 min.

$^1H$ NMR (400 MHz, DMSO-$d_6$) δ 9.31 (d, J=8.8 Hz, 1H), 8.59 (s, 1H), 8.19 (d, J=8.8 Hz, 1H), 8.12 (d, J=4.0 Hz, 1H), 8.03 (d, J=8.8 Hz, 1H), 7.95 (d, J=8.8 Hz, 1H), 7.74 (s, 1H), 7.20 (s, 1H), 6.93 (dd, J=17.6 Hz, 11.2 Hz, 1H), 6.32 (d, J=17.6 Hz, 1H), 5.52 (d, J=11.2 Hz, 1H), 3.60-3.40 (m, 3H), 1.20 (d, J=6.8 Hz, 3H). $^{19}F$ NMR (376 MHz, DMSO-$d_6$) δ-73.99.

Example 31: Synthesis of (15R)-15-methyl-5-[5-(morpholinomethyl)-2-vinyl-4-pyridyl]-11-thia-6,14,17-triazatetracyclo[8.8.0.0^2, 7.0^12,18]octadeca-1(10),2(7),3,5,8,12(18)-hexaen-13-one

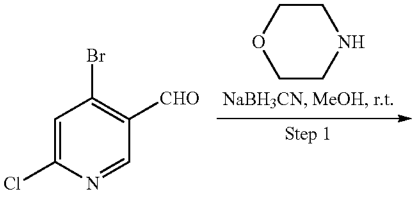

-continued

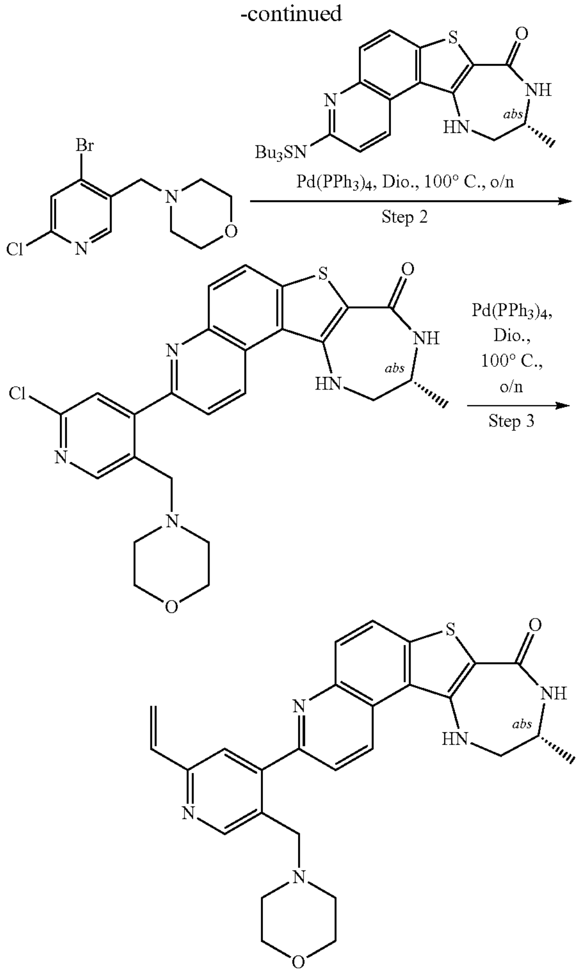

Step 1: Synthesis of 4-[(4-bromo-6-chloro-3-pyridyl)methyl]morpholine

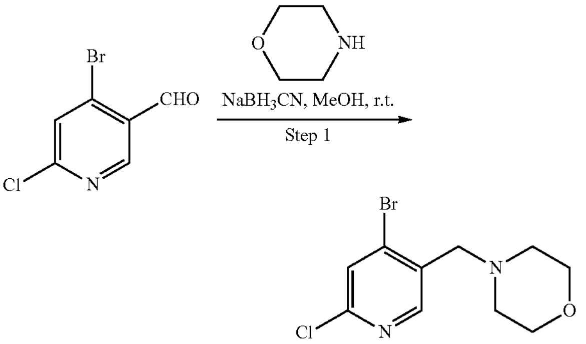

To a solution of 4-bromo-6-chloro-pyridine-3-carbaldehyde (100 mg, 0.450 mmol, 1.00 equiv) in methanol (5.0 mL) was added morpholine (79 mg, 0.910 mmol, 2.00 equiv). The resulting mixture was stirred at room temperature for 0.5 h. Then the $NaBH_3CN$ (116 mg, 1.81 mmol, 4.00 equiv) was added the resulting mixture and stirred at room temperature overnight. LCMS showed the reaction was completed. The resulting solution was diluted water (20 mL) and extracted with ethyl acetate (3×20 mL). The organic layers were washed with brine (2×20 mL), dried over anhydrous sodium sulfate, filtered and concentrated under reduce pressure. The residue was purified by column chromatography on silica gel with ethyl acetate/petroleum ether (1:2) to afford 4-[(4-bromo-6-chloro-3-pyridyl)methyl]morpholine (80 mg, 60%) as an white solid. LCMS (ESI, m/z): 291 and 293 $[M+H]^+$.

Step 2: Synthesis of (15R)-5-[2-chloro-5-(morpholinomethyl)-4-pyridyl]-15-methyl-11-thia-6,14,17-triazatetracyclo[8.8.0.0^2, 7.0^12,18]octadeca-1(10), 2(7),3,5,8, 12(18)-hexaen-13-one

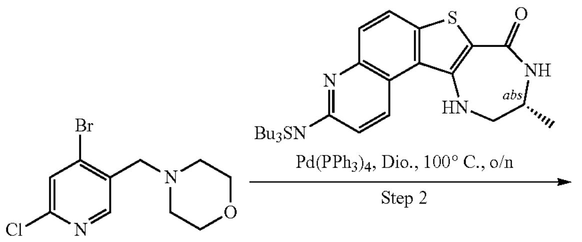

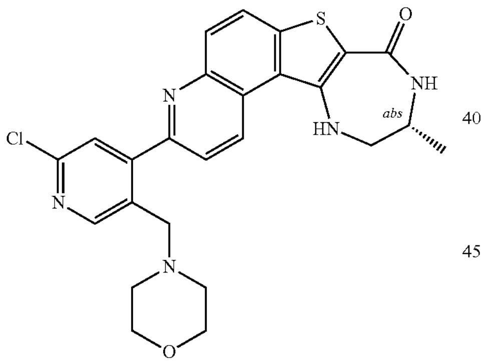

To a solution of 4-[(4-bromo-6-chloro-3-pyridyl)methyl]morpholine (60 mg, 0.210 mmol, 1.00 equiv) and (15R)-15-methyl-5-tributylstannyl-11-thia-6,14,17-triazatetracyclo[8.8.0.0^,7.0^12,18]octadeca-1(10),2(7),3,5,8,12(18)-hexaen-13-one (141 mg, 0.250 mmol, 1.20 equiv) in 1,4-dioxane (2.0 mL) was added $Pd(PPh_3)_4$(23 mg, 0.020 mmol, 0.10 equiv). The resulting mixture was stirred at 110° C. overnight under a nitrogen atmosphere. LCMS showed the reaction was completed. The resulting solution diluted with ethyl acetate (10 mL). The solid was collected by filtration and washed with ethyl acetate (2×5 mL). The solid was dried to give (15R)-5-[2-chloro-5-(morpholinomethyl)-4-pyridyl]-15-methyl-11-thia-6,14,17-triazatetracyclo [8.8.0.0^2, 7.0^12,18]octadeca-1(10),2(7),3,5,8, 12(18)-hexaen-13-one (80 mg, 78%) as a yellow solid. LCMS (ESI, m/z): 494 $[M+H]^+$.

Step 3: Synthesis of (15R)-15-methyl-5-[5-(morpholinomethyl)-2-vinyl-4-pyridyl]-11-thia-6,14,17-triazatetracyclo[8.8.0.0^2, 7.0^12,18]octadeca-1(10), 2(7),3,5,8,12(18)-hexaen-13-one

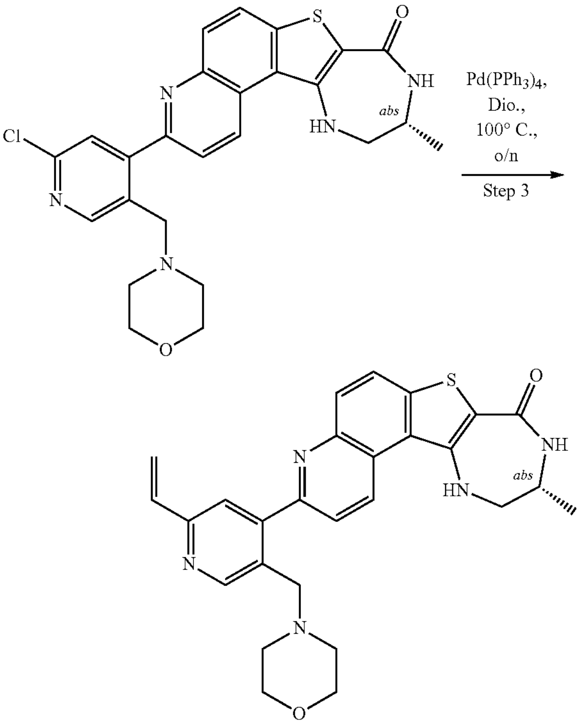

To a solution of (15R)-5-[2-chloro-5-(morpholinomethyl)-4-pyridyl]-15-methyl-11-thia-6,14,17-triazatetracyclo[8.8.0.0^,7.0^12,18]octadeca-1(10),2(7),3,5,8,12(18)-hexaen-13-one (40 mg, mmol, 1.00 equiv) and tributyl (vinyl)stannane (30 mg, 0.100 mmol, 1.20 equiv) in 1,4-dioxane (5.0 mL) was added $Pd(PPh_3)_4$(7 mg, 0.010 mmol, 0.10 equiv). The resulting mixture was stirred at 100° C. overnight under a nitrogen atmosphere. LCMS showed the reaction was completed. The resulting solution was concentrated under reduce pressure and the residue was purified by Prep-HPLC using the following gradient conditions: Column: X Bridge Prep C18 OBD Column, 19*150 mm, 5 μm; Mobile Phase A: Water (10 mmol/L $NH_4HCO_3$), Mobile Phase B: MeCN; Flow rate: 20 mL/min; Gradient: 25% B to 27% B in 6 min, 27% B; Wave Length: 254 nm; RT1(min): 4.55. Purification resulted in desired (15R)-15-methyl-5-[5-(morpholinomethyl)-2-vinyl-4-pyridyl]-11-thia-6,14,17-triazatetracyclo[8.8.0.0^2, 7.0^12,18]octadeca-1(10),2(7),3,5, 8,12(18)-hexaen-13-one (3.8 mg, 9%) as an orange solid. LCMS (ESI, m/z): 486 $[M+H]^+$. Analytic Conditions: Column: HALO C18 100A Column 3.0*33 mm, 3 um; Mobile Phase A: Water/5 mM $NH_4HCO_3$, Mobile Phase B: MeCN/0.05% TFA; Flow rate: 1.5000 mL/min; Gradient: 10% B to 95% B in 1.20 min; 254 nm; Rt: 0.880 min.

$^1$H NMR (400 MHz, DMSO-$d_6$) δ 9.44 (d, J=9.2 Hz, 1H), 8.85 (s, 1H), 8.29 (d, J=8.8 Hz, 1H), 8.25 (d, J=8.8 Hz, 1H), 8.17 (d, J=3.2 Hz, 1H), 8.03 (d, J=9.2 Hz, 1H), 7.99 (d, J=8.8 Hz, 1H), 7.27 (s, 1H), 7.03 (dd, J=17.2, 10.4 Hz, 1H), 6.48 (d, J=17.6 Hz, 1H), 5.67 (d, J=10.8 Hz, 1H), 4.64 (s, 2H), 4.10-3.90 (m, 3H), 3.80-3.62 (m, 4H), 3.56-3.45 (m, 4H), 1.21 (d, J=6.8 Hz, 3H). $^{19}F$ NMR (376 MHz, DMSO-$d_6$) δ-73.83

Example 32: Synthesis of (15R)-5-[2-ethynyl-5-(morpholinomethyl)-4-pyridyl]-15-methyl-11-thia-6,14,17-triazatetracyclo[8.8.0.0^2, 7.0^12,18]octadeca-1(10),2(7),3,5,8,12(18)-hexaen-13-one

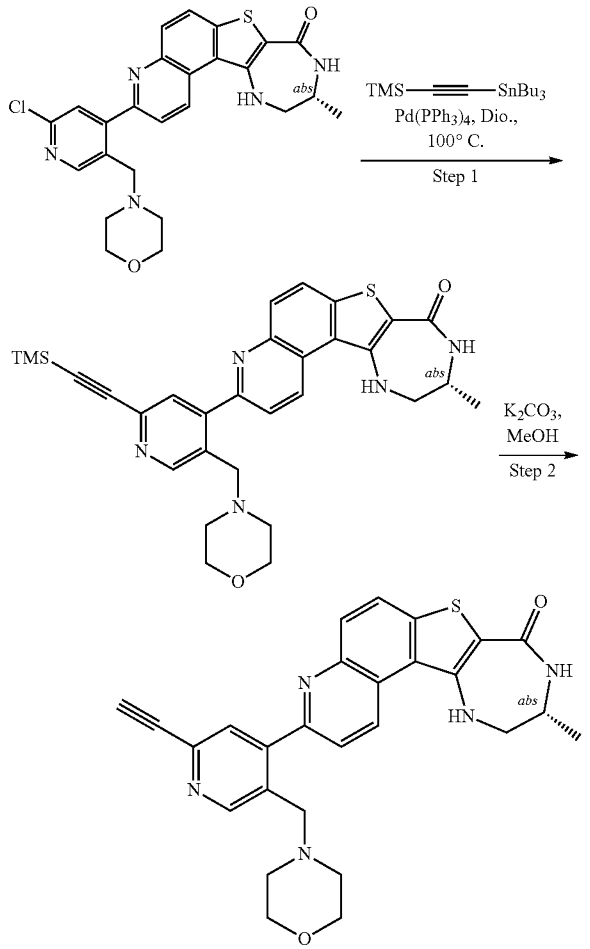

Step 1: Synthesis of (15R)-15-methyl-5-[5-(morpholinomethyl)-2-(2-trimethylsilylethynyl)-4-pyridyl]-11-thia-6,14,17-triazatetracyclo[8.8.0.0^2, 7.0^12, 18]octadeca-1(10),2(7),3,5,8,12(18)-hexaen-13-one

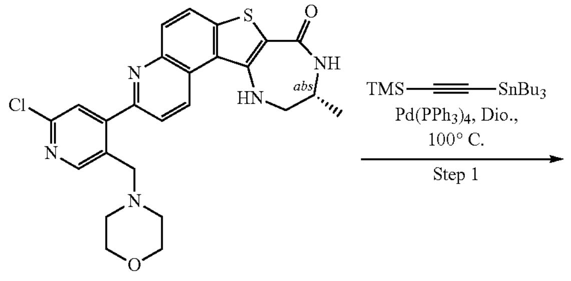

-continued

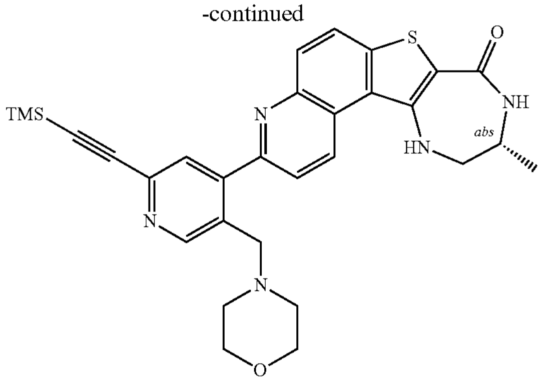

To a solution of (15R)-5-[2-chloro-5-(morpholinomethyl)-4-pyridyl]-15-methyl-11-thia-6,14,17-triazatetracyclo[8.8.0.0^,7.0^12,18]octadeca-1(10),2(7),3,5,8,12(18)-hexaen-13-one (50 mg, 0.100 mmol, 1.00 equiv) and trimethyl(2-tributylstannylethynyl)silane (78.39 mg, 0.200 mmol, 2.00 equiv) in 1,4-dioxane (2.0 mL) was added $Pd(PPh_3)_4$(11 mg, 0.010 mmol, 0.10 equiv). The resulting mixture was stirred at 100° C. overnight under a nitrogen atmosphere. LCMS showed the reaction was completed. The resulting solution was diluted with ethyl acetate (10 mL). The solid was collected by filtration and washed with ethyl acetate (3×50 mL). The solid was dried to give (15R)-15-methyl-5-[5-(morpholinomethyl)-2-(2-trimethylsilylethynyl)-4-pyridyl]-11-thia-6,14,17-triazatetracyclo[8.8.0.0^2, 7.0^12,18]octadeca-1(10),2(7),3,5,8,12(18)-hexaen-13-one (35 mg, 62%) as a yellow solid. LCMS (ESI, m/z): 556 $[M+H]^+$.

Step 2: Synthesis of (15R)-5-[2-ethynyl-5-(morpholinomethyl)-4-pyridyl]-15-methyl-11-thia-6,14,17-triazatetracyclo[8.8.0.0^2, 7.0^12,18]octadeca-1(10),2(7),3,5,8,12(18)-hexaen-13-one

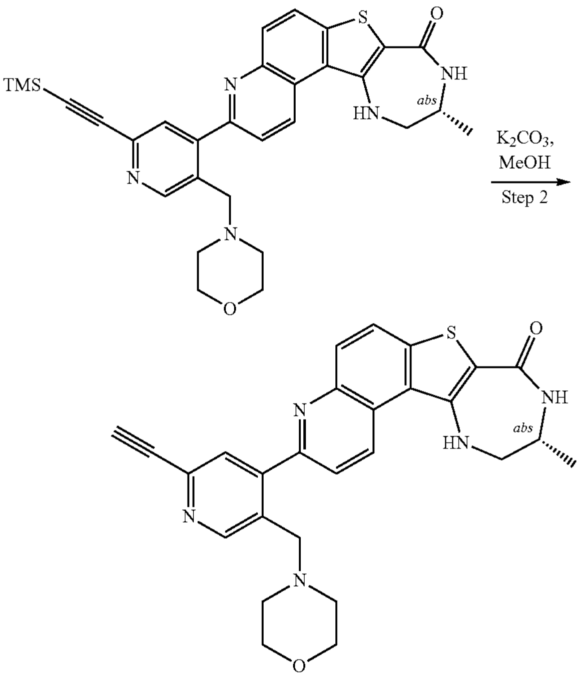

To a solution of (15R)-15-methyl-5-[5-(morpholinomethyl)-2-(2-trimethylsilylethynyl)-4-pyridyl]-11-thia-6,14,17-triazatetracyclo[8.8.0.0^,7.0^12,18]octadeca-1(10),2 (7),3,5,8,12(18)-hexaen-13-one (30 mg, 0.050 mmol, 1.00 equiv) in methanol (2.0 mL) was added $K_2CO_3$ (22 mg, 0.160 mmol, 3.00 equiv). The resulting mixture was stirred at room temperature for 30 minutes. LCMS showed the reaction was completed. The resulting solution was diluted DMSO (2.0 mL). The solid was filtered out and the filtration was by Prep-HPLC using the following gradient conditions: Column: X Bridge Prep OBD C18 Column, 30*150 mm, 5 μm; Mobile Phase A: Water (10 mmol/L $NH_4HCO_3$), Mobile Phase B: MeCN; Flow rate: 20 mL/min; Gradient: 35% B to 52% B in 4.7 min, 52% B; Wave Length: 254 nm; RT1(min): 4.58. Purification resulted in desired (15R)-5-[2-ethynyl-5-(morpholinomethyl)-4-pyridyl]-15-methyl-11-thia-6,14,17-triazatetracyclo[8.8.0.0^2, 7.0^12,18]octadeca-1(10),2(7),3,5,8,12(18)-hexaen-13-one (6.1 mg, 22%) as a yellow solid. LCMS (ESI, m/z): 484 $[M+H]^+$. Analytic Conditions: Column: HALO C18 100A Column 3.0*33 mm, 3.0 um; Mobile Phase A: Water/5 mM $NH_4HCO_3$, Mobile Phase B: Acetonitrile/0.05% TFA; Flow rate: 1.5000 mL/min; Gradient: 10% B to 95% B in 1.20 min; 254 nm; Rt: 0.856 min.

$^1$H NMR (400 MHz, DMSO-$d_6$) δ 9.28 (d, J=8.8 Hz, 1H), 8.72 (s, 1H), 8.19 (d, J=8.8 Hz, 1H), 8.13 (d, J=5.6 Hz, 1H), 8.05 (d, J=8.8 Hz, 1H), 8.01 (d, J=9.2 Hz, 1H), 7.77 (s, 1H), 7.18 (t, J=5.2 Hz, 1H), 4.41 (s, 1H), 3.76 (s, 2H), 3.65-3.61 (m, 1H), 3.55-3.45 (m, 2H), 3.33-3.31 (m, 4H), 2.22 (s, 4H), 1.21 (d, J=6.8 Hz, 3H).

Example 33: Synthesis of (R)-3-(5-((4-methoxypiperidin-1-yl)methyl)-2-vinylpyridin-4-yl)-10-methyl-9,10,11,12-tetrahydro-8H-[1,4]diazepino[5',6':4,5]thieno[3,2-f]quinolin-8-one

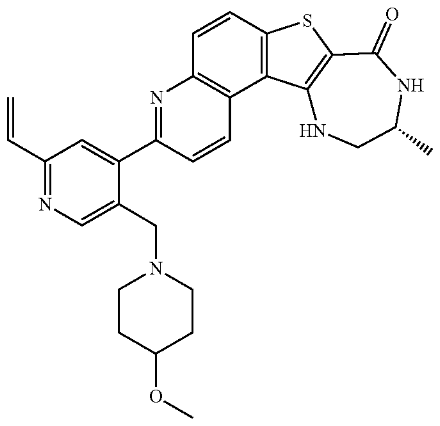 [SMILES: C=Cc1cc(-c2ccc3c(ccc4sc5c(c43)NC[C@@H](C)NC5=O)n2)c(CN2CCC(OC)CC2)cn1]

Step 1: Synthesis of 4-((4,6-dichloropyridin-2-yl)methyl)morpholine

A 20 mL reaction vial was charged with a stir bar, morpholine (49.0 μl, 0.568 mmol), 4,6-dichloropicolinaldehyde (100 mg, 0.568 mmol), acetic acid (65.1 μl, 1.136 mmol), and DCM (2841 μl) to give a colorless solution. The reaction mixture was stirred for 10 m at room temperature. Sodium triacetoxyborohydride (241 mg, 1.136 mmol) was added and the reaction was stirred at room temperature overnight. LC/MS indicates the reaction is complete. The reaction was quenched by washing with saturated sodium bicarbonate. The suspension was diluted in DCM and the layers were separated. The aqueous layer was extracted twice more with DCM. The organic layers were combined and washed with brine. The organic phase was concentrated under reduced pressure to yield 4-((4,6-dichloropyridin-2-yl)methyl)morpholine (142 mg, 0.575 mmol, 101% yield) as an oil. MS ESI m/z 328.5 $(M+H)^+$ Step 2: Synthesis of 4-((4-chloro-6-vinylpyridin-2-yl)methyl)morpholine A 20 mL reaction vial was charged with a stir bar, potassium vinyltrifluoroborate (72 mg, 0.538 mmol), 4-((4,6-dichloropyridin-2-yl)methyl)morpholine (140 mg, 0.567 mmol), Pd(dppf)Cl2, DCM adduct (46.3 mg, 0.057 mmol), cesium carbonate (461 mg, 1.416 mmol), Dioxane (2261 μl), and Water (567 μl) to give a orange suspension. The resulting mixture was degassed by bubbling of nitrogen for 5 min and then stirred at 60° C. for 16 h. LC MS indicated significant product formation. The reaction mixture was concentrated under reduced pressure, diluted in ethyl acetate, and filtered through a pad of Celite. The filtrate was concentrated under reduced pressure to yield the crude product, which was purified by flash chromatography (0-100% ethyl acetate in heptane; desired product eluted ~50%). The pure fractions were combined and concentrated to yield 4-((4-chloro-6-vinylpyridin-2-yl)methyl)morpholine (89 mg, 0.373 mmol, 66% yield) as a clear oil.

$^1$H NMR (400 MHz, CHLOROFORM-d) δ 7.40 (s, 1H), 7.28-7.25 (m, 1H), 6.78 (dd, J=17.4, 10.8 Hz, 1H), 6.22 (dd, J=17.4, 1.0 Hz, 1H), 5.55 (dd, J=10.9, 1.1 Hz, 1H), 3.79-3.76 (m, 4H), 3.67 (s, 2H), 2.56 (br s, 4H). MS ESI m/z 239.3, and 241.3 $(M+H)^+$ Step 3: Synthesis of (2-(morpholinomethyl)-6-vinylpyridin-4-yl)boronic acid A 20 mL reaction vial was charged with a stir bar, bis(pinacolato)diboron (62.2 mg, 0.245 mmol), 4-((4-chloro-6-vinylpyridin-2-yl)methyl)morpholine (45 mg, 0.189 mmol), potassium acetate (27.8 mg, 0.283 mmol), Pd(dppf)Cl2, DCM adduct (15.39 mg, 0.019 mmol), and Dioxane (1885 μl) to give a orange suspension. The reaction mixture was degassed by bubbling with nitrogen for 5 m. The vial was sealed and heated to 80° C. for 16 hours. LC MS shows the reaction is incomplete. PdCl2(dtbpf) (12.29 mg, 0.019 mmol) was added, the reaction was degassed by evacuating and backfilling with nitrogen 3 times, and the reaction was heated to 80° C. for 2 hours. LC/MS indicated the starting material was consumed. The crude product was concentrated under reduced pressure and diluted in ethyl acetate and water The layers were separated and the aqueous layer was extracted twice more with ethyl acetate. The combined organic layers were washed with brine and concentrated under reduced pressure to yield (2-(morpholinomethyl)-6-vinylpyridin-4-yl)boronic acid. The product will be used as a crude reaction mixture without further isolation. MS ESI m/z 249.3 $(M+H)^+$ Step 4: Synthesis of (R)-3-(5-((4-methoxypiperidin-1-yl)methyl)-2-vinylpyridin-4-yl)-10-methyl-9,10,11,12-tetrahydro-8H-[1,4]diazepino[5',6':4,5]thieno[3,2-f]quinolin-8-one A 4 mL reaction vial was charged with a stir bar, (R)-10-methyl-3-(tributylstannyl)-9,10,11,12-tetrahydro-8H-[1,4]diazepino[5',6':4,5]thieno[3,2-f]quinolin-8-one (506 μl, 0.101 mmol), 4-chloro-5-((4-methoxypiperidin-1-yl)methyl)-2-vinylpyridine (27 mg, 0.101 mmol), and tetrakis (11.70 mg, 10.12 μmol) in tetrakis (11.70 mg, 10.12 μmol) to give a yellow solution. The reaction mixture was degassed by evacuating and backfilling with nitrogen 3 times. The vial was sealed and heated to 100° C. for 16 h. LC MS indicated significant product present. The reaction mixture was concentrated under reduced pressure. The crude material was dissolved in ethyl acetate and water. The phases were separated. The aqueous layer was extracted twice more with ethyl acetate. The ethyl acetate was removed in vacuo. The crude material was purified via preparative LC/MS with the following conditions: Column: XBridge C18, 200 mm×19 mm, 5-m particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 11% B, 11-51% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation, affording (R)-3-(5-((4-methoxypiperidin-1-yl)methyl)-2-vinylpyridin-4-yl)-10-methyl-9,10,11,12-tetrahydro-8H-[1,4]diazepino[5',6':4,5]thieno[3,2-f]quinolin-8-one (0.9 mg, 0.002 mmol, 2% yield). HPLC retention time (TFA/AA): 1.23 m/1.32 m. MS ESI m/z 514.2 $(M+H)^+$

TABLE 2

Compounds in Table 2 were prepared in a similar fashion to (R)-3-(5-((4-methoxypiperidin-1-yl)methyl)-2-vinylpyridin-4-yl)-10-methyl-9,10,11,12-tetrahydro-8H-[1,4]diazepino[5',6':4,5]thieno[3,2-f]quinolin-8-one.

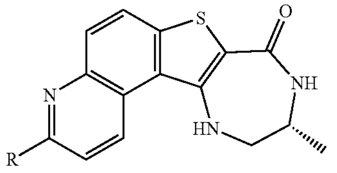

| Name | R | $M + H^+$ | 1H NMR (500 MHz, DMSO-d6) □ |
|---|---|---|---|
| (R)-3-(5-((3,3-difluoroazetidin-1-yl)methyl)-2-vinylpyridin-4-yl)-10-methyl-9,10,11,12-tetrahydro-8H-[1,4]diazepino[5',6':4,5]]thieno[3,2-f]quinolin-8-one | 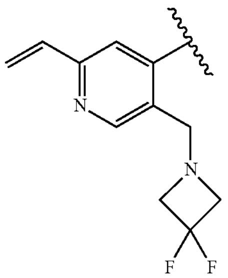 [SMILES: *c1cc(C=C)ncc1CN1CC(F)(F)C1] | 492.0 | HPLC retention time (TFA/AA): 1.13 m/1.61 m |
| (R)-10-methyl-3-(5-((4-(trifluoromethyl)piperidin-1-yl)methyl)-2-vinylpyridin-4-yl)-9,10,11,12-tetrahydro-8H-[1,4]diazepino[5',6':4,5]thieno[3,2-f]quinolin-8-one | 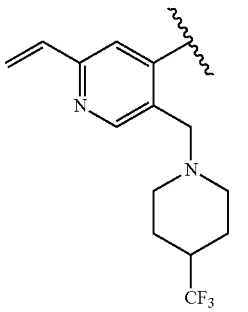 [SMILES: *c1cc(C=C)ncc1CN1CCC(C(F)(F)F)CC1] | 552.2 | $^1H$ NMR (500 MHz, DMSO-$d_6$) δ 9.28 (d, J = 8.8 Hz, 1H), 8.68 (s, 1H), 8.18 (d, J = 8.9 Hz, 1H), 8.10 (br d, J = 4.3 Hz, 1H), 8.01 (d, J = 8.9 Hz, 1H), 7.96 (d, J = 8.9 Hz, 1H), 7.68 (s, 1H), 7.17 (br t, J = 5.0 Hz, 1H), 6.94 (dd, J = 17.4, 10.9 Hz, 1H), 6.33 (br d, J = 17.5 Hz, 1H), 5.53 (d, J = 12.1 Hz, 1H), 3.79 (br d, J = 2.9 Hz, 2H), 3.66-3.56 (m, 1H), 2.74 (br s, 1H), 2.60-2.53 (m, 1H), 2.04 (br s, 1H), 1.87-1.76 (m, 2H), 1.69 (br d, J = 11.9 Hz, 1H), 1.51 (br d, J = 13.1 Hz, 1H), 1.21 (d, J=6.8 Hz, 4H), 1.17-1.04 (m, 2H). One proton obscured by water. |
| (R)-3-(5-((syn-2,6-dimethylmorpholino)methyl)-2-vinylpyridin-4-yl)-10-methyl-9,10,11,12-tetrahydro-8H-[1,4]diazepino[5',6':4,5]]thieno[3,2-f]quinolin-8-one | 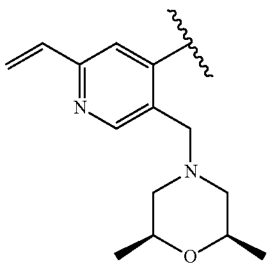 [SMILES: *c1cc(C=C)ncc1CN1C[C@@H](C)O[C@@H](C)C1] | 514.1 | $^1H$ NMR (500 MHz, DMSO-$d_6$) δ 9.45 (br d, J = 9.1 Hz, 1H), 8.87 (s, 1H), 8.31 (d, J = 8.9 Hz, 1H), 8.24 (d, J = 8.8 Hz, 1H), 8.16 (br d, J = 4.3 Hz, 1H), 8.03 (s, 1H), 7.95 (br s, 1H), 7.24 (br s, 1H), 7.03 (dd, J = 17.3, 10.8 Hz, 1H), 6.49 (d, J = 17.5 Hz, 1H), 5.68 (d, J = 12.1 Hz, 1H), 4.58 (br s, 2H), 4.06 (br s, 2H), 3.64 (br s, 2H), 2.93-2.75 (m, 2H), 1.24-1.12 (m, 9H). Four protons obscured by solvent. |

Example 34: Synthesis of (15R)-15-methyl-5-(2-morpholino-6-vinyl-4-pyridyl)-11-thia-6,14,17-triazatetracyclo[8.8.0.0^,7.0^12,18]octadeca-1(10),2(7),3,5,8,12(18)-hexaen-13-one

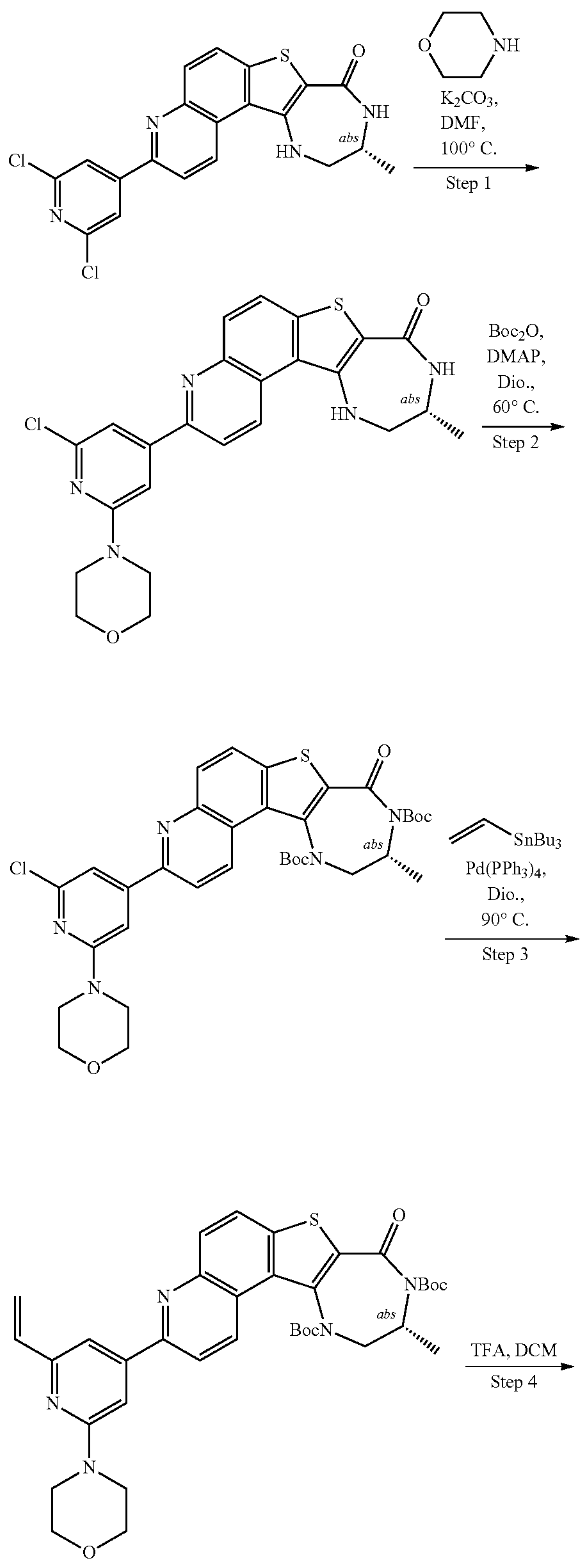

-continued

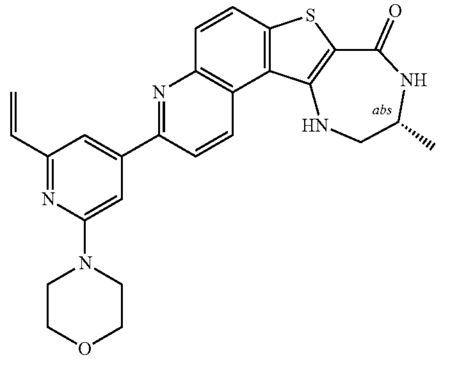

Step 1: Synthesis of (15R)-5-(2-chloro-6-morpholino-4-pyridyl)-15-methyl-11-thia-6,14,17-triazatetracyclo[8.8.0.0^,7.0^12,18]octadeca-1(10),2(7),3,5,8,12(18)-hexaen-13-one

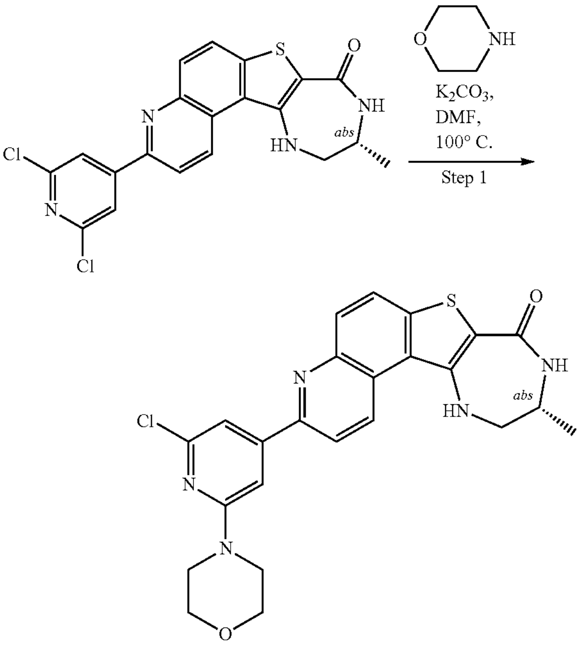

To a solution of (15R)-5-(2,6-dichloro-4-pyridyl)-15-methyl-11-thia-6,14,17-triazatetracyclo[8.8.0.0^,7.0^12,18] octadeca-1(10),2(7),3,5,8,12(18)-hexaen-13-one (200 mg, 0.470 mmol, 1.00 equiv) and $K_2CO_3$ (193 mg, 1.400 mmol, 3.00 equiv) in DMF (5.0 mL) was added morpholine (203 mg, 2.330 mmol, 5.00 equiv). The resulting mixture was stirred at 100° C. overnight under a nitrogen atmosphere. LCMS showed the reaction was completed. The resulting solution was diluted with water (50 mL), extracted with dichloromethane (3×50 mL). The combined organic layers were washed with brine (2×20 mL), dried over anhydrous sodium sulfate, filtered and concentrated under reduced pressure to give 100 mg crude product. The crude product was used directly for the next step without further purification. LCMS (ESI, m/z): 480 $(M+H)^+$.

Step 2: Synthesis of ditert-butyl (15R)-5-(2-chloro-6-morpholino-4-pyridyl)-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate

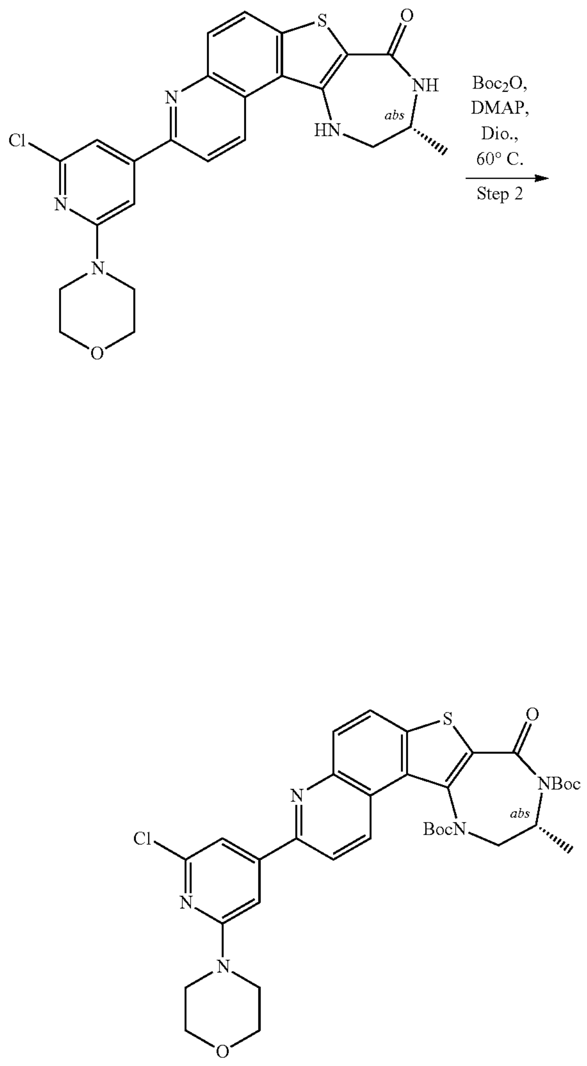

To a solution of (15R)-5-(2-chloro-6-morpholino-4-pyridyl)-15-methyl-11-thia-6,14,17-triazatetracyclo[8.8.0.0^,7.0^12,18]octadeca-1(10),2(7),3,5,8,12(18)-hexaen-13-one (100 mg, 0.210 mmol, 1.00 equiv) and $Boc_2O$ (182 mg, 0.830 mmol, 4.00 equiv) in 1,4-dioxane (5.0 mL) was added DMAP (3 mg, 0.020 mmol, 0.10 equiv). The resulting mixture was stirred at 60° C. for 2 h under a nitrogen atmosphere. LCMS showed the reaction was completed. The resulting solution was concentrated under reduced pressure and the residue was purified by column chromatography on silica gel with dichloromethane/ethyl acetate (1:1) to give ditert-butyl (15R)-5-(2-chloro-6-morpholino-4-pyridyl)-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (50 mg, 35%) as a yellow solid. LCMS (ESI, m/z): 680 $(M+H)^+$.

Step 3: Synthesis of ditert-butyl (15R)-15-methyl-5-(2-morpholino-6-vinyl-4-pyridyl)-13-oxo-11-thia-6,14,17-triazatetracyclo[8.8.0.0^,7.0^12,18]octadeca-1(10),2(7),3,5,8,12(18)-hexaene-14,17-dicarboxylate

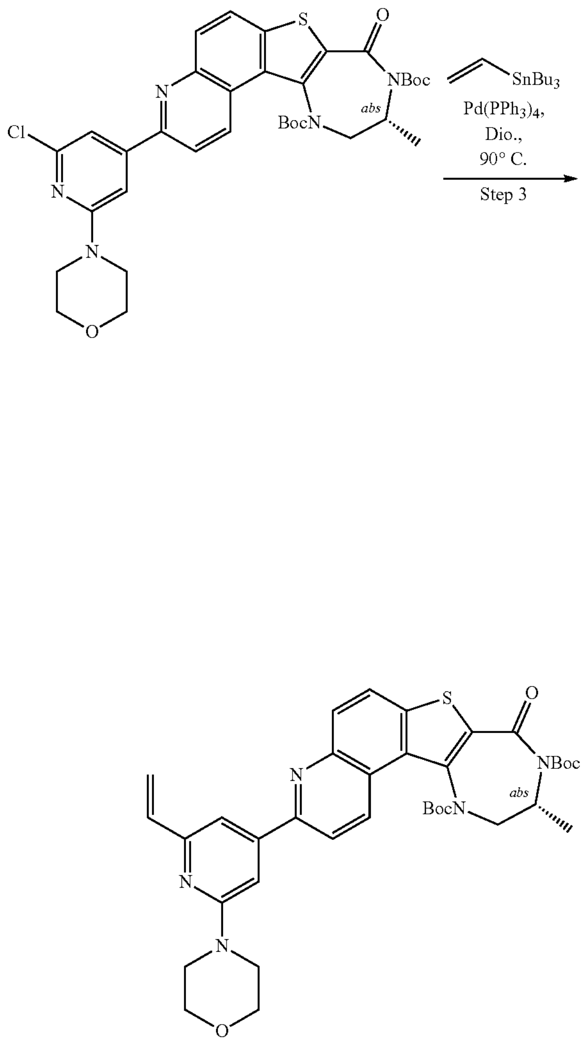

To a solution of ditert-butyl (15R)-5-(2-chloro-6-morpholino-4-pyridyl)-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (50 mg, 0.070 mmol, 1.00 equiv) and tributyl(vinyl)stannane (35 mg, 0.110 mmol, 1.50 equiv) in 1,4-dioxane (1.0 mL) was added $Pd(PPh_3)_4$(8 mg, 0.010 mmol, 0.10 equiv). The resulting mixture was stirred at 90° C. for 3 h under a nitrogen atmosphere. LCMS showed the reaction was completed. The resulting solution was concentrated under reduced pressure. The residue was purified by column chromatography on silica gel with dichloromethane/ethyl acetate (1:1) to give ditert-butyl (15R)-15-methyl-5-(2-morpholino-6-vinyl-4-pyridyl)-13-oxo-11-thia-6,14,17-triazatetracyclo[8.8.0.0^,7.0^12,18]octadeca-1(10),2(7),3,5,8,12(18)-hexaene-14,17-dicarboxylate (20 mg, 41%) as a yellow solid. LCMS (ESI, m/z): 672 $(M+H)^+$.

Step 4: Synthesis of (15R)-15-methyl-5-(2-morpholino-6-vinyl-4-pyridyl)-11-thia-6,14,17-triazatetracyclo[8.8.0.0^,7.0^12,18]octadeca-1(10),2(7),3,5,8,12(18)-hexaen-13-one

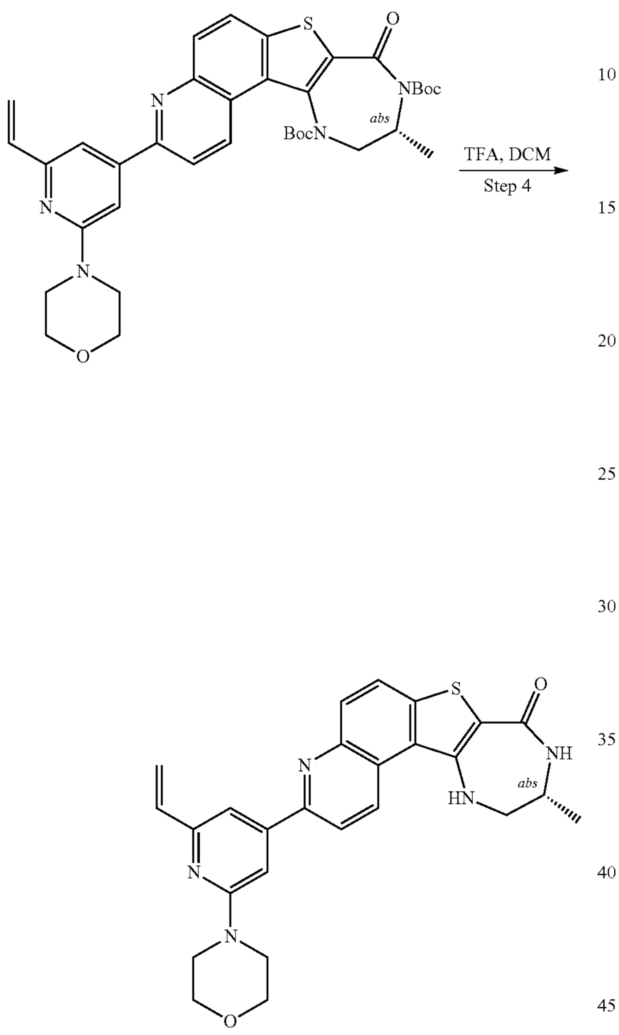

To a solution of ditert-butyl (15R)-15-methyl-5-(2-morpholino-6-vinyl-4-pyridyl)-13-oxo-11-thia-6,14,17-triazatetracyclo[8.8.0.0^,7.0^12,18]octadeca-1(10),2(7),3,5,8,12(18)-hexaene-14,17-dicarboxylate (20 mg, 0.030 mmol, 1.00 equiv) in DCM (1.0 mL) was added dropwise TFA (0.2 mL). The resulting mixture was stirred at room temperature for 1 h. LCMS showed the reaction was completed. The resulting solution was concentrated under reduced pressure. The residue was purified by Prep-HPLC using the following gradient: Column: Xselect CSH C18 OBD Column 30*150 mm 5 um; Mobile Phase A: Water (0.05% TFA), Mobile Phase B: MeCN; Flow rate: 60 mL/min; Gradient: 26% B to 56% B in 10 min, 56% B; Wave Length: 254 nm; RT1(min): 5.17. Purification resulting in desired (15R)-15-methyl-5-(2-morpholino-6-vinyl-4-pyridyl)-11-thia-6,14,17-triazatetracyclo[8.8.0.0^,7.0^12,18]octadeca-1(10),2(7),3,5,8,12(18)-hexaen-13-one (3.3 mg, 23%) as an orange solid. LCMS (ESI, m/z): 472 $(M+H)^+$. Analytic Conditions: Column: HALO AQ-C18 100A Column 3.0*30 mm, 2.0 um; Mobile Phase A: Water/0.05% TFA, Mobile Phase B: Acetonitrile/0.05% TFA; Flow rate: 1.2000 mL/min; Gradient: 20% B to 70% B in 2.10 min; 254 nm; Rt: 1.299

$^1H$ NMR (400 MHz, DMSO-$d_6$) δ 9.28 (d, J=8.8 Hz, 1H), 8.36 (d, J=8.8 Hz, 1H), 8.18 (d, J=9.2 Hz, 1H), 8.13 (d, J=4.4 Hz, 1H), 8.07 (d, J=8.8 Hz, 1H), 7.62 (d, J=12.4 Hz, 2H), 7.23 (s, 1H), 6.86 (dd, J=17.2, 10.8 Hz, 1H), 6.32 (dd, J=17.2, 2.0 Hz, 1H), 5.47 (dd, J=10.8, 2.0 Hz, 1H), 3.78 (t, J=4.8 Hz, 4H), 3.80-3.70 (m, 1H), 3.64 (t, J=4.8 Hz, 4H), 3.66-3.63 (m, 4H), 3.49 (s, 2H), 1.21 (d, J=6.4 Hz, 3H). $^{19}F$ NMR (376 MHz, DMSO-$d_6$) δ-74.70

Example 35: Synthesis of (15R)-5-[2-ethynyl-6-(4-methoxy-1-piperidyl)-4-pyridyl]-15-methyl-11-thia-6,14,17-triazatetracyclo[8.8.0.0^,7.0^12,18]octadeca-1(10),2(7),3,5,8,12(18)-hexaen-13-one

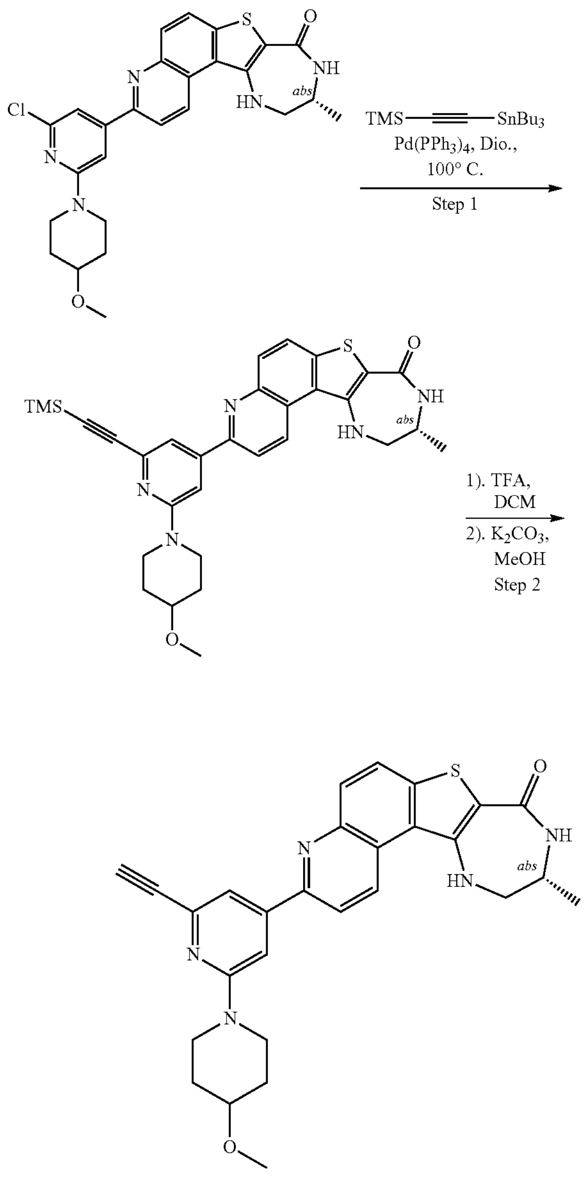

Step 1: Synthesis of ditert-butyl (15R)-5-[2-(4-methoxy-1-piperidyl)-6-(2-trimethylsilylethynyl)-4-pyridyl]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate

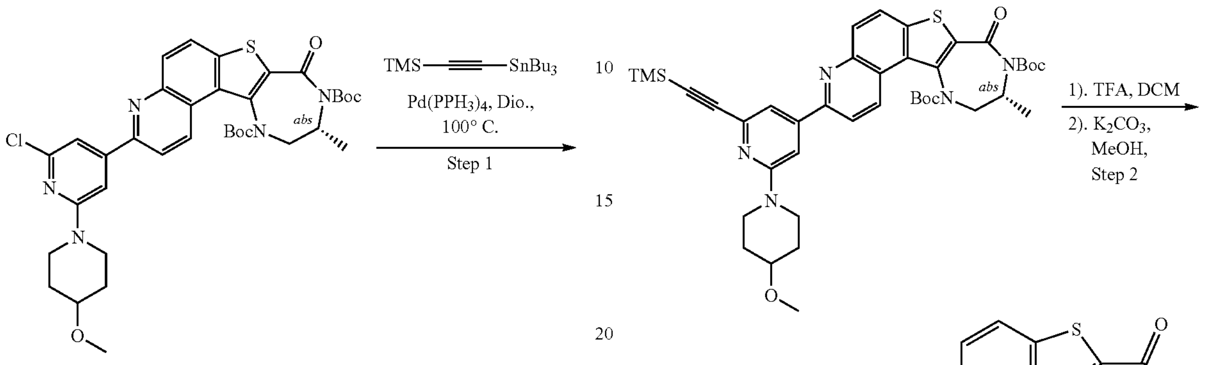

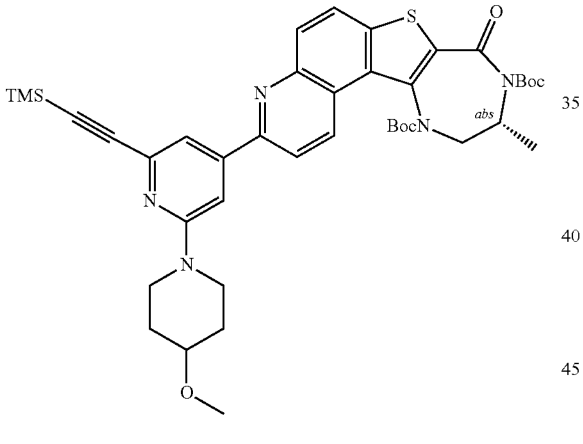

To a solution of ditert-butyl (15R)-5-[2-chloro-6-(4-methoxy-1-piperidyl)-4-pyridyl]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (50 mg, 0.070 mmol, 1.00 equiv) and trimethyl(2-tributylstannylethynyl)silane (41 mg, 0.110 mmol, 1.50 equiv) in 1,4-dioxane (2.0 mL) was added $Pd(PPh_3)_4$(8 mg, 0.010 mmol, 0.10 equiv). The resulting mixture was stirred at 100° C. for 6 h under a nitrogen atmosphere. LCMS showed the reaction was completed. The resulting solution was concentrated under reduce pressure. The residue was purified by column flash chromatography on silica gel with ethyl acetate/petroleum ether (2:1) to give ditert-butyl (15R)-5-[2-(4-methoxy-1-piperidyl)-6-(2-trimethylsilylethynyl)-4-pyridyl]-15-methyl-13-oxo-11-thia-6,14,17-triazatetracyclo[8.8.0.0^, 7.0^12,18]octadeca-1(10),2(7),3,5,8,12(18)-hexaene-14,17-dicarboxylate (50 mg, 92%) as a brown solid. LCMS (ESI, m/z): 771 $(M+H)^+$.

Step 2: Synthesis of (15R)-5-[2-ethynyl-6-(4-methoxy-1-piperidyl)-4-pyridyl]-15-methyl-11-thia-6,14,17-triazatetracyclo[8.8.0.0^,7.0^12,18]octadeca-1(10),2(7),3,5,8,12(18)-hexaen-13-one

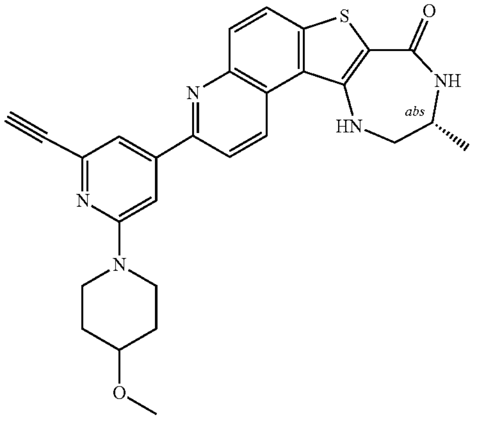

To a solution of ditert-butyl (15R)-5-[2-(4-methoxy-1-piperidyl)-6-(2-trimethylsilylethynyl)-4-pyridyl]-15-methyl-13-oxo-11-thia-6,14,17-triazatetracyclo[8.8.0.0^, 7.0^12,18]octadeca-1(10),2(7),3,5,8,12(18)-hexaene-14,17-dicarboxylate (50 mg, 0.060 mmol, 1.00 equiv) in DCM (2.5 mL) was added dropwise TFA (0.5 mL). The mixture was stirred at room temperature for 2 h. LCMS showed reaction was completed. The resulting solution was concentrated under reduced pressure. The residue was dissolved in methanol (2.0 mL) was added $K_2CO_3$ (11 mg, 0.080 mmol, 1.50 equiv). The resulting mixture was stirred at room temperature for 2 h. LCMS showed reaction was completed. The resulting solution was diluted with DMSO (3 mL). The solid was filtered out. The filtration was purified by Prep-HPLC using the following gradient conditions: Column: SunFire Prep C18 OBD Column, 19*150 mm, Sum; Mobile Phase A: Water (0.05% TFA), Mobile Phase B: MeCN; Flow rate: 20 mL/min; Gradient: 50% B to 50% B in 6 min, 50% B; Wave Length: 254 nm; RT1(min): 5.12. Purification resulted in desired (15R)-5-[2-ethynyl-6-(4-methoxy-1-piperidyl)-4-pyridyl]-15-methyl-11-thia-6,14,17-triazatetracyclo[8.8.0.0^,7.0^12,18]octadeca-1(10),2(7),3,5,8,12(18)-hexaen-13-one (9.0 mg, 33%) as an orange solid. LCMS (ESI, m/z): 498 $(M+H)^+$. Analytic Conditions: Column: HALO AQ-C18 100A Column 3.0*30 mm, 2.0 um; Mobile Phase A: Water/0.05% TFA, Mobile Phase B: Acetonitrile/0.05% TFA; Flow rate: 1.2000 mL/min; Gradient: 5% B to 100% B in 1.30 min; 254 nm; Rt: 1.196

$^1H$ NMR (400 MHz, DMSO-$d_6$) δ 9.27 (d, J=8.8 Hz, 1H), 8.37 (d, J=8.8 Hz, 1H), 8.18 (d, J=8.8 Hz, 1H), 8.12-8.03 (m, 2H), 7.71 (s, 1H), 7.68 (s, 1H), 7.19 (s, 1H), 4.23 (s, 1H), 4.11-4.03 (m, 2H), 3.55-3.42 (m, 4H), 3.33-3.28 (m, 5H), 2.02-1.89 (m, 2H), 1.54-1.42 (m, 2H), 1.21 (d, J=6.8 Hz, 3H). $^{19}F$ NMR (376 MHz, DMSO-$d_6$) δ-74.63

Example 36: Synthesis of (15R)-5-[2-ethynyl-6-(morpholinomethyl)-4-pyridyl]-15-methyl-11-thia-6,14,17-triazatetracyclo[8.8.0.0^,7.0^12,18]octadeca-1(10),2(7),3,5,8,12(18)-hexaen-13-one

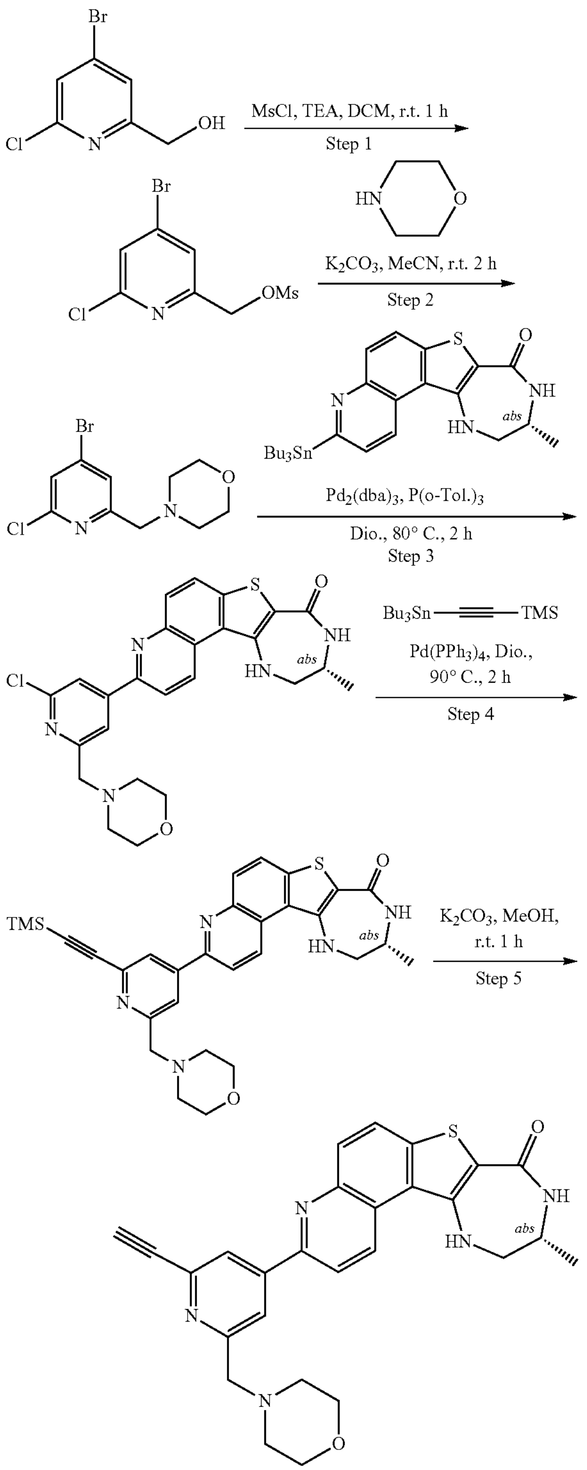

Step 1: Synthesis of (4-bromo-6-chloro-2-pyridyl)methyl methanesulfonate

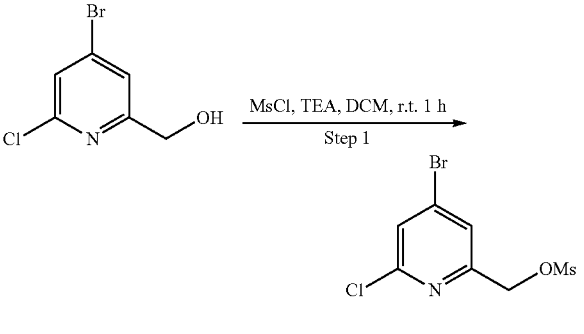

To a solution of (4-bromo-6-chloro-2-pyridyl)methanol (300 mg, 1.350 mmol, 1.00 equiv) and TEA (0.7 mL, 4.050 mmol, 3.00 equiv) in DCM (15.0 mL) was added dropwise methanesulfonyl chloride (185 mg, 1.620 mmol, 1.50 equiv) at 0° C. under a nitrogen atmosphere. The resulting mixture was stirred for 1 h at room temperature under a nitrogen atmosphere. LCMS showed the reaction was completed. The resulting solution was diluted with water (50 mL), extracted with dichloromethane (2×70 mL). The combined organic layers were washed with brine (2×30 mL), dried over anhydrous sodium sulfate, filtered and concentrated under reduce pressure to give crude (4-bromo-6-chloro-2-pyridyl) methyl methanesulfonate (350 mg, 87%). The crude product was used in the next step directly without further purification. LCMS (ESI, m/z): 300 $(M+H)^+$.

Step 2: Synthesis of 4-[(4-bromo-6-chloro-2-pyridyl)methyl]morpholine

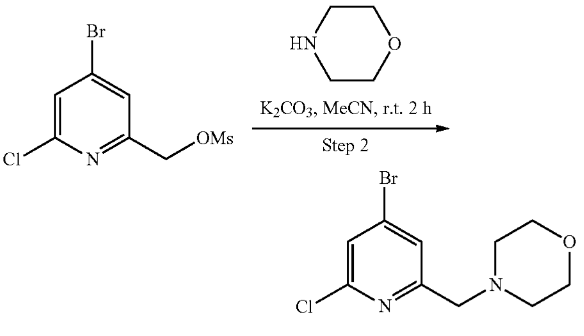

To a solution of 4-bromo-6-chloro-2-pyridyl)methyl methanesulfonate (300 mg, 1.000 mmol, 1.00 equiv) and $K_2CO_3$ (413 mg, 2.990 mmol, 3.00 equiv) in MeCN (10.0 mL) was added dropwise morpholine (130 mg, 1.500 mmol, 1.50 equiv). The resulting mixture was stirred at room temperature for 2 h. LCMS showed the reaction was completed. The resulting solution was diluted with ethyl acetate (30 mL). The solid was filtered out. The filtration was concentrated under reduce pressure and the residue was purified by column chromatography on silica gel with petroleum ether/ethyl acetate (1:5) to give 4-[(4-bromo-6-chloro-2-pyridyl)methyl]morpholine (280 mg, 96%) as a light yellow solid. LCMS (ESI, m/z): 291 $(M+H)^+$.

Step 3: Synthesis of (15R)-5-[2-chloro-6-(morpholinomethyl)-4-pyridyl]-15-methyl-11-thia-6,14,17-triazatetracyclo[8.8.0.0^,7.0^12,18]octadeca-1(10),2(7),3,5,8,12(18)-hexaen-13-one Step 4: Synthesis of give (15R)-15-methyl-5-[2-(morpholinomethyl)-6-(2-trimethylsilylethynyl)-4-pyridyl]-11-thia-6,14,17-triazatetracyclo[8.8.0.0^,7.0^12,18]octadeca-1(10),2(7),3,5,8,12(18)-hexaen-13-one

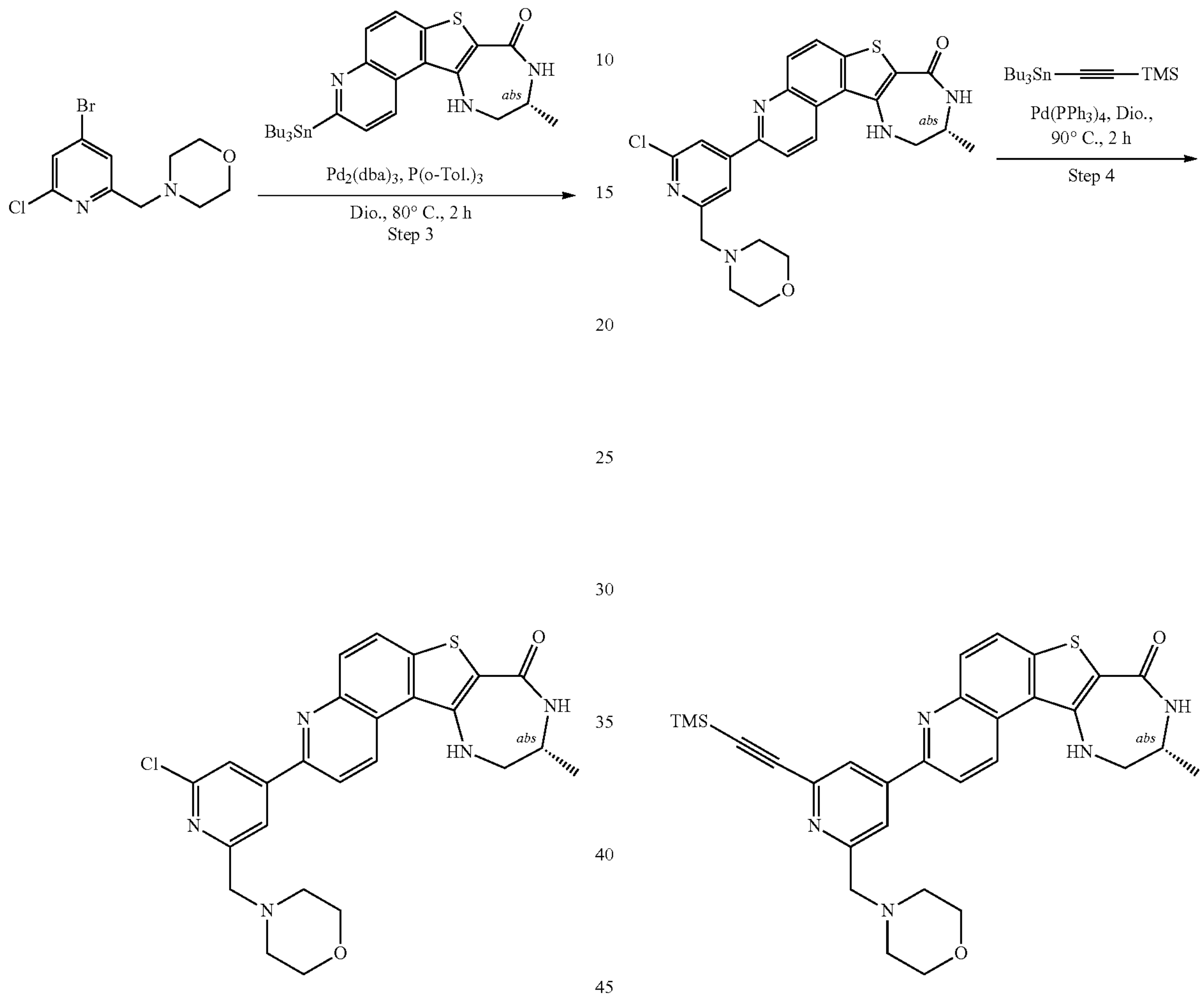

To a solution of 4-[(4-bromo-6-chloro-2-pyridyl)methyl]morpholine (100 mg, 0.340 mmol, 1.00 equiv) and (15R)-15-methyl-5-tributylstannyl-11-thia-6,14,17-triazatetracyclo[8.8.0.0^,7.0^12,18]octadeca-1(10),2(7),3,5,8,12(18)-hexaen-13-one (235 mg, 0.410 mmol, 1.20 equiv) in 1,4-dioxane (4.0 mL) was added P(o-Tol.)$_3$ (21 mg, 0.070 mmol, 0.20 equiv) and $Pd_2$(dba)$_3$ (63 mg, 0.070 mmol). The resulting mixture was stirred at 80° C. for 2 h under a nitrogen atmosphere. LCMS showed the reaction was completed. The resulting solution was diluted with water (20 mL) and extracted with ethyl acetate (2×30 mL). The combined organic layers were washed with brine (2×20 mL), dried over anhydrous sodium sulfate, filtered and concentrated under reduce pressure. The residue was purified by reverse flash chromatography with water (0.05% TFA)/MeCN (1:1) to give (15R)-5-[2-chloro-6-(morpholinomethyl)-4-pyridyl]-15-methyl-11-thia-6,14,17-triazatetracyclo[8.8.0.0^,7.0^12,18]octadeca-1(10),2(7),3,5,8,12(18)-hexaen-13-one (110 mg, 65%) as a light yellow solid. LCMS (ESI, m/z): 494 $(M+H)^+$.

To a solution of (15R)-5-[2-chloro-6-(morpholinomethyl)-4-pyridyl]-15-methyl-11-thia-6,14,17-triazatetracyclo[8.8.0.0^,7.0^12,18]octadeca-1(10),2(7),3,5,8,12(18)-hexaen-13-one (70 mg, 0.140 mmol, 1.00 equiv) and trimethyl(2-tributylstannylethynyl)silane (274 mg, 0.710 mmol, 5.00 equiv) in 1,4-dioxane (2.0 mL) was added $Pd(PPh_3)_4$(24 mg, 0.030 mmol, 0.20 equiv). The resulting solution was stirred at 80° C. for 2 h under nitrogen atmosphere. LCMS showed the reaction was completed. The resulting solution was diluted with water (20 mL), extracted with ethyl acetate (2×20 mL). The combined organic layers were washed with brine (2×20 mL), dried over anhydrous sodium sulfate, filtered and concentrated under reduce pressure. The residue was purified by reverse flash chromatography with water (0.05% TFA)/MeCN (1:2) to give (15R)-15-methyl-5-[2-(morpholinomethyl)-6-(2-trimethylsilylethynyl)-4-pyridyl]-11-thia-6,14,17-triazatetracyclo[8.8.0.0^,7.0^12,18]octadeca-1(10),2(7),3,5,8,12(18)-hexaen-13-one (50 mg, 63%) as a light yellow solid. LCMS (ESI, m/z): 556 $(M+H)^+$.

Step 5: Synthesis of (15R)-5-[2-ethynyl-6-(morpholinomethyl)-4-pyridyl]-15-methyl-11-thia-6,14,17-triazatetracyclo[8.8.0.0^,7.0^12,18]octadeca-1(10),2(7),3,5,8,12(18)-hexaen-13-one

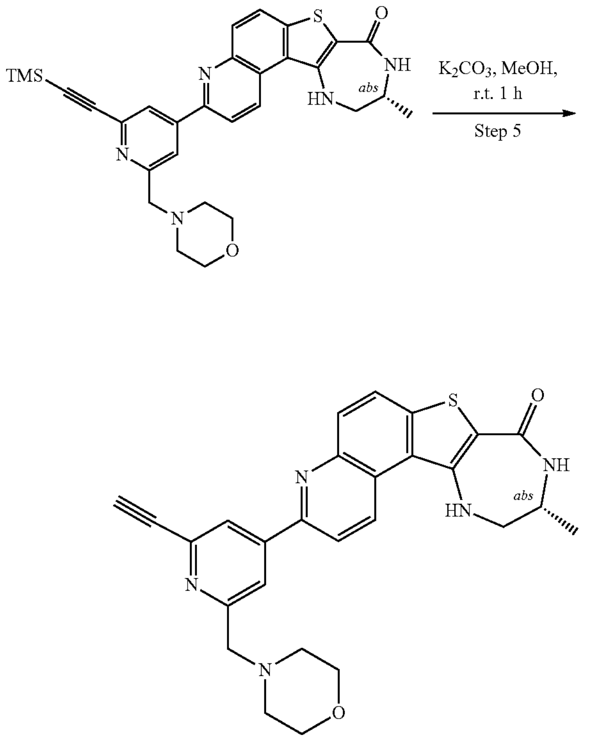

To a solution of (15R)-15-methyl-5-[2-(morpholinomethyl)-6-(2-trimethylsilylethynyl)-4-pyridyl]-11-thia-6,14,17-triazatetracyclo[8.8.0.0^,7.0^12,18]octadeca-1(10),2(7),3,5,8,12(18)-hexaen-13-one (50 mg, 0.090 mmol, 1.00 equiv) in methanol (1.0 mL) was added $K_2CO_3$ (37 mg, 0.270 mmol, 3.00 equiv). The resulting solution was stirred at room temperature for 1 h. LCMS showed the reaction was completed. The resulting solution was diluted with DMSO (3 mL). The solid was filtered out. The filtration was purified by Prep-HPLC using the following conditions: Column: SunFire Prep C18 OBD Column, 19*150 mm, 5 μm; Mobile Phase A: Water (0.05% TFA), Mobile Phase B: MeCN; Flow rate: 20 mL/min; Gradient: 20% B to 35% B in 6 min, 35% B; Wave Length: 254 nm; RT1(min): 4.98. Purification resulted in desired (15R)-5-[2-ethynyl-6-(morpholinomethyl)-4-pyridyl]-15-methyl-11-thia-6,14,17-triazatetracyclo[8.8.0.0^,7.0^12,18]octadeca-1(10),2(7),3,5,8,12(18)-hexaen-13-one (21.1 mg, 48%) as a yellow solid. LCMS (ESI, m z): 484 $[M+H]^+$. Analytic Conditions: Column: HALO C18 100A Column 3.0*30 mm, 2.0 um; Mobile Phase A: Water/0.05% TFA, Mobile Phase B: Acetonitrile/0.05% TFA; Flow rate: 1.2000 mL/min; Gradient: 5% B to 100% B in 1.30 min; 254 nm; Rt: 0.968 min.

$^1H$ NMR (400 MHz, DMSO-$d_6$) δ10.47 (s, 1H), 9.35 (d, J=9.2 Hz, 1H), 8.53 (d, J=8.8 Hz, 1H), 8.46 (d, J=8.8 Hz, 1H), 8.24 (d, J=8.8 Hz, 1H), 8.15 (d, J=4.0 Hz, 1H), 8.07 (d, J=8.8 Hz, 1H), 7.22 (t, J=4.4 Hz, 1H), 4.65 (s, 2H), 4.61 (s, 1H), 4.12-3.78 (m, 5H), 3.71-3.51 (m, 6H), 1.21 (d, J=6.8 Hz, 3H). $^{19}F$ NMR (376 MHz, DMSO-$d_6$) δ-73.80.

Example 37: Synthesis of (15R)-15-methyl-5-[2-[[(2R,6S)-2,6-dimethylmorpholin-4-yl]methyl]-6-vinyl-4-pyridyl]-11-thia-6,14,17-triazatetracyclo[8.8.0.0^,7.0^12,18]octadeca-1(10),2(7),3,5,8,12(18)-hexaen-13-one

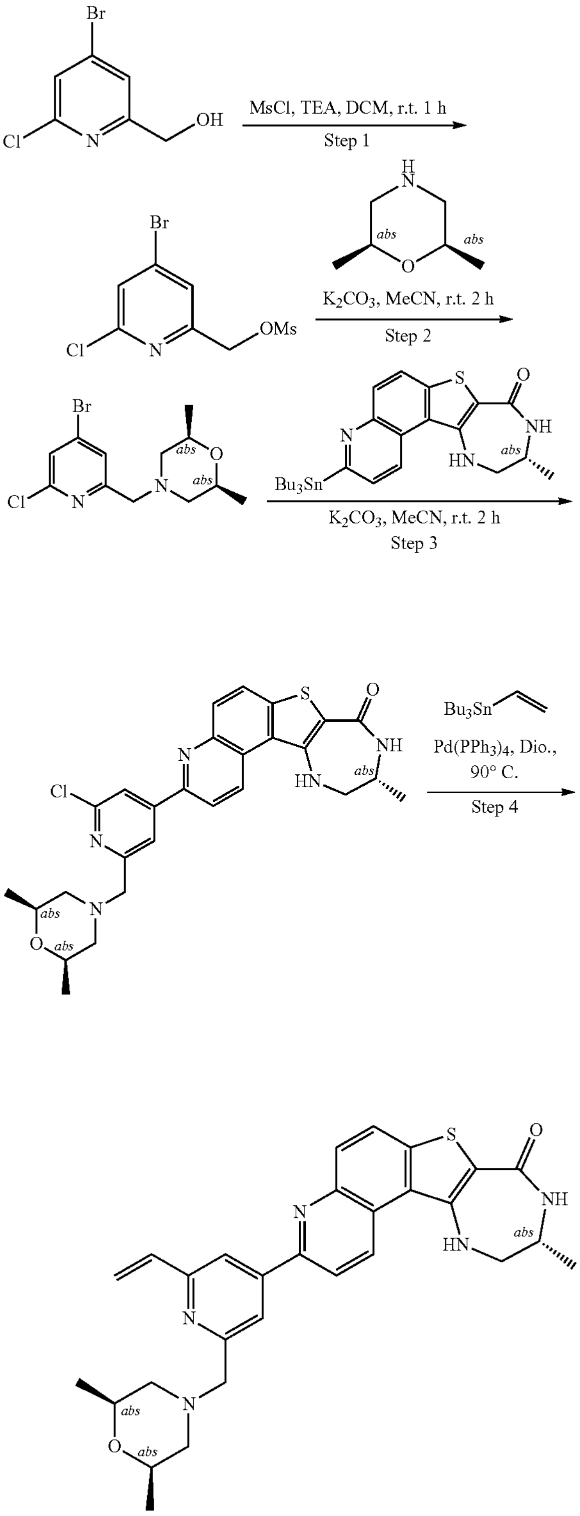

Step 1: Synthesis of (4-bromo-6-chloro-2-pyridyl)methyl methanesulfonate

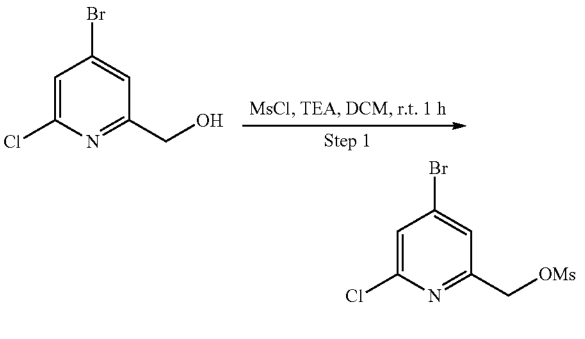

To a solution of (4-bromo-6-chloro-2-pyridyl)methanol (300 mg, 1.350 mmol, 1.00 equiv) and TEA (0.7 mL, 4.050 mmol, 3.00 equiv) in DCM (15.0 mL) was added dropwise methanesulfonyl chloride (185 mg, 1.620 mmol, 1.50 equiv) at 0° C. The resulting mixture was stirred for 1 h at room temperature under nitrogen atmosphere. LCMS showed the reaction was completed. The resulting solution was diluted with water (50 mL), extracted with dichloromethane (2×50 mL). The combined organic layers were washed with brine (2×30 mL), dried over anhydrous sodium sulfate, filtered and concentrated under reduce pressure to give crude (4-bromo-6-chloro-2-pyridyl)methyl methanesulfonate (350 mg, 87%). The crude product was used in the next step directly without further purification. LCMS (ESI, m/z): 300 $(M+H)^+$.

Step 2: Synthesis of (2R,6S)-4-[(4-bromo-6-chloro-2-pyridyl)methyl]-2,6-dimethyl-morpholine

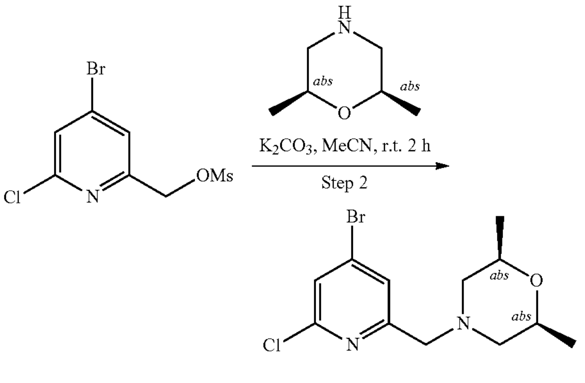

To a solution of (4-bromo-6-chloro-2-pyridyl)methyl methanesulfonate (100 mg, 0.330 mmol, 1.00 equiv) and $K_2CO_3$ (137 mg, 1.000 mmol, 3.00 equiv) in MeCN (3.0 mL) was added (2S,6R)-2,6-dimethylmorpholine (38 mg, 0.330 mmol, 1.00 equiv). The mixture was stirred at room temperature for 1 h under a nitrogen atmosphere. LCMS showed the reaction was completed. The resulting solution was diluted with ethyl acetate (30 mL). The solid was filtered out. The filtration was concentrated under reduce pressure and the residue was purified by column chromatography on silica gel with ethyl acetate to give (2R,6S)-4-[(4-bromo-6-chloro-2-pyridyl)methyl]-2,6-dimethyl-morpholine (80 mg, 75%) as a yellow solid. LCMS (ESI, m/z): 319 $(M+H)^+$.

Step 3: Synthesis of (15R)-5-[2-chloro-6-[[(2R,6S)-2,6-dimethylmorpholin-4-yl]methyl]-4-pyridyl]-15-methyl-11-thia-6,14,17-triazatetracyclo[8.8.0.0^, 7.0^12,18]octadeca-1(10),2(7),3,5,8,12(18)-hexaen-13-one

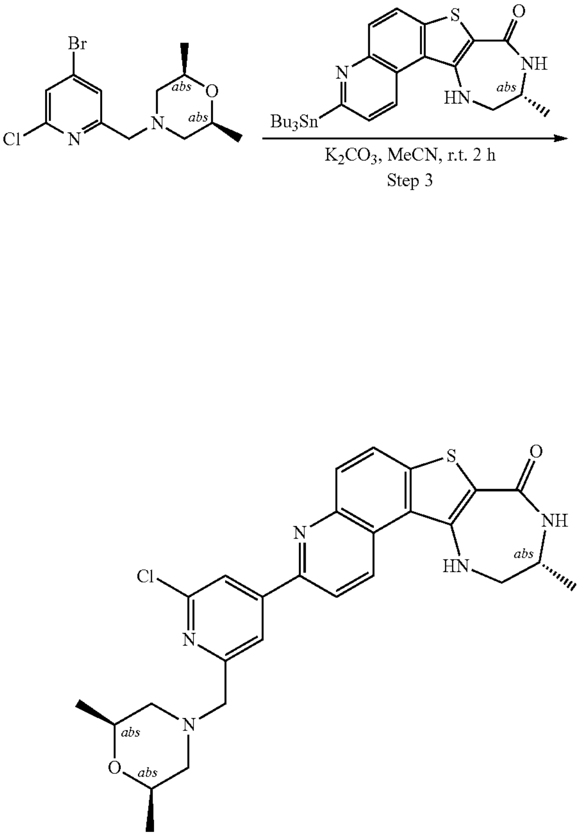

To a solution of (2R,6S)-4-[(4-bromo-6-chloro-2-pyridyl) methyl]-2,6-dimethyl-morpholine (100 mg, 0.310 mmol, 1.00 equiv) and (15R)-15-methyl-5-tributylstannyl-11-thia-6,14,17-triazatetracyclo[8.8.0.0^,7.0^12,18]octadeca-1(10), 2(7),3,5,8,12(18)-hexaen-13-one (215 mg, 0.380 mmol, 1.20 equiv) in 1,4-dioxane (5.0 mL) was added $P(o\text{-}Tol.)_3$ (19 mg, 0.060 mmol, 0.20 equiv) and $Pd_2(dba)_3$ (57 mg, 0.060 mmol, 0.20 equiv). The resulting mixture was stirred at 80° C. for 2 h under a nitrogen atmosphere. LCMS showed the reaction was completed. The resulting solution was diluted with water (20 mL), extracted with ethyl acetate (2×20 mL). The combined organic layers were washed with brine (2×20 mL), dried over anhydrous sodium sulfate, filtered and concentrated under reduce pressure. The residue was purified by reverse flash chromatography with water (0.05% TFA)/MeCN (1:2) to give (15R)-5-[2-chloro-6-[[(2R,6S)-2,6-dimethylmorpholin-4-yl]methyl]-4-pyridyl]-15-methyl-11-thia-6,14,17-triazatetracyclo[8.8.0.0^,7.0^12,18]octadeca-1(10),2(7),3,5,8,12(18)-hexaen-13-one (120 mg, 73%) as a light yellow solid. LCMS (ESI, m/z): 522 $(M+H)^+$.

Step 4: Synthesis of (15R)-15-methyl-5-[2-[[(2R,6S)-2,6-dimethylmorpholin-4-yl]methyl]-6-vinyl-4-pyridyl]-11-thia-6,14,17-triazatetracyclo[8.8.0.0^,7.0^12,18]octadeca-1(10),2(7),3,5,8,12(18)-hexaen-13-one

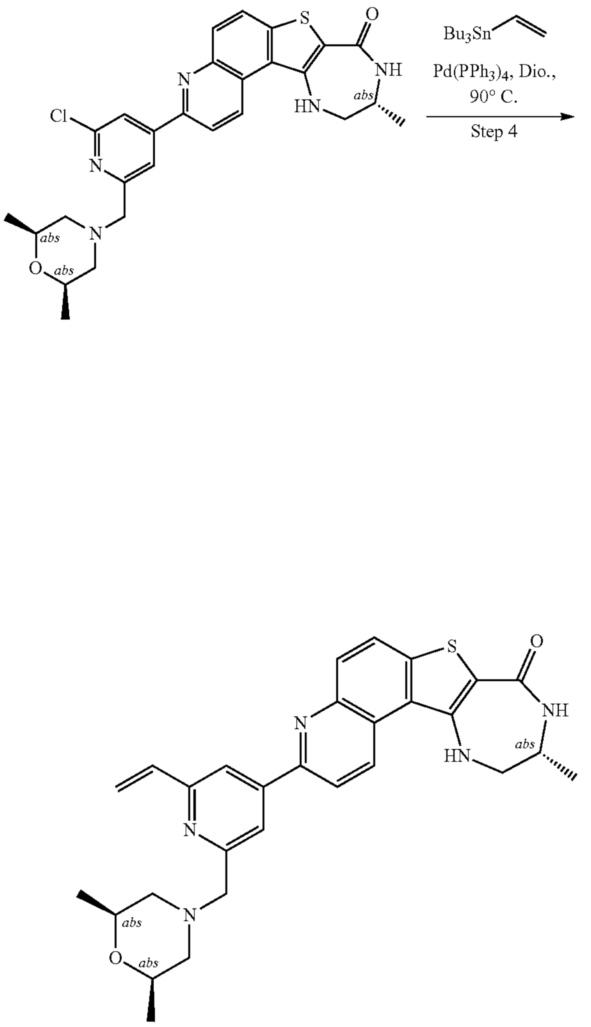

To a solution of rac-(15R)-5-[2-chloro-6-[[rac-(2R,6S)-2,6-dimethylmorpholin-4-yl]methyl]-4-pyridyl]-15-methyl-11-thia-6,14,17-triazatetracyclo[8.8.0.0^,7.0^12,18]octadeca-1(10),2(7),3,5,8,12(18)-hexaen-13-one (60 mg, 0.110 mmol, 1.00 equiv) and tributyl(vinyl)stannane (182 mg, 0.5700 mmol, 5.00 equiv) in 1,4-dioxane (2.0 mL) was added $Pd(PPh_3)_4$(27 mg, 0.020 mmol, 0.20 equiv). The resulting mixture was stirred at 80° C. for 2 h under a nitrogen atmosphere. LCMS showed the reaction was completed. The resulting solution was concentrated under reduce pressure. The residue was purified by Prep-HPLC with the following conditions: Column: SunFire Prep C18 OBD Column, 19*150 mm, 5 μm; Mobile Phase A: Water (0.05% TFA), Mobile Phase B: MeCN; Flow rate: 20 mL/min; Gradient: 28% B to 32% B in 6 min, 32% B; Wave Length: 254 nm; RT1(min): 6.15. Purification resulted in desired (15R)-15-methyl-5-[2-[[(2R,6S)-2,6-dimethylmorpholin-4-yl]methyl]-6-vinyl-4-pyridyl]-11-thia-6,14,17-triazatetracyclo[8.8.0.0^,7.0^12,18]octadeca-1(10),2(7),3,5,8,12(18)-hexaen-13-one (34.1 mg, 56%) as a light yellow solid. LCMS (ESI, m z): 514 $[M+H]^+$. Analytic Conditions: Column: HALO C18 100A Column 3.0*30 mm, 2.0 um; Mobile Phase A: Water/0.05% TFA, Mobile Phase B: Acetonitrile/0.05% TFA; Flow rate: 1.2000 mL/min; Gradient: 5% B to 60% B in 2.10 min; 254 nm; Rt: 1.730 min.

$^1H$ NMR (400 MHz, DMSO-$d_6$) δ 9.35 (d, J=8.8 Hz, 1H), 8.45 (s, 1H), 8.43 (d, J=9.2 Hz, 1H), 8.35 (s, 1H), 8.23 (d, J=8.8 Hz, 1H), 8.15 (d, J=4.4 Hz, 1H), 8.07 (d, J=9.2 Hz, 1H), 7.22 (t, J=4.4 Hz, 1H), 7.07 (dd, J=17.6, 10.8 Hz, 1H), 6.52 (dd, J=17.6, 1.2 Hz, 1H), 5.70 (dd, J=10.8, 1.2 Hz, 1H), 4.65 (s, 2H), 3.96-3.92 (m, 2H), 3.63-3.45 (m, 5H), 2.91-2.85 (m, 2H), 1.21 (d, J=6.8 Hz, 3H), 1.15 (d, J=9.2 Hz, 6H). $^{19}F$ NMR (376 MHz, DMSO-$d_6$) δ-73.98.

Example 38: Synthesis of (15R)-5-[2-[[(2R,6S)-2,6-dimethylmorpholin-4-yl]methyl]-6-ethynyl-4-pyridyl]-15-methyl-11-thia-6,14,17-triazatetracyclo[8.8.0.0^,7.0^12,18]octadeca-1(10),2(7),3,5,8,12(18)-hexaen-13-one

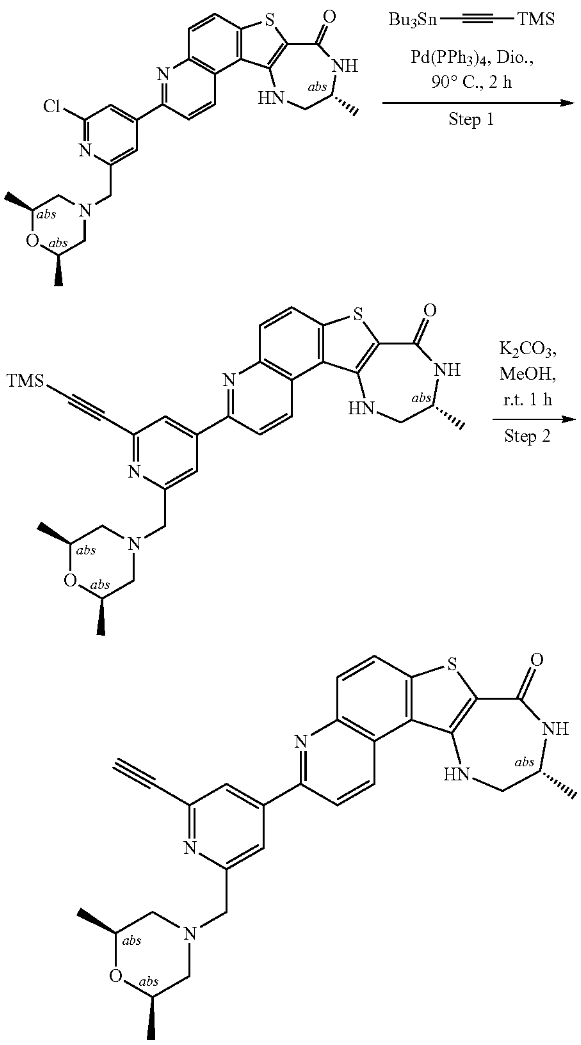

Step 1: Synthesis of (15R)-15-methyl-5-[2-[[(2R,6S)-2,6-dimethylmorpholin-4-yl]methyl]-6-(2-trimethylsilylethynyl)-4-pyridyl]-11-thia-6,14,17-triazatetracyclo[8.8.0.0^,7.0^12,18]octadeca-1(10),2(7),3,5,8,12(18)-hexaen-13-one

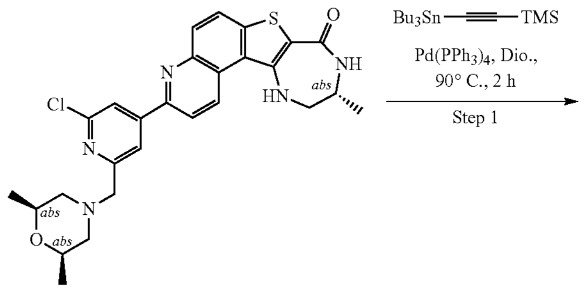

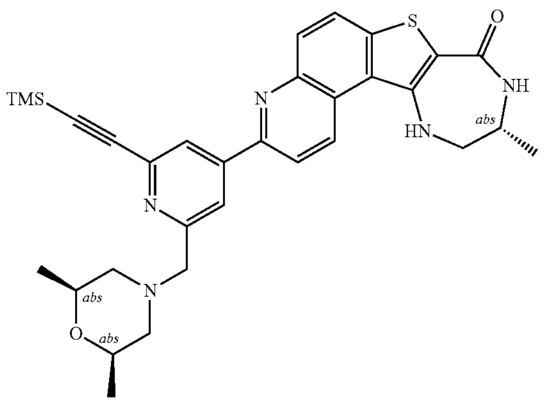

To a solution of rac-(15R)-5-[2-chloro-6-[[rac-(2R,6S)-2,6-dimethylmorpholin-4-yl]methyl]-4-pyridyl]-15-methyl-11-thia-6,14,17-triazatetracyclo[8.8.0.0^,7.0^12,18]octadeca-1(10),2(7),3,5,8,12(18)-hexaen-13-one (70 mg, 0.130 mmol, 1.00 equiv) and trimethyl(2-tributylstannylethynyl)silane (259 mg, 0.670 mmol, 5.00 equiv) in 1,4-dioxane (2.0 mL) was added $Pd(PPh_3)_4$(31 mg, 0.030 mmol, 0.20 equiv). The resulting mixture was stirred at 80° C. for 2 h under a nitrogen atmosphere. LCMS showed the reaction was completed. The resulting solution was concentrated under reduce pressure and the residue was purified by reverse flash chromatography with water (0.05% TFA)/MeCN (1:2) to give rac-(15R)-15-methyl-5-[2-[[rac-(2R,6S)-2,6-dimethylmorpholin-4-yl]methyl]-6-(2-trimethylsilylethynyl)-4-pyridyl]-11-thia-6,14,17-triazatetracyclo[8.8.0.0^,7.0^12,18]octadeca-1(10),2(7),3,5,8,12(18)-hexaen-13-one (60 mg, 77%) as a light yellow solid. LCMS (ESI, m/z): 584 $(M+H)^+$.

Step 2: Synthesis of (15R)-5-[2-[[(2R,6S)-2,6-dimethylmorpholin-4-yl]methyl]-6-ethynyl-4-pyridyl]-15-methyl-11-thia-6,14,17-triazatetracyclo[8.8.0.0^,7.0^12,18]octadeca-1(10),2(7),3,5,8,12(18)-hexaen-13-one

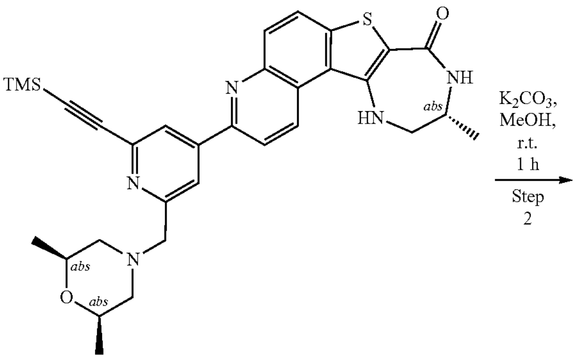

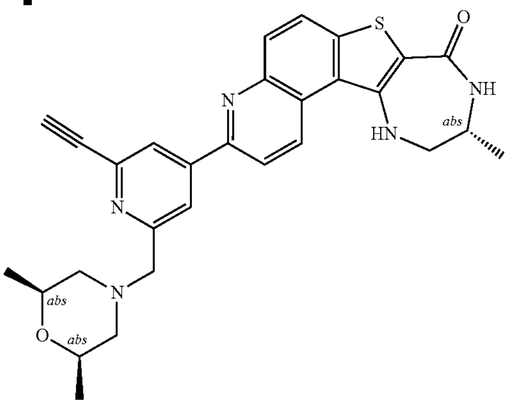

To a solution of (15R)-15-methyl-5-[2-[[(2R)-2-methylmorpholin-4-yl]methyl]-6-(2-trimethylsilylethynyl)-4-pyridyl]-11-thia-6,14,17-triazatetracyclo[8.8.0.0^,7.0^12,18]octadeca-1(10),2(7),3,5,8,12(18)-hexaen-13-one (60 mg, 0.110 mmol, 1.00 equiv) in methanol (2.0 mL) was added $K_2CO_3$ (58 mg, 0.4200 mmol, 4.00 equiv). The resulting mixture was stirred at room temperature for 1 h. LCMS showed the reaction was completed. The resulting solution was diluted with DMSO (3 mL). The solid was filtered out. The filtration was purified by Prep-HPLC used the following conditions: Column: Welch Utimate HS-C18, 21.2*250 mm, 7 μm; Mobile Phase A: Water (0.05% TFA), Mobile Phase B: MeCN; Flow rate: 25 mL/min; Gradient: 29% B to 30% B in 5 min, 30% B; Wave Length: 254/210 nm; RT1(min): 4.45. Purification resulted in desired (15R)-5-[2-[[(2R,6S)-2,6-dimethylmorpholin-4-yl]methyl]-6-ethynyl-4-pyridyl]-15-methyl-11-thia-6,14,17-triazatetracyclo[8.8.0.0^,7.0^12,18]octadeca-1(10),2(7),3,5,8,12(18)-hexaen-13-one (32.1 mg, 59%) as a light yellow solid. LCMS (ESI, m z): 512 $[M+H]^+$. Analytic Conditions: Column: HALO C18 100A Column 3.0*30 mm, 2.0 um; Mobile Phase A: Water/0.05% TFA, Mobile Phase B: Acetonitrile/0.05% TFA; Flow rate: 1.2000 mL/min; Gradient: 5% B to 65% B in 2.10 min; 254 nm; Rt: 1.607 min.

$^1H$ NMR (400 MHz, DMSO-$d_6$) δ 9.34 (d, J=9.2 Hz, 1H), 8.53 (s, 1H), 8.49 (s, 1H), 8.44 (d, J=8.8 Hz, 1H), 8.24 (d, J=8.8 Hz, 1H), 8.10 (d, J=8.8 Hz, 1H), 4.62 (s, 2H), 4.57 (s, 1H), 3.93-3.85 (m, 2H), 3.61-3.43 (m, 3H), 2.86 (t, J=12.0

Hz, 2H), 1.21 (d, J=6.8 Hz, 3H), 1.15 (d, J=6.4 Hz, 6H). $^{19}F$ NMR (376 MHz, DMSO-$d_6$) δ-74.01.

Example 39: Synthesis of (15R)-5-[2-[[(2R,6R)-2,6-dimethylmorpholin-4-yl]methyl]-6-vinyl-4-pyridyl]-15-methyl-11-thia-6,14,17-triazatetracyclo[8.8.0.0^,7.0^12,18]octadeca-1(10),2(7),3,5,8,12(18)-hexaen-13-one

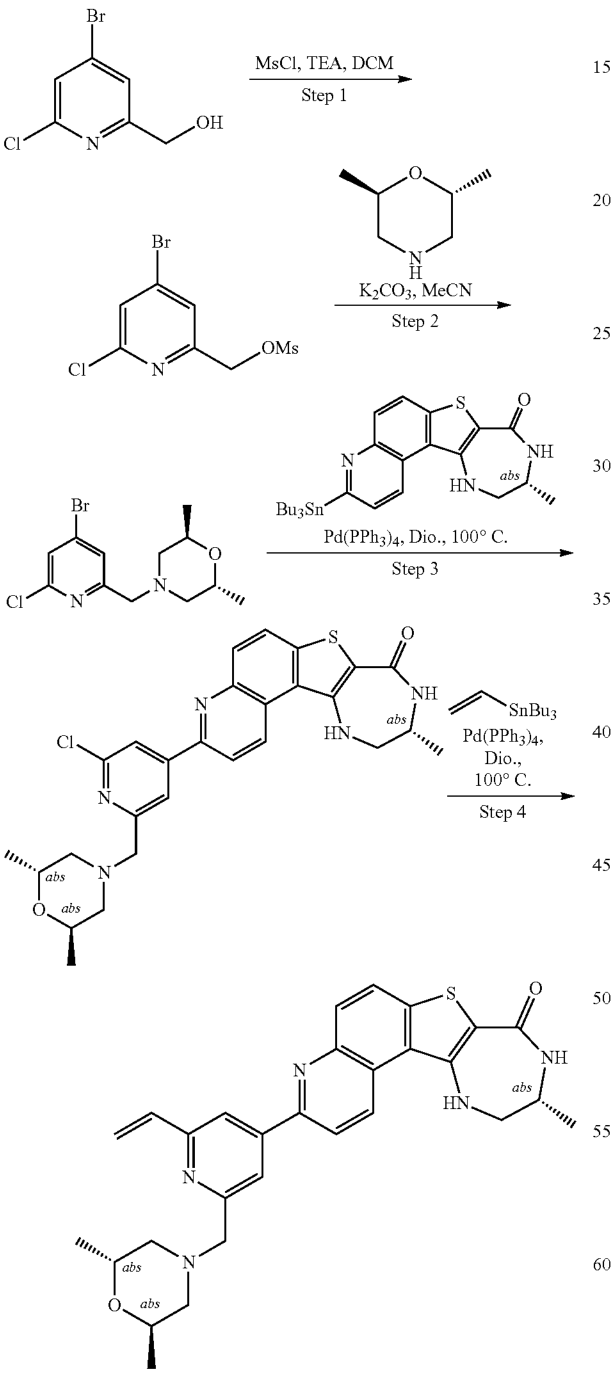

Step 1: Synthesis of (4-bromo-6-chloro-2-pyridyl)methyl methanesulfonate

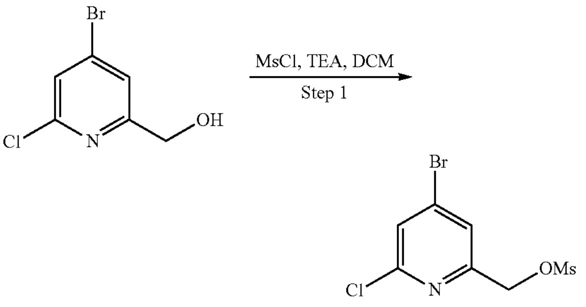

To a solution of (4-bromo-6-chloro-2-pyridyl)methanol (500 mg, 2.250 mmol, 1.00 equiv) and TEA (871 mg, 6.740 mmol, 3.00 equiv) in DCM (10.0 mL) was added dropwise methanesulfonyl chloride (309 mg, 2.700 mmol, 1.20 equiv). The resulting mixture was stirred at room temperature for 2 h under a nitrogen atmosphere. LCMS showed the reaction was completed. The resulting solution was diluted with water (50 mL), extracted with ethyl acetate (3×50 mL). The combined organic layers were washed with brine (2×50 mL), dried over anhydrous sodium sulfate, filtered and concentrated under reduced pressure to give 450 mg crude product. The crude product was used directly for the next step without further purification. LCMS (ESI, m/z): 300 $(M+H)^+$.

Step 2: Synthesis of (2R,6R)-4-[(4-bromo-6-chloro-2-pyridyl)methyl]-2,6-dimethyl-morpholine

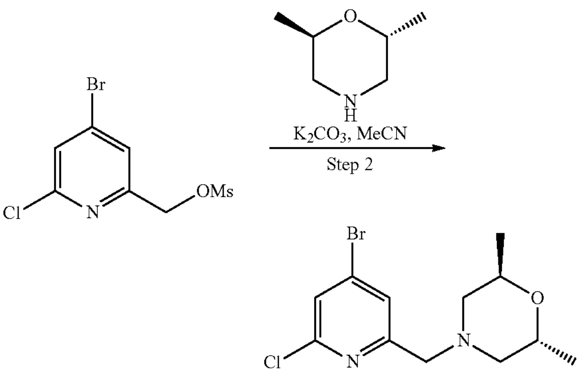

To a solution of (4-bromo-6-chloro-2-pyridyl)methyl methanesulfonate (400 mg, 1.330 mmol, 1.00 equiv) and (2R,6R)-2,6-dimethylmorpholine (184 mg, 1.600 mmol, 1.20 equiv) in MeCN (10.0 mL) was added $K_2CO_3$ (551 mg, 3.990 mmol, 3.00 equiv). The resulting mixture was stirred at room temperature for 3 h. LCMS showed the reaction was completed. The resulting solution was diluted with water (100 mL), extracted with ethyl acetate (3×50 mL). The combined organic layers were washed with brine (2×50 mL), dried over anhydrous sodium sulfate, filtered and concentrated under reduced pressure. The residue was purified by flash chromatography on silica gel with ethyl acetate/petroleum ether (1:2) to give (2R,6R)-4-[(4-bromo-6- chloro-2-pyridyl)methyl]-2,6-dimethyl-morpholine (400 mg, 94%) as an off-white solid. LCMS (ESI, m/z): 319(M+H)+.

Step 3: Synthesis of (15R)-5-[2-chloro-6-[[(2R,6R)-2,6-dimethylmorpholin-4-yl]methyl]-4-pyridyl]-15-methyl-11-thia-6,14,17-triazatetracyclo[8.8.0.0^,7.0^12,18]octadeca-1(10),2(7),3,5,8,12(18)-hexaen-13-one

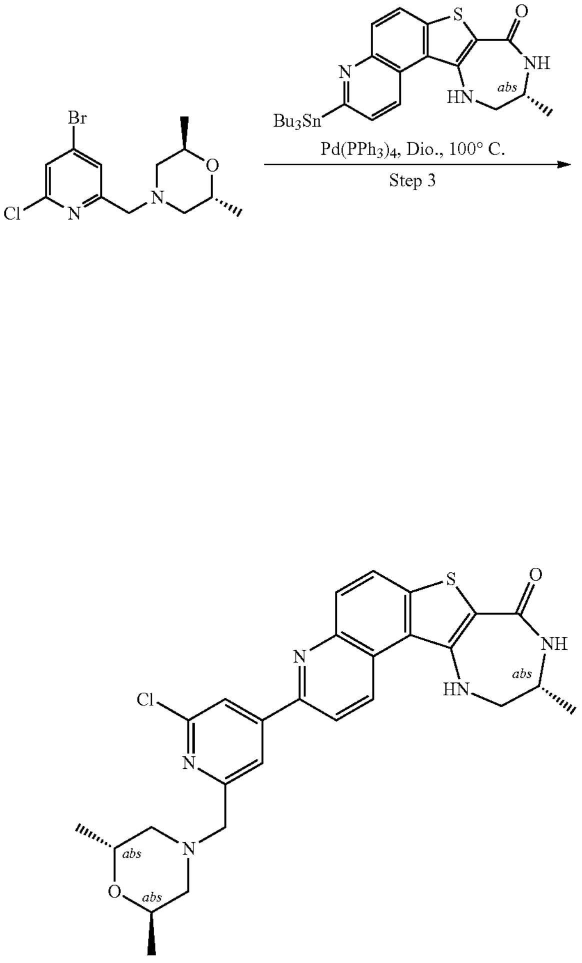

To a solution of (2R,6R)-4-[(4-bromo-6-chloro-2-pyridyl)methyl]-2,6-dimethyl-morpholine (380 mg, 1.190 mmol, 1.00 equiv) and (15R)-15-methyl-5-tributylstannyl-11-thia-6,14,17-triazatetracyclo[8.8.0.0^,7.0^12,18]octadeca-1(10),2(7),3,5,8,12(18)-hexaen-13-one (1.0 g, 1.780 mmol, 1.50 equiv) in 1,4-dioxane (10.0 mL) was added $Pd(PPh_3)_4$(137 mg, 0.120 mmol, 0.10 equiv). The resulting mixture was stirred at 100° C. for 3 h under a nitrogen atmosphere. LCMS showed the reaction was completed. The resulting solution was concentrated under reduced pressure. The residue was purified by column flash chromatography on silica gel with dichloromethane/ethyl acetate (1:1) to give (15R)-5-[2-chloro-6-[[(2R,6R)-2,6-dimethylmorpholin-4-yl]methyl]-4-pyridyl]-15-methyl-11-thia-6,14,17-triazatetracyclo[8.8.0.0^,7.0^12,18]octadeca-1(10),2(7),3,5,8,12(18)-hexaen-13-one (450 mg, 73%) as a yellow solid. LCMS (ESI, m/z): 522 $(M+H)^+$.

Step 4: Synthesis of (15R)-5-[2-[[(2R,6R)-2,6-dimethylmorpholin-4-yl]methyl]-6-vinyl-4-pyridyl]-15-methyl-11-thia-6,14,17-triazatetracyclo[8.8.0.0^,7.0^12,18]octadeca-1(10),2(7),3,5,8,12(18)-hexaen-13-one

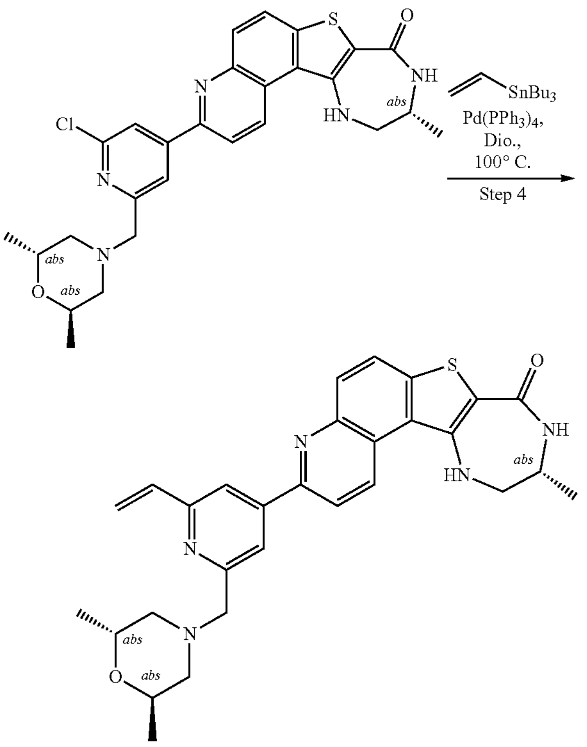

To a solution of (15R)-5-[2-chloro-6-[[(2R,6R)-2,6-dimethylmorpholin-4-yl]methyl]-4-pyridyl]-15-methyl-11-thia-6,14,17-triazatetracyclo[8.8.0.0^,7.0^12,18]octadeca-1(10),2(7),3,5,8,12(18)-hexaen-13-one (100 mg, 0.190 mmol, 1.00 equiv) and tributyl(vinyl)stannane (91 mg, 0.290 mmol, 1.50 equiv) in 1,4-dioxane (5.0 mL) was added $Pd(PPh_3)_4$(22 mg, 0.020 mmol, 0.10 equiv). The resulting mixture was stirred at 100° C. for 3 h under a nitrogen atmosphere. LCMS showed the reaction was completed. The resulting solution was concentrated under reduced pressure. The residue was purified by Prep-HPLC using the following gradient conditions: Column: Xselect CSH C18 OBD Column 30*150 mm 5 μm; Mobile Phase A: Water (0.1% FA), Mobile Phase B: MeCN; Flow rate: 60 mL/min; Gradient: 7% B to 37% B in 10 min, 37% B; Wave Length: 254 nm; RT1(min): 9.05. Purification resulted in desired (15R)-5-[2-[[(2R,6R)-2,6-dimethylmorpholin-4-yl]methyl]-6-vinyl-4-pyridyl]-15-methyl-11-thia-6,14,17-triazatetracyclo[8.8.0.0^,7.0^12,18]octadeca-1(10),2(7),3,5,8,12(18)-hexaen-13-one (6.1 mg, 6%) as a yellow solid. LCMS (ESI, m/z): 514 $(M+H)^+$. Analytic Conditions: Column: HALO AQ-C18 100A Column 3.0*30 mm, 2.0 um; Mobile Phase A: Water/0.05% TFA, Mobile Phase B: Acetonitrile/0.05% TFA; Flow rate: 1.2000 mL/min; Gradient: 5% B to 65% B in 2.10 min; 254 nm; Rt: 1.621

$^1H$ NMR (300 MHz, DMSO-$d_6$) δ 9.32 (d, J=9.0 Hz, 1H), 8.37 (d, J=8.4 Hz, 1H), 8.30-8.22 (m, 3H), 8.19 (s, 1H), 8.05 (d, J=9.0 Hz, 1H), 6.98 (dd, J=17.4, 10.5 Hz, 1H), 6.39 (d, J=17.1 Hz, 1H), 5.57 (d, J=12.0 Hz, 1H), 4.02 (s, 3H), 3.89-3.62 (m, 3H), 3.52-3.47 (m, 3H), 2.77-2.61 (m, 1H), 2.46-2.22 (m, 2H), 1.23-1.20 (m, 9H).

Example 40: Synthesis of (R)-3-(2,3-dimethyl-6-vinylpyridin-4-yl)-10-methyl-9,10,11,12-tetrahydro-8H-[1,4]diazepino[5',6':4,5]thieno[3,2-f]quinolin-8-one

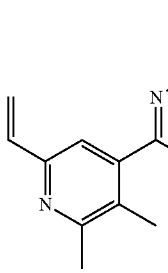

Step 1: Synthesis of 4-chloro-2,3-dimethyl-6-vinylpyridine

A 20 mL reaction vial was charged with a stir bar, potassium vinyltrifluoroborate (76 mg, 0.568 mmol), 4,6-dichloro-2,3-dimethylpyridine (100 mg, 0.568 mmol), Pd(dppf)Cl2, DCM adduct (46.4 mg, 0.057 mmol), and cesium carbonate (463 mg, 1.420 mmol), Dioxane (2272 μl), and Water (568 μl) to give a orange suspension. The resulting mixture was degassed by bubbling of N2 for 5 min and then sealed and stirred at 60° C. for 16 h. LC-MS indicated the desired product as the major product. The reaction mixture was concentrated under reduced pressure, diluted in ethyl acetate and filtered through a pad of Celite. The filtrate was concentrated under reduced pressure to yield the crude product. The crude product was purified by flash chromatography (0-100% ethyl acetate in heptane gradient; product eluted at 50% ethyl acetate), affording 4-chloro-2,3-dimethyl-6-vinylpyridine (53 mg, 0.316 mmol, 55.7% yield) as a clear oil.

$^1$H NMR (400 MHz, CHLOROFORM-d) δ 8.98 (d, J=8.6 Hz, 1H), 8.38 (s, 1H), 8.22-8.05 (m, 2H), 7.72-7.48 (m, 2H), 5.23-5.07 (m, 1H), 4.95 (br dd, J=13.8, 8.2 Hz, 1H), 3.25 (br dd, J=13.9, 4.6 Hz, 1H), 2.47-2.36 (m, 3H), 1.65-1.45 (m, 18H), 1.31-1.20 (m, 3H). MS ESI m/z 168.3 and 170.3 $(M+H)^+$ Step 2: Synthesis of (R)-3-(2,3-dimethyl-6-vinylpyridin-4-yl)-10-methyl-9,10,11,12-tetrahydro-8H-[1,4]diazepino[5',6':4,5]thieno[3,2-f]quinolin-8-one A 4 mL reaction vial was charged with a stir bar, (R)-10-methyl-3-(tributylstannyl)-9,10,11,12-tetrahydro-8H-[1,4]diazepino[5',6':4,5]thieno[3,2-f]quinolin-8-one (44.4 mg, 0.078 mmol), 4-chloro-2,3-dimethyl-6-vinylpyridine (13 mg, 0.078 mmol), and tetrakis (8.96 mg, 7.75 μmol), and Dioxane (388 μl) to give a yellow solution. The reaction mixture was degassed by evacuating and backfilling with nitrogen 3 times. The vial was sealed and heated to 100° C. for 16 h. LC MS indicated significant product formation. The reaction mixture was diluted with aqueous potassium fluoride and stirred for 2 h at room temperature. The reaction was diluted in DMF and filtered though a pad of Celite. The crude material was purified via preparative Reverse Phase chromatography with the following conditions: Column: XBridge C18, 19 mm×200 mm, 5 m particles; Mobile Phase A: 5:95 acetonitrile: water with 0.1% TFA; Mobile Phase B: 95:5 acetonitrile: water with 0.1% TFA; Gradient: a 0-min hold at 2% B, 2-42% B over 20 min, then a 4-min hold at 100% B; Flow Rate: 20 mL/min; Column Temperature: 25° C. Fraction collection was triggered by UV (220 nm) and MS (ESI+). Gradient: Fractions containing the desired product were combined and dried via centrifugal evaporation, affording (R)-3-(2,3-dimethyl-6-vinylpyridin-4-yl)-10-methyl-9,10,11,12-tetrahydro-8H-[1,4]diazepino[5',6':4,5]thieno[3,2-f]quinolin-8-one (7.3 mg, 0.018 mmol, 23% yield).

$^1$H NMR (500 MHz, DMSO-$d_6$) δ 9.35 (d, J=8.8 Hz, 1H), 8.22 (d, J=8.9 Hz, 1H), 8.12 (br d, J=4.1 Hz, 1H), 8.03 (d, J=8.8 Hz, 1H), 7.90 (d, J=8.7 Hz, 2H), 7.30-7.01 (m, 2H), 6.94 (dd, J=17.5, 11.0 Hz, 1H), 6.47 (br d, J=17.6 Hz, 1H), 5.74 (br d, J=11.2 Hz, 1H), 2.69 (s, 3H), 2.34 (s, 3H), 1.21 (d, J=6.8 Hz, 3H). 3 protons obscured by solvent peak. MS ESI m/z 415.2 $(M+H)^+$ Example 41: Synthesis of (15R)-5-[3-fluoro-2-(morpholinomethyl)-6-vinyl-4-pyridyl]-15-methyl-11-thia-6,14,17-triazatetracyclo[8.8.0.0^,7.0^12,18]octadeca-1(10),2(7),3,5,8,12(18)-hexaen-13-one

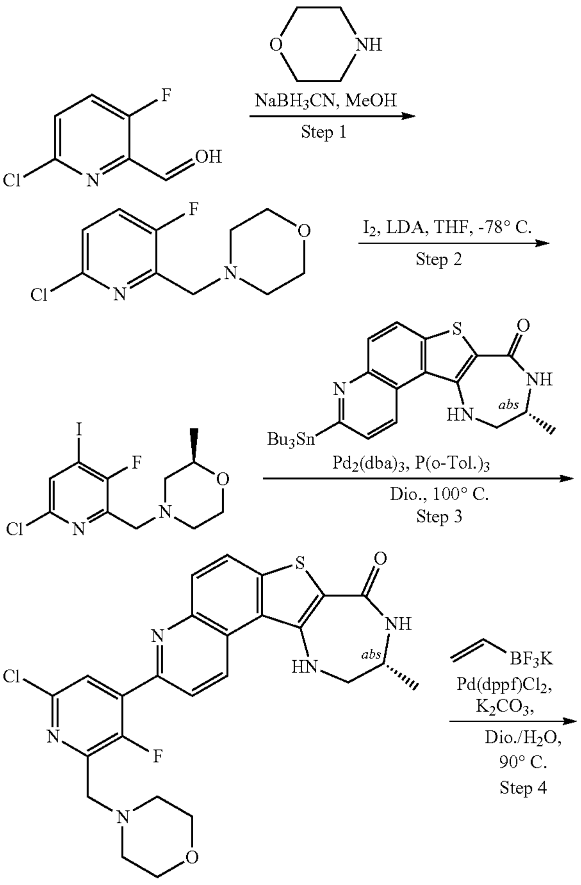

-continued

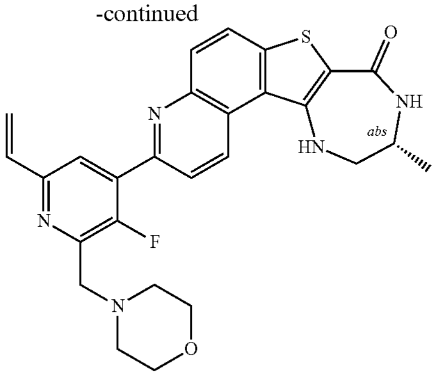

Step 1: Synthesis of 4-[(6-chloro-3-fluoro-2-pyridyl)methyl]morpholine

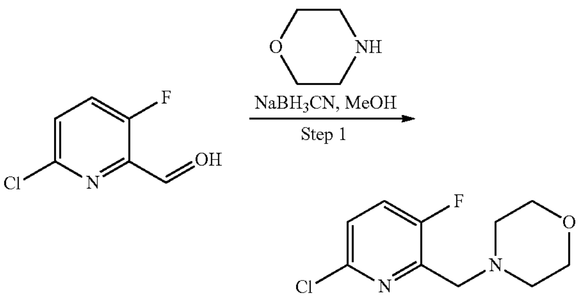

To a solution of 6-chloro-3-fluoro-pyridine-2-carbaldehyde (500 mg, 3.130 mmol, 1.00 equiv) in methanol (10.0 mL) was added morpholine (409 mg, 4.7 mmol, 1.50 equiv) and the pH of the resulting solution was adjusted to 5-6 with acetic acid. After 0.5 h, a solution of $NaBH_3CN$ (592 mg, 9.390 mmol, 3.00 equiv) in methanol (5.0 mL) was added the resulting solution and stirred for 1 h at room temperature. LCMS showed the reaction was completed. The resulting solution was diluted with a water (40 mL), extracted with ethyl acetate (3×40 mL). The combined organic layers were washed with brine (2×30 mL), dried over sodium sulfate, filtered and concentrated under reduce pressure The residue was purified by column chromatography on silica gel petroleum ether/ethyl acetate (2:1) to afforded 4-[(6-chloro-3-fluoro-2-pyridyl)methyl]morpholine (480 mg, 66%) as an off-white solid. LCMS (ESI, m/z): 231 $(M+H)^+$.

Step 2: Synthesis of 4-[(6-chloro-3-fluoro-4-iodo-2-pyridyl)methyl]morpholine

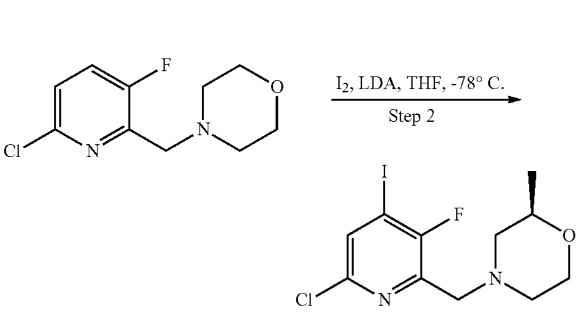

To a solution of 4-[(6-chloro-3-fluoro-2-pyridyl)methyl]morpholine (200 mg, 0.870 mmol, 1.00 equiv) in THF (5.0 mL) was added dropwise LDA (2M in THF) (0.65 mL, 1.300 mmol, 1.50 equiv) at −78° C. under a nitrogen atmosphere. After 0.5 h, a solution of $I_2$ (242 mg, 0.950 mmol, 1.10 equiv) in THF (4.0 mL) was added the resulting solution and stirred for 15 min at −78° C. under a nitrogen atmosphere. After 15 min at −78° C., the resulting solution was allowed to warm to room temperature. LCMS showed the reaction was completed. The resulting solution was quenched with saturated ammonium chloride aqueous (30 mL), extracted with ethyl acetate (3×30 mL). The combined organic layers were washed with saturated sodium thiosulfate (2×30 mL) aqueous, dried over sodium sulfate, filtered and concentrated under reduce pressure. The residue was purified by column chromatography on silica gel petroleum ether/ethyl acetate (2:1) to give 4-[(6-chloro-3-fluoro-4-iodo-2-pyridyl)methyl]morpholine (280 mg, 90%) as an off-white solid. LCMS (ESI, m z): 357 $[M+H]^+$.

Step 3: Synthesis of (15R)-5-[6-chloro-3-fluoro-2-(morpholinomethyl)-4-pyridyl]-15-methyl-11-thia-6,14,17-triazatetracyclo[8.8.0.0^,7.0^12,18]octadeca-1(10),2(7),3,5,8,12(18)-hexaen-13-one

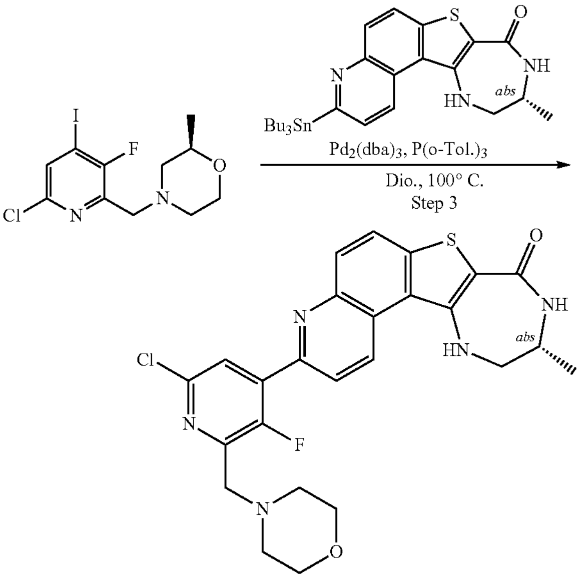

To a solution of (15R)-15-methyl-5-tributylstannyl-11-thia-6,14,17-triazatetracyclo[8.8.0.0^,7.0^12,18]octadeca-1(10),2(7),3,5,8,12(18)-hexaen-13-one (150 mg, 0.260 mmol, 1.00 equiv) and 4-[(6-chloro-3-fluoro-4-iodo-2-pyridyl)methyl]morpholine (93 mg, 0.260 mmol, 1.00 equiv) in 1,4-dioxane (5.0 mL) was added $Pd_2(dba)_3$ (27 mg, 0.0300 mmol, 0.10 equiv) and P(o-Tol.)$_3$ (8 mg, 0.030 mmol, 0.10 equiv). The resulting solution was stirred at 90° C. for 6 h under a nitrogen atmosphere. LCMS showed the reaction was completed. The resulting solution was diluted with ethyl acetate/petroleum ether (1:1) (20 mL). The precipitated solids were collected by filtration and washed with ethyl acetate/petroleum ether (1:1) (2×20 mL). The solid was dried to give (15R)-5-[6-chloro-3-fluoro-2-(morpholinomethyl)-4-pyridyl]-15-methyl-11-thia-6,14,17-triazatetracyclo[8.8.0.0^,7.0^12,18]octadeca-1(10),2(7),3,5,8,12

(18)-hexaen-13-one (110 mg, 81%) as a light-yellow solid. LCMS (ESI, m/z): 512 (M+H)+.

Step 4: Synthesis of (15R)-5-[3-fluoro-2-(morpholinomethyl)-6-vinyl-4-pyridyl]-15-methyl-11-thia-6,14,17-triazatetracyclo[8.8.0.0^,7.0^12,18]octadeca-1(10),2(7),3,5,8,12(18)-hexaen-13-one

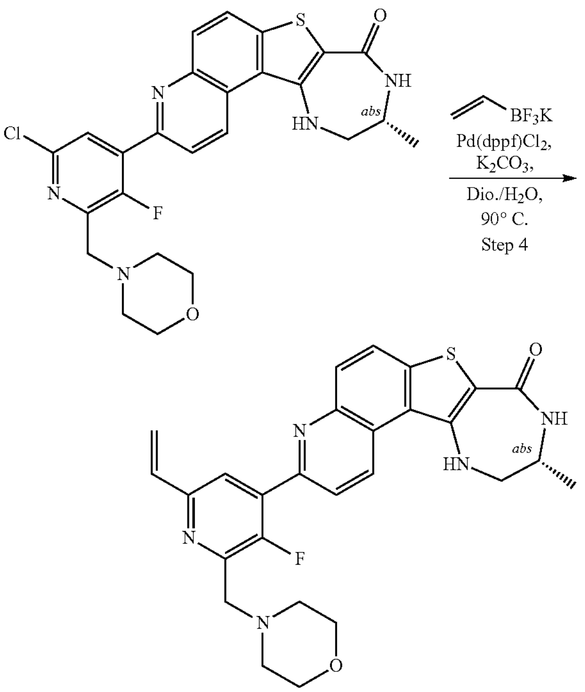

To a solution of (15R)-5-[6-chloro-3-fluoro-2-(morpholinomethyl)-4-pyridyl]-15-methyl-11-thia-6,14,17-triazatetracyclo[8.8.0.0^,7.0^12,18]octadeca-1(10),2(7),3,5,8,12(18)-hexaen-13-one (105 mg, 0.210 mmol, 1.00 equiv), $K_2CO_3$ (56 mg, 0.410 mmol, 2.00 equiv) and potassium; trifluoro(vinyl)boranuide (82 mg, 0.620 mmol, 3.00 equiv) in 1,4-dioxane (5.0 mL) and water (0.5 mL) was added $Pd(dppf)Cl_2$ (16 mg, 0.020 mmol, 0.10 equiv). The resulting mixture was stirred at 90° C. for 4 h under a nitrogen atmosphere. LCMS showed the reaction was completed. The resulting solution was diluted with water (30 mL). The solid was collected by filtration and washed with water (2×30 mL). The solid was purified by reverse flash chromatography with water (0.5% TFA)/MeCN (4:1) to give (15R)-5-[3-fluoro-2-(morpholinomethyl)-6-vinyl-4-pyridyl]-15-methyl-11-thia-6,14,17-triazatetracyclo[8.8.0.0^,7.0^12,18]octadeca-1(10),2(7),3,5,8,12(18)-hexaen-13-one (35.9 mg, 34%) as a yellow solid. LCMS (ESI, m z): 504 [M+H]+. Analytic Conditions: Column: HALO C18 100A Column 3.0*30 mm, 2.0 um; Mobile Phase A: Water/0.05% TFA, Mobile Phase B: Acetonitrile/0.05% TFA; Flow rate: 1.2000 mL/min; Gradient: 5% B to 60% B in 2.10 min; 254 nm; Rt: 1.602 min.

$^1H$ NMR (400 MHz, DMSO-$d_6$) δ 10.80-10.60 (m, 1H), 9.37 (d, J=9.2 Hz, 1H), 8.32-8.23 (m, 2H), 8.16-8.07 (m, 3H), 7.22 (s, 1H), 7.04 (dd, J=17.2, 10.8 Hz, 1H), 6.41 (d, J=17.6 Hz, 1H), 5.65 (d, J=11.2 Hz, 1H), 4.78 (s, 2H), 4.10-3.70 (m, 4H), 3.70-3.30 (m, 7H), 1.21 (d, J=6.8 Hz, 3H), $^{19}F$ NMR (376 MHz, DMSO-d6) δ-74.65, 131.37.

Example 42: Synthesis of (15R)-15-methyl-5-(5-vinyl-1,2,4-triazol-1-yl)-11-thia-6,14,17-triazatetracyclo[8.8.0.0^,7.0^12,18]octadeca-1(10),2(7),3,5,8,12(18)-hexaen-13-one

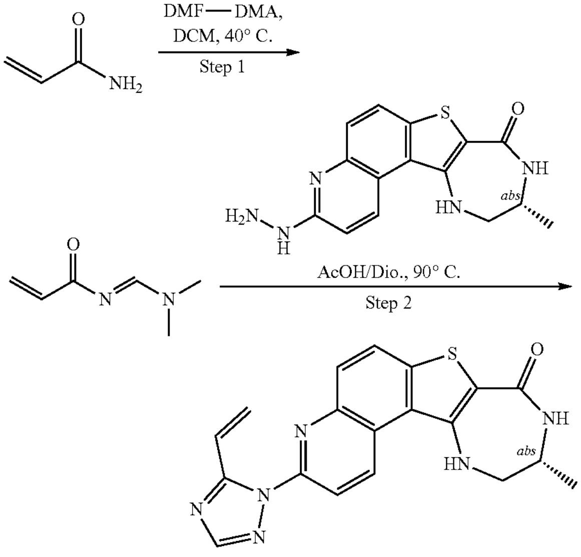

Step 1: Synthesis of (NE)-N-(dimethylaminomethylene)prop-2-enamide

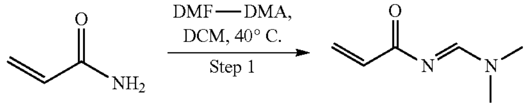

To a solution of prop-2-enamide (100 mg, 1.407 mmol, 1.00 equiv) in DCM (4.0 mL) was added 1,1-dimethoxy-N,N-dimethyl-methanamine (251 mg, 2.110 mmol, 1.50 equiv). The resulting mixture was stirred at 40° C. for 1 h under a nitrogen atmosphere. LCMS showed the reaction was completed. The resulting solution was concentrated under reduced pressure. The residue was used for the next step without further purification. LCMS (ESI, m/z): 127 (M+H)+.

Step 2: Synthesis of (15R)-15-methyl-5-(5-vinyl-1,2,4-triazol-1-yl)-11-thia-6,14,17-triazatetracyclo[8.8.0.0^,7.0^12,18]octadeca-1(10),2(7),3,5,8,12(18)-hexaen-13-one

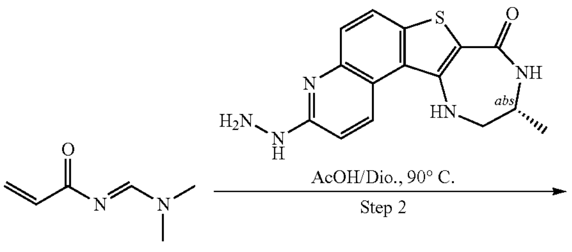

-continued

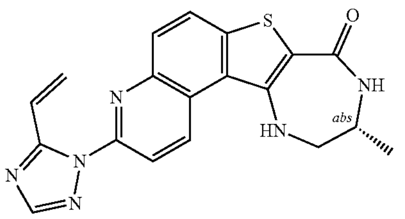

To a solution of (15R)-5-hydrazino-15-methyl-11-thia-6,14,17-triazatetracyclo[8.8.0.0^,7.0^12,18]octadeca-1(10),2(7),3,5,8,12(18)-hexaen-13-one (100 mg, 0.319 mmol, 1.00 equiv) and in 1,4-dioxane (2.0 mL) and acetic acid (2.0 mL) was added (NE)-N-(dimethylaminomethylene)prop-2-enamide (60 mg, 0.479 mmol, 1.50 equiv). The resulting mixture was stirred at 90° C. for 1.5 h under a nitrogen atmosphere. LCMS showed the reaction was completed. The resulting solution was concentrated under reduced pressure. The residue was purified by column chromatography on silica gel with dichloromethane/methanol (15:1) to afford 40 mg crude product. The crude product was purified by reverse flash chromatography with water (0.05% TFA)/MeCN (3:1) to give (15R)-15-methyl-5-(5-vinyl-1,2,4-triazol-1-yl)-11-thia-6,14,17-triazatetracyclo[8.8.0.0^,7.0^12,18]octadeca-1(10),2(7),3,5,8,12(18)-hexaen-13-one (11.8 mg, 10%) as a yellow solid. LCMS (ESI, m/z): 377 $(M+H)^+$. Analytic Conditions: Column: ACE Excel 2 C18 Column 3.0*30 mm, 2.0 um; Mobile Phase A: water+0.05% TFA, Mobile Phase B: Acetonitrile+0.05% TFA; Flow rate: 1.2000 mL/min; Gradient: 5% B to 70% B in 1.70 min; 254 nm; Rt: 1.351 min.

$^1$H NMR (300 MHz, DMSO-$d_6$+$D_2O$) δ 9.42 (d, J=9.3 Hz, 1H), 8.27 (s, 1H), 8.25 (d, J=9.0 Hz, 1H), 8.11 (d, J=9.3 Hz, 1H), 8.03 (d, J=9.0 Hz, 1H), 7.88 (dd, J=17.1, 11.1 Hz, 1H), 6.47 (dd, J=17.4, 1.8 Hz, 1H), 5.84 (dd, J=11.1, 1.8 Hz, 1H), 3.70-3.60 (m, 1H), 3.50-3.45 (m, 2H), 1.20 (d, J=6.6 Hz, 3H). $^{19}$F NMR (376 MHz, DMSO-$d_6$) δ-74.89.

Example 43: Synthesis of (15R)-5-(2-ethynylimidazol-1-yl)-15-methyl-11-thia-6,14,17-triazatetracyclo[8.8.0.0^,7.0^12,18]octadeca-1(10),2(7),3,5,8,12(18)-hexaen-13-one

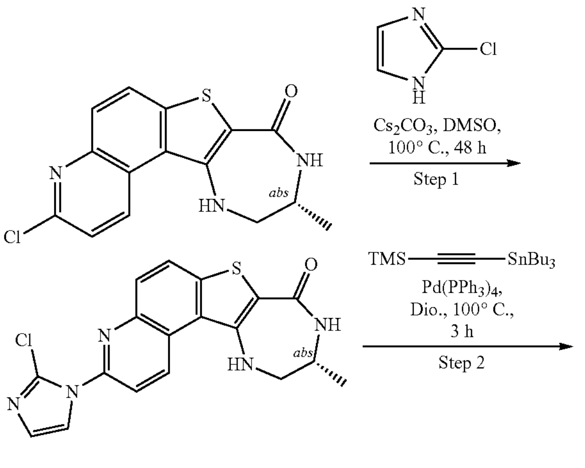

-continued

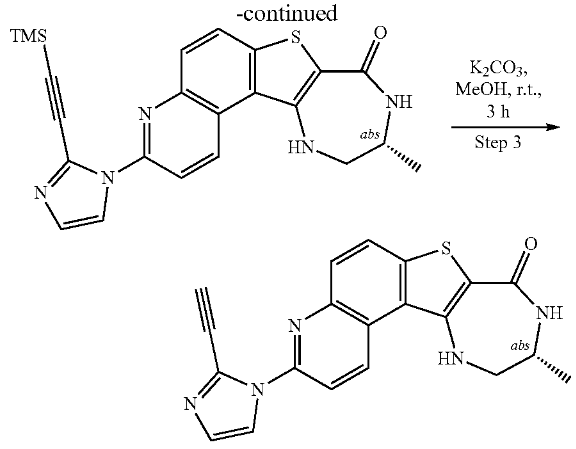

Step 1: Synthesis of (15R)-5-(2-chloroimidazol-1-yl)-15-methyl-11-thia-6,14,17-triazatetracyclo[8.8.0.0^,7.0^12,18]octadeca-1(10),2(7),3,5,8,12(18)-hexaen-13-one

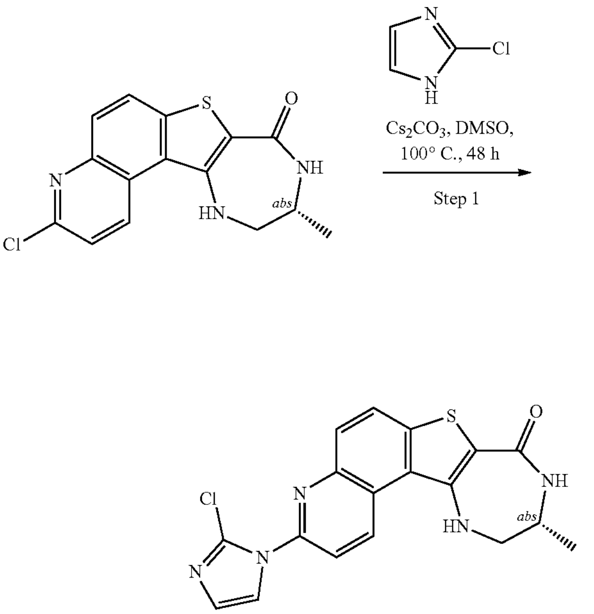

To solution of (15R)-5-chloro-15-methyl-11-thia-6,14,17-triazatetracyclo[8.8.0.0^2,7.0^12,18]octadeca-1(10),2(7),3,5,8,12(18)-hexaen-13-one (300 mg, 0.940 mmol, 1.00 equiv) and 2-chloro-1H-imidazole (290 mg, 2.830 mmol, 3.00 equiv) in DMSO (5.0 mL) was added $Cs_2CO_3$ (920 mg, 2.83 mmol, 3.00 equiv). The reaction mixture was stirred at 100° C. for 48 h under a nitrogen atmosphere. LCMS showed the reaction was major desired product. The resulting solution was diluted with water (30 mL). The solid was collected by filtration. The solid was purified by reverse flash chromatography with water (0.05% TFA)/MeCN (1:1) to give (15R)-5-(2-chloroimidazol-1-yl)-15-methyl-11-thia-6,14,17-triazatetracyclo[8.8.0.0^,7.0^12,18]octadeca-1(10),2(7),3,5,8,12(18)-hexaen-13-one (150 mg, 41%) as a yellow solid. LCMS (ESI, m/z): 384 $[M+H]^+$.

Step 2: Synthesis of (15R)-15-methyl-5-[2-(2-trimethylsilylethynyl)imidazol-1-yl]-11-thia-6,14,17-triazatetracyclo[8.8.0.0^,7.0^12,18]octadeca-1(10),2(7),3,5,8,12(18)-hexaen-13-one

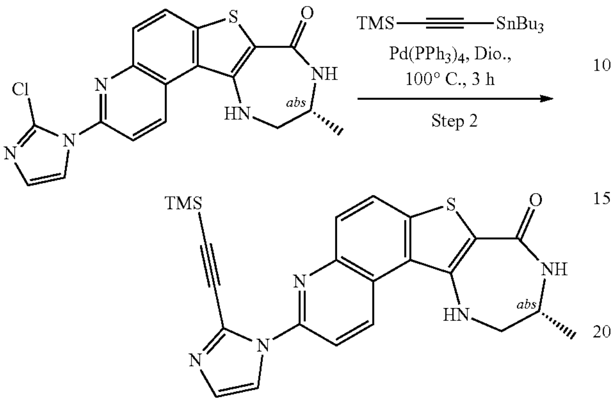

To a solution of (15R)-5-(2-chloroimidazol-1-yl)-15-methyl-11-thia-6,14,17-triazatetracyclo[8.8.0.0^,7.0^12,18]octadeca-1(10),2(7),3,5,8,12(18)-hexaen-13-one (75 mg, 0.200 mmol, 1.00 equiv) and trimethyl(2-tributylstannylethynyl)silane (91 mg, 0.230 mmol, 1.20 equiv) in 1,4-dioxane (5.0 mL) was added $Pd(PPh_3)_4$(18 mg, 0.020 mmol, 0.10 equiv). The reaction mixture was stirred 3 h for 100° C. under a nitrogen atmosphere. LCMS showed the reaction was completed. The resulting solution was diluted with petroleum ether (50 mL). The solid was collected by filtration and washed with petroleum ether (2×10 mL). The crude product was used directly for next step without further purification. LCMS (ESI, m/z): 446 $[M+H]^+$.

Step 3: Synthesis of (15R)-5-(2-ethynylimidazol-1-yl)-15-methyl-11-thia-6,14,17-triazatetracyclo[8.8.0.0^,7.0^12,18]octadeca-1(10),2(7),3,5,8,12(18)-hexaen-13-one

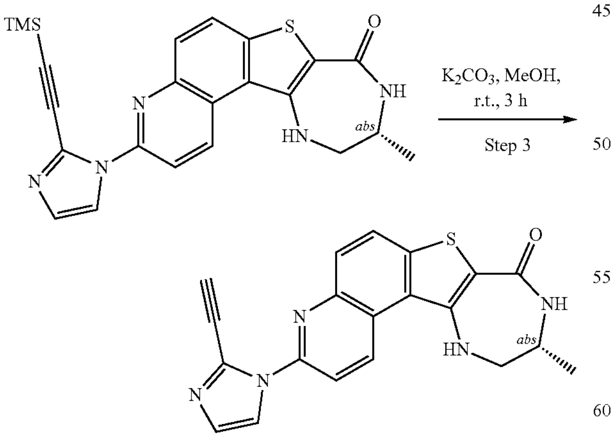

To solution of (15R)-15-methyl-5-[2-(2-trimethylsilylethynyl)imidazol-1-yl]-11-thia-6,14,17-triazatetracyclo[8.8.0.0^,7.0^12,18]octadeca-1(10),2(7),3,5,8,12(18)-hexaen-13-one (50 mg, 0.110 mmol, 1.00 equiv) in methanol (2.0 mL) was added $K_2CO_3$ (46 mg, 0.340 mmol, 3.00 equiv). The resulting mixture was stirred for 30 minutes at room temperature. LCMS showed the reaction was completed. The reaction solution was diluted with ethyl acetate (50 mL). The solid was filtered out. The filtration was concentrated under reduce pressure. The residue was purified by Prep-HPLC using the following gradient conditions: Column: XBridge Prep OBD C18 Column, 19*250 mm, 5 μm; Mobile Phase A: Water (10 mmol/L $NH_4HCO_3$), Mobile Phase B: MeCN; Flow rate: 25 mL/min; Gradient: 35% B to 39% B in 5 min, 39% B; Wave Length: 254 nm; RT1(min): 4.62. Purification resulted in the desired (15R)-5-(2-ethynylimidazol-1-yl)-15-methyl-11-thia-6,14,17-triazatetracyclo[8.8.0.0^,7.0^12,18]octadeca-1(10),2(7),3,5,8,12(18)-hexaen-13-one (6.7 mg, 15%) as a yellow solid. LCMS (ESI, m/z): 374 $[M+H]^+$. Analytic Conditions: Column: Shim-pack ScepterC18 Column 3.0*33 mm, 3.0 um; Mobile Phase A: Water/5mMNH$_4$HCO$_3$, Mobile Phase B: Acetonitrile; Flow rate: 1.5000 mL/min; Gradient: 10% B to 60% B in 1.85 min; 254 nm; Rt: 1.359 min.

$^1$H NMR (400 MHz, DMSO-d$_6$) δ 9.42 (d, J=9.2 Hz, 1H), 8.25 (d, J=8.8 Hz, 1H), 8.17 (d, J=9.2 Hz, 1H), 8.17 (s, 1H), 8.03 (s, 1H), 7.97 (d, J=8.8 Hz, 1H), 7.24 (s, 1H) 7.22 (t, J=5.2 Hz, 1H), 4.67 (s, 1H), 3.68-3.60 (m, 1H), 3.51-3.44 (m, 2H), 1.19 (d, J=6.8 Hz, 3H).

Example 44: Synthesis of (15R)-15-methyl-5-(3-methyl-5-vinyl-1,2,4-triazol-4-yl)-11-thia-6,14,17-triazatetracyclo[8.8.0.0^,7.0^12,18]octadeca-1(10),2(7),3,5,8,12(18)-hexaen-13-one

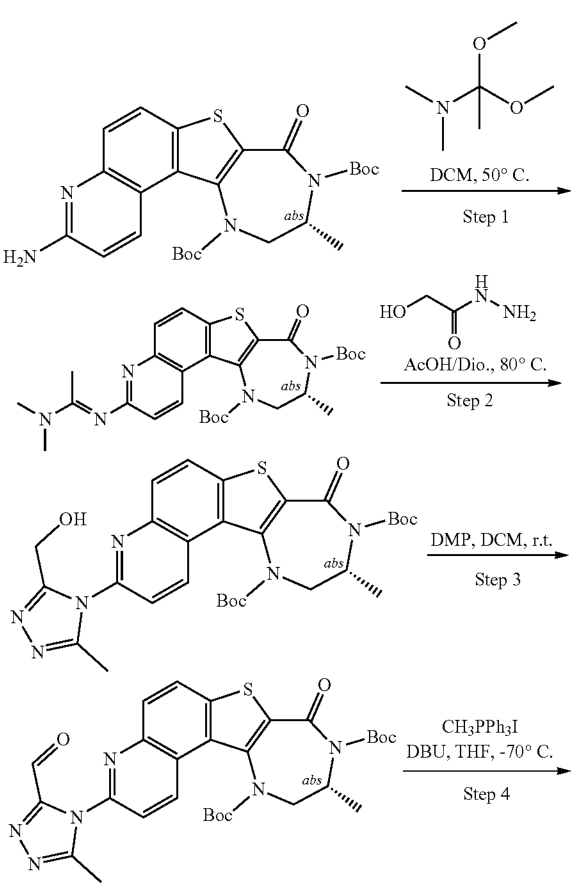

-continued

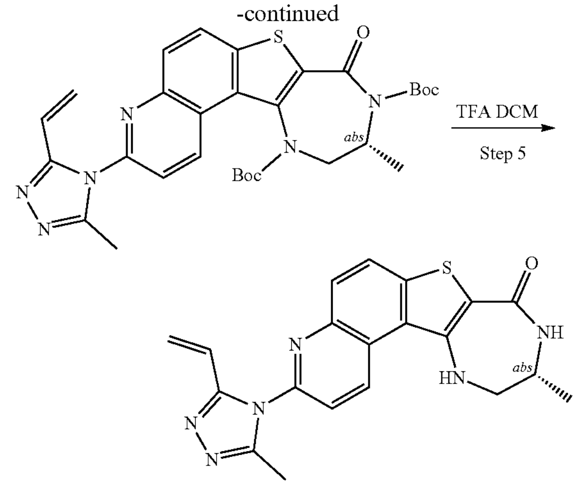

Step 1: Synthesis of ditert-butyl (15R)-5-[(E)-1-(dimethylamino)ethylideneamino]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate

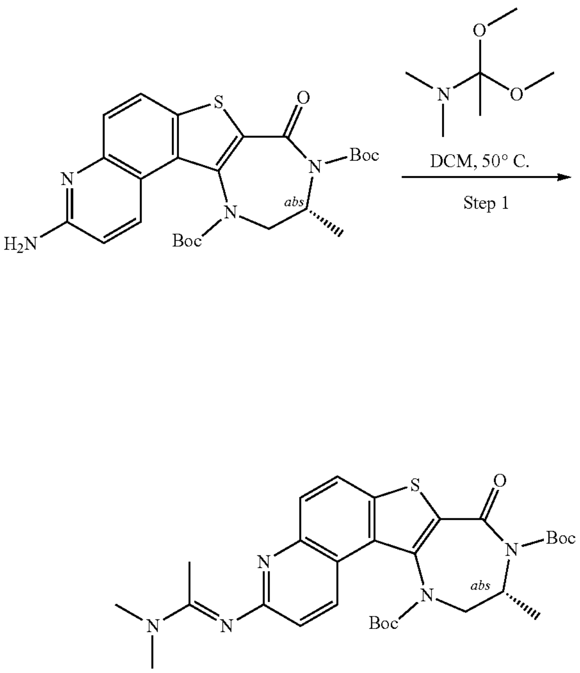

To a solution of ditert-butyl (15R)-5-amino-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (200 mg, 0.400 mmol, 1.00 equiv) in DCM (5.0 mL) was added 1,1-dimethoxy-N,N-dimethyl-ethanamine (160 mg, 1.200 mmol, 3.00 equiv). The resulting mixture was stirred at 50° C. for 4 h. LCMS showed the reaction was completed. The resulting solution was concentrated under reduced pressure. The residue was used directly for next step without further purification. LCMS (ESI, m/z): 568 $(M+H)^+$.

Step 2: Synthesis of ditert-butyl (15R)-5-[3-(hydroxymethyl)-5-methyl-1,2,4-triazol-4-yl]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate

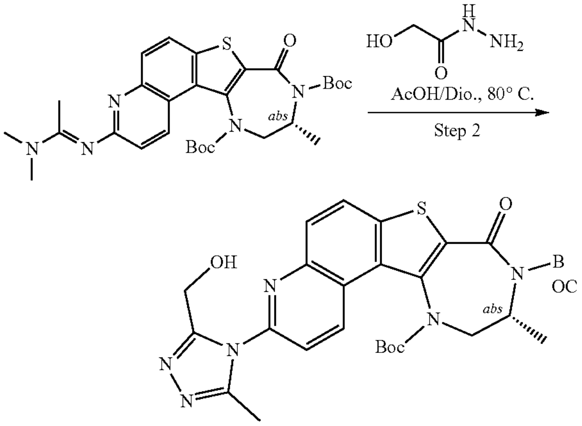

To a solution of ditert-butyl (15R)-5-[(E)-1-(dimethylamino)ethylideneamino]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (200 mg, 0.350 mmol, 1.00 equiv) in 1,4-dioxane (2.0 mL) and AcOH (2.0 mL) was added 2-hydroxyacetohydrazide (190 mg, 2.110 mmol, 6.00 equiv). The resulting mixture was stirred at 80° C. for 6 h under a nitrogen atmosphere. LCMS showed 50% desired product was formed. The resulting solution was diluted with a saturated sodium carbonate aqueous (50 ml), extracted with ethyl acetate (3x30 mL). The combined organic layers were washed with brine (2x20 mL), dried over anhydrous sodium sulfate, filtered and concentrated under reduced pressure. The residue was purified by column flash chromatography on silica gel with dichloromethane/methanol (15:1) to give ditert-butyl (15R)-5-[3-(hydroxymethyl)-5-methyl-1,2,4-triazol-4-yl]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (80 mg, 38%) as an orange solid. LCMS (ESI, m/z): 595 $(M+H)^+$.

Step 3: Synthesis of ditert-butyl (15R)-5-(3-formyl-5-methyl-1,2,4-triazol-4-yl)-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate

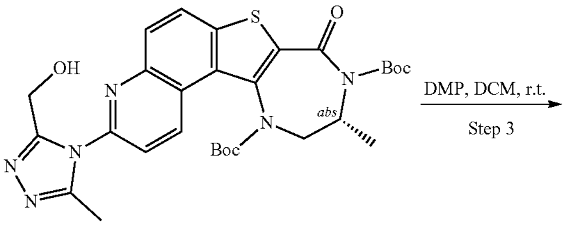

-continued

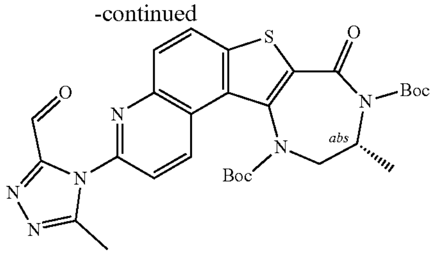

To a solution of ditert-butyl (15R)-5-[3-(hydroxymethyl)-5-methyl-1,2,4-triazol-4-yl]-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (80 mg, 0.130 mmol, 1.00 equiv) in DCM (5.0 mL) was added Dess-Martin periodinane (68 mg, 0.160 mmol, 1.20 equiv). The resulting mixture was stirred at room temperature for 1 h. LCMS showed the reaction was completed. The resulting mixture was diluted with water (30 mL), extracted with ethyl acetate (3×15 mL). The combined organic layers were washed saturated sodium thiosulfate aqueous (2×20 mL), dried over anhydrous sodium sulfate, filtered and concentrated under reduced pressure. The crude product was used for the next step directly without further purification. LCMS (ESI, m/z): 593 $(M+H)^+$.

Step 4: Synthesis of ditert-butyl(15R)-15-methyl-5-(3-methyl-5-vinyl-1,2,4-triazol-4-yl)-13-oxo-11-thia-6,14,17-triazatetracyclo[8.8.0.0^,7.0^12,18]octadeca-1(10),2(7),3,5,8,12(18)-hexaene-14,17-dicarboxylate

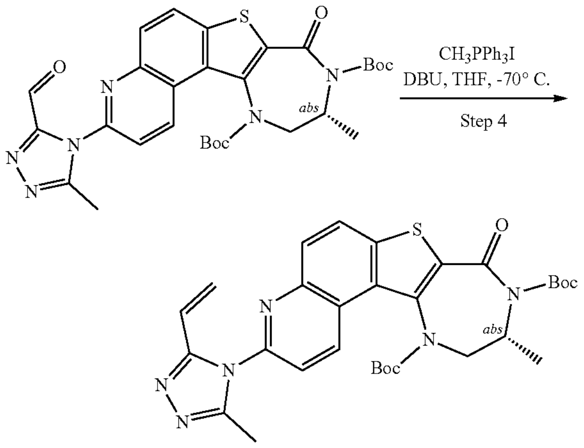

To a solution of $CH_3PPh_3I$ (132 mg, 0.330 mmol, 3.00 equiv) in THF (3.0 mL) was added dropwise DBU (33 mg, 0.220 mmol, 2.00 equiv) at −70° C. under a nitrogen atmosphere. After 30 min, a solution of ditert-butyl (15R)-5-(3-formyl-5-methyl-1,2,4-triazol-4-yl)-15-methyl-13-oxo-11-thia-6,14,17-triazatetracyclo[8.8.0.0^,7.0^12,18]octadeca-1(10),2(7),3,5,8,12(18)-hexaene-14,17-dicarboxylate (65 mg, 0.110 mmol, 1.00 equiv) in THE (3 mL) was added dropwise the resulting mixture. The reaction mixture was stirred for 1 h at −70° C., then was allowed to warm to room temperature. LCMS showed the reaction was completed. The resulting mixture was diluted with water (30 mL), extracted with ethyl acetate (3×15 mL). The combined organic layers were washed with brine (2×15 mL), dried over anhydrous sodium sulfate, filtered and concentrated under reduced pressure. The residue was purified by column flash chromatography on silica gel with dichloromethane/methanol (15:1) to give ditert-butyl (15R)-15-methyl-5-(3-methyl-5-vinyl-1,2,4-triazol-4-yl)-13-oxo-11-thia-6,14,17-triazatetracyclo[8.8.0.0^,7.0^12,18]octadeca-1(10),2(7),3,5,8,12(18)-hexaene-14,17-dicarboxylate (20 mg, 30%) as a brown oil. LCMS (ESI, m/z): 591 $(M+H)^+$.

Step 5: Synthesis of (15R)-15-methyl-5-(3-methyl-5-vinyl-1,2,4-triazol-4-yl)-11-thia-6,14,17-triazatetracyclo[8.8.0.0^,7.0^12,18]octadeca-1(10),2(7),3,5,8,12(18)-hexaen-13-one

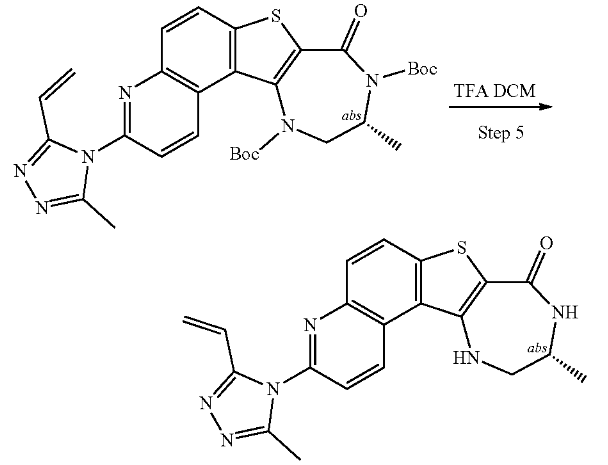

To a solution of ditert-butyl (15R)-15-methyl-5-(3-methyl-5-vinyl-1,2,4-triazol-4-yl)-13-oxo-11-thia-6,14,17-triazatetracyclo[8.8.0.0^,7.0^12,18]octadeca-1(10),2(7),3,5,8,12(18)-hexaene-14,17-dicarboxylate (20 mg, 0.030 mmol, 1.00 equiv) in DCM (1.0 mL) was added dropwise TFA (0.2 mL). The reaction was stirred at room temperature for 2 h. LCMS showed the reaction was completed. The resulting solution was concentrated under reduced pressure. The residue was purified by Prep-HPLC using the following gradient conditions: Column: XSelect CSH Prep C18 OBD Column, 19*150 mm, 5 μm; Mobile Phase A: Water (0.05% TFA), Mobile Phase B: MeCN; Flow rate: 25 mL/min; Gradient: 21% B to 27% B in 6.5 min, 27% B; Wave Length: 254/210 nm; RT1(min): 5.95. Purification resulted in desired (15R)-15-methyl-5-(3-methyl-5-vinyl-1,2,4-triazol-4-yl)-11-thia-6,14,17-triazatetracyclo[8.8.0.0^,7.0^12,18]octadeca-1(10),2(7),3,5,8,12(18)-hexaen-13-one (6.4 mg, 46%) as a yellow solid. LCMS (ESI, m/z): 391 $(M+H)^+$. Analytic Conditions: Column: XSelect HSS T3 100A Column 2.1*30 mm, 2.5 um; Mobile Phase A: Water/0.05% TFA, Mobile Phase B: Acetonitrile/0.05% TFA; Flow rate: 1.2000 mL/min; Gradient: 5% B to 50% B in 2.00 min; 254 nm; Rt: 1.429.

$^1H$ NMR (400 MHz, $CD_3OD-d_4$) δ9.50 (d, J=8.8 Hz, 1H), 8.24-8.12 (m, 1H), 8.07-7.99 (m, 1H), 7.80 (d, J=8.8 Hz, 1H), 6.58 (dd, J=17.6, 11.2 Hz, 1H), 6.22 (d, J=17.2 Hz, 1H), 5.72 (d, J=11.6 Hz, 1H), 3.82-3.72 (m, 1H), 3.72-3.45 (m, 2H), 2.54 (s, 3H), 1.33 (d, J=6.8 Hz, 3H). 19F NMR (376 MHz, $CD_3OD-d_4$) 6-77.36.

Example 45: Synthesis of (15R)-15-methyl-5-(3-methyl-5-vinyl-1,2,4-triazol-1-yl)-11-thia-6,14,17-triazatetracyclo[8.8.0.0^,7.0^12,18]octadeca-1(10),2(7),3,5,8,12(18)-hexaen-13-one

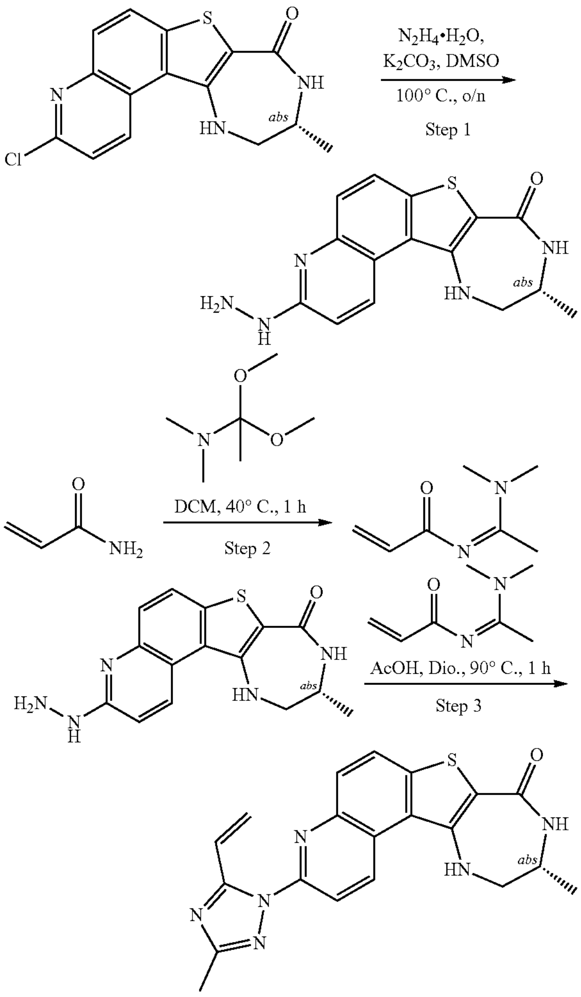

Step 1: Synthesis of (15R)-5-hydrazino-15-methyl-11-thia-6,14,17-triazatetracyclo[8.8.0.0^,7.0^12,18]octadeca-1(10),2(7),3,5,8,12(18)-hexaen-13-one

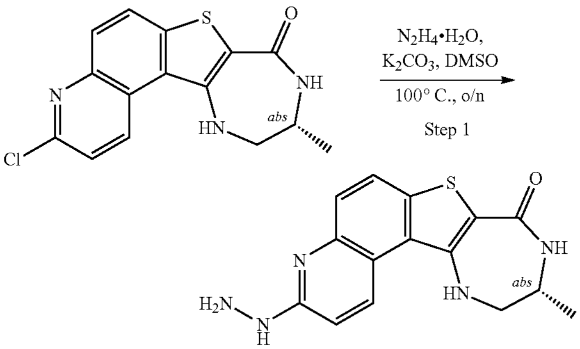

To a solution of (15R)-5-chloro-15-methyl-11-thia-6,14,17-triazatetracyclo[8.8.0.0^,7.0^12,18]octadeca-1(10),2(7),3,5,8,12(18)-hexaen-13-one (1.0 g, 3.150 mmol, 1.00 equiv) and $K_2CO_3$ (1.3 g, 9.440 mmol, 3.00 equiv) in DMSO (10.0 mL) was added $N_2H_4 \cdot H_2O$ (630 mg, 12.590 mmol, 4.00 equiv). The resulting mixture was stirred at 100° C. overnight under a nitrogen atmosphere. LCMS showed the reaction was completed. The resulting solution was purified by reverse flash chromatography with water (0.05% TFA)/MeCN (8:2) to give (15R)-5-hydrazino-15-methyl-11-thia-6,14,17-triazatetracyclo[8.8.0.0^,7.0^12,18]octadeca-1(10),2(7),3,5,8,12(18)-hexaen-13-one (950 mg, 96%) as a light yellow solid. LCMS (ESI, m/z): 314 $(M+H)^+$.

Step 2: Synthesis of (NE)-N-[1-(dimethylamino)ethylidene]prop-2-enamide

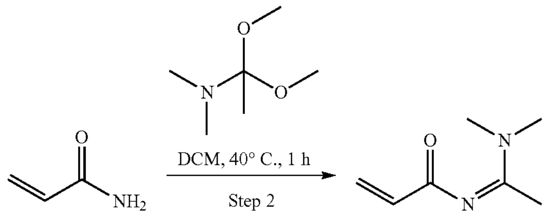

To a solution of prop-2-enamide (100 mg, 1.410 mmol, 1.00 equiv) in DCM (2.0 mL) was added 1,1-dimethoxy-N,N-dimethylethan-1-amine (281 mg, 2.110 mmol, 1.50 equiv). The resulting mixture was stirred at 40° C. for 1 h under a nitrogen atmosphere. LCMS showed the reaction was completed. The resulting solution was concentrated under reduced pressure. The residue was used for the next step directly without further purification. LCMS (ESI, m/z): 141 $(M+H)^+$.

Step 3: Synthesis of (15R)-15-methyl-5-(3-methyl-5-vinyl-1,2,4-triazol-1-yl)-11-thia-6,14,17-triazatetracyclo[8.8.0.0^,7.0^12,18]octadeca-1(10),2(7),3,5,8,12(18)-hexaen-13-one

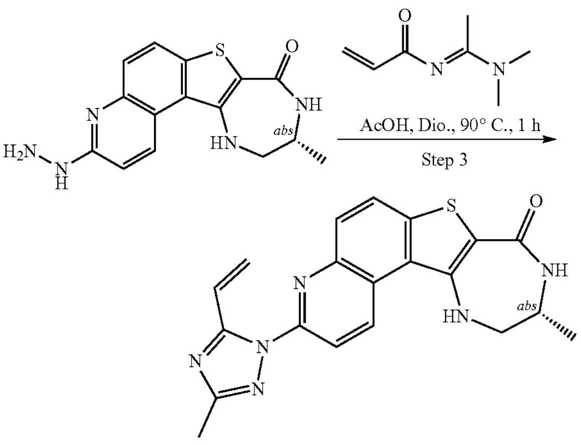

To a solution of and (15R)-5-hydrazino-15-methyl-11-thia-6,14,17-triazatetracyclo[8.8.0.0^,7.0^12,18]octadeca-1(10),2(7),3,5,8,12(18)-hexaen-13-one (100 mg, 0.320 mmol, 1.00 equiv) in 1,4-dioxane (2.0 mL) and acetic acid (2.0 mL) was added (NE)-N-[1-(dimethylamino)ethylidene]prop-2-enamide (89 mg, 0.640 mmol, 2.00 equiv). The resulting mixture was stirred at 90° C. for 1 h. LCMS showed the reaction was completed. The resulting mixture was adjusted pH to 7-8 with $NaHCO_3$, and extracted with dichloromethane (3×15 mL). The combined organic layers were washed with brine (10 mL), dried over anhydrous sodium sulfate, filtered and concentrated under reduced pressure. The residue was purified by column flash chromatography on silica gel with dichloromethane/methanol (15:1) to give 30 mg crude product. The crude product was purified by reverse flash chromatography with water (0.05% TFA)/MeCN (7:3) to give (15R)-15-methyl-5-(3-methyl-5-vinyl-1,2,4-triazol-1-yl)-11-thia-6,14,17-triazatetracyclo[8.8.0.0^,7.0^12,18]octadeca-1(10),2(7),3,5,8,12(18)-hexaen-13-one (16.5 mg, 13%) as a yellow solid. LCMS (ESI, m/z): 391 $(M+H)^+$. Analytic Conditions: Column: HALO C18 100A Column 3.0*30 mm, 2.7 um; Mobile Phase A: Water/0.05% TFA, Mobile Phase B: Acetonitrile/0.05% TFA; Flow rate: 1.5000 mL/min; Gradient: 5% B to 60% B in 1.80 min; 254 nm; Rt: 1.512.

$^1$H NMR (400 MHz, DMSO-$d_6$+$D_2O$) δ 9.39 (d, J=8.8 Hz, 1H), 8.23 (d, J=9.2 Hz, 1H), 8.06 (d, J=9.2 Hz, 1H), 8.01 (d, J=9.2 Hz, 1H), 7.87 (dd, J=17.2, 11.2 Hz, 1H), 6.42 (dd, J=17.6, 2.0 Hz, 1H), 5.80 (dd, J=11.2, 2.0 Hz, 1H), 3.64-3.61 (m, 1H), 3.50-3.40 (m, 2H), 2.41 (s, 3H), 1.21 (d, J=6.8 Hz, 3H). $^{19}$F NMR (376 MHz, DMSO-$d_6$) δ-74.85.

Example 46: Synthesis of (R)-10-methyl-3-(5-(methyl-d3)-2-vinylpyridin-4-yl-3-d)-9,10,11,12-tetrahydro-8H-[1,4]diazepino[5',6':4,5]thieno[3,2-f]quinolin-8-one

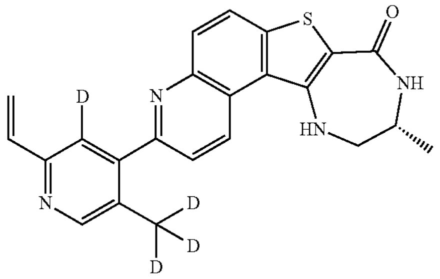 [SMILES: [2H]c1c(C=C)ncc(C([2H])([2H])[2H])c1-c1ccc2c(ccc3sc4c(c32)NC[C@@H](C)NC4=O)n1]

Step 1: Synthesis of (R)-(10-methyl-8-oxo-9,10,11,12-tetrahydro-8H-[1,4]diazepino[5',6':4,5]thieno[3,2-f]quinolin-3-yl)boronic acid A 40 mL reaction vial was charged with a stir bar, (R)-3-chloro-10-methyl-9,10,11,12-tetrahydro-8H-[1,4]diazepino[5',6':4,5]thieno[3,2-f]quinolin-8-one (2 g, 6.29 mmol), bis(pinacolato)diboron (1.758 g, 6.92 mmol), tricyclohexylphosphine (0.176 g, 0.629 mmol), Bis(dibenzylideneacetone)palladium(0) (0.181 g, 0.315 mmol), and potassium acetate (0.926 g, 9.44 mmol) in DMA (25.2 ml) to give a yellow suspension. The resulting mixture was degassed by bubbling of nitrogen for 5 min and then stirred at 80° C. for 16 h. LC-MS indicated the desired product as the major product, in a 2:1 ratio with proto-deboronated byproduct. (R)-(10-methyl-8-oxo-9,10,11,12-tetrahydro-8H-[1,4]diazepino[5',6':4,5]thieno[3,2-f]quinolin-3-yl)boronic acid will be used as a crude solution without further purification. MS ESI m/z 328.5 $(M+H)^+$

Step 2: Synthesis of 4-bromo-2-chloro-5-(methyl-d3)pyridine-3-d

A 40 mL reaction vial was charged with a stir bar, 4-bromo-2-chloro-5-methylpyridine (1 g, 4.84 mmol), and d6-DMSO (9.69 ml) to give a colorless solution. Potassium tert-butoxide (0.272 g, 2.422 mmol) was added, and the solution immediately turned burgundy. The reaction was heated to 50° C. for 15 minutes. LC MS indicated the reaction was complete. The reaction mixture was quenched by slow addition of saturated aqueous ammonium chloride, which left a brown suspension. The suspension was diluted in water and ethyl acetate. The layers were separated and the aqueous layer was extracted twice more with ethyl acetate. The combined organic layers were washed with water and concentrated under reduced pressure to yield the crude product as a brown oil. The crude product was dissolved in dichloromethane and purified by flash chromatography, affording 4-bromo-2-chloro-5-(methyl-d3)pyridine-3-d (368 mg, 1.748 mmol, 36% yield) as a clear oil.

$^1$H NMR (400 MHz, DMSO-$d_6$) δ 8.38-8.34 (m, 1H) MS ESI m/z 209.8, 211.8, and 213.7 $(M+H)^+$

Step 3: Synthesis of (R)-3-(2-chloro-5-(methyl-d3)pyridin-4-yl-3-d)-10-methyl-9,10,11,12-tetrahydro-8H-[1,4]diazepino[5',6':4,5]thieno[3,2-f]quinolin-8-one A 20 mL reaction vial was charged with a stir bar, 4-bromo-2-chloro-5-(methyl-d3)pyridine-3-d (65 mg, 0.309 mmol), (R)-(10-methyl-8-oxo-9,10,11,12-tetrahydro-8H-[1,4]diazepino[5',6':4,5]thieno[3,2-f]quinolin-3-yl)boronic acid (1.853 mL of DMA solution, 0.463 mmol), copper(I) chloride (30.6 mg, 0.309 mmol), and PdCl2(dtbpf) (20.13 mg, 0.031 mmol) to give a brown suspension. Aqueous potassium phosphate, tribasic (0.463 mL, 0.926 mmol) was added. The reaction mixture was degassed by evacuating and backfilling with nitrogen 3 times. The vial was sealed and heated to 80° C. for 2 hours. After 2 hours, LC/MS indicated nearly complete conversion to product. The reaction mixture was cooled to room temperature and filtered through a 0.45 um PTFE frit. The frit was washed with DMSO. The crude product was purified by reverse phase HPLC. Pure fractions were concentrated under reduced pressure to yield (R)-3-(2-chloro-5-(methyl-d3)pyridin-4-yl-3-d)-10-methyl-9,10,11,12-tetrahydro-8H-[1,4]diazepino[5',6':4,5]thieno[3,2-f]quinolin-8-one (42 mg, 0.102 mmol, 32.9% yield) as a yellow solid. MS ESI m/z 413.1 and 415.1 $(M+H)^+$ $^1$H NMR was not integrated due to the presence of two rotamers.

Step 4: Synthesis of (R)-10-methyl-3-(5-(methyl-d3)-2-vinylpyridin-4-yl-3-d)-9,10,11,12-tetrahydro-8H-[1,4]diazepino[5',6':4,5]thieno[3,2-f]quinolin-8-one A 4 mL reaction vial was charged with a stir bar, (R)-3-(2-chloro-5-(methyl-d3)pyridin-4-yl-3-d)-10-methyl-9,10,11,12-tetrahydro-8H-[1,4]diazepino[5',6':4,5]thieno[3,2-f]quinolin-8-one (42 mg, 0.102 mmol), PdCl2(dtbpf) (6.63 mg, 10.17 μmol), potassium trifluoro(vinyl)borate (27.2 mg, 0.203 mmol), and DMA (1017 μl) to give a brown solution. Aqueous potassium phosphate, tribasic (153 μl, 0.305 mmol) was added. The reaction mixture was degassed by evacuating and backfilling with nitrogen 3 times. The vial was sealed and heated to 80° C. for 16 h. LC MS indicated incomplete conversion. Potassium trifluoro(vinyl)borate (27.2 mg, 0.203 mmol) was added. The reaction mixture was degassed by evacuating and backfilling with nitrogen 3 times. The vial was sealed and heated to 80° C. for 3 h. LC MS indicated significant conversion. The reaction mixture was concentrated under reduced pressure. The crude material was purified via preparative Reverse Phase chromatography with the following conditions: Column: XBridge C18, 19 mm×200 mm, 5 m particles; Flow Rate: 20 mL/min;

Column Temperature: 25° C. Fraction collection was triggered by UV (220 nm) and MS (ESI+). Fractions containing the desired product were combined and dried via centrifugal evaporation, affording (R)-10-methyl-3-(5-(methyl-d3)-2-vinylpyridin-4-yl-3-d)-9,10,11,12-tetrahydro-8H-[1,4]diazepino[5',6':4,5]thieno[3,2-f]quinolin-8-one (12.3 mg, 0.03 mmol, 30% yield).

$^1$H NMR (500 MHz, DMSO-$d_6$) δ 9.31 (d, J=8.9 Hz, 1H), 8.57 (s, 1H), 8.19 (d, J=8.9 Hz, 1H), 8.11 (d, J=4.6 Hz, 1H), 8.03 (d, J=8.9 Hz, 1H), 7.94 (d, J=8.7 Hz, 1H), 7.19 (t, J=5.3 Hz, 1H), 6.96-6.89 (m, 1H), 6.29 (dd, J=17.4, 1.6 Hz, 1H), 5.50-5.46 (m, 1H), 3.63 (br s, 1H), 3.53-3.45 (m, 2H), 1.21 (d, J=6.8 Hz, 3H). MS ESI m/z 405.1 $(M+H)^+$

Example 47: Synthesis of R)-3-(2-bromo-4,5-dichloro-1H-imidazol-1-yl)-10-methyl-9,10,11,12-tetrahydro-8H-[1,4]diazepino[5',6':4,5]thieno[3,2-f]quinolin-8-one

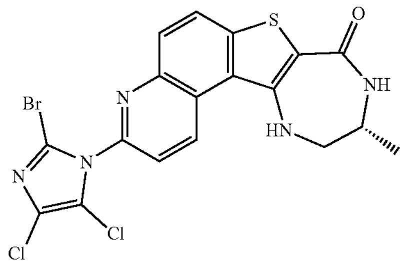 [SMILES: C[C@@H]1CNc2c(sc3ccc4nc(-n5c(Br)nc(Cl)c5Cl)ccc4c23)C(=O)N1]

A 4 mL reaction vial was charged with a stir bar, 2-bromo-4,5-dichloro-1H-imidazole (38.9 mg, 0.180 mmol), DIPEA (0.052 mL, 0.300 mmol), and tosyl-Cl (28.6 mg, 0.150 mmol) in DCE (1 mL). The mixture was stirred at rt for 10 min to give pink solution. (R)-9,12-bis(tert-butoxycarbonyl)-10-methyl-8-oxo-9,10,11,12-tetrahydro-8H-[1,4]diazepino[5',6':4,5]thieno[3,2-f]quinoline 4-oxide (30 mg, 0.060 mmol) was added and the resulting mixture was stirred at 100° C. overnight. Reaction mixture was diluted with DCM (10 mL), washed with 1N aq HCl (3 mL) and brine. Organic layer was separated, dried over Na2SO4, filtered, concentrated. Crude product obtained above was dissolved in Dioxane (1.5 mL), and HCl (0.225 mL, 0.901 mmol) (4N in dioxane) was added. After 4 h, more 4N HCl in dioxane (200 uL) was added. After total 20 h, reaction mixture was concentrated. The crude material was purified via preparative Reverse Phase chromatography with the following conditions: Column: XBridge C18, 19 mm×200 mm, 5 m particles; Mobile Phase A: 5:95 acetonitrile: water with 10 mM ammonium acetate; Mobile Phase B: 95:5 acetonitrile: water with 10 mM ammonium acetate; Gradient: a 0-min hold at 30% B, 30-70% B over 20 min, then a 4-min hold at 100% B; Flow Rate: 20 mL/min; Column Temperature: 25° C. Fraction collection was triggered by UV (220 nm) and MS (ESI+). Fractions containing the desired product were combined and dried via centrifugal evaporation, affording R)-3-(2-bromo-4,5-dichloro-1H-imidazol-1-yl)-10-methyl-9,10,11,12-tetrahydro-8H-[1,4]diazepino[5',6':4,5]thieno[3,2-f]quinolin-8-one (12.4 mg, 42% yield). MS ESI m/z 495.9 $(M+H)^+$ Example 48: Synthesis of (R)-3-(4,5-dichloro-2-vinyl-1H-imidazol-1-yl)-10-methyl-9,10,11,12-tetrahydro-8H-[1,4]diazepino[5',6':4,5]thieno[3,2-f]quinolin-8-one

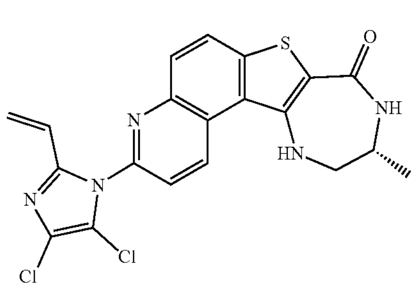 [SMILES: C=Cc1nc(Cl)c(Cl)n1-c1ccc2c(ccc3sc4c(c32)NC[C@@H](C)NC4=O)n1]

A 4 mL reaction vial was charged with a stir bar, 4,5-dichloro-2-vinyl-1H-imidazole (31.0 mg, 0.190 mmol), DIPEA (66.4 μl, 0.380 mmol), and tosyl-Cl (31.9 mg, 0.167 mmol) in DCE (1 mL). The mixture was stirred at rt for 10 min to give light yellow solution. (R)-9,12-bis(tert-butoxycarbonyl)-10-methyl-8-oxo-9,10,11,12-tetrahydro-8H-[1,4]diazepino[5',6':4,5]thieno[3,2-f]quinoline 4-oxide (38 mg, 0.076 mmol) was added and the resulting red-brown mixture was stirred at 100° C. for 3 h. Reaction mixture was cooled to RT, diluted with DCM (10 mL), washed with 1N aq HCl (3 mL) and brine. Organic layer was separated, dried over Na2SO4, filtered, concentrated to give crude product as a dark red oil. Crude product obtained above was dissolved in DCM (2 mL) and trifluoroacetic acid (400 μl, 5.19 mmol) was added. After stirring for 2 h, reaction mixture was concentrated. Purification by prep HPLC on ACCQ Prep (10-95% ACN-$H_2O$, 0.1% TFA, 25 min) gave BMS-A2E65-95-1 (R)-3-(4,5-dichloro-2-vinyl-1H-imidazol-1-yl)-10-methyl-9,10,11,12-tetrahydro-8H-[1,4]diazepino[5',6':4,5]thieno[3,2-f]quinolin-8-one, (14 mg, 0.025 mmol, 32.6% yield) as a yellow solid.

$^1$H NMR (400 MHz, DMSO-d6) δ 9.49 (d, J=8.9 Hz, 1H), 8.30 (d, J=8.9 Hz, 1H), 8.18 (d, J=4.4 Hz, 1H), 8.03-7.95 (m, 2H), 7.23 (br s, 1H), 6.38 (dd, J=17.2, 11.1 Hz, 1H), 6.04 (dd, J=17.2, 1.6 Hz, 1H), 5.47-5.41 (m, 1H), 3.68-3.58 (m, 1H), 3.56-3.42 (m, 2H), 1.20 (d, J=6.8 Hz, 3H). MS ESI m/z 444.2 $(M+H)^+$

Example 49: Synthesis of (R)-3-(5-(hydroxymethyl)-2-vinylpyridin-4-yl)-10-methyl-9,10,11,12-tetrahydro-8H-[1,4]diazepino[5',6':4,5]thieno[3,2-f]quinolin-8-one

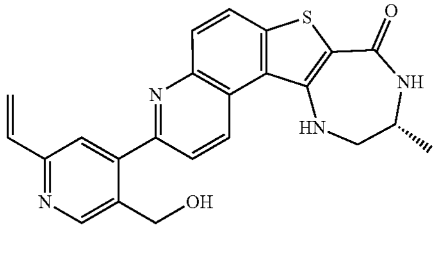 [SMILES: C=Cc1cc(-c2ccc3c(ccc4sc5c(c43)NC[C@@H](C)NC5=O)n2)c(CO)cn1]

Step 1: Synthesis of (4-bromo-6-chloropyridin-3-yl)methanol

A 20 mL reaction vial was charged with a stir bar4-bromo-6-chloronicotinaldehyde (417 mg, 1.892 mmol), and Ethanol (7566 μl) to give a colorless solution. sodium borohydride (75 mg, 1.986 mmol) was added portionwise, causing some gas to be evolved. The reaction was stirred at room temperature for 15 m. LC-MS indicated complete conversion. The reaction mixture was quenched by slowly adding saturated ammonium chloride. Ethyl acetate was added and the layers separated. The aqueous layer was extracted twice more with ethyl acetate. The combined organic layers were washed with water and then brine. The organic layers were concentrated under reduced pressure to give the crude product which was purified by flash chromatography to yield (4-bromo-6-chloropyridin-3-yl)methanol (216 mg, 0.971 mmol, 51.3% yield) as a white crystalline solid.

$^1$H NMR (400 MHz, CHLOROFORM-d) δ 8.47 (s, 1H), 7.59 (s, 1H), 4.81 (s, 2H). MS ESI m/z 221.7, 223.7, and 225.7 $(M+H)^+$ Step 2: Synthesis of (R)-3-(2-chloro-5-(hydroxymethyl)pyridin-4-yl)-10-methyl-9,10,11,12-tetrahydro-8H-[1,4]diazepino[5',6':4,5]thieno[3,2-f]quinolin-8-one A 4 mL reaction vial was charged with a stir bar, (R)-(10-methyl-8-oxo-9,10,11,12-tetrahydro-8H-[1,4]diazepino[5',6':4,5]thieno[3,2-f]quinolin-3-yl)boronic acid (2248 μl as a 0.2 M solution in DMA, 0.450 mmol), (4-bromo-6-chloropyridin-3-yl)methanol (50 mg, 0.225 mmol), copper (I) chloride (22.25 mg, 0.225 mmol), and PdCl2(dtbpf) (14.65 mg, 0.022 mmol) to give a yellow suspension. Aqueous potassium phosphate, tribasic (337 μl, 0.674 mmol) was added. The reaction mixture was degassed by evacuating and backfilling with nitrogen 3 times. The vial was sealed and heated to 80° C. for 2.5 hours. LC-MS indicated the completion of reaction. The reaction was cooled to room temperature and filtered through a 0.45 um PTFE frit. The frit was washed with additional DMF. The crude was purified by reverse phase HPLC (water and acetonitrile as mobile phases with 0.1% TFA additive), affording (R)-3-(2-chloro-5-(hydroxymethyl)pyridin-4-yl)-10-methyl-9,10,11,12-tetrahydro-8H-[1,4]diazepino[5',6':4,5]thieno[3,2-f]quinolin-8-one (15 mg, 0.035 mmol, 15.71% yield) as a yellow solid. MS ESI m/z 425.3 $(M+H)^+$ Step 3: Synthesis of (R)-3-(5-(hydroxymethyl)-2-vinylpyridin-4-yl)-10-methyl-9,10,11,12-tetrahydro-8H-[1,4]diazepino[5',6':4,5]thieno[3,2-f]quinolin-8-one A 4 mL reaction vial was charged with a stir bar, (R)-3-(2-chloro-5-(hydroxymethyl)pyridin-4-yl)-10-methyl-9,10,11,12-tetrahydro-8H-[1,4]diazepino[5',6':4,5]thieno[3,2-f]quinolin-8-one (15 mg, 0.035 mmol), potassium trifluoro(vinyl)borate (23.64 mg, 0.177 mmol), and PdCl2(dtbpf) (2.301 mg, 3.53 μmol), and DMA (353 μl) to give a yellow suspension. Potassium phosphate, tribasic (53.0 μl, 0.106 mmol) was added. The reaction mixture was degassed by evacuating and backfilling with nitrogen 3 times. The resulting mixture was stirred at 80° C. for 16 h. LC MS indicated significant product was present. The reaction mixture was filtered and the precipitate was washed with DMF. The crude material was purified via preparative Reverse Phase chromatography with the following conditions: Column: XBridge C18, 19 mm×200 mm, 5 μm particles; Mobile Phase A: 5:95 acetonitrile: water with 10 mM ammonium acetate; Mobile Phase B: 95:5 acetonitrile: water with 10 mM ammonium acetate; Gradient: a 0-min hold at 0% B, 0-53% B over 20 min, then a 4-min hold at 100% B; Flow Rate: 20 mL/min; Column Temperature: 25° C. Fraction collection was triggered by UV (220 nm) and MS (ESI+). Fractions containing the desired product were combined and dried via centrifugal evaporation, affording (R)-3-(5-(hydroxymethyl)-2-vinylpyridin-4-yl)-10-methyl-9,10,11,12-tetrahydro-8H-[1,4]diazepino[5',6':4,5]thieno[3,2-f]quinolin-8-one (3.8 mg, 0.009 mmol, 25% yield).

$^1$H NMR (500 MHz, DMSO-$d_6$) δ 9.33 (d, J=9.1 Hz, 1H), 8.79 (s, 1H), 8.21 (d, J=8.9 Hz, 1H), 8.14-8.08 (m, 2H), 8.02 (d, J=8.9 Hz, 1H), 7.80 (s, 1H), 7.20 (br s, 1H), 6.96 (dd, J=17.5, 10.8 Hz, 1H), 6.36 (d, J=17.4 Hz, 1H), 5.54 (d, J=12.1 Hz, 1H), 4.73 (s, 2H), 3.63 (br s, 1H), 3.51-3.48 (m, 2H), 1.21 (d, J=6.8 Hz, 3H). MS ESI m/z 417.0 $(M+H)^+$

Example 50: Synthesis of (R)-3-(5-(methoxymethyl)-2-vinylpyridin-4-yl)-10-methyl-9,10,11,12-tetrahydro-8H-[1,4]diazepino[5',6':4,5]thieno[3,2-f]quinolin-8-one

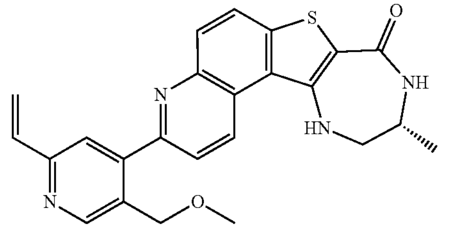 [SMILES: C=Cc1cc(-c2ccc3c(ccc4sc5c(c43)NC[C@@H](C)NC5=O)n2)c(COC)cn1]

Step 1: Synthesis of (4,6-dichloropyridin-3-yl)methanol

A 40 mL reaction vial was charged with a stir bar, 4,6-dichloronicotinaldehyde (1 g, 5.68 mmol) and acetic acid (0.651 ml, 11.36 mmol), and DCM (22.73 ml) to give a yellow solution. sodium triacetoxyborohydride (2.408 g, 11.36 mmol) was added portionwise at room temperature, resulting in a cloudy mixture. The reaction mixture was warmed to 40C for 2 hours on a heating block. After 2 hours, LC/MS indicated the reaction is complete. The vial was cooled to room temperature. The reaction was quenched with saturated sodium bicarbonate (added slowly), resulting in vigorous gas evolution. After gas evolution ceased, the mixture was transferred to a separatory funnel and additional saturated sodium bicarbonate and dichloromethane were added. After one hour of irregular mixing to ensure any remaining borohydride was removed, the layers were separated. The aqueous layer was extracted twice more with dichloromethane. The combined organic layers were washed with water and brine, and then concentrated under reduced pressure to yield the crude product. The crude product was dissolved in minimal dichloromethane and purified by flash chromatography (120 g silica column, 0-100% heptane in ethyl acetate). The pure fractions were combined and concentrated under reduced pressure to yield (4,6-dichloropyridin-3-yl)methanol (1.1 g, 6.18 mmol, 109% yield) as a white powder.

$^1$H NMR (400 MHz, CHLOROFORM-d) δ 8.51 (s, 1H), 7.41 (s, 1H), 4.84 (d, J=5.9 Hz, 2H), 1.96 (t, J=6.0 Hz, 1H). MS ESI m/z 178.2 and 180.2 $(M+H)^+$ Step 2: Synthesis of 2,4-dichloro-5-(methoxymethyl)pyridine A 20 mL reaction vial was charged with a stir bar, (4,6-dichloropyridin-3-yl)methanol (100 mg, 0.562 mmol) in THE (2809 μl) to give a colorless solution. sodium hydride (67.4 mg, 1.685 mmol) was added portionwise and stirred at room temperature for 15 minutes. Gas evolution quickly ceased. methyl iodide (105 μl, 1.685 mmol) was added dropwise. The reaction was stirred at room temperature for 3 days. LC-MS indicated the completion of reaction. The remaining sodium hydride was quenched by slow addition of saturated ammonium chloride. The mixture was extracted 3 times with DCM. The combined DCM layers were washed with water and brine and concentrated under reduced pressure to yield the crude product. The crude product was purified by flash chromatography to give 2,4-dichloro-5-(methoxymethyl)pyridine (74 mg, 0.385 mmol, 68.6% yield).

$^1$H NMR (400 MHz, CHLOROFORM-d) δ 8.45 (s, 1H), 7.40 (s, 1H), 4.56 (s, 2H), 3.52-3.46 (m, 3H). MS ESI m/z 191.8 $(M+H)^+$

Step 3: Synthesis of 4-chloro-5-(methoxymethyl)-2-vinylpyridine

A 20 mL reaction vial was charged with a stir bar, 2,4-dichloro-5-(methoxymethyl)pyridine (74 mg, 0.385 mmol), trifluoro(vinyl)borate, K+(51.6 mg, 0.385 mmol), Pd(dppf)Cl2, DCM adduct (31.5 mg, 0.039 mmol), and cesium carbonate (314 mg, 0.963 mmol) in Dioxane (1541 μl) and Water (385 μl) to give a orange suspension. The reaction mixture was degassed by evacuating and backfilling with nitrogen 3 times. The vial was sealed and heated to 70° C. for 16 hours. LC-MS indicated the completion of reaction. The aqueous layer was removed and the organic layer was concentrated under reduced pressure. The crude product was purified by flash chromatography to yield 4-chloro-5-(methoxymethyl)-2-vinylpyridine (48 mg, 0.261 mmol, 67.8% yield) as a colorless oil. MS ESI m/z 184.0 $(M+H)^+$

Step 4: Synthesis of (5-(methoxymethyl)-2-vinylpyridin-4-yl)boronic acid

A 20 mL reaction vial was charged with a stir bar, 4-chloro-5-(methoxymethyl)-2-vinylpyridine (48 mg, 0.261 mmol), bis(pinacolato)diboron (73.0 mg, 0.288 mmol), Bis (dibenzylideneacetone)palladium(0) (15.03 mg, 0.026 mmol), tricyclohexylphosphine (14.66 mg, 0.052 mmol), and potassium acetate (38.5 mg, 0.392 mmol) in Dioxane (2614 μl) to give a dark suspension. The reaction mixture was degassed by evacuating and backfilling with nitrogen 3 times. The vial was sealed and heated to 80° C. for 3 hours. LC-MS indicated the significant conversion of the starting material, affording (5-(methoxymethyl)-2-vinylpyridin-4-yl)boronic acid as a crude reaction mixture that will be used without further purification (estimated 50% conversion by LC MS). MS ESI m/z 193.8 $(M+H)^+$

Step 5: Synthesis of (R)-3-(5-(methoxymethyl)-2-vinylpyridin-4-yl)-10-methyl-9,10,11,12-tetrahydro-8H-[1,4]diazepino[5',6':4,5]thieno[3,2-f]quinolin-8-one A 4 mL reaction vial was charged with a stir bar, (R)-3-chloro-10-methyl-9,10,11,12-tetrahydro-8H-[1,4]diazepino [5',6':4,5]thieno[3,2-f]quinolin-8-one (65.9 mg, 0.207 mmol), (5-(methoxymethyl)-2-vinylpyridin-4-yl)boronic acid (259 μl, 0.2 M in dioxane as crude reaction mixture, 0.052 mmol), and PdCl2(dtbpf) (6.75 mg, 10.36 μmol) to give a dark suspension. Potassium phosphate, tribasic (155 μl, 0.311 mmol) was added as an aqueous solution. The reaction mixture was degassed by evacuating and backfilling with nitrogen 3 times. The resulting mixture was stirred at 60° C. for 16 h. LC MS indicated significant product was present. The reaction was concentrated under reduced pressure, and the crude product was dissolved in DMSO. The crude product was purified by reversed phase prep HPLC under acidic conditions to give 12 mg of product. The material was further purified via preparative Reverse Phase chromatography with the following conditions: Column: XBridge C18, 19 mm×200 mm, 5 m particles; Mobile Phase A: 5:95 acetonitrile: water with 10 mM ammonium acetate; Mobile Phase B: 95:5 acetonitrile: water with 10 mM ammonium acetate; Gradient: a 0-min hold at 19% B, 19-59% B over 20 min, then a 4-min hold at 100% B; Flow Rate: 20 mL/min; Column Temperature: 25° C. Fraction collection was triggered by UV (220 nm) and MS (ESI+). Fractions containing the desired product were combined and dried via centrifugal evaporation, affording (R)-3-(5-(methoxymethyl)-2-vinylpyridin-4-yl)-10-methyl-9,10,11,12-tetrahydro-8H-[1,4]diazepino[5',6':4,5]thieno[3,2-f]quinolin-8-one (7.2 mg, 0.017 mmol, 32% yield).

$^1$H NMR (500 MHz, DMSO-$d_6$) δ 9.28 (br d, J=8.8 Hz, 1H), 8.70 (s, 1H), 8.17 (d, J=8.9 Hz, 1H), 8.10-8.05 (m, 1H), 8.02 (d, J=9.2 Hz, 1H), 7.98 (br d, J=8.9 Hz, 1H), 7.76 (s, 1H), 7.18 (br t, J=5.1 Hz, 1H), 6.94 (dd, J=17.2, 10.9 Hz, 1H), 6.37-6.28 (m, 1H), 5.61-5.46 (m, 1H), 4.67 (s, 2H), 3.23-3.19 (m, 3H), 1.19 (d, J=6.7 Hz, 3H). 3 protons obscured by water peak. MS ESI m/z 431.1 $(M+H)^+$

TABLE 3

Compounds in Table 3 were prepared in a similar fashion to (R)-3-(5-(methoxymethyl)-2-vinylpyridin-4-yl)-10-methyl-9,10,11,12-tetrahydro-8H-[1,4]diazepino[5',6':4,5]thieno[3,2-f]quinolin-8-one.

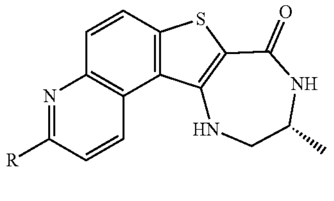

| Name | R | M + H$^+$ | 1H NMR (500 MHz, DMSO-d6) □ |
|---|---|---|---|
| (R)-3-(5-(ethoxymethyl)-2-vinylpyridin-4-yl)-10-methyl-9,10,11,12-tetrahydro-8H-[1,4]diazepino[5',6':4,5] thieno[3,2-f]quinolin-8-one | 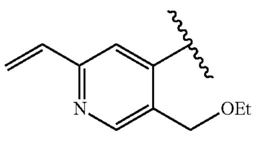 [SMILES: *c1cc(C=C)ncc1COCC] | 445.1 | $^1$H NMR (500 MHz, DMSO-$d_6$) δ 9.31 (d, J = 8.9 Hz, 1H), 8.75 (s, 1H), 8.20 (d, J = 8.9 Hz, 1H), 8.11 (br d, J = 4.0 Hz, 1H), 8.03 (d, J = 8.9 Hz, 2H), 7.86 (s, 1H), 6.97 (dd, J = 17.4, 10.6 Hz, 1H), 6.40 (d, J = 17.6 Hz, 1H), 5.60 (d, J = 11.1 Hz, 1H), 4.75 (s, 2H), 1.20 (d, J = 6.7 Hz, 3H), 1.02 (t, J = 7.0 Hz, 3H). 7 peaks obscured by solvent. |

Example 51: Synthesis of (15R)-15-methyl-5-[5-[2,2,2-trideuterio-1-hydroxy-1-(trideuteriomethyl)ethyl]-2-vinyl-4-pyridyl]-11-thia-6,14,17-triazatetracyclo[8.8.0.0^,7.0^12,18]octadeca-1(10),2(7),3,5,8,12(18)-hexaen-13-one

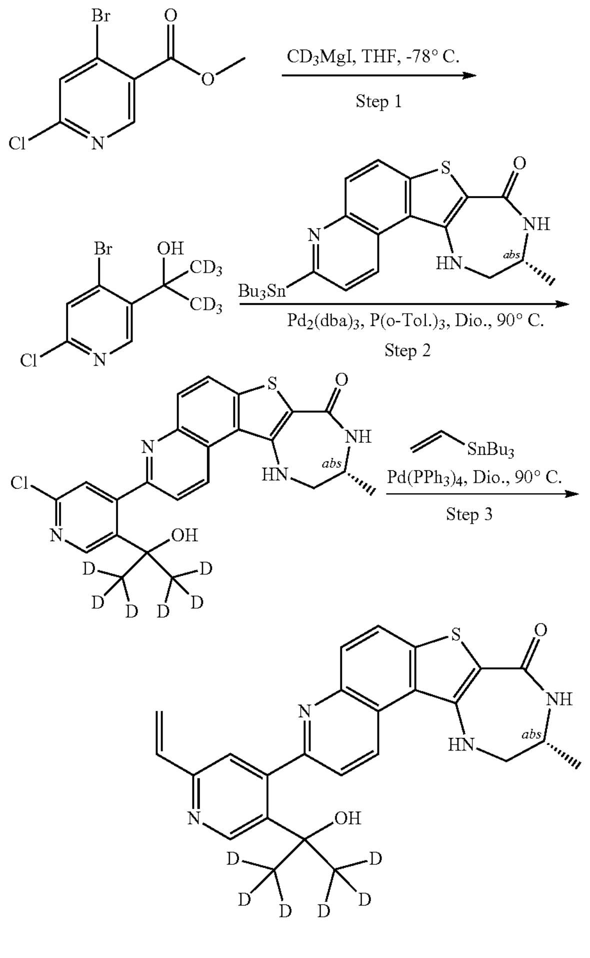

Step 1: Synthesis of 2-(4-bromo-6-chloro-3-pyridyl)-1,1,1,3,3,3-hexadeuterio-propan-2-ol

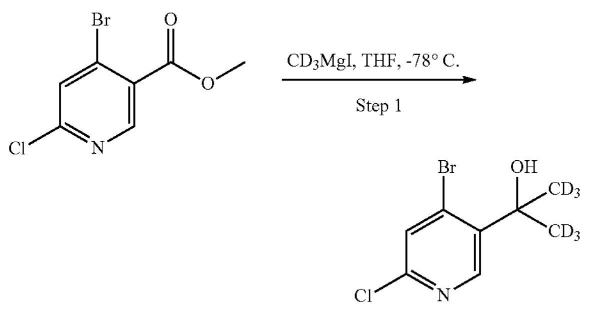

To a solution of methyl 4-bromo-6-chloro-pyridine-3-carboxylate (200 mg, 0.800 mmol, 1.00 equiv) in THF (8.0 mL) was added dropwise 1M iodo(trideuteriomethyl)magnesium in THF (8.0 mL, 8.000 mmol, 10.00 equiv) at −78° C. under nitrogen atmosphere. The resulting mixture was stirred at room temperature for 1 h under nitrogen atmosphere. LCMS showed the reaction was completed. The resulting solution was quenched with saturated ammonium chloride aqueous (20 mL), extracted with ethyl acetate (3×20 mL). The combined organic layers were washed with brine (2×10 mL), dried over anhydrous sodium sulfate, filtered and concentrated under reduce pressure. The residue was purified by column chromatography on silica gel with petroleum ether/ethyl acetate (1:1) to give 2-(4-bromo-6-chloro-3-pyridyl)-1,1,1,3,3,3-hexadeuterio-propan-2-ol (200 mg, 97%) as a light yellow solid. LCMS (ESI, m/z): 256 [M+H]+

Step 2: Synthesis of (15R)-5-[2-chloro-5-[2,2,2-trideuterio-1-hydroxy-1-(trideuteriomethyl)ethyl]-4-pyridyl]-15-methyl-11-thia-6,14,17-triazatetracyclo[8.8.0.0^,7.0^12,18]octadeca-1(10),2(7),3,5,8,12(18)-hexaen-13-one

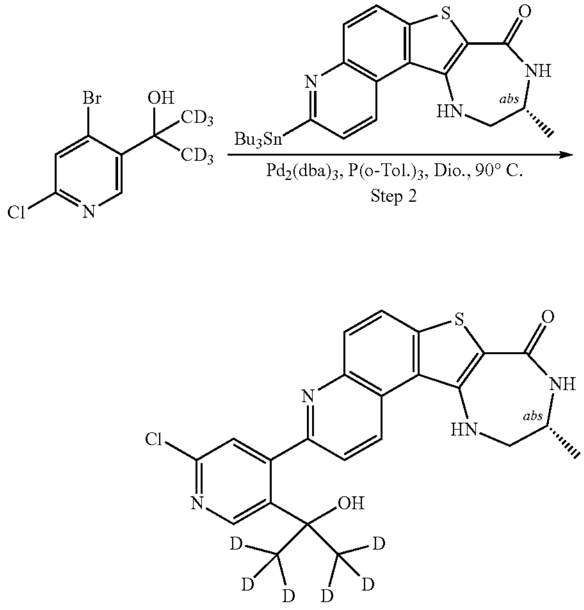

To a solution of 2-(4-bromo-6-chloro-3-pyridyl)-1,1,1,3,3,3-hexadeuterio-propan-2-ol (100 mg, 0.390 mmol, 1.00 equiv) and (15R)-15-methyl-5-tributylstannyl-11-thia-6,14,17-triazatetracyclo[8.8.0.0^,7.0^12,18]octadeca-1(10),2(7),3,5,8,12(18)-hexaen-13-one (268 mg, 0.470 mmol, 1.20 equiv) in 1,4-dioxane (4.0 mL) was added $Pd_2(dba)_3$ (81 mg, 0.080 mmol, 0.20 equiv) and $P(o\text{-}Tol.)_3$ (24 mg, 0.080 mmol, 0.20 equiv). The resulting mixture was stirred at 90° C. for 4 h under a nitrogen atmosphere. LCMS showed the reaction was completed. The resulting solution was diluted with ethyl acetate (20 mL). The solid was filtered out and the filtration was concentrated under reduced pressure. The residue was purified by reverse flash chromatography with water (0.05% TFA)/MeCN (1:3) to give (15R)-5-[2-chloro-5-[2,2,2-trideuterio-1-hydroxy-1-(trideuteriomethyl)ethyl]-4-pyridyl]-15-methyl-11-thia-6,14,17-triazatetracyclo[8.8.0.0^,7.0^12,18]octadeca-1(10),2(7),3,5,8,12(18)-hexaen-13-one (80 mg, 44%) as a yellow solid. LCMS (ESI, m/z): 459 $[M+H]^+$.

Step 3: Synthesis of (15R)-15-methyl-5-[5-[2,2,2-trideuterio-1-hydroxy-1-(trideuteriomethyl)ethyl]-2-vinyl-4-pyridyl]-11-thia-6,14,17-triazatetracyclo [8.8.0.0^,7.0^12,18]octadeca-1(10),2(7),3,5,8,12(18)-hexaen-13-one

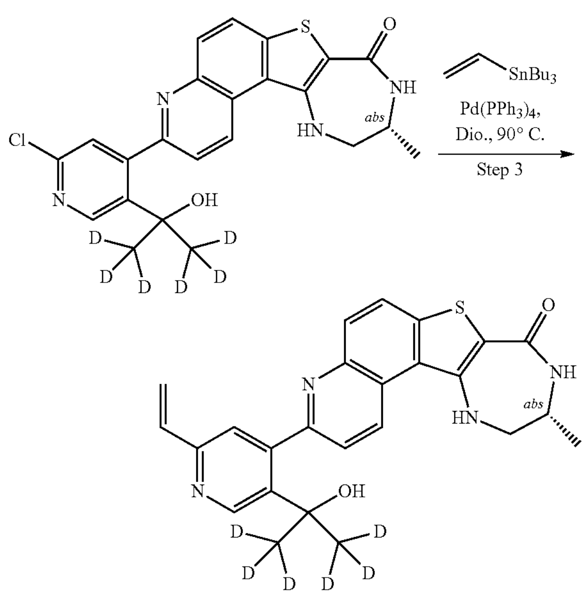

To a solution of (15R)-5-[2-chloro-5-[2,2,2-trideuterio-1-hydroxy-1-(trideuteriomethyl)ethyl]-4-pyridyl]-15-methyl-11-thia-6,14,17-triazatetracyclo[8.8.0.0^,7.0^12,18]octa-deca-1(10),2(7),3,5,8,12(18)-hexaen-13-one (70 mg, 0.150 mmol, 1.00 equiv), tributyl(vinyl)stannane (145 mg, 0.450 mmol, 3.00 equiv) in 1,4-dioxane (3.0 mL) was added $Pd(PPh_3)_4$(28 mg, 0.030 mmol, 0.20 equiv). The resulting mixture was stirred at 90° C. for 2 h under a nitrogen atmosphere. LCMS showed the reaction was completed. The resulting solution was diluted with ethyl acetate (10 mL). The solid was filtered out and the filtration was concentrated under reduced pressure. The residue was purified by reverse flash chromatography with water (0.05% TFA)/MeCN (1:2) to give 40 mg crude product. The crude product was purified by Prep-HPLC using the following conditions: Column: Welch Utimate HS-C18, 21.2*250 mm, 7 μm; Mobile Phase A: Water (0.05% TFA), Mobile Phase B: MeCN; Flow rate: 25 mL/min; Gradient: 30% B to 30% B in 6.5 min, 30% B; Wave Length: 254/210 nm; RT1(min): 5.68. Purification resulted in desired (15R)-15-methyl-5-[5-[2,2,2-trideuterio-1-hydroxy-1-(trideuteriomethyl)ethyl]-2-vinyl-4-pyridyl]-11-thia-6,14,17-triazatetracyclo[8.8.0.0^,7.0^12,18]octa-deca-1(10),2(7),3,5,8,12(18)-hexaen-13-one (21.1 mg, 29%) as a yellow solid. LCMS (ESI, m/z): 451 $[M+H]^+$. Analytic Conditions: column: HALO C18 Column 2.1*30 mm, 2.5 □m; mobile phase A: water+0.05% TFA, mobile phase B: acetonitrile+0.05% TFA; flow rate: 1.2000 mL/min; gradient: 5% B to 50% in 2.00 min. 254 nm; RT: 1.475 min.

$^1$H NMR (400 MHz, DMSO-$d_6$) δ 9.35 (d, J=8.8 Hz, 1H), 8.53 (s, 1H), 8.26 (d, J=9.2 Hz, 1H), 7.97 (d, J=8.8 Hz, 1H), 7.90 (d, J=8.8 Hz, 1H), 7.85 (s, 1H), 6.97 (dd, J=17.2, 10.8 Hz, 1H), 6.40 (d, J=17.2, 1H), 5.63 (d, J=12.0 Hz, 1H), 3.65-3.62 (m, 1H), 3.51-3.43 (m, 2H), 1.20 (d, J=6.8 Hz, 3H). $^{19}$F NMR (376 MHz, DMSO-$d_6$) δ-74.26.

Example 52: Synthesis of (15R)-15-methyl-5-[5-(2,2,2-trideuterio-1-hydroxy-ethyl)-2-vinyl-4-pyridyl]-11-thia-6,14,17-triazatetracyclo[8.8.0.0^,7.0^12,18] octadeca-1(10),2(7),3,5,8,12(18)-hexaen-13-one

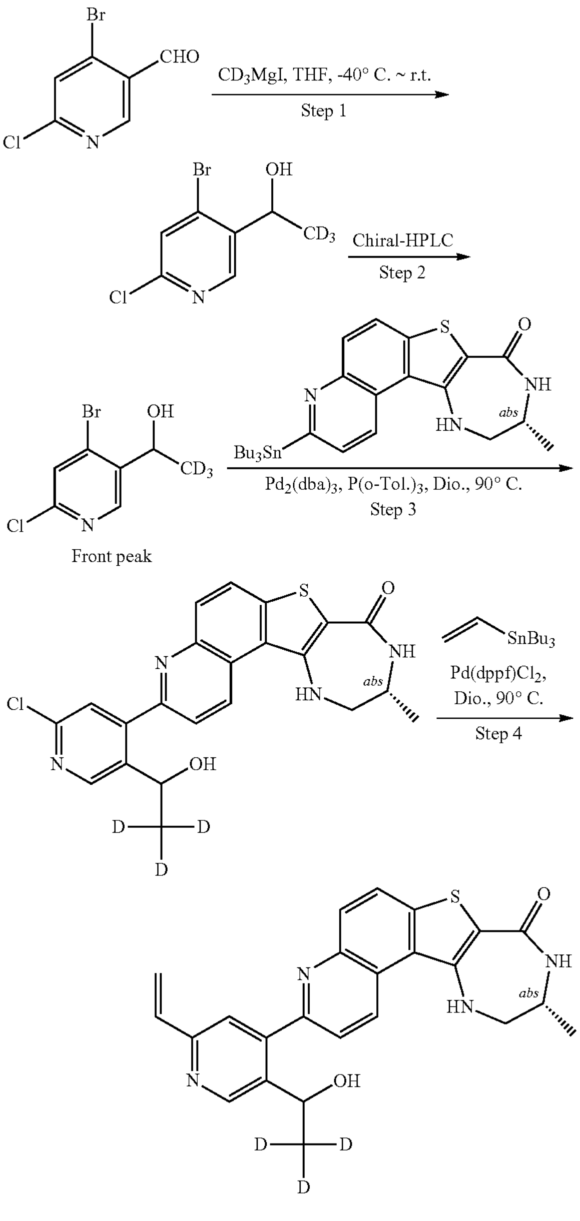

Step 1: Synthesis of 1-(4-bromo-6-chloro-3-pyridyl)-2,2,2-trideuterio-ethanol

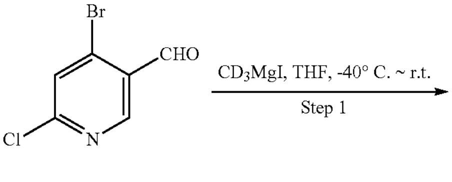

-continued

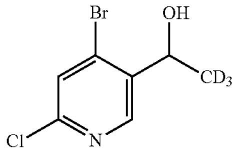

To a solution of 4-bromo-6-chloro-pyridine-3-carbaldehyde (330 mg, 1.500 mmol, 1.00 equiv) in THF (10.0 mL) was added dropwise 1M $CD_3MgI$ in THF (7.5 mL, 7.480 mmol, 5.00 equiv) at −40° C. The reaction mixture was stirred for 1 h at −40° C. and was allowed to warm to 0° C. under a nitrogen atmosphere. LCMS showed the reaction was completed. The resulting solution was quenched with saturated ammonium chloride aqueous (20 mL), extracted with ethyl acetate (3×20 mL). The combined organic layers were washed with brine (2×10 mL), dried over anhydrous sodium sulfate, filtered and concentrated under reduce pressure. The residue was purified by column chromatography on silica gel with petroleum ether/ethyl acetate (4:1) to give 1-(4-bromo-6-chloro-3-pyridyl)-2,2,2-trideuterio-ethanol (245 mg, 63%) as a colorless oil. LCMS (ESI, m z): 240 $(M+H)^+$.

Step 2: Synthesis of (1-(4-bromo-6-chloro-3-pyridyl)-2,2,2-trideuterio-ethanol

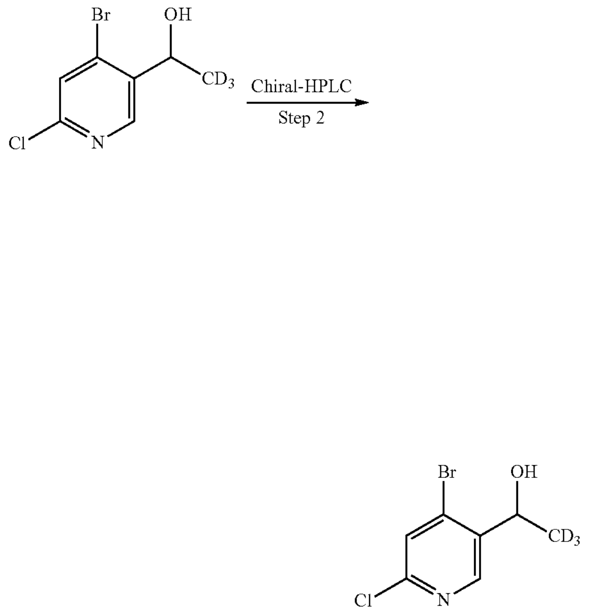

Front peak

The racemate (245 mg, purity: 97%) was separated by Chiral Prep-HPLC using the following gradient conditions: Column: CHIRAL ART Cellulose-SA, 2*25 cm, 5 μm; Mobile Phase A: hexane (0.1% 2M $NH_3$-MeOH), Mobile Phase B: EtOH; Flow rate: 20 mL/min; Gradient: 5% B to 5% B in 16 min; 220/254 nm; RT1: 10.62; RT2: 13.304. Purification resulted in front peak: (1-(4-bromo-6-chloro-3-pyridyl)-2,2,2-trideuterio-ethanol (125 mg, 51.02%, RT:1.87 min) as a colorless oil. LCMS (ESI, m z): 240 $[M+H]^+$.

Step 3: Synthesis of (15R)-5-[2-chloro-5-(2,2,2-trideuterio-1-hydroxy-ethyl)-4-pyridyl]-15-methyl-11-thia-6,14,17-triazatetracyclo[8.8.0.0^,7.0^12,18]octadeca-1(10),2(7),3,5,8,12(18)-hexaen-13-one

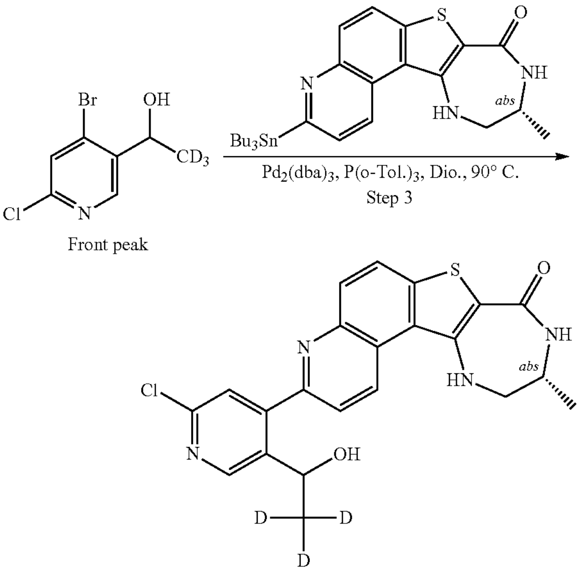

To a solution of 1-(4-bromo-6-chloro-3-pyridyl)-2,2,2-trideuterio-ethanol (110 mg, 0.460 mmol, 1.00 equiv) and (15R)-15-methyl-5-tributylstannyl-11-thia-6,14,17-triazatetracyclo[8.8.0.0^,7.0^12,18]octadeca-1(10),2(7),3,5,8,12(18)-hexaen-13-one (315 mg, 0.550 mmol, 1.20 equiv) in 1,4-dioxane (3.0 mL) was added $Pd_2(dba)_3$ (95 mg, 0.090 mmol, 0.20 equiv) and $P(o\text{-}Tol.)_3$ (56 mg, 0.180 mmol, 0.40 equiv). The resulting mixture was stirred at 90° C. for 3 h under a nitrogen atmosphere. LCMS showed the reaction was completed. The resulting solution was concentrated under reduced pressure. The residue was purified by reverse flash chromatography with water (0.05% TFA)/MeCN (3:2) to give (15R)-5-[2-chloro-5-(2,2,2-trideuterio-1-hydroxy-ethyl)-4-pyridyl]-15-methyl-11-thia-6,14,17-triazatetracyclo[8.8.0.0^,7.0^12,18]octadeca-1(10),2(7),3,5,8,12(18)-hexaen-13-one (80 mg, 39%) as a red solid. LCMS (ESI, m z): 442 $(M+H)^+$.

Step 4: Synthesis of (15R)-15-methyl-5-[5-(2,2,2-trideuterio-1-hydroxy-ethyl)-2-vinyl-4-pyridyl]-11-thia-6,14,17-triazatetracyclo[8.8.0.0^,7.0^12,18]octadeca-1(10),2(7),3,5,8,12(18)-hexaen-13-one

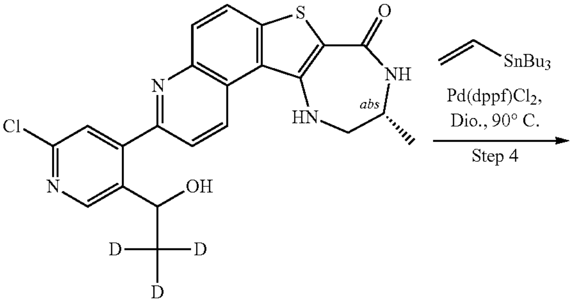

-continued

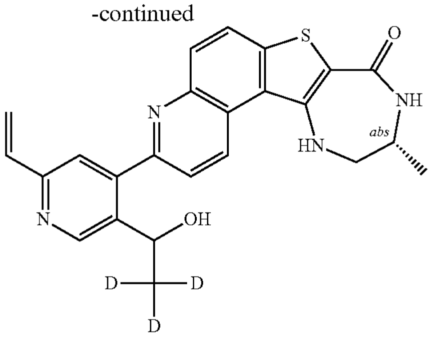

To a solution of (15R)-5-[2-chloro-5-(2,2,2-trideuterio-1-hydroxy-ethyl)-4-pyridyl]-15-methyl-11-thia-6,14,17-tri-azatetracyclo[8.8.0.0^2,7.0^12,18]octadeca-1(10),2(7),3,5,8,12(18)-hexaen-13-one (80 mg, 0.180 mmol, 1.00 equiv) and tributyl(vinyl)stannane (176 mg, 0.540 mmol, 3.00 equiv) in 1,4-dioxane (2.0 mL) was added Pd(dppf)$Cl_2$ (59 mg, 0.070 mmol, 0.40 equiv). The resulting mixture was stirred at 90° C. for 3 h under a nitrogen atmosphere. LCMS showed the reaction was completed. The resulting solution was concentrated under reduced pressure. The residue was purified by reverse flash chromatography with water (0.05% TFA)/MeCN (2:1) to give (15R)-15-methyl-5-[5-(2,2,2-tri-deuterio-1-hydroxy-ethyl)-2-vinyl-4-pyridyl]-11-thia-6,14,17-triazatetracyclo[8.8.0.0^,7.0^12,18]octadeca-1(10),2(7),3,5,8,12(18)-hexaen-13-one (33.9 mg, 42%) as an orange solid. LCMS (ESI, m z): 434 $(M+H)^+$. Analytic Conditions: Column: HALO C18 Column 3.0*30 mm, 2.7 um; Mobile Phase A: Water/0.05% TFA, Mobile Phase B: Acetonitrile/0.05% TFA; Flow rate: 1.5000 mL/min; Gradient: 5% B to 50% B in 1.70 min; 254 nm; Rt: 1.254 min.

$^1H$ NMR (400 MHz, DMSO-$d_6$) δ 9.35 (d, J=8.8 Hz, 1H), 8.91 (s, 1H), 8.22 (d, J=8.8 Hz, 1H), 8.15 (d, J=4.4 Hz, 1H), 8.01 (d, J=9.2 Hz, 1H), 7.98 (d, J=9.2 Hz, 1H), 7.81 (s, 1H), 7.22 (s, 1H), 6.96 (dd, J=17.2 Hz, 10.8 Hz, 1H), 6.41 (d, J=17.2 Hz, 1H), 5.63 (d, J=11.2 Hz, 1H), 5.16 (s, 1H), 3.68-3.60 (m, 1H), 3.53-3.45 (m, 2H), 1.20 (d, J=6.8 Hz, 3H). $^{19}F$ NMR (376 MHz, DMSO-$d_6$) δ-74.69.

Example 53: Synthesis of (15R)-15-methyl-5-[5-(2,2,2-trideuterio-1-hydroxy-ethyl)-2-vinyl-4-pyridyl]-11-thia-6,14,17-triazatetracyclo[8.8.0.0^,7.0^12,18]octadeca-1(10),2(7),3,5,8,12(18)-hexaen-13-one

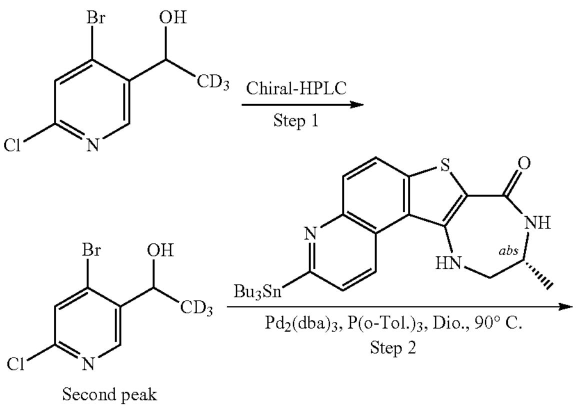

-continued

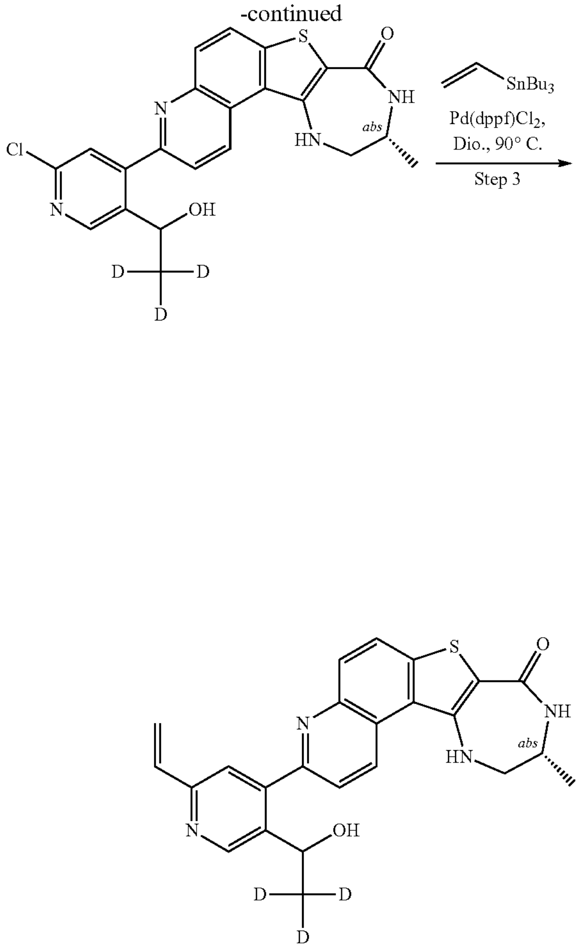

Step 1: Synthesis of (1-(4-bromo-6-chloro-3-pyridyl)-2,2,2-trideuterio-ethanol

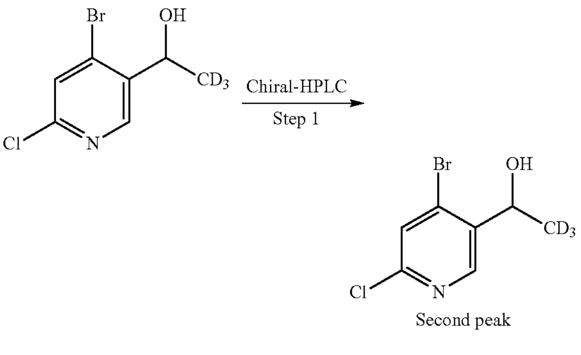

The racemate (245 mg, purity: 99%) was separated by Chiral Prep-HPLC using the following gradient conditions: Column: CHIRAL ART Cellulose-SA, 2*25 cm, 5 μm; Mobile Phase A: hexane (0.1% 2M $NH_3$-MeOH), Mobile Phase B: EtOH; Flow rate: 20 mL/min; Gradient: 5% B to 5% B in 16 min; 220/254 nm; RT1: 10.62; RT2: 13.304; Purification resulted in second peak: (1-(4-bromo-6-chloro-3-pyridyl)-2,2,2-trideuterio-ethanol (120 mg, 49%, RT: 2.40 min) as an off-white semi-oil. LCMS (ESI, m z): 240 $[M+H]^+$.

Step 2: Synthesis of (15R)-5-[2-chloro-5-(2,2,2-trideuterio-1-hydroxy-ethyl)-4-pyridyl]-15-methyl-11-thia-6,14,17-triazatetracyclo[8.8.0.0^,7.0^12,18]octadeca-1(10),2(7),3,5,8,12(18)-hexaen-13-one

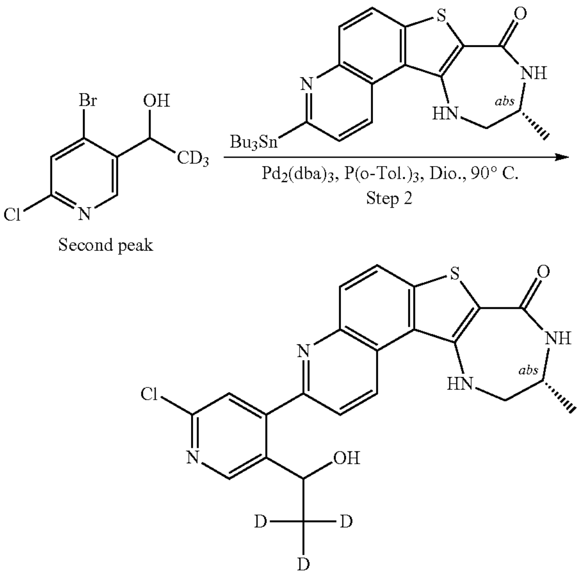

To a solution of 1-(4-bromo-6-chloro-3-pyridyl)-2,2,2-trideuterio-ethanol (120 mg, 0.500 mmol, 1.00 equiv) and (15R)-15-methyl-5-tributylstannyl-11-thia-6,14,17-triaza-tetracyclo[8.8.0.0^,7.0^12,18]octadeca-1(10),2(7),3,5,8,12(18)-hexaen-13-one (344 mg, 0.600 mmol, 1.20 equiv) in 1,4-dioxane (10.0 mL) was added $Pd_2(dba)_3$ (103 mg, 0.100 mmol, 0.20 equiv) and $P(o\text{-}Tol.)_3$ (61 mg, 0.200 mmol, 0.40 equiv). The resulting mixture was stirred at 90° C. for 3 h under a nitrogen atmosphere. LCMS showed the reaction was completed. The resulting solution was diluted with DMF (3.0 ml). The solid was filtered out and the filtration was purified by reverse flash chromatography with water (0.05% TFA)/MeCN (3:2) to give (15R)-5-[2-chloro-5-(2,2,2-trideuterio-1-hydroxy-ethyl)-4-pyridyl]-15-methyl-11-thia-6,14,17-triazatetracyclo[8.8.0.0^,7.0^12,18]octadeca-1(10),2(7),3,5,8,12(18)-hexaen-13-one (90 mg, 40%) as a red solid. LCMS (ESI, m z): 442 $(M+H)^+$.

Step 3: Synthesis of (15R)-15-methyl-5-[5-(2,2,2-trideuterio-1-hydroxy-ethyl)-2-vinyl-4-pyridyl]-11-thia-6,14,17-triazatetracyclo[8.8.0.0^,7.0^12,18]octa-deca-1(10),2(7),3,5,8,12(18)-hexaen-13-one

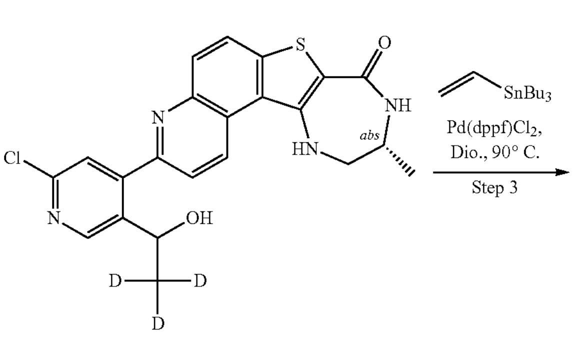

-continued

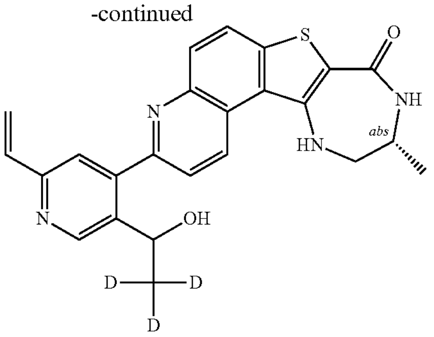

To a solution of (15R)-5-[2-chloro-5-(2,2,2-trideuterio-1-hydroxy-ethyl)-4-pyridyl]-15-methyl-11-thia-6,14,17-tri-azatetracyclo[8.8.0.0^,7.0^12,18]octadeca-1(10),2(7),3,5,8,12(18)-hexaen-13-one (80 mg, 0.180 mmol, 1.00 equiv) and tributyl(vinyl)stannane (176 mg, 0.540 mmol, 3.00 equiv) in 1,4-dioxane (5.0 mL) was added $Pd(dppf)Cl_2$ (60 mg, 0.070 mmol, 0.40 equiv). The resulting mixture was stirred at 90° C. for 3 h under a nitrogen atmosphere. LCMS showed the reaction was completed. The resulting solution was diluted with DMF (3.0 ml). The solid was filtered out and the filtration was purified by reverse flash chromatography with water (0.05% TFA)/MeCN (2:1) to give (15R)-15-methyl-5-[5-(2,2,2-trideuterio-1-hydroxy-ethyl)-2-vinyl-4-pyridyl]-11-thia-6,14,17-triazatetracyclo[8.8.0.0^,7.0^12,18]octa-deca-1(10),2(7),3,5,8,12(18)-hexaen-13-one (31.4 mg, 39%) as a yellow solid. LCMS (ESI, m/z): 434 $(M+H)^+$. Analytic Conditions: Column: HALO C18 Column 3.0*30 mm, 2.7 um; Mobile Phase A: Water/0.05% TFA, Mobile Phase B: Acetonitrile/0.05% TFA; Flow rate: 1.5000 mL/min; Gradient: 5% B to 50% B in 1.70 min; 254 nm; Rt: 1.246 min.

$^1H$ NMR (400 MHz, DMSO-$d_6$) δ 9.34 (d, J=8.8 Hz, 1H), 8.90 (s, 1H), 8.22 (d, J=8.8 Hz, 1H), 8.15 (d, J=4.4 Hz, 1H), 8.00 (d, J=8.8 Hz, 1H), 7.97 (d, J=8.8 Hz, 1H), 7.75 (s, 1H), 7.22 (s, 1H), 6.96 (dd, J=17.2 Hz, 10.8 Hz, 1H), 6.39 (d, J=17.2 Hz, 1H), 5.60 (d, J=11.2 Hz, 1H), 5.12 (s, 1H), 3.70-3.60 (m, 1H), 3.55-3.45 (m, 2H), 1.20 (d, J=6.8 Hz, 3H). $^{19}F$ NMR (376 MHz, DMSO-$d_6$) δ-74.54.

Example 54: Synthesis of (15R)-15-methyl-5-(5-vinylpyridazin-3-yl)-11-thia-6,14,17-triazatetracyclo[8.8.0.0^,7.0^12,18]octadeca-1(10),2,4,6,8,12(18)-hexaen-13-one

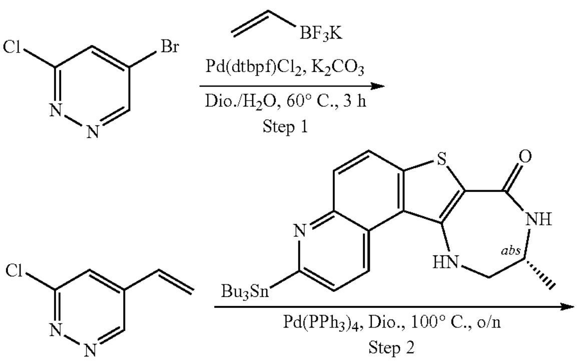

-continued

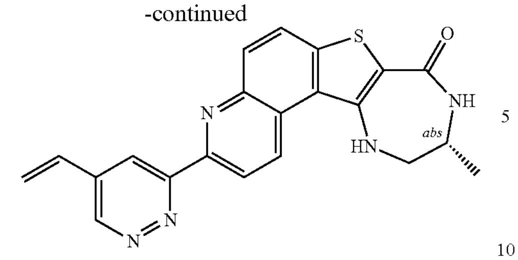

Step 1: Synthesis of 3-chloro-5-vinyl-pyridazine

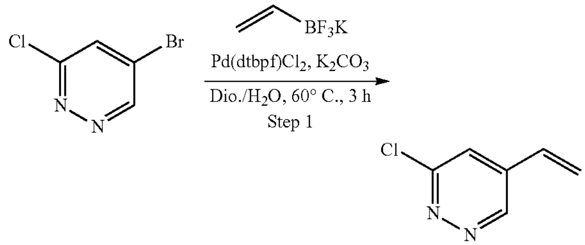

To a solution of 5-bromo-3-chloro-pyridazine (500 mg, 2.580 mmol, 1.00 equiv), potassium; trifluoro(vinyl)boranuide (693 mg, 5.170 mmol, 2.00 equiv) and $K_2CO_3$ (1.1 g, 7.750 mmol, 3.00 equiv) in 1,4-dioxane (10.0 mL) and water (1.0 mL) was added Pd(dtbpf)$Cl_2$ (168 mg, 0.260 mmol, 0.10 equiv). The resulting mixture was stirred at 60° C. for 3 h under a nitrogen atmosphere. LCMS showed the reaction was completed. The resulting solution was diluted with water (80 mL), extracted with ethyl acetate (3×25 mL). The combined organic layers were washed with brine (2×30 mL), dried over anhydrous sodium sulfate, filtered and concentrated under reduced pressure. The residue was purified by column flash chromatography on silica gel with ethyl acetate/petroleum ether (1:2) to give 3-chloro-5-vinyl-pyridazine (200 mg, 55%) as a colorless oil. LCMS (ESI, m/z): 141$(M+H)^+$.

Step 2: Synthesis of (15R)-15-methyl-5-(5-vinylpyridazin-3-yl)-11-thia-6,14,17-triazatetracyclo [8.8.0.0^,7.0^12,18]octadeca-1(10),2,4,6,8,12(18)-hexaen-13-one

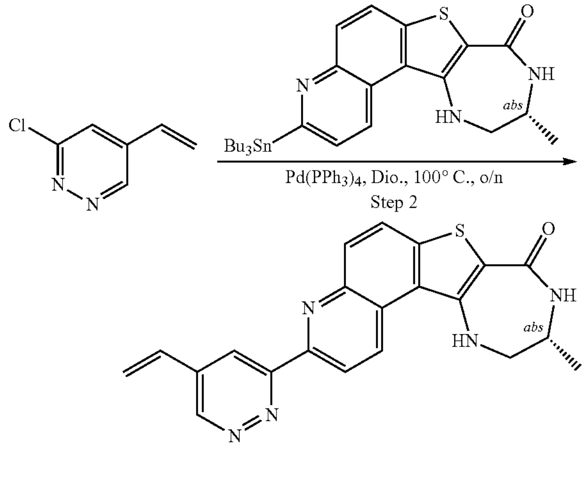

To a solution of 3-chloro-5-vinyl-pyridazine (200 mg, 1.420 mmol, 1.00 equiv) and (15R)-15-methyl-5-tributylstannyl-11-thia-6,14,17-triazatetracyclo[8.8.0.0^,7.0^12,18] octadeca-1(10),2,4,6,8,12(18)-hexaen-13-one (652 mg, 1.140 mmol, 0.80 equiv) in 1,4-dioxane (5.0 mL) was added $Pd(PPh_3)_4$(164 mg, 0.140 mmol, 0.10 equiv). The resulting mixture was stirred at 100° C. overnight under a nitrogen atmosphere. LCMS showed the reaction was completed. The resulting solution was concentrated under reduced pressure and the residue was purified by column flash chromatography on silica gel with ethyl acetate/petroleum (2:1) to give 40 mg crude product. The crude product was purified by Prep-HPLC using the following gradient conditions: Column: SunFire Prep C18 OBD Column, 19*150 mm, 5 μm; Mobile Phase A: Water (0.05% TFA), Mobile Phase B: MeCN; Flow rate: 25 mL/min; Gradient: 15% B to 60% B in 6.5 min, 60% B; Wave Length: 254/210 nm; RT1(min): 7.56. Purification resulted in desired (15R)-15-methyl-5-(5-vinylpyridazin-3-yl)-11-thia-6,14,17-triazatetracyclo [8.8.0.0^,7.0^12,18]octadeca-1(10),2,4,6,8,12(18)-hexaen-13-one (8.5 mg, 1%) as an orange solid. LCMS (ESI, m/z): 388 $(M+H)^+$. Analytic Conditions: Column: XSelect HSS T3 100A Column 2.1*30 mm, 2.5 um; Mobile Phase A: Water/0.05% TFA, Mobile Phase B: Acetonitrile/0.05% TFA; Flow rate: 1.2000 mL/min; Gradient: 5% B to 60% B in 2.10 min; 254 nm; Rt: 1.730

$^1H$ NMR (400 MHz, DMSO-$d_6$) δ 9.55 (d, J=2.0 Hz, 1H), 9.39 (d, J=8.8 Hz, 1H), 8.90 (d, J=9.2 Hz, 1H), 8.77 (s, 1H), 8.23 (d, J=8.8 Hz, 1H), 8.17 (d, J=9.2 Hz, 1H), 8.12 (d, J=8.8 Hz, 1H), 7.24 (t, J=5.6 Hz, 1H), 6.99 (dd, J=17.6, 11.2 Hz, 1H), 6.51 (d, J=17.6 Hz, 1H), 5.82 (d, J=11.2 Hz, 1H), 3.68-3.60 (m, 1H), 3.55-3.45 (m, 2H), 1.21 (d, J=6.4 Hz, 3H). $^{19}F$ NMR (376 MHz, DMSO-$d_6$) δ-74.34.

BIOLOGICAL EXAMPLES

Described below are in vitro assays used to measure the biological activity of provided compounds as selective inhibitors of MK2.

Mitogen-Activated Protein Kinase-Activated Protein Kinase 2 Omnia® Assay for Compound Potency Assessment:

The protocol below describes a continuous-read kinase assay optimized to measure potency of compounds against p38a activated, mitogen-activated protein kinase-activated protein kinase 2 (MAPKAP-K2 or MK2) enzyme. Further details of this assay are described by Life Technologies, Carlsbad, CA on their website at the following URL: http://tools.lifetechnologies.com/content/sfs/manuals/omnia_kinase_assay_man.pdf.

[Reagent] used:

[MK-2]=0.4 nM,

[ATP]=10 μM and

[ST3-Sox]=10 μM ($ATP^{app}K_M$=10 μM)

Briefly, 10× stock solutions of MK2 (PV3317, from Life Technologies), 1.13X ATP (AS001A), and Sox conjugated peptide substrate, S/T3-Sox, (KZN1031) were prepared in 1× kinase reaction buffer consisting of 20 mM Tris, pH 7.5, 5 mM $MgCl_2$, 1 mM EGTA, 5 mM β-glycerophosphate, 5% glycerol (10× stock, KB001A) and 0.2 mM DTT (DS001A). Enzyme solution (5 μL) was added to each of DMSO (5 μL) or serially diluted test compounds prepared in DMSO in a Corning (#3574) 384-well, white, non-binding surface microtiter plate (Corning, NY). Kinase reactions were started with the addition of 45 μL of the ATP-peptide substrate S/T3-Sox mix and monitored every 71 seconds for 120 minutes at $\lambda_{ex}360/\lambda_{em}485$ in a Synergy H4 plate reader from BioTek (Winooski, VT) at room temperature.

Background signals from the no enzyme control wells were subtracted from all progress curves. The initial linear portions of the net progress curves were fit according to a linear equation to yield the slope and percentage of inhibition (% inhibition) at each compound concentration. The net progress curves obtained during the first two hours of reactions were also fit according to an ascending single-exponential equation (Eq. 1) to yield $k_{obs}$ values at each compound concentration. Plots of % Inhibition versus inhibitor concentrations were fit according to a dose-response equation (Eq. 2) to generate $IC_{50}$ and Hill slope values while plots of $k_{obs}$ versus inhibitor concentration were fit according to Equation 3 (Eq. 3) to generate apparent $k_{inact}/K_1$ values using the GraphPad PRISM software (Version 6.00; GraphPad San Diego, CA).

$$F = V_0 \frac{(1 - e^{-k_{obs}t})}{k_{obs}} \quad \text{(Eq. 1)}$$

where F is the fluorescence intensity from the plate reader, $V_0$ is a constant reflecting the relationship between the instrument readout and product concentration, t is time, e is Euler's number, and $k_{obs}$ is the observed inactivation rate constant.

$$\% \text{ Inhibition} = \frac{100}{1 + \left(\frac{IC_{50}}{[I]}\right)^n} \quad \text{(Eq. 2)}$$

where % Inhibition is percentage of inhibition, $IC_{50}$ is half maximal inhibitory concentration, [I] is the inhibitor concentration, and n is the Hill slope.

$$k_{obs} = \frac{k_{inact}}{K_I} \frac{[I]}{2} \quad \text{(Eq. 3)}$$

where $k_{obs}$ is the observed inactivation rate constant, $k_{inact}$ is the apparent inactivation rate constant, $K_1$ is the apparent inhibition constant, and [I] is the inhibitor concentration. Results from this assay, showing $IC_{50}$ (i.e. the concentration at which a test compound inhibits substrate peptide phosphorylation 500%) are reported in nanomolar. Potency results for the compounds tested are shown in Table 4 in the column entitled "MK2 $IC_{50}$."

Table 4 shows data for selected compounds in various assays.

TABLE 4

| Compound Number | MK2 $IC_{50}$ (nM) |
|---|---|
| I-1 | 5 |
| I-2 | 133 |
| I-3 | 107 |
| I-4 | 1 |
| I-5 | 7 |
| I-6 | 912 |
| I-7 | 6 |
| I-8 | 75 |
| I-9 | 97 |
| I-10 | 291 |

TABLE 4-continued

| Compound Number | MK2 $IC_{50}$ (nM) |
|---|---|
| I-11 | 2 |
| I-12 | 87 |
| I-13 | 1 |
| I-14 | 12 |
| I-15 | 10 |
| I-16 | 26 |
| I-17 | 137 |
| I-18 | 4 |
| I-19 | 4 |
| I-20 | 224 |
| I-21 | 24 |
| I-22 | 2 |
| I-23 | 487 |
| I-24 | 98 |
| I-25 | 43 |
| I-26 | 684 |
| I-27 | 391 |
| I-28 | 18 |
| I-29 | 20 |
| I-30 | 16 |
| I-31 | 24 |
| I-32 | 245 |
| I-33 | 120 |
| I-34 | 13 |
| I-35 | 40 |
| I-36 | 12 |
| I-37 | 10 |
| I-38 | 5 |
| I-39 | 8 |
| I-40 | 25 |
| I-41 | 199 |
| I-42 | 233 |
| I-43 | 440 |
| I-44 | 1000 |
| I-45 | 160 |
| I-46 | 765 |
| I-47 | 429 |
| I-48 | 371 |
| I-49 | 474 |
| I-50 | 1000 |
| I-51 | 3 |
| I-52 | 116 |
| I-53 | 213 |
| I-54 | 61 |
| I-55 | 1 |
| I-56 | 194 |
| I-57 | 117 |
| I-58 | 16 |
| I-59 | 3 |
| I-60 | 58 |
| I-61 | 73 |
| I-62 | 27 |
| I-63 | 145 |
| I-64 | 4 |
| I-65 | 132 |
| I-66 | 9 |
| I-67 | 38 |
| I-68 | 472 |
| I-69 | 27 |
| I-70 | 64 |
| I-70 | 64 |
| I-71 | 39 |
| I-72 | 58 |
| I-73 | 75 |
| I-74 | 4 |
| I-75 | 470 |
| I-76 | 1 |
| I-77 | 13 |
| I-78 | 1 |
| I-79 | 568 |
| I-80 | 574 |
| I-81 | 90 |
| I-82 | 21 |
| I-83 | 83 |
| I-84 | 39 |
| I-85 | 11 |
| I-86 | 23 |

TABLE 4-continued

| Compound Number | MK2 $IC_{50}$ (nM) |
|---|---|
| I-87 | 283 |
| I-88 | 15 |
| I-89 | 26 |
| I-90 | 460 |
| I-91 | 26 |
| I-92 | 17 |
| I-93 | 238 |
| I-94 | 43 |
| I-95 | 42 |
| I-96 | 10 |
| I-97 | 60 |
| I-98 | 60 |
| I-99 | 2 |
| I-100 | 62 |
| I-101 | 8 |
| I-102 | 8 |
| I-103 | 46 |
| I-104 | 194 |
| I-105 | 118 |
| I-106 | 8 |
| I-107 | 22 |
| I-108 | 122 |
| I-109 | 4 |
| I-110 | 8 |
| I-111 | 104 |
| I-112 | 152 |
| I-113 | 53 |
| I-114 | 11 |
| I-115 | 37 |
| I-116 | 6 |
| I-117 | 6 |
| I-118 | 28 |
| I-119 | 981 |
| I-120 | 45 |
| I-121 | 11 |
| I-122 | 40 |
| I-123 | 31 |
| I-124 | 125 |
| I-125 | 2 |
| I-126 | 34 |
| I-127 | 50 |
| I-128 | 19 |
| I-129 | 106 |
| I-130 | 4 |
| I-131 | 3 |
| I-132 | 912 |
| I-133 | 255 |
| I-134 | 137 |
| I-135 | 15 |
| I-136 | 9 |
| I-137 | 3 |
| I-138 | 96 |
| I-139 | 2 |
| I-140 | 14 |
| I-141 | 111 |
| I-142 | 9 |
| I-143 | 59 |
| I-144 | 678 |
| I-145 | 273 |
| I-146 | 499 |
| I-147 | 104 |
| I-148 | 101 |
| I-149 | 95 |
| I-150 | 14 |
| I-151 | 23 |
| I-152 | 86 |
| I-153 | 23 |
| I-154 | 49 |
| I-155 | 95 |
| I-156 | 23 |
| I-157 | 214 |
| I-158 | 38 |
| I-159 | 189 |
| I-160 | 3 |
| I-161 | 2 |
| I-162 | 2 |
| I-163 | 109 |

TABLE 4-continued

| Compound Number | MK2 $IC_{50}$ (nM) |
|---|---|
| I-164 | 1 |
| I-165 | 81 |
| I-166 | 181 |
| I-168 | 260 |
| I-169 | 39 |
| I-170 | 18 |
| I-171 | 13 |
| I-172 | 97 |
| I-173 | 35 |
| I-174 | 98 |
| I-175 | 10 |
| I-176 | 70 |
| I-177 | 140 |
| I-178 | 185 |
| I-179 | 11 |
| I-180 | 184 |
| I-181 | 39 |
| I-182 | 1000 |
| I-183 | 839 |
| I-184 | 175 |
| I-185 | 7 |
| I-186 | 26 |
| I-187 | 8 |
| I-188 | 25 |
| I-189 | 206 |
| I-190 | 402 |
| I-191 | 289 |
| I-192 | 257 |
| I-193 | 526 |
| I-194 | 5 |
| I-195 | 13 |
| I-196 | 5 |
| I-197 | 5 |
| I-198 | 106 |
| I-199 | 636 |
| I-200 | 1000 |
| I-201 | 73 |
| I-202 | 674 |
| I-203 | 9 |
| I-204 | 555 |
| I-205 | 97 |
| I-206 | 4 |
| I-207 | 26 |
| I-208 | 285 |
| I-209 | 15 |
| I-210 | 91 |
| I-211 | 275 |
| I-212 | 92 |
| I-213 | 103 |
| I-214 | 2 |
| I-215 | 21 |
| I-216 | 11 |
| I-217 | 78 |
| I-218 | 79 |
| I-219 | 142 |
| I-220 | 177 |
| I-221 | 212 |
| I-223 | 1000 |
| I-224 | 2 |
| I-225 | 19 |
| I-226 | 7 |
| I-227 | 418 |
| I-228 | 128 |
| I-229 | 123 |
| I-230 | 44 |
| I-231 | 28 |
| I-232 | 77 |
| I-234 | 18 |
| I-236 | 157 |
| I-237 | 10 |
| I-238 | 6 |
| I-239 | 161 |
| I-240 | 107 |
| I-241 | 1000 |
| I-243 | 10 |
| I-245 | 74 |
| I-246 | 16 |

TABLE 4-continued

| Compound Number | MK2 $IC_{50}$ (nM) |
|---|---|
| I-247 | 360 |
| I-248 | 303 |
| I-249 | 4 |
| I-250 | 580 |
| I-251 | 192 |
| I-252 | 5 |
| I-253 | 6 |
| I-254 | 27 |
| I-255 | 1 |
| I-256 | 20 |
| I-257 | 1000 |
| I-258 | 1000 |
| I-259 | 15 |
| I-260 | 16 |
| I-261 | 1000 |
| I-262 | 35 |
| I-263 | 47 |
| I-265 | 210 |
| I-267 | 1000 |
| I-272 | 68 |
| I-273 | 153 |
| I-274 | 752 |

EMBODIMENTS

Embodiment 1. A compound of formula I:

I

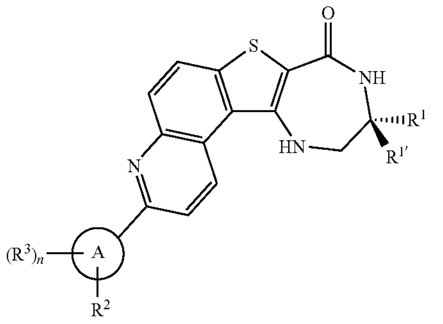

or a pharmaceutically acceptable salt thereof, wherein:

Ring A is a 5-6 membered heteroaryl ring having 1-3 heteroatoms independently selected from nitrogen, oxygen, and sulfur, provided that when Ring A is a 6-membered heteoaryl ring the heteroatom is nitrogen;

each $R^1$ and $R^{1'}$ is independently selected from hydrogen and $C_{1-4}$ aliphatic substituted with 0-3 instances of $R^x$, or:

$R^1$ and $R^{1'}$ may, together with the intervening atoms to which they are attached, form an optionally substituted 3- to 6-membered saturated, partially unsaturated heterocyclyl, carbocycle, or aryl ring having 0-3 heteroatoms independently selected from nitrogen, oxygen, and sulfur;

$R^x$ is —CN, —$NO_2$, halogen, —OR, —SR, —$N(R)_2$, —C(O)$N(R)_2$, —C(O)OR, —C(O)R, —N(R)C(O)R, —$SO_2N(R)_2$, or —N(R)$SO_2$;

$R^2$ is halogen, $C_2$-$C_6$ alkenyl, $C_2$-$C_6$ alkynyl, wherein the akynyl is optionally substituted with m instances of $R^y$;

each $R^y$ is independently selected from D, halogen, —CN, —$CO_2R$, —$N(R)_2$, and a 3- to 6-membered saturated or partially unsaturated heterocyclic ring having 1-3 heteroatoms independently selected from nitrogen, oxygen, and sulfur;

$R^3$ is optionally substituted $C_{1-6}$ aliphatic, —CN, halogen, —$(CH_2)_q$—$OR^4$, —$N(R)_2$, —C(O)OR, —$(CH_2)_r$-Cy, or —O—$(CH_2)_t$—$R^5$; or:

two $R^3$ groups, together with the intervening atoms to which they are attached, form an optionally substituted 5- to 6-membered saturated, partially unsaturated, or aryl ring having 0-3 heteroatoms independently selected from nitrogen, oxygen, and sulfur;

each $R^4$ is independently selected from hydrogen, optionally substituted $C_{1-6}$ aliphatic, and -Cy;

each $R^5$ is independently selected from —OR and -Cy;

each Cy is independently an optionally substituted ring selected from a 3- to 9-membered saturated or partially unsaturated monocyclic carbocyclic ring, a 3- to 9-membered saturated or partially unsaturated monocyclic heterocyclic ring having 1-3 heteroatoms independently selected from nitrogen, oxygen, and sulfur, phenyl, a 5- to 6-membered heteroaryl ring having 1-3 heteroatoms independently selected from nitrogen, oxygen, and sulfur, a 7- to 12-membered saturated or partially unsaturated fused, spirofused, or bridged bicyclic carbocyclic ring, or a 7- to 12-membered saturated or partially unsaturated fused, spirofused, or bridged bicyclic heterocyclic ring having 1-3 heteroatoms independently selected from nitrogen, oxygen, and sulfur;

each R is independently hydrogen or an optionally substituted $C_{1-6}$ aliphatic, or:

two R groups on the same nitrogen are taken together with the nitrogen to form a 3-7 membered saturated or partially unsaturated heterocyclic ring having 1-3 heteroatoms selected from nitrogen, oxygen, or sulfur;

each of m, n, q, and r is independently 0-4; and t is 1-4.

Embodiment 2. A compound of formula I:

I

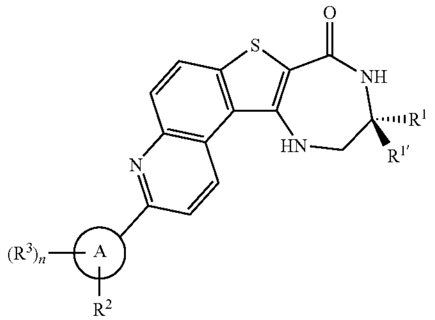

or a pharmaceutically acceptable salt thereof, wherein:

Ring A is a 5-6 membered heteroaryl ring having 1-3 heteroatoms independently selected from nitrogen, oxygen, and sulfur, provided that when Ring A is a 6-membered heteoaryl ring the 1-3 heteroatoms are each nitrogen;

each $R^1$ and $R^{1'}$ is independently selected from hydrogen and $C_{1-4}$ aliphatic substituted with 0-3 instances of $R^x$, or:

$R^1$ and $R^{1'}$ may, together with the intervening atoms to which they are attached, form an optionally substituted 3- to 6-membered saturated, or partially unsaturated, heterocyclyl, carbocycle, or aryl ring having 0-3 heteroatoms independently selected from nitrogen, oxygen, and sulfur;

$R^x$ is —CN, —$NO_2$, halogen, —OR, —SR, —$N(R)_2$, —$C(O)N(R)_2$, —C(O)OR, —C(O)R, —N(R)C(O)R, —$SO_2N(R)_2$, or —$N(R)SO_2$;

$R^2$ is halogen, —$(CH_2)_q$—CN, $C_2$-$C_6$ alkenyl, or $C_2$-$C_6$ alkynyl, wherein the alkenyl or akynyl is optionally substituted with m instances of $R^y$;

each $R^y$ is independently selected from D, halogen, —CN, —$CO_2R$, —$N(R)_2$, and a 3- to 6-membered saturated or partially unsaturated heterocyclic ring having 1-3 heteroatoms independently selected from nitrogen, oxygen, and sulfur;

each $R^3$ is independently selected from D, $C_{1-6}$ aliphatic, —CN, halogen, —$(CH_2)_q$—$OR^4$, —$N(R)_2$, —C(O)OR, —$(CH_2)_r$-Cy, or —O—$(CH_2)_t$—$R^5$, wherein the $C_{1-6}$ aliphatic is optionally substituted with one or more substituents each independently selected from D, halogen and —OR; or:

two $R^3$ groups, together with the intervening atoms to which they are attached, form an 5- to 6-membered saturated, partially unsaturated, heterocyclic, carbocyclic, or aryl ring having 0-3 heteroatoms independently selected from nitrogen, oxygen, and sulfur, wherein the heterocyclyl, carbocyclic, or aryl ring is optionally substituted with one or more substituents each independently selected from halogen, $C_{1-6}$ aliphatic, and —OR;

each $R^4$ is independently selected from hydrogen, $C_{1-6}$ aliphatic, and -Cy, wherein the $C_{1-6}$ aliphatic is optionally substituted with one or more substituents each independently selected from D, halogen and —OR;

each $R^5$ is independently selected from —OR and -Cy;

each Cy is independently a ring selected from a 3- to 9-membered saturated or partially unsaturated monocyclic carbocyclic ring, a 3- to 9-membered saturated or partially unsaturated monocyclic heterocyclic ring having 1-3 heteroatoms independently selected from nitrogen, oxygen, and sulfur, phenyl, a 5- to 6-membered heteroaryl ring having 1-3 heteroatoms independently selected from nitrogen, oxygen, and sulfur, a 7- to 12-membered saturated or partially unsaturated fused, spirofused, or bridged bicyclic carbocyclic ring, or a 7- to 12-membered saturated or partially unsaturated fused, spirofused, or bridged bicyclic heterocyclic ring having 1-3 heteroatoms independently selected from nitrogen, oxygen, and sulfur, wherein the ring is optionally substituted with one or more substituents each independently selected from D, halogen, oxo, R, and —$(CH_2)_q$—OR;

each R is independently hydrogen or a $C_{1-6}$ aliphatic optionally substituted with one or more substituents each selected from D, halogen, —OH, and —O—($C_{1-6}$ aliphatic), or:

two R groups on the same nitrogen are taken together with the nitrogen to form a 3-7 membered saturated or partially unsaturated heterocyclic ring having 1-3 heteroatoms selected from nitrogen, oxygen, or sulfur;

each of n, q, and r is independently 0-4; and t is 1-4.

Embodiment 3. The compound according to any one of the preceding embodiments, wherein Ring A is selected from:

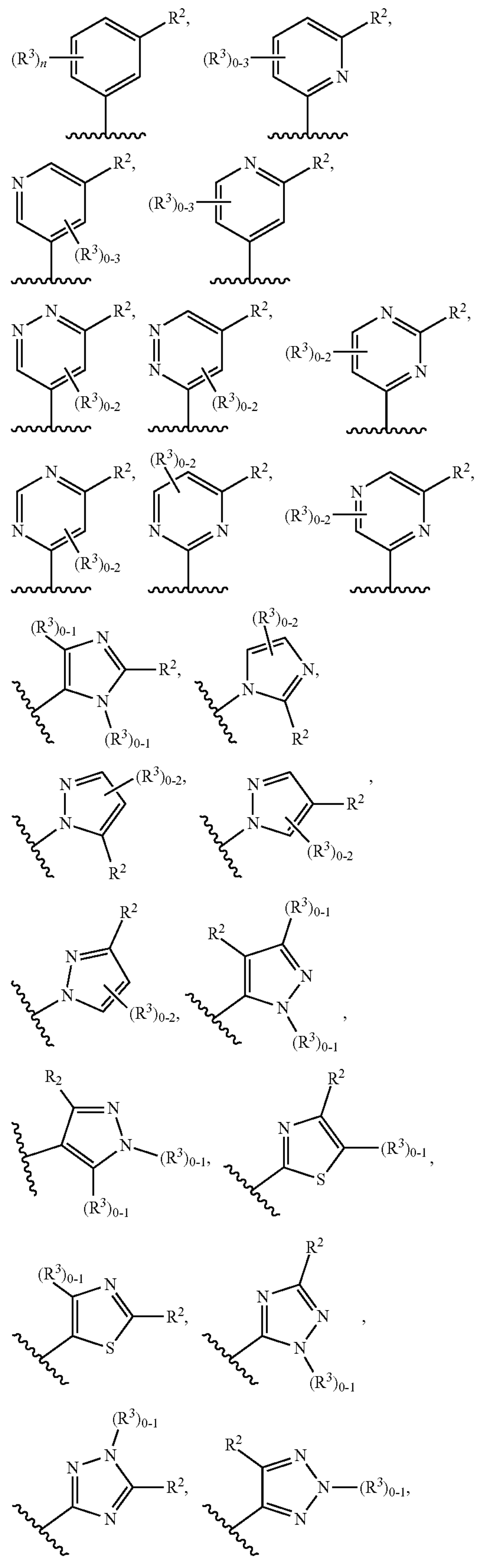

-continued

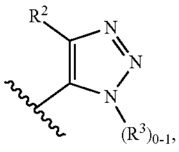

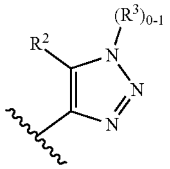

,

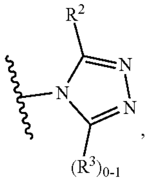

,

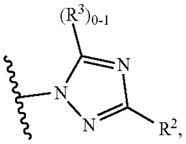

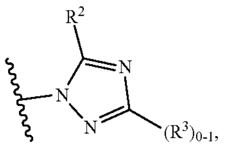

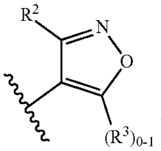

,

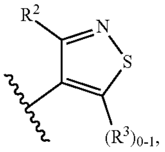

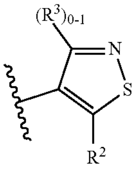

,

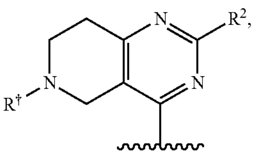

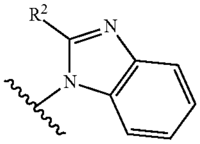

, and

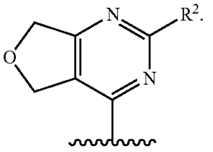

Embodiment 4. The compound according to any one of the preceding embodiments, wherein the compound is selected from any of formulae II, III, IV, or V:

II

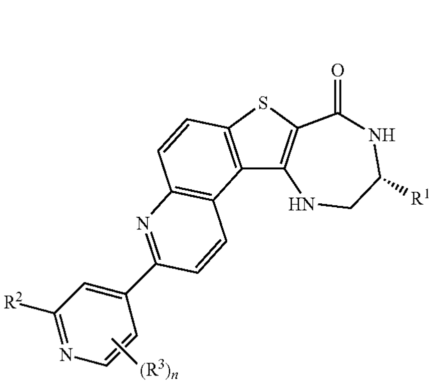

-continued

III

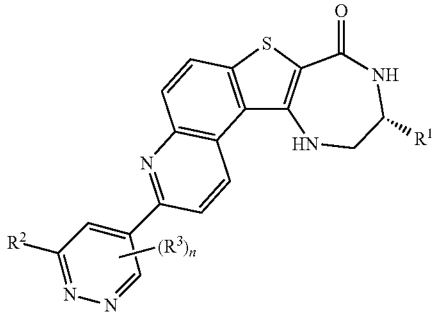

IV

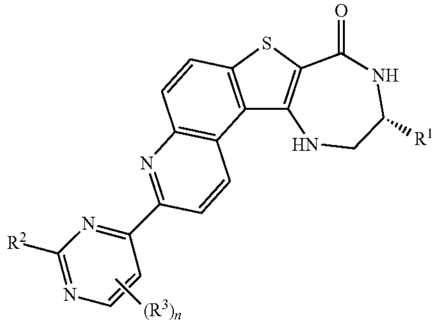

V

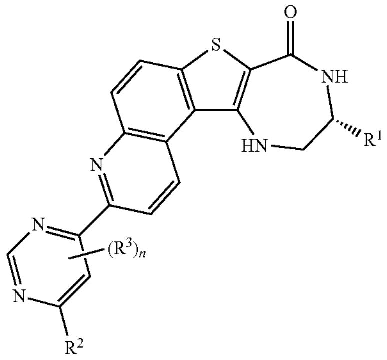

or a pharmaceutically acceptable salt thereof.

Embodiment 5. The compound according to any one of the preceding embodiments, wherein $R^2$ is halogen.

Embodiment 6. The compound according to any one of the preceding embodiments, wherein $R^2$ is —CN.

Embodiment 7. The compound according to any one of the preceding embodiments, wherein $R^2$ is $C_{2-6}$ aliphatic substituted with m instances of $R^y$, wherein the $C_{2-6}$ aliphatic has at least one unit of unsaturation.

Embodiment 8. The compound according to any one of the preceding embodiments, wherein m is 0.

Embodiment 9. The compound according to any one of the preceding embodiments, wherein $R^2$ is selected from:

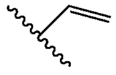

,

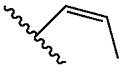

,

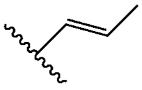

,

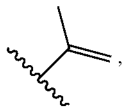

,

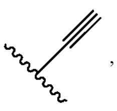

, and

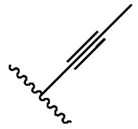

.

Embodiment 10. The compound according to any one of the preceding embodiments, wherein m is 1.

Embodiment 11. The compound according to any one of the preceding embodiments, wherein $R^y$ is halogen.

Embodiment 12. The compound according to any one of the preceding embodiments, wherein $R^y$ is —CN.

Embodiment 13. The compound according to any one of the preceding embodiments, wherein $R^y$ is $—CO_2R$.

Embodiment 14. The compound according to any one of the preceding embodiments, wherein $R^y$ is $—N(R)_2$.

Embodiment 15. The compound according to any one of the preceding embodiments, wherein $R^y$ is a 3- to 6-membered heterocyclic ring having 1-3 heteroatoms independently selected from nitrogen, oxygen, and sulfur.

Embodiment 16. The compound according to any one of the preceding embodiments, wherein $R^y$ is a 5-membered heterocyclic ring having 1 heteroatom selected from nitrogen, oxygen, and sulfur.

Embodiment 17. The compound according to any one of the preceding embodiments, wherein $R^y$ is a 6-membered heterocyclic ring having 1-2 heteroatoms independently selected from nitrogen, oxygen, and sulfur.

Embodiment 18. The compound according to any one of the preceding embodiments, wherein $R^2$ is selected from:

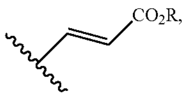

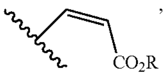

,

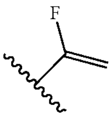

,

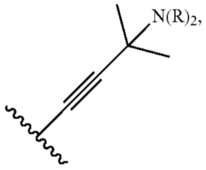

,

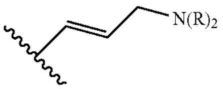

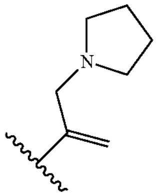

,

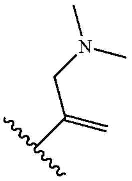

, and

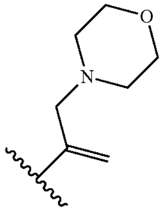

.

Embodiment 19. The compound according to any one of the preceding embodiments, wherein m is 3.

Embodiment 20. The compound according to any one of the preceding embodiments, wherein $R^y$ is halogen.

Embodiment 21. The compound according to any one of the preceding embodiments, wherein $R^y$ is D.

Embodiment 22. The compound according to any one of the preceding embodiments, wherein $R^2$ is selected from

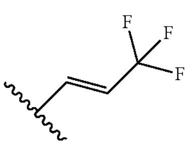

and

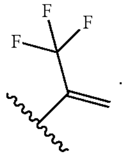

.

Embodiment 23. The compound according to any one of the preceding embodiments, wherein the compound is selected from formulae II-a, II-b, II-c, III-a, III-b, IV-a, IV-b, IV-c, V-a, V-b, or V-c:

II-a

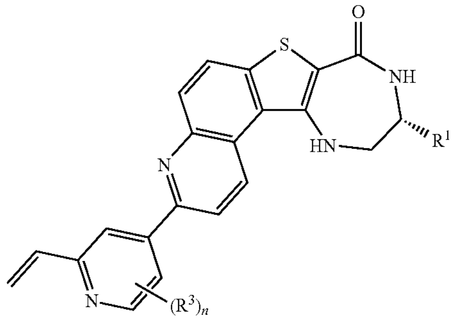

II-b

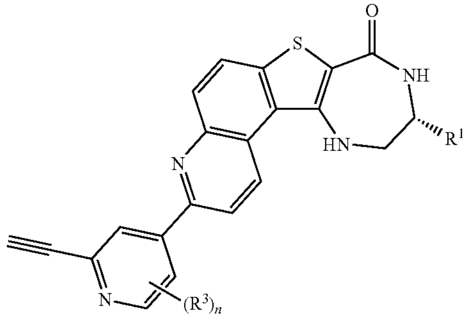

II-c

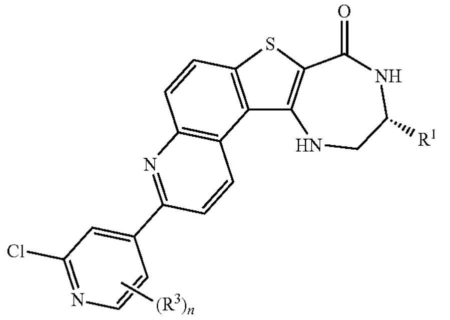

III-a

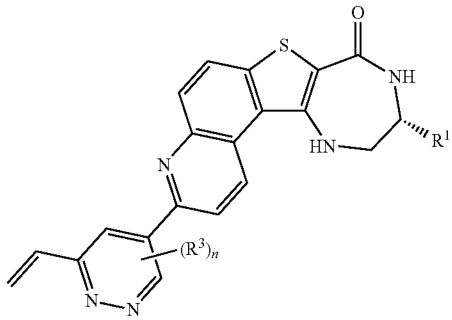

-continued
III-b
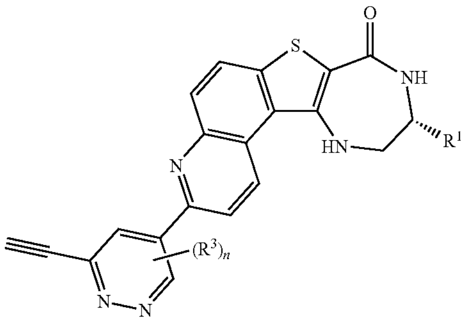
IV-a
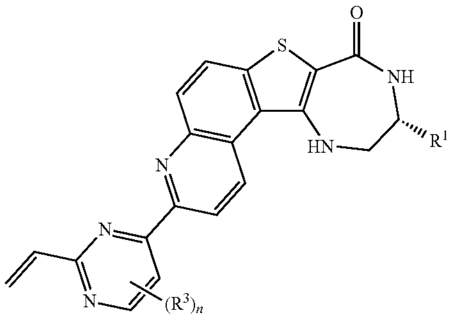
IV-b
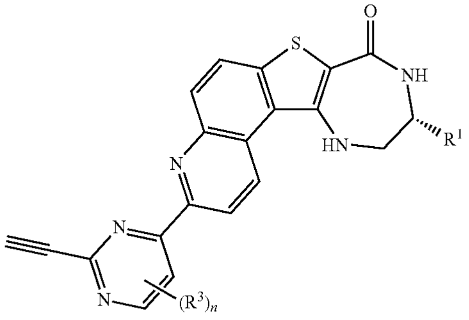
IV-c
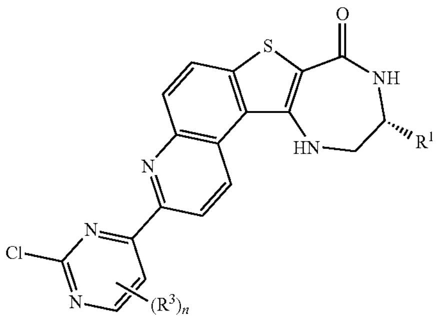
-continued
V-a
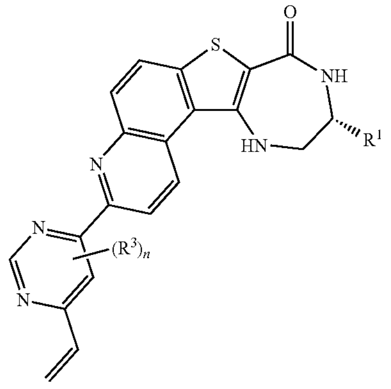
V-b
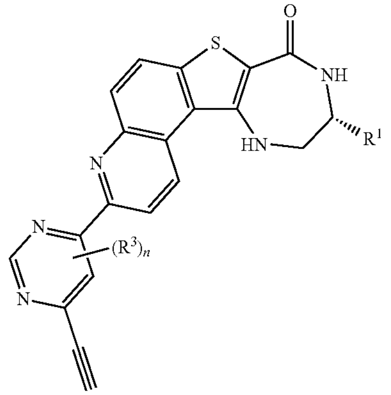
V-c
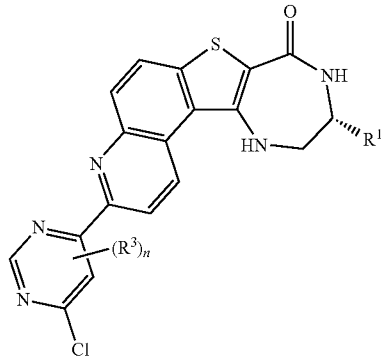
or a pharmaceutically acceptable salt thereof.
Embodiment 24. The compound according to any one of the preceding embodiments, wherein the compound is selected from formulae II-a-i, II-a-ii, II-b-i, II-b-ii, II-c-i, II-c-ii, III-a-i, III-b-i, IV-a-i, IV-a-ii, IV-b-i, IV-b-ii, IV-c-i, IV-c-ii, V-a-i, V-b-i, or V-c-i:

II-a-i
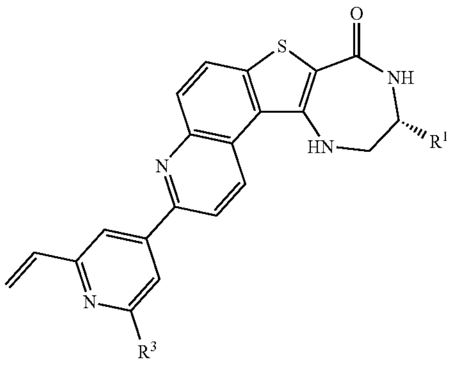
II-a-ii
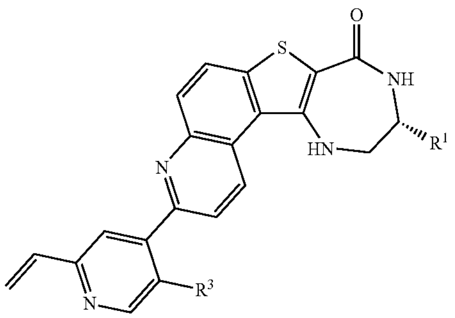
II-b-i
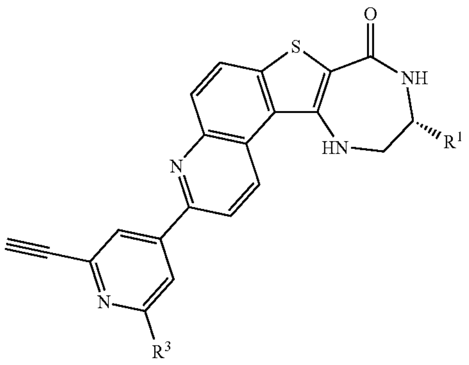
II-b-ii
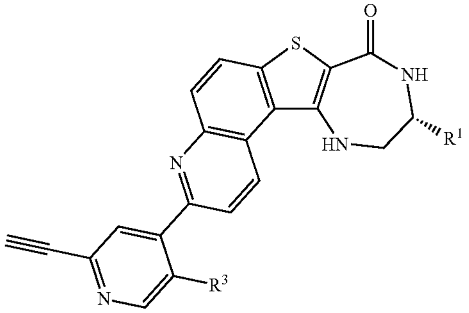
-continued
II-c-i
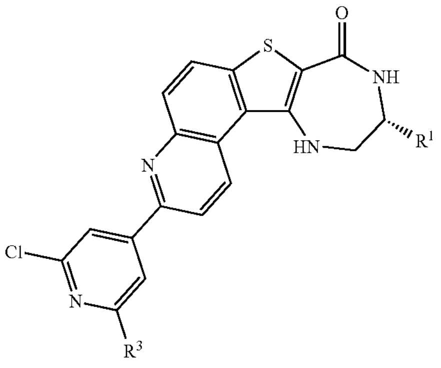
II-c-ii
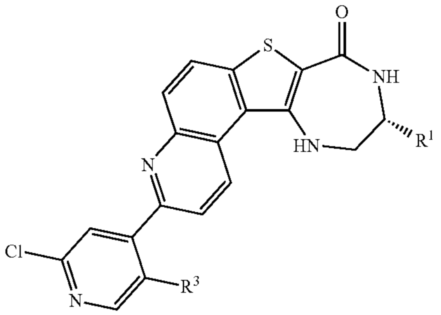
III-a-i
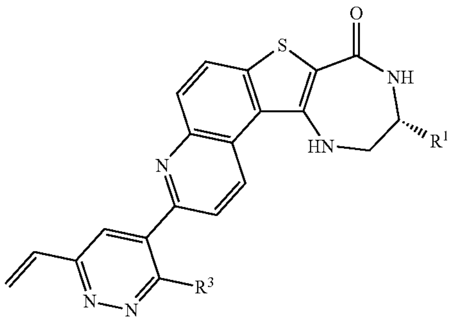
III-b-i
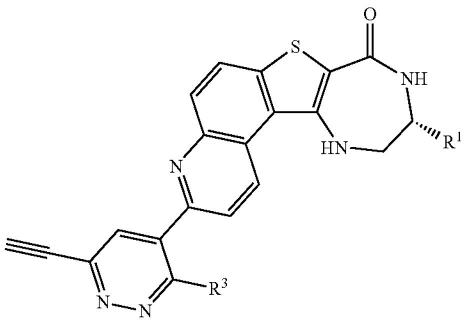

-continued
IV-a-i
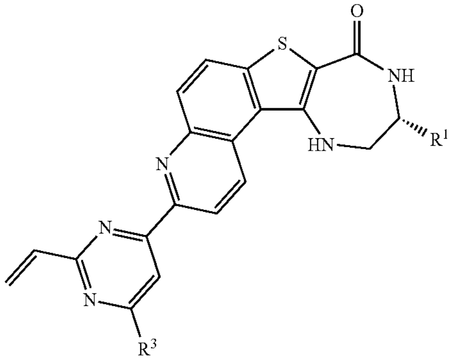
IV-a-ii
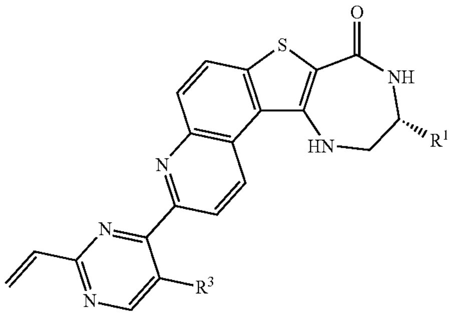
IV-b-i
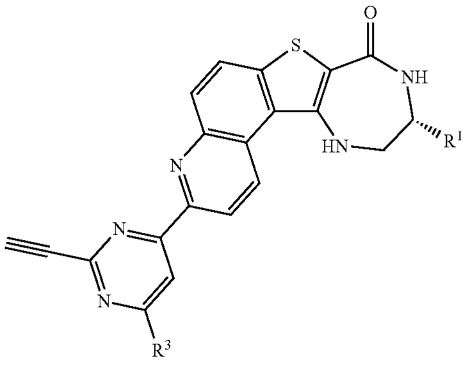
IV-b-ii
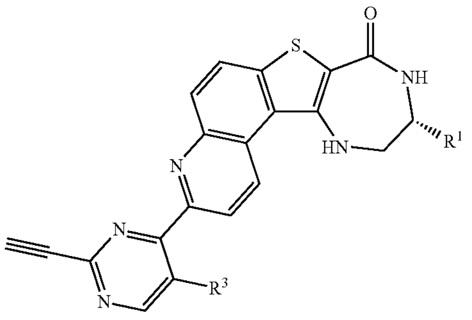
-continued
IV-c-i
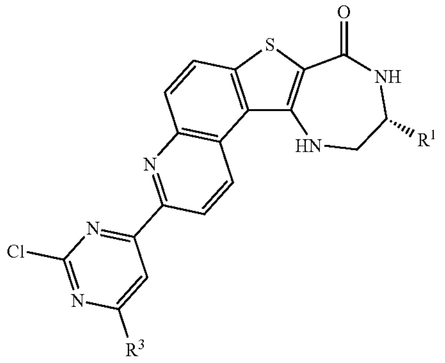
IV-c-ii
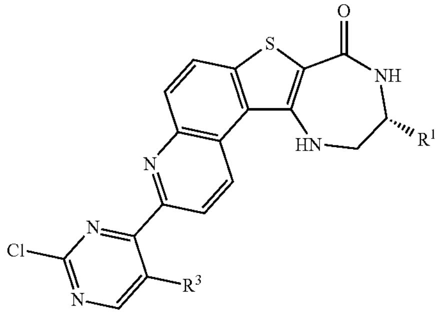
V-a-i
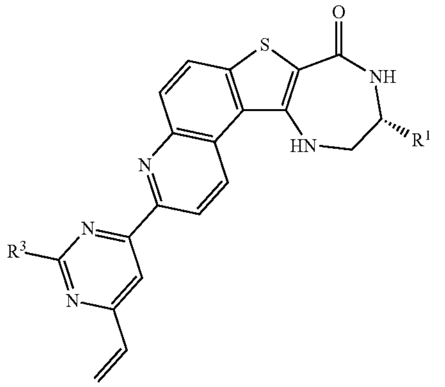
V-b-i
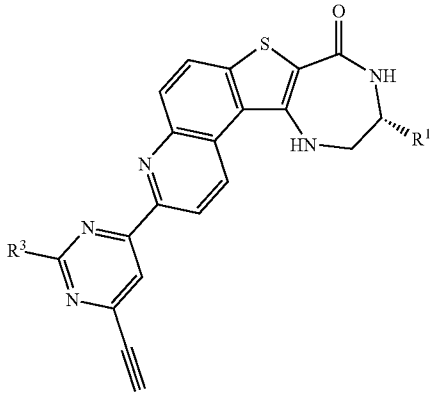

-continued

V-c-i

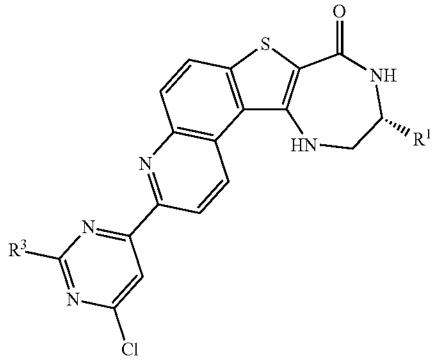

or a pharmaceutically acceptable salt thereof.

Embodiment 25. The compound according to any one of the preceding embodiments, wherein $R^1$ is $—CH_3$.

Embodiment 26. The compound according to any one of the preceding embodiments, wherein $R^1$ is $—CH_2F$ or $—CH_2OH$.

Embodiment 27. The compound according to any one of the preceding embodiments, wherein $R^3$ is —CN.

Embodiment 28. The compound according to any one of the preceding embodiments, wherein $R^3$ is $—N(R)_2$.

Embodiment 29. The compound according to any one of the preceding embodiments, wherein $R^3$ is —C(O)OR.

Embodiment 30. The compound according to any one of the preceding embodiments, wherein $R^3$ is halogen.

Embodiment 31. The compound according to any one of the preceding embodiments, wherein $R^3$ is optionally substituted $C_{1-6}$ aliphatic.

Embodiment 32. The compound according to any one of the preceding embodiments, wherein $R^3$ is $C_{1-6}$ aliphatic optionally substituted with halogen, $—N(R^\circ)_2$, and $—OR^\circ$.

Embodiment 33. The compound according to any one of the preceding embodiments, wherein $R^\circ$ is hydrogen.

Embodiment 34. The compound according to any one of the preceding embodiments, wherein $R^3$ is selected from $—CH_3$, $—CD_3$, $—CF_2H$, $—CF_3$, $—CH_2CH_3$,

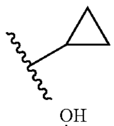
,
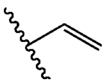
,
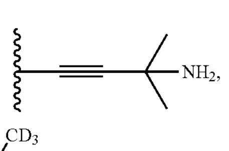

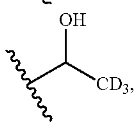
and
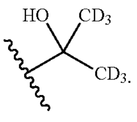

Embodiment 35. The compound according to any one of the preceding embodiments, wherein $R^3$ is $—(CH_2)_q—OR^4$.

Embodiment 36. The compound according to any one of the preceding embodiments, wherein q is 0.

Embodiment 37. The compound according to any one of the preceding embodiments, wherein q is 1.

Embodiment 38. The compound according to any one of the preceding embodiments, wherein $R^4$ is hydrogen.

Embodiment 39. The compound according to any one of the preceding embodiments, wherein $R^4$ is optionally substituted $C_{1-6}$ aliphatic.

Embodiment 40. The compound according to any one of the preceding embodiments, wherein $R^4$ is -Cy.

Embodiment 41. The compound according to any one of the preceding embodiments, wherein $R^3$ is selected from $—OCH_3$, $—OCF_2H$, $—OCF_3$, $—O(CH_2)_2CH_3$, $—O(CH_2)_2OCH_2CH_3$, $—CH_2OH$, $—CH_2OCH_3$, $—CH_2OCH_2CH_3$,

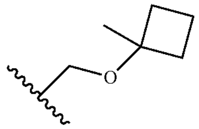
,
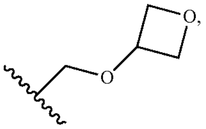

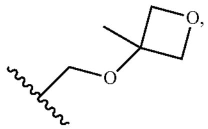

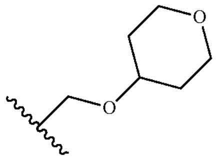
,
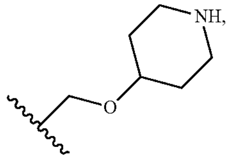
and

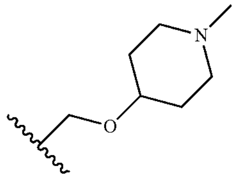
.

Embodiment 42. The compound according to any one of the preceding embodiments, wherein $R^3$ is $—(CH_2)_r$-Cy.

Embodiment 43. The compound according to any one of the preceding embodiments, wherein r is 0.

Embodiment 44. The compound according to any one of the preceding embodiments, wherein r is 1.

Embodiment 45. The compound according to any one of the preceding embodiments, wherein $R^3$ is selected from

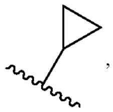
,
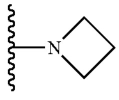
,
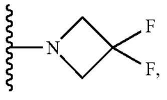

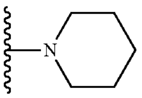
,
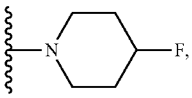

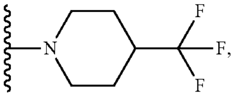

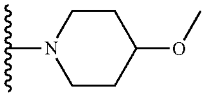
,

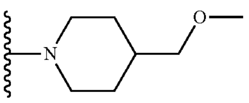

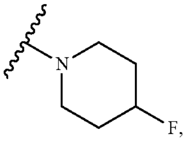
,

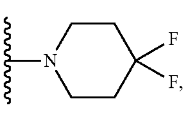

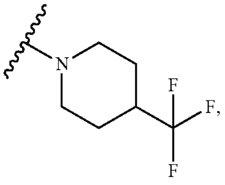

-continued

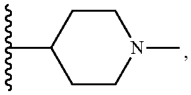,
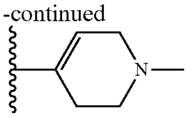,
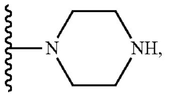,
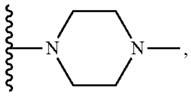,
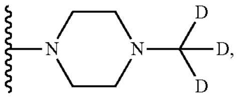,
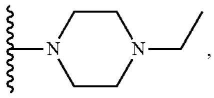,
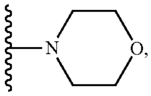,
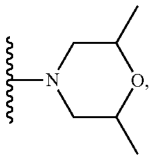,
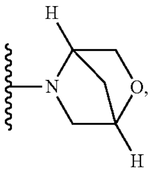,
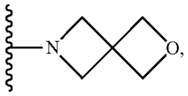,
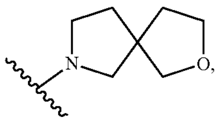,
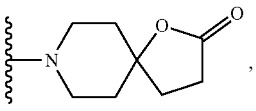,
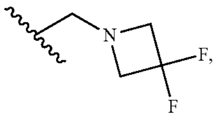,
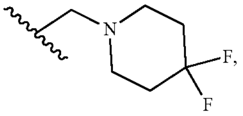,
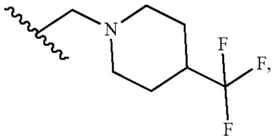,
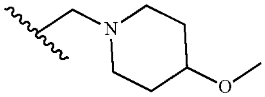,
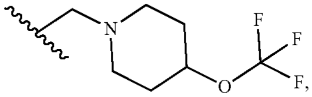,
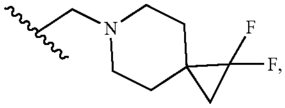,
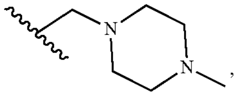,
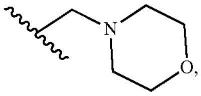,
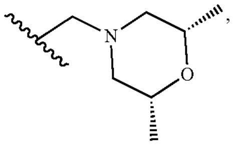,
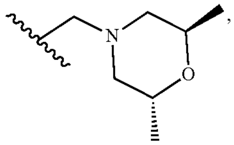, and
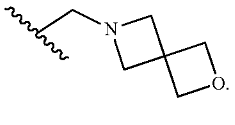.

Embodiment 46. The compound according to any one of the preceding embodiments, wherein $R^3$ is —O—$(CH_2)_t$—$R^5$.

Embodiment 47. The compound according to any one of the preceding embodiments, wherein t is 1.

Embodiment 48. The compound according to any one of the preceding embodiments, wherein t is 2.

Embodiment 49. The compound according to any one of the preceding embodiments, wherein $R^5$ is -Cy.

Embodiment 50. The compound according to any one of the preceding embodiments, wherein $R^5$ is —OR.

Embodiment 51. The compound according to any one of the preceding embodiments, wherein $R^3$ is selected from

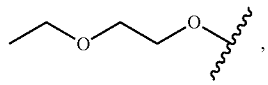,
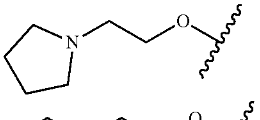 and
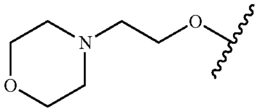.

Embodiment 52. The compound according to any one of the preceding embodiments, selected from the group consisting of:

(R)-3-(2-ethynyl-5-fluoropyrimidin-4-yl)-10-methyl-9,10,11,12-tetrahydro-8H-[1,4]diazepino[5',6':4,5]thieno[3,2-f]quinolin-8-one (I-1)

(R)-3-(5-fluoro-2-vinylpyrimidin-4-yl)-10-methyl-9,10,11,12-tetrahydro-8H-[1,4]diazepino[5',6':4,5]thieno[3,2-f]quinolin-8-one (I-2)

(R)-3-(2-chloro-5-(ethoxymethyl)pyrimidin-4-yl)-10-methyl-9,10,11,12-tetrahydro-8H-[1,4]diazepino[5',6':4,5]thieno[3,2-f]quinolin-8-one (I-3)

(R)-3-(2-chloro-5-(trifluoromethyl)pyrimidin-4-yl)-10-methyl-9,10,11,12-tetrahydro-8H-[1,4]diazepino[5',6':4,5]thieno[3,2-f]quinolin-8-one (I-4)

(R)-3-(5-(ethoxymethyl)-2-vinylpyrimidin-4-yl)-10-methyl-9,10,11,12-tetrahydro-8H-[1,4]diazepino[5',6':4,5]thieno[3,2-f]quinolin-8-one (I-5)

(R)-3-(2-chloro-5-methylpyrimidin-4-yl)-10-methyl-9,10,11,12-tetrahydro-8H-[1,4]diazepino[5',6':4,5]thieno[3,2-f]quinolin-8-one (I-6)

(R)-3-(6-chloro-2-(methoxymethyl)pyrimidin-4-yl)-10-methyl-9,10,11,12-tetrahydro-8H-[1,4]diazepino[5',6':4,5]thieno[3,2-f]quinolin-8-one (I-7)

(R)-3-(2-chloropyrimidin-4-yl)-10-methyl-9,10,11,12-tetrahydro-8H-[1,4]diazepino[5',6':4,5]thieno[3,2-f]quinolin-8-one (I-8)

(R)-2-chloro-4-(10-methyl-8-oxo-9,10,11,12-tetrahydro-8H-[1,4]diazepino[5',6':4,5]thieno[3,2-f]quinolin-3-yl)pyrimidine-5-carbonitrile (I-9)

(R)-3-(2-chloro-5-methoxypyrimidin-4-yl)-10-methyl-9,10,11,12-tetrahydro-8H-[1,4]diazepino[5',6':4,5]thieno[3,2-f]quinolin-8-one (I-10)

(R)-3-(6-chloropyrimidin-4-yl)-10-methyl-9,10,11,12-tetrahydro-8H-[1,4]diazepino[5',6':4,5]thieno[3,2-f]quinolin-8-one (I-11)

(R)-3-(5-(ethoxymethyl)-2-ethynylpyrimidin-4-yl)-10-methyl-9,10,11,12-tetrahydro-8H-[1,4]diazepino[5',6':4,5]thieno[3,2-f]quinolin-8-one (I-12)

(R)-3-(2-(methoxymethyl)-6-vinylpyrimidin-4-yl)-10-methyl-9,10,11,12-tetrahydro-8H-[1,4]diazepino[5',6':4,5]thieno[3,2-f]quinolin-8-one (I-13)

(R)-3-(6-chloro-2-((piperidin-4-yloxy)methyl)pyrimidin-4-yl)-10-methyl-9,10,11,12-tetrahydro-8H-[1,4]diazepino[5',6':4,5]thieno[3,2-f]quinolin-8-one (I-14)

(R)-3-(6-chloro-2-(((1-methylpiperidin-4-yl)oxy)methyl)pyrimidin-4-yl)-10-methyl-9,10,11,12-tetrahydro-8H-[1,4]diazepino[5',6':4,5]thieno[3,2-f]quinolin-8-one (I-15)

(R)-3-(2-chloro-6-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-16)

(R)-3-(6-chloro-2-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-17)

(R)-10-methyl-3-(6-(4-methylpiperazin-1-yl)-2-vinylpyrimidin-4-yl)-9,10,11,12-tetrahydro-8H-[1,4]diazepino[5',6':4,5]thieno[3,2-f]quinolin-8-one (I-18)

(R)-10-methyl-3-(2-(4-methylpiperazin-1-yl)-6-vinylpyrimidin-4-yl)-9,10,11,12-tetrahydro-8H-[1,4]diazepino[5',6':4,5]thieno[3,2-f]quinolin-8-one (I-19)

(R)-3-(2-chloro-5-((oxetan-3-yloxy)methyl)pyrimidin-4-yl)-10-methyl-9,10,11,12-tetrahydro-8H-[1,4]diazepino[5',6':4,5]thieno[3,2-f]quinolin-8-one (I-20)

(R)-10-methyl-3-(5-((oxetan-3-yloxy)methyl)-2-vinylpyrimidin-4-yl)-9,10,11,12-tetrahydro-8H-[1,4]diazepino[5',6':4,5]thieno[3,2-f]quinolin-8-one (I-21)

(R)-3-(2-(ethoxymethyl)-6-vinylpyrimidin-4-yl)-10-methyl-9,10,11,12-tetrahydro-8H-[1,4]diazepino[5',6':4,5]thieno[3,2-f]quinolin-8-one (I-22)

(R)-3-(6-chloro-2-(((tetrahydro-2H-pyran-4-yl)oxy)methyl)pyrimidin-4-yl)-10-methyl-9,10,11,12-tetrahydro-8H-[1,4]diazepino[5',6':4,5]thieno[3,2-f]quinolin-8-one (I-23)

(R)-3-(2-chloro-5-(((tetrahydro-2H-pyran-4-yl)oxy)methyl)pyrimidin-4-yl)-10-methyl-9,10,11,12-tetrahydro-8H-[1,4]diazepino[5',6':4,5]thieno[3,2-f]quinolin-8-one (I-24)

(R)-10-methyl-3-(5-(((tetrahydro-2H-pyran-4-yl)oxy)methyl)-2-vinylpyrimidin-4-yl)-9,10,11,12-tetrahydro-8H-[1,4]diazepino[5',6':4,5]thieno[3,2-f]quinolin-8-one (I-25)

(R)-10-methyl-3-(5-((1-methylcyclobutoxy)methyl)-2-vinylpyrimidin-4-yl)-9,10,11,12-tetrahydro-8H-[1,4]diazepino[5',6':4,5]thieno[3,2-f]quinolin-8-one (I-26)

(R)-3-(2-chloro-5-((1-methylcyclobutoxy)methyl)pyrimidin-4-yl)-10-methyl-9,10,11,12-tetrahydro-8H-[1,4]diazepino[5',6':4,5]thieno[3,2-f]quinolin-8-one (I-27)

(R)-3-(2-chloro-5-(((3-methyloxetan-3-yl)oxy)methyl)pyrimidin-4-yl)-10-methyl-9,10,11,12-tetrahydro-8H-[1,4]diazepino[5',6':4,5]thieno[3,2-f]quinolin-8-one (I-28)

(R)-10-methyl-3-(5-(((3-methyloxetan-3-yl)oxy)methyl)-2-vinylpyrimidin-4-yl)-9,10,11,12-tetrahydro-8H-[1,4]diazepino[5',6':4,5]thieno[3,2-f]quinolin-8-one (I-29)

(R)-3-(6-chloro-2-(ethoxymethyl)pyrimidin-4-yl)-10-methyl-9,10,11,12-tetrahydro-8H-[1,4]diazepino[5',6':4,5]thieno[3,2-f]quinolin-8-one (I-30)

(R)-3-(5-fluoro-2-(1-fluorovinyl)pyrimidin-4-yl)-10-methyl-9,10,11,12-tetrahydro-8H-[1,4]diazepino[5',6':4,5]thieno[3,2-f]quinolin-8-one (I-31)

(R)-3-(5-methoxy-2-vinylpyrimidin-4-yl)-10-methyl-9,10,11,12-tetrahydro-8H-[1,4]diazepino[5',6':4,5]thieno[3,2-f]quinolin-8-one (I-32)

(R)-10-methyl-3-(5-methyl-2-vinylpyrimidin-4-yl)-9,10,11,12-tetrahydro-8H-[1,4]diazepino[5',6':4,5]thieno[3,2-f]quinolin-8-one (I-33)

(R)-10-methyl-3-(6-vinylpyrimidin-4-yl)-9,10,11,12-tetrahydro-8H-[1,4]diazepino[5',6':4,5]thieno[3,2-f]quinolin-8-one (I34)

(R,E)-3-(2-(ethoxymethyl)-6-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-35)

(R,Z)-3-(2-(ethoxymethyl)-6-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-36)

(R)-3-(2-(ethoxymethyl)-6-(prop-1-en-2-yl)pyrimidin-4-yl)-10-methyl-9,10,11,12-tetrahydro-8H-[1,4]diazepino[5',6':4,5]thieno[3,2-f]quinolin-8-one (I-37)

(R)-3-(6-ethynylpyrimidin-4-yl)-10-methyl-9,10,11,12-tetrahydro-8H-[1,4]diazepino[5',6':4,5]thieno[3,2-f]quinolin-8-one (I-38)

(R)-3-(2-(ethoxymethyl)-6-ethynylpyrimidin-4-yl)-10-methyl-9,10,11,12-tetrahydro-8H-[1,4]diazepino[5',6':4,5]thieno[3,2-f]quinolin-8-one (I-39)

(R)-3-(2-ethynylpyrimidin-4-yl)-10-methyl-9,10,11,12-tetrahydro-8H-[1,4]diazepino[5',6':4,5]thieno[3,2-f]quinolin-8-one (I-40)

(R)-3-(2-ethynyl-5-methylpyrimidin-4-yl)-10-methyl-9,10,11,12-tetrahydro-8H-[1,4]diazepino[5',6':4,5]thieno[3,2-f]quinolin-8-one (I-41)

(R)-3-(2-ethynyl-5-methoxypyrimidin-4-yl)-10-methyl-9,10,11,12-tetrahydro-8H-[1,4]diazepino[5',6':4,5]thieno[3,2-f]quinolin-8-one (I-42)

(R)-3-(4-chloro-6-(4-methylpiperazin-1-yl)pyrimidin-2-yl)-10-methyl-9,10,11,12-tetrahydro-8H-[1,4]diazepino[5',6':4,5]thieno[3,2-f]quinolin-8-one (I-43)

(R)-3-(5-fluoro-2-(prop-1-yn-1-yl)pyrimidin-4-yl)-10-methyl-9,10,11,12-tetrahydro-8H-[1,4]diazepino[5',6':4,5]thieno[3,2-f]quinolin-8-one (I-44)

(R,E)-3-(5-fluoro-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-45)

(R,Z)-3-(5-fluoro-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-46)

(R)-3-(5-fluoro-2-(prop-1-en-2-yl)pyrimidin-4-yl)-10-methyl-9,10,11,12-tetrahydro-8H-[1,4]diazepino[5',6':4,5]thieno[3,2-f]quinolin-8-one (I-47)

(R,E)-3-(5-(ethoxymethyl)-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-48)

(R,Z)-3-(5-(ethoxymethyl)-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-49)

(R)-3-(5-(ethoxymethyl)-2-(prop-1-en-2-yl)pyrimidin-4-yl)-10-methyl-9,10,11,12-tetrahydro-8H-[1,4]diazepino[5',6':4,5]thieno[3,2-f]quinolin-8-one (I-50)

(R)-3-(6-ethynylpyridazin-4-yl)-10-methyl-9,10,11,12-tetrahydro-8H-[1,4]diazepino[5',6':4,5]thieno[3,2-f]quinolin-8-one (I-51)

(R)-3-(6-chloropyridin-2-yl)-10-methyl-9,10,11,12-tetrahydro-8H-[1,4]diazepino[5',6':4,5]thieno[3,2-f]quinolin-8-one (I-52)

(R)-10-methyl-3-(2-(prop-1-yn-1-yl)pyrimidin-4-yl)-9,10,11,12-tetrahydro-8H-[1,4]diazepino[5',6':4,5]thieno[3,2-f]quinolin-8-one (I-53)

(R)-10-methyl-3-(6-vinylpyridin-2-yl)-9,10,11,12-tetrahydro-8H-[1,4]diazepino[5',6':4,5]thieno[3,2-f]quinolin-8-one (I-54)

(R)-10-methyl-3-(2-vinylpyridin-4-yl)-9,10,11,12-tetrahydro-8H-[1,4]diazepino[5',6':4,5]thieno[3,2-f]quinolin-8-one (I-55)

(R)-3-(6-ethynylpyridin-2-yl)-10-methyl-9,10,11,12-tetrahydro-8H-[1,4]diazepino[5',6':4,5]thieno[3,2-f]quinolin-8-one (I56)

(R)-3-(2-ethynylpyridin-4-yl)-10-methyl-9,10,11,12-tetrahydro-8H-[1,4]diazepino[5',6':4,5]thieno[3,2-f]quinolin-8-one (I-57)

(R)-3-(2,6-dichloropyrimidin-4-yl)-10-methyl-9,10,11,12-tetrahydro-8H-[1,4]diazepino[5',6':4,5]thieno[3,2-f]quinolin-8-one (I-58)

(R)-3-(6-ethynyl-2-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-59)

(R)-3-(2-ethynyl-6-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-60)

(R)-3-(4-ethynyl-6-(4-methylpiperazin-1-yl)pyrimidin-2-yl)-10-methyl-9,10,11,12-tetrahydro-8H-[1,4]diazepino[5',6':4,5]thieno[3,2-f]quinolin-8-one (I-61)

(R)-10-methyl-3-(4-(4-methylpiperazin-1-yl)-6-vinylpyrimidin-2-yl)-9,10,11,12-tetrahydro-8H-[1,4]diazepino[5',6':4,5]thieno[3,2-f]quinolin-8-one (I-62)

(R)-3-(6-(3-amino-3-methylbut-1-yn-1-yl)-2-chloropyrimidin-4-yl)-10-methyl-9,10,11,12-tetrahydro-8H-[1,4]diazepino[5',6':4,5]thieno[3,2-f]quinolin-8-one (I-63)

(R)-3-(2-(3-amino-3-methylbut-1-yn-1-yl)-6-chloropyrimidin-4-yl)-10-methyl-9,10,11,12-tetrahydro-8H-[1,4]diazepino[5',6':4,5]thieno[3,2-f]quinolin-8-one (I-64)

(R)-3-(6-(3-amino-3-methylbut-1-yn-1-yl)-2-ethynylpyrimidin-4-yl)-10-methyl-9,10,11,12-tetrahydro-8H-[1,4]diazepino[5',6':4,5]thieno[3,2-f]quinolin-8-one (I-65)

(R)-3-(2-(3-amino-3-methylbut-1-yn-1-yl)-6-vinylpyrimidin-4-yl)-10-methyl-9,10,11,12-tetrahydro-8H-[1,4]diazepino[5',6':4,5]thieno[3,2-f]quinolin-8-one (I-66)

(R)-3-(2-(3-amino-3-methylbut-1-yn-1-yl)-6-ethynylpyrimidin-4-yl)-10-methyl-9,10,11,12-tetrahydro-8H-[1,4]diazepino[5',6':4,5]thieno[3,2-f]quinolin-8-one (I-67)

(R)-3-(2,6-dichloropyridin-4-yl)-10-methyl-9,10,11,12-tetrahydro-8H-[1,4]diazepino[5',6':4,5]thieno[3,2-f]quinolin-8-one (I-68)

(R)-3-(2-chloro-5-fluoropyridin-4-yl)-10-methyl-9,10,11,12-tetrahydro-8H-[1,4]diazepino[5',6':4,5]thieno[3,2-f]quinolin-8-one (I-69)

(R)-3-(5-fluoro-2-vinylpyridin-4-yl)-10-methyl-9,10,11,12-tetrahydro-8H-[1,4]diazepino[5',6':4,5]thieno[3,2-f]quinolin-8-one (I-70)

(R)-3-(2-ethynyl-5-fluoropyridin-4-yl)-10-methyl-9,10,11,12-tetrahydro-8H-[1,4]diazepino[5',6':4,5]thieno[3,2-f]quinolin-8-one (I-71)

(R)-3-(2-chloro-6-vinylpyridin-4-yl)-10-methyl-9,10,11,12-tetrahydro-8H-[1,4]diazepino[5',6':4,5]thieno[3,2-f]quinolin-8-one (I-72)

(R)-3-(2-chloro-6-ethynylpyridin-4-yl)-10-methyl-9,10,11,12-tetrahydro-8H-[1,4]diazepino[5',6':4,5]thieno[3,2-f]quinolin-8-one (I-73)

(R)-3-(6-chloro-2-(hydroxymethyl)pyrimidin-4-yl)-10-methyl-9,10,11,12-tetrahydro-8H-[1,4]diazepino[5',6':4,5]thieno[3,2-f]quinolin-8-one (I-74)

(R)-3-(2-chloro-5-(hydroxymethyl)pyrimidin-4-yl)-10-methyl-9,10,11,12-tetrahydro-8H-[1,4]diazepino[5',6':4,5]thieno[3,2-f]quinolin-8-one (I-75)

(R)-3-(2-(hydroxymethyl)-6-vinylpyrimidin-4-yl)-10-methyl-9,10,11,12-tetrahydro-8H-[1,4]diazepino[5',6':4,5]thieno[3,2-f]quinolin-8-one (I-76)

(R)-3-(5-(hydroxymethyl)-2-vinylpyrimidin-4-yl)-10-methyl-9,10,11,12-tetrahydro-8H-[1,4]diazepino[5',6':4,5]thieno[3,2-f]quinolin-8-one (I-77)

(R)-3-(6-ethynyl-2-(hydroxymethyl)pyrimidin-4-yl)-10-methyl-9,10,11,12-tetrahydro-8H-[1,4]diazepino[5',6':4,5]thieno[3,2-f]quinolin-8-one (I-78)

(R)-3-(2-ethynyl-5-(hydroxymethyl)pyrimidin-4-yl)-10-methyl-9,10,11,12-tetrahydro-8H-[1,4]diazepino[5',6':4,5]thieno[3,2-f]quinolin-8-one (I-79)

(R)-3-(2,6-divinylpyridin-4-yl)-10-methyl-9,10,11,12-tetrahydro-8H-[1,4]diazepino[5',6':4,5]thieno[3,2-f]quinolin-8-one (I-80)

(R)-3-(5-chloropyridin-3-yl)-10-methyl-9,10,11,12-tetrahydro-8H-[1,4]diazepino[5',6':4,5]thieno[3,2-f]quinolin-8-one (I-81)

(R)-10-methyl-3-(5-vinylpyridin-3-yl)-9,10,11,12-tetrahydro-8H-[1,4]diazepino[5',6':4,5]thieno[3,2-f]quinolin-8-one (I-82)

(R)-3-(5-ethynylpyridin-3-yl)-10-methyl-9,10,11,12-tetrahydro-8H-[1,4]diazepino[5',6':4,5]thieno[3,2-f]quinolin-8-one (I-83)

(R)-3-(2-chloro-6-(hydroxymethyl)pyrimidin-4-yl)-10-methyl-9,10,11,12-tetrahydro-8H-[1,4]diazepino[5',6':4,5]thieno[3,2-f]quinolin-8-one (I-84)

(R)-3-(6-(hydroxymethyl)-2-vinylpyrimidin-4-yl)-10-methyl-9,10,11,12-tetrahydro-8H-[1,4]diazepino[5',6':4,5]thieno[3,2-f]quinolin-8-one (I-85)

(R)-3-(2-ethynyl-6-(hydroxymethyl)pyrimidin-4-yl)-10-methyl-9,10,11,12-tetrahydro-8H-[1,4]diazepino[5',6':4,5]thieno[3,2-f]quinolin-8-one (I-86)

(R)-3-(2-chloro-6-((4-methylpiperazin-1-yl)methyl)pyrimidin-4-yl)-10-methyl-9,10,11,12-tetrahydro-8H-[1,4]diazepino[5',6':4,5]thieno[3,2-f]quinolin-8-one (I-87)

(R)-10-methyl-3-(6-((4-methylpiperazin-1-yl)methyl)-2-vinylpyrimidin-4-yl)-9,10,11,12-tetrahydro-8H-[1,4]diazepino[5',6':4,5]thieno[3,2-f]quinolin-8-one (I-88)

(R)-3-(2-ethynyl-6-((4-methylpiperazin-1-yl)methyl)pyrimidin-4-yl)-10-methyl-9,10,11,12-tetrahydro-8H-[1,4]diazepino[5',6':4,5]thieno[3,2-f]quinolin-8-one (I-89)

(R)-3-(6-(1-fluorovinyl)pyridin-2-yl)-10-methyl-9,10,11,12-tetrahydro-8H-[1,4]diazepino[5',6':4,5]thieno[3,2-f]quinolin-8-one (I-90)

(R)-3-(6-ethynyl-3-methoxypyridazin-4-yl)-10-methyl-9,10,11,12-tetrahydro-8H-[1,4]diazepino[5',6':4,5]thieno[3,2-f]quinolin-8-one (I-91)

(R)-3-(5-(difluoromethyl)-2-ethynylpyridin-4-yl)-10-methyl-9,10,11,12-tetrahydro-8H-[1,4]diazepino[5',6':4,5]thieno[3,2-f]quinolin-8-one (I-92)

(R)-3-(2-chloro-5-(difluoromethyl)pyridin-4-yl)-10-methyl-9,10,11,12-tetrahydro-8H-[1,4]diazepino[5',6':4,5]thieno[3,2-f]quinolin-8-one (I-93)

(R)-3-(2-chloro-6-(4-methylpiperazin-1-yl)pyridin-4-yl)-10-methyl-9,10,11,12-tetrahydro-8H-[1,4]diazepino[5',6':4,5]thieno[3,2-f]quinolin-8-one (I-94)

(R)-3-(2-ethynyl-6-(4-methylpiperazin-1-yl)pyridin-4-yl)-10-methyl-9,10,11,12-tetrahydro-8H-[1,4]diazepino[5',6':4,5]thieno[3,2-f]quinolin-8-one (I-95)

(R)-10-methyl-3-(2-(4-methylpiperazin-1-yl)-6-vinylpyridin-4-yl)-9,10,11,12-tetrahydro-8H-[1,4]diazepino[5',6':4,5]thieno[3,2-f]quinolin-8-one (I-96)

(R)-3-(2-chloro-6-(hydroxymethyl)pyridin-4-yl)-10-methyl-9,10,11,12-tetrahydro-8H-[1,4]diazepino[5',6':4,5]thieno[3,2-f]quinolin-8-one (I-97)

(R)-3-(2-ethynyl-6-(hydroxymethyl)pyridin-4-yl)-10-methyl-9,10,11,12-tetrahydro-8H-[1,4]diazepino[5',6':4,5]thieno[3,2-f]quinolin-8-one (I-98)

(R)-3-(2-(hydroxymethyl)-6-vinylpyridin-4-yl)-10-methyl-9,10,11,12-tetrahydro-8H-[1,4]diazepino[5',6':4,5]thieno[3,2-f]quinolin-8-one (I-99)

(R)-3-(6-chloro-1'-methyl-1',2',3',6'-tetrahydro-[2,4'-bipyridin]-4-yl)-10-methyl-9,10,11,12-tetrahydro-8H-[1,4]diazepino[5',6':4,5]thieno[3,2-f]quinolin-8-one (I-100)

(R)-10-methyl-3-(1'-methyl-6-vinyl-1',2',3',6'-tetrahydro-[2,4'-bipyridin]-4-yl)-9,10,11,12-tetrahydro-8H-[1,4]diazepino[5',6':4,5]thieno[3,2-f]quinolin-8-one (I-101)

(R)-3-(6-ethynyl-1'-methyl-1',2',3',6'-tetrahydro-[2,4'-bipyridin]-4-yl)-10-methyl-9,10,11,12-tetrahydro-8H-[1,4]diazepino[5',6':4,5]thieno[3,2-f]quinolin-8-one (I-102)
(R)-3-(2-chloro-6-(1-methylpiperidin-4-yl)pyridin-4-yl)-10-methyl-9,10,11,12-tetrahydro-8H-[1,4]diazepino[5',6':4,5]thieno[3,2-f]quinolin-8-one (I-103)
(R)-3-(6-ethynyl-3-(methylamino)pyridazin-4-yl)-10-methyl-9,10,11,12-tetrahydro-8H-[1,4]diazepino[5',6':4,5]thieno[3,2-f]quinolin-8-one (I-104)
(R)-3-(3-(dimethylamino)-6-ethynylpyridazin-4-yl)-10-methyl-9,10,11,12-tetrahydro-8H-[1,4]diazepino[5',6':4,5]thieno[3,2-f]quinolin-8-one (I-105)
(R)-10-methyl-3-(2-(1-methylpiperidin-4-yl)-6-vinylpyridin-4-yl)-9,10,11,12-tetrahydro-8H-[1,4]diazepino[5',6':4,5]thieno[3,2-f]quinolin-8-one (I-106)
(R)-3-(2-ethynyl-6-(1-methylpiperidin-4-yl)pyridin-4-yl)-10-methyl-9,10,11,12-tetrahydro-8H-[1,4]diazepino[5',6':4,5]thieno[3,2-f]quinolin-8-one (I-107)
(R)-3-(2-(1-fluorovinyl)pyridin-4-yl)-10-methyl-9,10,11,12-tetrahydro-8H-[1,4]diazepino[5',6':4,5]thieno[3,2-f]quinolin-8-one (I-108)
(R)-10-methyl-3-(5-methyl-2-vinylpyridin-4-yl)-9,10,11,12-tetrahydro-8H-[1,4]diazepino[5',6':4,5]thieno[3,2-f]quinolin-8-one (I-109)
(R)-10-methyl-3-(2-methyl-6-vinylpyridin-4-yl)-9,10,11,12-tetrahydro-8H-[1,4]diazepino[5',6':4,5]thieno[3,2-f]quinolin-8-one (I-110)
(R)-3-(2-ethynyl-5-methylpyridin-4-yl)-10-methyl-9,10,11,12-tetrahydro-8H-[1,4]diazepino[5',6':4,5]thieno[3,2-f]quinolin-8-one (I-111)
(R)-3-(2-ethynyl-6-methylpyridin-4-yl)-10-methyl-9,10,11,12-tetrahydro-8H-[1,4]diazepino[5',6':4,5]thieno[3,2-f]quinolin-8-one (I-112)
(R,E)-10-methyl-3-(2-(prop-1-en-1-yl)pyridin-4-yl)-9,10,11,12-tetrahydro-8H-[1,4]diazepino[5',6':4,5]thieno[3,2-f]quinolin-8-one (I-113)
(R,E)-3-(2-(3-(dimethylamino)prop-1-en-1-yl)pyridin-4-yl)-10-methyl-9,10,11,12-tetrahydro-8H-[1,4]diazepino[5',6':4,5]thieno[3,2-f]quinolin-8-one (I-114)
(R,E)-3-(6-(3-(dimethylamino)prop-1-en-1-yl)pyrimidin-4-yl)-10-methyl-9,10,11,12-tetrahydro-8H-[1,4]diazepino[5',6':4,5]thieno[3,2-f]quinolin-8-one (I-115)
(R)-10-methyl-3-(2-(3-(pyrrolidin-1-yl)prop-1-en-2-yl)pyridin-4-yl)-9,10,11,12-tetrahydro-8H-[1,4]diazepino[5',6':4,5]thieno[3,2-f]quinolin-8-one (I-116)
(R)-3-(2-(3-(dimethylamino)prop-1-en-2-yl)pyridin-4-yl)-10-methyl-9,10,11,12-tetrahydro-8H-[1,4]diazepino[5',6':4,5]thieno[3,2-f]quinolin-8-one (I-117)
(R)-10-methyl-3-(3-(2-(pyrrolidin-1-yl)ethoxy)-6-vinylpyridazin-4-yl)-9,10,11,12-tetrahydro-8H-[1,4]diazepino[5',6':4,5]thieno[3,2-f]quinolin-8-one (I-118)
(R)-3-(6-chloro-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one (I-119)
(R)-3-(6-ethynyl-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one (I-120)
(R)-3-(2-((4-methoxypiperidin-1-yl)methyl)-6-vinylpyridin-4-yl)-10-methyl-9,10,11,12-tetrahydro-8H-[1,4]diazepino[5',6':4,5]thieno[3,2-f]quinolin-8-one (I-121)
(R)-3-(2-ethynyl-6-((4-methoxypiperidin-1-yl)methyl)pyridin-4-yl)-10-methyl-9,10,11,12-tetrahydro-8H-[1,4]diazepino[5',6':4,5]thieno[3,2-f]quinolin-8-one (I-122)
(R)-3-(2-((4,4-difluoropiperidin-1-yl)methyl)-6-vinylpyridin-4-yl)-10-methyl-9,10,11,12-tetrahydro-8H-[1,4]diazepino[5',6':4,5]thieno[3,2-f]quinolin-8-one (I-123)
(R)-3-(2-((4,4-difluoropiperidin-1-yl)methyl)-6-ethynylpyridin-4-yl)-10-methyl-9,10,11,12-tetrahydro-8H-[1,4]diazepino[5',6':4,5]thieno[3,2-f]quinolin-8-one (I-124)
(R)-10-methyl-3-(2-((4-methylpiperazin-1-yl)methyl)-6-vinylpyridin-4-yl)-9,10,11,12-tetrahydro-8H-[1,4]diazepino[5',6':4,5]thieno[3,2-f]quinolin-8-one (I-125)
(R)-3-(2-ethynyl-6-((4-methylpiperazin-1-yl)methyl)pyridin-4-yl)-10-methyl-9,10,11,12-tetrahydro-8H-[1,4]diazepino[5',6':4,5]thieno[3,2-f]quinolin-8-one (I-126)
(R)-3-(3-methoxy-6-vinylpyridazin-4-yl)-10-methyl-9,10,11,12-tetrahydro-8H-[1,4]diazepino[5',6':4,5]thieno[3,2-f]quinolin-8-one (I-127)
(R)-10-methyl-3-(3-(methylamino)-6-vinylpyridazin-4-yl)-9,10,11,12-tetrahydro-8H-[1,4]diazepino[5',6':4,5]thieno[3,2-f]quinolin-8-one (I-128)
(R)-3-(3-(dimethylamino)-6-vinylpyridazin-4-yl)-10-methyl-9,10,11,12-tetrahydro-8H-[1,4]diazepino[5',6':4,5]thieno[3,2-f]quinolin-8-one (I-129)
(R)-3-(5-(difluoromethyl)-2-vinylpyridin-4-yl)-10-methyl-9,10,11,12-tetrahydro-8H-[1,4]diazepino[5',6':4,5]thieno[3,2-f]quinolin-8-one (I-130)
(R)-10-methyl-3-(2-(3-morpholinoprop-1-en-2-yl)pyridin-4-yl)-9,10,11,12-tetrahydro-8H-[1,4]diazepino[5',6':4,5]thieno[3,2-f]quinolin-8-one (I-131)
(R)-3-(6-chloro-3-(2-morpholinoethoxy)pyridazin-4-yl)-10-methyl-9,10,11,12-tetrahydro-8H-[1,4]diazepino[5',6':4,5]thieno[3,2-f]quinolin-8-one (I-132)
(R)-10-methyl-3-(3-(2-morpholinoethoxy)-6-vinylpyridazin-4-yl)-9,10,11,12-tetrahydro-8H-[1,4]diazepino[5',6':4,5]thieno[3,2-f]quinolin-8-one (I-133)
(R)-3-(6-ethynyl-3-(2-morpholinoethoxy)pyridazin-4-yl)-10-methyl-9,10,11,12-tetrahydro-8H-[1,4]diazepino[5',6':4,5]thieno[3,2-f]quinolin-8-one (I-134)
(R)-3-(2-(3-amino-3-methylbut-1-yn-1-yl)pyridin-4-yl)-10-methyl-9,10,11,12-tetrahydro-8H-[1,4]diazepino[5',6':4,5]thieno[3,2-f]quinolin-8-one (I-135)
(R)-10-methyl-3-(3-methyl-6-vinylpyridazin-4-yl)-9,10,11,12-tetrahydro-8H-[1,4]diazepino[5',6':4,5]thieno[3,2-f]quinolin-8-one (I-136)
methyl (R)-4-(10-methyl-8-oxo-9,10,11,12-tetrahydro-8H-[1,4]diazepino[5',6':4,5]thieno[3,2-f]quinolin-3-yl)-6-vinylpyridazine-3-carboxylate (I-137)
(R)-3-(3-methoxy-6-(3-morpholinoprop-1-en-2-yl)pyridazin-4-yl)-10-methyl-9,10,11,12-tetrahydro-8H-[1,4]diazepino[5',6':4,5]thieno[3,2-f]quinolin-8-one (I-138)
(R)-10-methyl-3-(6-(3-morpholinoprop-1-en-2-yl)pyrimidin-4-yl)-9,10,11,12-tetrahydro-8H-[1,4]diazepino[5',6':4,5]thieno[3,2-f]quinolin-8-one (I-139)
(R)-10-methyl-3-(2-(morpholinomethyl)-6-vinylpyridin-4-yl)-9,10,11,12-tetrahydro-8H-[1,4]diazepino[5',6':4,5]thieno[3,2-f]quinolin-8-one (I-140)
(R)-3-(2-((1,1-difluoro-6-azaspiro[2.5]octan-6-yl)methyl)-6-vinylpyridin-4-yl)-10-methyl-9,10,11,12-tetrahydro-8H-[1,4]diazepino[5',6':4,5]thieno[3,2-f]quinolin-8-one (I-141)
(R)-10-methyl-3-(5-(methyl-d3)-2-vinylpyridin-4-yl)-9,10,11,12-tetrahydro-8H-[1,4]diazepino[5',6':4,5]thieno[3,2-f]quinolin-8-one (I-142)
(R)-3-(5-chloro-2-vinylpyridin-4-yl)-10-methyl-9,10,11,12-tetrahydro-8H-[1,4]diazepino[5',6':4,5]thieno[3,2-f]quinolin-8-one (I-143)
(R)-3-(5-chloro-2-ethynylpyridin-4-yl)-10-methyl-9,10,11,12-tetrahydro-8H-[1,4]diazepino[5',6':4,5]thieno[3,2-f]quinolin-8-one (I-144)
(R,E)-3-(6-(3-(dimethylamino)prop-1-en-1-yl)-3-methoxypyridazin-4-yl)-10-methyl-9,10,11,12-tetrahydro-8H-[1,4]diazepino[5',6':4,5]thieno[3,2-f]quinolin-8-one (I-145)

(R)-10-methyl-3-(1-methyl-4-vinyl-1H-pyrazol-5-yl)-9,10,11,12-tetrahydro-8H-[1,4]diazepino[5',6':4,5]thieno[3,2-f]quinolin-8-one (I-146)

(R)-10-methyl-3-(3-vinyl-1H-pyrazol-1-yl)-9,10,11,12-tetrahydro-8H-[1,4]diazepino[5',6':4,5]thieno[3,2-f]quinolin-8-one (I-147)

(R)-10-methyl-3-(4-vinyl-H-pyrazol-yl)-9,10,11,12-tetrahydro-8H-[1,4]diazepino[5',6':4,5]thieno[3,2-f]quinolin-8-one (I-148)

(R)-10-methyl-3-(4-vinylthiazol-2-yl)-9,10,11,12-tetrahydro-8H-[1,4]diazepino[5',6':4,5]thieno[3,2-f]quinolin-8-one (I-149)

(R)-10-methyl-3-(2-vinyl-1H-imidazol-5-yl)-9,10,11,12-tetrahydro-8H-[1,4]diazepino[5',6':4,5]thieno[3,2-f]quinolin-8-one (I-150)

(R)-3-(2-chloro-1H-imidazol-5-yl)-10-methyl-9,10,11,12-tetrahydro-8H-[1,4]diazepino[5',6':4,5]thieno[3,2-f]quinolin-8-one (I-151)

(R)-3-(4-chloro-1H-pyrazol-1-yl)-10-methyl-9,10,11,12-tetrahydro-8H-[1,4]diazepino[5',6':4,5]thieno[3,2-f]quinolin-8-one (I-152)

(R)-10-methyl-3-(5-(morpholinomethyl)-2-vinylpyridin-4-yl)-9,10,11,12-tetrahydro-8H-[1,4]diazepino[5',6':4,5]thieno[3,2-f]quinolin-8-one (I-153)

(R)-3-(2-ethynyl-5-(morpholinomethyl)pyridin-4-yl)-10-methyl-9,10,11,12-tetrahydro-8H-[1,4]diazepino[5',6':4,5]thieno[3,2-f]quinolin-8-one (I-154)

(R)-3-(5-((4-methoxypiperidin-1-yl)methyl)-2-vinylpyridin-4-yl)-10-methyl-9,10,11,12-tetrahydro-8H-[1,4]diazepino[5',6':4,5]thieno[3,2-f]quinolin-8-one (I-155)

(R)-10-methyl-3-(2-morpholino-6-vinylpyridin-4-yl)-9,10,11,12-tetrahydro-8H-[1,4]diazepino[5',6':4,5]thieno[3,2-f]quinolin-8-one (I-156)

(R)-3-(2-ethynyl-6-morpholinopyridin-4-yl)-10-methyl-9,10,11,12-tetrahydro-8H-[1,4]diazepino[5',6':4,5]thieno[3,2-f]quinolin-8-one (I-157)

(R)-3-(2-(4-methoxypiperidin-1-yl)-6-vinylpyridin-4-yl)-10-methyl-9,10,11,12-tetrahydro-8H-[1,4]diazepino[5',6':4,5]thieno[3,2-f]quinolin-8-one (I-158)

(R)-3-(2-ethynyl-6-(4-methoxypiperidin-1-yl)pyridin-4-yl)-10-methyl-9,10,11,12-tetrahydro-8H-[1,4]diazepino[5',6':4,5]thieno[3,2-f]quinolin-8-one (I-159)

(R)-6-chloro-4-(10-methyl-8-oxo-9,10,11,12-tetrahydro-8H-[1,4]diazepino[5',6':4,5]thieno[3,2-f]quinolin-3-yl)nicotinonitrile (I-160)

(R)-4-(10-methyl-8-oxo-9,10,11,12-tetrahydro-8H-[1,4]diazepino[5',6':4,5]thieno[3,2-f]quinolin-3-yl)-6-vinylnicotinonitrile (I-161)

(R)-6-ethynyl-4-(10-methyl-8-oxo-9,10,11,12-tetrahydro-8H-[1,4]diazepino[5',6':4,5]thieno[3,2-f]quinolin-3-yl)nicotinonitrile (I-162)

(R)-10-methyl-3-(6-vinylpyrazin-2-yl)-9,10,11,12-tetrahydro-8H-[1,4]diazepino[5',6':4,5]thieno[3,2-f]quinolin-8-one (I-163)

(R)-10-methyl-3-(2-vinyl-1H-imidazol-1-yl)-9,10,11,12-tetrahydro-8H-[1,4]diazepino[5',6':4,5]thieno[3,2-f]quinolin-8-one (I-164)

(R)-3-(3-chloro-1H-pyrazol-1-yl)-10-methyl-9,10,11,12-tetrahydro-8H-[1,4]diazepino[5',6':4,5]thieno[3,2-f]quinolin-8-one (I-165)

(R)-10-methyl-3-(5-methyl-6-vinylpyrazin-2-yl)-9,10,11,12-tetrahydro-8H-[1,4]diazepino[5',6':4,5]thieno[3,2-f]quinolin-8-one (I-166)

(R)-10-methyl-3-(3-methyl-6-vinylpyrazin-2-yl)-9,10,11,12-tetrahydro-8H-[1,4]diazepino[5',6':4,5]thieno[3,2-f]quinolin-8-one (I-167)

(R)-3-(2-(4,4-difluoropiperidin-1-yl)-6-vinylpyridin-4-yl)-10-methyl-9,10,11,12-tetrahydro-8H-[1,4]diazepino[5',6':4,5]thieno[3,2-f]quinolin-8-one (I-168)

(R)-3-(2-ethynyl-6-(morpholinomethyl)pyridin-4-yl)-10-methyl-9,10,11,12-tetrahydro-8H-[1,4]diazepino[5',6':4,5]thieno[3,2-f]quinolin-8-one (I-169)

(R)-3-(6-ethynyl-3-methylpyridazin-4-yl)-10-methyl-9,10,11,12-tetrahydro-8H-[1,4]diazepino[5',6':4,5]thieno[3,2-f]quinolin-8-one (I-170)

(R)-10-methyl-3-(2-(4-(methyl-d3)piperazin-1-yl)-6-vinylpyridin-4-yl)-9,10,11,12-tetrahydro-8H-[1,4]diazepino[5',6':4,5]thieno[3,2-f]quinolin-8-one (I-171)

(R)-3-(2-ethynyl-6-(4-(methyl-d3)piperazin-1-yl)pyridin-4-yl)-10-methyl-9,10,11,12-tetrahydro-8H-[1,4]diazepino[5',6':4,5]thieno[3,2-f]quinolin-8-one (I-172)

(R)-3-(2-(4-ethylpiperazin-1-yl)-6-vinylpyridin-4-yl)-10-methyl-9,10,11,12-tetrahydro-8H-[1,4]diazepino[5',6':4,5]thieno[3,2-f]quinolin-8-one (I-173)

(R)-3-(2-(4-ethylpiperazin-1-yl)-6-ethynylpyridin-4-yl)-10-methyl-9,10,11,12-tetrahydro-8H-[1,4]diazepino[5',6':4,5]thieno[3,2-f]quinolin-8-one (I-174)

(R)-10-methyl-3-(2-(piperazin-1-yl)-6-vinylpyridin-4-yl)-9,10,11,12-tetrahydro-8H-[1,4]diazepino[5',6':4,5]thieno[3,2-f]quinolin-8-one (I-175)

(R)-3-(2-ethynyl-6-(piperazin-1-yl)pyridin-4-yl)-10-methyl-9,10,11,12-tetrahydro-8H-[1,4]diazepino[5',6':4,5]thieno[3,2-f]quinolin-8-one (I-176)

(R)-10-methyl-3-(2-(piperidin-1-yl)-6-vinylpyridin-4-yl)-9,10,11,12-tetrahydro-8H-[1,4]diazepino[5',6':4,5]thieno[3,2-f]quinolin-8-one (I-177)

(R)-3-(2-ethynyl-6-(piperidin-1-yl)pyridin-4-yl)-10-methyl-9,10,11,12-tetrahydro-8H-[1,4]diazepino[5',6':4,5]thieno[3,2-f]quinolin-8-one (I-178)

(R)-3-(2-(azetidin-1-yl)-6-vinylpyridin-4-yl)-10-methyl-9,10,11,12-tetrahydro-8H-[1,4]diazepino[5',6':4,5]thieno[3,2-f]quinolin-8-one (I-179)

(R)-3-(2-(azetidin-1-yl)-6-ethynylpyridin-4-yl)-10-methyl-9,10,11,12-tetrahydro-8H-[1,4]diazepino[5',6':4,5]thieno[3,2-f]quinolin-8-one (I-180)

(R)-10-methyl-3-(3-methyl-6-vinylpyrazin-2-yl)-9,10,11,12-tetrahydro-8H-[1,4]diazepino[5',6':4,5]thieno[3,2-f]quinolin-8-one (I-181)

(R)-3-(2-(4,4-difluoropiperidin-1-yl)-6-ethynylpyridin-4-yl)-10-methyl-9,10,11,12-tetrahydro-8H-[1,4]diazepino[5',6':4,5]thieno[3,2-f]quinolin-8-one (I-182)

(R)-3-(2-(3,3-difluoroazetidin-1-yl)-6-ethynylpyridin-4-yl)-10-methyl-9,10,11,12-tetrahydro-8H-[1,4]diazepino[5',6':4,5]thieno[3,2-f]quinolin-8-one (I-183)

(R)-3-(2-(3,3-difluoroazetidin-1-yl)-6-vinylpyridin-4-yl)-10-methyl-9,10,11,12-tetrahydro-8H-[1,4]diazepino[5',6':4,5]thieno[3,2-f]quinolin-8-one (I-184)

(R)-3-(2-(((2S,6R)-2,6-dimethylmorpholino)methyl)-6-vinylpyridin-4-yl)-10-methyl-9,10,11,12-tetrahydro-8H-[1,4]diazepino[5',6':4,5]thieno[3,2-f]quinolin-8-one (I-185)

(R)-3-(2-(((2S,6R)-2,6-dimethylmorpholino)methyl)-6-ethynylpyridin-4-yl)-10-methyl-9,10,11,12-tetrahydro-8H-[1,4]diazepino[5',6':4,5]thieno[3,2-f]quinolin-8-one (I-186)

(R)-3-(2-(((2R,6R)-2,6-dimethylmorpholino)methyl)-6-vinylpyridin-4-yl)-10-methyl-9,10,11,12-tetrahydro-8H-[1,4]diazepino[5',6':4,5]thieno[3,2-f]quinolin-8-one (I-187)

(R)-3-(2-(((2R,6R)-2,6-dimethylmorpholino)methyl)-6-ethynylpyridin-4-yl)-10-methyl-9,10,11,12-tetrahydro-8H-[1,4]diazepino[5',6':4,5]thieno[3,2-f]quinolin-8-one (I-188)

(R)-10-methyl-3-(2-((4-(trifluoromethoxy)piperidin-1-yl)methyl)-6-vinylpyridin-4-yl)-9,10,11,12-tetrahydro-8H-[1,4]diazepino[5',6':4,5]thieno[3,2-f]quinolin-8-one (I-189)

(R)-3-(2-ethynyl-6-((4-(trifluoromethoxy)piperidin-1-yl)methyl)pyridin-4-yl)-10-methyl-9,10,11,12-tetrahydro-8H-[1,4]diazepino[5',6':4,5]thieno[3,2-f]quinolin-8-one (I-190)

(R)-10-methyl-3-(6-methyl-2-vinyl-5,6,7,8-tetrahydropyrido[4,3-d]pyrimidin-4-yl)-9,10,11,12-tetrahydro-8H-[1,4]diazepino[5',6':4,5]thieno[3,2-f]quinolin-8-one (I-191)

(R)-3-(2-chloro-6-methyl-5,6,7,8-tetrahydropyrido[4,3-d]pyrimidin-4-yl)-10-methyl-9,10,11,12-tetrahydro-8H-[1,4]diazepino[5',6':4,5]thieno[3,2-f]quinolin-8-one (I-192)

(R)-3-(2-ethynyl-6-methyl-5,6,7,8-tetrahydropyrido[4,3-d]pyrimidin-4-yl)-10-methyl-9,10,11,12-tetrahydro-8H-[1,4]diazepino[5',6':4,5]thieno[3,2-f]quinolin-8-one (I-193)

(R)-3-(2,3-dimethyl-6-vinylpyridin-4-yl)-10-methyl-9,10,11,12-tetrahydro-8H-[1,4]diazepino[5',6':4,5]thieno[3,2-f]quinolin-8-one (I-194)

(R)-3-(5-ethyl-2-vinylpyridin-4-yl)-10-methyl-9,10,11,12-tetrahydro-8H-[1,4]diazepino[5',6':4,5]thieno[3,2-f]quinolin-8-one (I-195)

(R)-3-(5-cyclopropyl-2-vinylpyridin-4-yl)-10-methyl-9,10,11,12-tetrahydro-8H-[1,4]diazepino[5',6':4,5]thieno[3,2-f]quinolin-8-one (I-196)

(R)-10-methyl-3-(3-methyl-2-(morpholinomethyl)-6-vinylpyridin-4-yl)-9,10,11,12-tetrahydro-8H-[1,4]diazepino[5',6':4,5]thieno[3,2-f]quinolin-8-one (I-197)

(R)-3-(3-fluoro-2-(morpholinomethyl)-6-vinylpyridin-4-yl)-10-methyl-9,10,11,12-tetrahydro-8H-[1,4]diazepino[5',6':4,5]thieno[3,2-f]quinolin-8-one (I-198)

(R,E)-10-methyl-3-(2-(3,3,3-trifluoroprop-1-en-1-yl)pyridin-4-yl)-9,10,11,12-tetrahydro-8H-[1,4]diazepino[5',6':4,5]thieno[3,2-f]quinolin-8-one (I-199)

(R,E)-3-(3-methoxy-6-(3,3,3-trifluoroprop-1-en-1-yl)pyridazin-4-yl)-10-methyl-9,10,11,12-tetrahydro-8H-[1,4]diazepino[5',6':4,5]thieno[3,2-f]quinolin-8-one (I-200)

(10R)-3-(2-(2,6-dimethylmorpholino)-6-vinylpyridin-4-yl)-10-methyl-9,10,11,12-tetrahydro-8H-[1,4]diazepino[5',6':4,5]thieno[3,2-f]quinolin-8-one (I-201)

(R)-10-methyl-3-(2-(4-(trifluoromethyl)piperidin-1-yl)-6-vinylpyridin-4-yl)-9,10,11,12-tetrahydro-8H-[1,4]diazepino[5',6':4,5]thieno[3,2-f]quinolin-8-one (I-202)

(R)-10-methyl-3-(3-vinyl-4H-1,2,4-triazol-4-yl)-9,10,11,12-tetrahydro-8H-[1,4]diazepino[5',6':4,5]thieno[3,2-f]quinolin-8-one (I-203)

(R)-3-(3-ethynyl-4H-1,2,4-triazol-4-yl)-10-methyl-9,10,11,12-tetrahydro-8H-[1,4]diazepino[5',6':4,5]thieno[3,2-f]quinolin-8-one (I-204)

(R)-3-(2-chloro-1H-imidazol-1-yl)-10-methyl-9,10,11,12-tetrahydro-8H-[1,4]diazepino[5',6':4,5]thieno[3,2-f]quinolin-8-one (I-205)

(R)-10-methyl-3-(4-methyl-2-vinyl-1H-imidazol-1-yl)-9,10,11,12-tetrahydro-8H-[1,4]diazepino[5',6':4,5]thieno[3,2-f]quinolin-8-one (I-206)

(R)-10-methyl-3-(3-vinyl-1H-1,2,4-triazol-1-yl)-9,10,11,12-tetrahydro-8H-[1,4]diazepino[5',6':4,5]thieno[3,2-f]quinolin-8-one (I-207)

(R)-10-methyl-3-(1-methyl-5-vinyl-1H-1,2,4-triazol-3-yl)-9,10,11,12-tetrahydro-8H-[1,4]diazepino[5',6':4,5]thieno[3,2-f]quinolin-8-one (I-208)

(R)-10-methyl-3-(2-vinylthiazol-5-yl)-9,10,11,12-tetrahydro-8H-[1,4]diazepino[5',6':4,5]thieno[3,2-f]quinolin-8-one (I-209)

(R)-3-(3-chloro-1H-1,2,4-triazol-1-yl)-10-methyl-9,10,11,12-tetrahydro-8H-[1,4]diazepino[5',6':4,5]thieno[3,2-f]quinolin-8-one (I-210)

(R)-3-(5-((3,3-difluoroazetidin-1-yl)methyl)-2-vinylpyridin-4-yl)-10-methyl-9,10,11,12-tetrahydro-8H-[1,4]diazepino[5',6':4,5]thieno[3,2-f]quinolin-8-one (I-211)

(R)-10-methyl-3-(5-((4-(trifluoromethyl)piperidin-1-yl)methyl)-2-vinylpyridin-4-yl)-9,10,11,12-tetrahydro-8H-[1,4]diazepino[5',6':4,5]thieno[3,2-f]quinolin-8-one (I-212)

(R)-3-(5-(((2S,6R)-2,6-dimethylmorpholino)methyl)-2-vinylpyridin-4-yl)-10-methyl-9,10,11,12-tetrahydro-8H-[1,4]diazepino[5',6':4,5]thieno[3,2-f]quinolin-8-one (I-213)

(R)-10-methyl-3-(5-vinyl-1H-1,2,4-triazol-1-yl)-9,10,11,12-tetrahydro-8H-[1,4]diazepino[5',6':4,5]thieno[3,2-f]quinolin-8-one (I-214)

rac-(R)-8-(4-(10-methyl-8-oxo-9,10,11,12-tetrahydro-8H-[1,4]diazepino[5',6':4,5]thieno[3,2-f]quinolin-3-yl)-6-vinylpyridin-2-yl)-1-oxa-8-azaspiro[4.5]decan-2-one (I-215)

rac-(10R)-3-(2-(2-oxa-5-azabicyclo[2.2.1]heptan-5-yl)-6-vinylpyridin-4-yl)-10-methyl-9,10,11,12-tetrahydro-8H-[1,4]diazepino[5',6':4,5]thieno[3,2-f]quinolin-8-one (I-216)

(R)-3-(3-fluoro-2-vinylpyridin-4-yl)-10-methyl-9,10,11,12-tetrahydro-8H-[1,4]diazepino[5',6':4,5]thieno[3,2-f]quinolin-8-one (I-217)

(R)-3-(2-ethynyl-3-fluoropyridin-4-yl)-10-methyl-9,10,11,12-tetrahydro-8H-[1,4]diazepino[5',6':4,5]thieno[3,2-f]quinolin-8-one (I-218)

(R)-10-methyl-3-(3-methyl-2-vinylpyridin-4-yl)-9,10,11,12-tetrahydro-8H-[1,4]diazepino[5',6':4,5]thieno[3,2-f]quinolin-8-one (I-219)

(R)-3-(2-ethynyl-3-methylpyridin-4-yl)-10-methyl-9,10,11,12-tetrahydro-8H-[1,4]diazepino[5',6':4,5]thieno[3,2-f]quinolin-8-one (I-220)

(R)-3-(2-chloro-3-fluoropyridin-4-yl)-10-methyl-9,10,11,12-tetrahydro-8H-[1,4]diazepino[5',6':4,5]thieno[3,2-f]quinolin-8-one (I-221)

(R)-3-(2-ethynyl-1H-imidazol-1-yl)-10-methyl-9,10,11,12-tetrahydro-8H-[1,4]diazepino[5',6':4,5]thieno[3,2-f]quinolin-8-one (I-222)

(R)-10-methyl-3-(3-methyl-5-vinyl-4H-1,2,4-triazol-4-yl)-9,10,11,12-tetrahydro-8H-[1,4]diazepino[5',6':4,5]thieno[3,2-f]quinolin-8-one (I-223)

(R)-10-methyl-3-(3-methyl-5-vinyl-1H-1,2,4-triazol-1-yl)-9,10,11,12-tetrahydro-8H-[1,4]diazepino[5',6':4,5]thieno[3,2-f]quinolin-8-one (I-224)

(R)-10-methyl-3-(6-(3,3,3-trifluoroprop-1-en-2-yl)pyrazin-2-yl)-9,10,11,12-tetrahydro-8H-[1,4]diazepino[5',6':4,5]thieno[3,2-f]quinolin-8-one (I-225)

(R)-10-methyl-3-(3-(trifluoromethyl)-5-vinyl-1H-1,2,4-triazol-1-yl)-9,10,11,12-tetrahydro-8H-[1,4]diazepino[5',6':4,5]thieno[3,2-f]quinolin-8-one (I-226)

(R)-10-methyl-3-(5-methyl-3-vinylisoxazol-4-yl)-9,10,11,12-tetrahydro-8H-[1,4]diazepino[5',6':4,5]thieno[3,2-f]quinolin-8-one (I-227)

(R)-10-methyl-3-(3-vinylisothiazol-4-yl)-9,10,11,12-tetrahydro-8H-[1,4]diazepino[5',6':4,5]thieno[3,2-f]quinolin-8-one (I-228)

(R)-10-methyl-3-(5-vinylisothiazol-4-yl)-9,10,11,12-tetrahydro-8H-[1,4]diazepino[5',6':4,5]thieno[3,2-f]quinolin-8-one (I-229)

(R)-10-methyl-3-(1-methyl-3-vinyl-1H-pyrazol-4-yl)-9,10,11,12-tetrahydro-8H-[1,4]diazepino[5',6':4,5]thieno[3,2-f]quinolin-8-one (I-230)

(R)-3-(4,5-dimethyl-2-vinyl-1H-imidazol-1-yl)-10-methyl-9,10,11,12-tetrahydro-8H-[1,4]diazepino[5',6':4,5]thieno[3,2-f]quinolin-8-one (I-231)

(R)-10-methyl-3-(2-methyl-5-vinyl-2H-1,2,3-triazol-4-yl)-9,10,11,12-tetrahydro-8H-[1,4]diazepino[5',6':4,5]thieno[3,2-f]quinolin-8-one (I-232)

(R)-10-methyl-3-(1-methyl-4-vinyl-1H-1,2,3-triazol-5-yl)-9,10,11,12-tetrahydro-8H-[1,4]diazepino[5',6':4,5]thieno[3,2-f]quinolin-8-one (I-233)

ethyl (R)-5-(10-methyl-8-oxo-9,10,11,12-tetrahydro-8H-[1,4]diazepino[5',6':4,5]thieno[3,2-f]quinolin-3-yl)-2-vinylthiazole-4-carboxylate (I-234)

(R)-10-methyl-3-(1-methyl-5-vinyl-1H-1,2,3-triazol-4-yl)-9,10,11,12-tetrahydro-8H-[1,4]diazepino[5',6':4,5]thieno[3,2-f]quinolin-8-one (I-235)

(R)-10-methyl-3-(3-methyl-5-vinyl-1H-pyrazol-1-yl)-9,10,11,12-tetrahydro-8H-[1,4]diazepino[5',6':4,5]thieno[3,2-f]quinolin-8-one (I-236)

(R)-3-(2-((2-methoxyethyl)(methyl)amino)-6-vinylpyridin-4-yl)-10-methyl-9,10,11,12-tetrahydro-8H-[1,4]diazepino[5',6':4,5]thieno[3,2-f]quinolin-8-one (I-237)

(R)-3-(2-(2-oxa-6-azaspiro[3.3]heptan-6-yl)-6-vinylpyridin-4-yl)-10-methyl-9,10,11,12-tetrahydro-8H-[1,4]diazepino[5',6':4,5]thieno[3,2-f]quinolin-8-one (I-238)

(R)-3-(2-(4-fluoropiperidin-1-yl)-6-vinylpyridin-4-yl)-10-methyl-9,10,11,12-tetrahydro-8H-[1,4]diazepino[5',6':4,5]thieno[3,2-f]quinolin-8-one (I-239)

(R)-3-(2-(4-(methoxymethyl)piperidin-1-yl)-6-vinylpyridin-4-yl)-10-methyl-9,10,11,12-tetrahydro-8H-[1,4]diazepino[5',6':4,5]thieno[3,2-f]quinolin-8-one (I-240)

(R)-10-methyl-3-(3-(trifluoromethyl)-5-vinyl-1H-pyrazol-1-yl)-9,10,11,12-tetrahydro-8H-[1,4]diazepino[5',6':4,5]thieno[3,2-f]quinolin-8-one (I-241)

(R)-3-(2-bromo-4-(trifluoromethyl)-1H-imidazol-1-yl)-10-methyl-9,10,11,12-tetrahydro-8H-[1,4]diazepino[5',6':4,5]thieno[3,2-f]quinolin-8-one (I-242)

(10R)-3-(5-(1-hydroxyethyl-2,2,2-d3)-2-vinylpyridin-4-yl)-10-methyl-9,10,11,12-tetrahydro-8H-[1,4]diazepino[5',6':4,5]thieno[3,2-f]quinolin-8-one (I-243)

(R)-10-methyl-3-(5-(trifluoromethoxy)-2-vinylpyridin-4-yl)-9,10,11,12-tetrahydro-8H-[1,4]diazepino[5',6':4,5]thieno[3,2-f]quinolin-8-one (I-245)

(R)-1-(10-methyl-8-oxo-9,10,11,12-tetrahydro-8H-[1,4]diazepino[5',6':4,5]thieno[3,2-f]quinolin-3-yl)-1H-imidazole-2-carbonitrile (I-246)

(R)-3-(5-(difluoromethoxy)-2-vinylpyridin-4-yl)-10-methyl-9,10,11,12-tetrahydro-8H-[1,4]diazepino[5',6':4,5]thieno[3,2-f]quinolin-8-one (I-247)

(R)-3-(5-cyclopropyl-3-vinyl-1H-1,2,4-triazol-1-yl)-10-methyl-9,10,11,12-tetrahydro-8H-[1,4]diazepino[5',6':4,5]thieno[3,2-f]quinolin-8-one (I-248)

(R)-10-methyl-3-(5-(methyl-d3)-2-vinylpyridin-4-yl-3-d)-9,10,11,12-tetrahydro-8H-[1,4]diazepino[5',6':4,5]thieno[3,2-f]quinolin-8-one (I-249)

(R)-3-(2-bromo-4,5-dichloro-1H-imidazol-1-yl)-10-methyl-9,10,11,12-tetrahydro-8H-[1,4]diazepino[5',6':4,5]thieno[3,2-f]quinolin-8-one (I-250)

(R)-3-(4,5-dichloro-2-vinyl-1H-imidazol-1-yl)-10-methyl-9,10,11,12-tetrahydro-8H-[1,4]diazepino[5',6':4,5]thieno[3,2-f]quinolin-8-one (I-251)

(R)-3-(5-(hydroxymethyl)-2-vinylpyridin-4-yl)-10-methyl-9,10,11,12-tetrahydro-8H-[1,4]diazepino[5',6':4,5]thieno[3,2-f]quinolin-8-one (I-252)

(R)-3-(5-(methoxymethyl)-2-vinylpyridin-4-yl)-10-methyl-9,10,11,12-tetrahydro-8H-[1,4]diazepino[5',6':4,5]thieno[3,2-f]quinolin-8-one (I-253)

(S)-10-(fluoromethyl)-3-(5-methyl-2-vinylpyridin-4-yl)-9,10,11,12-tetrahydro-8H-[1,4]diazepino[5',6':4,5]thieno[3,2-f]quinolin-8-one (I-254)

(S)-10-(fluoromethyl)-3-(2-vinyl-1H-imidazol-1-yl)-9,10,11,12-tetrahydro-8H-[1,4]diazepino[5',6':4,5]thieno[3,2-f]quinolin-8-one (I-255)

(R)-3-(5-methoxy-2-vinylpyridin-4-yl)-10-methyl-9,10,11,12-tetrahydro-8H-[1,4]diazepino[5',6':4,5]thieno[3,2-f]quinolin-8-one (I-256)

(R)-10-methyl-3-(5-(trifluoromethyl)-3-vinyl-1H-pyrazol-1-yl)-9,10,11,12-tetrahydro-8H-[1,4]diazepino[5',6':4,5]thieno[3,2-f]quinolin-8-one (I-257)

(R)-3-(5-(2-hydroxypropan-2-yl-1,1,1,3,3,3-d6)-2-vinylpyridin-4-yl)-10-methyl-9,10,11,12-tetrahydro-8H-[1,4]diazepino[5',6':4,5]thieno[3,2-f]quinolin-8-one (I-258)

(10R)-3-(5-(1-hydroxyethyl-2,2,2-d3)-2-vinylpyridin-4-yl)-10-methyl-9,10,11,12-tetrahydro-8H-[1,4]diazepino[5',6':4,5]thieno[3,2-f]quinolin-8-one (I-259)

(10R)-3-(5-(1-hydroxyethyl-2,2,2-d3)-2-vinylpyridin-4-yl)-10-methyl-9,10,11,12-tetrahydro-8H-[1,4]diazepino[5',6':4,5]thieno[3,2-f]quinolin-8-one (I-260)

(R)-10-methyl-3-(5-methyl-3-vinyl-1H-1,2,4-triazol-1-yl)-9,10,11,12-tetrahydro-8H-[1,4]diazepino[5',6':4,5]thieno[3,2-f]quinolin-8-one (I-261)

(R)-3-(5-(ethoxymethyl)-2-vinylpyridin-4-yl)-10-methyl-9,10,11,12-tetrahydro-8H-[1,4]diazepino[5',6':4,5]thieno[3,2-f]quinolin-8-one (I-262)

(R)-3-(5-((2-oxa-6-azaspiro[3.3]heptan-6-yl)methyl)-2-vinylpyridin-4-yl)-10-methyl-9,10,11,12-tetrahydro-8H-[1,4]diazepino[5',6':4,5]thieno[3,2-f]quinolin-8-one (I-263)

(R)-10-methyl-3-(5-vinylpyridazin-3-yl)-9,10,11,12-tetrahydro-8H-[1,4]diazepino[5',6':4,5]thieno[3,2-f]quinolin-8-one (I-264)

(R,E)-10-methyl-3-(5-methyl-2-(prop-1-en-1-yl)pyridin-4-yl)-9,10,11,12-tetrahydro-8H-[1,4]diazepino[5',6':4,5]thieno[3,2-f]quinolin-8-one (I-265)

(R,E)-10-methyl-3-(2-(prop-1-en-1-yl)-1H-imidazol-1-yl)-9,10,11,12-tetrahydro-8H-[1,4]diazepino[5',6':4,5]thieno[3,2-f]quinolin-8-one (I-266)

(R)-2-(5-methyl-4-(10-methyl-8-oxo-9,10,11,12-tetrahydro-8H-[1,4]diazepino[5',6':4,5]thieno[3,2-f]quinolin-3-yl)pyridin-2-yl)acetonitrile (I-267)

(R)-10-methyl-3-(2-vinyl-1H-benzo[d]imidazol-1-yl)-9,10,11,12-tetrahydro-8H-[1,4]diazepino[5',6':4,5]thieno[3,2-f]quinolin-8-one (I-271)

(R)-3-(2-chloropyridin-4-yl)-10-methyl-9,10,11,12-tetrahydro-8H-[1,4]diazepino[5',6':4,5]thieno[3,2-f]quinolin-8-one (I-272)

(R)-3-(2-chloro-5-fluoropyrimidin-4-yl)-10-methyl-9,10,11,12-tetrahydro-8H-[1,4]diazepino[5',6':4,5]thieno[3,2-f]quinolin-8-one (I-273)

(R)-3-(6-chloro-3-fluoro-5-(trifluoromethyl)pyridin-2-yl)-10-methyl-9,10,11,12-tetrahydro-8H-[1,4]diazepino[5',6':4,5]thieno[3,2-f]quinolin-8-one (I-274)

Embodiment 53. A pharmaceutically acceptable composition comprising the compound according to any one of the preceding embodiments and a pharmaceutically acceptable carrier, adjuvant, or vehicle.

Embodiment 54. A method for inhibiting MK2 kinase, or a mutant thereof, activity in a biological sample comprising the step of contacting said biological sample with a compound according to any one of the preceding embodiments.

Embodiment 55. A method for inhibiting MK2 kinase, or a mutant thereof, activity in a patient comprising the step of administering to said patient the composition according to any of the preceding embodiments.

Embodiment 56. The method according to any one of the preceding embodiments, wherein the MK2 kinase, or a mutant thereof, activity is inhibited irreversibly.

Embodiment 57. The method according to any one of the preceding embodiments, wherein the MK2 kinase, or a mutant thereof, activity is inhibited irreversibly by covalently modifying Cys140 of MK2.

Embodiment 58. A method for treating an MK2-mediated disease or disorder in a patient in need thereof, comprising the step of administering to said patient the composition according to any one of the preceding embodiments.

Embodiment 59. The method according to any one of the preceding embodiments, wherein the MK2-mediated disease or disorder is an autoimmune disorder, chronic or acute inflammatory disorder, an auto-inflammatory disorder, a fibrotic disorder, a metabolic disorder, a neoplasia, or a cardiovascular or cerebrovascular disorder.

Embodiment 60. The method according to any one of the preceding embodiments, wherein the MK2-mediated disease or disorder is an autoimmune disorder, chronic or acute inflammatory disorder, or an auto-inflammatory disorder.

Embodiment 61. The method according to any one of the preceding embodiments, wherein the autoimmune disorder, chronic or acute inflammatory disorder, and/or auto-inflammatory disorder is selected from the group consisting of inflammatory bowel diseases, ulcerative colitis, Crohn's disease, multiple sclerosis, psoriasis, arthritis, rheumatoid arthritis, osteoarthritis, juvenile arthritis, psoriatic arthritis, reactive arthritis, ankylosing spondylitis, cryopyrin associated periodic syndromes, Muckle-Wells syndrome, familial cold auto-inflammatory syndrome, neonatal-onset multisystem inflammatory disease, TNF receptor associated periodic syndrome, acute and chronic pancreatitis, atherosclerosis, gout, ankylosing spondylitis, fibrotic disorders, hepatic fibrosis, idiopathic pulmonary fibrosis, nephropathy, sarcoidosis, scleroderma, anaphylaxis, diabetes, diabetes mellitus type 1, diabetes mellitus type 2, diabetic retinopathy, Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease, Sjogren's syndrome, familial Mediterranean fever, systemic lupus erythematosus, vasculitis syndromes, temporal, Takayasu's and giant cell arteritis, Behçet's disease, Wegener's granulomatosis, vitiligo, secondary hematologic manifestation of autoimmune diseases, anemias, drug-induced autoimmunity, Hashimoto's thyroiditis, hypophysitis, idiopathic thrombocytic pupura, metal-induced autoimmunity, myasthenia gravis, pemphigus, autoimmune deafness, Meniere's disease, Goodpasture's syndrome, Graves' disease, HW-related autoimmune syndromes, Gullain-Barre disease, Addison's disease, antiphospholipid syndrome, asthma, atopic dermatitis, Celiac disease, Cushing's syndrome, dermatomyositis, idiopathic adrenal adrenal atrophy, idiopathic thrombocytopenia, Kawasaki syndrome, Lambert-Eaton Syndrome, pernicious anemia, pollinosis, polyarteritis nodosa, primary biliary cirrhosis, primary sclerosing cholangitis, Raynaud's, Reiter's Syndrome, relapsing polychondritis, Schmidt's syndrome, thyrotoxidosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonary disease (COPD), vasculitis, graft vs. host reaction, graft vs. host disease, allograft rejections, acute allograft rejection, chronic allograft rejection, early transplantation rejection, acute allograft rejection, reperfusion injury, pain, acute pain, chronic pain, neuropathic pain, fibromyalgia, chronic infections, meningitis, encephalitis, myocarditis, gingivitis, post surgical trauma, tissue injury, traumatic brain injury, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

Embodiment 62. The method according to any one of the preceding embodiments, wherein the MK2-mediated disease or disorder is a fibrotic disorder.

Embodiment 63. The method according to any one of the preceding embodiments, wherein the fibrotic disorder is selected from the group consisting of systemic sclerosis/scleroderma, lupus nephritis, connective tissue disease, wound healing, surgical scarring, spinal cord injury, CNS scarring, acute lung injury, pulmonary fibrosis, idiopathic pulmonary fibrosis, cystic fibrosis, chronic obstructive pulmonary disease, adult respiratory distress syndrome, acute lung injury, drug-induced lung injury, glomerulonephritis, chronic kidney disease, diabetic nephropathy, hypertension-induced nephropathy, alimentary track or gastrointestinal fibrosis, renal fibrosis, hepatic or biliary fibrosis, liver fibrosis, nonalcoholic steatohepatitis, hepatitis C, hepatocellular carcinoma, cirrhosis, primary biliary cirrhosis, cirrhosis due to fatty liver disease cirrhosis due to alcoholic fatty liver disease, cirrhosis due to nonalcoholic steatosis/non-alcoholic fatty liver disease, radiation-induced fibrosis head and neck fibrosis, gastrointestinal fibrosis, pulmonary fibrosis, primary sclerosing cholangitis, restenosis, cardiac fibrosis, endomyocardial fibrosis, atrial fibrosis, ophthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

Embodiment 64. The method according to any one of the preceding embodiments, wherein the MK2-mediated disease or disorder is a metabolic disorder.

Embodiment 65. The method according to any one of the preceding embodiments, wherein the metabolic disorder is selected from the group consisting of obesity, steroid-resistance, glucose intolerance, and metabolic syndrome.

Embodiment 66. The method according to any one of the preceding embodiments, wherein the MK2-mediated disease or disorder is a neoplasia.

Embodiment 67. The method according to any one of the preceding embodiments, wherein the neoplasia is selected from the group consisting of angiogenesis disorders, multiple myeloma, leukemias, acute lymphocytic leukemia, acute and chronic myelogenous leukemia, chronic lymphocytic leukemia, acute lymphoblastic leukemia, promyelocytic leukemia, lymphomas, B-cell lymphoma, T-cell lymphoma, mantle cell lymphoma, hairy cell lymphoma, Burkitt's lymphoma, mast cell tumors, Hodgkin's disease, non-Hodgkin's disease, myelodysplastic syndrome, fibrosarcoma, rhabdomyosarcoma; astrocytoma, neuroblastoma, glioma, schwannomas, melanoma, seminoma, teratocarcinoma, osteosarcoma, xenoderma pigmentosum, keratoctanthoma, thyroid follicular cancer, Kaposi's sarcoma, melanoma, teratoma, rhabdomyosarcoma, metastatic and bone disorders, cancer of the bone, mouth/pharynx, esophagus, larynx, stomach, intestine, colon, rectum, lung, liver, pancreas, nerve, brain, head and neck, throat, ovary, uterus, prostate, testis, bladder, kidney, breast, gall bladder, cervix, thyroid, prostate, and skin, non-small cell lung cancer, small cell lung cancer, glioma, and glioblastoma multiforme.

Embodiment 68. The method according to any one of the preceding embodiments, wherein the MK2-mediated disease or disorder is a cardiovascular or cerebrovascular disorder.

Embodiment 69. The method according to any one of the preceding embodiments, wherein the cardiovascular or cerebrovascular disorder is selected from the group consisting of atherosclerosis, restenosis of an atherosclerotic coronary artery, acute coronary syndrome, myocardial infarction, cardiac-allograft vasculopathy, stroke, central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

We claim:

1. A compound of formula I:

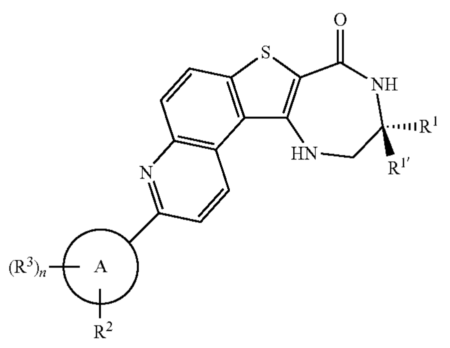

I or a pharmaceutically acceptable salt thereof, wherein:

Ring A is a 5-6 membered heteroaryl ring having 1-3 heteroatoms independently selected from nitrogen, oxygen, and sulfur, provided that when Ring A is a 6-membered heteroaryl ring the 1-3 heteroatoms are each nitrogen;

each $R^1$ and $R^{1'}$ is independently selected from -hydrogen and $C_{1-4}$ aliphatic substituted with 0-3 instances of $R^x$, or:

$R^1$ and $R^{1'}$ may, together with the intervening atoms to which they are attached, form an optionally substituted 3- to 6-membered saturated, or partially unsaturated, heterocyclyl, carbocycle, or aryl ring having 0-3 heteroatoms independently selected from nitrogen, oxygen, and sulfur;

$R^x$ is —CN, —$NO_2$, halogen, —OR, —SR, —$N(R)_2$, —$C(O)N(R)_2$, —C(O)OR, —C(O)R, —N(R)C(O)R, —$SO_2N(R)_2$, or —$N(R)SO_2$;

$R^2$ is —CN, $C_{2-6}$ aliphatic substituted with m instances of $R^y$, wherein the $C_{2-6}$ aliphatic has at least one unit of unsaturation, or $R^2$ is selected from the group consisting of

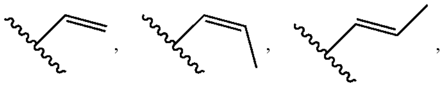

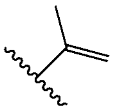,
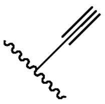, and
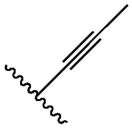;

each $R^y$ is independently selected from D, halogen, —CN, —$CO_2R$, —$N(R)_2$, and a 3- to 6-membered saturated or partially unsaturated heterocyclic ring having 1-3 heteroatoms independently selected from nitrogen, oxygen, and sulfur;

each $R^3$ is —$(CH_2)_r$-Cy, or $R^3$ is selected from the group consisting of

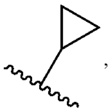,
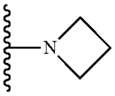,
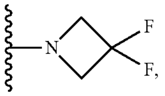

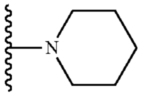,
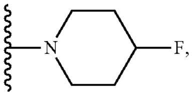

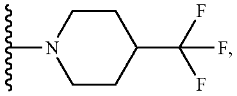
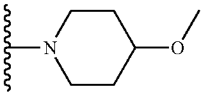,

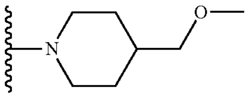,
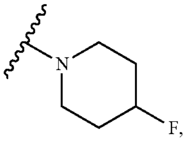

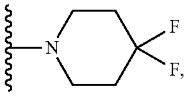
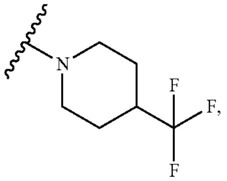

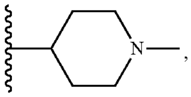,
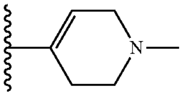,

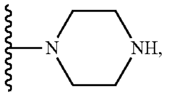
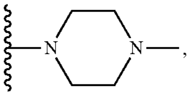,

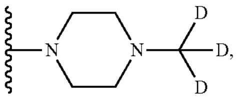
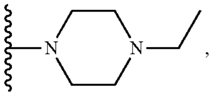,

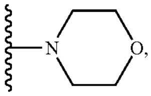
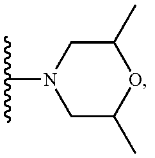

-continued

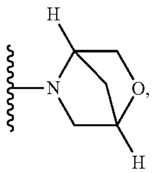
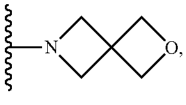

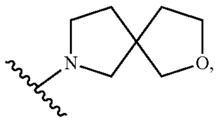
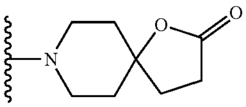,

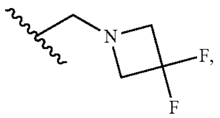
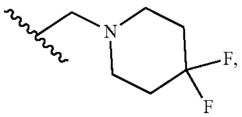

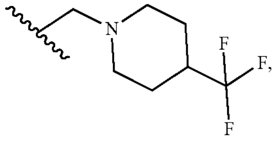

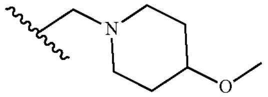,

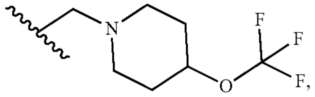

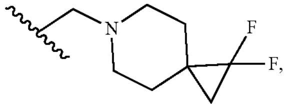

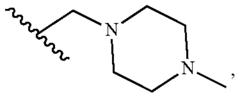,
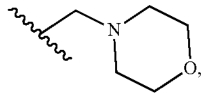

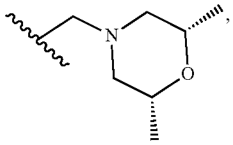,
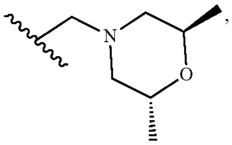,

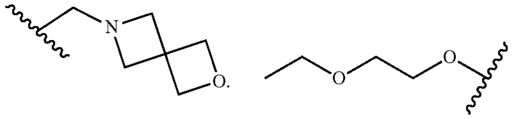

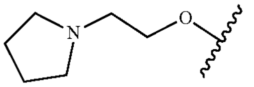 and

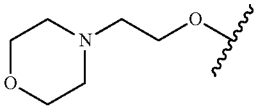;

each $R^4$ is independently selected from hydrogen, $C_{1-6}$ aliphatic, and —Cy, wherein the $C_{1-6}$ aliphatic is optionally substituted with one or more substituents each independently selected from D, halogen and —OR;

each $R^5$ is independently selected from —OR and —Cy;

each Cy is independently a ring selected from a 3- to 9-membered saturated or partially unsaturated monocyclic carbocyclic ring, a 3- to 9-membered saturated or partially unsaturated monocyclic heterocyclic ring having 1-3 heteroatoms independently selected from nitrogen, oxygen, and sulfur, phenyl, a 5- to 6-membered heteroaryl ring having 1-3 heteroatoms independently selected from nitrogen, oxygen, and sulfur, a 7- to 12-membered saturated or partially unsaturated fused, spirofused, or bridged bicyclic carbocyclic ring, or a 7- to 12-membered saturated or partially unsaturated fused, spirofused, or bridged bicyclic heterocyclic ring having 1-3 heteroatoms independently selected from nitrogen, oxygen, and sulfur, wherein the ring is optionally substituted with one or more substituents each independently selected from D, halogen, oxo, R, and $—(CH_2)_q—OR$;

each R is independently hydrogen or a $C_{1-6}$ aliphatic optionally substituted with one or more substituents each selected from D, halogen, —OH, and $—O—(C_{1-6}$ aliphatic), or:

two R groups on the same nitrogen are taken together with the nitrogen to form a 3-7 membered saturated or partially unsaturated heterocyclic ring having 1-3 heteroatoms selected from nitrogen, oxygen, or sulfur;

n is 0;

each of q, and r is independently 0-4; and tis 1-4.

2. The compound according to claim 1, wherein Ring A is selected from:

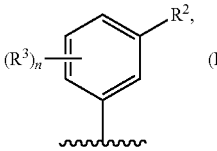 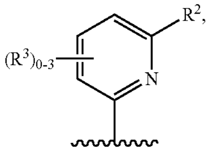

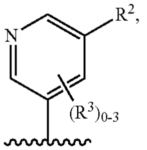 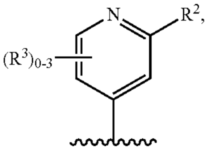 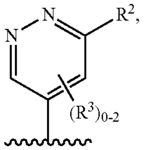

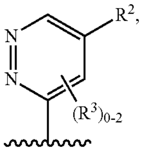 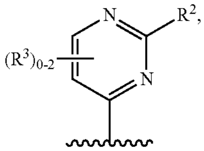 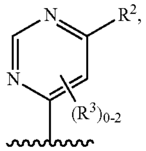

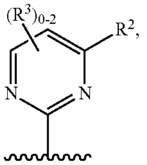 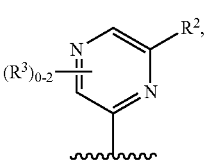

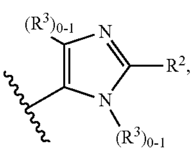 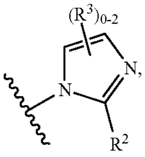

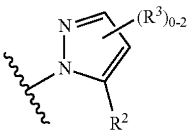 , 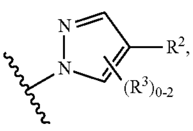

-continued

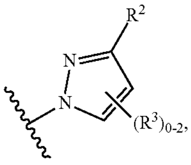 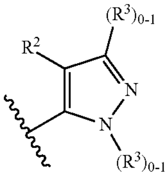 ,

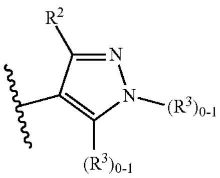 , 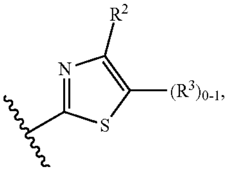

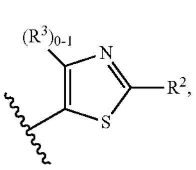 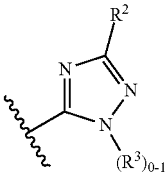 ,

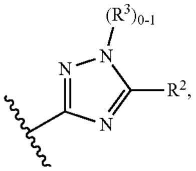 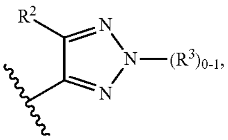

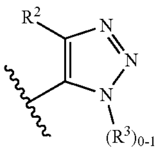 , 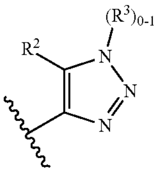 , 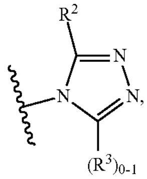

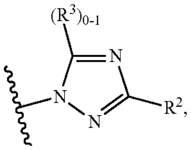 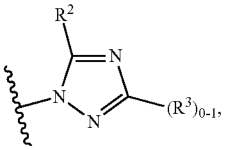

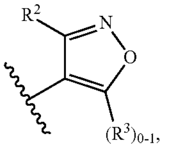 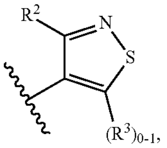 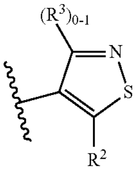 ,

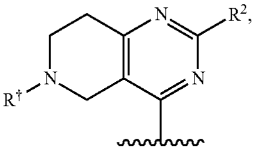 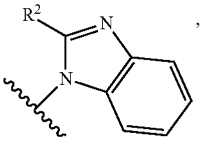 , and

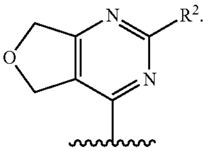

3. The compound according to claim 1, wherein the compound is selected from any of formulae II, III, IV, or V:

II

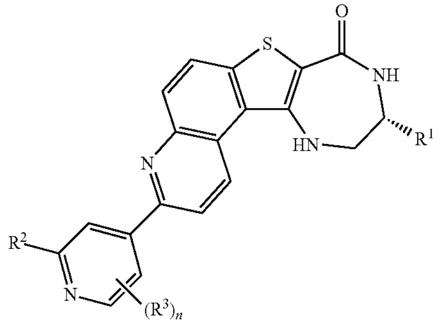

III

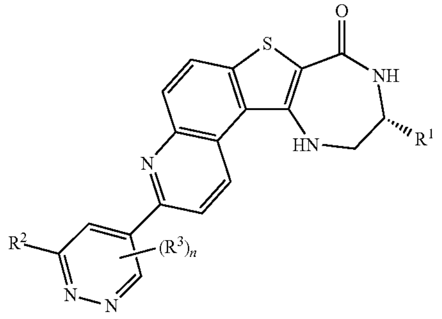

IV

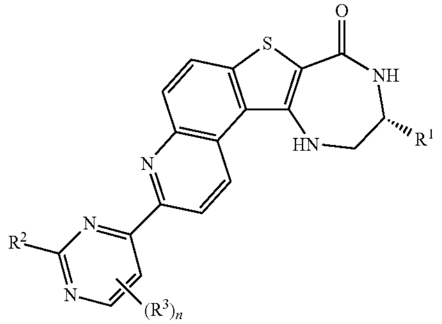

V

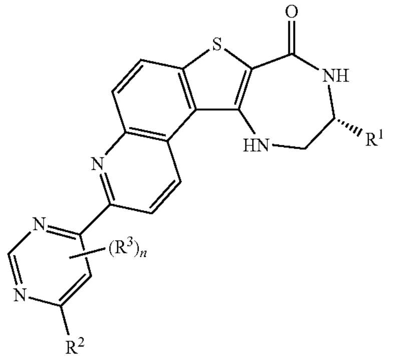

or a pharmaceutically acceptable salt thereof.

4. The compound according to claim 1, wherein $R^2$ is halogen.

5. The compound according to claim 1, wherein $R^2$ is selected from:

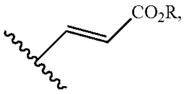 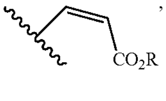 , 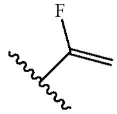 ,

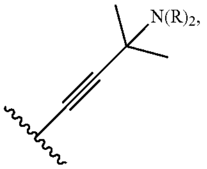 , 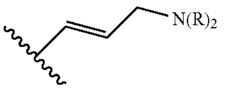

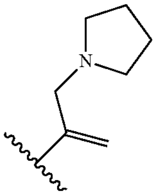 , 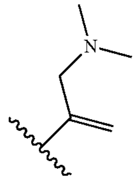 , and

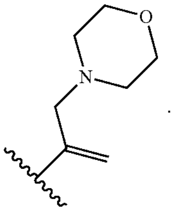 .

6. The compound according to claim 1, wherein $R^2$ is selected from

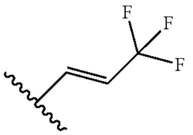 and 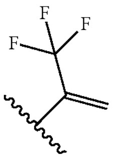 .

7. The compound according to claim 1, wherein the compound is selected from formulae II-a, II-b, II-c, III-a, III-b, IV-a, IV-b, IV-c, V-a, V-b, or V-c:

II-a

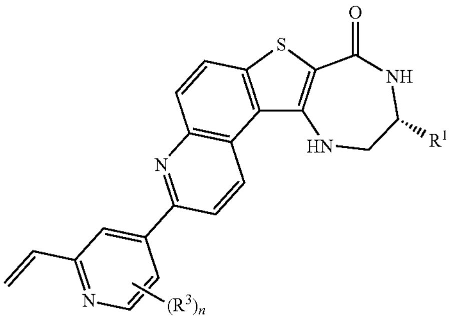

-continued
II-b
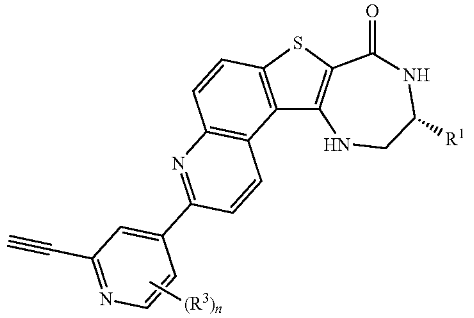
III-a
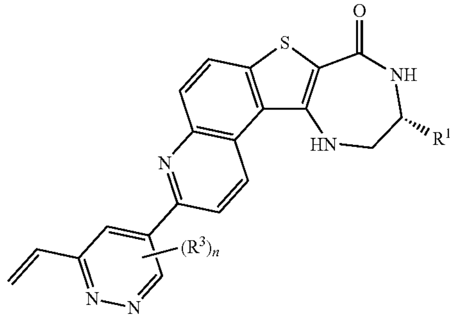
III-b
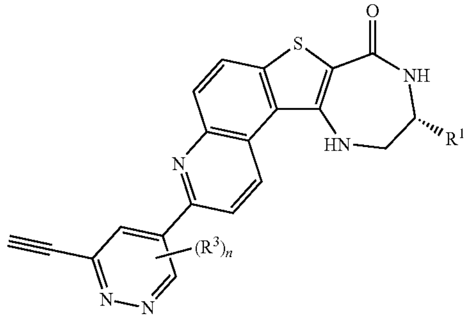
IV-a
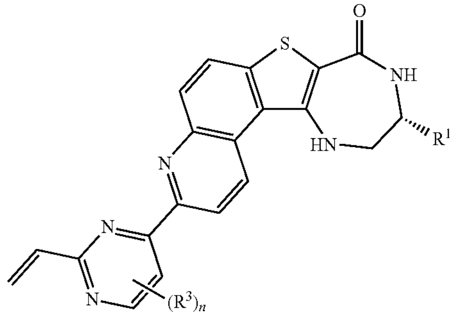
IV-b
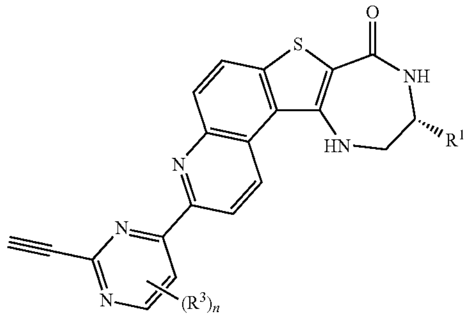
-continued
V-a
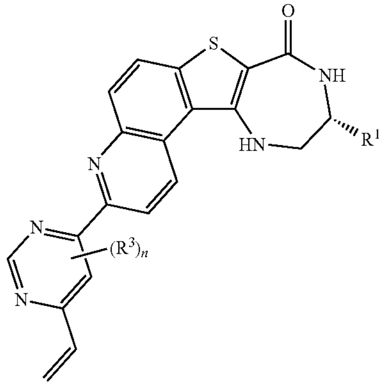
V-b
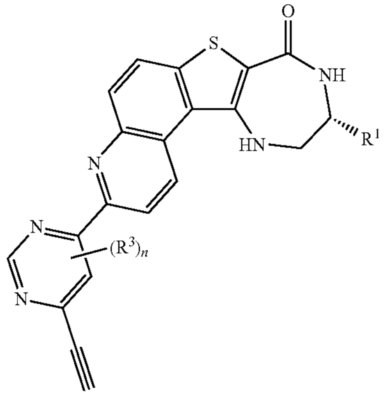
or a pharmaceutically acceptable salt thereof.
8. The compound according to claim 1, wherein the compound is selected from formulae II-a-i, II-a-ii, II-b-i, II-b-ii, II-c-i, II-c-ii, III-a-i, III-b-i, IV-a-i, IV-a-ii, IV-b-i, IV-b-ii, IV-c-i, IV-c-ii, V-a-i, V-b-i, or V-c-i:
II-a-i
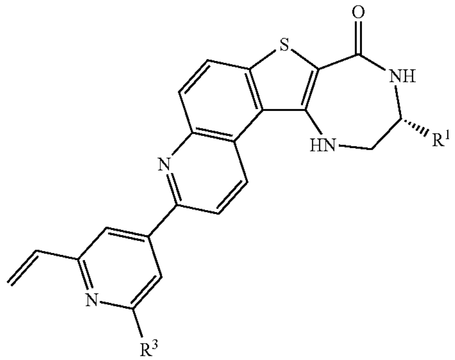

-continued
II-a-ii
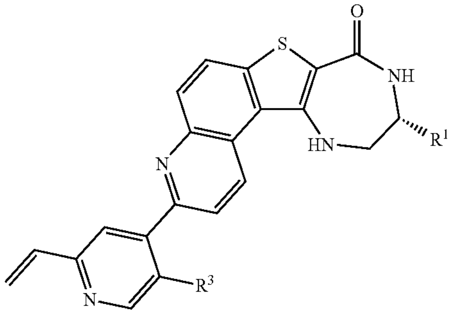
II-b-i
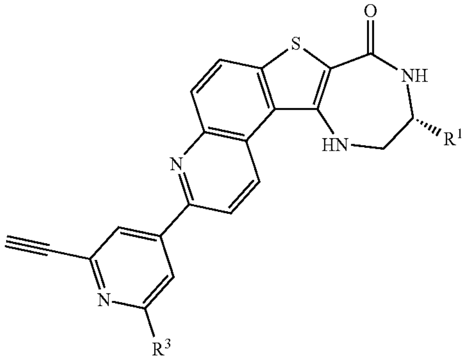
II-b-ii
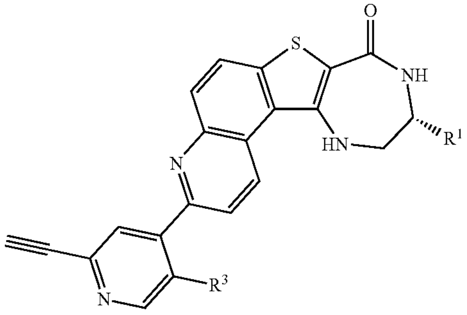
III-a-i
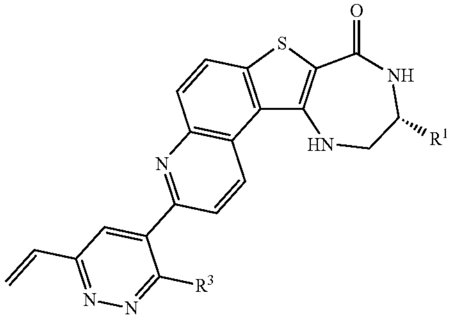
III-b-i
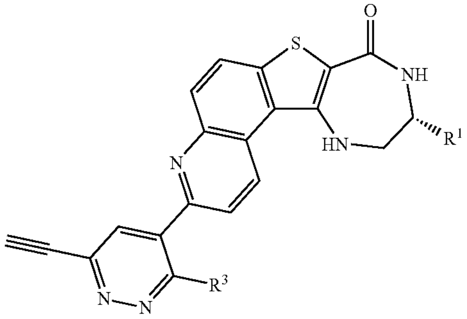
-continued
IV-a-i
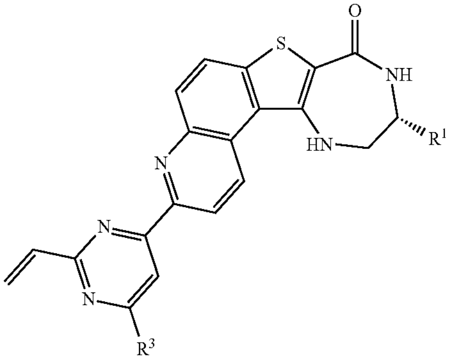
IV-a-ii
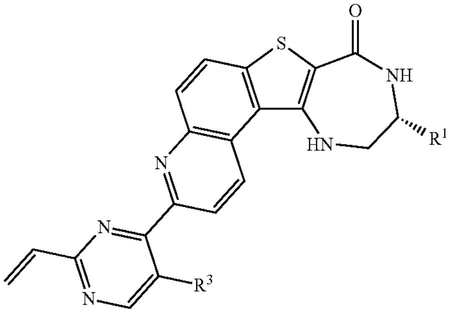
IV-b-i
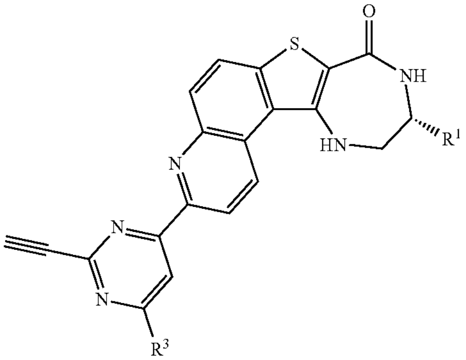
IV-b-ii
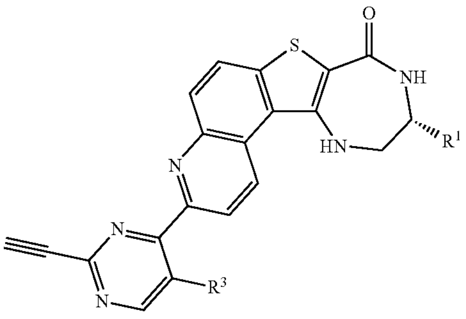

-continued

V-a-i

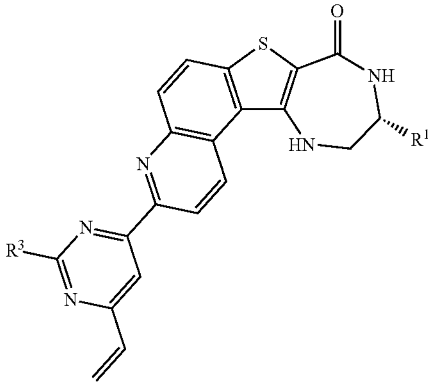

V-b-i

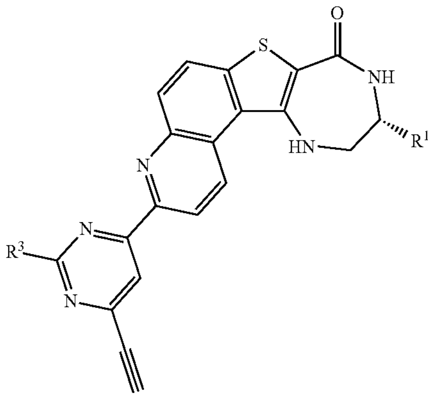

or a pharmaceutically acceptable salt thereof.

9. The compound according to claim 1, wherein $R^3$ is selected from —$CH_3$, —$CD_3$, —$CF_2H$, —$CF_3$, —$CH_2CH_3$,

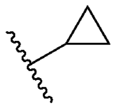 , 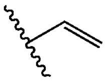 , 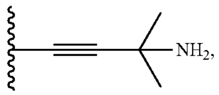

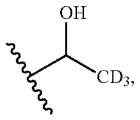 and 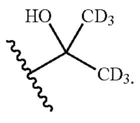

10. The compound according to claim 1, wherein $R^3$ is selected from —$OCH_3$, —$OCF_2H$, —$OCF_3$, —$O(CH_2)_2CH_3$, —$O(CH_2)_2OCH_2CH_3$, —$CH_2OH$, —$CH_2OCH_3$, —$CH_2OCH_2CH_3$,

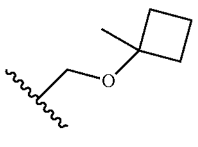 , 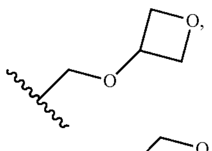

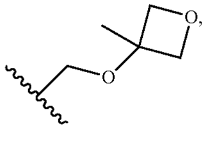 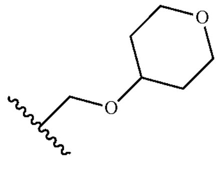 ,

-continued

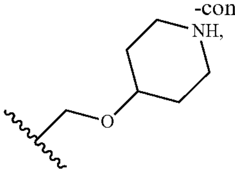 and

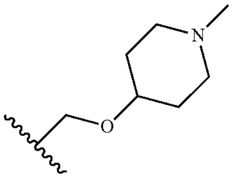 .

11. The compound of claim 1 or a pharmaceutically acceptable salt thereof, selected from the group consisting of:

(R)-3-(2-ethynyl-5-fluoropyrimidin-4-yl)-10-methyl-9,10,11,12-tetrahydro-8H-[1,4]diazepino[5',6':4,5]thieno[3,2-f]quinolin-8-one (I-1)

(R)-3-(5-fluoro-2-vinylpyrimidin-4-yl)-10-methyl-9,10,11,12-tetrahydro-8H-[1,4]diazepino[5',6':4,5]thieno[3,2-f]quinolin-8-one (I-2)

(R)-3-(2-chloro-5-(ethoxymethyl) pyrimidin-4-yl)-10-methyl-9,10,11,12-tetrahydro-8H-[1,4]diazepino[5',6':4,5]thieno[3,2-f]quinolin-8-one (I-3)

(R)-3-(2-chloro-5-(trifluoromethyl) pyrimidin-4-yl)-10-methyl-9,10,11,12-tetrahydro-8H-[1,4]diazepino[5',6':4,5]thieno[3,2-f]quinolin-8-one (I-4)

(R)-3-(5-(ethoxymethyl)-2-vinylpyrimidin-4-yl)-10-methyl-9,10,11,12-tetrahydro-8H-[1,4]diazepino[5',6':4,5]thieno[3,2-f]quinolin-8-one (I-5)

(R)-3-(2-chloro-5-methylpyrimidin-4-yl)-10-methyl-9,10,11,12-tetrahydro-8H-[1,4]diazepino[5',6':4,5]thieno[3,2-f]quinolin-8-one (I-6)

(R)-3-(6-chloro-2-(methoxymethyl)pyrimidin-4-yl)-10-methyl-9,10,11,12-tetrahydro-8H-[1,4]diazepino[5',6':4,5]thieno[3,2-f]quinolin-8-one (I-7)

(R)-3-(2-chloropyrimidin-4-yl)-10-methyl-9,10,11,12-tetrahydro-8H-[1,4]diazepino[5',6':4,5]thieno[3,2-f]quinolin-8-one (1-8)

(R)-2-chloro-4-(10-methyl-8-oxo-9,10,11,12-tetrahydro-8H-[1,4]diazepino[5',6':4,5]thieno[3,2-f]quinolin-3-yl)pyrimidine-5-carbonitrile (I-9)

(R)-3-(2-chloro-5-methoxypyrimidin-4-yl)-10-methyl-9,10,11,12-tetrahydro-8H-[1,4]diazepino[5',6':4,5]thieno[3,2-f]quinolin-8-one (I-10)

(R)-3-(6-chloropyrimidin-4-yl)-10-methyl-9,10,11,12-tetrahydro-8H-[1,4]diazepino[5',6':4,5]thieno[3,2-f]quinolin-8-one (I-11)

(R)-3-(5-(ethoxymethyl)-2-ethynylpyrimidin-4-yl)-10-methyl-9,10,11,12-tetrahydro-8H-[1,4]diazepino[5',6':4,5]thieno[3,2-f]quinolin-8-one (I-12)

(R)-3-(2-(methoxymethyl)-6-vinylpyrimidin-4-yl)-10-methyl-9,10,11,12-tetrahydro-8H-[1,4]diazepino[5',6':4,5]thieno[3,2-f]quinolin-8-one (I-13)

(R)-3-(6-chloro-2-((piperidin-4-yloxy)methyl)pyrimidin-4-yl)-10-methyl-9,10,11,12-tetrahydro-8H-[1,4]diazepino[5',6':4,5]thieno[3,2-f]quinolin-8-one (I-14)

(R)-3-(6-chloro-2-(((1-methylpiperidin-4-yl)oxy)methyl)pyrimidin-4-yl)-10-methyl-9,10,11,12-tetrahydro-8H-[1,4]diazepino[5',6':4,5]thieno[3,2-f]quinolin-8-one (I-15)

(R)-3-(2-chloro-6-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-16)

(R)-3-(6-chloro-2-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-17)

(R)-10-methyl-3-(6-(4-methylpiperazin-1-yl)-2-vinylpyrimidin-4-yl)-9,10,11,12-tetrahydro-8H-[1,4]diazepino[5',6':4,5]thieno[3,2-f]quinolin-8-one (I-18)

(R)-10-methyl-3-(2-(4-methylpiperazin-1-yl)-6-vinylpyrimidin-4-yl)-9,10,11,12-tetrahydro-8H-[1,4]diazepino[5',6':4,5]thieno[3,2-f]quinolin-8-one (I-19)

(R)-3-(2-chloro-5-((oxetan-3-yloxy)methyl)pyrimidin-4-yl)-10-methyl-9,10,11,12-tetrahydro-8H-[1,4]diazepino[5',6':4,5]thieno[3,2-f]quinolin-8-one (I-20)

(R)-10-methyl-3-(5-((oxetan-3-yloxy)methyl)-2-vinylpyrimidin-4-yl)-9,10,11,12-tetrahydro-8H-[1,4]diazepino[5',6':4,5]thieno[3,2-f]quinolin-8-one (I-21)

(R)-3-(2-(ethoxymethyl)-6-vinylpyrimidin-4-yl)-10-methyl-9,10,11,12-tetrahydro-8H-[1,4]diazepino[5',6':4,5]thieno[3,2-f]quinolin-8-one (I-22)

(R)-3-(6-chloro-2-(((tetrahydro-2H-pyran-4-yl)oxy)methyl)pyrimidin-4-yl)-10-methyl-9,10,11,12-tetrahydro-8H-[1,4]diazepino[5',6':4,5]thieno[3,2-f]quinolin-8-one (I-23)

(R)-3-(2-chloro-5-(((tetrahydro-2H-pyran-4-yl)oxy)methyl)pyrimidin-4-yl)-10-methyl-9,10,11,12-tetrahydro-8H-[1,4]diazepino[5',6':4,5]thieno[3,2-f]quinolin-8-one (I-24)

(R)-10-methyl-3-(5-(((tetrahydro-2H-pyran-4-yl)oxy)methyl)-2-vinylpyrimidin-4-yl)-9,10,11,12-tetrahydro-8H-[1,4]diazepino[5',6':4,5]thieno[3,2-f]quinolin-8-one (I-25)

(R)-10-methyl-3-(5-((1-methylcyclobutoxy)methyl)-2-vinylpyrimidin-4-yl)-9,10,11,12-tetrahydro-8H-[1,4]diazepino[5',6':4,5]thieno[3,2-f]quinolin-8-one (I-26)

(R)-3-(2-chloro-5-((1-methylcyclobutoxy)methyl)pyrimidin-4-yl)-10-methyl-9,10,11,12-tetrahydro-8H-[1,4]diazepino[5',6':4,5]thieno[3,2-f]quinolin-8-one (I-27)

(R)-3-(2-chloro-5-(((3-methyloxetan-3-yl)oxy)methyl)pyrimidin-4-yl)-10-methyl-9,10,11,12-tetrahydro-8H-[1,4]diazepino[5',6':4,5]thieno[3,2-f]quinolin-8-one (I-28)

(R)-10-methyl-3-(5-(((3-methyloxetan-3-yl)oxy)methyl)-2-vinylpyrimidin-4-yl)-9,10,11,12-tetrahydro-8H-[1,4]diazepino[5',6':4,5]thieno[3,2-f]quinolin-8-one (I-29)

(R)-3-(6-chloro-2-(ethoxymethyl)pyrimidin-4-yl)-10-methyl-9,10,11,12-tetrahydro-8H-[1,4]diazepino[5',6':4,5]thieno[3,2-f]quinolin-8-one (I-30)

(R)-3-(5-fluoro-2-(1-fluorovinyl)pyrimidin-4-yl)-10-methyl-9,10,11,12-tetrahydro-8H-[1,4]diazepino[5',6':4,5]thieno[3,2-f]quinolin-8-one (I-31)

(R)-3-(5-methoxy-2-vinylpyrimidin-4-yl)-10-methyl-9,10,11,12-tetrahydro-8H-[1,4]diazepino[5',6':4,5]thieno[3,2-f]quinolin-8-one (I-32)

(R)-10-methyl-3-(5-methyl-2-vinylpyrimidin-4-yl)-9,10,11,12-tetrahydro-8H-[1,4]diazepino[5',6':4,5]thieno[3,2-f]quinolin-8-one (I-33)

(R)-10-methyl-3-(6-vinylpyrimidin-4-yl)-9,10,11,12-tetrahydro-8H-[1,4]diazepino[5',6':4,5]thieno[3,2-f]quinolin-8-one (I-34)

(R,E)-3-(2-(ethoxymethyl)-6-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-35)

(R,Z)-3-(2-(ethoxymethyl)-6-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-36)

(R)-3-(2-(ethoxymethyl)-6-(prop-1-en-2-yl)pyrimidin-4-yl)-10-methyl-9,10,11,12-tetrahydro-8H-[1,4]diazepino[5',6':4,5]thieno[3,2-f]quinolin-8-one (I-37)

(R)-3-(6-ethynylpyrimidin-4-yl)-10-methyl-9,10,11,12-tetrahydro-8H-[1,4]diazepino[5',6':4,5]thieno[3,2-f]quinolin-8-one (I-38)

(R)-3-(2-(ethoxymethyl)-6-ethynylpyrimidin-4-yl)-10-methyl-9,10,11,12-tetrahydro-8H-[1,4]diazepino[5',6':4,5]thieno[3,2-f]quinolin-8-one (I-39)

(R)-3-(2-ethynylpyrimidin-4-yl)-10-methyl-9,10,11,12-tetrahydro-8H-[1,4]diazepino[5',6':4,5]thieno[3,2-f]quinolin-8-one (I-40)

(R)-3-(2-ethynyl-5-methylpyrimidin-4-yl)-10-methyl-9,10,11,12-tetrahydro-8H-[1,4]diazepino[5',6':4,5]thieno[3,2-f]quinolin-8-one (I-41)

(R)-3-(2-ethynyl-5-methoxypyrimidin-4-yl)-10-methyl-9,10,11,12-tetrahydro-8H-[1,4]diazepino[5',6':4,5]thieno[3,2-f]quinolin-8-one (I-42)

(R)-3-(4-chloro-6-(4-methylpiperazin-1-yl)pyrimidin-2-yl)-10-methyl-9,10,11,12-tetrahydro-8H-[1,4]diazepino[5',6':4,5]thieno[3,2-f]quinolin-8-one (I-43)

(R)-3-(5-fluoro-2-(prop-1-yn-1-yl)pyrimidin-4-yl)-10-methyl-9,10,11,12-tetrahydro-8H-[1,4]diazepino[5',6':4,5]thieno[3,2-f]quinolin-8-one (I-44)

(R,E)-3-(5-fluoro-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-45)

(R,Z)-3-(5-fluoro-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-46)

(R)-3-(5-fluoro-2-(prop-1-en-2-yl)pyrimidin-4-yl)-10-methyl-9,10,11,12-tetrahydro-8H-[1,4]diazepino[5',6':4,5]thieno[3,2-f]quinolin-8-one (I-47)

(R,E)-3-(5-(ethoxymethyl)-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-48)

(R,Z)-3-(5-(ethoxymethyl)-2-(prop-1-en-1-yl)pyrimidin-4-yl)-10-methyl-9,10,11,12-tetrahydro-8H-[1,4]diazepino[5',6':4,5]thieno[3,2-f]quinolin-8-one (I-49)

(R)-3-(5-(ethoxymethyl)-2-(prop-1-en-2-yl)pyrimidin-4-yl)-10-methyl-9,10,11,12-tetrahydro-8H-[1,4]diazepino[5',6':4,5]thieno[3,2-f]quinolin-8-one (I-50)

(R)-3-(6-ethynylpyridazin-4-yl)-10-methyl-9,10,11,12-tetrahydro-8H-[1,4]diazepino[5',6':4,5]thieno[3,2-f]quinolin-8-one (I-51)

(R)-3-(6-chloropyridin-2-yl)-10-methyl-9,10,11,12-tetrahydro-8H-[1,4]diazepino[5',6':4,5]thieno[3,2-f]quinolin-8-one (I-52)

(R)-10-methyl-3-(2-(prop-1-yn-1-yl)pyrimidin-4-yl)-9,10,11,12-tetrahydro-8H-[1,4]diazepino[5',6':4,5]thieno[3,2-f]quinolin-8-one (I-53)

(R)-10-methyl-3-(6-vinylpyridin-2-yl)-9,10,11,12-tetrahydro-8H-[1,4]diazepino[5',6':4,5]thieno[3,2-f]quinolin-8-one (I-54)

(R)-10-methyl-3-(2-vinylpyridin-4-yl)-9,10,11,12-tetrahydro-8H-[1,4]diazepino[5',6':4,5]thieno[3,2-f]quinolin-8-one (I-55)

(R)-3-(6-ethynylpyridin-2-yl)-10-methyl-9,10,11,12-tetrahydro-8H-[1,4]diazepino[5',6':4,5]thieno[3,2-f]quinolin-8-one (I-56)

(R)-3-(2-ethynylpyridin-4-yl)-10-methyl-9,10,11,12-tetrahydro-8H-[1,4]diazepino[5',6':4,5]thieno[3,2-f]quinolin-8-one (I-57)

(R)-3-(2,6-dichloropyrimidin-4-yl)-10-methyl-9,10,11,12-tetrahydro-8H-[1,4]diazepino[5',6':4,5]thieno[3,2-f]quinolin-8-one (I-58)

(R)-3-(6-ethynyl-2-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-59)

(R)-3-(2-ethynyl-6-(4-methylpiperazin-1-yl)pyrimidin-4-yl)-10-methyl-9,10,11,12-tetrahydro-8H-[1,4]diazepino[5',6':4,5]thieno[3,2-f]quinolin-8-one (I-60)

(R)-3-(4-ethynyl-6-(4-methylpiperazin-1-yl)pyrimidin-2-yl)-10-methyl-9,10,11,12-tetrahydro-8H-[1,4]diazepino[5',6':4,5]thieno[3,2-f]quinolin-8-one (I-61)

(R)-10-methyl-3-(4-(4-methylpiperazin-1-yl)-6-vinylpyrimidin-2-yl)-9,10,11,12-tetrahydro-8H-[1,4]diazepino[5',6':4,5]thieno[3,2-f]quinolin-8-one (I-62)

(R)-3-(6-(3-amino-3-methylbut-1-yn-1-yl)-2-chloropyrimidin-4-yl)-10-methyl-9,10,11,12-tetrahydro-8H-[1,4]diazepino[5',6':4,5]thieno[3,2-f]quinolin-8-one (I-63)

(R)-3-(2-(3-amino-3-methylbut-1-yn-1-yl)-6-chloropyrimidin-4-yl)-10-methyl-9,10,11,12-tetrahydro-8H-[1,4]diazepino[5',6':4,5]thieno[3,2-f]quinolin-8-one (I-64)

(R)-3-(6-(3-amino-3-methylbut-1-yn-1-yl)-2-ethynylpyrimidin-4-yl)-10-methyl-9,10,11,12-tetrahydro-8H-[1,4]diazepino[5',6':4,5]thieno[3,2-f]quinolin-8-one (I-65)

(R)-3-(2-(3-amino-3-methylbut-1-yn-1-yl)-6-vinylpyrimidin-4-yl)-10-methyl-9,10,11,12-tetrahydro-8H-[1,4]diazepino[5',6':4,5]thieno[3,2-f]quinolin-8-one (I-66)

(R)-3-(2-(3-amino-3-methylbut-1-yn-1-yl)-6-ethynylpyrimidin-4-yl)-10-methyl-9,10,11,12-tetrahydro-8H-[1,4]diazepino[5',6':4,5]thieno[3,2-f]quinolin-8-one (I-67)

(R)-3-(2,6-dichloropyridin-4-yl)-10-methyl-9,10,11,12-tetrahydro-8H-[1,4]diazepino[5',6':4,5]thieno[3,2-f]quinolin-8-one (I-68)

(R)-3-(2-chloro-5-fluoropyridin-4-yl)-10-methyl-9,10,11,12-tetrahydro-8H-[1,4]diazepino[5',6':4,5]thieno[3,2-f]quinolin-8-one (I-69)

(R)-3-(5-fluoro-2-vinylpyridin-4-yl)-10-methyl-9,10,11,12-tetrahydro-8H-[1,4]diazepino[5',6':4,5]thieno[3,2-f]quinolin-8-one (I-70)

(R)-3-(2-ethynyl-5-fluoropyridin-4-yl)-10-methyl-9,10,11,12-tetrahydro-8H-[1,4]diazepino[5',6':4,5]thieno[3,2-f]quinolin-8-one (I-71)

(R)-3-(2-chloro-6-vinylpyridin-4-yl)-10-methyl-9,10,11,12-tetrahydro-8H-[1,4]diazepino[5',6':4,5]thieno[3,2-f]quinolin-8-one (I-72)

(R)-3-(2-chloro-6-ethynylpyridin-4-yl)-10-methyl-9,10,11,12-tetrahydro-8H-[1,4]diazepino[5',6':4,5]thieno[3,2-f]quinolin-8-one (I-73)

(R)-3-(6-chloro-2-(hydroxymethyl)pyrimidin-4-yl)-10-methyl-9,10,11,12-tetrahydro-8H-[1,4]diazepino[5',6':4,5]thieno[3,2-f]quinolin-8-one (I-74)

(R)-3-(2-chloro-5-(hydroxymethyl)pyrimidin-4-yl)-10-methyl-9,10,11,12-tetrahydro-8H-[1,4]diazepino[5',6':4,5]thieno[3,2-f]quinolin-8-one (I-75)

(R)-3-(2-(hydroxymethyl)-6-vinylpyrimidin-4-yl)-10-methyl-9,10,11,12-tetrahydro-8H-[1,4]diazepino[5',6':4,5]thieno[3,2-f]quinolin-8-one (I-76)

(R)-3-(5-(hydroxymethyl)-2-vinylpyrimidin-4-yl)-10-methyl-9,10,11,12-tetrahydro-8H-[1,4]diazepino[5',6':4,5]thieno[3,2-f]quinolin-8-one (I-77)

(R)-3-(6-ethynyl-2-(hydroxymethyl)pyrimidin-4-yl)-10-methyl-9,10,11,12-tetrahydro-8H-[1,4]diazepino[5',6':4,5]thieno[3,2-f]quinolin-8-one (I-78)

(R)-3-(2-ethynyl-5-(hydroxymethyl)pyrimidin-4-yl)-10-methyl-9,10,11,12-tetrahydro-8H-[1,4]diazepino[5',6':4,5]thieno[3,2-f]quinolin-8-one (I-79)

(R)-3-(2,6-divinylpyridin-4-yl)-10-methyl-9,10,11,12-tetrahydro-8H-[1,4]diazepino[5',6':4,5]thieno[3,2-f]quinolin-8-one (I-80)

(R)-3-(5-chloropyridin-3-yl)-10-methyl-9,10,11,12-tetrahydro-8H-[1,4]diazepino[5',6':4,5]thieno[3,2-f]quinolin-8-one (I-81)

(R)-10-methyl-3-(5-vinylpyridin-3-yl)-9,10,11,12-tetrahydro-8H-[1,4]diazepino[5',6':4,5]thieno[3,2-f]quinolin-8-one (I-82)

(R)-3-(5-ethynylpyridin-3-yl)-10-methyl-9,10,11,12-tetrahydro-8H-[1,4]diazepino[5',6':4,5]thieno[3,2-f]quinolin-8-one (I-83)

(R)-3-(2-chloro-6-(hydroxymethyl)pyrimidin-4-yl)-10-methyl-9,10,11,12-tetrahydro-8H-[1,4]diazepino[5',6':4,5]thieno[3,2-f]quinolin-8-one (I-84)

(R)-3-(6-(hydroxymethyl)-2-vinylpyrimidin-4-yl)-10-methyl-9,10,11,12-tetrahydro-8H-[1,4]diazepino[5',6':4,5]thieno[3,2-f]quinolin-8-one (I-85)

(R)-3-(2-ethynyl-6-(hydroxymethyl)pyrimidin-4-yl)-10-methyl-9,10,11,12-tetrahydro-8H-[1,4]diazepino[5',6':4,5]thieno[3,2-f]quinolin-8-one (I-86)

(R)-3-(2-chloro-6-((4-methylpiperazin-1-yl)methyl)pyrimidin-4-yl)-10-methyl-9,10,11,12-tetrahydro-8H-[1,4]diazepino[5',6':4,5]thieno[3,2-f]quinolin-8-one (I-87)

(R)-10-methyl-3-(6-((4-methylpiperazin-1-yl)methyl)-2-vinylpyrimidin-4-yl)-9,10,11,12-tetrahydro-8H-[1,4]diazepino[5',6':4,5]thieno[3,2-f]quinolin-8-one (I-88)

(R)-3-(2-ethynyl-6-((4-methylpiperazin-1-yl)methyl)pyrimidin-4-yl)-10-methyl-9,10,11,12-tetrahydro-8H-[1,4]diazepino[5',6':4,5]thieno[3,2-f]quinolin-8-one (I-89)

(R)-3-(6-(1-fluorovinyl)pyridin-2-yl)-10-methyl-9,10,11,12-tetrahydro-8H-[1,4]diazepino[5',6':4,5]thieno[3,2-f]quinolin-8-one (I-90)

(R)-3-(6-ethynyl-3-methoxypyridazin-4-yl)-10-methyl-9,10,11,12-tetrahydro-8H-[1,4]diazepino[5',6':4,5]thieno[3,2-f]quinolin-8-one (I-91)

(R)-3-(5-(difluoromethyl)-2-ethynylpyridin-4-yl)-10-methyl-9,10,11,12-tetrahydro-8H-[1,4]diazepino[5',6':4,5]thieno[3,2-f]quinolin-8-one (I-92)

(R)-3-(2-chloro-5-(difluoromethyl)pyridin-4-yl)-10-methyl-9,10,11,12-tetrahydro-8H-[1,4]diazepino[5',6':4,5]thieno[3,2-f]quinolin-8-one (I-93)

(R)-3-(2-chloro-6-(4-methylpiperazin-1-yl)pyridin-4-yl)-10-methyl-9,10,11,12-tetrahydro-8H-[1,4]diazepino[5',6':4,5]thieno[3,2-f]quinolin-8-one (I-94)

(R)-3-(2-ethynyl-6-(4-methylpiperazin-1-yl)pyridin-4-yl)-10-methyl-9,10,11,12-tetrahydro-8H-[1,4]diazepino[5',6':4,5]thieno[3,2-f]quinolin-8-one (I-95)

(R)-10-methyl-3-(2-(4-methylpiperazin-1-yl)-6-vinylpyridin-4-yl)-9,10,11,12-tetrahydro-8H-[1,4]diazepino[5',6':4,5]thieno[3,2-f]quinolin-8-one (I-96)

(R)-3-(2-chloro-6-(hydroxymethyl)pyridin-4-yl)-10-methyl-9,10,11,12-tetrahydro-8H-[1,4]diazepino[5',6':4,5]thieno[3,2-f]quinolin-8-one (I-97)

(R)-3-(2-ethynyl-6-(hydroxymethyl)pyridin-4-yl)-10-methyl-9,10,11,12-tetrahydro-8H-[1,4]diazepino[5',6':4,5]thieno[3,2-f]quinolin-8-one (I-98)

(R)-3-(2-(hydroxymethyl)-6-vinylpyridin-4-yl)-10-methyl-9,10,11,12-tetrahydro-8H-[1,4]diazepino[5',6':4,5]thieno[3,2-f]quinolin-8-one (I-99)

(R)-3-(6-chloro-1'-methyl-1',2',3',6'-tetrahydro-[2,4'-bipyridin]-4-yl)-10-methyl-9,10,11,12-tetrahydro-8H-[1,4]diazepino[5',6':4,5]thieno[3,2-f]quinolin-8-one (I-100)

(R)-10-methyl-3-(1'-methyl-6-vinyl-1',2',3',6'-tetrahydro-[2,4'-bipyridin]-4-yl)-9,10,11,12-tetrahydro-8H-[1,4]diazepino[5',6':4,5]thieno[3,2-f]quinolin-8-one (I-101)

(R)-3-(6-ethynyl-1'-methyl-1',2',3',6'-tetrahydro-[2,4'-bipyridin]-4-yl)-10-methyl-9,10,11,12-tetrahydro-8H-[1,4]diazepino[5',6':4,5]thieno[3,2-f]quinolin-8-one (I-102)

(R)-3-(2-chloro-6-(1-methylpiperidin-4-yl)pyridin-4-yl)-10-methyl-9,10,11,12-tetrahydro-8H-[1,4]diazepino[5',6':4,5]thieno[3,2-f]quinolin-8-one (I-103)

(R)-3-(6-ethynyl-3-(methylamino)pyridazin-4-yl)-10-methyl-9,10,11,12-tetrahydro-8H-[1,4]diazepino[5',6':4,5]thieno[3,2-f]quinolin-8-one (I-104)

(R)-3-(3-(dimethylamino)-6-ethynylpyridazin-4-yl)-10-methyl-9,10,11,12-tetrahydro-8H-[1,4]diazepino[5',6':4,5]thieno[3,2-f]quinolin-8-one (I-105)

(R)-10-methyl-3-(2-(1-methylpiperidin-4-yl)-6-vinylpyridin-4-yl)-9,10,11,12-tetrahydro-8H-[1,4]diazepino[5',6':4,5]thieno[3,2-f]quinolin-8-one (I-106)

(R)-3-(2-ethynyl-6-(1-methylpiperidin-4-yl)pyridin-4-yl)-10-methyl-9,10,11,12-tetrahydro-8H-[1,4]diazepino[5',6':4,5]thieno[3,2-f]quinolin-8-one (I-107)

(R)-3-(2-(1-fluorovinyl)pyridin-4-yl)-10-methyl-9,10,11,12-tetrahydro-8H-[1,4]diazepino[5',6':4,5]thieno[3,2-f]quinolin-8-one (I-108)

(R)-10-methyl-3-(5-methyl-2-vinylpyridin-4-yl)-9,10,11,12-tetrahydro-8H-[1,4]diazepino[5',6':4,5]thieno[3,2-f]quinolin-8-one (I-109)

(R)-10-methyl-3-(2-methyl-6-vinylpyridin-4-yl)-9,10,11,12-tetrahydro-8H-[1,4]diazepino[5',6':4,5]thieno[3,2-f]quinolin-8-one (I-110)

(R)-3-(2-ethynyl-5-methylpyridin-4-yl)-10-methyl-9,10,11,12-tetrahydro-8H-[1,4]diazepino[5',6':4,5]thieno[3,2-f]quinolin-8-one (I-111)

(R)-3-(2-ethynyl-6-methylpyridin-4-yl)-10-methyl-9,10,11,12-tetrahydro-8H-[1,4]diazepino[5',6':4,5]thieno[3,2-f]quinolin-8-one (I-112)

(R,E)-10-methyl-3-(2-(prop-1-en-1-yl)pyridin-4-yl)-9,10,11,12-tetrahydro-8H-[1,4]diazepino[5',6':4,5]thieno[3,2-f]quinolin-8-one (I-113)

(R,E)-3-(2-(3-(dimethylamino)prop-1-en-1-yl)pyridin-4-yl)-10-methyl-9,10,11,12-tetrahydro-8H-[1,4]diazepino[5',6':4,5]thieno[3,2-f]quinolin-8-one (I-114)

(R,E)-3-(6-(3-(dimethylamino)prop-1-en-1-yl)pyrimidin-4-yl)-10-methyl-9,10,11,12-tetrahydro-8H-[1,4]diazepino[5',6':4,5]thieno[3,2-f]quinolin-8-one (I-115)

(R)-10-methyl-3-(2-(3-(pyrrolidin-1-yl)prop-1-en-2-yl)pyridin-4-yl)-9,10,11,12-tetrahydro-8H-[1,4]diazepino[5',6':4,5]thieno[3,2-f]quinolin-8-one (I-116)

(R)-3-(2-(3-(dimethylamino)prop-1-en-2-yl)pyridin-4-yl)-10-methyl-9,10,11,12-tetrahydro-8H-[1,4]diazepino[5',6':4,5]thieno[3,2-f]quinolin-8-one (I-117)

(R)-10-methyl-3-(3-(2-(pyrrolidin-1-yl)ethoxy)-6-vinylpyridazin-4-yl)-9,10,11,12-tetrahydro-8H-[1,4]diazepino[5',6':4,5]thieno[3,2-f]quinolin-8-one (I-118)

(R)-3-(6-chloro-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one (I-119)

(R)-3-(6-ethynyl-3-(2-(pyrrolidin-1-yl)ethoxy)pyridazin-4-yl)-10-methyl-9,10,11,12-tetrahydro-8H-[1,4]diazepino[5',6':4,5]thieno[3,2-f]quinolin-8-one (I-120)

(R)-3-(2-((4-methoxypiperidin-1-yl)methyl)-6-vinylpyridin-4-yl)-10-methyl-9,10,11,12-tetrahydro-8H-[1,4]diazepino[5',6':4,5]thieno[3,2-f]quinolin-8-one (I-121)

(R)-3-(2-ethynyl-6-((4-methoxypiperidin-1-yl)methyl)pyridin-4-yl)-10-methyl-9,10,11,12-tetrahydro-8H-[1,4]diazepino[5',6':4,5]thieno[3,2-f]quinolin-8-one (I-122)

(R)-3-(2-((4,4-difluoropiperidin-1-yl)methyl)-6-vinylpyridin-4-yl)-10-methyl-9,10,11,12-tetrahydro-8H-[1,4]diazepino[5',6':4,5]thieno[3,2-f]quinolin-8-one (I-123)

(R)-3-(2-((4,4-difluoropiperidin-1-yl)methyl)-6-ethynylpyridin-4-yl)-10-methyl-9,10,11,12-tetrahydro-8H-[1,4]diazepino[5',6':4,5]thieno[3,2-f]quinolin-8-one (I-124)

(R)-10-methyl-3-(2-((4-methylpiperazin-1-yl)methyl)-6-vinylpyridin-4-yl)-9,10,11,12-tetrahydro-8H-[1,4]diazepino[5',6':4,5]thieno[3,2-f]quinolin-8-one (I-125)

(R)-3-(2-ethynyl-6-((4-methylpiperazin-1-yl)methyl)pyridin-4-yl)-10-methyl-9,10,11,12-tetrahydro-8H-[1,4]diazepino[5',6':4,5]thieno[3,2-f]quinolin-8-one (I-126)

(R)-3-(3-methoxy-6-vinylpyridazin-4-yl)-10-methyl-9,10,11,12-tetrahydro-8H-[1,4]diazepino[5',6':4,5]thieno[3,2-f]quinolin-8-one (I-127)

(R)-10-methyl-3-(3-(methylamino)-6-vinylpyridazin-4-yl)-9,10,11,12-tetrahydro-8H-[1,4]diazepino[5',6':4,5]thieno[3,2-f]quinolin-8-one (I-128)

(R)-3-(3-(dimethylamino)-6-vinylpyridazin-4-yl)-10-methyl-9,10,11,12-tetrahydro-8H-[1,4]diazepino[5',6':4,5]thieno[3,2-f]quinolin-8-one (I-129)

(R)-3-(5-(difluoromethyl)-2-vinylpyridin-4-yl)-10-methyl-9,10,11,12-tetrahydro-8H-[1,4]diazepino[5',6':4,5]thieno[3,2-f]quinolin-8-one (I-130)

(R)-10-methyl-3-(2-(3-morpholinoprop-1-en-2-yl)pyridin-4-yl)-9,10,11,12-tetrahydro-8H-[1,4]diazepino[5',6':4,5]thieno[3,2-f]quinolin-8-one (I-131)

(R)-3-(6-chloro-3-(2-morpholinoethoxy)pyridazin-4-yl)-10-methyl-9,10,11,12-tetrahydro-8H-[1,4]diazepino[5',6':4,5]thieno[3,2-f]quinolin-8-one (I-132)

(R)-10-methyl-3-(3-(2-morpholinoethoxy)-6-vinylpyridazin-4-yl)-9,10,11,12-tetrahydro-8H-[1,4]diazepino[5',6':4,5]thieno[3,2-f]quinolin-8-one (I-133)

(R)-3-(6-ethynyl-3-(2-morpholinoethoxy)pyridazin-4-yl)-10-methyl-9,10,11,12-tetrahydro-8H-[1,4]diazepino[5',6':4,5]thieno[3,2-f]quinolin-8-one (I-134)

(R)-3-(2-(3-amino-3-methylbut-1-yn-1-yl)pyridin-4-yl)-10-methyl-9,10,11,12-tetrahydro-8H-[1,4]diazepino[5',6':4,5]thieno[3,2-f]quinolin-8-one (I-135)

(R)-10-methyl-3-(3-methyl-6-vinylpyridazin-4-yl)-9,10,11,12-tetrahydro-8H-[1,4]diazepino[5',6':4,5]thieno[3,2-f]quinolin-8-one (I-136)

methyl (R)-4-(10-methyl-8-oxo-9,10,11,12-tetrahydro-8H-[1,4]diazepino[5',6':4,5]thieno[3,2-f]quinolin-3-yl)-6-vinylpyridazine-3-carboxylate (I-137)

(R)-3-(3-methoxy-6-(3-morpholinoprop-1-en-2-yl)pyridazin-4-yl)-10-methyl-9,10,11,12-tetrahydro-8H-[1,4]diazepino[5',6':4,5]thieno[3,2-f]quinolin-8-one (I-138)

(R)-10-methyl-3-(6-(3-morpholinoprop-1-en-2-yl)pyrimidin-4-yl)-9,10,11,12-tetrahydro-8H-[1,4]diazepino[5',6':4,5]thieno[3,2-f]quinolin-8-one (I-139)

(R)-10-methyl-3-(2-(morpholinomethyl)-6-vinylpyridin-4-yl)-9,10,11,12-tetrahydro-8H-[1,4]diazepino[5',6':4,5]thieno[3,2-f]quinolin-8-one (I-140)

(R)-3-(2-((1,1-difluoro-6-azaspiro[2.5]octan-6-yl)methyl)-6-vinylpyridin-4-yl)-10-methyl-9,10,11,12-tetrahydro-8H-[1,4]diazepino[5',6':4,5]thieno[3,2-f]quinolin-8-one (I-141)

(R)-10-methyl-3-(5-(methyl-d3)-2-vinylpyridin-4-yl)-9,10,11,12-tetrahydro-8H-[1,4]diazepino[5',6':4,5]thieno[3,2-f]quinolin-8-one (I-142)

(R)-3-(5-chloro-2-vinylpyridin-4-yl)-10-methyl-9,10,11,12-tetrahydro-8H-[1,4]diazepino[5',6':4,5]thieno[3,2-f]quinolin-8-one (I-143)

(R)-3-(5-chloro-2-ethynylpyridin-4-yl)-10-methyl-9,10,11,12-tetrahydro-8H-[1,4]diazepino[5',6':4,5]thieno[3,2-f]quinolin-8-one (I-144)

(R,E)-3-(6-(3-(dimethylamino)prop-1-en-1-yl)-3-methoxypyridazin-4-yl)-10-methyl-9,10,11,12-tetrahydro-8H-[1,4]diazepino[5',6':4,5]thieno[3,2-f]quinolin-8-one (I-145)

(R)-10-methyl-3-(1-methyl-4-vinyl-1H-pyrazol-5-yl)-9,10,11,12-tetrahydro-8H-[1,4]diazepino[5',6':4,5]thieno[3,2-f]quinolin-8-one (I-146)

(R)-10-methyl-3-(3-vinyl-1H-pyrazol-1-yl)-9,10,11,12-tetrahydro-8H-[1,4]diazepino[5',6':4,5]thieno[3,2-f]quinolin-8-one (I-147)

(R)-10-methyl-3-(4-vinyl-1H-pyrazol-1-yl)-9,10,11,12-tetrahydro-8H-[1,4]diazepino[5',6':4,5]thieno[3,2-f]quinolin-8-one (I-148)

(R)-10-methyl-3-(4-vinylthiazol-2-yl)-9,10,11,12-tetrahydro-8H-[1,4]diazepino[5',6':4,5]thieno[3,2-f]quinolin-8-one (I-149)

(R)-10-methyl-3-(2-vinyl-1H-imidazol-5-yl)-9,10,11,12-tetrahydro-8H-[1,4]diazepino[5',6':4,5]thieno[3,2-f]quinolin-8-one (I-150)

(R)-3-(2-chloro-1H-imidazol-5-yl)-10-methyl-9,10,11,12-tetrahydro-8H-[1,4]diazepino[5',6':4,5]thieno[3,2-f]quinolin-8-one (I-151)

(R)-3-(4-chloro-1H-pyrazol-1-yl)-10-methyl-9,10,11,12-tetrahydro-8H-[1,4]diazepino[5',6':4,5]thieno[3,2-f]quinolin-8-one (I-152)

(R)-10-methyl-3-(5-(morpholinomethyl)-2-vinylpyridin-4-yl)-9,10,11,12-tetrahydro-8H-[1,4]diazepino[5',6':4,5]thieno[3,2-f]quinolin-8-one (I-153)

(R)-3-(2-ethynyl-5-(morpholinomethyl)pyridin-4-yl)-10-methyl-9,10,11,12-tetrahydro-8H-[1,4]diazepino[5',6':4,5]thieno[3,2-f]quinolin-8-one (I-154)

(R)-3-(5-((4-methoxypiperidin-1-yl)methyl)-2-vinylpyridin-4-yl)-10-methyl-9,10,11,12-tetrahydro-8H-[1,4]diazepino[5',6':4,5]thieno[3,2-f]quinolin-8-one (I-155)

(R)-10-methyl-3-(2-morpholino-6-vinylpyridin-4-yl)-9,10,11,12-tetrahydro-8H-[1,4]diazepino[5',6':4,5]thieno[3,2-f]quinolin-8-one (I-156)

(R)-3-(2-ethynyl-6-morpholinopyridin-4-yl)-10-methyl-9,10,11,12-tetrahydro-8H-[1,4]diazepino[5',6':4,5]thieno[3,2-f]quinolin-8-one (I-157)

(R)-3-(2-(4-methoxypiperidin-1-yl)-6-vinylpyridin-4-yl)-10-methyl-9,10,11,12-tetrahydro-8H-[1,4]diazepino[5',6':4,5]thieno[3,2-f]quinolin-8-one (I-158)

(R)-3-(2-ethynyl-6-(4-methoxypiperidin-1-yl)pyridin-4-yl)-10-methyl-9,10,11,12-tetrahydro-8H-[1,4]diazepino[5',6':4,5]thieno[3,2-f]quinolin-8-one (I-159)

(R)-6-chloro-4-(10-methyl-8-oxo-9,10,11,12-tetrahydro-8H-[1,4]diazepino[5',6':4,5]thieno[3,2-f]quinolin-3-yl)nicotinonitrile (I-160)

(R)-4-(10-methyl-8-oxo-9,10,11,12-tetrahydro-8H-[1,4]diazepino[5',6':4,5]thieno[3,2-f]quinolin-3-yl)-6-vinylnicotinonitrile (I-161)

(R)-6-ethynyl-4-(10-methyl-8-oxo-9,10,11,12-tetrahydro-8H-[1,4]diazepino[5',6':4,5]thieno[3,2-f]quinolin-3-yl)nicotinonitrile (I-162)

(R)-10-methyl-3-(6-vinylpyrazin-2-yl)-9,10,11,12-tetrahydro-8H-[1,4]diazepino[5',6':4,5]thieno[3,2-f]quinolin-8-one (I-163)

(R)-10-methyl-3-(2-vinyl-1H-imidazol-1-yl)-9,10,11,12-tetrahydro-8H-[1,4]diazepino[5',6':4,5]thieno[3,2-f]quinolin-8-one (I-164)

(R)-3-(3-chloro-1H-pyrazol-1-yl)-10-methyl-9,10,11,12-tetrahydro-8H-[1,4]diazepino[5',6':4,5]thieno[3,2-f]quinolin-8-one (I-165)

(R)-10-methyl-3-(5-methyl-6-vinylpyrazin-2-yl)-9,10,11,12-tetrahydro-8H-[1,4]diazepino[5',6':4,5]thieno[3,2-f]quinolin-8-one (I-166)

(R)-10-methyl-3-(3-methyl-6-vinylpyrazin-2-yl)-9,10,11,12-tetrahydro-8H-[1,4]diazepino[5',6':4,5]thieno[3,2-f]quinolin-8-one (I-167)

(R)-3-(2-(4,4-difluoropiperidin-1-yl)-6-vinylpyridin-4-yl)-10-methyl-9,10,11,12-tetrahydro-8H-[1,4]diazepino[5',6':4,5]thieno[3,2-f]quinolin-8-one (I-168)

(R)-3-(2-ethynyl-6-(morpholinomethyl)pyridin-4-yl)-10-methyl-9,10,11,12-tetrahydro-8H-[1,4]diazepino[5',6':4,5]thieno[3,2-f]quinolin-8-one (I-169)

(R)-3-(6-ethynyl-3-methylpyridazin-4-yl)-10-methyl-9,10,11,12-tetrahydro-8H-[1,4]diazepino[5',6':4,5]thieno[3,2-f]quinolin-8-one (I-170)

(R)-10-methyl-3-(2-(4-(methyl-d3)piperazin-1-yl)-6-vinylpyridin-4-yl)-9,10,11,12-tetrahydro-8H-[1,4]diazepino[5',6':4,5]thieno[3,2-f]quinolin-8-one (I-171)

(R)-3-(2-ethynyl-6-(4-(methyl-d3)piperazin-1-yl)pyridin-4-yl)-10-methyl-9,10,11,12-tetrahydro-8H-[1,4]diazepino[5',6':4,5]thieno[3,2-f]quinolin-8-one (I-172)

(R)-3-(2-(4-ethylpiperazin-1-yl)-6-vinylpyridin-4-yl)-10-methyl-9,10,11,12-tetrahydro-8H-[1,4]diazepino[5',6':4,5]thieno[3,2-f]quinolin-8-one (I-173)

(R)-3-(2-(4-ethylpiperazin-1-yl)-6-ethynylpyridin-4-yl)-10-methyl-9,10,11,12-tetrahydro-8H-[1,4]diazepino[5',6':4,5]thieno[3,2-f]quinolin-8-one (I-174)

(R)-10-methyl-3-(2-(piperazin-1-yl)-6-vinylpyridin-4-yl)-9,10,11,12-tetrahydro-8H-[1,4]diazepino[5',6':4,5]thieno[3,2-f]quinolin-8-one (I-175)

(R)-3-(2-ethynyl-6-(piperazin-1-yl)pyridin-4-yl)-10-methyl-9,10,11,12-tetrahydro-8H-[1,4]diazepino[5',6':4,5]thieno[3,2-f]quinolin-8-one (I-176)

(R)-10-methyl-3-(2-(piperidin-1-yl)-6-vinylpyridin-4-yl)-9,10,11,12-tetrahydro-8H-[1,4]diazepino[5',6':4,5]thieno[3,2-f]quinolin-8-one (I-177)

(R)-3-(2-ethynyl-6-(piperidin-1-yl)pyridin-4-yl)-10-methyl-9,10,11,12-tetrahydro-8H-[1,4]diazepino[5',6':4,5]thieno[3,2-f]quinolin-8-one (I-178)

(R)-3-(2-(azetidin-1-yl)-6-vinylpyridin-4-yl)-10-methyl-9,10,11,12-tetrahydro-8H-[1,4]diazepino[5',6':4,5]thieno[3,2-f]quinolin-8-one (I-179)

(R)-3-(2-(azetidin-1-yl)-6-ethynylpyridin-4-yl)-10-methyl-9,10,11,12-tetrahydro-8H-[1,4]diazepino[5',6':4,5]thieno[3,2-f]quinolin-8-one (I-180)

(R)-10-methyl-3-(3-methyl-6-vinylpyrazin-2-yl)-9,10,11,12-tetrahydro-8H-[1,4]diazepino[5',6':4,5]thieno[3,2-f]quinolin-8-one (I-181)

(R)-3-(2-(4,4-difluoropiperidin-1-yl)-6-ethynylpyridin-4-yl)-10-methyl-9,10,11,12-tetrahydro-8H-[1,4]diazepino[5',6':4,5]thieno[3,2-f]quinolin-8-one (I-182)

(R)-3-(2-(3,3-difluoroazetidin-1-yl)-6-ethynylpyridin-4-yl)-10-methyl-9,10,11,12-tetrahydro-8H-[1,4]diazepino[5',6':4,5]thieno[3,2-f]quinolin-8-one (I-183)

(R)-3-(2-(3,3-difluoroazetidin-1-yl)-6-vinylpyridin-4-yl)-10-methyl-9,10,11,12-tetrahydro-8H-[1,4]diazepino[5',6':4,5]thieno[3,2-f]quinolin-8-one (I-184)

(R)-3-(2-(((2S,6R)-2,6-dimethylmorpholino)methyl)-6-vinylpyridin-4-yl)-10-methyl-9,10,11,12-tetrahydro-8H-[1,4]diazepino[5',6':4,5]thieno[3,2-f]quinolin-8-one (I-185)

(R)-3-(2-(((2S,6R)-2,6-dimethylmorpholino)methyl)-6-ethynylpyridin-4-yl)-10-methyl-9,10,11,12-tetrahydro-8H-[1,4]diazepino[5',6':4,5]thieno[3,2-f]quinolin-8-one (I-186)

(R)-3-(2-(((2R,6R)-2,6-dimethylmorpholino)methyl)-6-vinylpyridin-4-yl)-10-methyl-9,10,11,12-tetrahydro-8H-[1,4]diazepino[5',6':4,5]thieno[3,2-f]quinolin-8-one (I-187)

(R)-3-(2-(((2R,6R)-2,6-dimethylmorpholino)methyl)-6-ethynylpyridin-4-yl)-10-methyl-9,10,11,12-tetrahydro-8H-[1,4]diazepino[5',6':4,5]thieno[3,2-f]quinolin-8-one (I-188)

(R)-10-methyl-3-(2-((4-(trifluoromethoxy)piperidin-1-yl)methyl)-6-vinylpyridin-4-yl)-9,10,11,12-tetrahydro-8H-[1,4]diazepino[5',6':4,5]thieno[3,2-f]quinolin-8-one (I-189)

(R)-3-(2-ethynyl-6-((4-(trifluoromethoxy)piperidin-1-yl)methyl)pyridin-4-yl)-10-methyl-9,10,11,12-tetrahydro-8H-[1,4]diazepino[5',6':4,5]thieno[3,2-f]quinolin-8-one (I-190)

(R)-10-methyl-3-(6-methyl-2-vinyl-5,6,7,8-tetrahydropyrido[4,3-d]pyrimidin-4-yl)-9,10,11,12-tetrahydro-8H-[1,4]diazepino[5',6':4,5]thieno[3,2-f]quinolin-8-one (I-191)

(R)-3-(2-chloro-6-methyl-5,6,7,8-tetrahydropyrido[4,3-d]pyrimidin-4-yl)-10-methyl-9,10,11,12-tetrahydro-8H-[1,4]diazepino[5',6':4,5]thieno[3,2-f]quinolin-8-one (I-192)

(R)-3-(2-ethynyl-6-methyl-5,6,7,8-tetrahydropyrido[4,3-d]pyrimidin-4-yl)-10-methyl-9,10,11,12-tetrahydro-8H-[1,4]diazepino[5',6':4,5]thieno[3,2-f]quinolin-8-one (I-193)

(R)-3-(2,3-dimethyl-6-vinylpyridin-4-yl)-10-methyl-9,10,11,12-tetrahydro-8H-[1,4]diazepino[5',6':4,5]thieno[3,2-f]quinolin-8-one (I-194)

(R)-3-(5-ethyl-2-vinylpyridin-4-yl)-10-methyl-9,10,11,12-tetrahydro-8H-[1,4]diazepino[5',6':4,5]thieno[3,2-f]quinolin-8-one (I-195)

(R)-3-(5-cyclopropyl-2-vinylpyridin-4-yl)-10-methyl-9,10,11,12-tetrahydro-8H-[1,4]diazepino[5',6':4,5]thieno[3,2-f]quinolin-8-one (I-196)

(R)-10-methyl-3-(3-methyl-2-(morpholinomethyl)-6-vinylpyridin-4-yl)-9,10,11,12-tetrahydro-8H-[1,4]diazepino[5',6':4,5]thieno[3,2-f]quinolin-8-one (I-197)

(R)-3-(3-fluoro-2-(morpholinomethyl)-6-vinylpyridin-4-yl)-10-methyl-9,10,11,12-tetrahydro-8H-[1,4]diazepino[5',6':4,5]thieno[3,2-f]quinolin-8-one (I-198)

(R,E)-10-methyl-3-(2-(3,3,3-trifluoroprop-1-en-1-yl)pyridin-4-yl)-9,10,11,12-tetrahydro-8H-[1,4]diazepino[5',6':4,5]thieno[3,2-f]quinolin-8-one (I-199)

(R,E)-3-(3-methoxy-6-(3,3,3-trifluoroprop-1-en-1-yl)pyridazin-4-yl)-10-methyl-9,10,11,12-tetrahydro-8H-[1,4]diazepino[5',6':4,5]thieno[3,2-f]quinolin-8-one (I-200)

(10R)-3-(2-(2,6-dimethylmorpholino)-6-vinylpyridin-4-yl)-10-methyl-9,10,11,12-tetrahydro-8H-[1,4]diazepino[5',6':4,5]thieno[3,2-f]quinolin-8-one (I-201)

(R)-10-methyl-3-(2-(4-(trifluoromethyl)piperidin-1-yl)-6-vinylpyridin-4-yl)-9,10,11,12-tetrahydro-8H-[1,4]diazepino[5',6':4,5]thieno[3,2-f]quinolin-8-one (I-202)

(R)-10-methyl-3-(3-vinyl-4H-1,2,4-triazol-4-yl)-9,10,11,12-tetrahydro-8H-[1,4]diazepino[5',6':4,5]thieno[3,2-f]quinolin-8-one (I-203)

(R)-3-(3-ethynyl-4H-1,2,4-triazol-4-yl)-10-methyl-9,10,11,12-tetrahydro-8H-[1,4]diazepino[5',6':4,5]thieno[3,2-f]quinolin-8-one (I-204)

(R)-3-(2-chloro-1H-imidazol-1-yl)-10-methyl-9,10,11,12-tetrahydro-8H-[1,4]diazepino[5',6':4,5]thieno[3,2-f]quinolin-8-one (I-205)

(R)-10-methyl-3-(4-methyl-2-vinyl-1H-imidazol-1-yl)-9,10,11,12-tetrahydro-8H-[1,4]diazepino[5',6':4,5]thieno[3,2-f]quinolin-8-one (I-206)

(R)-10-methyl-3-(3-vinyl-1H-1,2,4-triazol-1-yl)-9,10,11,12-tetrahydro-8H-[1,4]diazepino[5',6':4,5]thieno[3,2-f]quinolin-8-one (I-207)

(R)-10-methyl-3-(1-methyl-5-vinyl-1H-1,2,4-triazol-3-yl)-9,10,11,12-tetrahydro-8H-[1,4]diazepino[5',6':4,5]thieno[3,2-f]quinolin-8-one (I-208)

(R)-10-methyl-3-(2-vinylthiazol-5-yl)-9,10,11,12-tetrahydro-8H-[1,4]diazepino[5',6':4,5]thieno[3,2-f]quinolin-8-one (I-209)

(R)-3-(3-chloro-1H-1,2,4-triazol-1-yl)-10-methyl-9,10,11,12-tetrahydro-8H-[1,4]diazepino[5',6':4,5]thieno[3,2-f]quinolin-8-one (I-210)

(R)-3-(5-((3,3-difluoroazetidin-1-yl)methyl)-2-vinylpyridin-4-yl)-10-methyl-9,10,11,12-tetrahydro-8H-[1,4]diazepino[5',6':4,5]thieno[3,2-f]quinolin-8-one (I-211)

(R)-10-methyl-3-(5-((4-(trifluoromethyl)piperidin-1-yl)methyl)-2-vinylpyridin-4-yl)-9,10,11,12-tetrahydro-8H-[1,4]diazepino[5',6':4,5]thieno[3,2-f]quinolin-8-one (I-212)

(R)-3-(5-(((2S,6R)-2,6-dimethylmorpholino)methyl)-2-vinylpyridin-4-yl)-10-methyl-9,10,11,12-tetrahydro-8H-[1,4]diazepino[5',6':4,5]thieno[3,2-f]quinolin-8-one (I-213)

(R)-10-methyl-3-(5-vinyl-1H-1,2,4-triazol-1-yl)-9,10,11,12-tetrahydro-8H-[1,4]diazepino[5',6':4,5]thieno[3,2-f]quinolin-8-one (I-214)

rac-(R)-8-(4-(10-methyl-8-oxo-9,10,11,12-tetrahydro-8H-[1,4]diazepino[5',6':4,5]thieno[3,2-f]quinolin-3-yl)-6-vinylpyridin-2-yl)-1-oxa-8-azaspiro[4.5]decan-2-one (I-215)

rac-(10R)-3-(2-(2-oxa-5-azabicyclo[2.2.1]heptan-5-yl)-6-vinylpyridin-4-yl)-10-methyl-9,10,11,12-tetrahydro-8H-[1,4]diazepino[5',6':4,5]thieno[3,2-f]quinolin-8-one (I-216)

(R)-3-(3-fluoro-2-vinylpyridin-4-yl)-10-methyl-9,10,11,12-tetrahydro-8H-[1,4]diazepino[5',6':4,5]thieno[3,2-f]quinolin-8-one (I-217)

(R)-3-(2-ethynyl-3-fluoropyridin-4-yl)-10-methyl-9,10,11,12-tetrahydro-8H-[1,4]diazepino[5',6':4,5]thieno[3,2-f]quinolin-8-one (I-218)

(R)-10-methyl-3-(3-methyl-2-vinylpyridin-4-yl)-9,10,11,12-tetrahydro-8H-[1,4]diazepino[5',6':4,5]thieno[3,2-f]quinolin-8-one (I-219)

(R)-3-(2-ethynyl-3-methylpyridin-4-yl)-10-methyl-9,10,11,12-tetrahydro-8H-[1,4]diazepino[5',6':4,5]thieno[3,2-f]quinolin-8-one (I-220)

(R)-3-(2-chloro-3-fluoropyridin-4-yl)-10-methyl-9,10,11,12-tetrahydro-8H-[1,4]diazepino[5',6':4,5]thieno[3,2-f]quinolin-8-one (I-221)

(R)-3-(2-ethynyl-1H-imidazol-1-yl)-10-methyl-9,10,11,12-tetrahydro-8H-[1,4]diazepino[5',6':4,5]thieno[3,2-f]quinolin-8-one (I-222)

(R)-10-methyl-3-(3-methyl-5-vinyl-4H-1,2,4-triazol-4-yl)-9,10,11,12-tetrahydro-8H-[1,4]diazepino[5',6':4,5]thieno[3,2-f]quinolin-8-one (I-223)

(R)-10-methyl-3-(3-methyl-5-vinyl-1H-1,2,4-triazol-1-yl)-9,10,11,12-tetrahydro-8H-[1,4]diazepino[5',6':4,5]thieno[3,2-f]quinolin-8-one (I-224)

(R)-10-methyl-3-(6-(3,3,3-trifluoroprop-1-en-2-yl)pyrazin-2-yl)-9,10,11,12-tetrahydro-8H-[1,4]diazepino[5',6':4,5]thieno[3,2-f]quinolin-8-one (I-225)

(R)-10-methyl-3-(3-(trifluoromethyl)-5-vinyl-1H-1,2,4-triazol-1-yl)-9,10,11,12-tetrahydro-8H-[1,4]diazepino[5',6':4,5]thieno[3,2-f]quinolin-8-one (I-226)

(R)-10-methyl-3-(5-methyl-3-vinylisoxazol-4-yl)-9,10,11,12-tetrahydro-8H-[1,4]diazepino[5',6':4,5]thieno[3,2-f]quinolin-8-one (I-227)

(R)-10-methyl-3-(3-vinylisothiazol-4-yl)-9,10,11,12-tetrahydro-8H-[1,4]diazepino[5',6':4,5]thieno[3,2-f]quinolin-8-one (I-228)

(R)-10-methyl-3-(5-vinylisothiazol-4-yl)-9,10,11,12-tetrahydro-8H-[1,4]diazepino[5',6':4,5]thieno[3,2-f]quinolin-8-one (I-229)

(R)-10-methyl-3-(1-methyl-3-vinyl-1H-pyrazol-4-yl)-9,10,11,12-tetrahydro-8H-[1,4]diazepino[5',6':4,5]thieno[3,2-f]quinolin-8-one (I-230)

(R)-3-(4,5-dimethyl-2-vinyl-1H-imidazol-1-yl)-10-methyl-9,10,11,12-tetrahydro-8H-[1,4]diazepino[5',6':4,5]thieno[3,2-f]quinolin-8-one (I-231)

(R)-10-methyl-3-(2-methyl-5-vinyl-2H-1,2,3-triazol-4-yl)-9,10,11,12-tetrahydro-8H-[1,4]diazepino[5',6':4,5]thieno[3,2-f]quinolin-8-one (I-232)

(R)-10-methyl-3-(1-methyl-4-vinyl-1H-1,2,3-triazol-5-yl)-9,10,11,12-tetrahydro-8H-[1,4]diazepino[5',6':4,5]thieno[3,2-f]quinolin-8-one (I-233) ethyl (R)-5-(10-methyl-8-oxo-9,10,11,12-tetrahydro-8H-[1,4]diazepino[5',6':4,5]thieno[3,2-f]quinolin-3-yl)-2-vinylthiazole-4-carboxylate (I-234)

(R)-10-methyl-3-(1-methyl-5-vinyl-1H-1,2,3-triazol-4-yl)-9,10,11,12-tetrahydro-8H-[1,4]diazepino[5',6':4,5]thieno[3,2-f]quinolin-8-one (I-235)

(R)-10-methyl-3-(3-methyl-5-vinyl-1H-pyrazol-1-yl)-9,10,11,12-tetrahydro-8H-[1,4]diazepino[5',6':4,5]thieno[3,2-f]quinolin-8-one (I-236)

(R)-3-(2-((2-methoxyethyl)(methyl)amino)-6-vinylpyridin-4-yl)-10-methyl-9,10,11,12-tetrahydro-8H-[1,4]diazepino[5',6':4,5]thieno[3,2-f]quinolin-8-one (I-237)

(R)-3-(2-(2-oxa-6-azaspiro[3.3]heptan-6-yl)-6-vinylpyridin-4-yl)-10-methyl-9,10,11,12-tetrahydro-8H-[1,4]diazepino[5',6':4,5]thieno[3,2-f]quinolin-8-one (I-238)

(R)-3-(2-(4-fluoropiperidin-1-yl)-6-vinylpyridin-4-yl)-10-methyl-9,10,11,12-tetrahydro-8H-[1,4]diazepino[5',6':4,5]thieno[3,2-f]quinolin-8-one (I-239)

(R)-3-(2-(4-(methoxymethyl)piperidin-1-yl)-6-vinylpyridin-4-yl)-10-methyl-9,10,11,12-tetrahydro-8H-[1,4]diazepino[5',6':4,5]thieno[3,2-f]quinolin-8-one (I-240)

(R)-10-methyl-3-(3-(trifluoromethyl)-5-vinyl-1H-pyrazol-1-yl)-9,10,11,12-tetrahydro-8H-[1,4]diazepino[5',6':4,5]thieno[3,2-f]quinolin-8-one (I-241)

(R)-3-(2-bromo-4-(trifluoromethyl)-1H-imidazol-1-yl)-10-methyl-9,10,11,12-tetrahydro-8H-[1,4]diazepino[5',6':4,5]thieno[3,2-f]quinolin-8-one (I-242)

(10R)-3-(5-(1-hydroxyethyl-2,2,2-d3)-2-vinylpyridin-4-yl)-10-methyl-9,10,11,12-tetrahydro-8H-[1,4]diazepino[5',6':4,5]thieno[3,2-f]quinolin-8-one (I-243)

di-tert-butyl (R)-10-methyl-3-(5-methyl-2-vinylpyridin-4-yl)-8-oxo-10,11-dihydro-8H-[1,4]diazepino[5',6':4,5]thieno[3,2-f]quinoline-9,12-dicarboxylate (I-244)

(R)-10-methyl-3-(5-(trifluoromethoxy)-2-vinylpyridin-4-yl)-9,10,11,12-tetrahydro-8H-[1,4]diazepino[5',6':4,5]thieno[3,2-f]quinolin-8-one (I-245)

(R)-1-(10-methyl-8-oxo-9,10,11,12-tetrahydro-8H-[1,4]diazepino[5',6':4,5]thieno[3,2-f]quinolin-3-yl)-1H-imidazole-2-carbonitrile (I-246)

(R)-3-(5-(difluoromethoxy)-2-vinylpyridin-4-yl)-10-methyl-9,10,11,12-tetrahydro-8H-[1,4]diazepino[5',6':4,5]thieno[3,2-f]quinolin-8-one (I-247)

(R)-3-(5-cyclopropyl-3-vinyl-1H-1,2,4-triazol-1-yl)-10-methyl-9,10,11,12-tetrahydro-8H-[1,4]diazepino[5',6':4,5]thieno[3,2-f]quinolin-8-one (I-248)

(R)-10-methyl-3-(5-(methyl-d3)-2-vinylpyridin-4-yl-3-d)-9,10,11,12-tetrahydro-8H-[1,4]diazepino[5',6':4,5]thieno[3,2-f]quinolin-8-one (I-249)

(R)-3-(2-bromo-4,5-dichloro-1H-imidazol-1-yl)-10-methyl-9,10,11,12-tetrahydro-8H-[1,4]diazepino[5',6':4,5]thieno[3,2-f]quinolin-8-one (I-250)

(R)-3-(4,5-dichloro-2-vinyl-1H-imidazol-1-yl)-10-methyl-9,10,11,12-tetrahydro-8H-[1,4]diazepino[5',6':4,5]thieno[3,2-f]quinolin-8-one (I-251)

(R)-3-(5-(hydroxymethyl)-2-vinylpyridin-4-yl)-10-methyl-9,10,11,12-tetrahydro-8H-[1,4]diazepino[5',6':4,5]thieno[3,2-f]quinolin-8-one (I-252)

(R)-3-(5-(methoxymethyl)-2-vinylpyridin-4-yl)-10-methyl-9,10,11,12-tetrahydro-8H-[1,4]diazepino[5',6':4,5]thieno[3,2-f]quinolin-8-one (I-253)

(S)-10-(fluoromethyl)-3-(5-methyl-2-vinylpyridin-4-yl)-9,10,11,12-tetrahydro-8H-[1,4]diazepino[5',6':4,5]thieno[3,2-f]quinolin-8-one (I-254)

(S)-10-(fluoromethyl)-3-(2-vinyl-1H-imidazol-1-yl)-9,10,11,12-tetrahydro-8H-[1,4]diazepino[5',6':4,5]thieno[3,2-f]quinolin-8-one (I-255)

(R)-3-(5-methoxy-2-vinylpyridin-4-yl)-10-methyl-9,10,11,12-tetrahydro-8H-[1,4]diazepino[5',6':4,5]thieno[3,2-f]quinolin-8-one (I-256)

(R)-10-methyl-3-(5-(trifluoromethyl)-3-vinyl-1H-pyrazol-1-yl)-9,10,11,12-tetrahydro-8H-[1,4]diazepino[5',6':4,5]thieno[3,2-f]quinolin-8-one (I-257)

(R)-3-(5-(2-hydroxypropan-2-yl-1,1,1,3,3,3-d6)-2-vinylpyridin-4-yl)-10-methyl-9,10,11,12-tetrahydro-8H-[1,4]diazepino[5',6':4,5]thieno[3,2-f]quinolin-8-one (I-258)

(10R)-3-(5-(1-hydroxyethyl-2,2,2-d3)-2-vinylpyridin-4-yl)-10-methyl-9,10,11,12-tetrahydro-8H-[1,4]diazepino[5',6':4,5]thieno[3,2-f]quinolin-8-one (I-259)

(10R)-3-(5-(1-hydroxyethyl-2,2,2-d3)-2-vinylpyridin-4-yl)-10-methyl-9,10,11,12-tetrahydro-8H-[1,4]diazepino[5',6':4,5]thieno[3,2-f]quinolin-8-one (I-260)

(R)-10-methyl-3-(5-methyl-3-vinyl-1H-1,2,4-triazol-1-yl)-9,10,11,12-tetrahydro-8H-[1,4]diazepino[5',6':4,5]thieno[3,2-f]quinolin-8-one (I-261)

(R)-3-(5-(ethoxymethyl)-2-vinylpyridin-4-yl)-10-methyl-9,10,11,12-tetrahydro-8H-[1,4]diazepino[5',6':4,5]thieno[3,2-f]quinolin-8-one (I-262)

(R)-3-(5-((2-oxa-6-azaspiro[3.3]heptan-6-yl)methyl)-2-vinylpyridin-4-yl)-10-methyl-9,10,11,12-tetrahydro-8H-[1,4]diazepino[5',6':4,5]thieno[3,2-f]quinolin-8-one (I-263)

(R)-10-methyl-3-(5-vinylpyridazin-3-yl)-9,10,11,12-tetrahydro-8H-[1,4]diazepino[5',6':4,5]thieno[3,2-f]quinolin-8-one (I-264)

(R,E)-10-methyl-3-(5-methyl-2-(prop-1-en-1-yl)pyridin-4-yl)-9,10,11,12-tetrahydro-8H-[1,4]diazepino[5',6':4,5]thieno[3,2-f]quinolin-8-one (I-265)

(R,E)-10-methyl-3-(2-(prop-i-en-1-yl)-1H-imidazol-1-yl)-9,10,11,12-tetrahydro-8H-[1,4]diazepino[5',6':4,5]thieno[3,2-f]quinolin-8-one (I-266)

(R)-2-(5-methyl-4-(10-methyl-8-oxo-9,10,11,12-tetrahydro-8H-[1,4]diazepino[5',6':4,5]thieno[3,2-f]quinolin-3-yl)pyridin-2-yl)acetonitrile (I-267)

1'-fluoro-2'-(2-((2-methoxyethyl)(methyl)amino)-6-vinylpyridin-4-yl)-1-methyl-6',8',9',11'-tetrahydrospiro[azetidine-3,10'-pyrido[3',4':4,5]pyrrolo[2,3-f]isoquinolin]-7'(5'H)-one (I-268)

2'-(2-(2-oxa-7-azaspiro[4.4]nonan-7-yl)-6-vinylpyridin-4-yl)-1'-fluoro-1-methyl-6',8',9',11'-tetrahydrospiro[azetidine-3,10'-pyrido[3',4':4,5]pyrrolo[2,3-f]isoquinolin]-7'(5'H)-one (I-269)

1'-fluoro-2'-(2-(4-(methoxymethyl)piperidin-1-yl)-6-vinylpyridin-4-yl)-1-methyl-6',8',9',11'-tetrahydrospiro[azetidine-3,10'-pyrido[3',4':4,5]pyrrolo[2,3-f]isoquinolin]-7'(5'H)-one (I-270)

(R)-10-methyl-3-(2-vinyl-1H-benzo[d]imidazol-1-yl)-9,10,11,12-tetrahydro-8H-[1,4]diazepino[5',6':4,5]thieno[3,2-f]quinolin-8-one (I-271)

(R)-3-(2-chloropyridin-4-yl)-10-methyl-9,10,11,12-tetrahydro-8H-[1,4]diazepino[5',6':4,5]thieno[3,2-f]quinolin-8-one (I-272)

(R)-3-(2-chloro-5-fluoropyrimidin-4-yl)-10-methyl-9,10,11,12-tetrahydro-8H-[1,4]diazepino[5',6':4,5]thieno[3,2-f]quinolin-8-one (I-273)

(R)-3-(6-chloro-3-fluoro-5-(trifluoromethyl)pyridin-2-yl)-10-methyl-9,10,11,12-tetrahydro-8H-[1,4]diazepino[5',6':4,5]thieno[3,2-f]quinolin-8-one (I-274).

12. A compound which is (R)-10-methyl-3-(5-methyl-2-vinylpyridin-4-yl)-9,10,11,12-tetrahydro-8H-[1,4]diazepino[5',6':4,5]thieno[3,2-f]quinolin-8-one.

13. A compound which is (R)-10-methyl-3-(5-methyl-2-vinylpyridin-4-yl)-9,10,11,12-tetrahydro-8H-[1,4]diazepino[5',6':4,5]thieno[3,2-f]quinolin-8-one, or a pharmaceutically acceptable salt thereof.

* * * * *